(12) United States Patent
Lee et al.

(10) Patent No.: US 11,649,255 B2
(45) Date of Patent: May 16, 2023

(54) INDAZOLES AS HEMATOPOIETIC PROGENITOR KINASE 1 (HPK1) INHIBITORS AND METHODS USING SAME

(71) Applicant: 1st Biotherapeutics, Inc., Gyeonggi-do (KR)

(72) Inventors: Jinhwa Lee, Gyeonggi-do (KR); Suyeon Jo, Gyeonggi-do (KR); Keonseung Lim, Gyeonggi-do (KR); A Yeong Park, Gyeonggi-do (KR); Gadhe Changdev Gorakshnath, Seoul (KR); Hwajung Nam, Busan (KR); Yeonguk Jeon, Gyeonggi-do (KR); Yejin Hwang, Gyeonggi-do (KR); Jae Eun Kim, Gyeonggi-do (KR); Misoon Kim, Gyeonggi-do (KR); Seung Mook Lim, Gyeonggi-do (KR)

(73) Assignee: 1ST Biotherapeutics, Inc., Gyeonggi-do (KR)

( * ) Notice: Subject to any disclaimer, the term of this patent is extended or adjusted under 35 U.S.C. 154(b) by 0 days.

(21) Appl. No.: 17/485,711

(22) Filed: Sep. 27, 2021

(65) Prior Publication Data
US 2022/0098193 A1 Mar. 31, 2022

Related U.S. Application Data

(60) Provisional application No. 63/084,059, filed on Sep. 28, 2020.

(51) Int. Cl.
| | |
|---|---|
| *C07F 7/08* | (2006.01) |
| *C07D 487/04* | (2006.01) |
| *C07D 417/04* | (2006.01) |
| *C07D 417/14* | (2006.01) |
| *C07D 471/04* | (2006.01) |
| *C07D 513/04* | (2006.01) |
| *C07F 9/6558* | (2006.01) |

(52) U.S. Cl.
CPC .......... *C07F 7/0812* (2013.01); *C07D 417/04* (2013.01); *C07D 417/14* (2013.01); *C07D 471/04* (2013.01); *C07D 487/04* (2013.01); *C07D 513/04* (2013.01); *C07F 9/65583* (2013.01); *C07B 2200/05* (2013.01)

(58) Field of Classification Search
CPC .. C07F 9/65583; C07F 7/0812; C07D 471/04; C07D 417/14; C07D 487/04; C07D 417/04; C07D 513/04

USPC .......................................................... 514/80
See application file for complete search history.

(56) References Cited

U.S. PATENT DOCUMENTS

| | | |
|---|---|---|
| 8,975,406 B2 | 3/2015 | Menet et al. |
| 8,993,580 B2 | 3/2015 | Ren et al. |
| 2019/0100500 A1 | 4/2019 | Lee et al. |

FOREIGN PATENT DOCUMENTS

| | | | |
|---|---|---|---|
| CN | 109721620 A | 5/2019 | |
| WO | WO-2009/017822 A2 | 2/2009 | |
| WO | WO-2009017822 A2 * | 2/2009 | ........... C07D 277/82 |
| WO | WO-2010/008847 A2 | 1/2010 | |
| WO | WO-2010008847 A2 * | 1/2010 | ........... C07D 513/04 |
| WO | WO-2010/100144 A1 | 9/2010 | |
| WO | WO-2013/130855 A1 | 9/2013 | |

OTHER PUBLICATIONS

International Search Report from corresponding PCT Application No. PCT/IB2021/058795, dated Dec. 24, 2021.
Written Opinion of the International Searching Authority from corresponding PCT Application No. PCT/IB2021/058795, dated Dec. 24, 2021.

* cited by examiner

*Primary Examiner* — Kahsay Habte
(74) *Attorney, Agent, or Firm* — Harness, Dickey & Pierce, P.L.C.

(57) ABSTRACT

The present disclosure provides a compound of Formula (I) or pharmaceutically acceptable salts thereof, a composition comprising the compound, methods of using the compound for the treatment of various disorders associated with HPK1, and methods of preparing these compounds.

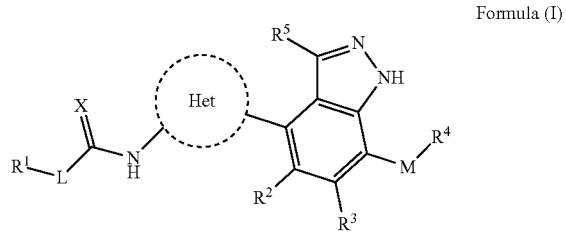

Formula (I)

19 Claims, No Drawings

INDAZOLES AS HEMATOPOIETIC PROGENITOR KINASE 1 (HPK1) INHIBITORS AND METHODS USING SAME

CROSS-REFERENCE TO RELATED APPLICATIONS

This application claims the benefit and priority to U.S. Provisional Patent Application No. 63/084,059, filed on 28 Sep. 2020. The entire disclosure of the application identified in this paragraph is incorporated herein by reference.

FIELD

The present disclosure is directed to inhibitors of hematopoietic progenitor kinase 1 (HPK1), pharmaceutical compositions comprising the inhibitors, methods of using the inhibitors for the treatment of various disorders associated with HPK1, and methods of preparing these compounds.

BACKGROUND

Immunotherapy is treatment that uses the human body's own immune system to help fight cancer and other disorders. This relatively new approach has achieved remarkable clinical successes in the treatment of a variety of tumor types in recent years, especially with the treatment of immune checkpoint inhibitors and chimeric antigen T-cell therapy. The most investigated checkpoint inhibitors including CTLA4, PD-1, or PD-L1 inhibitors have demonstrated significant antitumor activity by overcoming immunosuppressive mechanisms at the tumor site.

Hematopoietic progenitor kinase 1 (HPK1, MAP4K1) is a serine/threonine kinase and a member of MAP4K. HPK1 is prominently expressed in subsets of hematopoietic cell lineages. HPK1 is a newly identified as a critical negative regulator in the activation of T lymphocytes and dendritic cells. It has been recently demonstrated that the important roles for kinase activity of HPK1 in anticancer immunity as a new intracellular checkpoint molecule as well as potential advantages of combination therapy with current checkpoint regimens. HPK1 inhibition is expected to have dual functions, 1. prolonged activation of T cells; 2. enhanced APC functions by dendritic cells. This dual targeting may synergistically work together for efficient immune responses in tumor microenvironment. Thus, HPK1 has been validated as a novel target for anticancer immunotherapy. Examples of cancers that are treatable using the compounds of the present disclosure include, but are not limited to, all forms of carcinomas, melanomas, blastomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

Inhibition of HPK1 with small molecule inhibitors has the potential for the treatment of cancer and other disorders [Hernandez, S., et. al. (2018) Cell Reports 25, 80-94].

SUMMARY

The present disclosure provides novel indazole compounds and pharmaceutically acceptable salts as effective HPK1 inhibitors and dual activators of T cell and dendritic cell.

One embodiment of the invention is a compound represented by Formula (I):

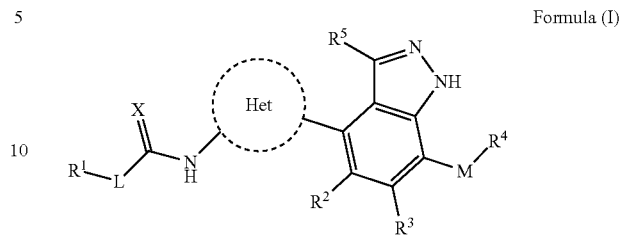

Formula (I)

or a pharmaceutically acceptable salt, hydrate, solvate thereof, wherein $R^1$, $R^2$, $R^3$, $R^4$, $R^5$, Het, M, and L are as defined in the detailed descriptions.

In another embodiment, there is provided a pharmaceutical composition comprising a pharmaceutically acceptable carrier or diluent and a compound of Formula (I) or a pharmaceutically acceptable salt thereof.

In yet another embodiment, there is provided a method of treating a subject with a disease or disorder associated with modulation of HPK1 comprising: administering to the subject a therapeutically effective amount of a compound of Formula (I) or a pharmaceutically acceptable salt thereof.

DETAILED DESCRIPTION

The following description is merely exemplary in nature and is not intended to limit the present disclosure, application, or uses.

Definitions

The generic terms used in the present disclosure are herein defined for clarity.

This specification uses the terms "substituent", "radical", "group", "moiety", and "fragment" interchangeably.

As used herein, the term "alkenyl" refers to a straight or branched hydrocarbonyl group with at least one site of unsaturation, i.e., a carbon-carbon, sp2 double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

As used herein, the term "alkoxy" is RO— where R is alkyl. Non-limiting examples of alkoxy groups include methoxy, ethoxy and propoxy.

As used herein, the term "alkoxyalkyl" refers to an alkyl moiety substituted with an alkoxy group. Examples of alkoxyalkyl groups include methoxymethyl, methoxyethyl, methoxypropyl and ethoxyethyl.

As used herein, the term "alkoxycarbonyl" is ROC(O)—, where R is an alkyl group as defined herein. In various embodiments, R is a $C_1$-$C_{10}$ alkyl group or a $C_1$-$C_6$ alkyl group.

As used herein, the term "alkyl" refers to a straight or branched chain hydrocarbonyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl. "lower alkyl" means alkyl having from 1 to 4 carbon atoms.

As used herein, if the term "$C_1$-$C_6$" is used, it means the number of carbon atoms is from 1 to 6. For example, $C_1$-$C_6$ alkyl means an alkyl which carbon number is any integer of from 1 to 6.

As used herein, the term "alkylamino" refers to an amino group substituted with one or more alkyl groups. "N-(alkyl) amino" is RNH— and "N,N-(alkyl)$_2$amino" is $R_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamino.

As used herein, the term "alkylaminoalkyl" refers to an alkyl moiety substituted with an alkylamino group, wherein alkylamino is as defined herein. Examples of alkylaminoakyl groups include methylaminomethyl and ethylaminomethyl.

As used herein, the term "alkynyl" refers to a straight or branched carbon-chain group with at least one site of unsaturation, i.e., a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$alkynyl group. Examples of alkynyl groups include acetylenic (—C≡CH) and propargyl (—CH$_2$CE CH).

As used herein, the term "aryl" refers to any monocyclic or bicyclic carbon ring of up to 7 atoms in each ring, wherein at least one ring is aromatic, or an aromatic ring system of 5 to 14 carbon atoms which includes a carbocyclic aromatic group fused with a 5- or 6-membered cycloalkyl group. Representative examples of aryl groups include, but are not limited to, phenyl, tolyl, xylyl, naphthyl, tetrahydronaphthyl, anthracenyl, fluorenyl, indenyl, azulenyl and indanyl. A carbocyclic aromatic group can be unsubstituted or optionally substituted.

As used herein, the term "cycloalkyl" is a hydrocarbyl group containing at least one saturated or partially unsaturated ring structure, and attached via a ring carbon. In various embodiments, it refers to a saturated or a partially unsaturated $C_3$-$C_{12}$cyclic moiety, examples of which include cyclopropyl, cyclobutyl, cyclopentyl, cyclopentenyl, cyclohexyl, cyclohexenyl, cycloheptyl and cyclooctyl. "Cycloalkyloxy" is RO—, where R is cycloalkyl.

As used herein, the terms "halogen" and "halo" refers to chloro (—Cl), bromo (—Br), fluoro (—F) or iodo (—I). "Haloalkoxy" refers to an alkoxy group substituted with one or more halo groups and examples of haloalkoxy groups include, but are not limited to, —OCF$_3$, —OCHF$_2$ and —OCH$_2$F. "Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl. "Haloalkyl" refers to an alkyl moiety substituted with one or more halo groups. Examples of haloalkyl groups include —CF$_3$ and —CHF$_2$.

As used herein, the term "heteroalkyl" refers to a straight- or branched-chain alkyl group having from 2 to 14 carbons (in some embodiments, 2 to 10 carbons) in the chain, one or more of which has been replaced by a heteroatom selected from S, O, P and N. Exemplary heteroalkyls include alkyl ethers, secondary and tertiary alkyl amines, amides, alkyl sulfides, and the like.

As used herein, the term "heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof "Heterocyclyloxy" is RO—, where R is heterocyclyl. "Heterocyclylthio" is RS—, where R is heterocyclyl.

As used herein, the term "3- or 4-membered heterocyclyl" refers to a monocyclic ring having 3 or 4 ring atoms wherein at least one ring atom is heteroatom selected from the group consisting of N, O and S. Non-limiting examples of 3- or 4-membered heterocyclyl include aziridinyl, 2H-azirinyl, oxiranyl, thiiranyl, azetidinyl, 2,3-dihyroazetyl, azetyl, 1,3-diazetidinyl, oxetanyl, 2H-oxetyl, thietanyl, and 2H-thietyl.

As used herein, the term "heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl. "Heteroaryloxy" is RO—, where R is heteroaryl.

As used herein, the term "hydroxyalkoxy" refers to an alkoxy group substituted with a hydroxyl group (—OH), wherein alkoxy is as defined herein. An example of hydroxyalkoxy is hydroxyethoxy.

As used herein, the term "hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

As used herein, the term "pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

As used herein, the term "pharmaceutically acceptable carrier" refers to a diluent, adjuvant, excipient, or carrier, or other ingredient which is pharmaceutically acceptable and with which a compound of the invention is administered.

As used herein, the term "pharmaceutically acceptable salt" refers to a salt which may enhance desired pharmacological activity. Examples of pharmaceutically acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo [2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

As used herein, the term "substituted" means any of above groups (i.e., alkyl, aryl, heteroaryl, heterocycle or cycloalkyl) wherein at least one hydrogen atom of the moiety being substituted is replaced with a substituent. In one embodiment, each carbon atom of the group being substituted is substituted with no more than two substituents. In another embodiment, each carbon atom of the group being substituted is substituted with no more than one substituent. In the case of a keto substituent, two hydrogen atoms are replaced with an oxygen which is attached to the carbon via a double bond. Unless specifically defined, substituents include halo, hydroxyl, (lower) alkyl, haloalkyl, mono- or di-alkylamino, aryl, heterocycle, —NO$_2$, B(OH)$_2$, BPin, —NR$_a$R$_b$, —NR$_a$C(=O)R$_b$, —NR$_a$C(=O)NR$_a$R$_b$, —NR$_a$C(=O)OR$_b$, —NR$_a$SO$_2$R$_b$, —OR$_a$, —CN, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —NR$_a$SO$_2$R$_b$, —PO$_3$R$_a$, —PO(OR$_a$)(OR$_b$), —SO$_2$R$_a$, —S(O)R$_a$, —SO(N)R$_a$ (e.g., sulfoximine), —(R$_a$)S=NR$_b$ (e.g., sulfilimine) and —SR$_a$, wherein R$_a$ and R$_b$ are the same or different and independently —H, halo, amino, alkyl, haloalkyl, aryl or heterocycle, or wherein R$_a$ and R$_b$ taken together with the nitrogen atom to which they are attached form a heterocycle. R$_a$ and R$_b$ may be in the plural based on atoms which those are attached to.

As used herein, the term "therapeutically effective amount" means when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

As used herein, the term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

Compounds

The present disclosure provides a compound of Formula (I):

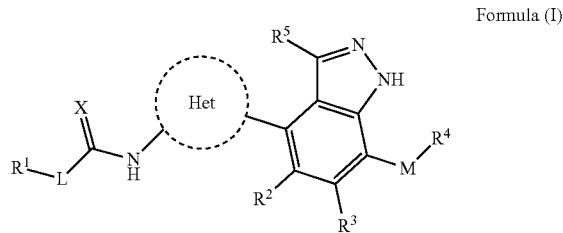

Formula (I)

or a pharmaceutically acceptable salt, hydrate, or solvate, thereof, wherein:

X is O or S;

L is a bond, —O—, —S—, or —NR$^6$—;

R$^1$ is alkyl, cycloalkyl, aryl, heteroaryl, or heterocyclyl, wherein R$^1$ is optionally substituted with one or more substituents independently selected from R$^7$;

R$^6$ is —H or C$_{1-6}$ alkyl;

R$^7$ is C$_{1-6}$ alkyl, C$_{2-6}$ alkenyl, C$_{2-6}$ alkynyl, cycloalkyl, aryl, heteroaryl, heterocyclyl, halo, oxo, cyano, hydroxy, —C(O)R$^9$, —C(O)OR$^9$, —C(O)NR$^{10}$R$^{11}$, —OR$^9$, —OC(O)R$^9$, —OC(O)NR$^{10}$R$^{11}$, —SR$^9$, —S(O)R$^9$, —S(O)$_2$R$^9$, —S(O)(=NH)R$^{10}$, —S(O)$_2$NR$^{10}$R$^{11}$, —NR$^{10}$R$^{11}$, —N(R$^6$)NR$^{10}$R$^{11}$, —N(R$^6$)OR$^9$, —N(R$^6$)C(O)R$^9$, —N(R$^6$)C(O)OR$^9$, —N(R$^6$)C(O)NR$^{10}$R$^{11}$, —N(R$^6$)S(O)$_2$R$^9$, —N(R$^6$)S(O)$_2$NR$^{10}$R$^{11}$, or —P(O)R$^{12}$R$^{13}$;

R$^9$ is —H, C$_{1-6}$ alkyl, C$_{1-6}$ haloalkyl, C$_{2-6}$ alkenyl, C$_{2-6}$ alkynyl, cycloalkyl, aryl, heteroaryl, or heterocyclyl;

Each R$^{10}$ and R$^{11}$ is independently —H, C$_{1-6}$ alkyl, C$_{2-6}$ alkenyl, C$_{2-6}$ alkynyl, cycloalkyl, aryl, heteroaryl, or heterocyclyl, or R$^{10}$ and R$^{11}$ are taken together with the nitrogen atom to which they are attached to form a 4- to 12-membered heterocyclyl optionally substituted with one or more groups selected from the group consisting of halo, hydroxyl, alkyl, alkenyl, alkynyl, haloalkyl, hydroxyalkyl, —CN, —NO$_2$, —NR$^{10}$R$^{11}$, —NR$^{10}$C(=O)R$^9$, —NR$^{10}$C(=O)NR$^{10}$R$^{11}$, —NR$^{10}$C(=O)OR$^9$, —OR$^9$, —C(=O)R$^9$, —C(=O)OR$^9$, —C(=O)NR$^{10}$R$^{11}$, —OC(=O)R$^9$, —OC(=O)OR$^9$, and —OC(=O)NR$^{10}$R$^{11}$;

Each R$^{12}$ and R$^{13}$ is independently C$_{1-6}$ alkyl, C$_{1-6}$ alkoxy, C$_{3-8}$ cycloalkyl, aryl, heteroaryl, heterocyclyl, or R$^{12}$ and R$^{13}$ are taken together with the phosphorus atom to which they are attached to form a 4- to 8-membered heterocyclyl optionally substituted with one or more groups selected from the group consisting of halo, hydroxyl, alkyl, alkenyl, alkynyl, haloalkyl, hydroxyalkyl, —CN, —NO$_2$, —NR$^{10}$R$^{11}$, —NR$^{10}$C(=O)R$^9$, —NR$^{10}$C(=O)NR$^{10}$R$^{11}$, —NR$^{10}$C(=O)OR$^9$, —OR$^9$, —C(=O)R$^9$, —C(=O)OR$^9$, —C(=O)NR$^{10}$R$^{11}$, —OC(=O)R$^9$, —OC(=O)OR$^9$, and —OC(=O)NR$^{10}$R$^{11}$; Het is selected from the group consisting of:

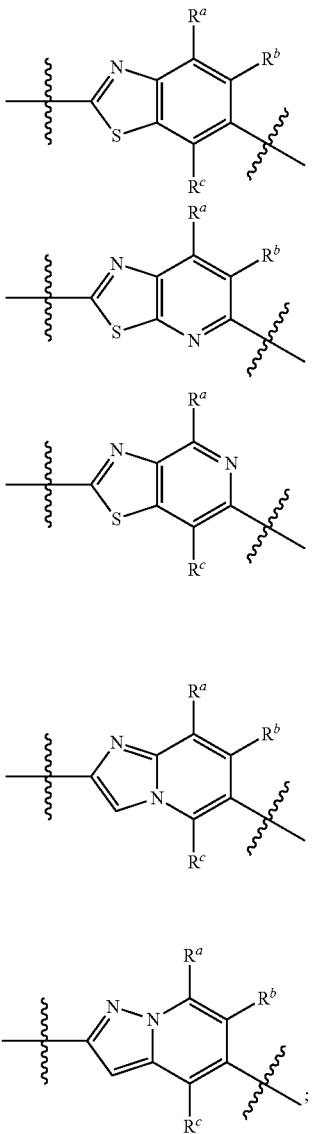

Each of R$^a$, R$^b$ and R$^c$ is independently —H, -D, halo, CF$_3$, CF$_2$H, CH$_2$F, CN, OR$^9$ or NR$^{10}$R$^{11}$;

R$^2$ is —H, -D, —CD$_3$, C$_{1-6}$ alkyl, C$_{2-6}$ alkenyl, C$_{2-6}$ alkynyl, cycloalkyl, aryl, heteroaryl, heterocyclyl, halo, hydroxyl, —CD$_2$OH, —CN, —NO$_2$, haloalkyl, trimethylsilylethoxymethyl, —C(O)R$^9$, —C(O)OR$^9$, —C(O)NR$^{10}$R$^{11}$, —OR$^9$, —OC(O)R$^9$, —OC(O)NR$^{10}$R$^{11}$, —SR$^9$, —S(O)R$^9$, —S(O)$_2$R$^9$, —S(O)(=NH)R$_{10}$, —S(O)$_2$NR$^{10}$R$^{11}$, —NR$^{10}$R$^{11}$, —N(R$^6$)NR$^{10}$R$^{11}$, —N(R$^6$)OR$^9$, —N(R$^6$)C(O)R$^9$, —N(R$^6$)C(O)R$^9$, —N(R$^6$)C(O)OR$^9$, —N(R$^6$)C(O)NR$^{10}$R$^{11}$, —N(R$^6$)S(O)$_2$R$^9$, —N(R$^6$)S(O)$_2$NR$^{10}$R$^{11}$, or —P(O)R$^{12}$R$^{13}$ wherein the C$_{1-6}$ alkyl, C$_{2-6}$ alkenyl, C$_{2-6}$ alkynyl, cycloalkyl, aryl, heteroaryl, or heterocyclyl is optionally substituted with one or more groups selected from the group consisting of halo, hydroxyl, alkyl, alkenyl, alkynyl, haloalkyl, hydroxyalkyl, —CN, —NO$_2$, —NR$^{10}$R$^{11}$, —NR$^{10}$C(=O)R$^9$, —NR$^{10}$C(=O)NR$^{10}$R$^{11}$, —NR$^{10}$C(=O)OR$^9$, —OR$^9$, —C(=O)R$^9$, —C(=O)OR$^9$, —C(=O)NR$^{10}$R$^{11}$, —OC(=O)R$^9$, —OC(=O)OR$^9$, and —OC(=O)NR$^{10}$R$^{11}$;

R$^3$ is —H, -D, —CD$_3$, C$_{1-6}$ alkyl, C$_{2-6}$ alkenyl, C$_{2-6}$ alkynyl, cycloalkyl, aryl, heteroaryl, heterocyclyl, halo, cyano, hydroxy, —CH$_2$OH, —CD$_2$OH, —OH, —CN, —NO$_2$, haloalkyl, —C(O)R$^9$, —C(O)OR$^9$, —C(O)NR$^{10}$R$^{11}$, —OR$^9$, —OC(O)R$^9$, —OC(O)NR$^{10}$R$^{11}$, —SR$^9$, —S(O)R$^9$, —S(O)$_2$R$^9$, —S(O)(=NH)R$_{10}$, —S(O)$_2$NR$^{10}$R$^{11}$, —NR$^{10}$R$^{11}$, —N(R$^6$)NR$^{10}$R$^{11}$, —N(R$^6$)OR$^9$, —N(R$^6$)C(O)R$^9$, —N(R$^6$)C(O)OR$^9$, —N(R$^6$)C(O)NR$^{10}$R$^{11}$, —N(R$^6$)S(O)$_2$R$^9$, —N(R$^6$)S(O)$_2$NR$^{10}$R$^{11}$, or —P(O)R$^{12}$R$^{13}$;

M is a bond, —O—, —S—, or —NR$^6$—;

R$^6$ is —H or C$_{1-6}$ alkyl;

R$^4$ is —H, -D, C$_{1-6}$ alkyl, C$_{2-6}$ alkenyl, C$_{2-6}$ alkynyl, cycloalkyl, aryl, heteroaryl, heterocyclyl, halo, cyano, hydroxy, —C(O)R$^9$, —C(O)OR$^9$, —C(O)NR$^{10}$R$^{11}$, —S(O)$_2$R$^9$, —S(O)(=NH)R$^{10}$, —S(O)$_2$NR$^{10}$R$^{11}$, or —P(O)R$^{12}$R$^{13}$, wherein C$_{1-6}$ alkyl, C$_{2-6}$ alkenyl, C$_{2-6}$ alkynyl, cycloalkyl, aryl, heteroaryl, or heterocyclyl is optionally substituted with one or more groups selected from the group consisting of halo, hydroxyl, alkyl, alkenyl, alkynyl, haloalkyl, hydroxyalkyl, —CN, —CD$_3$, —NO$_2$, —NR$^{10}$R$^{11}$, —NR$^{10}$C(=O)R$^9$, —NR$^{10}$C(=O)NR$^{10}$R$^{11}$, —NR$^{10}$C(=O)OR$^9$, —NR$^{10}$S(O)$_2$R$^9$, —OR$^9$, —C(=O)R$^9$, —C(=O)OR$^9$, —C(=O)NR$^{10}$R$^{11}$, —OC(=O)R$^9$, —OC(=O)OR$^9$, and —OC(=O)NR$^{10}$R$^{11}$; and R$^5$ is —H, -D, —CD$_3$, C$_{1-6}$ alkyl, C$_{2-6}$ alkenyl, C$_{2-6}$ alkynyl, cycloalkyl, halo, hydroxyl, —CH$_2$OH, —CD$_2$OH, —CN or haloalkyl.

In various embodiments, L is a bond, and R$^1$ is cycloalkyl which is optionally substituted with one or more groups selected from the group consisting of C$_{1-6}$ alkyl, C$_{2-6}$ alkenyl, C$_{2-6}$ alkynyl, cycloalkyl, halo, cyano, hydroxy, —C(O)R$^9$, —C(O)OR$^9$, —C(O)NR$^{10}$R$^{11}$, —OR$^9$, —OC(O)R$^9$, —OC(O)NR$^{10}$R$^{11}$, —NR$^{10}$R$^{11}$, —N(R$^6$)NR$^{10}$R$^{11}$, —N(R$^6$)OR$^9$, —N(R$^6$)C(O)R$^9$, —N(R$^6$)C(O)OR$^9$, and —N(R$^6$)C(O)NR$^{10}$R$^{11}$. In various embodiments, each of R$^2$ and R$^3$ is independently —H, halo, alkylthio, haloalkyl, or alkyl. In various embodiments, M is a bond, —O—, or —NR$^6$—; and R$^4$ is —H, -D, C$_{1-6}$ alkyl, C$_{2-6}$ alkenyl, C$_{2-6}$ alkynyl, cycloalkyl, aryl, heteroaryl, heterocyclyl, halo, cyano, hydroxy, —C(O)R$^9$, —C(O)NR$^{10}$R$^{11}$, —S(O)$_2$R$^9$, —S(O)(=NH)R$^{10}$, or —S(O)$_2$NR$^{10}$R$^{11}$, wherein the C$_{1-6}$ alkyl, C$_{2-6}$ alkenyl, C$_{2-6}$ alkynyl, cycloalkyl, aryl, heteroaryl, or heterocyclyl is optionally substituted with one or more groups selected from the group consisting of halo, hydroxy, alkyl, alkenyl, alkynyl, haloalkyl, hydroxyalkyl, —CN, —CD$_3$, —NR$^{10}$R$^{11}$, —NR$^{10}$S(O)$_2$R$^9$, and —NR$^{10}$C(=O)R$^9$.

In another embodiment, there is provided a compound represented by Formula (II):

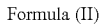
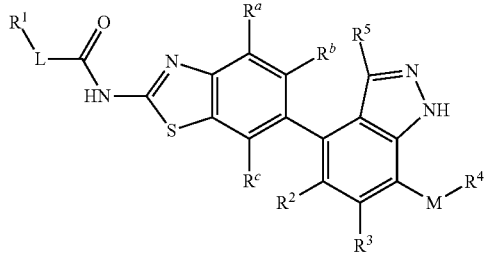

wherein $R^1$, $R^2$, $R^3$, $R^4$, $R^5$, $R^a$, $R^b$, M, and L are as defined above for Formula (I).

In various embodiments, L is a bond, $R^1$ is cyclopropyl which is optionally substituted with one or more groups selected from the group consisting of halo, $C_{1-3}$ alkylthio, $C_{1-3}$ alkyl, $C_{1-3}$ hydroxyalkyl and $C_{1-3}$ haloalkyl; $R^2$ is —H, alkyl, halo, haloalkyl, or alkylthio; $R^3$ is —H, alkyl, or halo; M is a bond, —O—, —S— or —NR$^6$—; $R^4$ is —H, halo, alkyl, hydroxyalkyl, haloalkyl, haloalkenyl, cycloalkyl, cyanoalkyl, dimethylamino, dimethylaminoethyl, dimethylaminocarbonyl, methylaminooxoethyl, aminocarbonylalkyl, acetamindoethyl, propionamidoethyl, formamidoethyl, aminoalkyl, methylaminocarbonylmethyl, alkoxyalkyl, azetidinyl, or azetidinylmethyl; and $R^5$ is —H, alkyl, or halo.

Non-limiting exemplary compounds of Formula (II) include the compound of Examples 1-145 of Table 1. In particular embodiments, the compound is selected from the group consisting of: the compounds of Examples 58, 80, 82, 85, 87, 92, 94, 97, 98, 110, 111, 118, 123, 125, 129, and 134.

In another embodiment, there is provided a compound represented by Formula (III):

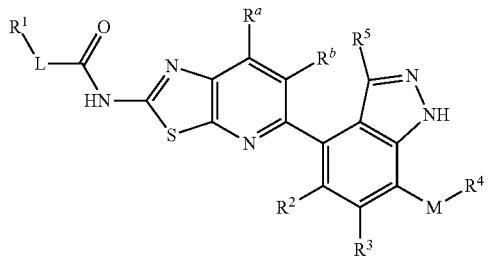

wherein $R^1$, $R^2$, $R^3$, $R^4$, $R^5$, $R^a$, $R^b$, M, and L are as defined above for Formula (I).

In some embodiments, L is a bond, $R^1$ is cyclopropyl which is optionally substituted with one or more groups selected from the group consisting of halo, $C_{1-3}$ alkyl, $C_{1-3}$ hydroxyalkyl and $C_{1-3}$ haloalkyl; $R^2$ is —H, alkyl, halo, haloalkyl, or alkylthio; $R^3$ is —H, alkyl, or halo; M is a bond, —O—, —S— or —NR$^6$—; $R^4$ is —H, halo, alkyl, hydroxyalkyl, dimethylamino, dimethylaminoethyl, dimethylaminocarbonyl, methylaminooxoethyl, aminocarbonylalkyl, acetamindoethyl, or alkoxyalkyl; and $R^5$ is —H, alkyl, or halo.

Non-limiting exemplary compounds of Formula (III) include the compound of Examples 146-218 of Table 1. In particular embodiments, the compound is selected from the group consisting of the compounds of Examples 149, 152, 156, 159, 161-163, 167, 169, 170, 172-175, 178, 184, 193, 194, 196, 199, and 218.

In another embodiment, there is provided a compound represented by Formula (IV):

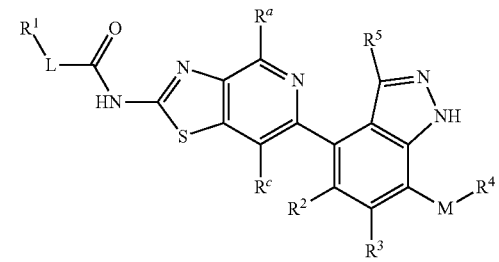

wherein $R^1$, $R^2$, $R^3$, $R^4$, $R^5$, $R^a$, $R^b$, M, and L are as defined above for Formula (I).

In some embodiments, L is a bond, $R^1$ is cyclopropyl which is optionally substituted with one or more groups selected from the group consisting of halo, $C_{1-3}$ alkyl, $C_{1-3}$ hydroxyalkyl and $C_{1-3}$ haloalkyl; $R^2$ is —H, alkyl, halo, haloalkyl, or alkylthio; $R^3$ is —H, alkyl, or halo; M is a bond, —O—, —S— or —NR$^6$—; $R^4$ is —H, halo, alkyl, hydroxyalkyl, haloalkyl, haloalkenyl, cycloalkyl, cyanoalkyl, dimethylamino, dimethylaminoethyl, dimethylaminocarbonyl, methylaminooxoethyl, aminocarbonylalkyl, acetamindoethyl, propionamidoethyl, formamidoethyl, cycloalkylalkyl, cycloalkyl(hydroxy)alkyl, hydroxycycloalkyl, methoxycycloalkyl, cycloalkyl(methoxy)methyl, alkoxyalkyl, alkenyl, methylsulfonamidoethyl, imidazolylethyl, dioxanyl, cyclobutanylcarbonylaminoethyl, difluoroacetamidoethyl, trifluoroacetamidoethyl, methylthiomethyl, methylthioethyl, azetidinyl, azetidinylmethyl, cyclopropylcarbonylamino(cyano)methyl, cyano(difluoroacetamido)methyl, propanyl-1,1,1,3,3,3-d6)amino, tetrahydrofuranyl, methylimidazolylethyl, furanyl, pyrrolyl, methylpyrrolyl, isoxazolyl, tetrazolylalkyl, methylpyrazolyl, or methylpyrazolylmethyl; and $R^5$ is —H, alkyl, or halo.

Non-limiting exemplary compounds of Formula (IV) include the compound of Examples 219 and 220 of Table 1.

In another embodiment, there is provided a compound represented by Formula (V):

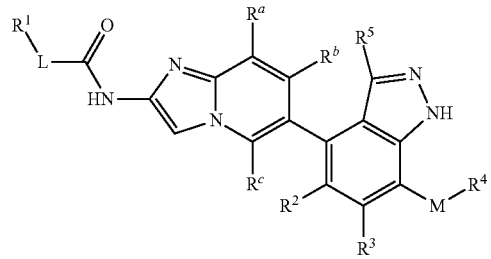

wherein $R^1$, $R^2$, $R^3$, $R^4$, $R^5$, $R^a$, $R^b$, M, and L are as defined above for Formula (I).

In some embodiments, L is a bond, and $R^1$ is cycloalkyl which is optionally substituted with one or more groups selected from the group consisting of $C_{1-6}$ alkyl, $C_{2-6}$ alkenyl, $C_{2-6}$ alkynyl, cycloalkyl, halo, cyano, hydroxy, —C(O)

R⁹, —C(O)OR⁹, —C(O)NR¹⁰R¹¹, —OR⁹, —OC(O)R⁹, —OC(O)NR¹⁰R¹¹, —NR¹⁰R¹¹, —N(R⁶)NR¹⁰R¹¹, —N(R⁶)OR⁹, —N(R⁶)C(O)R⁹, —N(R⁶)C(O)OR⁹, and —N(R⁶)C(O)NR¹⁰R¹¹. In some other embodiments, R¹ is cycloalkyl which is optionally substituted with one or more groups selected from the group consisting of halo, $C_{1-3}$ alkyl, $C_{1-3}$ hydroxyalkyl and $C_{1-3}$ haloalkyl.

Non-limiting exemplary compounds of Formula (V) include the compound of Examples 221-445 of Table 1.

In some embodiments, R¹ is cyclopropyl which is optionally substituted with one or more groups selected from the group consisting of halo, $C_1$-$C_3$ alkyl, $C_1$-$C_3$ hydroxyalkyl and $C_1$-$C_3$ haloalkyl; R² is —H, alkyl, alkylthio, haloalkyl, or halo; R³ is —H, alkyl, or halo; M is a bond, —O—, or —NR⁶—; R⁴ is —H, halo, alkyl, monoalkylamino, or dialkylamino; R⁵ is —H, alkyl, or halo. Non-limiting exemplary compounds include one selected from the group consisting of:

(1S,2S)—N-(6-(5-chloro-7-(dimethylamino)-6-fluoro-1H-indazol-4-yl)imidazo[1,2-a]pyridin-2-yl)-2-fluorocyclopropane-1-carboxamide;
(1S,2S)—N-(6-(7-(dimethylamino)-6-fluoro-5-methyl-1H-indazol-4-yl)imidazo[1,2-a]pyridin-2-yl)-2-fluorocyclopropane-1-carboxamide;
(1S,2S)—N-(6-(7-(dimethylamino)-6-fluoro-5-(methylthio)-1H-indazol-4-yl)imidazo[1,2-a]pyridin-2-yl)-2-fluorocyclopropane-1-carboxamide;
(1S,2S)—N-(6-(7-(dimethylamino)-6-fluoro-5-(trifluoromethyl)-1H-indazol-4-yl)imidazo[1,2-a]pyridin-2-yl)-2-fluorocyclopropane-1-carboxamide;
(1S,2S)—N-(6-(5-chloro-6-fluoro-7-(isopropylamino)-1H-indazol-4-yl)imidazo[1,2-a]pyridin-2-yl)-2-fluorocyclopropane-1-carboxamide; and
(1S,2S)—N-(6-(5-chloro-6-fluoro-7-isopropyl-1H-indazol-4-yl)imidazo[1,2-a]pyridin-2-yl)-2-fluorocyclopropane-1-carboxamide.

In some embodiments, R¹ is cyclopropyl which is optionally substituted with one or more groups selected from the group consisting of halo, $C_{1-3}$ alkyl, $C_{1-3}$ hydroxyalkyl and $C_{1-3}$ haloalkyl; R² is —H, alkyl, halo, haloalkyl, or alkylthio; R³ is —H, alkyl, or halo; M is a bond, —O—, —S— or —NR⁶—; R⁴ is —H, halo, alkyl, hydroxyalkyl, haloalkyl, haloalkenyl, cycloalkyl, monoalkylamino, or dialkylamino; and R⁵ is —H, alkyl, or halo. Non-limiting exemplary compounds include one selected from the group consisting of: the compounds of Examples 258, 261, 265, 266, 269, 272, 275, 280, 288, 291, 293, 296, 297, 300, 304, 306, 310, 318, 320, 324, 327, 329, 330, 332, 334, 336, 341, 345, 349, 353, 356, 358, 359, 361, 366, 371, 372, 374, 390, 391, 393, 404, 405, 408, 410, 414, 417, 419, 422, 423, 425, 426, 428, 430, 433, 434, 436, 439, 441, and 445.

In some embodiments, R¹ is cyclopropyl which is optionally substituted with one or more groups selected from the group consisting of halo, $C_{1-3}$ alkyl, $C_{1-3}$ hydroxyalkyl and $C_{1-3}$ haloalkyl; R² is —H, alkyl, halo, haloalkyl, or alkylthio; R³ is —H, alkyl, or halo; M is a bond, —O—, —S— or —NR⁶—; R⁴ is —H, halo, alkyl, alkylcarbonyl, dialkylaminocarbonyl, oxopyrrolidinyl, hydroxyalkyl, haloalkyl, haloalkenyl, cycloalkyl, pyridinyl, monoalkylamino, or dialkylamino; and R⁵ is —H, alkyl, or halo. Non-limiting exemplary compounds include one selected from the group consisting of the compounds of Examples 258, 261, 265, 266, 268, 269, 271-273 275, 280, 281, 288, 290, 291, 293, 296-298, 300, 304, 306, 307, 310, 316, 318, 320, 324, 326, 327, 329, 330-334, 336, 339, 341, 345, 346, 349, 353, 356, 358, 359, 361-363, 365-367, 370-374, 377-379, 383, 388, 390, 391, 393, 398, 401, 404-406, 408-410, 414, 415, 417, 419, 421-426, 428, 430, 433, 434, 436, 439, 441, and 445.

In another embodiment, there is provided a compound represented by Formula (VI):

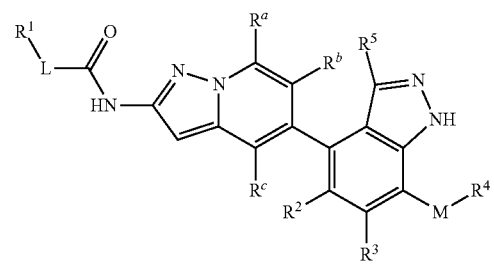

Formula (VI)

wherein R¹, R², R³, R⁴, R⁵, Rᵃ, Rᵇ, M, and L are as defined above for Formula (I).

In some embodiments, L is a bond, R¹ is cyclopropyl which is optionally substituted with one or more groups selected from the group consisting of halo, $C_{1-3}$ alkyl, $C_{1-3}$ hydroxyalkyl and $C_{1-3}$ haloalkyl; R² is —H, alkyl, halo, haloalkyl, or alkylthio; R³ is —H, alkyl, or halo; M is a bond, —O—, —S— or —NR⁶—; R⁴ is —H, halo, alkyl, hydroxyalkyl, haloalkyl, haloalkylamidoalkyl, haloalkylcarbonylaminoalkyl, alkylamidoalkyl, hydroxyhaloalkyl, haloalkenyl, cycloalkyl, cyano, cyanoalkyl, dimethylamino, dimethylaminoethyl, methylaminocarbonyl, dimethylaminocarbonyl, methylaminooxoethyl, aminocarbonylalkyl, acetamindoethyl, dialkylaminocycloalkyl, aminocycloalkyl, methylaminocycloalkyl, cycloalkylalkyl, cycloalkyl(hydroxy)alkyl, cycloalkylamidoalkyl, cycloalkylaminocarbonyl, hydroxycycloalkyl, methoxycycloalkyl, cycloalkyl(methoxy)methyl, alkoxycarbonyl, alkylcarbonyl, alkylamidoalkyl, alkoxyalkyl, alkenyl, methylsulfonamidoethyl, imidazolylethyl, dioxanyl, azetidinyl, azetidinylmethyl, tetrahydrofuranyl, furanyl, pyrimidinyl, pyridinyl, pyrrolyl, halopyrrolidinyl, pyrrolidinyl, methylpyrrolyl, isoxazolyl, tetrazolylalkyl, triazinyl, methylpyrazolyl, or methylpyrazolylmethyl; and R⁵ is —H, alkyl, or halo.

Non-limiting exemplary compounds of Formula (VI) include the compound of Examples 446-666 of Table 1. In particular embodiments, the compound is selected from the group consisting of the compounds of Examples 464, 466, 467, 476, 477, 480, 484, 485, 487, 488, 490-494, 496, 497, 502-505, 509, 513, 514, 519-521, 523-525, 529-532, 534, 541, 543, 548, 550, 552, 556-558, 561-565, 568-574, 577, 579, 581, 585, 586, 588, 592, 596-600, 602, 607, 612, 615, 617-619, 621, 623, 625, 629, 634, 636-642, 644, 646, 650-652, 655-657, and 659-665.

In an embodiment, there is provided a pharmaceutical composition comprising a pharmaceutically acceptable carrier or diluent and a compound of Formula (I) or a pharmaceutically acceptable salt thereof.

Medical Uses and Methods of Treatment Using the Compounds

The present disclosure provides a method of treating a subject with a disease or disorder associated with modulation of HPK1 comprising: administering to the subject in need thereof a therapeutically effective amount of the compound of Formula (I) or a pharmaceutically acceptable salt thereof. In some embodiments, the disease or disorder associated with modulation of HPK1 is a cancer, metastasis, inflammation, or immune disease including autoimmune disease.

In some other embodiments, the disease is cancer, metastasis, inflammation or auto-immune disease. In particular embodiments, the cancer is selected from the group consisting of carcinomas, melanomas, blastomas, sarcomas, lymphomas and leukemias, including without limitation, bladder carcinoma, brain tumors, breast cancer, cervical cancer, colorectal cancer, esophageal cancer, endometrial cancer, hepatocellular carcinoma, laryngeal cancer, lung cancer, osteosarcoma, ovarian cancer, pancreatic cancer, prostate cancer, renal carcinoma and thyroid cancer, acute lymphocytic leukemia, acute myeloid leukemia, ependymoma, Ewing's sarcoma, glioblastoma, medulloblastoma, neuroblastoma, osteosarcoma, rhabdomyosarcoma, rhabdoid cancer, and nephroblastoma (Wilm's tumor).

In some embodiments, the autoimmune disease is an inflammatory bowel disease, Addison's disease, alopecia areata, ankylosing spondylitis, antiphospholipid syndrome, hemolytic anemia, autoimmune hepatitis, Behcet's disease, Berger's disease, bullous pemphigoid, cardiomyopathy, celiac sprue, chronic fatigue immune dysfunction syndrome (CFIDS), chronic inflammatory demyelinating polyneuropathy, Churg-Strauss syndrome, cicatricial pemphigoid, cold agglutinin disease, type 1 diabetes, discoid lupus, essential mixed cryoglobulinemia, Graves' disease, Guillain-Barre syndrome, Hashimoto's thyroiditis, hypothyroidism, autoimmune lymphoproliferative syndrome (ALPS), idiopathic pulmonary fibrosis, idiopathic thrombocytopenia purpura (ITP), juvenile arthritis, lichen planus, lupus erythematosus, Meniere's disease, mixed connective tissue disease, multiple sclerosis, myasthenia gravis, pemphigus vulgaris, pernicious anemia, polychondritis, autoimmune polyglandular syndromes, polymyalgia rheumatica, polymyositis, dermatomyositis, primary agammaglobulinemia, primary biliary cirrhosis, psoriasis, psoriatic arthritis, Raynaud's phenomenon, Reiter's syndrome, rheumatic fever, rheumatoid arthritis, sarcoidosis, scleroderma, Sjogren's syndrome, stiff-man syndrome, Takayasu arteritis, giant cell arteritis, ulcerative colitis, uveitis, vasculitis, or granulomatosis with polyangiitis.

In another embodiment, there is provided the use of a compound of Formula (I) or a pharmaceutically acceptable salt thereof for the manufacture of a medicament for inhibiting HPK1 activity in a subject in need of inhibition of HPK1 activity. In some embodiments, the use includes treatment of cancer.

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development. In one embodiment, the suitable subject to be treated according to the present disclosure is human.

The compounds of the present disclosure are generally administered in a therapeutically effective amount. The compounds of the present disclosure can be administered by any suitable route in the form of a pharmaceutical composition adapted to such a route, and in a dose effective for the treatment intended. An effective dosage is typically in the range of about 0.01 to about 1000 mg per kg body weight per day, preferably about 0.01 to about 500 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20$^{th}$ ed., 2000 can be used.

Pharmaceutical Compositions, Dosage Forms and Administration Routes

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration). Suitable compositions for oral administration include solid, liquid, gel or powder formulations, and have a dosage form such as tablet, lozenge, capsule, granule or powder. Compositions for oral administration may be formulated as immediate or modified release, including delayed or sustained release, optionally with enteric coating. Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release. Most parenteral formulations are aqueous solutions containing excipients, including salts, buffering agents and isotonic agents. Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Transdermal Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical or transdermal administration can also be performed by electroporation, iontophoresis, phonophoresis and the like. Compositions for topical administration may be formulated as immediate or modified release, including delayed or sustained release.

Combination Therapy

A pharmaceutical composition according to the present disclosure may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by HPK1. Examples of such active ingredients are, without limitation, agents to treat cancer, metastasis, inflammation, or auto-immune pathogenesis. In some embodiments, the compound of Formula (I) is administered with anti-PD-1 agent, anti-PD-L1 agent, or anti-CTLA4 agent.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* (7th ed.), *Remington: The Science and Practice of Pharmacy* (20th ed.), *Encyclopedia of Pharmaceutical Technology* (3rd ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

The present disclosure provides a compound having various pharmacological effects by inhibiting HPK1 activity, a pharmaceutical composition having the compound as an effective agent, a medical use, particularly for treating a disease or disorder modulated by HPK1, of the compound, and a method of treatment or prevention comprising administering the compound to a subject in need of such treatment or prevention. The compounds of the present disclosure and pharmaceutically acceptable salts thereof have good safety and high selectivity for HPK1, and thus exhibit superior property as a drug.

Compound Preparation

The following Preparative Examples illustrate the preparation of intermediate compounds that are useful for preparing compounds of formula (I). The novel intermediate compounds described herein, as well as the synthetic processes useful for preparing the intermediate compounds represent embodiments of the current invention.

Intermediate 1A. 1-(tetrahydro-2H-pyran-2-yl)-5-(thiophen-2-yl)-1H-indazol-4-yl trifluoromethanesulfonate

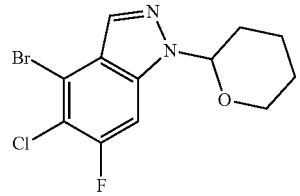 [SMILES: Fc1cc2c(cnn2C2CCCCO2)c(Br)c1Cl]

Step 1) 3-bromo-4-chloro-5-fluoro-2-methylaniline

To a solution of 3-bromo-5-fluoro-2-methylaniline (50 g, 245 mmol, 1 eq) in AcOH (100 mL) was added N-chlorosuccinimide (36 g, 270 mmol, 1.1 eq). The mixture was stirred at 25° C. for 16 hr. The mixture was concentrated under vacuum and the residue was extracted with Dichloromethane (200 mL*2). The combined organic layers were washed with sat. NaHCO$_3$ 200 mL, dried over Na$_2$SO$_4$, filtered and concentrated under reduced pressure to give a residue. The crude product (66 g, crude) was obtained as a black oil.

Step 2) 4-bromo-5-chloro-6-fluoro-1H-indazole

To a solution of 3-bromo-4-chloro-5-fluoro-2-methylaniline (25.8 g, 108 mmol, 1 eq) in AcOH (1.96 L, 0.05 M), H$_2$O (0.065 L, 1.5 M) was added sodium nitrite (8.96 g, 130 mmol, 1.2 eq). The mixture was stirred at 25° C. for 16 hr. The mixture was concentrated under vacuum and the residue was extracted with Dichloromethane (1 L*2). The combined organic layers were washed with sat. NaHCO$_3$ (1 L), dried over Na$_2$SO$_4$, filtered and concentrated under reduced pressure to give a residue. The crude product (23.6 g, crude) was obtained as a brown solid.

Step 3) 4-bromo-5-chloro-6-fluoro-1-(tetrahydro-2H-pyran-2-yl)-1H-indazole

To a solution of 4-bromo-5-chloro-6-fluoro-1H-indazole (1.98 g, 7.97 mmol, 1 eq) in THP (40 mL) was added 3,4-dihydro-2H-pyran (2.18 ml, 23.9 mmol, 3 eq) and p-toluenesulfonic acid monohydrate (300 mg, 1.59 mmol, 0.2 eq). The reaction mixture was stirred 70° C. for 14 hours. The reaction mixture was extracted with Ethyl Acetate and dried over MgSO$_4$. The organic residue was purified by column chromatography (silical gel, Hex:Ethyl acetate=1:0 to 4:1). 4-bromo-5-chloro-6-fluoro-1-(tetrahydro-2H-pyran-2-yl)-1H-indazole (1.51 g, 4.54 mmol, 57% yield) was obtained.

$^1$H NMR (400 MHz, DMSO-d$_6$) δ 8.16 (s, 1H), 8.00 (dd, J=9.3, 1.1 Hz, 1H), 5.85 (dd, J=9.6, 2.5 Hz, 1H), 3.87 (d, J=12.6 Hz, 1H), 3.79-3.72 (m, 1H), 2.38-2.30 (m, 1H), 2.04-1.94 (m, 2H), 1.77-1.55 (m, 3H).

Intermediate 1B. 4-bromo-5-chloro-6-fluoro-7-iodo-2-(tetrahydro-2H-pyran-2-yl)-2H-indazole

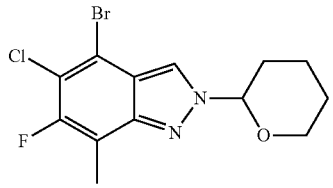

Step 1)
4-bromo-5-chloro-6-fluoro-7-iodo-1H-indazole

To a solution of 4-bromo-5-chloro-6-fluoro-1H-indazole (2 g, 8.02 mmol) in sulfuric acid (1.7 mL) was added N-iodosuccinimide (2.7 g, 12.03 mmol) portionwise. The mixture was stirred at 0° C. for 3 h. After the reaction completed, the mixture was poured into ice water and quenched by solid NaOH and then extracted with Dichloromethane. The combined organic residue was concentrated in vacuo. (2.99 g, crude).
$^1$H NMR (400 MHz, DMSO-$d_6$) δ 13.91 (s, 1H), 8.27 (d, J=1.6 Hz, 1H).

Step 2) 4-bromo-5-chloro-6-fluoro-7-iodo-2-(tetrahydro-2H-pyran-2-yl)-2H-indazole To a solution of 4-bromo-5-chloro-6-fluoro-7-iodo-1H-indazole (2.99 g, 7.97 mmol, 1 eq) in THF (40 mL) was added 3,4-dihydro-2H-pyran (2.18 ml, 23.9 mmol, 3 eq) and p-toluenesulfonic acid monohydrate (300 mg, 1.59 mmol, 0.2 eq). The reaction mixture was stirred 60° C. for 16 hours. The reaction mixture was extracted with Ethyl Acetate and dried over MgSO$_4$. The organic residue was purified by column chromatography (silical gel, Hex:Ethyl acetate=1:0 to 4:1). 4-bromo-5-chloro-6-fluoro-7-iodo-2-(tetrahydro-2H-pyran-2-yl)-2H-indazole (1.64 g, 7.97 mmol, 60.7% yield) was obtained.
$^1$H NMR (400 MHz, DMSO-$d_6$) δ 8.84 (s, 1H), 5.80 (dd, J=9.9, 2.7 Hz, 1H), 5.66 (s, 1H), 4.02 (t, J=6.6 Hz, 1H), 3.85-3.70 (m, 1H), 2.33-2.21 (m, 1H), 2.08-1.91 (m, 2H), 1.79-1.45 (m, 4H).

Intermediate 1C. 4-bromo-5-chloro-6-fluoro-2-(tetrahydro-2H-pyran-2-yl)-2H-indazol-7-amine

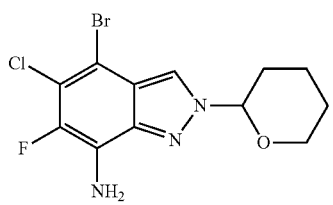

Step 1)
4-bromo-5-chloro-6-fluoro-7-nitro-1H-indazole

To a mixture of HNO$_3$ (12.63 g, 200.43 mmol, 9.02 mL, 5 eq) in H$_2$SO$_4$ (50 mL) stirred at 0° C. was added 4-bromo-5-chloro-6-fluoro-1H-indazole (10 g, 40.09 mmol, 1 eq) slowly. After the addition the mixture was stirred at 0° C. for 2 hr. TLC (Petroleum ether:Ethyl acetate=3:1) showed all the reactant was consumed and a main new point showed up. Poured the mixture into ice-water, extracted with ethyl acetate (50 mL*3), the combined organic phase was dried over Na$_2$SO$_4$, filtered and the filtrate was concentrated to obtain 4-bromo-5-chloro-6-fluoro-7-nitro-1H-indazole (12 g, crude) as a yellow solid.

Step 2) 4-bromo-5-chloro-6-fluoro-7-nitro-2-(tetrahydro-2H-pyran-2-yl)-2H-indazole To a solution of 4-bromo-5-chloro-6-fluoro-7-nitro-1H-indazole (2.34 g, 7.97 mmol, 1 eq) in THF (40 mL) was added 3,4-dihydro-2H-pyran (2.18 ml, 23.9 mmol, 3 eq) and p-toluenesulfonic acid monohydrate (300 mg, 1.59 mmol, 0.2 eq). The reaction mixture was stirred 60° C. for 14 hours. The reaction mixture was extracted with Ethyl Acetate and dried over MgSO$_4$. The organic residue was purified by column chromatography (silical gel, Hex:Ethyl acetate=1:0 to 4:1). 4-bromo-5-chloro-6-fluoro-7-nitro-2-(tetrahydro-2H-pyran-2-yl)-2H-indazole (1.65 g, 4.35 mmol, 54.7% yield) was obtained.

Step 3) 4-bromo-5-chloro-6-fluoro-2-(tetrahydro-2H-pyran-2-yl)-2H-indazol-7-amine To a solution of 4-bromo-5-chloro-6-fluoro-7-nitro-2-(tetrahydro-2H-pyran-2-yl)-2H-indazole (600 mg, 1.58 mmol, 1 eq) in EtOH (5 mL) and H$_2$O (5 mL) were added NH$_4$Cl (508.66 mg, 9.51 mmol, 6 eq) and Fe (531.04 mg, 9.51 mmol, 6 eq), then the reaction mixture was stirred at 80° C. for 1 hour. The reaction mixture was filtered, and the filtrate was diluted with ethyl acetate (20 mL), and the mixture was washed with water (20 mL*2), after then the organic layer was dried over Na$_2$SO$_4$, filtered and concentrated under reduced pressure to give a residue. The residue was purified by prep-TLC (SiO$_2$, Petroleum ether/Ethyl acetate=1:1). 4-bromo-5-chloro-6-fluoro-2-(tetrahydro-2H-pyran-2-yl)-2H-indazol-7-amine (390 mg, 1.12 mmol, 70.59% yield) was obtained as a yellow oil.
$^1$H NMR (400 MHz, DMSO-$d_6$) δ 8.41 (s, 1H), 5.85 (br s, 2H), 5.71 (br d, J=8.0 Hz, 1H), 4.00 (br d, J=11.3 Hz, 1H), 3.77-3.59 (m, 1H), 2.29-2.17 (m, 1H), 2.10-1.91 (m, 2H), 1.78-1.54 (m, 3H).

Intermediate 1D. 4-bromo-5-chloro-6-fluoro-N,N-dimethyl-1-(tetrahydro-2H-pyran-2-yl)-1H-indazol-7-amine

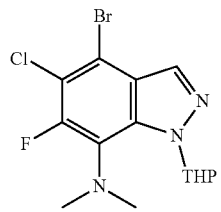

Step 1)
4-bromo-5-chloro-6-fluoro-7-nitro-1H-indazole

To a solution of Intermediate 1A (900 mg, 3.61 mmol, 1 eq) in H$_2$SO$_4$ (10 mL) (98% purity) was added HNO$_3$ (419.69 mg, 4.33 mmol, 299.78 uL, 1.2 eq) (65% purity) dropwise at −15° C., then the reaction mixture was stirred at 0° C. for 2 hours. The reaction mixture was slowly poured into ice water (20 mL), then the mixture's pH was adjusted to pH=7 by using saturated aqueous solution of NaOH, after then the mixture was extracted with ethyl acetate (30 mL*2), the combined organic layers were dried over $Na_2SO_4$, filtered and concentrated under reduced pressure to give a residue. 4-bromo-5-chloro-6-fluoro-7-nitro-1H-indazole (900 mg, crude) was obtained as a yellow solid.

$^1$H NMR (400 MHz, DMSO-$d_6$) δ 14.36 (br s, 1H), 8.37 (br s, 1H).

Step 2) 4-bromo-5-chloro-6-fluoro-7-nitro-1-(tetrahydro-2H-pyran-2-yl)-1H-indazole To a solution of 4-bromo-5-chloro-6-fluoro-7-nitro-1H-indazole (900 mg, 3.06 mmol, 1 eq) (crude) in DCM (10 mL) were added TsOH.$H_2O$ (58.14 mg, 305.64 umol, 0.1 eq) and DHP (771.27 mg, 9.17 mmol, 838.34 uL, 3 eq), then the reaction mixture was stirred at 20° C. for 2 hours. The reaction mixture was diluted with dichloromethane (20 mL), and the mixture was washed with saturated aqueous solution of $NaHCO_3$ (15 mL*2), the organic layer was dried over $Na_2SO_4$, filtered and concentrated under reduced pressure to give a residue. The residue was purified by column chromatography (SiO2, Petroleum ether/Ethyl acetate=40/1 to 25:1, 4-bromo-5-chloro-6-fluoro-7-nitro-1-(tetrahydro-2H-pyran-2-yl)-1H-indazole came out at Petroleum ether/Ethyl acetate=40/1, 4-bromo-5-chloro-6-fluoro-7-nitro-2-(tetrahydro-2H-pyran-2-yl)-2H-indazole came out at Petroleum ether/Ethyl acetate=25/1). 4-bromo-5-chloro-6-fluoro-7-nitro-1-(tetrahydro-2H-pyran-2-yl)-1H-indazole (200 mg, 528.29 umol, 17.28% yield) was obtained as a brown solid. 4-bromo-5-chloro-6-fluoro-7-nitro-2-(tetrahydro-2H-pyran-2-yl)-2H-indazole (600 mg, 1.58 mmol, 51.85% yield) was obtained as a yellow solid.

4-bromo-5-chloro-6-fluoro-7-nitro-1-(tetrahydro-2H-pyran-2-yl)-1H-indazole $^1$HNMR (400 MHz, DMSO-$d_6$) δ 8.43 (s, 1H), 5.50 (dd, J=2.8, 7.8 Hz, 1H), 3.45-3.38 (m, 2H), 2.35-2.27 (m, 1H), 2.23-2.14 (m, 1H), 1.92 (td, J=4.6, 13.6 Hz, 1H), 1.68 (ddt, J=4.0, 10.1, 13.9 Hz, 1H), 1.59-1.36 (m, 2H).

4-bromo-5-chloro-6-fluoro-7-nitro-2-(tetrahydro-2H-pyran-2-yl)-2H-indazole $^1$H NMR (400 MHz, DMSO-$d_6$) δ 8.99 (s, 1H), 5.86 (dd, J=2.7, 9.7 Hz, 1H), 4.08-3.96 (m, 1H), 3.81-3.68 (m, 1H), 2.28-2.14 (m, 1H), 2.14-2.02 (m, 1H), 2.02-1.89 (m, 1H), 1.78-1.67 (m, 1H), 1.64-1.56 (m, 2H).

Step 3) 4-bromo-5-chloro-6-fluoro-1-(tetrahydro-2H-pyran-2-yl)-1H-indazol-7-amine To a solution of 4-bromo-5-chloro-6-fluoro-7-nitro-1-(tetrahydro-2H-pyran-2-yl)-1H-indazole (200 mg, 528.29 umol, 1 eq) in EtOH (5 mL) and $H_2O$ (5 mL) were added $NH_4Cl$ (169.55 mg, 3.17 mmol, 6 eq) and Fe (177.03 mg, 3.17 mmol, 6 eq), then the reaction mixture was stirred at 80° C. for 2 hours. The reaction mixture was filtered, and the filtrate was concentrated to remove EtOH, then the mixture was diluted with ethyl acetate (20 mL), and the mixture was washed with water (20 mL*2), after then the organic layer was dried over $Na_2SO_4$, filtered and concentrated under reduced pressure to give a residue. 4-bromo-5-chloro-6-fluoro-1-(tetrahydro-2H-pyran-2-yl)-1H-indazol-7-amine (140 mg, crude) was obtained as a yellow solid.

Step 4) 4-bromo-5-chloro-6-fluoro-N,N-dimethyl-1-(tetrahydro-2H-pyran-2-yl)-1H-indazol-7-amine To a solution of 4-bromo-5-chloro-6-fluoro-1-(tetrahydro-2H-pyran-2-yl)-1H-indazol-7-amine (120 mg, 344.24 umol, 1 eq) in THF (5 mL) was added NaH (34.42 mg, 860.59 umol, 60% purity, 2.5 eq) in portions at 0° C. under $N_2$, then the mixture was stirred at 0° C. for 30 mins under $N_2$, after then MeI (293.16 mg, 2.06 mmol, 128.58 uL, 6 eq) was added dropwise, and the reaction mixture was stirred at 20° C. for 12 hours under $N_2$. The reaction mixture was poured into saturated aqueous solution of $NH_4Cl$ (20 mL), then the mixture was extracted with ethyl acetate (20 mL*2), the combined organic layers were dried over $Na_2SO_4$, filtered and concentrated under reduced pressure to give a residue. The residue was purified by prep-TLC (SiO$_2$, Petroleum ether/Ethyl acetate=5:1). Intermediate 1E (30 mg, 78.06 umol, 22.68% yield, 98% purity) was obtained as a yellow oil.

Intermediate 1E. 4-bromo-5-chloro-6-fluoro-N-isopropyl-2-(tetrahydro-2H-pyran-2-yl)-2H-indazol-7-amine

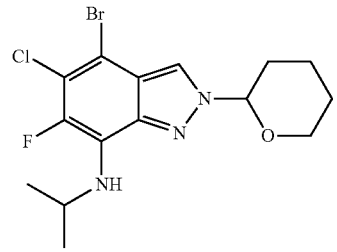

To a solution of Intermediate 1B (100 mg, 0.218 mmol, 1 eq) in 2-methyl-2-butanol (1.09 mL) was added Xantphos Pd G3 (21 mg, 21.8 μmol, 0.1 eq) and $Cs_2CO_3$ (142 mg, 0.436 mmol, 2.0 eq). The mixture was degassed and purged with $N_2$ for 3 times, and then propan-2-amine (0.19 mL, 2.18 mmol, 10 eq) was added. The mixture was stirred at 90° C. for 3 hr in sealed tube. The reaction mixture was diluted with $H_2O$ (40 mL), and then the mixture was extracted with DCM (50 mL*3). The combined organic layers were dried over $Na_2SO_4$, filtered and the filtrate was concentrated in vacuum to give a residue. The residue was purified by silica gel chromatography (product came out at Hexane/Ethyl acetate=10/1) to afford Intermediate 1E (47 mg, 0.120 mmol, 55% yield) as beige color solid.

$^1$H NMR (400 MHz, DMSO-$d_6$) δ 8.43 (s, 1H), 5.74 (dd, J=9.6, 2.5 Hz, 1H), 5.29 (dd, J=9.9, 3.3 Hz, 1H), 4.63-4.57 (m, 1H), 3.99 (d, J=11.0 Hz, 1H), 3.74-3.68 (m, 1H), 2.23-2.17 (m, 1H), 2.05-1.95 (m, 2H), 1.74-1.57 (m, 3H), 1.23-1.18 (m, 6H).

Intermediate 1F. 4-bromo-5-chloro-6-fluoro-N-isopropyl-N-methyl-2-(tetrahydro-2H-pyran-2-yl)-2H-indazol-7-amine

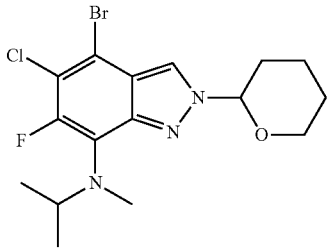

To a solution of Intermediate 1E (600 mg, 1.54 mmol, 1.0 eq) in Methanol (7.7 mL) was added formaldehyde (0.572 mL, 7.68 mmol, 5.0 eq) and acetic acid (88 μL, 1.54 mmol, 1.0 eq). The mixture was stirred at room temperature for 10 min. Sodium cyanoborohydride (290 mg, 4.61 mmol, 3.0 eq) was added and then the mixture was stirred room temperature for 16 hr. The reaction mixture was quenched by $H_2O$ and extracted with Ethyl acetate (150 mL*3). The combined organic layers were dried over $Na_2SO_4$, filtered and the filtrate was concentrated in vacuum to give a residue. The residue was purified by silica gel chromatography (product came out at Hexane/Ethyl acetate=100/4) to afford Intermediate 1F (292 mg, 0.722 mmol, 47% yield) as brown color oil.

$^1$H NMR (400 MHz, DMSO-$d_6$) δ 8.51 (s, 1H), 5.75 (dd, J=9.3, 2.7 Hz, 1H), 4.14-4.05 (m, 1H), 4.00-3.93 (m, 1H), 3.78-3.67 (m, 1H), 2.92 (d, J=4.4 Hz, 3H), 2.23-2.20 (m, 1H), 2.05-1.95 (m, 2H), 1.75-1.60 (m, 3H), 1.17 (d, J=6.6 Hz, 6H).

Intermediate 1G. 4-bromo-5-chloro-N-ethyl-6-fluoro-N-methyl-1H-indazol-7-amine

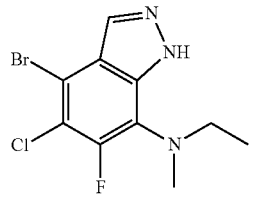

Step 1) 4-bromo-5-chloro-6-fluoro-1H-indazol-7-amine

To a solution of 4-bromo-5-chloro-6-fluoro-7-nitro-1H-indazole (12 g, 40.75 mmol, 1 eq) in EtOH (100 mL) and $H_2O$ (40 mL) was added Fe (6.83 g, 122.26 mmol, 3 eq) and $NH_4Cl$ (6.54 g, 122.26 mmol, 3 eq). The reaction mixture was heated to 80° C. and reacted for 2 hr. The reaction mixture was filtered through a celite cake, the filtrate was concentrated to give the crude product. The residue was purified by column chromatography (SiO$_2$, Petroleum ether/Ethyl acetate=20/1 to 3/1). 4-bromo-5-chloro-6-fluoro-1H-indazol-7-amine (5 g, 18.90 mmol, 46.39% yield) was obtained as a yellow solid.

Step 2) N-(4-bromo-5-chloro-6-fluoro-1H-indazol-7-yl)acetamide

To a solution 4-bromo-5-chloro-6-fluoro-1H-indazol-7-amine (3 g, 11.34 mmol, 1 eq) in AcOH (30 mL) was added $Ac_2O$ (1.39 g, 13.61 mmol, 1.27 mL, 1.2 eq), the reaction mixture was heated to 80° C. and reacted for 3 hr. The solvent was removed under vacuum. The residue was purified by column chromatography (SiO$_2$, Petroleum ether/Ethyl acetate=50/1 to 4/1) to obtain N-(4-bromo-5-chloro-6-fluoro-1H-indazol-7-yl)acetamide (3 g, 9.79 mmol, 86.29% yield) as a yellow solid.

Step 3) 4-bromo-5-chloro-N-ethyl-6-fluoro-1H-indazol-7-amine

To a solution of LAH (520.00 mg, 13.70 mmol, 1.5 eq) in THF (50 mL) was added a solution of N-(4-bromo-5-chloro-6-fluoro-1H-indazol-7-yl)acetamide (2.8 g, 9.13 mmol, 1 eq) in THF (100 mL) drop-wise under $N_2$ at 0° C., after the addition, the reaction mixture was allowed to warm to 25° C., and reacted for 16 hr. The mixture was poured into water (500 mL), extracted with ethyl acetate (100 mL*2), the combined organic phase was dried over $Na_2SO_4$, filtered and the filtrate was concentrated to give the crude. The residue was purified by column chromatography (SiO$_2$, Petroleum ether/Ethyl acetate=50/1 to 2/1) to obtain 4-bromo-5-chloro-N-ethyl-6-fluoro-1H-indazol-7-amine (1 g, 3.42 mmol, 37.42% yield) as a yellow solid.

Step 4) 4-bromo-5-chloro-N-ethyl-6-fluoro-N-methyl-1H-indazol-7-amine

To a solution of 4-bromo-5-chloro-N-ethyl-6-fluoro-1H-indazol-7-amine (1.4 g, 4.79 mmol, 1 eq) and HCHO (718.48 mg, 23.93 mmol, 659.16 uL, 5 eq) in MeOH (50 mL) was added NaBH3CN (902.21 mg, 14.36 mmol, 3 eq) and AcOH (287.38 mg, 4.79 mmol, 273.70 uL, 1 eq). The reaction mixture was stirred at 25° C. for 16 hr. The solvent was removed under vacuum. The residue was purified by column chromatography (SiO$_2$, Petroleum ether/Ethyl acetate=50/1 to 5/1) to obtain 4-bromo-5-chloro-N-ethyl-6-fluoro-N-methyl-1H-indazol-7-amine (1.4 g, 4.57 mmol, 95.42% yield) as a white solid.

Intermediate 1H. 4-bromo-5-chloro-6-fluoro-7-methyl-1-(tetrahydro-2H-pyran-2-yl)-1H-indazole

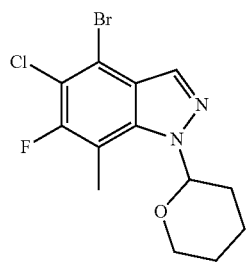

To a solution of 4-bromo-5-chloro-6-fluoro-1-(tetrahydro-2H-pyran-2-yl)-1H-indazole (0.5 g, 1.50 mmol, 1 eq) in THF (10 mL) was added dropwise LDA (2 M, 1.87 mL, 2.5 eq) at −78° C. After addition, the mixture was stirred at this temperature for 2.5 hr, and then MeI (319.12 mg, 2.25 mmol, 139.97 uL, 1.5 eq) was added dropwise at −78° C.

The resulting mixture was stirred at 20° C. for 16 hr. The mixture was poured into saturated NH$_4$Cl and extracted with EA 20 mL. The organic layer was concentrated. The residue was purified by column chromatography (SiO$_2$, Petroleum ether/Ethyl acetate=20/1 to 10/1). We got the desired product 4-bromo-5-chloro-6-fluoro-7-methyl-1-(tetrahydro-2H-pyran-2-yl)-1H-indazole (0.38 g, 1.09 mmol, 72.93% yield) was obtained as white solid.

Intermediate 1I. 4-bromo-6-fluoro-N,N-dimethyl-5-(methylthio)-1H-indazol-7-amine

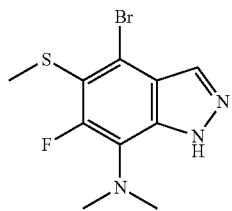

Step 1) 4-bromo-6-fluoro-7-nitro-1H-indazole

To a solution of 4-bromo-6-fluoro-1H-indazole (10 g, 46.51 mmol, 1 eq) in H$_2$SO$_4$ (80 mL) (98% purity) was added KNO$_3$ (4.70 g, 46.51 mmol, 1 eq) at 0° C. in portions, then the mixture was stirred at 0° C. for 1 h. The reaction mixture was then poured into ice water (200 mL), and the mixture was extracted with ethyl acetate (100 mL*2), the combined organic layers were washed with saturated aqueous solution of NaHCO$_3$ (100 mL*2) and brine (100 mL), dried over Na$_2$SO$_4$, filtered and concentrated under reduced pressure to give a residue. The residue was purified by silica gel chromatography (200-300 mesh silica gel, Petroleum ether/Ethyl acetate=15/1 to 1/1, product 4-bromo-6-fluoro-7-nitro-1H-indazole came out at Petroleum ether/Ethyl acetate=8/1) to afford 4-bromo-6-fluoro-7-nitro-1H-indazole (2.7 g, 10.38 mmol, 22.32% yield) as yellow solid and crude product. The cured product was purified by MPLC (Petroleum ether/Ethyl acetate) to afford 4-bromo-6-fluoro-7-nitro-1H-indazole (3.57 g, 13.73 mmol, 29.52% yield) as yellow solid.

Step 2)
4-bromo-6-fluoro-5-iodo-7-nitro-1H-indazole

To a solution of 4-bromo-6-fluoro-7-nitro-1H-indazole (2.7 g, 10.38 mmol, 1 eq) in H$_2$SO$_4$ (30 mL) was added NIS (7.01 g, 31.15 mmol, 3 eq) at 25° C. The reaction mixture was stirred at 50° C. for 16 h. The reaction mixture was quenched by ice water (50 mL). Then the mixture was extracted with ethyl acetate (50 mL*3). The combined organic layers were washed with Na$_2$SO$_3$ aqueous solution (20 mL*2), NaHCO$_3$ aqueous solution (20 mL*2) and brine (20 mL), dried over sodium sulfate, filtered and the filtrate was concentrated in vacuum to give 4-bromo-6-fluoro-5-iodo-7-nitro-1H-indazole (3.4 g, 8.81 mmol, 84.85% yield) as yellow solid.

$^1$H NMR (400 MHz, DMSO-d$_6$) δ 14.28 (br s, 1H), 8.30 (s, 1H).

Step 3)
4-bromo-6-fluoro-5-iodo-1H-indazol-7-amine

To a solution of 4-bromo-6-fluoro-5-iodo-7-nitro-1H-indazole (3.4 g, 8.81 mmol, 1 eq) in EtOH (50 mL) and H$_2$O (25 mL) was added NH$_4$Cl (2.83 g, 52.86 mmol, 6 eq), then Fe (2.95 g, 52.86 mmol, 6 eq) was added in portions at 60° C. The mixture was stirred at 80° C. for 1 h. The reaction mixture was filtered through celite while it was still hot. Then the filtrate was concentrated in vacuum to remove EtOH. The resulting aqueous phase was extracted with ethyl acetate (50 mL*2). The combined organic layers were washed with brine (50 mL), dried over sodium sulfate, filtered and the filtrate was concentrated in vacuum to give a residue. The residue was purified by silica gel chromatography (MPLC, Petroleum ether/Ethyl acetate=5/1 to 2/1, product came out at Petroleum ether/Ethyl acetate=2/1) to afford 4-bromo-6-fluoro-5-iodo-1H-indazol-7-amine (2.2 g, 6.18 mmol, 70.16% yield) as gray solid.

$^1$H NMR (400 MHz, DMSO-d$_6$) δ 13.09 (br s, 1H), 7.86 (d, J=1.7 Hz, 1H), 5.62 (s, 2H).

Step 4) 4-bromo-6-fluoro-5-iodo-N,N-dimethyl-1H-indazol-7-amine

To a solution of 4-bromo-6-fluoro-5-iodo-1H-indazol-7-amine (2.2 g, 6.18 mmol, 1 eq) in MeOH (50 mL) was added AcOH (1.11 g, 18.54 mmol, 1.06 mL, 3 eq), HCHO (5.02 g, 61.81 mmol, 4.60 mL, 10 eq), then NaBH$_3$CN (3.88 g, 61.81 mmol, 10 eq) was added in portions under 40° C. Gas released and the temperature rise. The suspension was stirred at 25° C. for 16 h. The reaction mixture was poured into water (50 mL), then the mixture was concentrated to remove MeOH, after then the mixture was extracted with ethyl acetate (50 mL*2), and the combined organic layers were washed with brine (50 mL), dried over sodium sulfate, filtered and concentrated under reduced pressure to give a residue. The residue was purified by silica gel chromatography (200-300 mesh silica gel, Petroleum ether/Ethyl acetate=15/1 to 8/1, product came out at Petroleum ether/Ethyl acetate=8/1) to afford 4-bromo-6-fluoro-5-iodo-N,N-dimethyl-1H-indazol-7-amine (2.05 g, 5.34 mmol, 86.37% yield) as off-white solid.

Step 5) 4-bromo-6-fluoro-N,N-dimethyl-5-(methylthio)-1H-indazol-7-amine

To a 100 mL bottle equipped with a magnetic stir bar was added 4-bromo-6-fluoro-5-iodo-N,N-dimethyl-1H-indazol-7-amine (1.2 g, 3.13 mmol, 1 eq), NaSMe (328.56 mg, 4.69 mmol, 1.5 eq), Xantphos (361.65 mg, 625.02 umol, 0.2 eq), K$_2$CO$_3$ (1.30 g, 9.38 mmol, 3 eq), dioxane (20 mL) and Pd$_2$(dba)$_3$ (286.17 mg, 312.51 umol, 0.1 eq) sequentially. The bottle was evacuated and backfilled with nitrogen. Then the mixture was stirred at 90° C. for 16 h under nitrogen atmosphere. The residue was purified by silica gel chromatography (200-300 mesh silica gel, Petroleum ether/Ethyl acetate=20/1 to 8/1, product came out at Petroleum ether/Ethyl acetate=10/1) to afford 4-bromo-6-fluoro-N,N-dimethyl-5-(methylthio)-1H-indazol-7-amine (540 mg, 1.78 mmol, 56.81% yield) as orange solid.

$^1$H NMR (400 MHz, DMSO-d$_6$) δ 13.59 (br s, 1H), 8.00 (d, J=1.6 Hz, 1H), 2.91 (d, J=2.4 Hz, 6H), 2.39 (s, 3H).

Intermediate 1J. 4-bromo-6-fluoro-N,N-dimethyl-5-(trifluoromethyl)-1H-indazol-7-amine

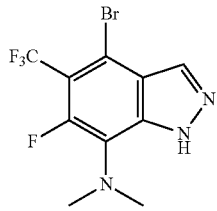

To a solution of 4-bromo-6-fluoro-5-iodo-N,N-dimethyl-1H-indazol-7-amine (1.0 g, 2.61 mmol, 1 eq) and methyl 2,2-difluoro-2-(fluorosulfonyl)acetate (1.00 g, 5.22 mmol, 664.45 uL, 2 eq) in DMF (10 mL) was added CuI (994.63 mg, 5.22 mmol, 2 eq). The mixture was stirred at 100° C. for 6 hr under $N_2$ atmosphere. The reaction mixture was filtered and the filtrate was diluted with water 50 mL and extracted with Ethyl acetate (50 mL*2). The combined organic layers were washed with brine (50 mL*3), dried over anhydrous $Na_2SO_4$, filtered and the filtrate was concentrated under reduced pressure to give a residue. The residue was purified by silical gel column chromatography (Petroleum ether: Ethyl acetate=1:0 to 10:1). 4-bromo-6-fluoro-N,N-dimethyl-5-(trifluoromethyl)-1H-indazol-7-amine (502 mg, 1.54 mmol, 58.91% yield) was obtained as a yellow solid.

Intermediate 1K.
4-bromo-5-ethyl-6-fluoro-1H-indazole

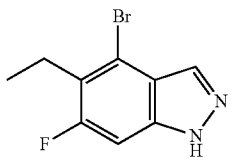

Step 1)
4-bromo-5-ethyl-6-fluoro-2-trityl-2H-indazole

To a solution of diisopropylamine (132.75 mg, 1.31 mmol, 185.41 uL, 1.2 eq) in THF (5 mL) was added slowly n-BuLi (2.5 M, 481.04 uL, 1.1 eq) at −78° C. for 0.5 hr under $N_2$ atmosphere. Then a solution of 4-bromo-6-fluoro-2-trityl-2H-indazole (500 mg, 1.09 mmol, 1 eq) in THF (2 mL) was added dropwise to the solution. After the mixture was stirred at −78° C. for 0.5 hr, a solution of EtI (204.62 mg, 1.31 mmol, 104.93 uL, 1.2 eq) in THF (2 mL) was added to the mixture and the solution were warmed to 15° C. and stirred for 2 hr under $N_2$ atmosphere. The reaction mixture was quenched by addition with saturated $NH_4Cl$ aqueous 3 mL at 15° C., was diluted with water 20 mL and extracted with Ethyl acetate (30 mL*2). The combined organic layers were washed with brine (30 mL*2), dried over $Na_2SO_4$, filtered and the filtrate was concentrated under reduced pressure to give a residue. 4-bromo-5-ethyl-6-fluoro-2-trityl-2H-indazole (500 mg, crude) was obtained as a yellow solid.

Step 2) 4-bromo-5-ethyl-6-fluoro-1H-indazole

To a solution of 4-bromo-5-ethyl-6-fluoro-2-trityl-2H-indazole (500 mg, 1.03 mmol, 1 eq) in DCM (6 mL) was added TFA (3.08 g, 27.01 mmol, 2.00 mL, 26.22 eq). The mixture was stirred at 15° C. for 4 hr. The reaction mixture pH was adjusted to 7 with saturated $NaHCO_3$ aqueous, and the mixture was extracted with Dichloromethane (30 mL*2). The combined organic layers were washed with brine (30 mL*2), dried over $Na_2SO_4$, filtered and the filtrate was concentrated under reduced pressure to give a residue. The residue was purified by prep-HPLC (column: Phenomenex luna C18 150*40 mm*15 um; mobile phase: [water (0.1% TFA)-ACN]; B %: 40%-70%, 10 min). The fraction was concentrated under reduced pressure to remove ACN, the aqueous pH was adjusted to 7 with saturated $NaHCO_3$ aqueous. The aqueous was extracted with Ethyl acetate (10 mL*2). The combined organic layers were washed with brine (10 mL*2), dried over $Na_2SO_4$, filtered and the filtrate was concentrated under reduced pressure to give a product. 4-bromo-5-ethyl-6-fluoro-1H-indazole (70 mg, 287.98 umol, 27.96% yield) was obtained as a yellow solid.

$^1$H NMR (400 MHz, DMSO-$d_6$) δ 13.39 (br s, 1H), 8.01-7.98 (m, 1H), 7.41 (d, J=9.9 Hz, 1H), 2.83 (dq, J=2.4, 7.5 Hz, 2H), 1.14 (t, J=7.5 Hz, 3H).

Intermediate 1L. 4-bromo-6-fluoro-1-(tetrahydro-2H-pyran-2-yl)-1H-indazol-5-amine

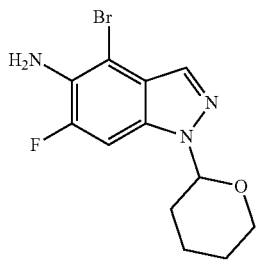

Step 1) 6-fluoro-5-nitro-1H-indazole

To a solution of 6-fluoro-1H-indazole (4.4 g, 32.32 mmol, 1 eq) in $H_2SO_4$ (30 mL) was added $HNO_3$ (2.44 g, 38.79 mmol, 1.75 mL, 1.2 eq) dropwise at −15° C., the reaction mixture was stirred at 0° C. for 2 hours. The reaction mixture was slowly poured into ice water (100 mL), then the mixture was extracted with ethyl acetate (100 mL*2), the combined organic layers were dried over $Na_2SO_4$, filtered and concentrated under reduced pressure to give 6-fluoro-5-nitro-1H-indazole (5.4 g, crude) was obtained as a yellow solid.

Step 2) 6-fluoro-5-nitro-1-(tetrahydro-2H-pyran-2-yl)-1H-indazole

To a mixture of 6-fluoro-5-nitro-1H-indazole (4.9 g, 27.05 mmol, 1 eq) (crude) in DCM (50 mL) were added DHP (6.83 g, 81.16 mmol, 7.42 mL, 3 eq) and TsOH.$H_2O$ (514.60 mg, 2.71 mmol, 0.1 eq), and the reaction mixture was stirred at 15° C. for 1 hour. The reaction mixture was poured into saturated solution of $NaHCO_3$ (100 mL), then the mixture was extracted with dichloromethane (50 mL*2), the combined organic layers were dried over $Na_2SO_4$, filtered and concentrated under reduced pressure to give a residue. The residue was purified by column chromatography ($SiO_2$, Petroleum ether/Ethyl acetate=20/1 to 15:1 6-fluoro-5-nitro-1-(tetrahydro-2H-pyran-2-yl)-1H-indazole (3 g, 11.31 mmol, 41.81% yield) was obtained as a yellow solid.

¹H NMR (400 MHz, DMSO-d₆) δ 8.78 (d, J=7.3 Hz, 1H), 8.41 (s, 1H), 7.97 (d, J=12.1 Hz, 1H), 5.90 (dd, J=2.1, 9.7 Hz, 1H), 3.94-3.85 (m, 1H), 3.82-3.72 (m, 1H), 2.43-2.28 (m, 1H), 2.10-1.93 (m, 2H), 1.82-1.34 (m, 3H).

Step 3) 6-fluoro-1-(tetrahydro-2H-pyran-2-yl)-1H-indazol-5-amine

To a solution of 6-fluoro-5-nitro-1-(tetrahydro-2H-pyran-2-yl)-1H-indazole (2.9 g, 10.93 mmol, 1 eq) in MeOH (30 mL) was added wet Pd/C (300 mg, 10% purity) under N₂ atmosphere. The suspension was degassed and purged with H₂ for 3 times. The mixture was stirred under H₂ (15 Psi) at 15° C. for 4 hours. The reaction mixture was filtered, and the filtrate was concentrated under reduced pressure to give a residue. The residue was purified by column chromatography (SiO₂, Petroleum ether/Ethyl acetate=15/1 to 8:1). 6-fluoro-1-(tetrahydro-2H-pyran-2-yl)-1H-indazol-5-amine (1.5 g, 5.87 mmol, 53.65% yield, 92% purity) was obtained as a brick-red solid.

¹H NMR (400 MHz, DMSO-d₆) δ 7.82 (s, 1H), 7.43 (d, J=11.6 Hz, 1H), 6.98 (d, J=8.6 Hz, 1H), 5.66 (dd, J=2.3, 9.7 Hz, 1H), 4.91 (s, 2H), 3.85 (br d, J=12.1 Hz, 1H), 3.77-3.62 (m, 1H), 2.42-2.27 (m, 1H), 2.07-1.96 (m, 1H), 1.95-1.86 (m, 1H), 1.76-1.63 (m, 1H), 1.59-1.51 (m, 2H); LCMS (electrospray) m/z 236.1 (M+H)+.

Step 4) 4-bromo-6-fluoro-1-(tetrahydro-2H-pyran-2-yl)-1H-indazol-5-amine

To a solution of 6-fluoro-1-(tetrahydro-2H-pyran-2-yl)-1H-indazol-5-amine (1.45 g, 5.67 mmol, 1 eq) in MeCN (10 mL) was added NBS (1.21 g, 6.80 mmol, 1.2 eq) in portions at 0° C. The mixture was stirred at 0° C. for 2 hours. The reaction mixture was concentrated to give a residue. Then the residue was dissolved in ethyl acetate (30 mL), and the mixture was washed with brine (15 mL*2), the organic layer was dried over Na₂SO₄, filtered and concentrated under reduced pressure to give a residue. The residue was purified by column chromatography (SiO₂, Petroleum ether/Ethyl acetate=20/1). 4-bromo-6-fluoro-1-(tetrahydro-2H-pyran-2-yl)-1H-indazol-5-amine (1.3 g, 4.14 mmol, 72.98% yield) was obtained as a brown solid.

¹H NMR (400 MHz, DMSO-d₆) δ 7.80 (s, 1H), 7.60 (d, J=10.6 Hz, 1H), 5.71 (dd, J=2.5, 9.6 Hz, 1H), 5.15 (s, 2H), 3.88-3.82 (m, 1H), 3.76-3.68 (m, 1H), 2.36-2.27 (m, 1H), 2.02 (br dd, J=4.6, 8.5 Hz, 1H), 1.96-1.90 (m, 1H), 1.76-1.65 (m, 1H), 1.60-1.52 (m, 2H).

Intermediate 1M. 3-(4-bromo-5-chloro-6-fluoro-1H-indazol-7-yl)cyclopentan-1-ol

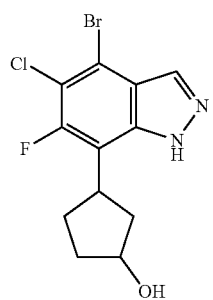

Step 1) 4-bromo-5-chloro-6-fluoro-1-(tetrahydro-2H-pyran-2-yl)-1H-indazole-7-carbaldehyde To a mixture of Intermediate 1A (3 g, 8.99 mmol, 1 eq) in THF (60 mL) was added LDA (2 M, 17.99 mL, 4 eq) dropwise at −78° C. under N₂. The mixture was stirred at −78° C. for 1 h. After then, HCO₂Et (3.17 g, 35.97 mmol, 3.52 mL, 4 eq) in THF (8 mL) was added dropwise at −78° C., then the mixture was stirred at −78° C. for 2 h. The reaction mixture was quenched by addition of saturated NH₄Cl solution (20 mL) at −78° C., and then extracted with EA (30 mL*3). The combined organic layers were washed with brine (30 mL*2), dried over Na₂SO₄, filtered and concentrated under reduced pressure to give a residue. The residue was purified by column chromatography (SiO₂, Petroleum ether/Ethyl acetate=30/1 to 20/1). 4-bromo-5-chloro-6-fluoro-1-(tetrahydro-2H-pyran-2-yl)-1H-indazole-7-carbaldehyde (2.78 g, 7.69 mmol, 85.49% yield) was obtained as an off-white solid.

¹H NMR (400 MHz, DMSO-d₆) δ 10.40 (s, 1H), 8.35 (s, 1H), 6.09 (dd, J=2.6, 8.9 Hz, 1H), 3.71-3.63 (m, 1H), 3.63-3.52 (m, 1H), 2.42-2.30 (m, 1H), 2.21-2.10 (m, 1H), 2.07-1.95 (m, 1H), 1.77-1.63 (m, 2H), 1.60-1.40 (m, 2H); LCMS (electrospray) m/z 278.9 (M+H)+.

Step 2) 1-(4-bromo-5-chloro-6-fluoro-1-(tetrahydro-2H-pyran-2-yl)-1H-indazol-7-yl)but-3-en-1-ol To a mixture of 4-bromo-5-chloro-6-fluoro-1-(tetrahydro-2H-pyran-2-yl)-1H-indazole-7-carbaldehyde (2.2 g, 6.08 mmol, 1 eq) in THF (60 mL) was added allyl magnesium bromide (1 M, 9.13 mL, 1.5 eq) dropwise at 0° C. under N₂. The mixture was stirred at 0° C. for 2 h. The reaction mixture was quenched by addition of saturated NH₄Cl solution (20 mL) at 0° C., and then extracted with EA (30 mL*3). The combined organic layers were washed with brine (30 mL*2), dried over anhydrous Na₂SO₄, filtered and concentrated under reduced pressure to give a residue. The residue was purified by column chromatography (SiO₂, Petroleum ether/Ethyl acetate=10/1 to 5/1). 1-(4-bromo-5-chloro-6-fluoro-1-(tetrahydro-2H-pyran-2-yl)-1H-indazol-7-yl)but-3-en-1-ol (2 g, 4.95 mmol, 81.43% yield) was obtained as a colorless oil.

¹H NMR (400 MHz, DMSO-d₆) δ 8.25-8.21 (m, 1H), 8.20-8.18 (m, 1H), 6.61 (br d, J=9.0 Hz, 1H), 6.23 (d, J=4.0 Hz, 1H), 6.18 (br d, J=8.3 Hz, 1H), 5.95 (d, J=5.0 Hz, 1H), 5.90-5.75 (m, 2H), 5.36 (dt, J=4.3, 7.5 Hz, 1H), 5.30 (td, J=5.9, 7.9 Hz, 1H), 5.10-4.97 (m, 4H), 3.97 (br d, J=11.5 Hz, 1H), 3.89 (br d, J=11.3 Hz, 1H), 3.69-3.55 (m, 2H), 2.87-2.74 (m, 2H), 2.70-2.55 (m, 4H), 2.06 (br d, J=10.8 Hz, 3H), 1.96-1.87 (m, 1H), 0.90-0.78 (m, 1H); LCMS (electrospray) m/z 302.9 (M+H)+.

Step 3) 4-bromo-7-(3-bromocyclopentyl)-5-chloro-6-fluoro-1H-indazole

To a mixture of 1-(4-bromo-5-chloro-6-fluoro-1-(tetrahydro-2H-pyran-2-yl)-1H-indazol-7-yl)but-3-en-1-ol (2 g, 4.95 mmol, 1 eq) in DCM (20 mL) was added Br₂ (1.19 g, 7.43 mmol, 383.11 uL, 1.5 eq) in DCM (2 mL) dropwise at −20° C. under N₂. The mixture was stirred at −10° C. for 3 h. The mixture was quenched by addition of Na₂SO₃ solution (30 mL), and then diluted with DCM (30 mL). The organic layer was washed with Na₂SO₃ solution (30 mL*2), dried over anhydrous Na₂SO₄, filtered and concentrated to obtain a residue. The residue was dissolved in MeOH (15 mL), and then K₂CO₃ (2.05 g, 14.86 mmol, 3 eq) was added and the resulting mixture was stirred at 20° C. for 16 h. The reaction was quenched by addition of water (20 mL), and extracted with EA (30 mL*3), dried by $Na_2SO_4$, filtered and concentrated to obtain a residue. The residue was purified by column chromatography ($SiO_2$, Petroleum ether/Ethyl acetate=10/1 to 3:1). The crude product was purified by reversed-phase HPLC (0.1% FA condition). 4-bromo-7-(3-bromocyclopentyl)-5-chloro-6-fluoro-1H-indazole (300 mg, 752.91 umol, 15.20% yield) was obtained as a white solid.

$^1$H NMR (400 MHz, DMSO-$d_6$) δ 13.44-13.37 (m, 2H), 8.14-8.11 (m, 2H), 5.71-5.67 (m, 1H), 5.44 (dt, J=1.2, 7.5 Hz, 1H), 4.97 (s, 1H), 4.83-4.76 (m, 2H), 4.47 (dd, J=3.7, 10.1 Hz, 1H), 4.22 (dd, J=5.5, 10.1 Hz, 1H), 4.15 (dd, J=2.3, 10.6 Hz, 1H), 3.20-3.13 (m, 1H), 2.69-2.64 (m, 1H), 2.34-2.27 (m, 2H); LCMS (electrospray) m/z 398.8 (M+H)+.

Step 4) 3-(4-bromo-5-chloro-6-fluoro-1H-indazol-7-yl)cyclopentyl acetate

To a mixture of 4-bromo-7-(3-bromocyclopentyl)-5-chloro-6-fluoro-1H-indazole (100 mg, 250.97 umol, 1 eq) in DMSO (2 mL) was added KOAc (73.89 mg, 752.91 umol, 3 eq) in one portion at 20° C. under $N_2$. The mixture was then heated to 70° C. and stirred for 3 h. The reaction was quenched by addition of water (15 mL), and then extracted with EA (20 mL*3), the combined organic layers were washed with brine (20 mL*2), dried by $Na_2SO_4$, filtered and concentrated to give a residue. 3-(4-bromo-5-chloro-6-fluoro-1H-indazol-7-yl)cyclopentyl acetate (100 mg, crude, brown oil) was used directly in the next step without further purification.

LCMS (electrospray) m/z 378.8 (M+H)+.

Step 5) 3-(4-bromo-5-chloro-6-fluoro-1H-indazol-7-yl)cyclopentan-1-ol

To a mixture of 3-(4-bromo-5-chloro-6-fluoro-1H-indazol-7-yl)cyclopentyl acetate (80 mg, 211.87 umol, 1 eq) in MeOH (4 mL) and $H_2O$ (0.8 mL) was added $K_2CO_3$ (442.15 mg, 3.20 mmol, 15.1 eq) in one portion at 20° C. under $N_2$. The mixture was stirred at 20° C. for 2 h. The reaction mixture was quenched by addition of water (15 mL) at 20° C., and then extracted with ethyl acetate (20 mL*3). The combined organic layers were washed with brine (20 mL*1), dried over $Na_2SO_4$, filtered and concentrated under reduced pressure to give a residue. The residue was purified by column chromatography ($SiO_2$, Petroleum ether/Ethyl acetate=3/1 to 1/2). 3-(4-bromo-5-chloro-6-fluoro-1H-indazol-7-yl)cyclopentan-1-ol (50 mg, 149.01 umol, 70.33% yield) was obtained as a white solid.

LCMS (electrospray) m/z 336.9 (M+H)+.

Intermediate 1N. 4-bromo-6-fluoro-N-isopropyl-2-(tetrahydro-2H-pyran-2-yl)-5-(trifluoromethyl)-2H-indazol-7-amine

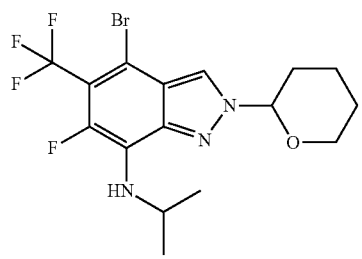

Step 1) 5-fluoro-2-iodo-4-(trifluoromethyl)aniline

To a solution of 3-fluoro-4-(trifluoromethyl)aniline (4 g, 22.33 mmol, 1 eq) in MeCN (40 mL) was added NIS (5.53 g, 24.57 mmol, 1.1 eq) at 15° C., then reaction mixture was stirred at 15° C. for 15 h. The reaction mixture was diluted with $H_2O$ (100 mL) and extracted with EtOAc (100 mL*3). The combined organic layers were dried over $Na_2SO_4$, filtered and concentrated under reduced pressure to give a residue. 5-fluoro-2-iodo-4-(trifluoromethyl)aniline (5.6 g, crude) was obtained as a brown oil.

LCMS (electrospray) m/z 305.9 (M+H)+.

Step 2) 5-fluoro-2-methyl-4-(trifluoromethyl)aniline

To a solution of 5-fluoro-2-iodo-4-(trifluoromethyl)aniline (6.0 g, 19.67 mmol, 1 eq) and 2,4,6-trimethyl-1,3,5,2,4,6-trioxatriborinane (8.82 g, 29.51 mmol, 9.82 mL, 42% purity, 1.5 eq) in DME (60 mL) were added $Pd(PPh_3)_4$ (1.14 g, 983.57 umol, 0.05 eq) and $K_2CO_3$ (8.16 g, 59.01 mmol, 3 eq) at 15° C., then reaction mixture was stirred at 100° C. for 60 h. The reaction mixture was concentrated under reduced pressure to afford the residue. The residue was purified by column chromatography ($SiO_2$, Petroleum ether/Ethyl acetate=5/1 to 3/1, Petroleum ether/Ethyl acetate=2:1, Rf=0.3). 5-fluoro-2-methyl-4-(trifluoromethyl)aniline (1.6 g, 4.06 mmol, 20.64% yield, 49% purity) was obtained as a yellow oil.

LCMS (electrospray) m/z 194.1.9 (M+H)+.

Step 3) 6-fluoro-5-(trifluoromethyl)-1H-indazole

To a solution of 5-fluoro-2-methyl-4-(trifluoromethyl) aniline (1 g, 5.18 mmol, 1 eq) in AcOH (15 mL) were added $NaNO_2$ (357.25 mg, 5.18 mmol, 1 eq) and $H_2O$ (3 mL) at 0° C., then the reaction mixture was stirred at 15° C. for 2 h. The reaction was quenched by addition of $H_2O$ (60 mL) at 20° C. and the resulting mixture was extracted with EtOAc (50 mL*3). The combined organic layers were washed with $H_2O$ (50 mL*3), dried over $Na_2SO_4$, filtered and concentrated under reduced pressure to give a residue. Residue was purified by column (SiO2, Petroleum ether/Ethyl acetate=10/1 to 5/1, Petroleum ether/Ethyl acetate=3:1, Rf=0.5). 6-fluoro-5-(trifluoromethyl)-1H-indazole (500 mg, 2.45 mmol, 47.31% yield) was obtained as a yellow solid.

LCMS (electrospray) m/z 205.2 (M+H)+.

Step 4) 6-fluoro-7-nitro-5-(trifluoromethyl)-1H-indazole

To a solution of 6-fluoro-5-(trifluoromethyl)-1H-indazole (500 mg, 2.45 mmol, 1 eq) in $H_2SO_4$ (5 mL, 95% purity) was added $KNO_3$ (249 mg, 2.46 mmol, 1.01 eq) at 0° C., then the reaction mixture was stirred at 15° C. for 15 hr. The reaction mixture was diluted with water (100 mL) and extracted with Ethyl acetate (50 mL*2). The combined organic layers were treated with saturated sodium bicarbonate solution until pH=7, dried over $Na_2SO_4$, filtered and concentrated under reduced pressure to give a residue. 6-fluoro-7-nitro-5-(trifluoromethyl)-1H-indazole (500 mg) was obtained as a yellow solid.

LCMS (electrospray) m/z 250.2 (M+H)+.

Step 5) 6-fluoro-7-nitro-2-(tetrahydro-2H-pyran-2-yl)-5-(trifluoromethyl)-2H-indazole To a solution of 6-fluoro-7-nitro-5-(trifluoromethyl)-1H-indazole (500 mg, 2.01 mmol, 1 eq) in THF (10 mL) was added PPTS (50.44 mg, 200.71 umol, 0.1 eq) and DHP (844.13 mg, 10.04 mmol, 917.53 uL, 5 eq) at 0° C., then the reaction mixture was stirred at 60° C. for 15 hr. The reaction mixture was diluted with solvent H₂O (50 mL) and extracted with EtOAc (50 mL*3). The combined organic layers were washed with H₂O (50 mL*3), dried over Na₂SO₄, filtered and concentrated under reduced pressure to give a residue. 6-fluoro-7-nitro-2-(tetrahydro-2H-pyran-2-yl)-5-(trifluoromethyl)-2H-indazole (1 g, crude) was obtained as yellow oil.

Step 6) 6-fluoro-2-(tetrahydro-2H-pyran-2-yl)-5-(trifluoromethyl)-2H-indazol-7-amine To a solution of 6-fluoro-7-nitro-2-(tetrahydro-2H-pyran-2-yl)-5-(trifluoromethyl)-2H-indazole (800 mg, 2.40 mmol, 1 eq) and H₂O (2 mL) in EtOH (10 mL) was added NH₄Cl (642.08 mg, 12.00 mmol, 5 eq) and Fe (268.13 mg, 4.80 mmol, 2 eq) at 0° C., then the reaction mixture was stirred at 60° C. for 1 hr. The reaction mixture was diluted with H₂O (20 mL) and extracted with EtOAc (20 mL*3). The combined organic layers were washed with H₂O (30 mL*2), dried over Na₂SO₄, filtered and concentrated under reduced pressure to give a residue. The residue was purified by column chromatography (SiO₂, Petroleum ether/Ethyl acetate=10/1 to 5/1, Petroleum ether:Ethyl acetate=3:1, Rf=0.3). 6-fluoro-2-(tetrahydro-2H-pyran-2-yl)-5-(trifluoromethyl)-2H-indazol-7-amine (500 mg, 1.65 mmol, 68.68% yield) was obtained as a yellow solid
LCMS (electrospray) m/z 220.2 (M+H)+.

Step 7) 4-bromo-6-fluoro-2-(tetrahydro-2H-pyran-2-yl)-5-(trifluoromethyl)-2H-indazol-7-amine To a solution of 6-fluoro-2-(tetrahydro-2H-pyran-2-yl)-5-(trifluoromethyl)-2H-indazol-7-amine (200 mg, 659.51 umol, 1 eq) in DMF (1 mL) was added NBS (129.12 mg, 725.46 umol, 1.1 eq) at 20° C., then the reaction mixture was stirred at 20° C. for 2 hr. The reaction mixture was diluted with H₂O (10 mL) and extracted with EtOAc (10 mL*3). The combined organic layers were washed with H₂O (10 mL*2), dried over Na₂SO₄, filtered and concentrated under reduced pressure to give a residue. 4-bromo-6-fluoro-2-(tetrahydro-2H-pyran-2-yl)-5-(trifluoromethyl)-2H-indazol-7-amine (120 mg, crude) was obtained as a yellow solid.
LCMS (electrospray) m/z 297.9 (M+H)+.

Step 8) 4-bromo-6-fluoro-N-isopropyl-5-(trifluoromethyl)-1H-indazol-7-amine

To a solution of 4-bromo-6-fluoro-2-(tetrahydro-2H-pyran-2-yl)-5-(trifluoromethyl)-2H-indazol-7-amine (100 mg, 335.53 umol, 1 eq) in MeOH (1 mL) were added AcOH (40.30 mg, 671.06 umol, 38.38 uL, 2 eq) and acetone (97.44 mg, 1.68 mmol, 123.34 uL, 5 eq) at 20° C., NaBH₃CN (105.42 mg, 1.68 mmol, 5 eq) was then added and the reaction mixture was stirred at 20° C. for 2 hr. After then, acetone (97.44 mg, 1.68 mmol, 123.34 uL, 5 eq), NaBH₃CN (105.43 mg, 1.68 mmol, 5 eq) and AcOH (60.45 mg, 1.01 mmol, 57.57 uL, 3 eq) were added to the mixture and the reaction mixture was stirred at 20° C. for 20 hr. The reaction mixture was diluted with H₂O (10 mL) and extracted with EtOAc (10 mL*3). The combined organic layers were washed with H₂O (10 mL*2), dried over Na₂SO₄, filtered and concentrated under reduced pressure to give a residue. The residue was purified by prep-TLC (Petroleum ether:Ethyl acetate=3:1, Rf=0.4). 4-bromo-6-fluoro-N-isopropyl-5-(trifluoromethyl)-1H-indazol-7-amine (60 mg, 165.83 umol, 49.42% yield, 94% purity) was obtained as a white solid.
LCMS (electrospray) m/z 340.1 (M+H)+.

Step 9) 4-bromo-6-fluoro-N-isopropyl-2-(tetrahydro-2H-pyran-2-yl)-5-(trifluoromethyl)-2H-indazol-7-amine To a solution of 4-bromo-6-fluoro-N-isopropyl-5-(trifluoromethyl)-1H-indazol-7-amine (50 mg, 147.01 umol, 1 eq) in THF (1 mL) were added PPTS (3.69 mg, 14.70 umol, 0.1 eq) and DHP (61.83 mg, 735.05 umol, 67.21 uL, 5 eq) at 0° C., then the reaction mixture was stirred at 60° C. for 2 hr. The reaction mixture was diluted with H₂O (50 mL) and extracted with EtOAc (50 mL*3). The combined organic layers were washed with H₂O (50 mL*3), dried over Na₂SO₄, filtered and concentrated under reduced pressure to give a residue. Residue was purified by prep-TLC (Petroleum ether:Ethyl acetate=5:1, Rf=0.6). 4-bromo-6-fluoro-N-isopropyl-2-(tetrahydro-2H-pyran-2-yl)-5-(trifluoromethyl)-2H-indazol-7-amine (50 mg, 117.86 umol, 80.17% yield) was obtained as a yellow oil.
LCMS (electrospray) m/z 424.1 (M+H)+.

Intermediate IO. 4-bromo-5-cyclopropyl-6-fluoro-1-(tetrahydro-2H-pyran-2-yl)-1H-indazole

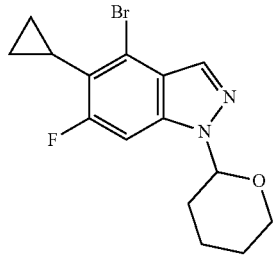

Step 1) 3-bromo-5-fluoro-2-methylaniline

To a mixture of 1-bromo-5-fluoro-2-methyl-3-nitrobenzene (23 g, 98.28 mmol, 1 eq) in EtOH (80 mL) and H₂O (80 mL) was added Fe (27.44 g, 491.41 mmol, 5 eq) and NH₄Cl (26.29 g, 491.41 mmol, 5 eq). The mixture was stirred at 100° C. for 3 h. The mixture was filtered and the filtrate was concentrated at reduced pressure to remove EtOH. The resulting mixture was extracted with DCM (50 mL*3). The combined organic phase was washed with brine (50 mL*2), dried over Na₂SO₄, filtered and concentrated at reduced pressure to give a residue to give 3-bromo-5-fluoro-2-methylaniline (20.6 g, crude) as yellow liquid.
¹H NMR (400 MHz, DMSO-d₆) δ 6.59 (br d, J=8.4 Hz, 1H), 6.42 (br d, J=11.2 Hz, 1H), 5.51 (br s, 2H), 2.09 (s, 3H).

Step 2) 3-bromo-5-fluoro-4-iodo-2-methylaniline

To a mixture of 3-bromo-5-fluoro-2-methylaniline (18 g, 88.22 mmol, 1 eq) (crude) in CH₃CN (150 mL) was added NIS (19.85 g, 88.22 mmol, 1 eq) in portions at 0° C. The mixture was stirred at 30° C. for 3 h. After 3 h, LCMS showed compound 2 was remained and desired mass was detected, too. Then the mixture was stirred at 30° C. for another 12 h. LCMS showed there was no compound 2 remained and one main peak with desired mass was detected. The mixture was quenched with saturated Na$_2$SO$_3$ (200 mL) and the resulting mixture was extracted with EtOAc (50 mL*3). The combined organic phase was washed with brine (50 mL*2), dried over Na$_2$SO$_4$, filtered and concentrated at reduced pressure to give a residue. The residue was purified by silica gel chromatography (1000 mesh silica gel, Petroleum ether/Ethyl acetate=50/1, 30/1; TLC (Petroleum ether:Ethyl acetate=10:1; Rf=0.28)) to give 3-bromo-5-fluoro-4-iodo-2-methylaniline (22 g, 66.68 mmol, 75.58% yield) as brown solid.

$^1$H NMR (400 MHz, DMSO-d$_6$) δ 6.55 (d, J=10.5 Hz, 1H), 5.67 (s, 2H), 2.25 (d, J=0.8 Hz, 3H).

Step 3) 4-bromo-6-fluoro-5-iodo-1H-indazole

To a mixture of 3-bromo-5-fluoro-4-iodo-2-methylaniline (22 g, 66.68 mmol, 1 eq) in CH$_3$COOH (200 mL) was added NaNO$_2$ (5.52 g, 80.02 mmol, 1.2 eq) which was dissolved water (40 mL) at 0° C. The mixture was stirred at 30° C. for 16 h. The mixture was poured into saturated NaHCO$_3$ (1000 mL) and the resulting mixture was extracted with EtOAc (200 mL*3). The combined organic phase was washed with brine (100 mL*2), dried over Na$_2$SO$_4$, filtered and concentrated at reduced pressure to give a residue. The residue was purified by silica gel chromatography (1000 mesh silica gel, Petroleum ether/Ethyl acetate=15/1, 5/1) to give 4-bromo-6-fluoro-5-iodo-1H-indazole (7.5 g, 22.00 mmol, 32.99% yield) as brown solid.

$^1$HNMR (400 MHz, DMSO-d$_6$) δ 13.58 (br s, 1H), 8.00 (s, 1H), 7.51 (d, J=8.1 Hz, 1H), 3.32 (s, 1H).

Step 4) 4-bromo-6-fluoro-5-iodo-1-(tetrahydro-2H-pyran-2-yl)-1H-indazole

To a mixture of 4-bromo-6-fluoro-5-iodo-1H-indazole (7.5 g, 22.00 mmol, 1 eq) and 4-methylbenzenesulfonic acid; hydrate (418.47 mg, 2.20 mmol, 0.1 eq) in DCM (100 mL) was added DHP (5.55 g, 66.00 mmol, 6.03 mL, 3 eq) slowly. The mixture was stirred at 30° C. for 1 h. The mixture was washed with saturated NaHCO$_3$ (30 mL*3) and brine (30 mL*3). The organic phase was dried over Na$_2$SO$_4$, filtered and concentrated at reduced pressure to give a residue. The residue was purified by silica gel chromatography (1000 mesh silica gel, Petroleum ether/Ethyl acetate=100/1, 50/1) to give 4-bromo-6-fluoro-5-iodo-1-(tetrahydro-2H-pyran-2-yl)-1H-indazole (7.4 g, 17.41 mmol, 79.14% yield) as yellow solid.

$^1$H NMR (400 MHz, DMSO-d$_6$) δ 8.06 (s, 1H), 7.80 (dd, J=0.7, 8.4 Hz, 1H), 5.83 (dd, J=2.4, 9.6 Hz, 1H), 3.88-3.85 (m, 1H), 3.80-3.70 (m, 2H), 2.40-2.27 (m, 1H), 2.07-1.94 (m, 2H), 1.81-1.63 (m, 2H), 1.62-1.53 (m, 2H).

Step 5) 4-bromo-5-cyclopropyl-6-fluoro-1-(tetrahydro-2H-pyran-2-yl)-1H-indazole

To a mixture of 4-bromo-6-fluoro-5-iodo-1-(tetrahydro-2H-pyran-2-yl)-1H-indazole (1.5 g, 3.53 mmol, 1 eq) and cyclopropylboronic acid (303.14 mg, 3.53 mmol, 1 eq) in dioxane (10 mL) and H$_2$O (2.5 mL) was added Na$_2$CO$_3$ (748.10 mg, 7.06 mmol, 2 eq) and Pd(dppf)Cl$_2$ (258.23 mg, 352.91 umol, 0.1 eq) under N$_2$. The mixture was stirred at 80° C. for 16 h. The mixture was concentrated at reduced pressure to give a residue. The residue was purified by prep-TLC (Petroleum ether:Ethyl acetate=20:1) to give 4-bromo-5-cyclopropyl-6-fluoro-1-(tetrahydro-2H-pyran-2-yl)-1H-indazole (0.21 g, 619.10 umol, 17.54% yield) as colorless oil.

$^1$H NMR (400 MHz, CDCl$_3$) δ 7.98 (d, J=0.6 Hz, 1H), 7.20 (d, J=10.4 Hz, 1H), 5.61 (dd, J=2.8, 9.1 Hz, 1H), 4.03-3.94 (m, 1H), 3.76-3.69 (m, 1H), 2.55-2.42 (m, 1H), 2.19-2.06 (m, 2H), 1.91-1.86 (m, 1H), 1.81-1.64 (m, 3H), 1.12-1.05 (m, 2H), 0.87-0.81 (m, 2H).

Intermediate 1P.
4-bromo-6-fluoro-5-isopropyl-1H-indazole

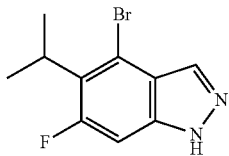

Step 1) 4-bromo-6-fluoro-5-(prop-1-en-2-yl)-1-(tetrahydro-2H-pyran-2-yl)-1H-indazole To a mixture of 4-bromo-6-fluoro-5-iodo-1-(tetrahydro-2H-pyran-2-yl)-1H-indazole (1.5 g, 3.53 mmol, 1 eq) and potassium; trifluoro(isopropenyl)boranuide (626.67 mg, 4.23 mmol, 1.2 eq) in dioxane (10 mL) and H$_2$O (2 mL) was added Pd(dppf)Cl$_2$ (258.23 mg, 352.91 umol, 0.1 eq) and Na$_2$CO$_3$ (748.10 mg, 7.06 mmol, 2 eq) under N$_2$. The mixture was stirred at 80° C. for 16 h. The mixture was concentrated at reduced pressure to give a residue. The residue was purified by silica gel chromatography (1000 mesh silica gel, Petroleum ether/Ethyl acetate=100/1, 50/1; TLC (Petroleum ether:Ethyl acetate=10:1; Rf=0.61)) to give 0.9 g of yellow oil. This oil was purified by prep-TLC (Petroleum ether:Ethyl acetate=20:1) to give 4-bromo-6-fluoro-5-(prop-1-en-2-yl)-1-(tetrahydro-2H-pyran-2-yl)-1H-indazole (0.55 g, 1.62 mmol, 45.94% yield) as yellow oil.

$^1$H NMR (400 MHz, CDCl$_3$) δ 8.00 (d, J=0.6 Hz, 1H), 7.28 (d, J=0.9 Hz, 0.5H), 7.26 (d, J=0.7 Hz, 0.5H), 5.64 (dd, J=2.8, 9.0 Hz, 1H), 5.46 (t, J=1.6 Hz, 1H), 5.01 (s, 1H), 4.05-3.97 (m, 1H), 3.80-3.69 (m, 1H), 2.57-2.42 (m, 1H), 2.19-2.09 (m, 2H), 2.07 (s, 3H), 1.81-1.66 (m, 4H).

Step 2) 4-bromo-6-fluoro-5-isopropyl-1-(tetrahydro-2H-pyran-2-yl)-1H-indazole

To a solution of 4-bromo-6-fluoro-5-(prop-1-en-2-yl)-1-(tetrahydro-2H-pyran-2-yl)-1H-indazole (0.4 g, 1.18 mmol, 1 eq) in MeOH (10 mL) was added PtO$_2$ under N$_2$. The suspension was degassed under vacuum and purged with H$_2$ several times. The mixture was stirred under H$_2$ (15 Psi) at 30° C. for 2.5 h. The mixture was filtered and the filtrate was concentrated at reduced pressure to give a residue The residue was purified by silica gel chromatography (300-400 mesh silica gel, Petroleum ether/Ethyl acetate=50/1) to give 4-bromo-6-fluoro-5-isopropyl-1-(tetrahydro-2H-pyran-2-yl)-1H-indazole (0.3 g, 879.20 umol, 74.56% yield) as colorless oil.

Step 3) 4-bromo-6-fluoro-5-isopropyl-1H-indazole

To a solution of 4-bromo-6-fluoro-5-isopropyl-1-(tetrahydro-2H-pyran-2-yl)-1H-indazole (0.3 g, 879.20 umol, 1 eq) in DCM (1 mL) was added TFA (2.30 g, 20.14 mmol, 1.49 mL, 22.91 eq). The mixture was stirred at 30° C. for 0.5 h. The mixture was concentrated at reduced pressure to give a residue. The residue was diluted with DCM (10 mL) and the resulting mixture was adjusted pH to about 8 with TEA. The mixture was concentrated at reduced pressure to give a residue. The residue was purified by silica gel chromatography (300-400 mesh silica gel, Petroleum ether/Ethyl acetate=30/1, 5/1) to give 4-bromo-6-fluoro-5-isopropyl-1H-indazole (0.2 g, 777.90 umol, 88.48% yield) as colorless oil.

$^1$H NMR (400 MHz, CDCl$_3$) δ 8.04 (s, 1H), 7.11 (d, J=11.2 Hz, 1H), 3.75-3.63 (m, 1H), 1.38 (dd, J=1.7, 7.1 Hz, 6H).

Intermediate 1Q.
4-bromo-6-fluoro-5-methoxy-1H-indazole

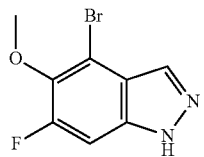

Step 1)
2-bromo-4-fluoro-3-methoxy-1-methylbenzene

To a solution of 2-bromo-6-fluoro-3-methylphenol (4.8 g, 23.41 mmol, 1 eq) in acetone (50 mL) were added K$_2$CO$_3$ (6.47 g, 46.82 mmol, 2 eq) and iodomethane (9.97 g, 70.24 mmol, 4.37 mL, 3 eq), and the mixture was stirred at 25° C. for 1 hour. The reaction mixture was concentrated to give a residue. The residue was dissolved in ethyl acetate (50 mL), and the mixture was filtered, and the filtrate was concentrated to give a residue (4.6 g, 21.00 mmol, 89.70% yield) as a yellow oil.

$^1$H NMR (400 MHz, CHLOROFORM-d) δ 7.05-6.85 (m, 2H), 3.95 (d, J=1.2 Hz, 3H), 2.38 (s, 3H).

Step 2)
3-bromo-1-fluoro-2-methoxy-4-methyl-5-nitrobenzene

To a solution of 2-bromo-4-fluoro-3-methoxy-1-methylbenzene (4.4 g, 20.09 mmol, 1 eq) in H$_2$SO$_4$ (40 mL) (98%) was added KNO$_3$ (2.23 g, 22.10 mmol, 1.1 eq) in portions at 0° C., and the mixture was stirred at 25° C. for 1 hour. The reaction mixture was poured slowly into ice water (200 mL), then the mixture was extracted with ethyl acetate (200 mL*2), the combined organic layers were dried over Na$_2$SO$_4$, filtered and concentrated under reduced pressure to give a residue. 3-bromo-1-fluoro-2-methoxy-4-methyl-5-nitrobenzene (4.6 g, crude) was obtained as a brown oil.

$^1$H NMR (400 MHz, CHLOROFORM-d) δ 7.70 (d, J=10.9 Hz, 1H), 4.08 (d, J=2.7 Hz, 3H), 2.61 (d, J=1.1 Hz, 3H).

Step 3)
3-bromo-5-fluoro-4-methoxy-2-methylaniline

To a solution of 3-bromo-1-fluoro-2-methoxy-4-methyl-5-nitrobenzene (4.6 g, 17.42 mmol, 1 eq) in EtOH (30 mL) and H$_2$O (30 mL) were added Fe (5.84 g, 104.53 mmol, 6 eq) and NH$_4$Cl (5.59 g, 104.53 mmol, 6 eq), and the mixture was stirred at 80° C. for 2 hours. The reaction mixture was filtered, and the filtrate was concentrated to remove EtOH, then the mixture was diluted with EA (50 mL), and the mixture was washed with water (20 mL*2), after then the organic layer was dried over Na$_2$SO$_4$, filtered and concentrated under reduced pressure to give a residue. 3-bromo-5-fluoro-4-methoxy-2-methylaniline (3.5 g, crude) was obtained as a brown oil.

$^1$H NMR (400 MHz, CHLOROFORM-d) δ 6.44 (d, J=11.9 Hz, 1H), 3.83 (s, 3H), 3.76-3.48 (m, 2H), 2.24 (d, J=1.0 Hz, 3H).

Step 4) 4-bromo-6-fluoro-5-methoxy-1H-indazole

To a mixture of 3-bromo-5-fluoro-4-methoxy-2-methylaniline (3.5 g, 14.95 mmol, 1 eq) (crude) in AcOH (20 mL) was added a solution of NaNO$_2$ (1.24 g, 17.94 mmol, 1.2 eq) in H$_2$O (4 mL) dropwise at 0° C., then the mixture was stirred at 25° C. for 12 hr. The reaction mixture was diluted with ice water (100 mL), and the mixture was adjusted to pH 7 by using KOH, then the mixture was extracted with EA (100 mL*2), the combined organic layers were washed with brine (50 mL*2), dried over Na$_2$SO$_4$, filtered and concentrated under reduced pressure to give a residue. The residue was purified by column chromatography (SiO$_2$, Petroleum ether/Ethyl acetate=20/1 to 15:1). 4-bromo-6-fluoro-5-methoxy-1H-indazole (600 mg, 2.45 mmol, 16.37% yield) was obtained as a brown solid.

$^1$H NMR (400 MHz, DMSO-d$_6$) δ 13.44 (br s, 1H), 8.00 (s, 1H), 7.52 (br d, J=10.4 Hz, 1H), 3.84 (s, 3H).

Synthesis of Formula (I) Compounds

Synthetic methods A to J were used to prepare the compounds of the following. Below, the illustrating synthetic examples of some compounds of the present disclosure are described, and other compounds can be prepared by the similar method to the one described below with different starting or reacting materials.

Synthetic Method A

Example 2. (1S,2S)-2-fluoro-N-(6-(5-methyl-1H-indazol-4-yl)benzo[d]thiazol-2-yl)cyclopropane-1-carboxamide

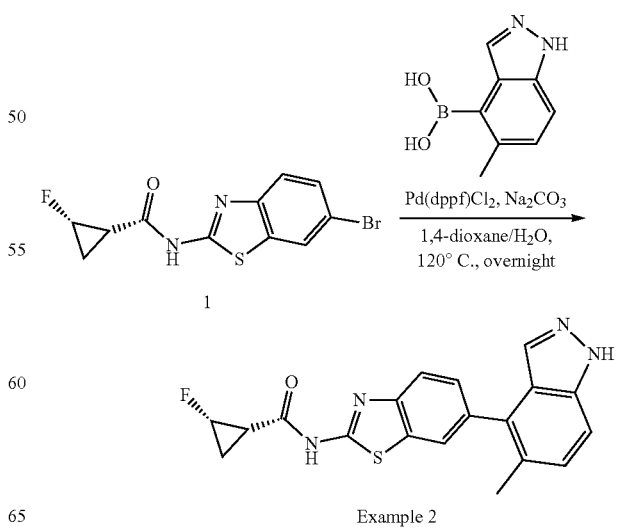

Example 2

To a solution of Compound 1 (0.2 g, 0.462 mmol, 1 eq) (5-methyl-1H-indazol-4-yl)boronic acid (0.081 g, 0.462 mmol, 1 eq) in dioxane (4 mL) and H₂O (1 mL) was added Na₂CO₃ (0.146 g, 1.38 mmol, 3 eq) and Pd(dppf)Cl₂ (33 mg, 0.046 mmol, 0.1 eq). The mixture was stirred at 110° C. for 16 hr. The reaction mixture was diluted with water (10 mL) and extracted with ethyl acetate (10 mL×2). The combined organic layers were dried over Na₂SO₄, filtered and concentrated under reduced pressure to give a residue. The residue was purified by column chromatography to get Example 2 (135 mg, 0.369 mmol, 80% yield) was obtained as a yellow solid.

¹H NMR (400 MHz, DMSO-d₆) δ 13.04 (s, NH), 12.76 (s, CONH), 8.05 (s, 1H), 7.86 (d, J=8.0 Hz, 1H), 7.63 (s, 2H), 7.49-7.44 (m, 2H), 7.31 (d, J=8.4 Hz, 1H), 5.05 (td, J12=3.3 Hz, J13=65.7 Hz, 1H), 2.24 (s, 3H), 2.23-2.24 (m, 1H), 1.78-1.73 (m, 1H), 1.31-1.23 (m, 1H); LCMS (electrospray) m/z 367.1 (M+H)+.

Synthetic Method B

Example 58. (1S,2S)—N-(6-(5-chloro-6-fluoro-7-(methylthio)-1H-indazol-4-yl)benzo[d]thiazol-2-yl)-2-fluorocyclopropane-1-carboxamide. 2 TFA Step 1) (1S,2S)—N-(6-(5-chloro-6-fluoro-7-(methylthio)-2-(tetrahydro-2H-pyran-2-yl)-2H-indazol-4-yl)benzo[d]thiazol-2-yl)-2-fluorocyclopropane-1l-carboxamide To a solution of Compound 3 (4.4 g, 11.59 mmol, 1 eq) in dioxane (100 mL) and H₂O (20 mL) was added Compound 2 (4.20 g, 11.59 mmol, 1 eq), Pd(dppf)Cl₂ (847.97 mg, 1.16 mmol, 0.1 eq) and Na₂CO₃ (2.46 g, 23.18 mmol, 2 eq) under N₂. The reaction mixture was stirred at 90° C. for 12 hr. Water (100 mL) was added and the aqueous phase was extracted with EA (200 mL*2). The combined organic phase was washed with saturated brine (200 mL*2), and concentrated in vacuum. The mixture was purified by column chromatography on silica gel (Petroleum ether:Ethyl acetate=10:1 to 1:1) to give product. Compound 4 (3.9 g, 7.29 mmol, 62.90% yield) as a light yellow solid.

¹H NMR (400 MHz, DMSO-d₆) δ 8.00-7.95 (m, 2H), 7.92-7.85 (m, 1H), 7.59 (dd, J=1.8, 8.4 Hz, 1H), 5.70 (dd, J=2.5, 9.5 Hz, 1H), 5.07-4.79 (m, 1H), 3.82-3.63 (m, 1H), 2.72 (d, J=0.9 Hz, 3H), 2.35-2.23 (m, 1H), 2.04-1.94 (m, 2H), 1.81-1.48 (m, 4H), 1.46-1.33 (m, 2H).

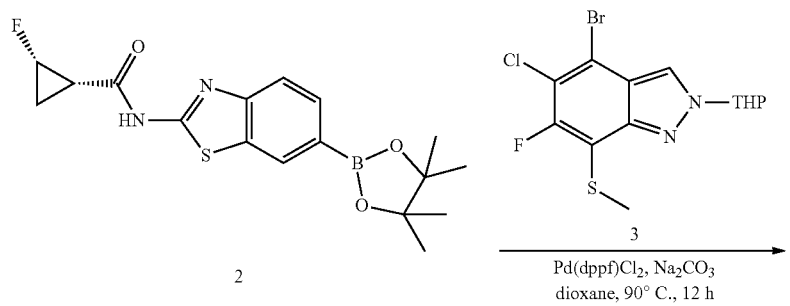

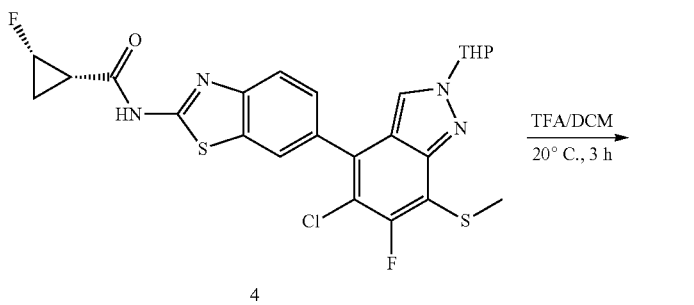

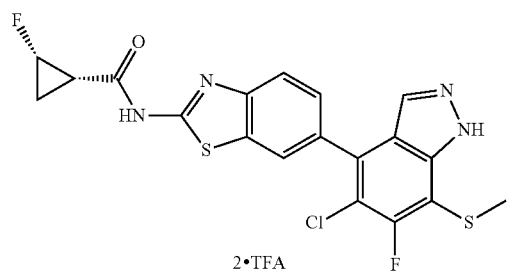

Example 58

Step 2) (1S,2S)—N-(6-(5-chloro-6-fluoro-7-(methylthio)-1H-indazol-4-yl)benzo[d]thiazol-2-yl)-2-fluorocyclopropane-1-carboxamide. 2 TFA salt To a solution of Compound 4 (3.80 g, 7.10 mmol, 1 eq) in DCM (100 mL) was added TFA (9.86 g, 86.51 mmol, 6.41 mL, 12.18 eq) under $N_2$. The reaction mixture was stirred at 20° C. for 4 hr. DCM (10 ml) was added, Then the MeOH (200 ml) was slowly added. The reaction mixture was stirred at 20° C. for 0.5 hr. The reaction mixture was filtered and the filter cake was concentrated to give product. The filtrate was concentrated in vacuum to give product. Then the crude product was lyophilized to afford Example 58 (3.1 g, 4.26 mmol, 59.98% yield, 2 TFA) as a light yellow solid.

$^1$H NMR (400 MHz, DMSO-$d_6$) δ 13.76 (br s, 1H), 12.82 (br s, 1H), 8.19 (d, J=1.7 Hz, 1H), 7.96-7.82 (m, 2H), 7.59 (dd, J=1.8, 8.4 Hz, 1H), 5.26-4.85 (m, 1H), 2.57 (s, 3H), 2.30-2.19 (m, 1H), 1.84-1.69 (m, 1H), 1.33 (tdd, J=6.4, 9.0, 12.9 Hz, 1H); LCMS (electrospray) m/z 450.8 (M+H)+.

Synthetic Method C

Example 149. (1S,2S)—N-(5-(5-chloro-7-ethoxy-6-fluoro-1H-indazol-4-yl)thiazolo[5,4-b]pyridin-2-yl)-2-fluorocyclopropane-1-carboxamide. 2 TFA

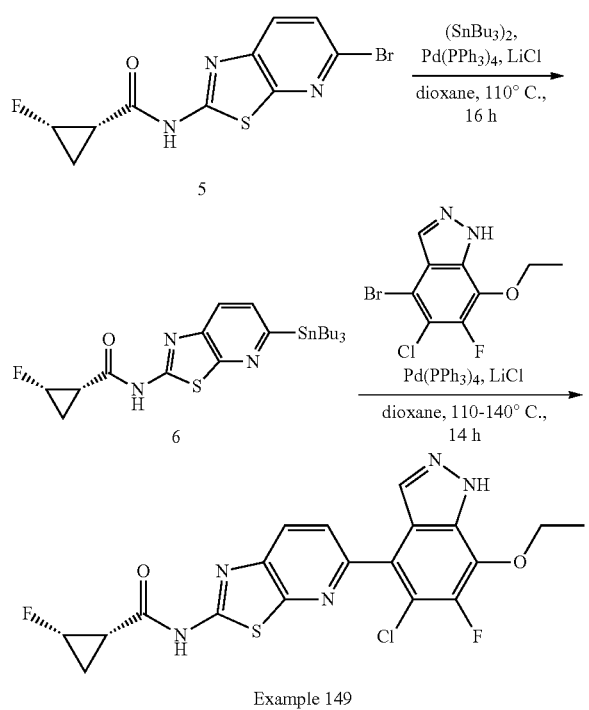

Example 149

Step 1) (1S,2S)-2-fluoro-N-(5-(tributylstannyl)thiazolo[5,4-b]pyridin-2-yl)cyclopropane-1-carboxamide To a solution of Compound 5 (2.5 g, 7.91 mmol, 1 eq) in dioxane (30 mL) was added (SnBu$_3$)$_2$ (6.88 g, 11.86 mmol, 5.93 mL, 1.5 eq), Pd(PPh$_3$)$_4$ (913.78 mg, 790.77 umol, 0.1 eq) and LiCl (1.01 g, 23.72 mmol, 485.85 uL, 3 eq). The mixture was stirred at 110° C. for 16 hr under $N_2$ atmosphere. The reaction mixture was filtered and the filtrate was concentrated under reduced pressure to give a residue. The residue was purified by column chromatography (Silical gel, Petroleum ether:Ethyl acetate=10:1 to 3:1). Compound 6 (1.3 g, 2.47 mmol, 31.24% yield) was obtained as a yellow oil.

Step 2) (1S,2S)—N-(5-(5-chloro-7-ethoxy-6-fluoro-1H-indazol-4-yl)thiazolo[5,4-b]pyridin-2-yl)-2-fluorocyclopropane-1-carboxamide. 2 TFA To a solution of 4-bromo-5-chloro-7-ethoxy-6-fluoro-1H-indazole (100 mg, 264.81 umol, 1 eq) in dioxane (2 mL) were added Compound 6 (167.24 mg, 317.77 umol, 1.2 eq), Pd(PPh$_3$)$_4$ (30.60 mg, 26.48 umol, 0.1 eq) and LiCl (33.68 mg, 794.42 umol, 16.27 uL, 3 eq). The mixture was stirred at 140° C. for 2 hr under microwave. After then, the reaction mixture was added with saturated $K_2CO_3$ aqueous 10 mL and stirred at 20° C. for 15 min. The mixture was diluted with water 10 mL and extracted with Ethyl acetate (20 mL*2). The combined organic layers were washed with brine (20 mL*2), dried over $Na_2SO_4$, filtered and the filtrate was concentrated under reduced pressure to give a residue. The residue was purified by prep-TLC (Silical gel plate, Petroleum ether:Ethyl acetate=1:2) to give a crude product. The crude product was purified by prep-HPLC (column: Phenomenex luna C18 150*25 mm*10 um; mobile phase: [water (0.1% TFA)-ACN]; B %: 55%-85%, 10 min). Example 149 (60 mg, 112.36 umol, 42.43% yield) was obtained as a yellow oil.

$^1$H NMR (400 MHz, DMSO-$d_6$) δ 12.97 (s, 1H), 8.28 (d, J=8.4 Hz, 1H), 7.95 (s, 1H), 7.81 (d, J=8.4 Hz, 1H), 6.12-6.06 (m, 1H), 5.20-4.96 (m, 1H), 4.46-4.34 (q, J=7.0 Hz, 2H), 3.97 (m, 1H), 3.73-3.61 (m, 1H), 2.47-2.40 (m, 1H), 2.32-2.22 (m, 1H), 2.04 (m, 2H), 1.83-1.69 (m, 2H), 1.57 (m, 2H), 1.49 (t, J=7.0 Hz, 3H), 1.41-1.28 (m, 1H).

Synthetic Method D

Example 152. (1S,2S)—N-(5-(5-ethyl-6-fluoro-1H-indazol-4-yl)thiazolo[5,4-b]pyridin-2-yl)-2-fluorocyclopropane-1-carboxamide

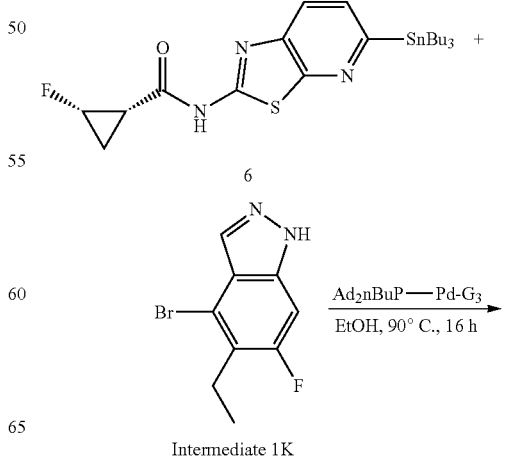

Intermediate 1K

-continued

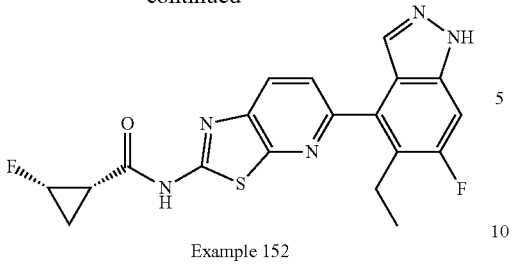

Example 152

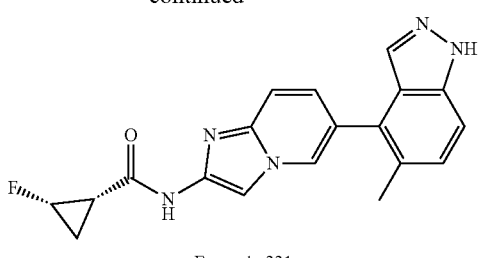

Example 221

To a solution of Intermediate 1K (45 mg, 185.13 umol, 1 eq) in EtOH (2 mL) were added Compound 6 (116.92 mg, 222.15 umol, 1.2 eq) and Ad₂nBuP-Pd-G3 (13.48 mg, 18.51 umol, 0.1 eq). The mixture was stirred at 80° C. for 16 hr under N₂ atmosphere. The reaction mixture was diluted with water 20 mL and extracted with Ethyl acetate (20 mL*2). The combined organic layers were washed with brine (20 mL*2), dried over Na₂SO₄, filtered and the filtrate was concentrated under reduced pressure to give a residue. The residue was purified by prep-HPLC (column: Phenomenex luna C18 150*25 mm*10 um; mobile phase: [water (0.1% TFA)-ACN]; B %: 33%-63%, 10 min) to give a crude product. The crude product was purified by prep-TLC (Silical gel plate, Petroleum ether:Ethyl acetate=1:1). Example 152 (9.7 mg, 24.29 umol, 13.12% yield, 100% purity) was obtained as a white solid.

¹H NMR (400 MHz, DMSO-d₆) δ 13.18 (br s, 1H), 12.94 (br s, 1H), 8.26 (d, J=8.2 Hz, 1H), 7.72 (s, 1H), 7.68 (d, J=8.3 Hz, 1H), 7.42 (d, J=10.1 Hz, 1H), 5.20-4.95 (m, 1H), 2.65 (dq, J=2.4, 7.2 Hz, 2H), 2.27 (m, 1H), 1.85-1.69 (m, 1H), 1.34 (m, 1H), 1.11 (t, J=7.0 Hz, 3H); LCMS (electrospray) m/z 400.4 (M+H)+.

Synthetic Method E

Example 221. (1S,2S)-2-fluoro-N-(6-(5-methyl-1H-indazol-4-yl)imidazo[1,2-a]pyridin-2-yl)cyclopropane-1-carboxamide

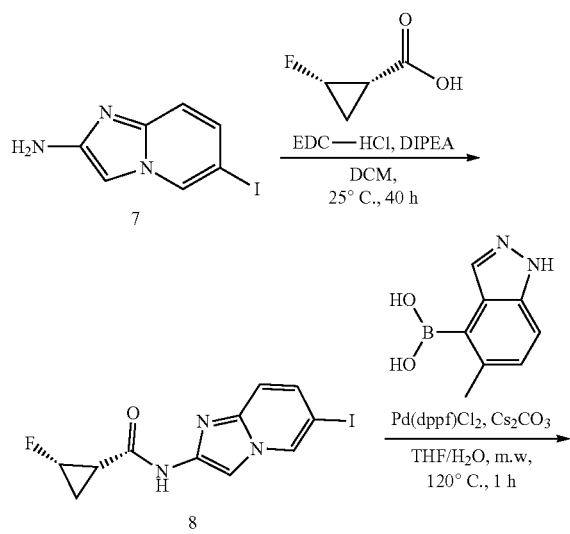

Step 1) (1S,2S)-2-fluoro-N-(6-iodoimidazo[1,2-a]pyridin-2-yl)cyclopropane-1-carboxamide A mixture of Compound 7 (5.890 g, 22.737 mmol), (1S,2S)-2-fluorocyclopropane-1-carboxylic acid (3.076 g, 29.558 mmol) and 1-Ethyl-3-(3-dimethylaminopropyl)carbodiimide hydrochloride (EDC-HCl, 6.538 g, 34.105 mmol) in dichloromethane (100 mL) was treated at the room temperature with N,N-diisopropylethylamine (2.376 mL, 13.642 mmol), stirred at the same temperature for 40 hr. The precipitates were collected by filtration, washed by dichloromethane, and dried to give Compound 8 as beige solid (3.870 g, 49.3%).

¹H NMR (400 MHz, DMSO-d₆) δ 10.99 (s, 1H), 8.87 (s, 1H), 8.02 (s, 1H), 7.36~7.23 (m, 2H), 4.97~4.77 (m, 1H), 2.09~2.07 (m, 1H), 1.65~1.57 (m, 1H), 1.16~1.09 (m, 1H).

Step 2) (1S,2S)-2-fluoro-N-(6-(5-methyl-1H-indazol-4-yl)imidazo[1,2-a]pyridin-2-yl)cyclopropane-1-carboxamide Compound 8 (0.750 g, 2.173 mmol), (5-methyl-1H-indazol-4-yl)boronic acid (0.459 g, 2.608 mmol), [1,1'-bis(diphenylphosphino)ferrocene]dichloropalladium(II) (Pd(dppf)Cl₂, 0.159 g, 0.217 mmol) and cesium carbonate (1.416 g, 4.346 mmol) in tetrahydrofuran (15 mL)/water (4 mL) was mixed at the room temperature and then heated at 120° C. under the microwaves for 1 hr, cooled down to the room temperature, filtered through a celite pad to remove solids, and partitioned between ethyl acetate and saturated aqueous sodium bicarbonate solution. The organic layer was washed with aqueous saturated sodium chloride solution, separated, dried (anhydrous MgSO4), filtered, and concentrated in vacuo. The residue was chromatographed (SiO₂, 30 g cartridge; ethyl acetate/hexane=100%) to give the crude product which was crystallized at the room temperature using diethylether (5 mL). The resulting precipitates were filtered, washed by diethylether, and dried to give Example 221 as light yellow solid (0.550 g, 72.4%).

¹H NMR (400 MHz, DMSO-d₆) δ 12.77 (s, 1H), 9.70 (s, 1H), 9.00 (s, 1H), 8.66 (d, J=9.2 Hz, 1H), 8.59 (s, 1H), 8.55 (d, J=9.2 Hz, 1H), 8.33 (d, J=8.0 Hz, 1H), 8.14 (d, J=8.8 Hz, 1H), 5.91~5.71 (m, 1H), 3.11 (s, 3H), 3.05~3.00 (m, 1H), 2.54~2.48 (m, 1H), 2.07~2.03 (m, 1H); LCMS (electrospray) m/z 350.0 (M+H)+.

Synthetic Method F

Example 223. N-(6-(5-chloro-1H-indazol-4-yl)imidazo[1,2-a]pyridin-2-yl)cyclopropanecarboxamide. dihydrochloride

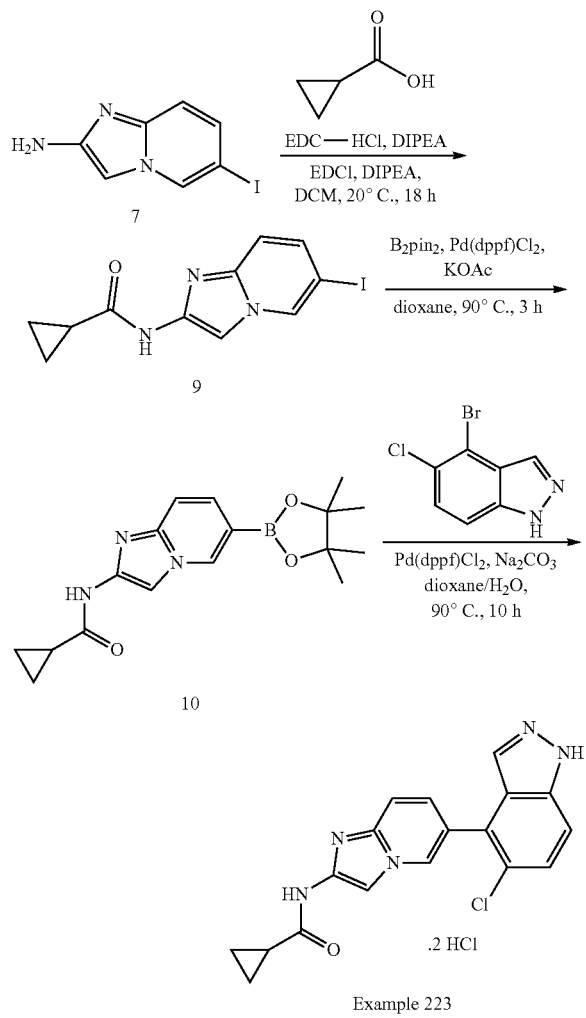

Example 223

Step 1) (2-amino-6-iodoimidazo[1,2-a]pyridin-3-yl)(cyclopropyl)methanone

To a solution of cyclopropanecarboxylic acid (3.17 g, 36.78 mmol, 2.91 mL, 1.3 eq) in DCM (50 mL) was added EDCI (6.51 g, 33.95 mmol, 1.2 eq), HOBt (4.59 g, 33.95 mmol, 1.2 eq) and TEA (8.59 g, 84.89 mmol, 11.82 mL, 3 eq). The mixture was stirred at 20° C. for 1 hr. then added Compound 7 (6 g, 28.30 mmol, 1 eq). The final mixture was stirred at 20° C. for 18 hr. The mixture was poured into H$_2$O (200 mL) and extracted with Ethyl acetate (300 mL*3), the organic phase was washed with brine (500 mL*2) and dried with anhydrous sodium sulfate (Na$_2$SO$_4$), filtered and concentrated in vacuum. The residue was purified by trituration with Ethyl acetate (50 mL), filtered and the filter cake was concentrated. Compound 9 (1.9 g, 6.78 mmol, 23.96% yield) was obtained as yellow solid.

$^1$H NMR (400 MHz, DMSO-d$_6$) δ 9.70 (d, J=1.2 Hz, 1H), 7.60 (dd, J=2.1, 9.3 Hz, 1H), 7.32 (d, J=9.3 Hz, 1H), 6.62 (s, 2H), 2.46-2.37 (m, 1H), 1.02-0.90 (m, 4H).

Step 2) (1S,2S)-2-fluoro-N-(6-(5-methyl-1H-indol-4-yl)imidazo[1,2-a]pyridin-2-yl)cyclopropane-1-carboxamide dihydrochloride To a solution of Compound 9 (10.22 g, 31.27 mmol, 1 eq) and 4,4,5,5-tetramethyl-2-(4,4,5,5-tetramethyl-1,3,2-dioxaborolan-2-yl)-1,3,2-dioxaborolane (11.12 g, 43.78 mmol, 1.4 eq) in dioxane (100 mL) was added KOAc (9.21 g, 93.82 mmol, 3 eq) and Pd(dppf)Cl$_2$ (1.14 g, 1.56 mmol, 0.05 eq). The mixture was heated to 90° C. for 3 hr. The residue was poured into water (200 mL). The aqueous phase was extracted with ethyl acetate (200 mL*2). The combined organic phase was washed with brine (300 mL), dried with anhydrous Na$_2$SO$_4$, filtered and concentrated in vacuum. TLC (Petroleum ether/Ethyl acetate=0:1) showed a main spot. The residue was purified by silica gel chromatography eluted with Petroleum ether/Ethyl acetate=0:1. Compound 10 (11 g, crude) was obtained as yellow solid. The crude was purified by triturated with Petroleum ether (20 mL) and Ethyl acetate (4 mL), filtered and the filter cake was concentrated. Compound 10 (6.3 g, 19.26 mmol, 48.46% yield) was obtained as white solid.

Step 3) N-(6-(5-chloro-1H-indazol-4-yl)imidazo[1,2-a]pyridin-2-yl)cyclopropanecarboxamide. Dihydrochloride To a solution of Compound 10 (100 mg, 305.64 umol, 1 eq) and 4-bromo-5-chloro-1H-indazole (84.90 mg, 366.76 umol, 1.2 eq) in dioxane (3 mL) and H$_2$O (1 mL) was added Na$_2$CO$_3$ (97.18 mg, 916.91 umol, 3 eq) and Pd(dppf)Cl$_2$ (11.18 mg, 15.28 umol, 0.05 eq). The mixture was stirred at 90° C. for 10 hr. The mixture was poured into Petroleum ether (10 mL), filtered with silica gel and the filtrate was concentrated in vacuum. The residue was purified by prep-HPLC (column: Phenomenex Synergi C18 150*25*10 um; mobile phase: [water (0.05% HCl)-ACN]; B %: 14%-34%, 9 min), followed by lyophilization. Example 223 (36.8 mg, 85.95 umol, 28.12% yield, 99.2% purity, 2 HCl) was obtained as white solid.

$^1$H NMR (400 MHz, METHANOL-d$_4$) δ 8.92 (s, 1H), 8.13 (s, 1H), 7.99-7.91 (m, 3H), 7.68 (dd, J=1.0, 8.9 Hz, 1H), 7.58 (d, J=8.9 Hz, 1H), 1.95-1.87 (m, 1H), 1.12-1.07 (m, 2H), 1.05-0.98 (m, 2H); LCMS (electrospray) m/z 352.0 (M+H)+.

Synthetic Method G

Example 231. N-(6-(5-bromo-6-fluoro-1H-indazol-4-yl)imidazo[1,2-a]pyridin-2-yl)cyclopropanecarboxamide. 2 TFA salt

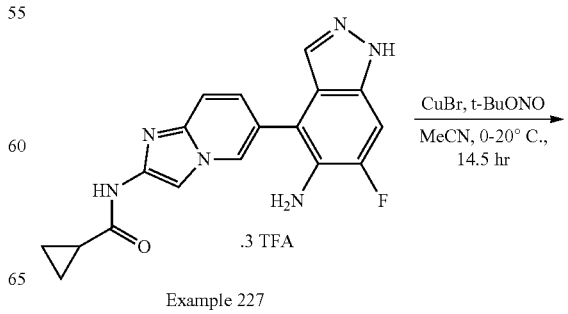

Example 227

-continued

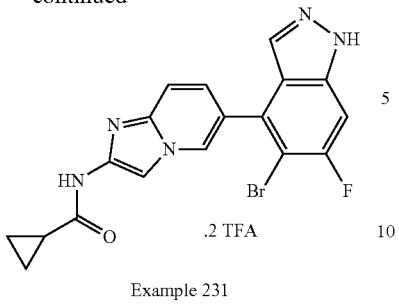

Example 231

A mixture of CuBr (137.29 mg, 957.04 umol, 29.15 uL, 1 eq) and t-BuONO (98.69 mg, 957.04 umol, 113.83 uL, 1 eq) in MeCN (5 mL) was stirred at 0° C. for 30 mins, after then a solution of Example 227 (662 mg, 957.04 umol, 1 eq) in MeCN (1 mL) was added, and the mixture was stirred at 20° C. for 2 hours, after then CuBr (137.29 mg, 957.04 umol, 29.15 uL, 1 eq) and t-BuONO (98.69 mg, 957.04 umol, 113.83 uL, 1 eq) were added, and the mixture was stirred at 20° C. for another 12 hours. The reaction mixture was concentrated to give a residue, then the residue was dissolved in ethyl acetate (50 mL), after then the mixture was washed with diluted ammonium hydroxide (3%, 20 mL*2), the organic layer was washed with brine (20 mL), dried over $Na_2SO_4$, filtered and concentrated under reduced pressure to give a residue. The residue was purified by prep-HPLC (column: Phenomenex Synergi C18 150*25*10 um; mobile phase: [water (0.1% TFA)-ACN]; B %: 20%-50%, 9 min). Example 231 (14 mg, 22.01 umol, 2.3% yield, 2TFA) was obtained as a yellow solid.

$^1$H NMR (400 MHz, DMSO-$d_6$) δ 13.49 (br s, 1H), 11.05 (s, 1H), 8.78 (s, 1H), 8.14 (s, 1H), 7.92 (s, 1H), 7.64 (d, J=8.7 Hz, 1H), 7.57 (d, J=9.2 Hz, 1H), 7.32 (dd, J=1.7, 9.2 Hz, 1H), 2.05-1.86 (m, 1H), 0.85-0.79 (m, 4H); LCMS (electrospray) m/z 414.1 (M+H)+.

Synthetic Method H

Example 258. (1S,2S)—N-(6-(5-chloro-7-(dimethyl-amino)-6-fluoro-1H-indazol-4-yl)imidazo[1,2-a]pyridin-2-yl)-2-fluorocyclopropane-1-carboxamide

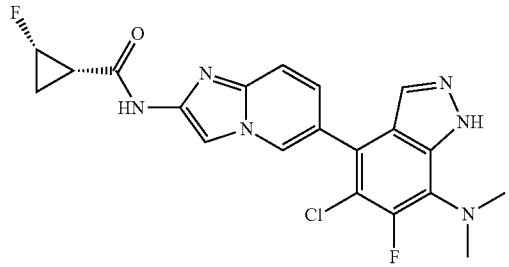

Example 258

Step 1) (1S,2S)—N-(6-(5-chloro-7-(dimethyl-amino)-6-fluoro-1-(tetrahydro-2H-pyran-2-yl)-1H-indazol-4-yl)imidazo[1,2-a]pyridin-2-yl)-2-fluorocyclopropane-1-carboxamide To a solution of Intermediate 1D (30 mg, 78.06 umol, 1 eq) and Compound 11 (32.33 mg, 93.67 umol, 1.2 eq) in dioxane (1 mL) and $H_2O$ (0.2 mL) were added Pd(dppf)Cl$_2$ (5.71 mg, 7.81 umol, 0.1 eq) and $Na_2CO_3$ (24.82 mg, 234.17 umol, 3 eq), then the mixture was stirred at 80° C. for 12 hours under $N_2$. The reaction mixture was concentrated to give a residue. The residue was purified by prep-TLC (SiO$_2$, Dichloromethane:Methanol=10:1). Compound 12 (34 mg, 57.44 umol, 73.59% yield, 87% purity) was obtained as a yellow oil.

Step 2) (1S,2S)—N-(6-(5-chloro-7-(dimethyl-amino)-6-fluoro-1H-indazol-4-yl)imidazo[1,2-a]pyridin-2-yl)-2-fluorocyclopropane-1-carboxamide To a solution of Compound 12 (34 mg, 57.44 umol, 1 eq) in dioxane (1 mL) was added HCl/dioxane (4 M, 1 mL, 69.64 eq), then the mixture was stirred at 20° C. for 2 hours under $N_2$. The reaction mixture was diluted with ethyl acetate (20 mL), and the mixture was washed with saturated aqueous solution of NaHCO$_3$ (15 mL*2), the organic layer was dried over $Na_2SO_4$, filtered and concentrated under reduced pressure to give a residue. The residue was purified by prep-HPLC (column: Phenomenex luna C$_{18}$ 150*25 10u; mobile phase: [water (0.1% TFA)-ACN]; B %: 23%-53%, 10 min). Example 258 (8.7 mg, 13.05 umol, 22.72% yield, 2 TFA) was obtained as a white solid.

$^1$H NMR (400 MHz, DMSO-$d_6$) δ 13.55 (br s, 1H), 11.21 (s, 1H), 8.80 (s, 1H), 8.17 (s, 1H), 7.95 (s, 1H), 7.62 (d, J=9.2 Hz, 1H), 7.43 (d, J=9.2 Hz, 1H), 5.08-4.77 (m, 1H), 3.01 (s, 3H), 3.00 (s, 3H), 2.16 (td, J=7.0, 13.8 Hz, 1H), 1.76-1.57 (m, 1H), 1.27-1.11 (m, 1H); LCMS (electrospray) m/z 431.2 (M+H)+.

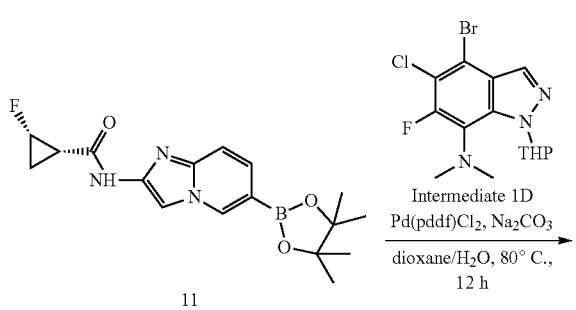

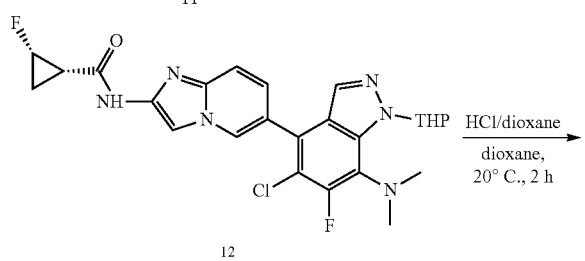

Synthetic Method I

Example 393. (1S,2S)—N-(6-(7-(1-(2H-tetrazol-2-yl)ethyl)-5-chloro-6-fluoro-1H-indazol-4-yl)imidazo[1,2-a]pyridin-2-yl)-2-fluorocyclopropane-1-carboxamide

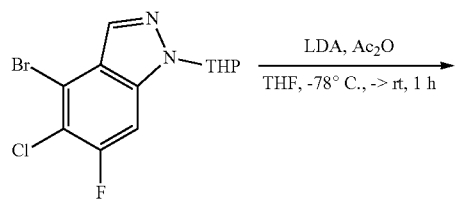

Intermediate 1A

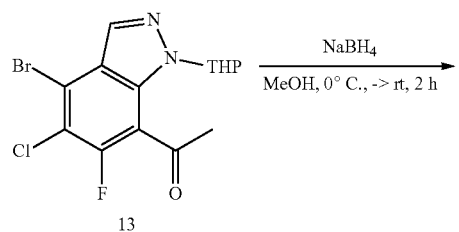

13

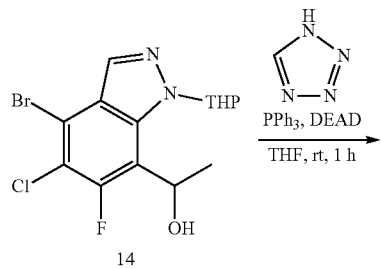

14

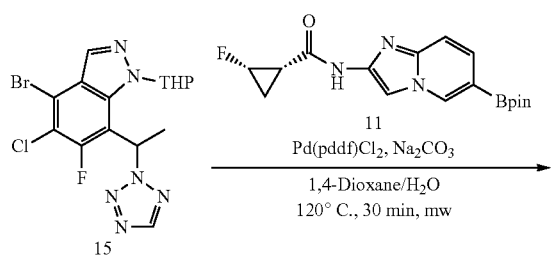

15

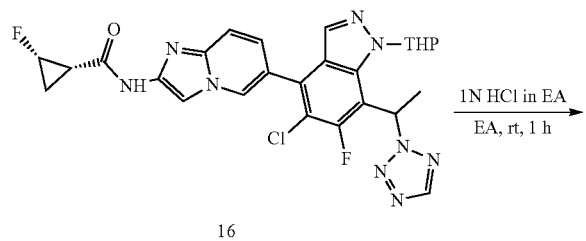

16

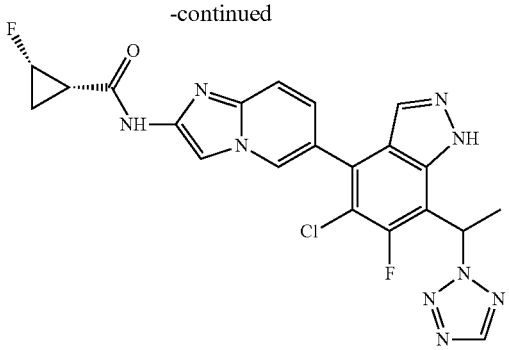

Example 393

Step 1) 1-(4-bromo-5-chloro-6-fluoro-1-(tetrahydro-2H-pyran-2-yl)-1H-indazol-7-yl)ethan-1-one To a solution of Intermediate 1A (3.29 g, 9.86 mmol, 1 eq) in THF (49 mL) was cooled to −78° C. then, LDA (7.39 mL, 14.7 mmol, 1.5 eq) was added slowly to reaction mixture, stirred at the same temperature for 30 min. Then acetic anhydride (1.11 mL, 11.8 mmol, 1.2 eq) was added dropwise and the reaction mixture was stirred at rt for 2 hrs. After the Intermediate 1A was consumed, quenched with water and extracted with DCM, separated, dried over anhydrous MgSO₄, filtered, and concentrated in vacuo. The residue was purified by silica gel chromatography (product came out at Hexane/Ethyl acetate=10/1) to afford Compound 13 (1.86 g, 4.95 mmol, 50.2% yield) as an orange solid.

Step 2) 1-(4-bromo-5-chloro-6-fluoro-1-(tetrahydro-2H-pyran-2-yl)-1H-indazol-7-yl)ethan-1-ol To a solution of Compound 13 (1.86 mg, 4.95 mmol, 1 eq) in MeOH (24 mL) were cooled to 0° C. then sodium borohydride (375 mg, 9.90 mmol, 2 eq) was added portionwise. The reaction mixture was stirred at rt for 2 hrs. After the Compound 13 was consumed, the reaction mixture was concentrated and extracted with DCM, washed with water, separated, dried over anhydrous MgSO₄, filtered, and concentrated in vacuo. The residue was purified by silica gel chromatography (product came out at Hexane/Ethyl acetate=7/3) to afford Compound 14 (615 mg, 1.62 mmol, 32% yield) as an ivory solid.

Step 3) 7-(1-(2H-tetrazol-2-yl)ethyl)-4-bromo-5-chloro-6-fluoro-1-(tetrahydro-2H-pyran-2-yl)-1H-indazole To a solution of Compound 14 (100 mg, 0.265 mmol, 1.0 eq) in THF (1.33 mL) was added 1H-tetrazole (0.89 mL, 0.398 mmol, 1.5 eq) and PPh₃ (104 mg, 0.398 mmol, 1.5 eq). The mixture was cooled to 0° C. and DEAD (0.181 mL, 0.398 mmol, 1.5 eq) was added slowly at 0° C. The mixture was stirred at room temperature for 1 hr. The reaction mixture was extracted with DCM (30 mL*3). The combined organic layers were dried over Na₂SO₄, filtered and the filtrate was concentrated in vacuum. The crude product was purified by silica gel chromatography (product came out Hexane/Ethyl acetate=10/2) to afford Compound 15 (62 mg, 0.144 mmol, 54% yield) as a white color solid.

Step 4) (1S,2S)—N-(6-(7-(1-(2H-tetrazol-2-yl)ethyl)-5-chloro-6-fluoro-1-(tetrahydro-2H-pyran-2-yl)-1H-indazol-4-yl)imidazo[1,2-a]pyridin-2-yl)-2-fluorocyclopropane-1-carboxamide To a solution of Compound 15 (62 mg, 0.144 mmol, 1 eq) in 1,4-Dioxane (0.577 mL)/H₂O (0.144 mL) were added Compound 11 (54 mg, 0.159 mmol, 1.1 eq), Pd(dppf)Cl₂ (5 mg, 0.007 mmol, 0.05 eq), Na₂CO₃ (30 mg, 0.289 mmol, 2 eq). The mixture was degassed and purged with N₂ for 3 times. The mixture was stirred at 120° C. for 30 min in microwave reactor. The reaction mixture was filtered through celite and filtrate was extracted with DCM. The combined organic layers were dried over Na₂SO₄, filtered and the filtrate was concentrated in vacuum to give a residue. The residue was purified by silica gel chromatography (product came out at Hexane/Ethyl acetate=2/8) to afford Compound 16 (68 mg, 0.120 mmol, 83%) as a yellow solid.

Step 5) (1S,2S)—N-(6-(7-(1-(2H-tetrazol-2-yl)ethyl)-5-chloro-6-fluoro-1H-indazol-4-yl)imidazo[1,2-a]pyridin-2-yl)-2-fluorocyclopropane-1-carboxamide To a solution of Compound 16 (66 mg, 0.116 mmol, 1 eq) in Ethyl acetate (0.6 mL) was added 1 N HCl in EA solution (1.16 mL, 1.16 mmol, 10 eq). The mixture was stirred at room temperature for 1 hr. The reaction mixture was quenched by saturated NaHCO₃ and extracted with EA, dried over Na₂SO₄, filtered and the filtrate was concentrated in vacuum. The crude product was purified by silica gel chromatography (product came out at DCM/MeOH=10/1) to afford Example 393 (4 mg, 0.008 mmol, 7%) as an ivory solid.

¹H NMR (400 MHz, DMSO-d₆) δ 13.77 (s, 1H), 11.07 (s, 1H), 8.99 (s, 1H), 8.80 (s, 1H), 8.14-8.04 (m, 2H), 7.58-7.54 (m, 1H), 7.35 (dd, J=9.3, 1.6 Hz, 1H), 6.74 (q, J=7.1 Hz, 1H), 5.00-4.79 (m, 1H), 2.23 (d, J=7.2 Hz, 3H), 2.16-2.09 (m, 1H), 1.68-1.57 (m, 1H), 1.18-1.09 (m, 1H)); LCMS (electrospray) m/z 485.10 (M+H)+.

Synthetic Method J

Example 446. (1S,2S)-2-fluoro-N-(5-(5-methyl-1H-indazol-4-yl)pyrazolo[1,5-a]pyridin-2-yl)cyclopropanecarboxamide

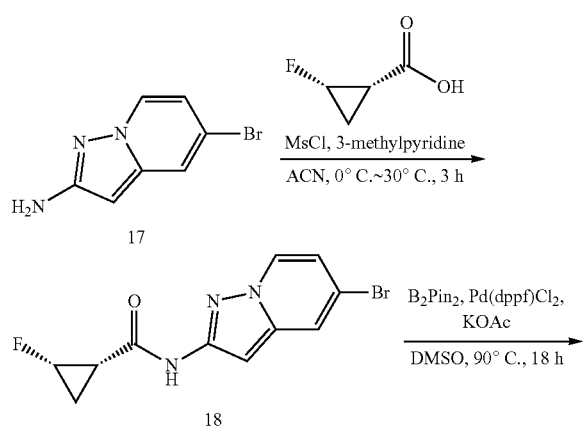

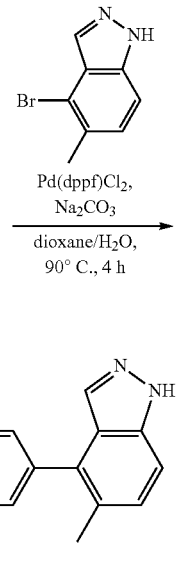

Example 446

Step 1) (1S,2S)—N-(5-bromopyrazolo[1,5-a]pyridin-2-yl)-2-fluorocyclopropane-1-carboxamide To a mixture of Compound 17 (3.1 g, 14.62 mmol, 1 eq) and (1S,2S)-2-fluorocyclopropanecarboxylic acid (1.67 g, 16.08 mmol, 1.1 eq) in CH₃CN (40 mL) was added MsCl (3.35 g, 29.24 mmol, 2.26 mL, 2 eq) and 3-methylpyridine (6.81 g, 73.10 mmol, 7.12 mL, 5 eq) slowly at 0° C. under N₂. The mixture was stirred at 30° C. for 3 h. The mixture was concentrated at reduced pressure. The residue was dissolved with ethyl acetate (200 mL) and the resulting mixture was washed with 10% citric acid (30 mL*2), saturated Na₂CO₃ (30 mL*2), brine (30 mL*2), dried over Na₂SO₄, filtered and concentrated at reduced pressure to give a residue. The residue was purified by silica gel chromatography (1000 mesh silica gel, Petroleum ether/Ethyl acetate=5/1, 3/1) to give Compound 18 (2.3 g, 7.72 mmol, 52.81% yield) as white solid.

Step 2) (1S,2S)-2-fluoro-N-(5-(4,4,5,5-tetramethyl-1,3,2-dioxaborolan-2-yl)pyrazolo[1,5-a]pyridin-2-yl)cyclopropane-1-carboxamide Compound 18 (0.345 g, 1.159 mmol), 4,4,4',4',5,5,5',5'-octamethyl-2,2'-bi(1,3,2-dioxaborolane, 0.588 g, 2.318 mmol), [1,1'-bis(diphenylphosphino)ferrocene]dichloropalladium(II) (Pd(dppf)Cl₂, 0.084 g, 0.115 mmol) and potassium acetate (0.398 g, 4.056 mmol) were mixed at the room temperature in DMSO (10 mL) and then stirred at 90° C. for 18 h, cooled down to the room temperature, filtered through a celite pad to remove solids, and partitioned between ethyl acetate and water. The organic layer was washed with aqueous saturated sodium chloride solution, separated, dried with anhydrous MgSO₄, filtered, and concentrated in vacuo. The residue was chromatographed (SiO₂, 12 g cartridge; ethyl acetate/hexane=0% to 100%) to give Compound 19 as brown solid (0.289 g, 72.3%).

Step 3) (1S,2S)-2-fluoro-N-(5-(5-methyl-1H-indazol-4-yl)pyrazolo[1,5-a]pyridin-2-yl)cyclopropanecarboxamide To a mixture of Compound 19 (6 g*, 17.34 mmol, 1 eq) and 4-bromo-5-methyl-1H-indazole (3.6 g, 17.34 mmol, 1 eq) in dioxane (120 mL) and H₂O (24 mL) was added Na₂CO₃ (3.67 g, 34.68 mmol, 2 eq) and Pd(dppf)Cl₂ (1.28 g, 1.73 mmol, 0.1 eq) under N₂. The mixture was stirred at 90° C. for 4 h. The mixture was concentrated at reduced pressure to give a residue. The residue was purified by silica gel chromatography (1000 mesh silica gel, Petroleum ether/ Ethyl acetate=5/1, 1/1; TLC (Petroleum ether:Ethyl acetate=1:1; Rf=0.08) to give 2.5 g of yellow solid. This solid was triturated with CH₃CN (10 mL) for two times. The mixture was filtered and the filtered cake was collected. The cake was dispersed with H₂O/CH₃CN (5:1; 10 mL) and the resulting mixture was lyophilizated for third times to give Example 446 (1.53 g, 4.37 mmol, 25.20% yield, 96.98% purity) as pale solid.

¹H NMR (400 MHz, DMSO-d₆) δ 13.09 (s, 1H), 11.13 (s, 1H), 8.61 (d, J=7.1 Hz, 1H), 7.74 (s, 1H), 7.63 (d, J=0.9 Hz, 1H), 7.49 (d, J=8.6 Hz, 1H), 7.32 (d, J=8.6 Hz, 1H), 6.91 (s, 1H), 6.86 (dd, J=1.9, 7.0 Hz, 1H), 5.06-4.98 (m, 1H), 4.88-4.84 (m, 1H), 2.34 (s, 3H), 2.15 (td, J=6.9, 13.8 Hz, 1H), 1.74-1.61 (m, 1H), 1.21-1.13 (m, 1H); LCMS (electrospray) m/z 350.1 (M+H)+.

Table 1 below shows the compounds of Examples along with general synthetic methods used to make the compound and characterization data.

TABLE 1

Compounds of Examples

| Ex # | Structure/Name | ¹H NMR/MS (M + 1) | Method |
|---|---|---|---|
| 1 | 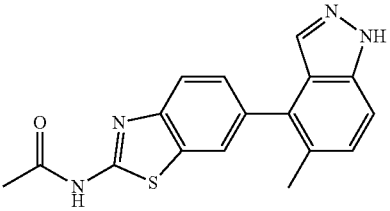<br>N-(6-(5-methyl-1H-indazol-4-yl)benzo[d]thiazol-2-yl)cyclopropanecarboxamide | ¹H NMR (400 MHz, DMSO-d₆) δ 13.04 (s, NH), 12.69 (s, CONH), 8.03 (s, 1H), 7.84 (d, J = 8.4 Hz, 1H), 7.63 (s, 1H), 7.48-7.44 (m, 1H), 7.31 (d, J = 8.4 Hz, 1H), 2.30 (s, 3H), 2.02 (t, J = 5.6 Hz, 1H), 0.97 (t, J = 4.0 Hz, 4H); LCMS (electrospray) m/z 349.0 (M + H)+. | A |
| 2 | 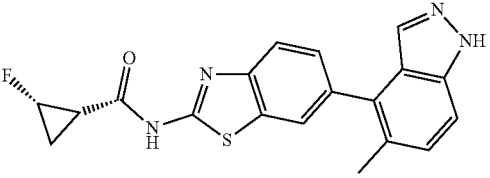<br>(1S,2S)-2-fluoro-N-(6-(5-methyl-1H-indazol-4-yl)benzo[d]thiazol-2-yl)cyclopropane-1-carboxamide | ¹H NMR (400 MHz, DMSO-d₆) δ 13.04 (s, NH), 12.76 (s, CONH), 8.05 (s, 1H), 7.86 (d, J = 8.0 Hz, 1H), 7.63 (s, 2H), 7.49-7.44 (m, 2H), 7.31 (d, J = 8.4 Hz, 1H), 5.05 (td, J12 = 3.3 Hz, J13 = 65.7 Hz, 1H), 2.24 (s, 3H), 2.23-2.24 (m, 1H), 1.78-1.73 (m, 1H), 1.31-1.23 (m, 1H); LCMS (electrospray) m/z 367.1 (M + H)+. | A |
| 3 | 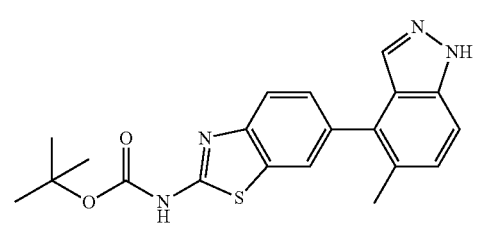 [SMILES: Cc1ccc2[nH]ncc2c1-c1ccc2nc(NC(=O)OC(C)(C)C)sc2c1]<br>tert-butyl (6-(5-methyl-1H-indazol-4-yl)benzo[d]thiazol-2-yl)carbamate | ¹H NMR (400 MHz, DMSO-d₆) δ 13.03 (s, 1H), 11.80 (s, 1H), 7.99 (s, 1H), 7.78 (d, 8.4 Hz, 1H), 7.63 (s, 1H), 7.46-7.42 (m, 2H), 7.31 (d, 8.4 Hz, 1H), 2.30 (s, 3H), 1.52 (s, 9H); LCMS (electrospray) m/z 381.1 (M + H)+. | A |
| 4 | 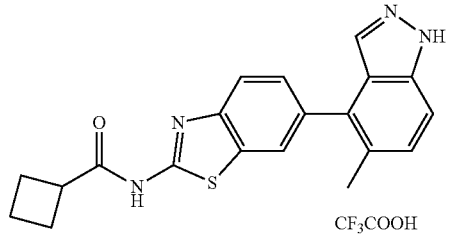<br>N-(6-(5-methyl-1H-indazol-4-yl)benzo[d]thiazol-2-yl)cyclobutanecarboxamide. 2 TFA | ¹H NMR (400 MHz, DMSO-d₆) δ 13.02 (br s, 1H), 12.28 (br s, 1H), 8.04 (d, J = 1.3 Hz, 1H), 7.83 (d, J = 8.3 Hz, 1H), 7.63 (s, 1H), 7.50-7.43 (m, 2H), 7.31 (d, J = 8.4 Hz, 1H), 3.44 (quin, J = 8.5 Hz, 1H), 2.32-2.13 (m, 7H), 2.06-1.92 (m, 1H), 1.90-1.78 (m, 1H); LCMS (electrospray) m/z 363.2 (M + H)+. | A |

TABLE 1-continued

Compounds of Examples

| Ex # | Structure/Name | ¹H NMR/MS (M + 1) | Method |
|---|---|---|---|
| 5 | 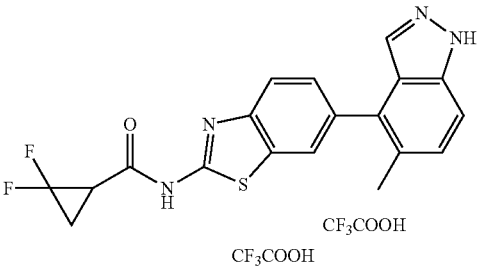 [SMILES: Cc1ccc2[nH]ncc2c1-c1ccc2nc(NC(=O)C3CC3(F)F)sc2c1 ; "CF3COOH" ; "CF3COOH"]<br>2,2-difluoro-N-(6-(5-methyl-1H-indazol-4-yl)benzo[d]thiazol-2-yl)cyclopropane-1-carboxamide. 2 TFA salt | ¹H NMR (400 MHz, DMSO-d₆) δ 13.21-12.83 (m, 2H), 8.08 (d, J = 1.2 Hz, 1H), 7.89 (d, J = 8.3 Hz, 1H), 7.64 (s, 1H), 7.52-7.43 (m, 2H), 7.32 (d, J = 8.6 Hz, 1H), 3.02 (td, J = 9.5, 13.0 Hz, 1H), 2.30 (s, 3H), 2.23-2.11 (m, 2H); LCMS (electrospray) m/z 385.0 (M + H)+. | A |
| 6 | 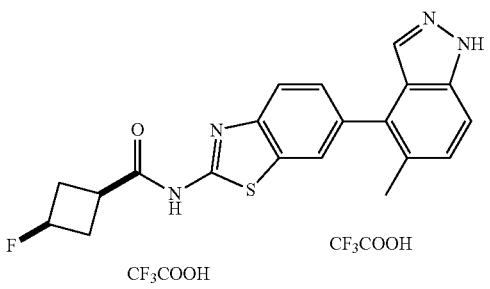<br>(1S,3S)-3-fluoro-N-(6-(5-methyl-1H-indazol-4-yl)benzo[d]thiazol-2-yl)cyclobutane-1-carboxamide. 2 TFA | ¹H NMR (400 MHz, DMSO-d₆) δ 13.05 (br s, 1H), 12.50 (s, 1H), 8.06 (d, J = 1.3 Hz, 1H), 7.85 (d, J = 8.3 Hz, 1H), 7.63 (s, 1H), 7.50-7.44 (m, 2H), 7.32 (d, J = 8.6 Hz, 1H), 5.19-4.95 (m, 1H), 2.97-2.85 (m, 1H), 2.66-2.57 (m, 2H), 2.45-2.35 (m, 2H), 2.30 (s, 3H); LCMS (electrospray) m/z 381.1 (M + H)+. | A |
| 7 | 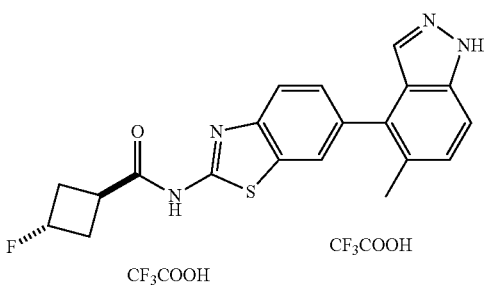<br>(1R,3R)-3-fluoro-N-(6-(5-methyl-1H-indazol-4-yl)benzo[d]thiazol-2-yl)cyclobutane-1-carboxamide. 2 TFA | ¹H NMR (400 MHz, DMSO-d₆) δ 13.03 (br s, 1H), 12.48 (s, 1H), 8.06 (d, J = 1.3 Hz, 1H), 7.85 (d, J = 8.3 Hz, 1H), 7.63 (s, 1H), 7.50-7.43 (m, 2H), 7.32 (d, J = 8.6 Hz, 1H), 5.37-5.15 (m, 1H), 3.45 (br d, J = 3.1 Hz, 1H), 2.65-2.55 (m, 2H), 2.45-2.35 (m, 2H), 2.30 (s, 3H); LCMS (electrospray) m/z 381.1 (M + H)+. | A |
| 8 | 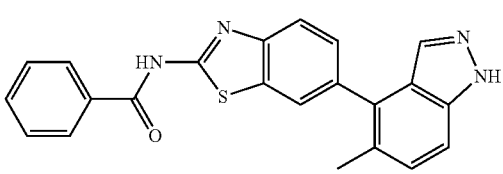 [SMILES: Cc1ccc2[nH]ncc2c1-c1ccc2nc(NC(=O)c3ccccc3)sc2c1]<br>N-(6-(5-methyl-1H-indazol-4-yl)benzo[d]thiazol-2-yl)benzamide | ¹H NMR (400 MHz, DMSO-d₆) δ 13.04(s, 1H), 12.93(s, 1H), 8.16(dd, J = 8.4 Hz, J = 2.0 Hz, 2H), 8.10(s, 1H), 7.91(d, J = 7.6 Hz, 1H), 7.70-7.65(m, 2H), 7.60-7.57(m, 2H), 7.53(dd, J = 8.4 Hz, 2.0 Hz, 1H), 7.47(d, J = 8.4 Hz, 1H), 7.32(d, J = 8.8 Hz, 1H), 2.32(s, 3H); LCMS (electrospray) m/z 385.1 (M + H)+. | A |

TABLE 1-continued

Compounds of Examples

| Ex # | Structure/Name | ¹H NMR/MS (M + 1) | Method |
|---|---|---|---|
| 9 | 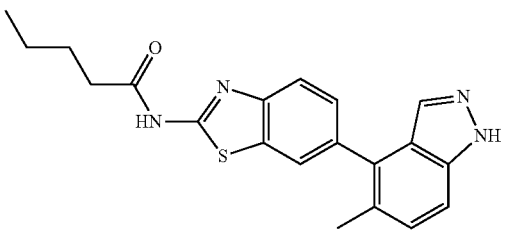 [SMILES: CCCCC(=O)Nc1nc2ccc(-c3c(C)ccc4[nH]ncc34)cc2s1]<br>N-(6-(5-methyl-1H-indazol-4-yl)benzo[d]thiazol-2-yl)pentanamide | ¹H NMR (400 MHz, DMSO-$d_6$) δ 12.99 (s, NH), 12.31 (s, NH), 7.99 (s, 1H), 7.80 (d, J = 8.0 Hz, 1H), 7.58 (s, 1H), 7.44-7.40 (m, 2H), 7.27 (d, J = 8.0 Hz, 1H), 2.26 (s, 3H), 1.59 (m, 2H), 1.31-1.29 (m, 2H), 0.89-0.85 (m, 3H); LCMS (electrospray) m/z 365.1 (M + H)+. | A |
| 10 | 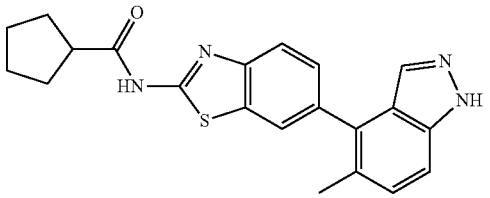 [SMILES: Cc1ccc2[nH]ncc2c1-c1ccc2nc(NC(=O)C3CCCC3)sc2c1]<br>N-(6-(5-methyl-1H-indazol-4-yl)benzo[d]thiazol-2-yl)cyclopentanecarboxamide | ¹H NMR (400 MHz, DMSO-$d_6$) δ 12.98 (s, NH), 12.32 (s, NH), 7.99 (s, 1H), 7.80 (d, J = 8.0 Hz, 1H), 7.58 (s, 1H), 7.44-7.40 (m, 2H), 7.27 (d, J = 8.0 Hz, 1H), 2.96 (m, 1H), 2.26 (s, 3H), 1.89 (m, 2H), 1.79-1.49 (m, 4H), 1.24-1.20 (m, 1H), 0.83-0.80 (m, 1H); LCMS (electrospray) m/z 377.1 (M + H)+. | A |
| 11 | 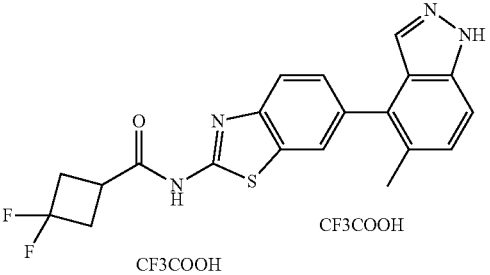<br>3,3-difluoro-N-(6-(5-methyl-1H-indazol-4-yl)benzo[d]thiazol-2-yl)cyclobutane-1-carboxamide. 2 TFA | ¹H NMR (400 MHz, DMSO-$d_6$) δ 13.08 (br s, 1H), 12.60 (br s, 1H), 8.07 (d, J = 1.3 Hz, 1H), 7.86 (d, J = 8.2 Hz, 1H), 7.64 (s, 1H), 7.51-7.43 (m, 2H), 7.32 (d, J = 8.6 Hz, 1H), 3.38-3.25 (m, 1H), 2.98-2.81 (m, 4H), 2.30 (s, 3H); LCMS (electrospray) m/z 377.1 (M + H)+. | A |
| 12 | 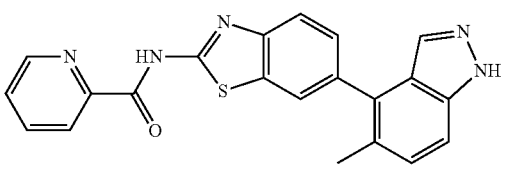 [SMILES: Cc1ccc2[nH]ncc2c1-c1ccc2nc(NC(=O)c3ccccn3)sc2c1]<br>N-(6-(5-methyl-1H-indazol-4-yl)benzo[d]thiazol-2-yl)picolinamide | ¹H NMR (400 MHz, DMSO-$d_6$) d 13.00 (s, 1H), 12.17 (s, 1H), 8.82 (d, J = 4.4 Hz, 1H), 8.24 (d, J = 8.0 Hz, 1H), 8.16-8.12 (m, 2H), 7.93 (d, J = 8.8 Hz, 1H), 7.76 (dd, J = 7.2, 4.8 Hz, 1H), 7.64 (s, 1H), 7.52 (dd, J = 8.4, 1.6 Hz, 1H), 7.47 (d, J = 8.4 Hz, 1H), 7.32 (d, J = 8.4 Hz, 1H), 2.32 (s, 3H); LCMS (electrospray) m/z 386.1 (M + H)+. | A |
| 13 | 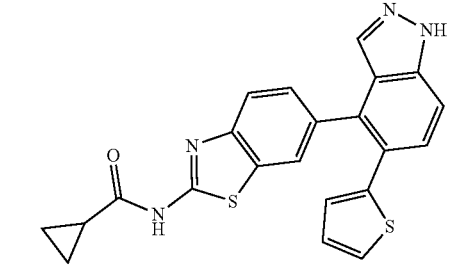 [SMILES: O=C(Nc1nc2ccc(-c3c(-c4cccs4)ccc4[nH]ncc34)cc2s1)C1CC1]<br>N-(6-(5-(thiophen-2-yl)-1H-indazol-4-yl)benzo[d]thiazol-2-yl)cyclopropanecarboxamide | ¹H NMR (400 MHz, DMSO-$d_6$) δ 13.31(s, 1H), 12.74(brs, 1H), 8.43(s, 1H), 7.93(d, J = 1.6 Hz, 1H), 7.73(d, J = 2.4 Hz, 1H), 7.71(s, 1H), 7.60(d, J = 3.2 Hz, 2H), 7.36-7.34(m, 1H), 7.31(dd, J = 8.4 Hz, J = 1.2 Hz, 1H), 6.92-6.89(m, 1H), 6.86-6.85(m, 1H), 2.03-1.98(m, 1H), 0.99-0.95(m, 4H); LCMS (electrospray) m/z 417.0 (M + H)+. | B |

TABLE 1-continued

Compounds of Examples

| Ex # | Structure/Name | ¹H NMR/MS (M + 1) | Method |
|---|---|---|---|
| 14 | 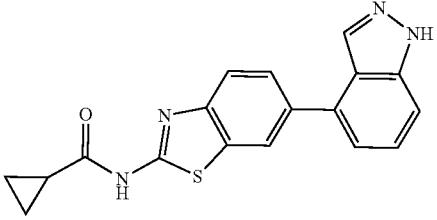 [SMILES: O=C(Nc1nc2ccc(-c3cccc4[nH]ncc34)cc2s1)C1CC1]<br>N-(6-(1H-indazol-4-yl)benzo[d]thiazol-2-yl)cyclopropanecarboxamide | ¹H NMR (400 MHz, DMSO-d$_6$) δ 13.07(s, 1H), 12.62(s, 1H), 8.25(s, 1H), 8.08(s, 1H), 8.03(s, 1H), 7.77-7.67(m, 3H), 7.59(d, J = 8.0 Hz, 1H), 2.00-1.96(m, 1H), 0.96-0.92(m, 4H); LCMS (electrospray) m/z 335.1 (M + H)+. | A |
| 15 | 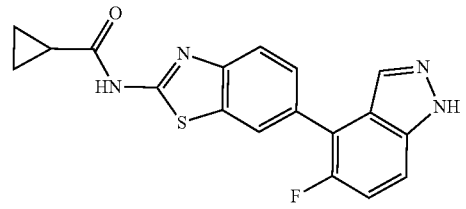 [SMILES: O=C(Nc1nc2ccc(-c3c(F)ccc4[nH]ncc34)cc2s1)C1CC1]<br>N-(6-(5-fluoro-1H-indazol-4-yl)benzo[d]thiazol-2-yl)cyclopropanecarboxamide | ¹H NMR (400 MHz, DMSO-d$_6$) δ 13.27(s, 1H), 12.69(s, 1H), 8.21(s, 1H), 8.00(s, 1H), 7.84(d, J = 8.4 Hz, 1H), 7.65(dd, J = 8.4 Hz, J = 1.6 Hz, 1H), 7.54(dd, J = 10.8 Hz, J = 9.2 Hz, 1H), 2.02-1.96(m 1H), 0.95-0.93(m, 4H); LCMS (electrospray) m/z 353.1 (M + H)+. | B |
| 16 | 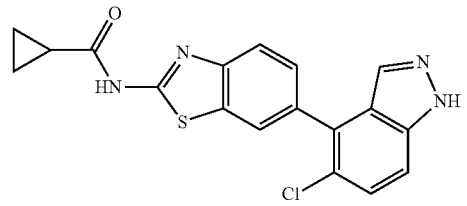 [SMILES: O=C(Nc1nc2ccc(-c3c(Cl)ccc4[nH]ncc34)cc2s1)C1CC1]<br>N-(6-(5-chloro-1H-indazol-4-yl)benzo[d]thiazol-2-yl)cyclopropanecarboxamide | ¹H NMR (400 MHz, DMSO-d$_6$) δ 13.38(s, 1H), 12.74(s, 1H), 8.09(d, J = 1.6 Hz, 1H), 7.83(d, J = 8.8 Hz, 1H), 7.72(s, 1H), 7.55(d, J = 8.8 Hz, 1H), 7.51(dd, J = 8.4 Hz, J = 1.6 Hz, 1H), 7.46(d, J = 8.8 Hz, 1H), 2.02-1.97(m, 1H), 0.97-0.93(m, 4H); LCMS (electrospray) m/z 369.0 (M + H)+. | B |
| 17 | 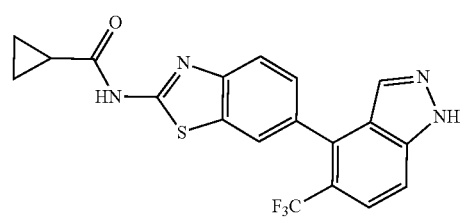 [SMILES: O=C(Nc1nc2ccc(-c3c(C(F)(F)F)ccc4[nH]ncc34)cc2s1)C1CC1]<br>N-(6-(5-(trifluoromethyl)-1H-indazol-4-yl)benzo[d]thiazol-2-yl)cyclopropanecarboxamide | ¹H NMR (400 MHz, DMSO-d$_6$) δ 13.58(s, 1H), 12.74(s, 1H), 8.03(d, J = 1.6 Hz, 1H), 7.84(d, J = 8.0 Hz, 1H), 7.75(s, 2H), 7.71(s, 1H), 7.44(dd, J = 8.8 Hz, 1.6 Hz, 1H), 20.4-2.00(m, 1H), 0.99-0.96(m, 4H); LCMS (electrospray) m/z 403.0 (M + H)+. | B |
| 18 | 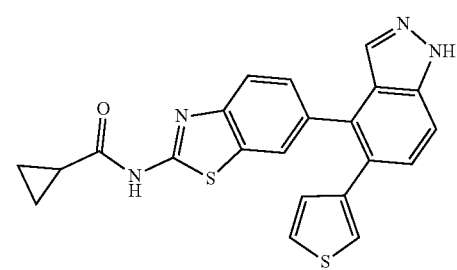 [SMILES: O=C(Nc1nc2ccc(-c3c(-c4ccsc4)ccc4[nH]ncc34)cc2s1)C1CC1]<br>N-(6-(5-(thiophen-3-yl)-1H-indazol-4-yl)benzo[d]thiazol-2-yl)cyclopropanecarboxamide | ¹H NMR (400 MHz, DMSO-d$_6$) δ 13.19(s, 1H), 12.64(s, 1H), 7.84(s, 1H), 7.75(s, 1H), 7.65(d, J = 8.0 Hz, 1H), 7.55(d, J = 8.0 Hz, 1H), 7.48(d, J = 8.0 Hz, 1H), 7.29-7.20(m, 3H), 6.63(d, J = 4.0 Hz, 1H), 3.66-3.62(m, 1H), 2.01-1.92(m, 1H), 0.98-0.85(m, 4H); LCMS (electrospray) m/z 417.1 (M + H)+. | B |

TABLE 1-continued

Compounds of Examples

| Ex # | Structure/Name | ¹H NMR/MS (M + 1) | Method |
|---|---|---|---|
| 19 | 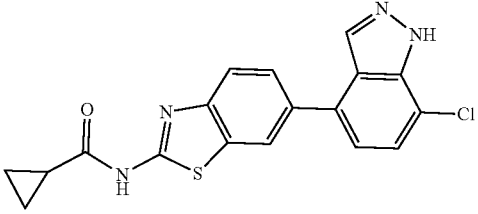 [SMILES: O=C(Nc1nc2ccc(-c3ccc(Cl)c4[nH]ncc34)cc2s1)C1CC1]<br>N-(6-(7-chloro-1H-indazol-4-yl)benzo[d]thiazol-2-yl)cyclopropanecarboxamide | ¹H NMR (400 MHz, DMSO-d$_6$) δ 13.75(s, 1H), 12.71(s, 1H), 8.35(s, 2H), 7.86(d, J = 6.8 Hz, 1H), 7.79(s, 1H), 7.53(d, J = 6.8 Hz, 1H), 7.28(d, J = 6.0 Hz, 1H), 2.05-1.95(m, 1H), 1.10-0.90(m, 4H); LCMS (electrospray) m/z 369.0 (M + H)+. | B |
| 20 | 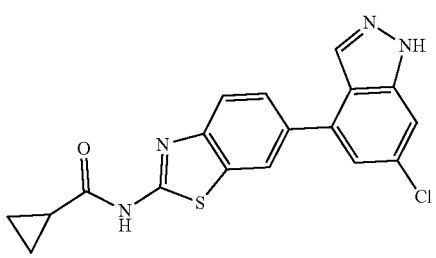 [SMILES: O=C(Nc1nc2ccc(-c3cc(Cl)cc4[nH]ncc34)cc2s1)C1CC1]<br>N-(6-(6-chloro-1H-indazol-4-yl)benzo[d]thiazol-2-yl)cyclopropanecarboxamide | ¹H NMR (400 MHz, DMSO-d$_6$) δ 13.36(s, 1H), 12.73(s, 1H), 8.39(s, 1H), 8.27(s, 1H), 7.88-7.81(m, 2H), 7.62(s, 1H), 7.31(s, 1H), 2.04-1.99(m, 1H), 0.99-0.97(m, 4H); LCMS (electrospray) m/z 369.0 (M + H)+. | B |
| 21 | 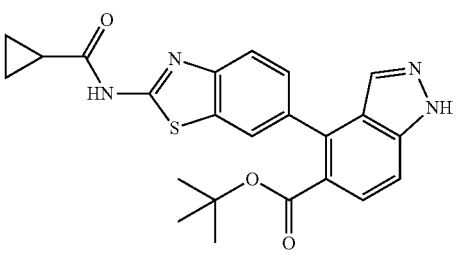 [SMILES: CC(C)(C)OC(=O)c1ccc2[nH]ncc2c1-c1ccc2nc(NC(=O)C3CC3)sc2c1]<br>tert-butyl 4-(2-(cyclopropanecarboxamido)benzo[d]thiazol-6-yl)-1H-indazole-5-carboxylate | ¹H NMR (400 MHz, DMSO-d$_6$) δ 13.42 (s, NH), 12.70(s, NH), 7.95 (s, 1H), 7.84-7.82 (m, 2H), 7.75 (d, J = 8.4 Hz, 1H), 7.60(d, J = 9.6 Hz, 1H), 7.44(d, J = 10.0 Hz, 1H), 2.02-1.98(m, 1H), 1.08 (s, 9 H), 0.98-0.96 (m, 4H); LCMS (electrospray) m/z 435.1 (M + H)+. | B |
| 22 | 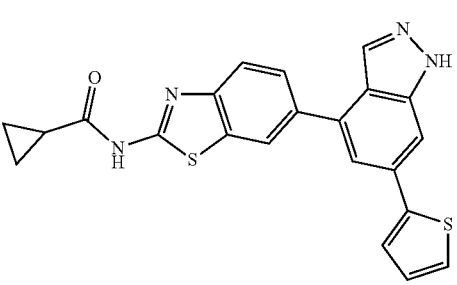 [SMILES: O=C(Nc1nc2ccc(-c3cc(-c4cccs4)cc4[nH]ncc34)cc2s1)C1CC1]<br>N-(6-(6-(thiophen-2-yl)-1H-indazol-4-yl)benzo[d]thiazol-2-yl)cyclopropanecarboxamide | ¹H NMR (400 MHz, DMSO-d$_6$) δ 13.28(s, 1H), 12.74(s, 1H), 8.43(s, 1H), 8.23(s, 1H), 7.88-7.87(m, 2H), 7.72-7.71(m, 2H), 7.61-7.59(m, 2H), 7.19(dd, J = 5.2 Hz, J = 3.2 Hz, 1H), 2.07-2.00(m, 1H), 1.01-0.97(m, 4H); LCMS (electrospray) m/z 417.0 (M + H)+. | B |

TABLE 1-continued

Compounds of Examples

| Ex # | Structure/Name | ¹H NMR/MS (M + 1) | Method |
|---|---|---|---|
| 23 | 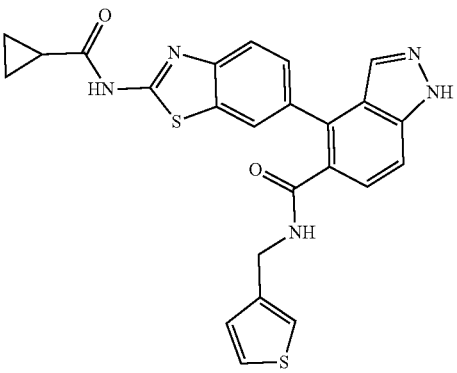 [SMILES: O=C(NCc1ccsc1)c1ccc2[nH]ncc2c1-c1ccc2nc(NC(=O)C3CC3)sc2c1]<br>4-(2-(cyclopropanecarboxamido)benzo[d]thiazol-6-yl)-N-(thiophen-3-ylmethyl)-1H-indazole-5-carboxamide | ¹H NMR (400 MHz, DMSO-$d_6$) δ 13.31 (s, NH), 12.71 (s, NH), 8.45-8.42 (m, 1H), 8.02 (s, 1H), 7.90 (s, 1H), 7.72-7.70 (d, J = 8.0 Hz, 1H), 7.48-7.50 (d, J = 8.4 Hz, 1H), 7.46 (m, 4H), 6.76 (m, 1H), 4.24 (d, J = 5.2 Hz, 1H), 2.03-2.01 (m, 1H), 0.99-0.97 (m, 4H); LCMS (electrospray) m/z 474.1 (M + H)+. | B |
| 24 | 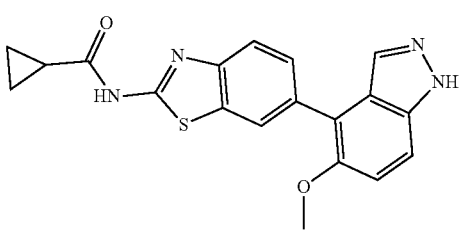 [SMILES: COc1ccc2[nH]ncc2c1-c1ccc2nc(NC(=O)C3CC3)sc2c1]<br>N-(6-(5-methoxy-1H-indazol-4-yl)benzo[d]thiazol-2-yl)cyclopropanecarboxamide | ¹H NMR (400 MHz, DMSO-$d_6$) δ 13.03(s, 1H), 12.67(s, 1H), 8.11(d, J = 3.2 Hz, 1H), 7.82-7.80(m, 2H), 7.60(dd, J = 8.4 Hz, 1.6 Hz, 1H), 7.53(d, J = 9.2 Hz, 1H), 7.34(d, J = 8.4 Hz, 1H), 3.75(s, 3H), 2.05-1.98(m, 1H), 0.98-0.96(m, 4H); LCMS (electrospray) m/z 365.1 (M + H)+. | B |
| 25 | 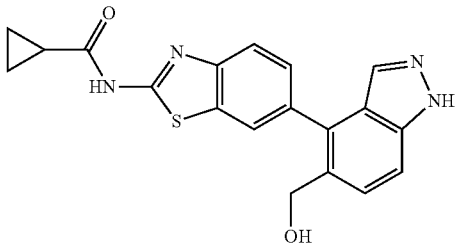 [SMILES: O=C(Nc1nc2ccc(-c3c(CO)ccc4[nH]ncc34)cc2s1)C1CC1]<br>N-(6-(5-(hydroxymethyl)-1H-indazol-4-yl)benzo[d]thiazol-2-yl)cyclopropanecarboxamide | ¹H NMR (400 MHz, DMSO-$d_6$) δ 13.13(s, 1H), 12.72(s, 1H), 8.07(d, J = 1.6 Hz, 1H), 7.84(d, J = 8.0 Hz, 1H), 7.71(s, 1H), 7.58-7.53(m, 3H), 5.15-5.08(m, 1H), 4.45(d, J = 5.2 Hz, 2H), 2.04-1.99(m, 1H), 1.02-0.96(m, 4H); LCMS (electrospray) m/z 365.0 (M + H)+. | B |
| 26 | 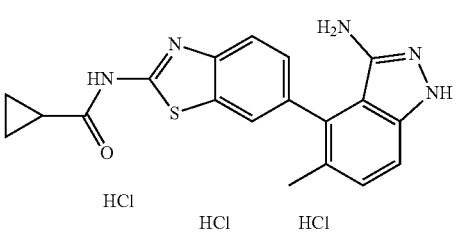 [SMILES: Cc1ccc2[nH]nc(N)c2c1-c1ccc2nc(NC(=O)C3CC3)sc2c1 ; Cl ; Cl ; Cl]<br>N-(6-(3-amino-5-methyl-1H-indazol-4-yl)benzo[d]thiazol-2-yl)cyclopropanecarboxamide. 3 HCl | ¹H NMR (400 MHz, DMSO-$d_6$) δ 13.03 (s, NH), 12.77 (s, NH), 7.97 (s, 1H), 7.86 (d, J = 8.4 Hz, 1H), 7.49-7.38 (m, 3H), 4.20 (br, NH2), 2.10 (m, 1H), 1.99 (s, 3H), 0.99-0.96 (m, 4H); LCMS (electrospray) m/z 364.1 (M + H)+. | B |

TABLE 1-continued

Compounds of Examples

| Ex # | Structure/Name | ¹H NMR/MS (M + 1) | Method |
|---|---|---|---|
| 27 | N-(6-(5-hydroxy-1H-indazol-4-yl)benzo[d]thiazol-2-yl)cyclopropanecarboxamide | ¹H NMR (400 MHz, DMSO-d$_6$) δ 12.85 (s, 1H), 12.61 (s, 1H), 9.02 (s, 1H), 8.11 (s, 1H), 7.77-7.75 (m, 2H), 7.65 (d, J = 9.2 Hz, 1H), 7.34 (d, J = 8.6 Hz, 1H), 7.07 (d, J = 8.6 Hz, 1H), 1.97 (quin, J = 6.2 Hz, 1H), 0.94 (d, J = 6.0 Hz, 4H); LCMS (electrospray) m/z 351.40 (M + H)+. | B |
| 28 | N-(6-(5-ethyl-1H-indazol-4-yl)benzo[d]thiazol-2-yl)cyclopropanecarboxamide | ¹H NMR (400 MHz, DMSO-d$_6$) δ 13.04(s, 1H), 12.69(s, 1H), 7.99(d, J = 1.2 Hz, 1H), 7.84(d, J = 8.4 Hz, 1H), 7.55(s, 1H), 7.50(d, J = 8.4 Hz, 1H), 7.42(dd, J = 7.6 Hz, 1.6 Hz, 1H), 7.35(d, J = 9.2 Hz, 1H), 2.0(q, J = 7.6 Hz, 2H), 2.05-1.99(m, 1H), 1.08(t, J = 7.6 Hz, 3H), 0.98-0.96(m, 4H); LCMS (electrospray) m/z 363.1 (M + H)+. | B |
| 29 | N-(6-(5-cyano-1H-indazol-4-yl)benzo[d]thiazol-2-yl)cyclopropanecarboxamide | ¹H NMR (400 MHz, DMSO-d$_6$) δ 13.68(s, 1H), 12.76(s, 1H), 8.28(d, J = 1.6 Hz, 1H), 8.07(s, 1H), 7.89(d, J = 8.4 Hz, 1H), 7.75(d, J = 9.2 Hz, 1H), 7.69(dd, J = 8.4 Hz, J = 1.6 Hz, 2H), 2.03-1.96(m, 1H), 0.96-0.94(m, 4H); LCMS: m/z = 403.0 (M + H+)LCMS (electrospray) m/z 360.1 (M + H)+. | B |
| 30 | (1S,2S)-N-(6-(5-chloro-1H-indazol-4-yl)benzo[d]thiazol-2-yl)-2-fluorocyclopropane-1-carboxamide | ¹H NMR (400 MHz, DMSO-d$_6$) 13.37(s, 1H), 12.76(s, 1H), 8.15(d, J = 1.6 Hz, 1H), 7.88(d, J = 8.4 Hz, 1H), 7.77(brs, 1H), 7.60-7.55(m, 2H), 7.50(d, J = 9.2 Hz, 1H), 5.16-4.95(m, 1H), 2.28-2.21(m, 1H), 1.81-1.71(m, 1H), 1.38-1.28(m, 1H); LCMS (electrospray) m/z 387.0 (M + H)+. | B |

TABLE 1-continued

Compounds of Examples

| Ex # | Structure/Name | ¹H NMR/MS (M + 1) | Method |
|---|---|---|---|
| 31 | (1S,2S)-N-(6-(5-(2-(dimethylamino)ethoxy)-1H-indazol-4-yl)benzo[d]thiazol-2-yl)-2-fluorocyclopropane-1-carboxamide. 3 HCl | ¹H NMR (400 MHz, DMSO-d$_6$) 12.85(s, 1H), 12.76(s, 1H), 8.19 (s, 1H), 7.81-7.78 (m, 2H), 7.68 (d, J = 9.2 Hz, 1H), 7.56 (d, J = 8.6 Hz, 1H), 7.34 (d, J = 8.6 Hz, 1H), 5.16-4.95 (m, 1H), 4.26 (t, J = 4.4 Hz, 2H), 3.32 (t, J = 4.4 Hz, 2H), 2.45 (s, 6H), 2.28-2.21(m, 1H), 1.78-1.68 (m, 1H), 1.38-1.28(m, 1H); LCMS (electrospray) m/z 440.10 (M + H)+. | B |
| 32 | N-(6-(5-methyl-1H-indazol-4-yl)benzo[d]thiazol-2-yl)cyclopropanecarbothioamide | ¹H NMR (400 MHz, DMSO-d$_6$) δ 14.14 (s, NH), 13.08 (s, NH), 8.12 (s, 1H), 7.94-7.92 (m, 1H), 7.65 (s, 1H), 7.55 (dd, J12 = 1.6 Hz, J13 = 8.4 Hz, 1H), 7.47 (d, J = 8.4 Hz, 1H), 7.32 (d, J = 8.8 Hz, 1H), 2.75 (m, 1H), 2.31 (s, 3H), 1.21-1.17 (m, 4H); LCMS (electrospray) m/z 365.0 (M + H)+. | A |
| 33 | (1S,2S)-N-(6-(5-(difluoromethyl)-1H-indazol-4-yl)benzo[d]thiazol-2-yl)-2-fluorocyclopropane-1-carboxamide | ¹H NMR (400 MHz, DMSO-d$_6$) δ 13.50(s, 1H), 12.85(s, 1H), 8.11(s, 1H), 7.91(d, J = 8.4 Hz, 2H), 7.85(s, 1H), 7.72(d, J = 4.0 Hz, 2H), 7.50(d, J = 8.8 Hz, 1H), 6.82(t, J = 55.2 Hz, 1H), 5.14-4.98(m, 1H), 2.25-2.22(m, 1H), 1.82-1.72(m, 1H), 1.37-1.30(m, 1H); 19F NMR (400 MHz, DMSO-d6) δ −102.50(d, J = 56.8 Hz, 1H), −103.08(d, J = 56.8 Hz, 1H), 219.66-219.92(m, 1H); LCMS (electrospray) m/z = 403.0 (M + H+) | B |
| 34 | (1S,2S)-2-fluoro-N-(6-(5-(2-methoxyethoxy)-1H-indazol-4-yl) benzo[d]thiazol-2-yl)cyclopropane-1-carboxamide. 2 HCl | ¹H NMR (400 MHz, DMSO-d$_6$) 12.85(s, 1H), 12.77(s, 1H), 8.21 (s, 1H), 7.86 (s, 1H), 7.83 (d, J = 8.4 Hz, 1H), 7.68 (d, J = 8.4 Hz, 1H), 7.52 (d, J = 9.2 Hz, 1H), 7.32 (d, J = 9.2 Hz, 1H), 5.13-4.96 (m, 1H), 4.08 (t, J = 4.6 Hz, 2H), 3.53 (t, J = 4.4 Hz, 2H), 3.21 (s, 3H), 2.29-2.22(m, 1H), 1.80-1.70 (m, 1H), 1.36-1.27(m, 1H); LCMS (electrospray) m/z 427.10 (M + H)+. | B |

TABLE 1-continued

Compounds of Examples

| Ex # | Structure/Name | ¹H NMR/MS (M + 1) | Method |
|---|---|---|---|
| 35 | 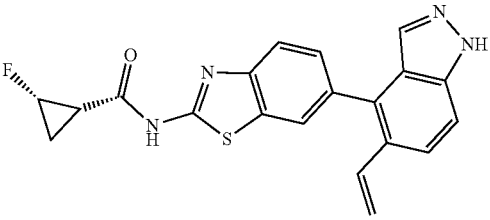<br>(1S,2S)-2-fluoro-N-(6-(5-vinyl-1H-indazol-4-yl)benzo[d]thiazol-2-yl)cyclopropane-1-carboxamide | ¹H NMR (400 MHz, DMSO-$d_6$) δ 13.22(s, 1H), 12.78(s, 1H), 8.02(d, J = 1.6 Hz, 1H), 7.86(d, J = 8.0 Hz, 1H), 7.77(d, J = 8.8 Hz, 1H), 7.70(s, 1H), 7.55(d, J = 8.8 Hz, 1H), 7.43(dd, J = 8.4 Hz, J = 2.0 Hz, 1H), 6.69(dd, J = 17.6 Hz, J = 10.8 Hz, 1H), 5.76(d, J = 16.4 Hz, 1H), 5.16(d, J = 12.0 hz, 1H), 5.13-4.94(m, 1H), 2.24-2.20(m, 1H), 1.72-1.71(m, 1H), 1.35-1.28(m, 1H); LCMS (electrospray) m/z = 379.1 (M + H+) | B |
| 36 | 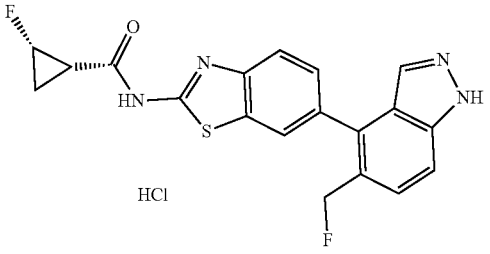<br>(1S,2S)-2-fluoro-N-(6-(5-(fluoromethyl)-1H-indazol-4-yl)benzo[d]thiazol-2-yl)cyclopropane-1-carboxamide. 2 HCl | ¹H NMR (400 MHz, DMSO-$d_6$) δ 12.77(s, 1H), 8.13(dd, J = 4.4 Hz, 1.6 Hz, 1H), 7.92(dd, J = 8.4 Hz, 6.4 Hz, 1H), 7.88(d, J = 7.6 Hz, 1H), 7.64-7.54(m, 3H), 5.10-4.92(m, 1H), 5.39-5.27(m, 1H), 4.73-4.60(m, 1H), 2.22-2.21(m, 1H), 1.69-1.68(m, 1H), 1.30-1.25(m, 1H); LCMS (electrospray) m/z = 383.1. (M + H+) | B |
| 37 | 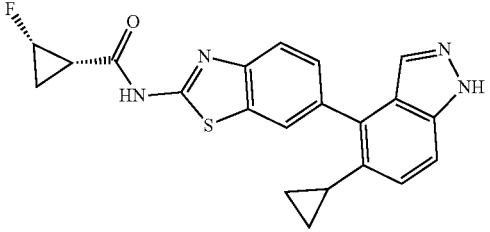 [SMILES: O=C(Nc1nc2ccc(-c3c(C4CC4)ccc4[nH]ncc34)cc2s1)[C@@H]1C[C@@H]1F]<br>(1S,2S)-N-(6-(5-cyclopropyl-1H-indazol-4-yl)benzo[d]thiazol-2-yl)-2-fluorocyclopropane-1-carboxamide | ¹H NMR (400 MHz, DMSO-$d_6$) δ 13.01(s, 1H), 12.74(s, 1H), 8.07(s, 1H), 7.83(dd, J = 8.4 Hz, 1H), 7.58(s, 1H), 7.51(d, J = 8.0 Hz, 1H), 7.41(d, J = 8.8 Hz, 1H), 6.95(dd, J = 8.4 Hz, 1.2 Hz, 1H), 5.10-4.92(m, 1H), 2.21-2.17(m, 1H), 1.94-1.90(m, 1H), 1.74-1.69(m, 1H), 1.30-1.11(m, 1H), 0.82-0.75(m, 1H), 0.60-0.59(m, 1H); LCMS (electrospray) m/z = 393.1 (M + H+) | B |
| 38 | 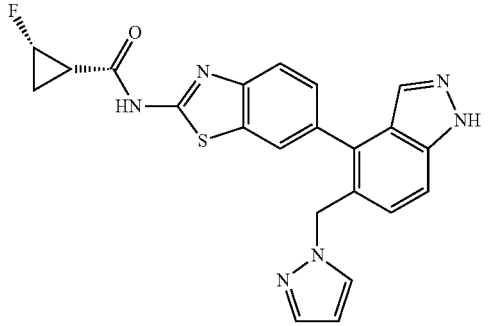<br>(1S,2S)-N-(6-(5-((1H-pyrazol-1-yl)methyl)-1H-indazol-4-yl)benzo[d]thiazol-2-yl)-2-fluorocyclopropane-1-carboxamide | ¹H NMR (400 MHz, DMSO-$d_6$) δ 12.79(s, 1H), 8.06(d, J = 2.0 Hz, 1H), 7.84(d, J = 8.0 Hz, 1H), 7.67(s, 1H), 7.55-7.53(m, 2H), 7.48(d, J = 8.8 Hz, 1H), 7.39(d, J = 1.2 Hz, 1H), 7.16(d, J = 8.8 Hz, 1H), 6.18-6.17(m, 1H), 5.29(s, 2H), 5.10-4.93(m, 1H), 2.23-2.20(m, 1H), 1.76-1.68(m, 1H), 1.31-1.27(m, 1H); LCMS (electrospray) m/z = 433.1 (M + H+) | B |

TABLE 1-continued

Compounds of Examples

| Ex # | Structure/Name | $^1$H NMR/MS (M + 1) | Method |
|---|---|---|---|
| 39 | 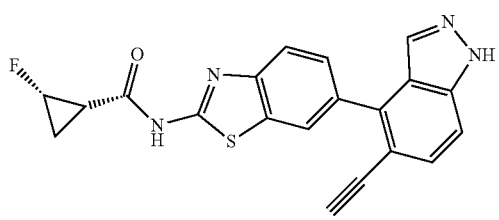<br>(1S,2S)-N-(6-(5-ethynyl-1H-indazol-4-yl)benzo[d]thiazol-2-yl)-2-fluorocyclopropane-1-carboxamide | $^1$H NMR (400 MHz, DMSO-d$_6$) δ 13.35(s, 1H), 12.77(s, 1H), 8.20(d, J = 2.0 Hz, 1H), 7.87(s, 1H), 7.83(d, J = 8.4 Hz, 1H), 7.66(dd, J = 8.4 Hz, 1.6 Hz, 1H), 7.51(d, J = 3.2 Hz, 1H), 5.12-4.91(m, 1H), 3.91(s, 1H), 2.21-2.18(m, 1H), 1.75-1.68(m, 1H), 1.29-1.23(m, 1H); LCMS (electrospray) m/z = 377.1 (M + H+) | B |
| 40 | 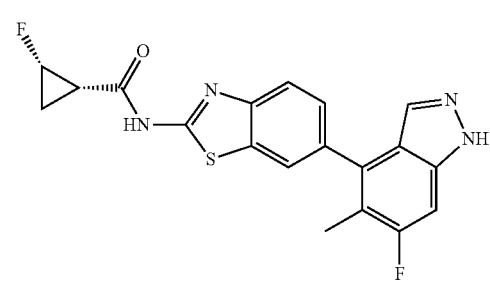 [SMILES: Cc1c(F)cc2[nH]ncc2c1-c1ccc2nc(NC(=O)[C@@H]3C[C@@H]3F)sc2c1]<br>(1S,2S)-2-fluoro-N-(6-(6-fluoro-5-methyl-1H-indazol-4-yl)benzo[d]thiazol-2-yl)cyclopropane-1-carboxamide | $^1$H NMR (400 MHz, DMSO-d$_6$) δ 13.15 (s, NH), 12.80 (s, NH), 8.09 (s, 1H), 7.88 (d, J = 8.0 Hz, 1H), 7.67 (s, 1H), 7.50 (d, J = 8.0 Hz, 1H), 7.35 (d, J = 9.6 Hz, 1H), 4.96-5.15 (m, 1H), 2.25-2.22 (m, 1H), 2.18 (s, 3H), 1.79-1.72 (m, 1H), 1.33-1.31 (m, 1H); LCMS (electrospray) m/z 385.1 (M + H)+. | B |
| 41 | 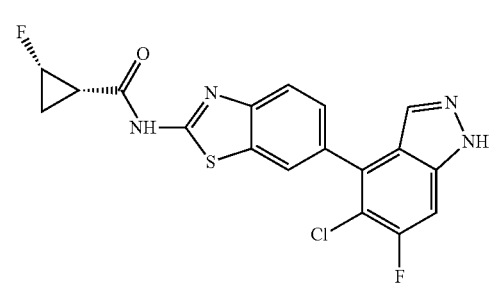 [SMILES: O=C(Nc1nc2ccc(-c3c(Cl)c(F)cc4[nH]ncc34)cc2s1)[C@@H]1C[C@@H]1F]<br>(1S,2S)-N-(6-(5-chloro-6-fluoro-1H-indazol-4-yl)benzo[d]thiazol-2-yl)-2-fluorocyclopropane-1-carboxamide | $^1$H NMR (400 MHz, DMSO-d$_6$) δ 13.15 (s, NH), 12.80 (s, NH), 8.09 (s, 1H), 7.88 (d, J = 8.0 Hz, 1H), 7.67 (s, 1H), 7.50 (d, J = 8.0 Hz, 1H), 7.35 (d, J = 9.6 Hz, 1H), 4.96-5.15 (m, 1H), 2.25-2.22 (m, 1H), 2.18 (s, 3H), 1.79-1.72 (m, 1H), 1.33-1.31 (m, 1H); LCMS (electrospray) m/z 385.1 (M + H)+. | B |
| 42 | 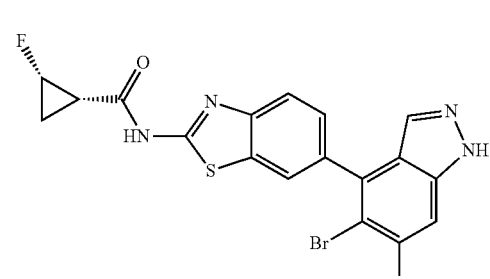<br>(1S,2S)-N-(6-(5-bromo-6-fluoro-1H-indazol-4-yl)benzo[d]thiazol-2-yl)-2-fluorocyclopropane-1-carboxamide | $^1$H NMR (400 MHz, DMSO-d$_6$) δ 13.46 (s, NH), 12.83 (s, NH), 8.19 (s, 1H), 7.90 (d, J = 8.4 Hz, 1H), 7.80 (s, 1H), 7.64 (d, J = 8.8 Hz, 1H), 5.16-4.95 (m, 1H), 2.28-2.21 (m, 1H), 1.79-1.72 (m, 1H), 1.35-1.28 (m, 1H); LCMS (electrospray) m/z = 405.0 (M + H+) | B |

TABLE 1-continued

Compounds of Examples

| Ex # | Structure/Name | ¹H NMR/MS (M + 1) | Method |
|---|---|---|---|
| 43 | 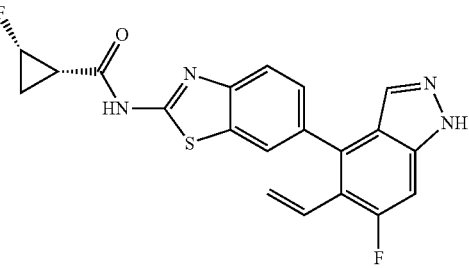<br>(1S,2S)-2-fluoro-N-(6-(6-fluoro-5-vinyl-1H-indazol-4-yl)benzo[d]thiazol-2-yl)cyclopropane-1-carboxamide | ¹H NMR (400 MHz, DMSO-$d_6$) δ 13.59 (s, NH), 12.79 (s, NH), 8.05 (s, 1H), 7.87 (d, J = 8.0 Hz, 1H), 7.71 s, 1H), 7.46-7.40 (m, 2H), 6.48 (dd, J12 = 11.8 Hz, J13 = 17.8 Hz, 1H), 5.35 (dd, J12 = 2.6 Hz, J13 = 14.2 Hz, 1H), 5.16-4.95 (m, 1H), 2.26-2.21 (m, 1H), 1.79-1.72 (m, 1H), 1.35-1.29 (m, 1H); LCMS (electrospray) m/z 449.0 (M + H)+. | B |
| 44 | 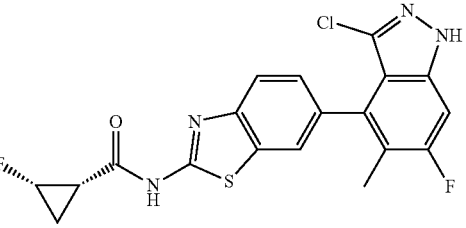<br>(1S,2S)-N-(6-(3-chloro-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 13.34 (s, 1H), 12.77 (d, J = 3.2 Hz, 1H), 7.88 (d, J = 1.6 Hz, 1H), 7.80 (d, J = 8.4 Hz, 1H), 7.38 (d, J = 9.6 Hz, 1H), 7.30 (dd, J = 2.0, 6.4 Hz, 1H), 5.10 (m, 0.5H), 4.93 (m, 0.5H), 2.20 (m, 1H), 2.00 (m, 3H), 1.71 (m, 1H), 1.28 (m, 1H), LCMS (electrospray) m/z 419.05 (M + H)+. | B |
| 45 | 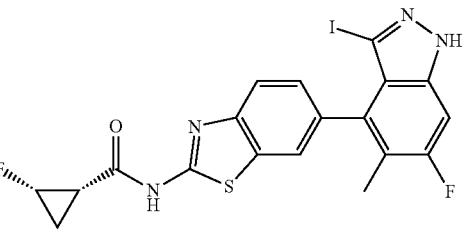<br>(1S,2S)-2-fluoro-N-(6-(6-fluoro-3-iodo-5-methyl-1H-indazol-4-yl)benzo[d]thiazol-2-yl)cyclopropane-1-carboxamide | ¹H NMR (400 MHz, DMSO-$d_6$) δ 13.55 (s, 1H), 12.79 (d, J = 3.6 Hz, 1H), 7.87 (d, J = 2.0 Hz, 1H), 7.86 (d, J = 7.6 Hz, 1H), 7.41 (d, J = 10.0 Hz, 1H), 7.28 (dd, J = 1.6 Hz, 1H), 5.14 (m, 0.5H), 4.97 (m, 0.5H), 2.23 (m, 1H), 2.00 (m, 3H), 1.76 (m, 1H), 1.31 (m, 1H), LCMS (electrospray) m/z 511.00 (M + H)+. | B |
| 46 | 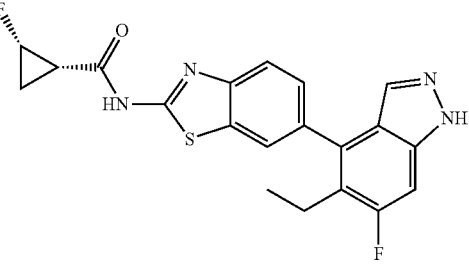<br>(1S,2S)-N-(6-(5-ethyl-6-fluoro-1H-indazol-4-yl)benzo[d]thiazol-2-yl)-2-fluorocyclopropane-1-carboxamide | ¹H NMR (400 MHz, DMSO-$d_6$) δ 13.15 (s, NH), 12.80 (s, NH), 8.04 (s, 1H), 7.87 (d, J = 8.0 Hz, 1H), 7.56 (s, 1H), 7.44 (d, J = 8.4 Hz, 1H), 5.15-4.96 (m, 1H), 2.58-2.54 (m, 2H), 2.25-2.22 (m, 1H), 1.78-1.72 (m, 1H), 1.33-1.30 (m, 1H), 1.06 (t, 3H); LCMS (electrospray) m/z 399.1 (M + H)+. | B |

TABLE 1-continued

Compounds of Examples

| Ex # | Structure/Name | ¹H NMR/MS (M + 1) | Method |
|---|---|---|---|
| 47 | 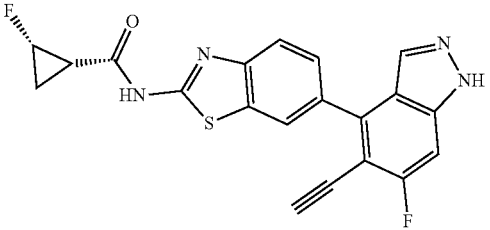<br>(1S,2S)-N-(6-(5-ethynyl-6-fluoro-1H-indazol-4-yl)benzo[d]thiazol-2-yl)-2-fluorocyclopropane-1-carboxamide | ¹H NMR (400 MHz, DMSO-$d_6$) δ 13.41(s, 1H), 12.78(s, 1H), 8.23(d, J = 1.6 Hz, 1H), 7.89(s, 1H), 7.84(d, J = 8.4 Hz, 1H), 7.67(d, J = 8.4 Hz, 1H), 7.46(d, J = 9.6 Hz, 1H), 5.11-4.92(m, 1H), 4.19(s, 1H), 2.21-2.18(m, 1H), 1.77-1.67(m, 1H), 1.33-1.25(m, 1H); LCMS (electrospray) m/z 395.1 (M + H+) | B |
| 48 | 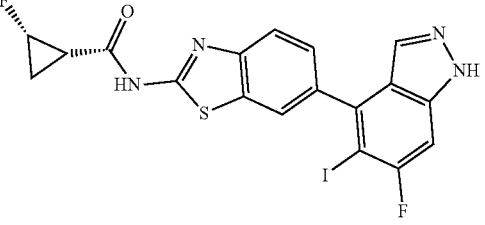<br>(1S,2S)-2-fluoro-N-(6-(6-fluoro-5-iodo-1H-indazol-4-yl)benzo[d]thiazol-2-yl)cyclopropane-1-carboxamide | ¹H NMR (400 MHz, DMSO-$d_6$) δ 13.34(s, 1H), 12.77(s, 1H), 8.01(d, J = 2.0 Hz, 1H), 7.84(d, J = 8.4 Hz, 1H), 7.60(s, 1H), 7.45(d, J = 8.4 Hz, 1H), 7.41(dd, J = 8.4 Hz, J = 1.2 Hz, 1H), 5.12-4.92(m, 1H), 2.21-2.19(m, 1H), 1.76-1.69(m, 1H), 1.31-1.26(m, 1H); LCMS (electrospray) m/z 497.0 (M + H+) | B |
| 49 | 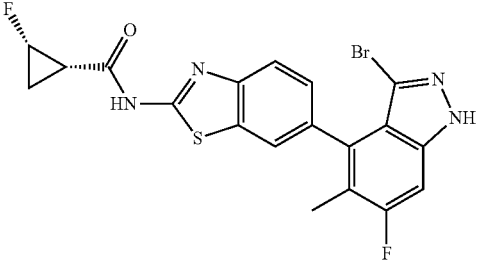 [SMILES: Cc1c(F)cc2[nH]nc(Br)c2c1-c1ccc2nc(NC(=O)[C@@H]3C[C@@H]3F)sc2c1]<br>(1S,2S)-N-(6-(3-bromo-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 13.49 (s, 1H), 12.78 (d, J = 3.6 Hz, 1H), 7.89 (d, J = 1.6 Hz, 1H), 7.84 (d, J = 8.4 Hz, 1H), 7.43 (d, J = 10 Hz, 1H), 7.31 (dd, J = 1.6, 6.8 Hz, 1H), 5.14 (m, 0.5H), 4.95 (m, 0.5H), 2.24 (m, 1H), 2.02 (t, J = 2.4 Hz, 3H), 1.75 (m, 1H), 1.31 (m, 1H); LCMS (electrospray) m/z 464.00 (M + H)+. | B |
| 50 | 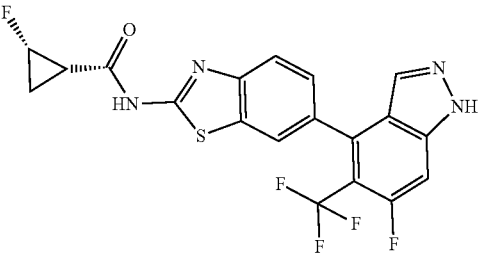<br>(1S,2S)-2-fluoro-N-(6-(6-fluoro-5-(trifluoromethyl)-1H-indazol-4-yl)benzo[d]thiazol-2-yl)cyclopropane-1-carboxamide | ¹H NMR (400 MHz, DMSO-$d_6$) δ 13.67(s, 1H), 12.82(s, 1H), 8.03(s, 1H), 7.82(d, J = 8.4 Hz, 1H), 7.66-7.64(m, 1H), 7.41(d, J = 8.4 Hz, 1H), 5.15-4.95(m, 1H), 2.26-2.23(m, 1H), 1.79-1.72(m, 1H), 1.34-1.28(m, 1H); LCMS (electrospray) LCMS: m/z 439.1 (M + H+) | B |

TABLE 1-continued

Compounds of Examples

| Ex # | Structure/Name | ¹H NMR/MS (M + 1) | Method |
|---|---|---|---|
| 51 | 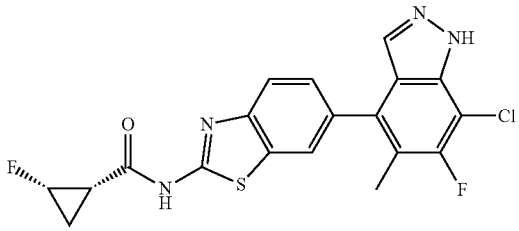 [SMILES: Cc1c(F)c(Cl)c2[nH]ncc2c1-c1ccc2nc(NC(=O)[C@@H]3C[C@@H]3F)sc2c1]<br>(1S,2S)-N-(6-(7-chloro-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 13.75 (s, 1H), 12.82 (s, 1H), 8.09 (d, J = 1.6 Hz, 1H), 7.88 (d, J = 8.4 Hz, 1H), 7.79 (brs, 1H), 7.50 (dd, J = 1.6, 6.4 Hz, 1H), 5.14 (m, 0.5H), 4.97 (m, 0.5H), 2.23 (m, 4H), 1.76 (m, 1H), 1.32 (m, 1H); LCMS (electrospray) m/z 419.00 (M + H)+. | B |
| 52 | 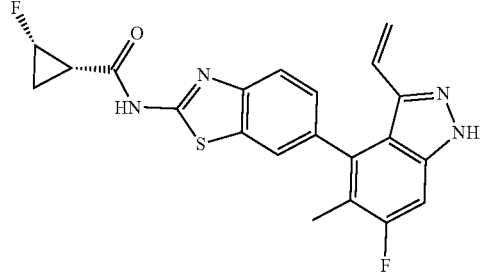 [SMILES: C=Cc1n[nH]c2cc(F)c(C)c(-c3ccc4nc(NC(=O)[C@@H]5C[C@@H]5F)sc4c3)c12]<br>(1S,2S)-2-fluoro-N-(6-(6-fluoro-5-methyl-3-vinyl-1H-indazol-4-yl)benzo[d]thiazol-2-yl)cyclopropane-1-carboxamide | ¹H NMR (400 MHz, DMSO-$d_6$) δ 13.16 (s, 1H), 12.81 (s, 1H), 7.91 (d, J = 1.6 Hz, 1H), 7.87 (d, J = 8.4 Hz, 1H), 7.33 (m, 2H), 5.73 (m, 1H), 5.59 (m, 1H), 5.14 (m, 0.5H), 4.97 (m, 0.5H), 4.84 (m, 1H), 2.25 (m, 1H), 2.01 (t, J = 2.4 Hz, 3H) 1.76 (m, 1H), 1.32 (m, 1H); LCMS (electrospray) m/z 411.10 (M + H)+. | B |
| 53 | 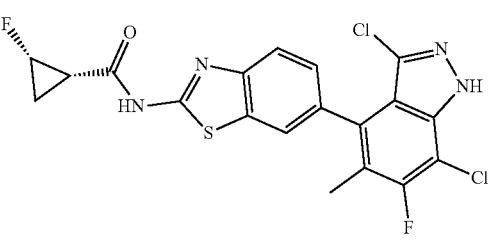 [SMILES: Cc1c(F)c(Cl)c2[nH]nc(Cl)c2c1-c1ccc2nc(NC(=O)[C@@H]3C[C@@H]3F)sc2c1]<br>(1S,2S)-N-(6-(3,7-dichloro-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 14.00(s, 1H), 12.80(s, 1H), 7.92(d, J = 1.2 Hz, 1H), 7.84(d, J = 8.4 Hz, 1H), 7.34(dd, J = 8.4 Hz, J = 1.6 Hz, 1H), 5.15-4.97(m, 1H), 2.26-2.24(m, 1H), 2.08(s, 3H), 1.79-1.76(m, 1H), 1.32-1.27(m, 1H); LCMS (electrospray) m/z 454.0 (M + H+) | B |
| 54 | 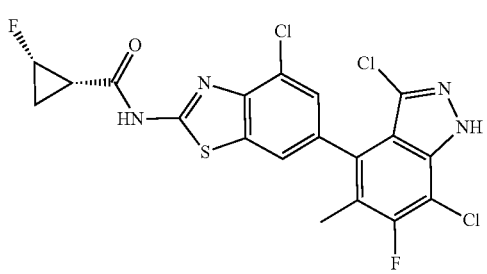 [SMILES: Cc1c(F)c(Cl)c2[nH]nc(Cl)c2c1-c1cc(Cl)c2nc(NC(=O)[C@@H]3C[C@@H]3F)sc2c1]<br>(1S,2S)-N-(4-chloro-6-(3,7-dichloro-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 14.03(s, 1H), 13.21(s, 1H), 7.94(d, J = 1.6 Hz, 1H), 7.50(d, J = 1.6 Hz, 1H), 5.14-4.95(m, 1H), 2.25-2.22(m, 1H), 2.09(s, 3H), 1.80-1.70(m, 1H), 1.36-1.29(m, 1H); LCMS (electrospray) m/z 487.0 (M + H+) | B |

TABLE 1-continued

Compounds of Examples

| Ex # | Structure/Name | ¹H NMR/MS (M + 1) | Method |
|---|---|---|---|
| 55 | 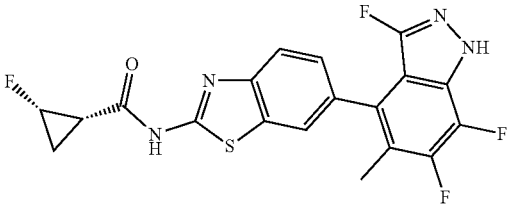 [SMILES: Cc1c(F)c(F)c2[nH]nc(F)c2c1-c1ccc2nc(NC(=O)[C@@H]3C[C@@H]3F)sc2c1]<br>(1S,2S)-2-fluoro-N-(6-(3,6,7-trifluoro-5-methyl-1H-indazol-4-yl)benzo[d]thiazol-2-yl)cyclopropane-1-carboxamide | ¹H NMR (400 MHz, DMSO-$d_6$) δ 13.33(s, 1H), 12.80(s, 1H), 8.06(s, 1H), 7.84(d, J = 8.0 Hz, 1H), 7.43-7.41(m, 1H), 5.13-4.97(m, 1H), 2.23-2.20(m, 1H), 2.16(s, 3H), 1.77-1.72(m, 1H), 1.44-1.41(m, 1H); LCMS (electrospray): m/z 421.0 (M + H+) | B |
| 56 | 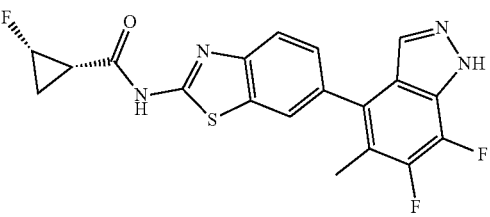 [SMILES: Cc1c(F)c(F)c2[nH]ncc2c1-c1ccc2nc(NC(=O)[C@@H]3C[C@@H]3F)sc2c1]<br>(1S,2S)-N-(6-(6,7-difluoro-5-methyl-1H-indazol-4-yl)benzo[d]thiazol-2-yl)-2-fluorocyclopropane-1-carboxamide | ¹H NMR (400 MHz, DMSO-$d_6$) δ 12.78 (s, 1H), 12.60 (s, 1H), 8.09 (s, 1H), 8.06 (s, 1H), 7.84 (d, J = 8.0 Hz, 1H), 7.43-7.41 (m, 1H), 5.13-4.97 (m, 1H), 2.23-2.20 (m, 1H), 2.16 (s, 3H), 1.77-1.72 (m, 1H), 1.44-1.41 (m, 1H); LCMS (electrospray): m/z 403.0 (M + H)+. | B |
| 57 | 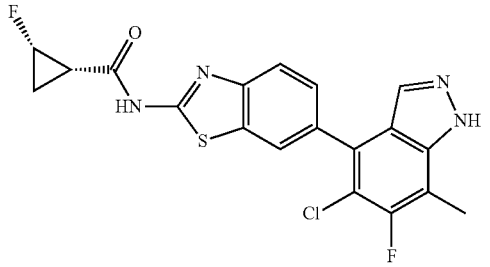 [SMILES: Cc1c(F)c(Cl)c(-c2ccc3nc(NC(=O)[C@@H]4C[C@@H]4F)sc3c2)c2cn[nH]c12]<br>(1S,2S)-N-(6-(5-chloro-6-fluoro-7-methyl-1H-indazol-4-yl)benzo[d]thiazol-2-yl)-2-fluorocyclopropane-1-carboxamide | ¹H NMR (400 MHz, DMSO-$d_6$) δ 13.59 (s, 1H), 12.81 (s, 1H), 8.15 (s, 1H), 7.88 (d, J = 8.0 Hz, 1H), 7.82 (s, 1H), 7.34 (dd, J = 8.4 Hz, J = 1.6 Hz, 1H), 5.18-5.12 (m, 0.5H), 5.01-4.96 (m, 0.5H), 2.50 (t, J = 1.6 Hz, 3H), 2.29-2.21 (m, 1H), 1.85-1.72 (m, 1H), 1.38-1.29 (m, 1H); LCMS (electrospray) m/z 419.0 (M + H)+. | B |
| 58 | 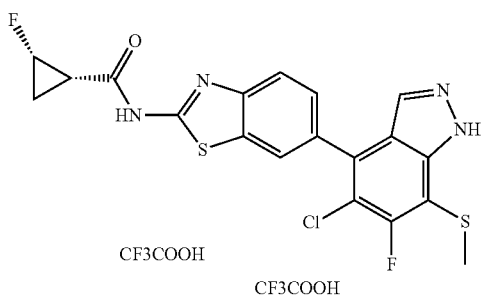 [SMILES: CSc1c(F)c(Cl)c(-c2ccc3nc(NC(=O)[C@@H]4C[C@@H]4F)sc3c2)c2cn[nH]c12 ; "CF3COOH" ; "CF3COOH"]<br>(1S,2S)-N-(6-(5-chloro-6-fluoro-7-(methylthio)-1H-indazol-4-yl)benzo[d]thiazol-2-yl)-2-fluorocyclopropane-1-carboxamide. 2 TFA | ¹H NMR (400 MHz, DMSO-$d_6$) δ 13.76 (br s, 1H), 12.82 (br s, 1H), 8.19 (d, J = 1.7 Hz, 1H), 7.96-7.82 (m, 2H), 7.59 (dd, J = 1.8, 8.4 Hz, 1H), 5.26-4.85 (m, 1H), 2.57 (s, 3H), 2.30-2.19 (m, 1H), 1.84-1.69 (m, 1H), 1.33 (tdd, J = 6.4, 9.0, 12.9 Hz, 1H); LCMS (electrospray) m/z 450.8 (M + H)+. | B |

TABLE 1-continued

Compounds of Examples

| Ex # | Structure/Name | ¹H NMR/MS (M + 1) | Method |
|------|----------------|-------------------|--------|
| 59 | 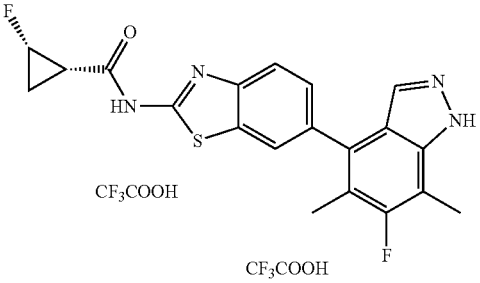 [SMILES: Cc1c(F)c(C)c2[nH]ncc2c1-c1ccc2nc(NC(=O)[C@@H]3C[C@@H]3F)sc2c1 ; "CF3COOH" ; "CF3COOH"]<br>CF₃COOH<br><br>(1S,2S)-2-fluoro-N-(6-(6-fluoro-5,7-dimethyl-1H-indazol-4-yl)benzo[d]thiazol-2-yl)cyclopropane-1-carboxamide. 2 TFA | ¹H NMR (400 MHz, DMSO-d₆) δ 13.36 (s, 1H), 12.77 (br s, 1H), 8.04 (s, 1H), 7.87 (dd, J12 = 4.8 Hz, J13 = 8.4 Hz, 1H), 7.66 (s, 1H), 7.45 (d, J = 7,6 Hz, 1H), 5.14-4.95 (m, 1H), 2.49 (d, J = 1.7 Hz, 3H), 2.21 (d, J = 2.8 Hz, 3H), 2.18-2.10 (m, 1H), 1.75-1.61 (m, 1H), 1.27-1.10 (m, 1H); LCMS (electrospray) m/z 399.1 (M + H)+. | B |
| 60 | 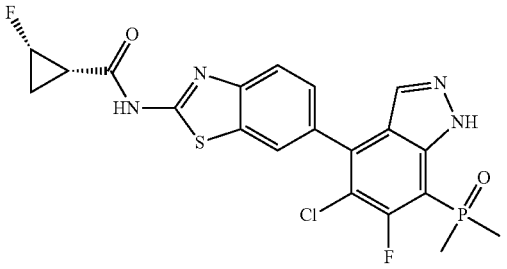 [SMILES: CP(C)(=O)c1c(F)c(Cl)c(-c2ccc3nc(NC(=O)[C@@H]4C[C@@H]4F)sc3c2)c2cn[nH]c12]<br><br>(1S,2S)-N-(6-(5-chloro-7-(dimethylphosphoryl)-6-fluoro-1H-indazol-4-yl)benzo[d]thiazol-2-yl)-2-fluorocyclopropane-1-carboxamide | ¹H NMR (400 MHz, DMSO-d₆) δ 12.87 (s, 1H), 12.85 (s, 1H), 8.22 (s, 1H), 7.88 (m, 2H), 7.60 (dd, J12 = 1.8 Hz, J13 = 8.2 Hz, 1H), 5.13-4.97 (m, 1H), 2.28-2.21 (m, 1H), 1.95 (s, 3H), 1.92 (s, 3H), 1.81-1.71 (m, 1H), 1.37-1.28 (m, 1H); LCMS (electrospray) m/z 481.1 (M + H)+. | B |
| 61 | 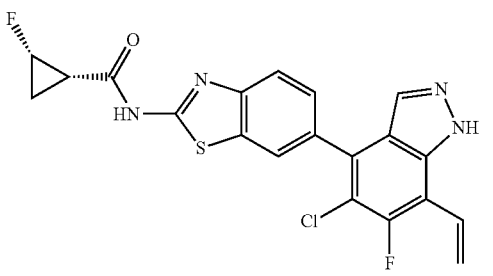 [SMILES: C=Cc1c(F)c(Cl)c(-c2ccc3nc(NC(=O)[C@@H]4C[C@@H]4F)sc3c2)c2cn[nH]c12]<br><br>(1S,2S)-N-(6-(5-chloro-6-fluoro-7-vinyl-1H-indazol-4-yl)benzo[d]thiazol-2-yl)-2-fluorocyclopropane-1-carboxamide | ¹H NMR (400 MHz, DMSO-d₆) δ 13.70 (s, 1H), 12.82 (s, 1H), 8.19 (d, J = 2.0 Hz, 1H), 7.90 (d, J = 8.4 Hz, 2H), 7.59 (dd, J = 6.8 Hz, J = 2.0 Hz, 1H), 7.10 (q, J = 12.4 Hz, 1H), 6.22 (brs, 1H), 5.81 (d, J = 11.6 Hz, 1H), 5.16-5.12 (m, 0.5H), 4.99-4.96 (m, 0.5H), 2.28-2.21 (m, 1H), 1.81-1.71 (m, 1H), 1.37-1.28 (m, 1H); LCMS (electrospray) m/z 431.0 (M + H)+. | B |
| 62 | 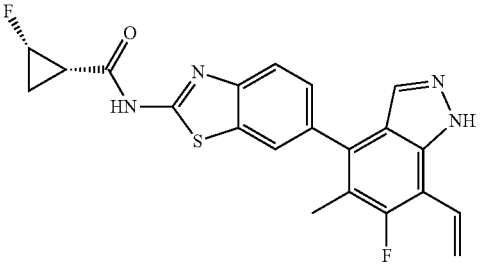 [SMILES: C=Cc1c(F)c(C)c(-c2ccc3nc(NC(=O)[C@@H]4C[C@@H]4F)sc3c2)c2cn[nH]c12]<br><br>(1S,2S)-2-fluoro-N-(6-(6-fluoro-5-methyl-7-vinyl-1H-indazol-4-yl)benzo[d]thiazol-2-yl)cyclopropane-1-carboxamide | ¹H NMR (400 MHz, DMSO-d₆) δ 13.37 (s, 1H), 12.79 (s, 1H), 8.08 (s, 1H), 7.88 (d, J = 8.4 Hz, 1H), 7.49 (d, J = 8.0 Hz, 1H), 7.11-7.09 (m, 1H), 6.16 (d, J = 18.4 Hz, 1H), 5.70 (d, J = 12.0 Hz, 1H), 5.14-4.97 (m, 1H), 2.28-2.21 (m, 1H), 2.20 (s, 3H), 1.81-1.71 (m, 1H), 1.37-1.28 (m, 1H); LCMS (electrospray) m/z 411.1 (M + H)+. | B |

TABLE 1-continued

Compounds of Examples

| Ex # | Structure/Name | ¹H NMR/MS (M + 1) | Method |
|---|---|---|---|
| 63 | 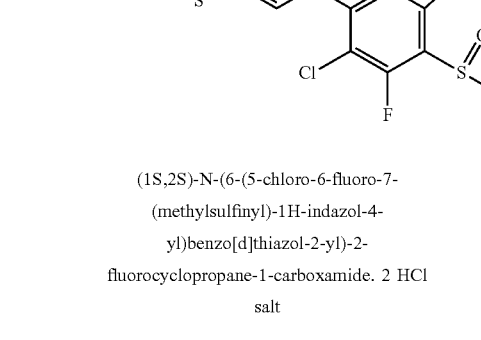<br>(1S,2S)-N-(6-(5-chloro-6-fluoro-7-(methylsulfinyl)-1H-indazol-4-yl)benzo[d]thiazol-2-yl)-2-fluorocyclopropane-1-carboxamide. 2 HCl salt | ¹H NMR (400 MHz, DMSO-$d_6$) δ 12.85 (s, 1H), 8.22 (s, 1H), 7.96-7.89 (m, 2H), 7.49 (d, J = 8.0 Hz, 1H), 7.11-7.09 (m, 1H), 7.60 (d, J = 8.0 Hz, 1H), 5.14-4.97 (m, 1H), 3.19 (s, 3H), 2.28-2.21 (m, 1H), 1.79-1.73 (m, 1H), 1.37-1.28 (m, 1H); LCMS (electrospray) m/z 467.0 (M + H)+. | B |
| 64 | 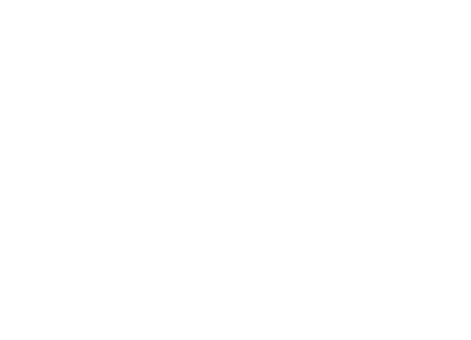<br>(1S,2S)-2-fluoro-N-(6-(6-fluoro-5-methyl-7-(methylthio)-1H-indazol-4-yl)benzo[d]thiazol-2-yl)cyclopropane-1-carboxamide | ¹H NMR (400 MHz, DMSO-$d_6$) δ 12.79 (br s, 1H), 8.08 (s, 1H), 7.87 (d, J = 8.0 Hz, 1H), 7.73 (s, 1H), 7.49 (d, J = 9.6 Hz, 1H), 5.14-4.96 (m, 1H), 3.17 (s, 3H), 2.54 (s, 3H), 2.16 (td, J = 6.9, 13.8 Hz, 1H), 1.74-1.60 (m, 1H), 1.25-1.11 (m, 1H); LCMS (electrospray) m/z 431.0 (M + H)+. | B |
| 65 | 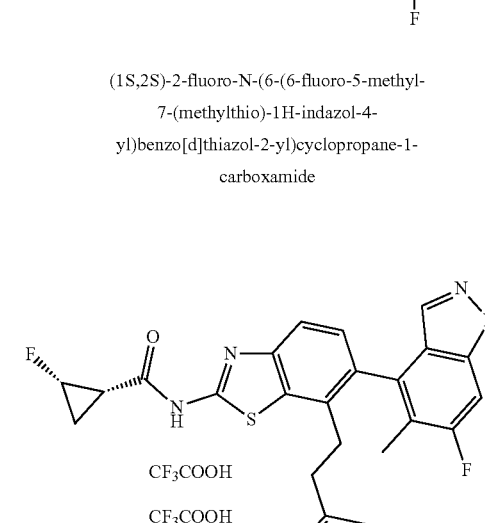<br>(1S,2S)-2-fluoro-N-(6-(6-fluoro-5-methyl-1H-indazol-4-yl)-7-(2-(pyridin-4-yl)ethyl)benzo[d]thiazol-2-yl)cyclopropane-1-carboxamide. 3 TFA | ¹H NMR (400 MHz, METHANOL-$d_4$) δ 8.44-8.32 (m, 2H), 7.84-7.76 (m, 1H), 7.42-7.25 (m, 5H), 5.07-5.01 (m, 1H), 3.27-2.97 (m, 5H), 2.24-2.15 (m, 1H), 2.06 (br d, J = 2.2 Hz, 3H), 1.96-1.81 (m, 1H), 1.38-1.28 (m, 1H); LCMS (electrospray) m/z 490.2 (M + H)+. | B |

TABLE 1-continued

Compounds of Examples

| Ex # | Structure/Name | $^1$H NMR/MS (M + 1) | Method |
|---|---|---|---|
| 66 | 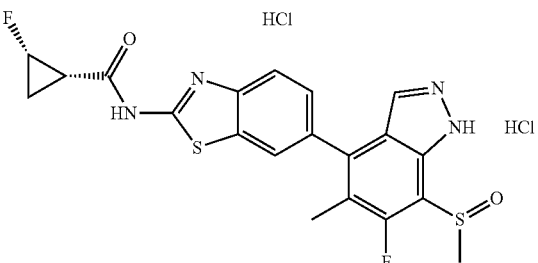<br>(1S,2S)-2-fluoro-N-(6-(6-fluoro-5-methyl-7-(methylsulfinyl)-1H-indazol-4-yl)benzo[d]thiazol-2-yl)cyclopropane-1-carboxamide. 2 HCl | $^1$H NMR (400 MHz, DMSO-$d_6$) δ 13.36 (br s, 1H), 12.81 (s, 1H), 8.12 (s, 1H), 7.90 (d, J = 8.4 Hz, 1H), 7.51 (d, J = 8.4 Hz, 1H), 5.14-4.96 (m, 1H), 3.13 (s, 3H), 2.32 (s, 3H), 2.16 (td, J = 6.9, 13.8 Hz, 1H), 1.74-1.60 (m, 1H), 1.25-1.11 (m, 1H); LCMS (electrospray) m/z 447.1 (M + H)+. | B |
| 67 | 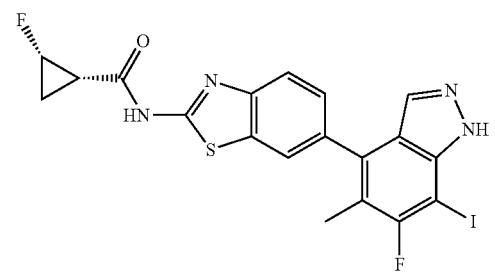 [SMILES: Cc1c(F)c(I)c2[nH]ncc2c1-c1ccc2nc(NC(=O)[C@@H]3C[C@@H]3F)sc2c1]<br>(1S,2S)-2-fluoro-N-(6-(6-fluoro-7-iodo-5-methyl-1H-indazol-4-yl)benzo[d]thiazol-2-yl)cyclopropane-1-carboxamide | $^1$H NMR (400 MHz, DMSO-$d_6$) δ 13.35 (s, 1H), 12.79 (s, 1H), 8.08 (s, 1H), 7.87 (d, J = 8.4 Hz, 1H), 7.83 (br s, 1H), 7.48 (dd, J = 1.6, 6.8 Hz, 1H), 5.14-4.96 (m, 1H), 2.26-2.18 (m, 4H), 1.82-1.71 (m, 1H), 1.36-1.28 (m, 1H); LCMS (electrospray) m/z 511.00 (M + H)+. | B |
| 68 | 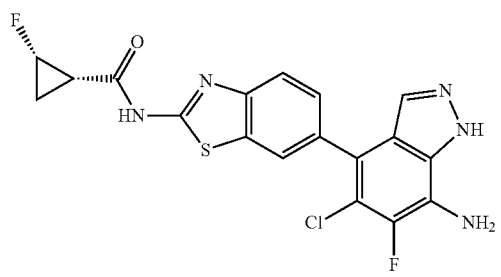 [SMILES: Nc1c(F)c(Cl)c(-c2ccc3nc(NC(=O)[C@@H]4C[C@@H]4F)sc3c2)c2cn[nH]c12]<br>(1S,2S)-N-(6-(7-amino-5-chloro-6-fluoro-1H-indazol-4-yl)benzo[d]thiazol-2-yl)-2-fluorocyclopropane-1-carboxamide | $^1$H NMR (400 MHz, DMSO-$d_6$) δ 12.94 (s, 1H), 12.76 (s, 1H), 8.08 (d, J = 1.6 Hz, 1H), 7.84 (d, J = 8.4 Hz, 1H), 7.71 (s, 1H), 7.52 (dd, J = 2.4, 6.4 Hz, 1H), 5.69 (s, 2H), 5.16-4.94 (m, 1H), 2.27-2.20 (m, 1H), 1.81-1.70 (m, 1H), 1.36-1.27 (m, 1H); LCMS (electrospray) m/z 420.00 (M + H)+. | B |
| 69 | 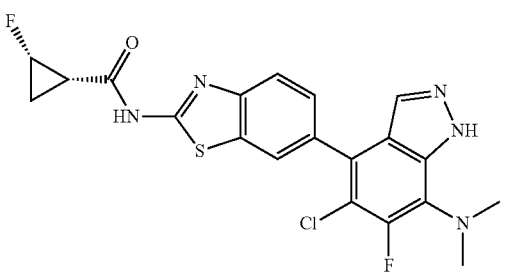 [SMILES: CN(C)c1c(F)c(Cl)c(-c2ccc3nc(NC(=O)[C@@H]4C[C@@H]4F)sc3c2)c2cn[nH]c12]<br>(1S,2S)-N-(6-(5-chloro-7-(dimethylamino)-6-fluoro-1H-indazol-4-yl)benzo[d]thiazol-2-yl)-2-fluorocyclopropane-1-carboxamide | $^1$H NMR (400 MHz, DMSO-$d_6$) δ 13.47 (s, 1H), 12.79 (s, 1H), 8.13 (d, J = 1.6 Hz, 1H), 7.87 (d, J = 8.4 Hz, 1H), 7.76 (s, 1H), 7.55 (dd, J = 1.6, 6.8 Hz, 1H), 5.16-4.95 (m, 1H), 2.99 (s, 6H), 2.28-2.21 (m, 1H), 1.81-1.71 (m, 1H), 1.36-1.28 (m, 1H); LCMS (electrospray) m/z 448.10 (M + H)+. | B |

TABLE 1-continued

Compounds of Examples

| Ex # | Structure/Name | ¹H NMR/MS (M + 1) | Method |
|---|---|---|---|
| 70 | 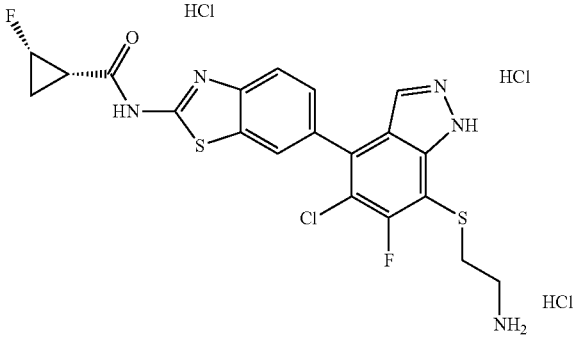 [SMILES: Cl ; NCCSc1c(F)c(Cl)c(-c2ccc3nc(NC(=O)[C@@H]4C[C@@H]4F)sc3c2)c2cn[nH]c12 ; Cl ; Cl](1S,2S)-N-(6-(7-((2-aminoethyl)thio)-5-chloro-6-fluoro-1H-indazol-4-yl)benzo[d]thiazol-2-yl)-2-fluorocyclopropane-1-carboxamide. 3 HCl | ¹H NMR (400 MHz, DMSO-$d_6$) δ 13.70 (br s, 1H), 12.81 (s, 1H), 8.15 (s, 1H), 7.96 (br s, 2H), 7.90-7.86 (m, 2H), 7.55 (d, J = 8.4 Hz, 1H), 5.11-4.92 (m, 1H), 3.14 (m, 2H), 2.88 (m, 2H), 2.16 (td, J = 6.9, 13.8 Hz, 1H), 1.74-1.60 (m, 1H), 1.25-1.11 (m, 1H); LCMS (electrospray) m/z 480.1 (M + H)+. | B |
| 71 | 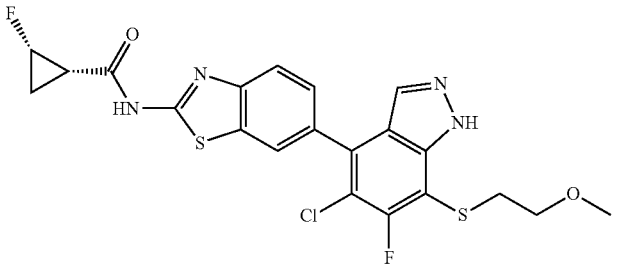 [SMILES: COCCSc1c(F)c(Cl)c(-c2ccc3nc(NC(=O)[C@@H]4C[C@@H]4F)sc3c2)c2cn[nH]c12](1S,2S)-N-(6-(5-chloro-6-fluoro-7-((2-methoxyethyl)thio)-1H-indazol-4-yl)benzo[d]thiazol-2-yl)-2-fluorocyclopropane-1-carboxamide | ¹H NMR (400 MHz, DMSO-$d_6$) δ 13.76 (s, 1H), 12.82 (s, 1H), 8.17 (d, J = 0.8 Hz, 1H), 7.88 (s, 1H), 7.86 (d, J = 8.4 Hz, 1H), 7.58 (dd, J = 1.6, 6.8 Hz, 1H), 5.14-4.94 (m, 1H), 3.50 (t, J = 6.0 Hz, 2H), 3.20 (s, 3H), 3.17 (t, J = 6.4 Hz, 2H), 2.26-2.19 (m, 1H), 1.80-1.70 (m, 1H), 1.35-1.26 (m, 1H); LCMS (electrospray) m/z 495.10 (M + H)+. | B |
| 72 | 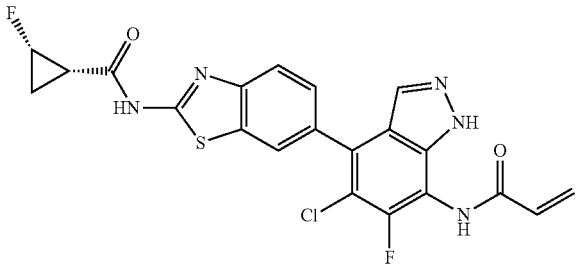 [SMILES: C=CC(=O)Nc1c(F)c(Cl)c(-c2ccc3nc(NC(=O)[C@@H]4C[C@@H]4F)sc3c2)c2cn[nH]c12](1S,2S)-N-(6-(7-acrylamido-5-chloro-6-fluoro-1H-indazol-4-yl)benzo[d]thiazol-2-yl)-2-fluorocyclopropane-1-carboxamide | ¹H NMR (400 MHz, DMSO-$d_6$) δ 13.29 (s, 1H), 10.42 (s, 1H), 7.80 (s, 1H), 7.75 (d, J = 1.6 Hz, 1H), 7.49 (d, J = 8.4 Hz, 1H), 7.31 (dd, J = 1.6, 6.8 Hz, 1H), 6.58 (q, J = 10 Hz, 1H), 6.32 (dd, J = 1.6, 15.2 HZ, 1H), 5.83 (d, J = 10 Hz, 1H), 4.86-4.65 (m, 1H), 1.95 (d, J = 14 Hz, 1H), 1.85 (m, 1H), 1.69-1.55 (m, 1H), 0.95-0.87 (m, 1H); LCMS (electrospray) m/z 474.00 (M + H)+. | B |

TABLE 1-continued

Compounds of Examples

| Ex # | Structure/Name | ¹H NMR/MS (M + 1) | Method |
|---|---|---|---|
| 73 | 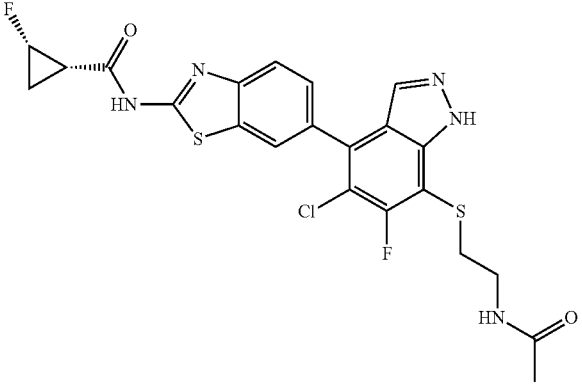 [SMILES: CC(=O)NCCSc1c(F)c(Cl)c(-c2ccc3nc(NC(=O)[C@@H]4C[C@@H]4F)sc3c2)c2cn[nH]c12]<br>(1S,2S)-N-(6-(7-((2-acetamidoethyl)thio)-5-chloro-6-fluoro-1H-indazol-4-yl)benzo[d]thiazol-2-yl)-2-fluorocyclopropane-1-carboxamide | ¹H NMR (400 MHz, DMSO-$d_6$) δ 13.78 (br s, 1H), 12.81 (s, 1H), 8.18 (s, 1H), 7.99 (t, J = 5.2 Hz, 1H), 7.89-7.87 (m, 2H), 7.59 (d, J = 8.4 Hz, 1H), 5.13-4.96 (m, 1H), 3.29 (m, 2H), 3.00 (m, 2H), 2.16 (td, J = 6.9, 13.8 Hz, 1H), 1.75 (s, 3H), 1.74-1.60 (m, 1H), 1.25-1.11 (m, 1H); LCMS (electrospray) m/z 522.1 (M + H)+. | B |
| 74 | 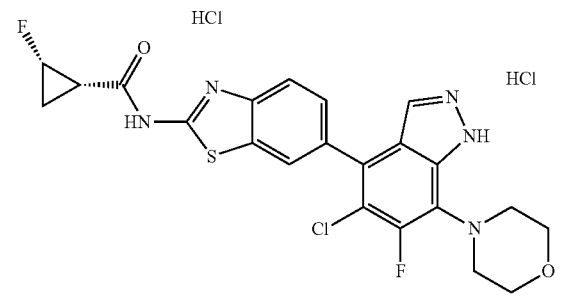 [SMILES: Cl ; O=C(Nc1nc2ccc(-c3c(Cl)c(F)c(N4CCOCC4)c4[nH]ncc34)cc2s1)[C@@H]1C[C@@H]1F ; Cl]<br>(1S,2S)-N-(6-(5-chloro-6-fluoro-7-morpholino-1H-indazol-4-yl)benzo[d]thiazol-2-yl)-2-fluorocyclopropane-1-carboxamide. 2 HCl | ¹H NMR (400 MHz, DMSO-$d_6$) δ 13.50 (br s, 1H), 12.82 (s, 1H), 8.14 (s, 1H), 7.88 (d, J = 8.4 Hz, 1H), 7.81 (s, 1H), 7.55 (d, J = 8.4 Hz, 1H), 5.14-4.76 (m, 1H), 3.83 (m, 4H), 3.28 (m, 4H), 2.16 (td, J = 6.9, 13.8 Hz, 1H), 1.74-1.60 (m, 1H), 1.25-1.11 (m, 1H); LCMS (electrospray) m/z 490.1 (M + H)+. | B |
| 75 | 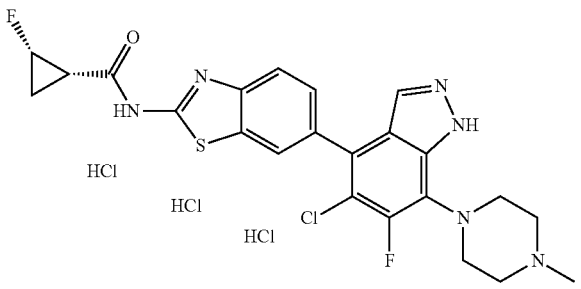 [SMILES: CN1CCN(c2c(F)c(Cl)c(-c3ccc4nc(NC(=O)[C@@H]5C[C@@H]5F)sc4c3)c3cn[nH]c23)CC1 ; Cl ; Cl ; Cl]<br>(1S,2S)-N-(6-(5-chloro-6-fluoro-7-(4-methylpiperazin-1-yl)-1H-indazol-4-yl)benzo[d]thiazol-2-yl)-2-fluorocyclopropane-1-carboxamide. 3 HCl | ¹H NMR (400 MHz, DMSO-$d_6$) δ 13.60 (s, 1H), 12.82 (s, 1H), 8.13 (s, 1H), 7.88 (d, J = 8.4 Hz, 1H), 7.84 (s, 1H), 7.54 (d, J = 8.4 Hz, 1H), 5.16-4.97 (m, 1H), 3.55 (br s, 6H), 3.39 (br s, 2H), 2.90 (d, J = 8.0 Hz, 3H), 2.19-2.10 (m, 1H), 1.73-1.60 (m, 1H), 1.35-1.28 (m, 1H); LCMS (electrospray) m/z 503.1 (M + H)+. | B |

TABLE 1-continued

Compounds of Examples

| Ex # | Structure/Name | ¹H NMR/MS (M + 1) | Method |
|------|----------------|-------------------|--------|
| 76 | 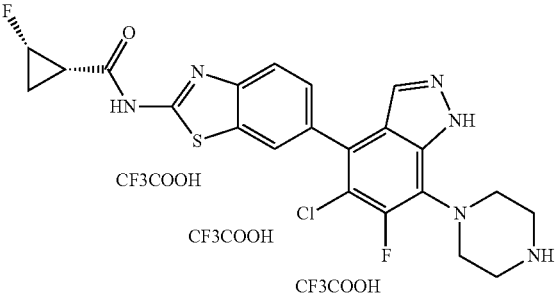 [SMILES: O=C(Nc1nc2ccc(-c3c(Cl)c(F)c(N4CCNCC4)c4[nH]ncc34)cc2s1)[C@@H]1C[C@@H]1F ; "CF3COOH" ; "CF3COOH" ; "CF3COOH"]<br>(1S,2S)-N-(6-(5-chloro-6-fluoro-7-(piperazin-1-yl)-1H-indazol-4-yl)benzo[d]thiazol-2-yl)-2-fluorocyclopropane-1-carboxamide. 3 TFA | ¹H NMR (400 MHz, DMSO-$d_6$) δ 13.56 (s, 1H), 12.82 (s, 1H), 8.71 (br s, 1H), 8.13 (s, 1H), 7.89 (d, J = 8.4 Hz, 1H), 7.84 (s, 1H), 7.54 (d, J = 8.4 Hz, 1H), 5.13-4.98 (m, 1H), 3.38 (br s, 4H), 2.66 (br s, 4H), 2.19-2.10 (m, 1H), 1.79-1.73 (m, 1H), 1.35-1.28 (m, 1H); LCMS (electrospray) m/z 489.1 (M + H)+. | B |
| 77 | 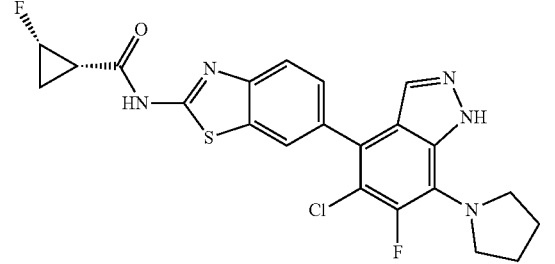 [SMILES: O=C(Nc1nc2ccc(-c3c(Cl)c(F)c(N4CCCC4)c4[nH]ncc34)cc2s1)[C@@H]1C[C@@H]1F]<br>(1S,2S)-N-(6-(5-chloro-6-fluoro-7-(pyrrolidin-1-yl)-1H-indazol-4-yl)benzo[d]thiazol-2-yl)-2-fluorocyclopropane-1-carboxamide | ¹H NMR (400 MHz, DMSO-$d_6$) δ 13.18 (s, 1H), 12.78 (s, 1H), 8.08 (s, 1H), 7.84 (d, J = 8.4 Hz, 1H), 7.73 (s, 1H), 7.51 (d, J = 8.4 Hz, 1H), 5.12-4.96 (m, 1H), 3.65 (br s, 4H), 2.19-2.10 (m, 1H), 1.95 (br s, 4H), 1.77-1.73 (m, 1H), 1.35-1.28 (m, 1H); LCMS (electrospray) m/z 473.1 (M + H)+. | B |
| 78 | 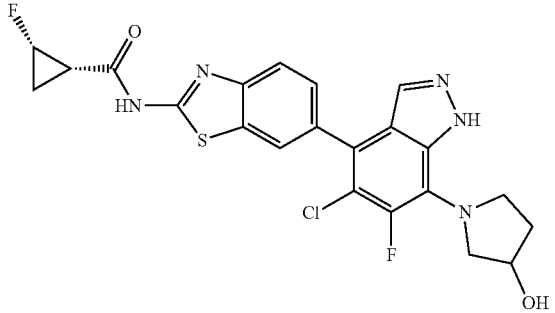 [SMILES: O=C(Nc1nc2ccc(-c3c(Cl)c(F)c(N4CCC(O)C4)c4[nH]ncc34)cc2s1)[C@@H]1C[C@@H]1F]<br>(1S,2S)-N-(6-(5-chloro-6-fluoro-7-(3-hydroxypyrrolidin-1-yl)-1H-indazol-4-yl)benzo[d]thiazol-2-yl)-2-fluorocyclopropane-1-carboxamide | ¹H NMR (400 MHz, DMSO-$d_6$) δ 13.17 (s, 1H), 12.79 (s, 1H), 8.09 (s, 1H), 7.85 (d, J = 8.4 Hz, 1H), 7.75 (s, 1H), 7.83 (d, J = 6.4, Hz, 1H), 5.14-4.97 (m, 2H), 4.41 (s, 1H), 3.97 (s, 2H), 3.73-3.35 (m, 2H), 2.29-2.18 (m, 1H), 2.10-1.98 (m, 1H), 1.94-1.85 (m, 1H), 1.82-1.70 (m, 1H), 1.38-1.27 (m, 1H); LCMS (electrospray) m/z 490.10 (M + H)+. | B |

TABLE 1-continued

Compounds of Examples

| Ex # | Structure/Name | ¹H NMR/MS (M + 1) | Method |
|---|---|---|---|
| 79 | 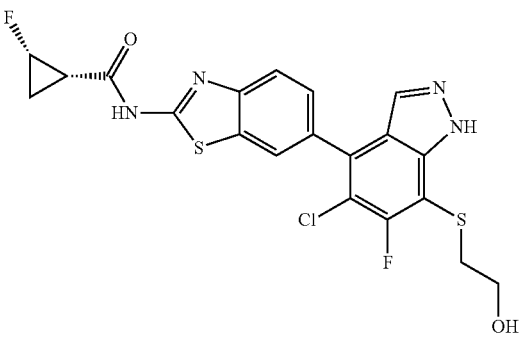 [SMILES: O=C(Nc1nc2ccc(-c3c(Cl)c(F)c(SCCO)c4[nH]ncc34)cc2s1)[C@@H]1C[C@@H]1F]<br><br>(1S,2S)-N-(6-(5-chloro-6-fluoro-7-((2-hydroxyethyl)thio)-1H-indazol-4-yl)benzo[d]thiazol-2-yl)-2-fluorocyclopropane-1-carboxamide | ¹H NMR (400 MHz, DMSO-d$_6$) δ 13.75 (s, 1H), 12.84 (s, 1H), 8.20 (s, 1H), 7.94-7.82 (m, 2H), 7.60 (d, J = 8.4 Hz, 1H), 7.83 (d, J = 6.4, Hz, 1H), 5.18-4.87 (m, 2H), 3.52 (q, J = 5.2 Hz, 2H), 3.06 (t, J = 5.6 Hz, 2H), 2.29-2.18 (m, 1H), 1.83-1.69 (m, 1H), 1.39-1.27 (m, 1H); LCMS (electrospray) m/z 481.05 (M + H)+. | B |
| 80 | 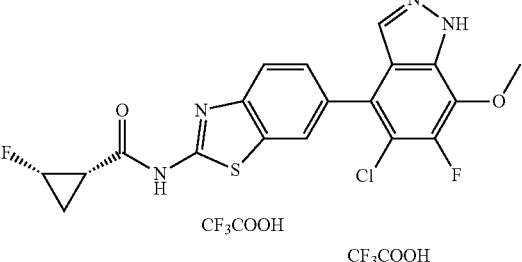<br><br>(1S,2S)-N-(6-(5-chloro-6-fluoro-7-methoxy-1H-indazol-4-yl)benzo[d]thiazol-2-yl)-2-fluorocyclopropane-1-carboxamide. 2 TFA | ¹H NMR (400 MHz, DMSO-d$_6$) δ 13.78 (br s, 1H), 12.81 (s, 1H), 8.14 (d, J = 1.4 Hz, 1H), 7.88 (d, J = 8.4 Hz, 1H), 7.86-7.79 (m, 1H), 7.55 (dd, J = 1.8, 8.4 Hz, 1H), 5.25-4.85 (m, 1H), 4.15 (s, 3H), 2.30-2.18 (m, 1H), 1.85-1.68 (m, 1H), 1.33 (tdd, J = 6.4, 9.0, 12.7 Hz, 1H); LCMS (electrospray) m/z 435.3 (M + H)+. | B |
| 81 | 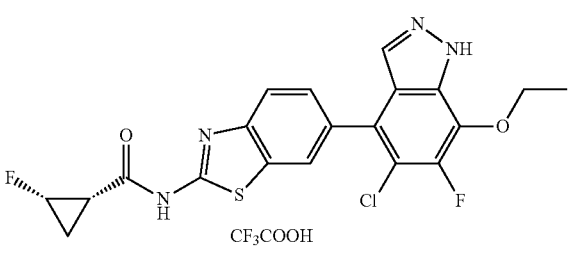<br><br>(1S,2S)-N-(6-(5-chloro-7-ethoxy-6-fluoro-1H-indazol-4-yl)benzo[d]thiazol-2-yl)-2-fluorocyclopropane-1-carboxamide. 2 TFA | ¹H NMR (400 MHz, DMSO-d$_6$) δ13.77 (s, 1H), 12.82 (s, 1H), 8.16 (d, J = 1.5 Hz, 1H), 7.92-7.87 (m, 1H), 7.84-7.80 (m, 1H), 7.62-7.53 (m, 1H), 5.27-4.92 (m, 1H), 4.38 (q, J = 7.0 Hz, 2H), 2.30-2.20 (m, 1H), 1.88-1.71 (m, 1H), 1.42 (t, J = 7.0 Hz, 3H), 1.38-1.29 (m, 1H); LCMS (electrospray) m/z 449.1 (M + H)+. | B |

TABLE 1-continued

Compounds of Examples

| Ex # | Structure/Name | ¹H NMR/MS (M + 1) | Method |
|---|---|---|---|
| 82 | 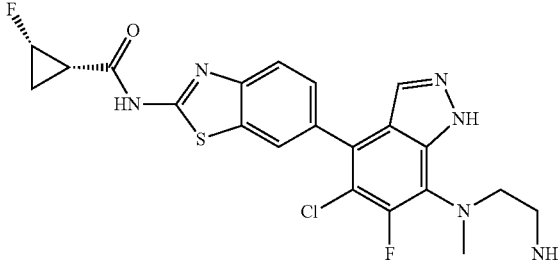<br>(1S,2S)-N-(6-(7-((2-aminoethyl)(methyl)amino)-5-chloro-6-fluoro-1H-indazol-4-yl)benzo[d]thiazol-2-yl)-2-fluorocyclopropane-1-carboxamide | ¹H NMR (400 MHz, DMSO-d$_6$) δ 7.91 (s, 1H), 7.74 (s, 1H), 7.66 (d, J = 8.4 Hz, 1H), 7.40 (dd, J = 1.6, 6.8, Hz, 1H), 5.02-4.78 (m, 1H), 3.23 (t, J = 5.6 Hz, 2H), 2.99 (d, J = 4 Hz, 3H), 2.80 (t, J = 6.0 2H), 2.09-1.99 (m, 1H), 1.74-1.62 (m, 1H), 1.16-1.07 (m, 1H); LCMS (electrospray) m/z 477.10 (M + H)+. | B |
| 83 | 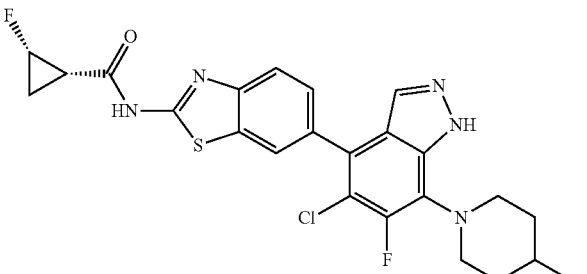<br>(1S,2S)-N-(6-(7-(4-aminopiperidin-1-yl)-5-chloro-6-fluoro-1H-indazol-4-yl)benzo[d]thiazol-2-yl)-2-fluorocyclopropane-1-carboxamide | ¹H NMR (400 MHz, DMSO-d$_6$) δ 8.07 (d, J = 1.6 Hz, 1H), 7.82 (d, J = 8.0 Hz, 1H), 7.78 (s, 1H), 7.51 (dd, J = 2.0, 6.4 Hz, 1H), 5.14-4.91 (m, 1H), 3.48 (m, 2H), 3.16 (t, J = 12 Hz 2H), 2.87-2.78(m, 1H), 2.24-2.15 (m, 1H), 1.85 (d, J = 10.4 Hz, 2H), 1.80-1.68 (m, 1H), 1.66-1.54 (m, 2H), 1.33-1.24 (m, 1H); LCMS (electrospray) m/z 503.10 (M + H)+. | B |
| 84 | 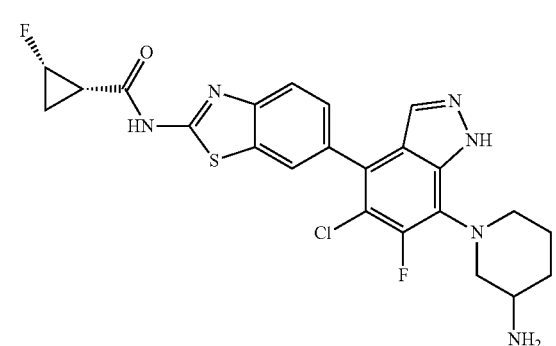<br>(1S,2S)-N-(6-(7-(3-aminopiperidin-1-yl)-5-chloro-6-fluoro-1H-indazol-4-yl)benzo[d]thiazol-2-yl)-2-fluorocyclopropane-1-carboxamide | ¹H NMR (400 MHz, DMSO-d$_6$) δ 8.10 (d, J = 1.6 Hz, 1H), 7.85 (d, J = 8.4 Hz, 1H), 7.79 (s, 1H), 7.53 (dd, J = 1.6, 8.0 Hz, 1H), 5.15-4.93 (m, 1H), 3.26-3.17 (m, 2H), 3.12-2.96 (m, 2H), 2.89-2.81 (m, 1H), 2.26-2.17 (m, 1H), 1.91-1.68 (m, 4H), 1.35-1.23 (m, 2H); LCMS (electrospray) m/z 503.1 (M + H)+. | B |

TABLE 1-continued

Compounds of Examples

| Ex # | Structure/Name | ¹H NMR/MS (M + 1) | Method |
|---|---|---|---|
| 85 | 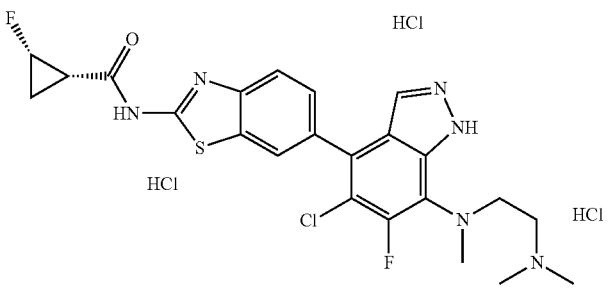 [SMILES: CN(C)CCN(C)c1c(F)c(Cl)c(-c2ccc3nc(NC(=O)[C@@H]4C[C@@H]4F)sc3c2)c2cn[nH]c12 ; Cl ; Cl ; Cl]<br>(1S,2S)-N-(6-(5-chloro-7-((2-(dimethylamino)ethyl)(methyl)amino)-6-fluoro-1H-indazol-4-yl)benzo[d]thiazol-2-yl)-2-fluorocyclopropane-1-carboxamide. 3 HCl | ¹H NMR (400 MHz, DMSO-d₆) δ 13.94 (s, 1H), 12.83 (s, 1H), 8.15 (s, 1H), 7.89 (d, J = 8.0 Hz, 1H), 7.82 (s, 1H), 7.56 (d, J = 8.0 Hz, 1H), 5.14-4.97 (m, 1H), 3.61 (s, 3H), 3.41-3.38 (m, 2H), 2.87-2.84 (m, 2H), 2.78 (s, 6H), 2.26-2.23 (m, 1H), 1.73-1.65 (m, 1H), 1.31-1.23 (m, 1H); LCMS (electrospray) m/z 505.1 (M + H)+. | B |
| 86 | 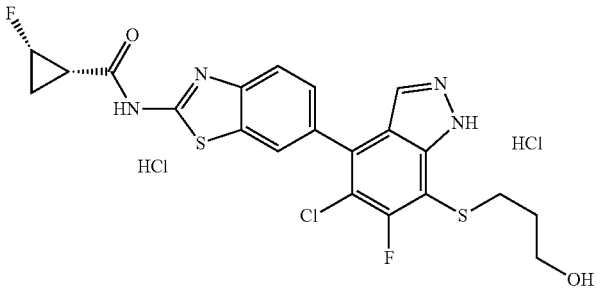 [SMILES: O=C(Nc1nc2ccc(-c3c(Cl)c(F)c(SCCCO)c4[nH]ncc34)cc2s1)[C@@H]1C[C@@H]1F ; Cl ; Cl]<br>(1S,2S)-N-(6-(5-chloro-6-fluoro-7-((3-hydroxypropyl)thio)-1H-indazol-4-yl)benzo[d]thiazol-2-yl)-2-fluorocyclopropanecarboxamide. 2 HCl | ¹H NMR (400 MHz, DMSO-d₆) δ 13.94 (s, 1H), 12.85 (s, 1H), 8.19 (s, 1H), 7.89 (d, J = 8.0 Hz, 1H), 7.82 (s, 1H), 7.60 (d, J = 8.0 Hz, 1H), 5.14-4.97 (m, 1H), 3.61-3.57 (m, 2H), 3.04-3.01 (m, 2H), 2.87-2.84 (m, 2H), 2.26-2.23 (m, 1H), 1.73-1.65 (m, 1H), 1.64-1.61 (m, 2H), 1.31-1.23 (m, 1H); LCMS (electrospray) m/z 495.1 (M + H)+. | B |
| 87 | 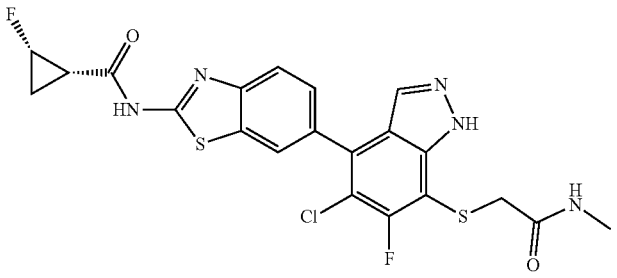 [SMILES: CNC(=O)CSc1c(F)c(Cl)c(-c2ccc3nc(NC(=O)[C@@H]4C[C@@H]4F)sc3c2)c2cn[nH]c12]<br>(1S,2S)-N-(6-(5-chloro-6-fluoro-7-((2-(methylamino)-2-oxoethyl)thio)-1H-indazol-4-yl)benzo[d]thiazol-2-yl)-2-fluorocyclopropanecarboxamide | ¹H NMR (400 MHz, DMSO-d₆) δ 13.86 (s, 1H), 12.84 (s, 1H), 8.19 (d, J = 1.6 Hz, 1H), 8.13-8.05 (m, 1H), 7.95-7.85 (m, 2H), 7.59 (dd, J = 1.6, 8.4 Hz, 1H), 5.18-4.95 (m, 1H), 3.66 (s, 2H), 2.58 (d, J = 1.4 Hz, 3H), 2.29-2.21 (m, 1H), 1.83-1.69 (m, 1H), 1.38-1.28 (m, 1H); LCMS (electrospray) m/z 509.1 (M + H)+. | B |

TABLE 1-continued

Compounds of Examples

| Ex # | Structure/Name | $^1$H NMR/MS (M + 1) | Method |
|---|---|---|---|
| 88 | 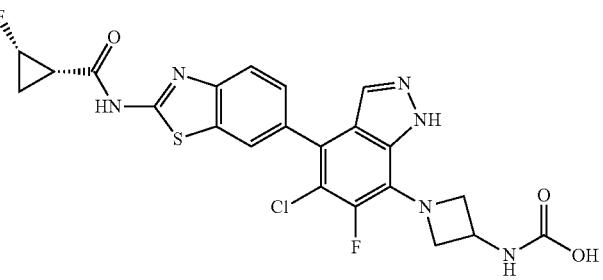<br>(1-(5-chloro-6-fluoro-4-(2-((1S,2S)-2-fluorocyclopropane-1-carboxamido)benzo[d]thiazol-6-yl)-1H-indazol-7-yl)azetidin-3-yl)carbamic acid | $^1$H NMR (400 MHz, DMSO-d$_6$) δ 13.56 (s, 1H), 12.83 (s, 1H), 8.19 (d, J = 1.6 Hz, 1H), 7.93-7.81 (m, 2H), 7.59 (dd, J = 2.0, 8.0 Hz, 1H), 7.20 (s, 1H), 5.17-4.95 (m, 2H), 4.01 (s, J = 8.8 Hz, 1H), 3.91-3.82 (m, 1H), 3.67-3.60 (m, 1H), 3.55 (t, J = 5.2 Hz, 2H), 2.29-2.21 (m, 1H), 1.83-1.70 (m, 1H), 1.38-1.28 (m, 1H); LCMS (electrospray) m/z 519.1 (M + H)+. | B |
| 89 | 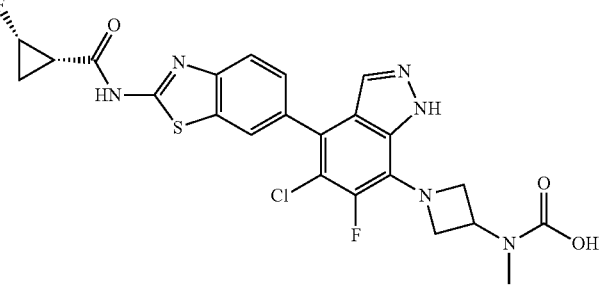<br>(1-(5-chloro-6-fluoro-4-(2-((1S,2S)-2-fluorocyclopropane-1-carboxamido)benzo[d]thiazol-6-yl)-1H-indazol-7-yl)azetidin-3-yl)(methyl)carbamic acid | $^1$H NMR (400 MHz, DMSO-d$_6$) δ 13.25 (s, 1H), 12.78 (s, 1H), 8.09 (d, J = 1.6 Hz, 1H), 7.90-7.70 (m, 2H), 7.52 (dd, J = 1.6, 8.4 Hz, 1H), 7.20 (s, 1H), 5.67-5.47 (s, 1H), 5.17-4.93 (m, 1H), 4.43-4.16 (m, 2H), 4.04-3.96 (m, 1H), 3.89-3.52 (m, 2H), 2.86 (s, 3H), 2.29-2.20 (m, 1H), 1.83-1.68 (m, 1H), 1.38-1.27 (m, 1H); LCMS (electrospray) m/z 533.1 (M + H)+ | B |
| 90 | 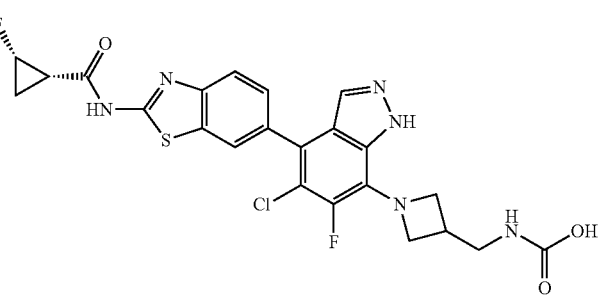<br>((1-(5-chloro-6-fluoro-4-(2-((1S,2S)-2-fluorocyclopropane-1-carboxamido)benzo[d]thiazol-6-yl)-1H-indazol-7-yl)azetidin-3-yl)methyl)carbamic acid | $^1$H NMR (400 MHz, DMSO-d$_6$) δ 13.13 (s, 1H), 12.78 (s, 1H), 8.10 (d, J = 1.6 Hz, 1H), 7.89-7.68 (m, 2H), 7.52 (dd, J = 2.4, 8.8 Hz, 1H), 7.21 (s, 1H), 5.82-5.62 (s, 1H), 5.17-4.94 (m, 1H), 4.33-4.23 (m, 1H), 4.15-4.06 (m, 1H), 3.67-3.43 (m, 2H), 3.34-3.26 (m, 1H), 3.12-3.05 (m, 1H), 2.31-2.15 (m, 2H), 1.84-1.69 (m, 1H), 1.39-1.26 (m, 1H); LCMS (electrospray) m/z 533.1 (M + H)+. | B |

TABLE 1-continued

Compounds of Examples

| Ex # | Structure/Name | ¹H NMR/MS (M + 1) | Method |
|---|---|---|---|
| 91 | 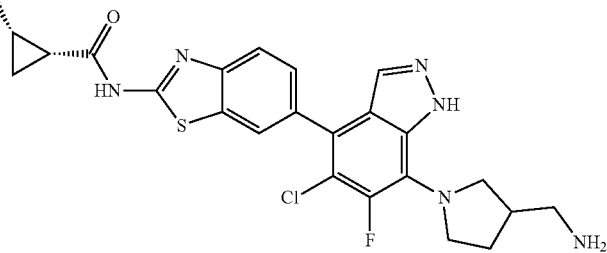<br>(1S,2S)-N-(6-(7-(3-(aminomethyl)pyrrolidin-1-yl)-5-chloro-6-fluoro-1H-indazol-4-yl)benzo[d]thiazol-2-yl)-2-fluorocyclopropanecarboxamide | ¹H NMR (400 MHz, DMSO-$d_6$) δ 7.85 (s, 1H), 7.76 (s, 1H), 7.63 (d, J = 8.4 Hz, 1H), 7.36 (dd, J = 1.6, 8.4 Hz, 1H), 5.02-4.78 (m, 1H), 4.04-3.87 (m, 1H), 3.78-3.61 (m, 2H), 3.58-3.48 (m, 1H), 2.72-2.59 (m, 2H), 2.34-2.26 (m, 1H), 2.09-1.92 (m, 2H), 1.74-1.61 (m, 4H), 1.15-1.02 (m, 1H); LCMS (electrospray) m/z 503.1 (M + H)+. | B |
| 92 | 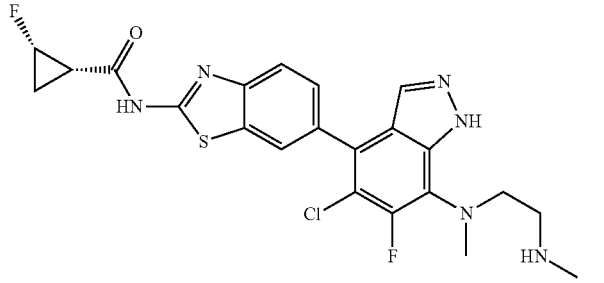 [SMILES: CNCCN(C)c1c(F)c(Cl)c(-c2ccc3nc(NC(=O)[C@@H]4C[C@@H]4F)sc3c2)c2cn[nH]c12]<br>(1S,2S)-N-(6-(5-chloro-6-fluoro-7-(methyl(2-(methylamino)ethyl)amino)-1H-indazol-4-yl)benzo[d]thiazol-2-yl)-2-fluorocyclopropane-1-carboxamide | ¹H NMR (400 MHz, DMSO-$d_6$) δ 13.42 (s, 1H), 12.82 (s, 1H), 8.22 (s, 1H), 8.14 (s, 1H), 7.90 (d, J = 8.0 Hz, 1H), 7.85 (s, 1H), 7.55 (d, J = 8.0 Hz, 1H), 5.14-4.97 (m, 1H), 2.89 (m, 2H), 2.65 (t, J = 5.2 Hz, 2H), 2.26-2.23 (m, 1H), 1.73-1.65 (m, 1H), 1.31-1.23 (m, 1H); LCMS (electrospray) m/z 491.1 (M + H)+. | B |
| 93 | 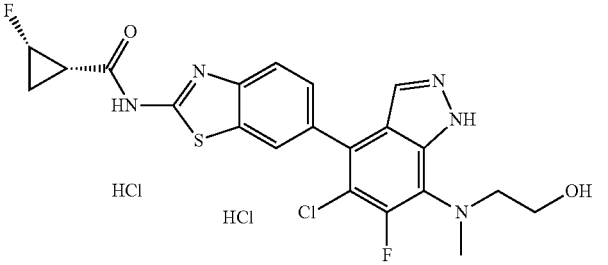 [SMILES: CN(CCO)c1c(F)c(Cl)c(-c2ccc3nc(NC(=O)[C@@H]4C[C@@H]4F)sc3c2)c2cn[nH]c12 ; Cl ; Cl]<br>(1S,2S)-N-(6-(5-chloro-6-fluoro-7-((2-hydroxyethyl)(methyl)amino)-1H-indazol-4-yl)benzo[d]thiazol-2-yl)-2-fluorocyclopropanecarboxamide. 2 HCl | ¹H NMR (400 MHz, DMSO-$d_6$) δ 13.42 (s, 1H), 12.81 (s, 1H), 8.22 (s, 1H), 8.14 (s, 1H), 7.87 (d, J = 8.4 Hz, 1H), 7.78 (s, 1H), 7.55 (d, J = 8.8 Hz, 1H), 5.14-4.96 (m, 1H), 3.64-3.61 (m, 2H), 3.35-3.32 (m, 2H), 3.02 (s, 3H), 2.26-2.23 (m, 1H), 1.73-1.65 (m, 1H), 1.31-1.23 (m, 1H); LCMS (electrospray) m/z 478.1 (M + H)+. | B |

TABLE 1-continued

Compounds of Examples

| Ex # | Structure/Name | ¹H NMR/MS (M + 1) | Method |
|---|---|---|---|
| 94 | (1S,2S)-N-(6-(7-((azetidin-3-ylmethyl)(methyl)amino)-5-chloro-6-fluoro-1H-indazol-4-yl)benzo[d]thiazol-2-yl)-2-fluorocyclopropanecarboxamide. 3 TFA | ¹H NMR (400 MHz, DMSO-$d_6$) δ 13.51 (s, 1H), 12.82 (s, 1H), 8.49 (br, 1H), 8.38 (br, 1H), 8.14 (s, 1H), 7.89 (d, J = 8.4 Hz, 1H), 7.72 (s, 1H), 7.55 (d, J = 8.8 Hz, 1H), 5.16-4.97 (m, 1H), 3.96-3.91 (m, 2H), 3.67-3.64 (m, 2H), 2.90 (s, 3H), 2.26-2.23 (m, 1H), 1.79-1.72 (m, 1H), 1.37-1.30 (m, 1H), 1.08 (t, J = 7.2 Hz, 1H); LCMS (electrospray) m/z 503.1 (M + H)+. | B |
| 95 | (1S,2S)-N-(6-(7-((azetidin-3-ylmethyl)amino)-5-chloro-6-fluoro-1H-indazol-4-yl)benzo[d]thiazol-2-yl)-2-fluorocyclopropanecarboxamide. 3 TFA | ¹H NMR (400 MHz, DMSO-$d_6$) δ 13.18 (s, 1H), 12.78 (s, 1H), 8.57 (br, 2H), 8.08 (s, 1H), 7.85 (d, J = 8.4 Hz, 1H), 7.77 (s, 1H), 7.51 (dd, J = 8.0 Hz, J = 1.6 Hz, 1H), 5.16-4.95 (m, 1H), 4.00 (m, 2H), 3.92 (m, 2H), 3.71 (br, 2H), 3.05 (br, 1H), 2.25-2.20 (m, 1H), 1.78-1.68 (m, 1H), 1.36-1.28 (m, 1H), 1.08 (t, J = 7.2 Hz, 1H); LCMS (electrospray) m/z 489.1 (M + H)+. | B |
| 96 | (1S,2S)-2-fluoro-N-(6-(7-methoxy-5-methyl-1H-indazol-4-yl)benzo[d]thiazol-2-yl)cyclopropanecarboxamide. 2 TFA | ¹H NMR (400 MHz, DMSO-$d_6$) δ 13.26 (br s, 1H), 12.74 (s, 1H), 8.00 (d, J = 1.4 Hz, 1H), 7.83 (d, J = 8.3 Hz, 1H), 7.60 (s, 1H), 7.44 (dd, J = 1.7, 8.3 Hz, 1H), 6.81 (s, 1H), 5.16-4.94 (m, 1H), 3.98 (s, 3H), 2.31 (s, 3H), 2.27-2.19 (m, 1H), 1.82-1.68 (m, 1H), 1.32 (tdd, J = 6.3, 9.0, 12.8 Hz, 1H); LCMS(electrospray) m/z 397.4 (M + H+). | B |
| 97 | (1S,2S)-2-fluoro-N-(6-(6-fluoro-7-methoxy-5-methyl-1H-indazol-4-yl)benzo[d]thiazol-2-yl)cyclopropanecarboxamide. 2 TFA | ¹H NMR (400 MHz, DMSO-$d_6$) δ 13.44 (br s, 1H), 12.76 (s, 1H), 8.04 (d, J = 1.3 Hz, 1H), 7.86 (d, J = 8.3 Hz, 1H), 7.69 (s, 1H), 7.46 (dd, J = 1.7, 8.3 Hz, 1H), 5.18-4.89 (m, 1H), 4.08 (d, J = 0.9 Hz, 3H), 2.29-2.22 (m, 1H), 2.20 (d, J = 3.2 Hz, 3H), 1.83-1.69 (m, 1H), 1.32 (tdd, J = 6.4, 8.8, 12.8 Hz, 1H); LCMS(electrospray) m/z 415.4 (M + H+). | B |

TABLE 1-continued

Compounds of Examples

| Ex # | Structure/Name | ¹H NMR/MS (M + 1) | Method |
|---|---|---|---|
| 98 | 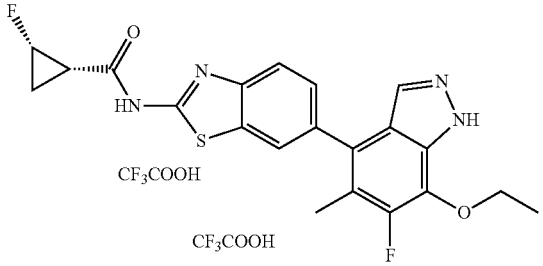 [SMILES: CCOc1c(F)c(C)c(-c2ccc3nc(NC(=O)[C@@H]4C[C@@H]4F)sc3c2)c2cn[nH]c12 ; "CF3COOH" ; "CF3COOH"]<br>(1S,2S)-N-(6-(7-ethoxy-6-fluoro-5-methyl-1H-indazol-4-yl)benzo[d]thiazol-2-yl)-2-fluorocyclopropanecatboxamide. 2 TFA | ¹H NMR (400 MHz, DMSO-$d_6$) 13.42 (br s, 1H), 12.78 (s, 1H), 8.05 (d, J = 1.3 Hz, 1H), 7.86 (d, J = 8.3 Hz, 1H), 7.68 (s, 1H), 7.47 (dd, J = 1.5, 8.3 Hz, 1H), 5.22-4.90 (m, 1H), 4.30 (br d, J = 7.1 Hz, 2H), 2.23 (br d, J = 7.0 Hz, 1H), 2.19 (d, J = 3.1 Hz, 3H), 1.80-1.70 (m, 1H), 1.39 (t, J = 7.0 Hz, 3H), 1.35-1.28 (m, 1H); LCMS(electrospray) m/z 429.4 (M + H+). | B |
| 99 | 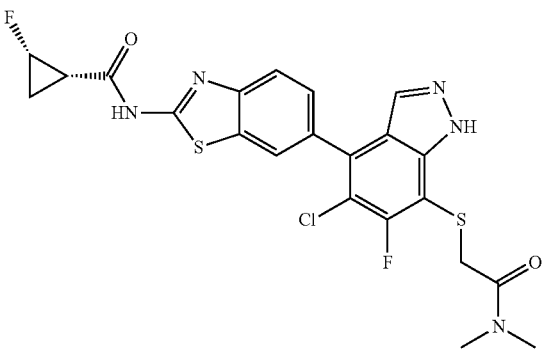 [SMILES: CN(C)C(=O)CSc1c(F)c(Cl)c(-c2ccc3nc(NC(=O)[C@@H]4C[C@@H]4F)sc3c2)c2cn[nH]c12]<br>(1S,2S)-N-(6-(5-chloro-7-((2-(dimethylamino)-2-oxoethyl)thio)-6-fluoro-1H-indazol-4-yl)benzo[d]thiazol-2-yl)-2-fluorocyclopropane-1-carboxamide | ¹H NMR (400 MHz, DMSO-$d_6$) δ 13.76 (s, 1H), 12.84 (s, 1H), 8.19 (d, J = 2.0 Hz, 1H), 7.94-7.84 (m, 2H), 7.59 (dd, J = 1.6, 8.0 Hz, 1H), 5.17-4.95 (m, 1H), 4.03 (s, 2H), 3.01 (s, 3H), 2.81 (s, 3H), 2.29-2.20 (m, 1H), 1.82-1.70 (m, 1H), 1.38-1.28 (m, 1H); LCMS (electrospray) m/z 522.10 (M + H)+. | B |
| 100 | 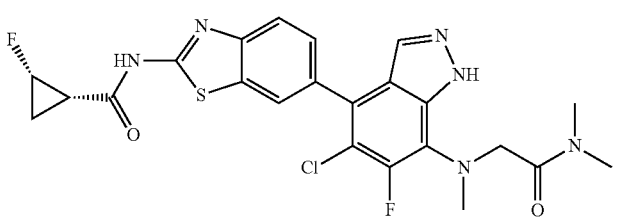 [SMILES: CN(C)C(=O)CN(C)c1c(F)c(Cl)c(-c2ccc3nc(NC(=O)[C@@H]4C[C@@H]4F)sc3c2)c2cn[nH]c12]<br>(1S,2S)-N-(6-(5-chloro-7-((2-(dimethylamino)-2-oxoethyl)(methyl)amino)-6-fluoro-1H-indazol-4-yl)benzo[d]thiazol-2-yl)-2-fluorocyclopropane-1-carboxamide | ¹H NMR (400 MHz, DMSO-$d_6$) δ 13.42 (s, 1H), 12.80 (s, 1H), 8.12 (s, 1H), 7.87 (d, J = 8.4 Hz, 1H), 7.77 (s, 1H), 7.54 (dd, J = 8.0 Hz, J = 1.6 Hz, 1H), 5.14-4.96 (m, 1H), 3.62 (s, 2H), 3.37 (s, 6H), 3.15 (s, 3H), 2.25-2.20 (m, 1H), 1.78-1.68 (m, 1H), 1.34-1.28 (m, 1H); LCMS (electrospray) m/z 519.1 (M + H)+. | B |
| 101 | 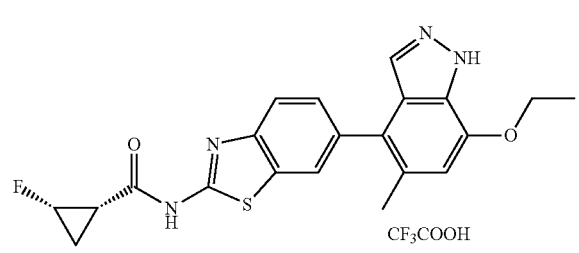<br>(1S,2S)-N-(6-(7-ethoxy-5-methyl-1H-indazol-4-yl)benzo[d]thiazol-2-yl)-2-fluorocyclopropane-1-carboxamide. 2 TFA | ¹H NMR (400 MHz, DMSO-$d_6$) δ 13.22 (br s, 1H), 12.74 (s, 1H), 8.00 (d, J = 1.3 Hz, 1H), 7.83 (d, J = 8.3 Hz, 1H), 7.60 (s, 1H), 7.44 (dd, J = 1.8, 8.3 Hz, 1H), 6.79 (s, 1H), 5.17-4.93 (m, 1H), 4.27 (q, J = 7.1 Hz, 2H), 2.29 (s, 3H), 2.27-2.20 (m, 1H), 1.82-1.69 (m, 1H), 1.46 (t, J = 7.0 Hz, 3H), 1.32 (tdd, J = 6.4, 8.9, 12.8 Hz, 1H); LCMS(electrospray) m/z 410.9 (M + H+). | B |

TABLE 1-continued

Compounds of Examples

| Ex # | Structure/Name | ¹H NMR/MS (M + 1) | Method |
|---|---|---|---|
| 102 | 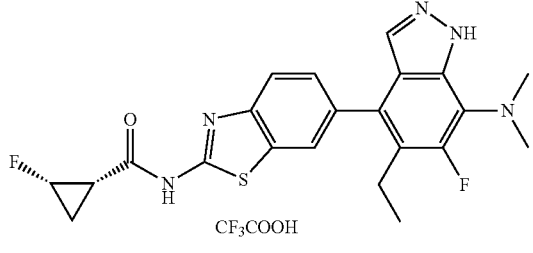<br>(1S,2S)-N-(6-(7-(dimethylamino)-5-ethyl-6-fluoro-1H-indazol-4-yl)benzo[d]thiazol-2-yl)-2-fluorocyclopropane-1-carboxamide. 2 TFA | ¹H NMR (400 MHz, DMSO-$d_6$) δ 13.16 (br s, 1H), 12.77 (s, 1H), 8.00 (d, J = 1.6 Hz, 1H), 7.85 (d, J = 8.3 Hz, 1H), 7.55 (s, 1H), 7.42 (dd, J = 1.6, 8.3 Hz, 1H), 5.18-4.93 (m, 1H), 2.96 (s, 3H), 2.96 (s, 3H), 2.56-2.52 (m, 2H), 2.29-2.20 (m, 1H), 1.82-1.71 (m, 1H), 1.32 (tdd, J = 6.6, 9.0, 12.8 Hz, 1H), 1.07 (t, J = 7.4 Hz, 3H); LCMS(electrospray) m/z 442.2 (M + H+). | B |
| 103 | 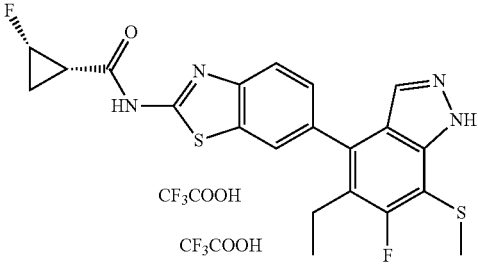 [SMILES: CCc1c(F)c(SC)c2[nH]ncc2c1-c1ccc2nc(NC(=O)[C@@H]3C[C@@H]3F)sc2c1 ; "CF3COOH" ; "CF3COOH"]<br>(1S,2S)-N-(6-(5-ethyl-6-fluoro-7-(methylthio)-1H-indazol-4-yl)benzo[d]thiazol-2-yl)-2-fluorocyclopropane-1-carboxamide. 2 TFA | ¹H NMR (400 MHz, DMSO-$d_6$) δ 13.44 (br s, 1H), 12.80 (s, 1H), 8.05 (d, J = 1.3 Hz, 1H), 7.88 (d, J = 8.1 Hz, 1H), 7.64 (s, 1H), 7.45 (dd, J = 1.8, 8.3 Hz, 1H), 5.18-4.92 (m, 1H), 2.59 (br d, J = 6.9 Hz, 2H), 2.52 (br s, 3H), 2.29-2.20 (m, 1H), 1.82-1.70 (m, 1H), 1.37-1.28 (m, 1H), 1.08 (t, J = 7.3 Hz, 3H); LCMS(electrospray) m/z 445.3 (M + H+). | B |
| 104 | 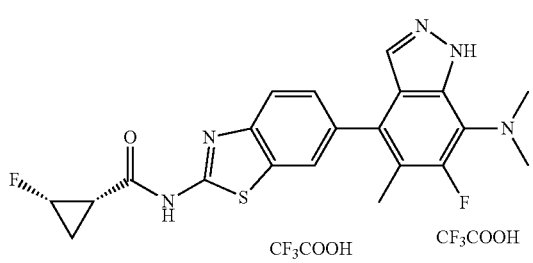 [SMILES: Cc1c(F)c(N(C)C)c2[nH]ncc2c1-c1ccc2nc(NC(=O)[C@@H]3C[C@@H]3F)sc2c1 ; "CF3COOH" ; "CF3COOH"]<br>(1S,2S)-N-(6-(7-(dimethylamino)-6-fluoro-5-methyl-1H-indazol-4-yl)benzo[d]thiazol-2-yl)-2-fluorocyclopropane-1-carboxamide. 2 TFA | ¹H NMR (400 MHz, DMSO-$d_6$) δ 13.15 (br s, 1H), 12.77 (br s, 1H), 8.03 (s, 1H), 7.85 (d, J = 8.3 Hz, 1H), 7.64 (s, 1H), 7.46 (br d, J = 8.3 Hz, 1H), 5.18-4.89 (m, 1H), 2.95 (s, 6H), 2.28-2.22 (m, 1H), 2.16 (br d, J = 3.2 Hz, 3H), 1.83-1.69 (m, 1H), 1.38-1.24 (m, 1H); LCMS(electrospray) m/z 428.2 (M + H+). | B |
| 105 | 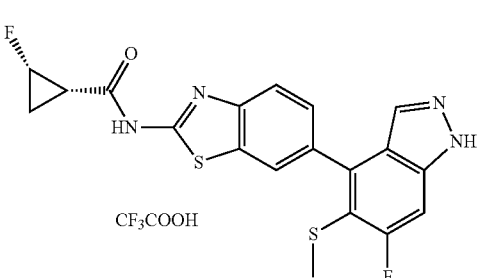<br>(1S,2S)-2-fluoro-N-(6-(6-fluoro-5-(methylthio)-1H-indazol-4-yl)benzo[d]thiazol-2-yl)cyclopropane-1-carboxamide. 2 TFA | ¹H NMR (400 MHz, CHLOROFORM-d) δ 12.79 (br s, 1H), 8.09 (d, J = 1.6 Hz, 1H), 7.86 (d, J = 8.3 Hz, 1H), 7.71 (s, 1H), 7.51 (dd, J = 1.8, 8.3 Hz, 1H), 7.48 (d, J = 9.3 Hz, 1H), 5.21-4.92 (m, 1H), 2.28-2.22 (m, 1H), 2.21 (s, 3H), 1.83-1.69 (m, 1H), 1.32 (ddd, J = 2.6, 6.4, 12.8 Hz, 1H); LCMS(electrospray) m/z 417.1 (M + H+). | B |

TABLE 1-continued

Compounds of Examples

| Ex # | Structure/Name | ¹H NMR/MS (M + 1) | Method |
|---|---|---|---|
| 106 | 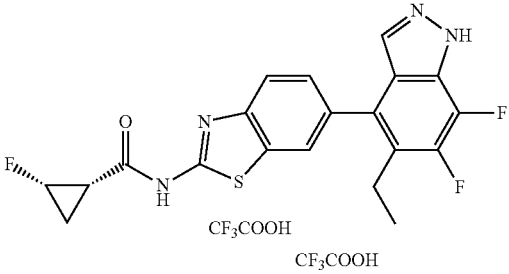 [SMILES: CCc1c(F)c(F)c2[nH]ncc2c1-c1ccc2nc(NC(=O)[C@@H]3C[C@@H]3F)sc2c1 ; "CF3COOH" ; "CF3COOH"]<br>(1S,2S)-N-(6-(5-ethyl-6,7-difluoro-1H-indazol-4-yl)benzo[d]thiazol-2-yl)-2-fluorocyclopropane-1-carboxamide. 2 TFA | ¹H NMR (400 MHz, DMSO-$d_6$) δ 13.84 (br s, 1H), 12.79 (s, 1H), 8.03 (d, J = 1.6 Hz, 1H), 7.88 (d, J = 8.3 Hz, 1H), 7.70 (br s, 1H), 7.43 (dd, J = 1.8, 8.3 Hz, 1H), 5.23-4.89 (m, 1H), 2.61 (br d, J = 6.0 Hz, 2H), 2.29-2.20 (m, 1H), 1.82-1.69 (m, 1H), 1.37-1.27 (m, 1H), 1.09 (t, J = 7.4 Hz, 3H); LCMS(electrospray) m/z 417.1 (M + H+). | B |
| 107 | 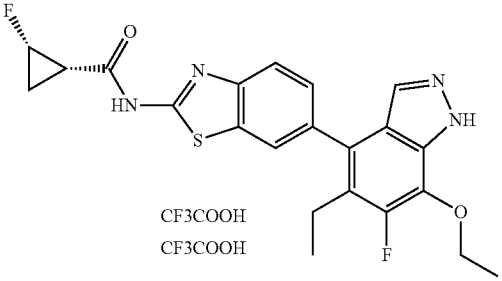 [SMILES: CCOc1c(F)c(CC)c(-c2ccc3nc(NC(=O)[C@@H]4C[C@@H]4F)sc3c2)c2cn[nH]c12 ; "CF3COOH" ; "CF3COOH"]<br>(1S,2S)-N-(6-(7-ethoxy-5-ethyl-6-fluoro-1H-indazol-4-yl)benzo[d]thiazol-2-yl)-2-fluorocyclopropane-1-carboxamide. 2 TFA | ¹H NMR (400 MHz, DMSO-$d_6$) δ 13.43 (s, 1H), 12.78 (s, 1H), 8.02 (s, 1H), 7.87 (d, J = 8.4 Hz, 1H), 7.59 (s, 1H), 7.45-7.42 (m, 1H), 5.15-4.97 (m, 1H), 4.34-4.28 (m, 2H), 2.59-2.53 (m, 2H), 2.27-2.23 (m, 1H), 1.85-1.75 (m, 1H), 1.40 (t, J = 6.8 Hz, 3H), 1.36-1.32 (m, 1H), 1.09 (t, J = 7.2 Hz, 3H); LCMS(electrospray) m/z 443.2 (M + H+). | B |
| 108 | 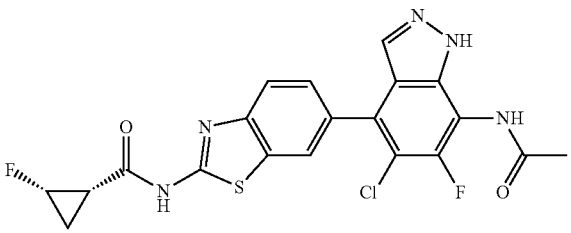<br>(1S,2S)-N-(6-(7-acetamido-5-chloro-6-fluoro-1H-indazol-4-yl)benzo[d]thiazol-2-yl)-2-fluorocyclopropane-1-carboxamide. 1 TFA | ¹H NMR (400 MHz, DMSO-$d_6$) δ 13.27 (s, 1H), 12.82 (s, 1H), 10.11 (s, 1H), 8.20 (d, J = 1.6 Hz, 1H), 7.91 (d, J = 8.4 Hz, 1H), 7.81 (d, J = 1.1 Hz, 1H), 7.60 (dd, J = 1.7, 8.3 Hz, 1H), 5.18-4.96 (m, 1H), 2.26 (ddd, J = 2.2, 4.5, 6.5 Hz, 1H), 2.19 (s, 3H), 1.77 (tdd, J = 3.2, 6.8, 19.9 Hz, 1H), 1.33 (tdd, J = 6.3, 9.0, 12.8 Hz, 1H); LCMS(electrospray) m/z 462.1 (M + H+). | B |
| 109 | 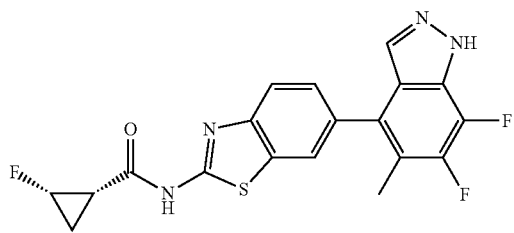 [SMILES: Cc1c(F)c(F)c2[nH]ncc2c1-c1ccc2nc(NC(=O)[C@@H]3C[C@@H]3F)sc2c1]<br>(1S,2S)-N-(6-(6,7-difluoro-5-methyl-1H-indazol-4-yl)benzo[d]thiazol-2-yl)-2-fluorocyclopropane-1-carboxamide | ¹H NMR (400 MHz, DMSO-$d_6$) δ 14.35-13.37 (m, 1H), 12.79 (s, 1H), 8.07 (d, J = 1.6 Hz, 1H), 7.88 (d, J = 8.3 Hz, 1H), 7.79 (br s, 1H), 7.48 (dd, J = 1.8, 8.3 Hz, 1H), 5.22-4.90 (m, 1H), 2.27-2.19 (m, 4H), 1.83-1.69 (m, 1H), 1.32 (tdd, J = 6.4, 9.0, 12.9 Hz, 1H); LCMS(electrospray) m/z 403.2 (M + H+). | B |

TABLE 1-continued

Compounds of Examples

| Ex # | Structure/Name | ¹H NMR/MS (M + 1) | Method |
|---|---|---|---|
| 110 | <br>CF₃COOH<br><br>(1S,2S)-N-(6-(7-(dimethylamino)-6-fluoro-5-(methylthio)-1H-indazol-4-yl)benzo[d]thiazol-2-yl)-2-fluorocyclopropane-1-carboxamide. 1 TFA | ¹H NMR (400 MHz, DMSO-d₆) δ 13.36 (br s, 1H), 12.77 (s, 1H), 8.04 (d, J = 1.5 Hz, 1H), 7.84 (d, J = 8.3 Hz, 1H), 7.67 (s, 1H), 7.48 (dd, J = 1.7, 8.3 Hz, 1H), 5.16-4.94 (m, 1H), 2.97 (d, J = 2.1 Hz, 6H), 2.27-2.22 (m, 1H), 2.20 (s, 3H), 1.83-1.69 (m, 1H), 1.39-1.26 (m, 1H); LCMS(electrospray) m/z 460 (M + H+). | B |
| 111 | 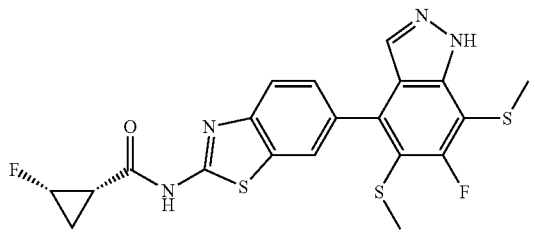<br>CF₃COOH<br><br>(1S,2S)-2-fluoro-N-(6-(6-fluoro-5,7-bis(methylthio)-1H-indazol-4-yl)benzo[d]thiazol-2-yl)cyclopropane-1-carboxamide. 1 TFA | ¹H NMR (400 MHz, DMSO-d₆) δ 13.77-13.52 (m, 1H), 12.80 (s, 1H), 8.09 (d, J = 1.5 Hz, 1H), 7.86 (d, J = 8.4 Hz, 1H), 7.78 (s, 1H), 7.52 (dd, J = 1.8, 8.3 Hz, 1H), 5.20-4.93 (m, 1H), 2.55 (s, 3H), 2.30-2.24 (m, 1H), 2.22 (s, 3H), 1.83-1.70 (m, 1H), 1.32 (tdd, J = 6.4, 8.9, 12.8 Hz, 1H); LCMS(electrospray) m/z 462.05 (M + H+). | B |
| 112 | 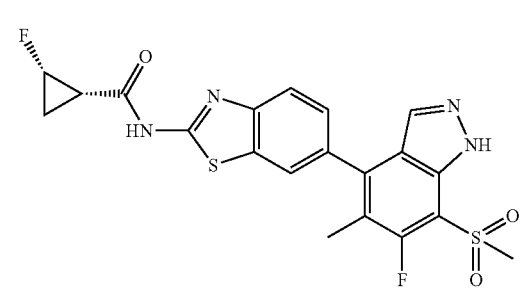 [SMILES: Cc1c(F)c(S(C)(=O)=O)c2[nH]ncc2c1-c1ccc2nc(NC(=O)[C@@H]3C[C@@H]3F)sc2c1]<br><br>(1S,2S)-2-fluoro-N-(6-(6-fluoro-5-methyl-7-(methylsulfonyl)-1H-indazol-4-yl)benzo[d]thiazol-2-yl)cyclopropane-1-carboxamide | ¹H NMR (400 MHz, DMSO-d₆) δ 13.16 (s, 1H), 12.83 (s, 1H), 8.14 (d, J = 1.5 Hz, 1H), 7.92 (d, J = 8.3 Hz, 1H), 7.85 (d, J = 1.2 Hz, 1H), 7.53 (dd, J = 1.7, 8.3 Hz, 1H), 5.19-4.94 (m, 1H), 3.50 (s, 3H), 2.29 (br s, 1H), 2.24 (d, J = 2.9 Hz, 3H), 1.85-1.69 (m, 1H), 1.41-1.24 (m, 1H); LCMS(electrospray) m/z 463.1 (M + H+). | B |
| 113 | 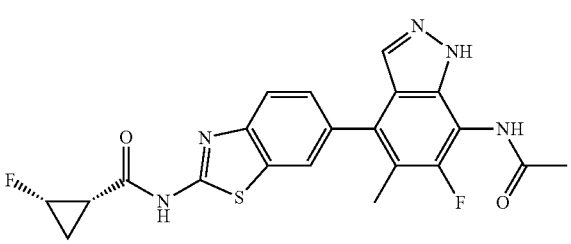 [SMILES: CC(=O)Nc1c(F)c(C)c(-c2ccc3nc(NC(=O)[C@@H]4C[C@@H]4F)sc3c2)c2cn[nH]c12]<br><br>(1S,2S)-N-(6-(7-acetamido-6-fluoro-5-methyl-1H-indazol-4-yl)benzo[d]thiazol-2-yl)-2-fluorocyclopropane-1-carboxamide | ¹H NMR (400 MHz, DMSO-d₆) δ 12.94-12.86 (m, 1H), 12.83-12.74 (m, 1H), 9.90 (br s, 1H), 8.09 (br s, 1H), 7.88 (br d, J = 7.9 Hz, 1H), 7.66 (br s, 1H), 7.49 (br d, J = 7.4 Hz, 1H), 5.19-4.95 (m, 1H), 2.28-2.23 (m, 1H), 2.20 (br s, 3H), 2.16 (br s, 3H), 1.84-1.69 (m, 1H), 1.42-1.25 (m, 1H); LCMS(electrospray) m/z 442.0 (M + H+). | B |

TABLE 1-continued

Compounds of Examples

| Ex # | Structure/Name | ¹H NMR/MS (M + 1) | Method |
|---|---|---|---|
| 114 | 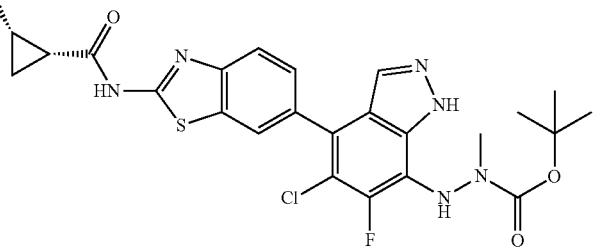<br>tert-butyl 2-(5-chloro-6-fluoro-4-(2-((1S,2S)-2-fluorocyclopropane-1-carboxamido)benzo[d]thiazol-6-yl)-1H-indazol-7-yl)-1-methylhydrazine-1-carboxylate | ¹H NMR (400 MHz, DMSO-$d_6$) δ 13.05 (s, 1H), 10.78 (s, 1H), 8.08 (s, 1H), 7.83 (d, J = 8.4 Hz, 1H), 7.72 (s, 1H), 7.12 (d, J = 8.0 Hz, 1H), 6.45 (d, J = 12.4 Hz, 1H), 5.14-4.95 (m, 1H), 3.37 (s, 3H), 2.25-2.20 (m, 1H), 1.78-1.68 (m, 1H), 1.34-1.28 (m, 10H); LCMS (electrospray) m/z 549.1 (M + H)+. | B |
| 115 | 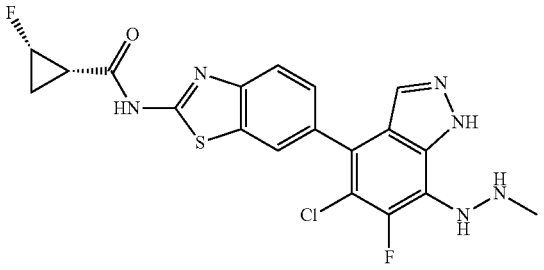 [SMILES: CNNc1c(F)c(Cl)c(-c2ccc3nc(NC(=O)[C@@H]4C[C@@H]4F)sc3c2)c2cn[nH]c12]<br>(1S,2S)-N-(6-(5-chloro-6-fluoro-7-(2-methylhydrazineyl)-1H-indazol-4-yl)benzo[d]thiazol-2-yl)-2-fluorocyclopropane-1-carboxamide | ¹H NMR (400 MHz, DMSO-$d_6$) δ 12.88 (s, 1H), 12.79 (s, 1H), 8.25 (s, 1H), 8.11 (s, 1H), 7.89 (d, J = 8.4 Hz, 1H), 7.76 (s, 1H), 7.52 (d, J = 8.0 Hz, 1H), 6.45 (d, J = 12.4 Hz, 1H), 5.13-4.96 (m, 1H), 4.04-3.99 (m, 1H), 3.23 (s, 3H), 2.25-2.20 (m, 1H), 1.78-1.68 (m, 1H), 1.34-1.28 (m, 1H); LCMS (electrospray) m/z 449.1 (M + H)+. | B |
| 116 | 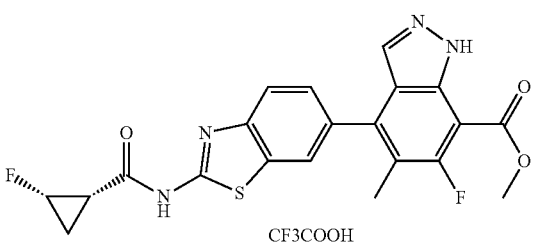<br>CF3COOH<br>methyl 6-fluoro-4-(2-((1S,2S)-2-fluorocyclopropane-1-carboxamido)benzo[d]thiazol-6-yl)-5-methyl-1H-indazole-7-carboxylate. 1 TFA | ¹H NMR (400 MHz, DMSO-$d_6$) δ 13.28 (s, 1H), 12.87-12.78 (m, 1H), 8.14 (d, J = 1.5 Hz, 1H), 7.91 (d, J = 8.3 Hz, 1H), 7.80 (d, J = 1.3 Hz, 1H), 7.53 (dd, J = 1.8, 8.4 Hz, 1H), 5.18-4.95 (m, 1H), 3.98 (s, 3H), 2.21 (d, J = 3.1 Hz, 3H), 1.91-1.88 (m, 1H), 1.69 (br d, J = 2.8 Hz, 1H), 1.34-1.29 (m, 1H); LCMS(electrospray) m/z 443.1(M + H+). | B |
| 117 | 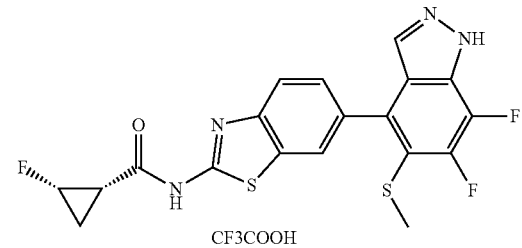 [SMILES: CSc1c(F)c(F)c2[nH]ncc2c1-c1ccc2nc(NC(=O)[C@@H]3C[C@@H]3F)sc2c1 ; "CF3COOH"]<br>CF3COOH<br>(1S,2S)-N-(6-(6,7-difluoro-5-(methylthio)-1H-indazol-4-yl)benzo[d]thiazol-2-yl)-2-fluorocyclopropane-1-carboxamide 2,2,2-trifluoroacetate. 1 TFA | ¹H NMR (400 MHz, DMSO-$d_6$) δ 14.07 (br s, 1H), 12.81 (s, 1H), 8.08 (d, J = 1.5 Hz, 1H), 7.86 (d, J = 8.4 Hz, 2H), 7.50 (dd, J = 1.8, 8.3 Hz, 1H), 5.19-4.94 (m, 1H), 2.29-2.20 (m, 4H), 1.84-1.68 (m, 1H), 1.38-1.26 (m, 1H); LCMS(electrospray) m/z 435.1 (M + H+). | B |

TABLE 1-continued

Compounds of Examples

| Ex # | Structure/Name | $^1$H NMR/MS (M + 1) | Method |
|---|---|---|---|
| 118 | <br>(1S,2S)-N-(6-(7-ethoxy-6-fluoro-5-(methylthio)-1H-indazol-4-yl)benzo[d]thiazol-2-yl)-2-fluorocyclopropane-1-carboxamide. 1 TFA | $^1$H NMR (400 MHz, DMSO-d$_6$) δ 13.87-13.43 (m, 1H), 12.78 (s, 1H), 8.07 (s, 1H), 7.85 (d, J = 8.4 Hz, 1H), 7.73 (s, 1H), 7.50 (dd, J = 1.3, 8.4 Hz, 1H), 5.21-4.93 (m, 1H), 4.35 (q, J = 7.0 Hz, 2H), 2.30-2.19 (m, 4H), 1.84-1.70 (m, 1H), 1.41 (t, J = 7.0 Hz, 3H), 1.37-1.27 (m, 1H); LCMS(electrospray) m/z 461.2 (M + H+). | B |
| 119 | 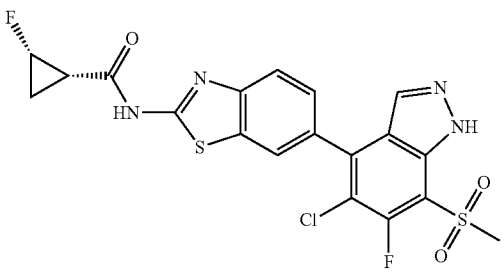 [SMILES: CS(=O)(=O)c1c(F)c(Cl)c(-c2ccc3nc(NC(=O)[C@@H]4C[C@@H]4F)sc3c2)c2cn[nH]c12]<br>(1S,2S)-N-(6-(5-chloro-6-fluoro-7-(methylsulfonyl)-1H-indazol-4-yl)benzo[d]thiazol-2-yl)-2-fluorocyclopropane-1-carboxamide | $^1$H NMR (400 MHz, DMSO-d$_6$) δ 13.47 (br s, 1H), 12.87 (s, 1H), 8.24 (d, J = 1.6 Hz, 1H), 8.00 (s, 1H), 7.94 (d, J = 8.4 Hz, 1H), 7.62 (dd, J = 1.8, 8.4 Hz, 1H), 5.17-4.95 (m, 1H), 3.56 (s, 3H), 2.29-2.22 (m, 1H), 1.83-1.71 (m, 1H), 1.37-1.29 (m, 1H); LCMS(electrospray) m/z 483 (M + H+). | B |
| 120 | 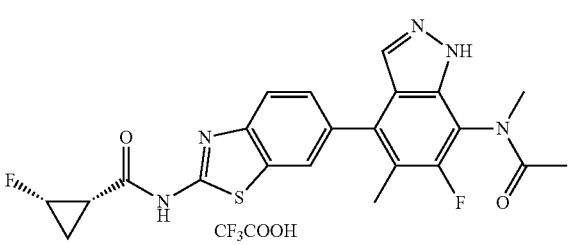 [SMILES: CC(=O)N(C)c1c(F)c(C)c(-c2ccc3nc(NC(=O)[C@@H]4C[C@@H]4F)sc3c2)c2cn[nH]c12 ; "CF3COOH"]<br>(1S,2S)-2-fluoro-N-(6-(6-fluoro-5-methyl-7-(N-methylacetamido)-1H-indazol-4-yl)benzo[d]thiazol-2-yl)cyclopropane-1-carboxamide. 1 TFA | $^1$H NMR (400 MHz, DMSO-d$_6$) δ 11.22-11.13 (m, 1H), 8.66 (d, J = 7.1 Hz, 1H), 7.95-7.87 (m, 1H), 7.72-7.70 (m, 1H), 6.96-6.93 (m, 1H), 6.92-6.89 (m, 1H), 5.07-4.81 (m, 1H), 3.21 (s, 3H), 2.30-2.25 (m, 3H), 2.25-2.23 (m, 1H), 2.20-2.09 (m, 1H), 1.79 (s, 3H), 1.74-1.63 (m, 1H), 1.28-1.09 (m, 1H); LCMS(electrospray) m/z 456.1 (M + H+) | B |
| 121 | 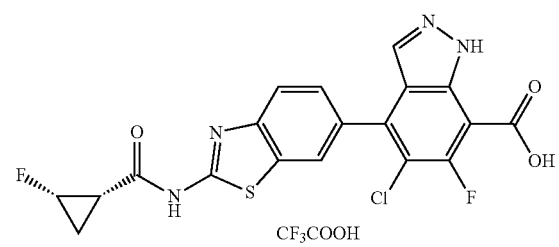<br>5-chloro-6-fluoro-4-(2-((1S,2S)-2-fluorocyclopropane-1-carboxamido)benzo[d]thiazol-6-yl)-1H-indazole-7-carboxylic acid. 1 TFA | $^1$H NMR (400 MHz, DMSO-d$_6$) δ 13.45 (br s, 1H), 12.85 (s, 1H), 8.23 (d, J = 1.6 Hz, 1H), 7.94-7.88 (m, 2H), 7.62 (dd, J = 1.8, 8.4 Hz, 1H), 5.21-4.90 (m, 1H), 2.29-2.17 (m, 1H), 1.85-1.62 (m, 1H), 1.42-1.26 (m, 1H); LCMS(electrospray) m/z 449.2 (M + H+). | B |

TABLE 1-continued

Compounds of Examples

| Ex # | Structure/Name | ¹H NMR/MS (M + 1) | Method |
|---|---|---|---|
| 122 | 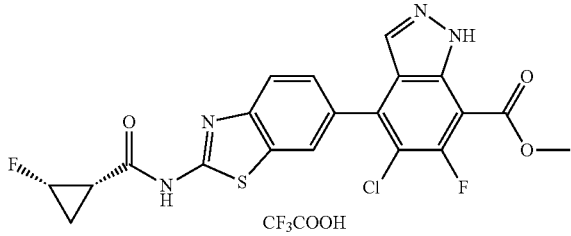<br>methyl 5-chloro-6-fluoro-4-(2-((1S,2S)-2-fluorocyclopropane-1-carboxamido)benzo[d]thiazol-6-yl)-1H-indazole-7-carboxylate. 1 TFA | ¹H NMR (400 MHz, DMSO-d$_6$) δ 13.57 (s, 1H), 12.86 (s, 1H), 8.36-8.16 (m, 1H), 7.96-7.91 (m, 2H), 7.63 (dd, J = 1.8, 8.4 Hz, 1H), 5.22-4.90 (m, 1H), 4.00 (s, 3H), 2.30-2.20 (m, 1H), 1.83-1.68 (m, 1H), 1.45-1.21 (m, 1H); LCMS(electrospray) m/z 463.1 (M + H+). | B |
| 123 | 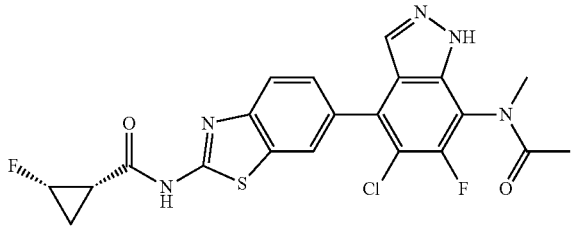<br>(1S,2S)-N-(6-(5-chloro-6-fluoro-7-(N-methylacetamido)-1H-indazol-4-yl)benzo[d]thiazol-2-yl)-2-fluorocyclopropane-1-carboxamide. 1 TFA | ¹H NMR (400 MHz, DMSO-d$_6$) δ 14.06-13.79 (m, 1H), 12.83 (s, 1H), 8.21 (d, J = 1.6 Hz, 1H), 7.91-7.89 (m, 1H), 7.63 (d, J = 1.7 Hz, 1H), 7.62-7.59 (m, 1H), 5.15-4.96 (m, 1H), 3.23 (s, 3H), 2.27-2.23 (m, 1H), 1.82 (s, 3H), 1.76-1.69 (m, 1H), 1.36-1.30 (m, 1H); LCMS(electrospray) m/z 476.1 (M + H+). | B |
| 124 | 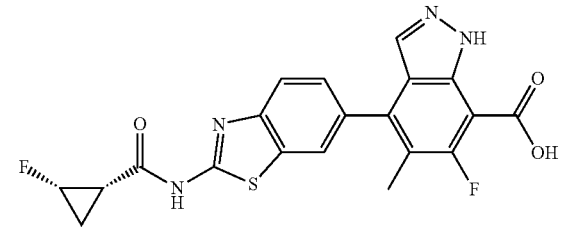 [SMILES: Cc1c(F)c(C(=O)O)c2[nH]ncc2c1-c1ccc2nc(NC(=O)[C@@H]3C[C@@H]3F)sc2c1]<br>6-fluoro-4-(2-((1S,2S)-2-fluorocyclopropane-1-carboxamido)benzo[d]thiazol-6-yl)-5-methyl-1H-indazole-7-carboxylic acid | ¹H NMR (400 MHz, DMSO-d$_6$) δ 12.94 (br s, 1H), 8.10 (d, J = 1.5 Hz, 1H), 7.91(d, J = 8.3 Hz, 1H), 7.68 (s, 1H), 7.51 (dd, J = 1.7, 8.3 Hz, 1H), 5.19-4.92 (m, 1H), 2.31-2.25 (m, 1H), 2.19 (d, J = 3.1 Hz, 3H), 1.82-1.71 (m, 1H), 1.37-1.28 (m, 1H); LCMS(electrospray) m/z 429.1(M + H+). | B |
| 125 | 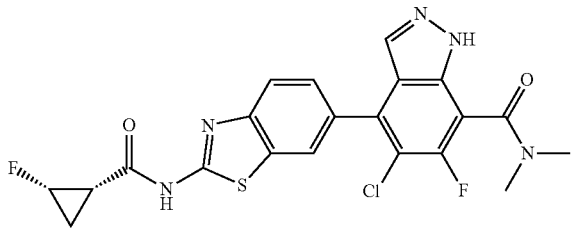 [SMILES: CN(C)C(=O)c1c(F)c(Cl)c(-c2ccc3nc(NC(=O)[C@@H]4C[C@@H]4F)sc3c2)c2cn[nH]c12]<br>5-chloro-6-fluoro-4-(2-((1S,2S)-2-fluorocyclopropane-1-carboxamido)benzo[d]thiazol-6-yl)-N,N-dimethyl-1H-indazole-7-carboxamide | ¹H NMR (400 MHz, DMSO-d$_6$) δ 13.86-13.55 (m, 1H), 8.21 (d, J = 1.5 Hz, 1H), 7.92 (s, 1H), 7.90 (s, 1H), 7.61 (dd, J = 1.8, 8.4 Hz, 1H), 5.17-4.94 (m, 1H), 3.13 (s, 3H), 2.94 (s, 3H), 2.28-2.22 (m, 1H), 1.81-1.72 (m, 1H), 1.36-1.28 (m, 1H); LCMS(electrospray) m/z 475.9 (M + H+). | B |

TABLE 1-continued

Compounds of Examples

| Ex # | Structure/Name | ¹H NMR/MS (M + 1) | Method |
|---|---|---|---|
| 126 | (1S,2S)-N-(6-(5-chloro-6,7-difluoro-1H-indazol-4-yl)benzo[d]thiazol-2-yl)-2-fluorocyclopropane-1-carboxamide | ¹H NMR (400 MHz, DMSO-$d_6$) δ 8.16 (d, J = 1.6 Hz, 1H), 7.95 (d, J = 3.2 Hz, 1H), 7.89 (d, J = 8.3 Hz, 1H), 7.56 (dd, J = 1.8, 8.3 Hz, 1H), 5.18-4.93 (m, 1H), 2.29-2.20 (m, 1H), 1.83-1.70 (m, 1H), 1.32 (tdd, J = 6.4, 9.0, 12.8 Hz, 1H); LCMS(electrospray) m/z 423.1 (M + H+). | B |
| 127 | 5-chloro-6-fluoro-4-(2-((1S,2S)-2-fluorocyclopropane-1-carboxamido)benzo[d]thiazol-6-yl)-N-methyl-1H-indazole-7-carboxamide | ¹H NMR (400 MHz, DMSO-$d_6$) δ 13.71-13.47 (s, 1H), 12.98-12.70 (s, 1H), 8.65-8.55 (s, 1H), 8.21 (s, 1H), 7.97-7.88 (m, 1H), 7.85 (s, 1H), 7.63-7.56 (m, 1H), 5.20-4.91 (m, 1H), 2.91 (br d, J = 4.3 Hz, 3H), 2.30-2.21 (m, 1H), 1.84-1.69 (m, 1H), 1.41-1.28 (m, 1H); LCMS(electrospray) m/z 462.0 (M + H+). | B |
| 128 | (1S,2S)-N-(6-(7-acetyl-5-chloro-6-fluoro-1H-indazol-4-yl)benzo[d]thiazol-2-yl)-2-fluorocyclopropane-1-carboxamide | ¹H NMR (400 MHz, DMSO-$d_6$) δ 13.69 (s, 1H), 12.86 (s, 1H), 8.24 (d, J = 1.5 Hz, 1H), 7.97-7.87 (m, 2H), 7.63 (dd, J = 1.7, 8.4 Hz, 1H), 5.22-4.92 (m, 1H), 2.77 (d, J = 6.2 Hz, 3H), 2.31-2.21 (m, 1H), 1.83-1.70 (m, 1H), 1.25-1.32 (m, J = 2.5, 6.3, 12.8 Hz, 1H); LCMS(electrospray) m/z 447.2 (M + H+). | B |
| 129 | (1S,2S)-N-(6-(7-(azetidin-3-yl(methyl)amino)-5-chloro-6-fluoro-1H-indazol-4-yl)benzo[d]thiazol-2-yl)-2-fluorocyclopropane-1-carboxamide | ¹H NMR (400 MHz, DMSO-$d_6$) δ 8.14 (s, 1H), 7.92-7.82 (m, 2H), 7.59-7.51 (m, 1H), 5.18-4.92 (m, 1H), 4.51-4.40 (m, 1H), 4.11-3.85 (m, 3H), 2.94 (s, 3H), 2.89-2.16 (m, 1H), 2.03-1.88 (m, 1H), 1.83-1.68 (m, 1H), 1.38-1.27 (m, 1H); LCMS (electrospray) m/z 489.10 (M + H)+. | B |

TABLE 1-continued

Compounds of Examples

| Ex # | Structure/Name | ¹H NMR/MS (M + 1) | Method |
|---|---|---|---|
| 130 | 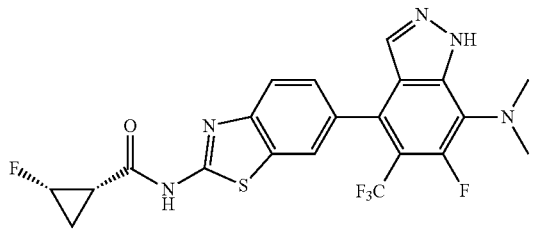 [SMILES: CN(C)c1c(F)c(C(F)(F)F)c(-c2ccc3nc(NC(=O)[C@@H]4C[C@@H]4F)sc3c2)c2cn[nH]c12]<br>(1S,2S)-N-(6-(7-(dimethylamino)-6-fluoro-5-(trifluoromethyl)-1H-indazol-4-yl)benzo[d]thiazol-2-yl)-2-fluorocyclopropane-1-carboxamide | ¹H NMR (400 MHz, DMSO-$d_6$) δ 13.86-13.56 (m, 1H), 12.93-12.67 (m, 1H), 8.01 (s, 1H), 7.82 (d, J = 8.3 Hz, 1H), 7.63 (s, 1H), 7.40 (br d, J = 8.5 Hz, 1H), 5.20-4.90 (m, 1H), 3.01 (s, 6H), 2.28-2.18 (m, 1H), 1.82-1.69 (m, 1H), 1.31 (ddd, J = 2.4, 6.4, 12.5 Hz, 1H); LCMS(electrospray) m/z 482.1 (M + H+). | B |
| 131 | 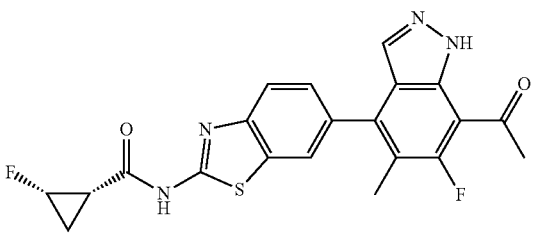 [SMILES: CC(=O)c1c(F)c(C)c(-c2ccc3nc(NC(=O)[C@@H]4C[C@@H]4F)sc3c2)c2cn[nH]c12]<br>(1S,2S)-N-(6-(7-acetyl-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 13.39 (s, 1H), 12.82 (br d, J = 1.7 Hz, 1H), 8.13 (s, 1H), 7.91 (d, J = 8.3 Hz, 1H), 7.76 (s, 1H), 7.52 (dd, J = 1.4, 8.3 Hz, 1H), 5.18-4.92 (m, 1H), 2.74 (d, J = 6.2 Hz, 3H), 2.24 (br d, J = 3.2 Hz, 3H), 1.86-1.66 (m, 1H), 1.32 (tdd, J = 6.5, 8.8, 12.7 Hz, 1H); LCMS(electrospray) m/z 427.10 (M + H+). | B |
| 132 | 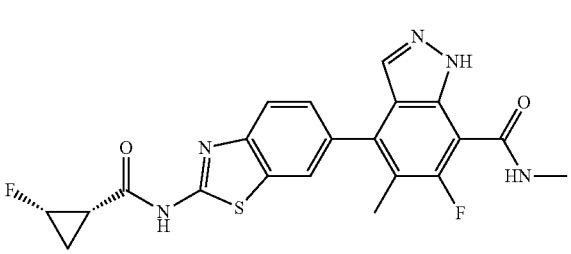<br>6-fluoro-4-(2-((1S,2S)-2-fluorocyclopropane-1-carboxamido)benzo[d]thiazol-6-yl)-N,5-dimethyl-1H-indazole-7-carboxamide | ¹H NMR (400 MHz, DMSO-$d_6$) δ 13.19 (s, 1H), 12.81 (br s, 1H), 8.11 (d, J = 1.5 Hz, 1H), 7.90 (d, J = 8.3 Hz, 1H), 7.70 (d, J = 1.1 Hz, 1H), 7.50 (dd, J = 1.7, 8.3 Hz, 1H), 5.18-4.93 (m, 1H), 2.90 (d, J = 4.5 Hz, 3H), 2.29-2.24 (m, 1H), 2.22 (d, J = 3.1 Hz, 3H), 1.87-1.67 (m, 1H), 1.33 (tdd, J = 6.4, 8.9, 12.7 Hz, 1H); LCMS(electrospray) m/z 442.1 (M + H+). | B |
| 133 | 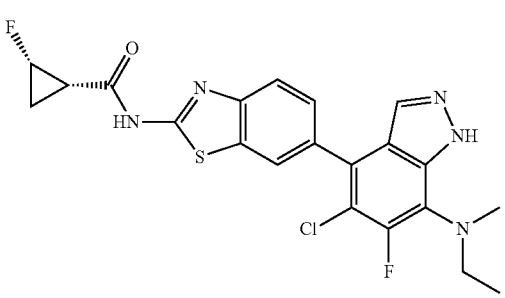 [SMILES: CCN(C)c1c(F)c(Cl)c(-c2ccc3nc(NC(=O)[C@@H]4C[C@@H]4F)sc3c2)c2cn[nH]c12]<br>(1S,2S)-N-(6-(5-chloro-7-(ethyl(methyl)amino)-6-fluoro-1H-indazol-4-yl)benzo[d]thiazol-2-yl)-2-fluorocyclopropane-1-carboxamide | ¹H NMR (400 MHz, DMSO-$d_6$) δ 13.45 (br s, 1H), 12.81 (s, 1H), 8.15 (d, J = 1.5 Hz, 1H), 7.89 (d, J = 8.4 Hz, 1H), 7.78 (s, 1H), 7.57 (dd, J = 1.8, 8.4 Hz, 1H), 5.17-4.92 (m, 1H), 3.26 (q, J = 6.4 Hz, 2H), 2.98 (s, 3H), 2.30-2.21 (m, 1H), 1.85-1.70 (m, 1H), 1.33 (tdd, J = 6.5, 8.8, 12.8 Hz, 1H), 1.09 (t, J = 7.1 Hz, 3H); LCMS(electrospray) m/z 462.1(M + H+). | B |

TABLE 1-continued

Compounds of Examples

| Ex # | Structure/Name | ¹H NMR/MS (M + 1) | Method |
|---|---|---|---|
| 134 | 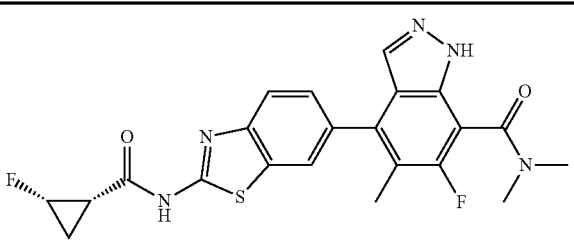<br>6-fluoro-4-(2-((1S,2S)-2-fluorocyclopropane-1-carboxamido)benzo[d]thiazol-6-yl)-N,N,5-trimethyl-1H-indazole-7-carboxamide | ¹H NMR (400 MHz, DMSO-$d_6$) δ 13.38 (br s, 1H), 8.10 (d J = 1.3 Hz, 1H), 7.88 (d J = 8.3 Hz, 1H), 7.74 (s, 1H), 7.51 (dd, J = 1.8, 8.4 Hz, 1H), 5.18-4.91 (m, 1H), 3.12 (s, 3H), 2.93 (s, 3H), 2.24 (br d, J = 2.1 Hz, 1H), 2.21 (d, J = 2.8 Hz, 3H), 1.83-1.67 (m, 1H), 1.31 (ddd, J = 2.8, 6.3, 12.7 Hz, 1H); LCMS(electrospray) m/z 455.9 (M + H+). | B |
| 135 | 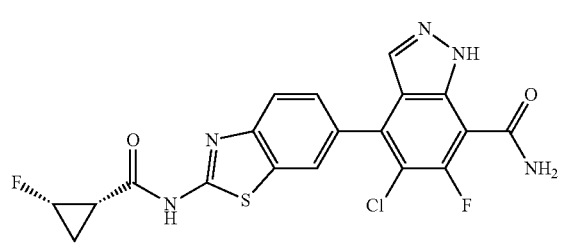 [SMILES: NC(=O)c1c(F)c(Cl)c(-c2ccc3nc(NC(=O)[C@@H]4C[C@@H]4F)sc3c2)c2cn[nH]c12]<br>5-chloro-6-fluoro-4-(2-((1S,2S)-2-fluorocyclopropane-1-carboxamido)benzo[d]thiazol-6-yl)-1H-indazole-7-carboxamide | ¹H NMR (400 MHz, DMSO-$d_6$) δ 13.50 (s, 1H), 12.85 (s, 1H), 8.21 (d, J = 1.4 Hz, 1H), 8.04 (s, 2H), 7.92 (d, J = 8.4 Hz, 1H), 7.84 (s, 1H), 7.60 (dd, J = 1.7, 8.3 Hz, 1H), 5.20-4.94 (m, 1H), 2.32-2.18 (m, 1H), 1.84-1.69 (m, 1H), 1.29~1.36(m, 1H); LCMS(electrospray) m/z 448.1 (M + H+). | B |
| 136 | 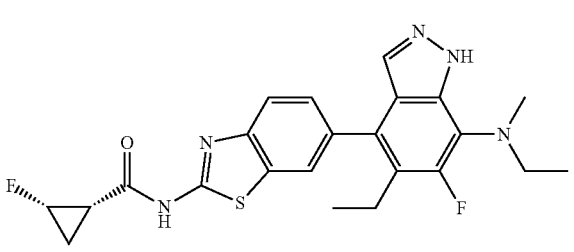 [SMILES: CCc1c(F)c(N(C)CC)c2[nH]ncc2c1-c1ccc2nc(NC(=O)[C@@H]3C[C@@H]3F)sc2c1]<br>(1S,2S)-N-(6-(5-ethyl-7-(ethyl(methyl)amino)-6-fluoro-1H-indazol-4-yl)benzo[d]thiazol-2-yl)-2-fluorocyclopropane-1-carboxamide | ¹H NMR (400 MHz, DMSO-$d_6$) δ 13.12 (br s, 1H), 12.76 (br d, J = 12.7 Hz, 1H), 8.00 (s, 1H), 7.85 (d, J = 8.3 Hz, 1H), 7.54 (s, 1H), 7.43 (dd, J = 1.6, 8.2 Hz, 1H), 5.21-4.89 (m, 1H), 3.21 (q, J = 6.9 Hz, 2H), 2.94 (s, 3H), 2.55 (br d, J = 7.6 Hz, 2H), 2.28-2.19 (m, 1H), 1.83-1.68 (m, 1H), 1.37-1.26 (m, 1H), 1.07 (dt, J = 4.0, 7.1 Hz, 6H); LCMS(electrospray) m/z 456.2 (M + H+). | B |
| 137 | 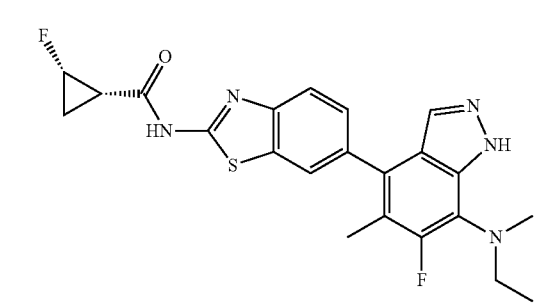 [SMILES: CCN(C)c1c(F)c(C)c(-c2ccc3nc(NC(=O)[C@@H]4C[C@@H]4F)sc3c2)c2cn[nH]c12]<br>(1S,2S)-N-(6-(7-(ethyl(methyl)amino)-6-fluoro-5-methyl-1H-indazol-4-yl)benzo[d]thiazol-2-yl)-2-fluorocyclopropane-1-carboxamide | ¹H NMR (400 MHz, DMSO-$d_6$) δ 13.11 (s, 1H), 8.04 (d, J = 1.4 Hz, 1H), 7.85 (d, J = 8.6 Hz, 1H), 7.64 (s, 1H), 7.47 (dd, J = 1.8, 8.3 Hz, 1H), 5.19-4.89 (m, 1H), 3.23-3.17 (m, 2H), 2.93 (d, J = 1.9 Hz, 3H), 2.28-2.20 (m, 1H), 2.17 (d, J = 3.1 Hz, 3H), 1.85-1.68 (m, 1H), 1.38-1.23 (m, 1H), 1.06 (t, J = 7.1 Hz, 3H); LCMS(electrospray) m/z 441.14 (M + H+). | B |

TABLE 1-continued

Compounds of Examples

| Ex # | Structure/Name | ¹H NMR/MS (M + 1) | Method |
|---|---|---|---|
| 138 | 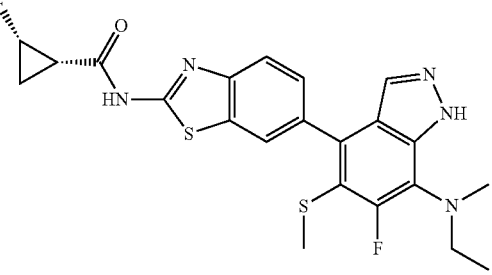<br>(1S,2S)-N-(6-(7-(ethyl(methyl)amino)-6-fluoro-5-(methylthio)-1H-indazol-4-yl)benzo[d]thiazol-2-yl)-2-fluorocyclopropane-1-carboxamide | ¹H NMR (400 MHz, DMSO-$d_6$) δ 13.34 (br s, 1H), 8.04 (d, J = 1.3 Hz, 1H), 7.83 (d, J = 8.2 Hz, 1H), 7.68 (s, 1H), 7.49 (dd, J = 1.7, 8.3 Hz, 1H), 5.16-4.94 (m, 1H), 3.23 (q, J = 7.1 Hz, 2H), 2.95 (d, J = 2.0 Hz, 3H), 2.28-2.22 (m, 1H), 2.20 (s, 3H), 1.82-1.68 (m, 1H), 1.31 (tdd, J = 6.2, 8.9, 12.6 Hz, 1H), 1.07 (t, J = 7.1 Hz, 3H); LCMS(electrospray) m/z 474.1 (M + H+). | B |
| 139 | 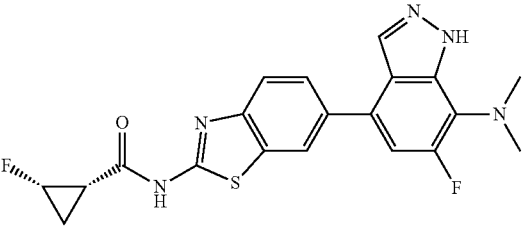<br>(1S,2S)-N-(6-(7-(dimethylamino)-6-fluoro-1H-indazol-4-yl)benzo[d]thiazol-2-yl)-2-fluorocyclopropane-1-carboxamide | ¹H NMR (400 MHz, DMSO-$d_6$) δ 13.31 (s, 1H), 12.77 (s, 1H), 8.33 (s, 1H), 8.24 (br s, 1H), 7.89-7.81 (m, 1H), 7.80-7.74 (m, 1H), 7.13 (br d, J = 13.7 Hz, 1H), 5.17-4.92 (m, 1H), 2.95 (br s, 6H), 2.27-2.18 (m, 1H), 1.82-1.69 (m, 1H), 1.31 (br s, 1H); LCMS(electrospray) m/z 414.2 (M + H+). | B |
| 140 | 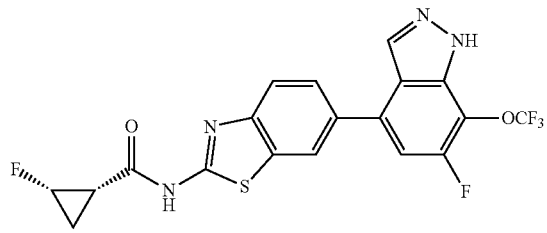 [SMILES: O=C(Nc1nc2ccc(-c3cc(F)c(OC(F)(F)F)c4[nH]ncc34)cc2s1)[C@@H]1C[C@@H]1F]<br>(1S,2S)-2-fluoro-N-(6-(6-fluoro-7-(trifluoromethoxy)-1H-indazol-4-yl)benzo[d]thiazol-2-yl)cyclopropane-1-carboxamide | ¹H NMR (400 MHz, DMSO-$d_6$) δ 14.04 (br s, 1H), 12.83 (br s, 1H), 8.47-8.36 (m, 2H), 7.92-7.83 (m, 2H), 7.45 (br d, J = 11.7 Hz, 1H), 5.19-4.95 (m, 1H), 2.30-2.20 (m, 1H), 1.84-1.70 (m, 1H), 1.34 (ddd, J = 2.4, 6.2, 12.9 Hz, 1H); LCMS(electrospray) m/z 455.2 (M + H+). | B |
| 141 | 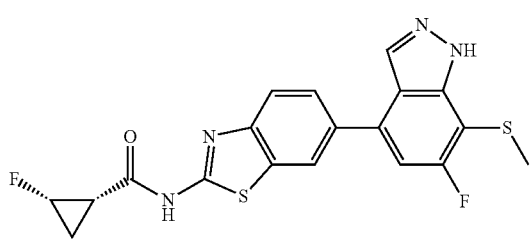 [SMILES: CSc1c(F)cc(-c2ccc3nc(NC(=O)[C@@H]4C[C@@H]4F)sc3c2)c2cn[nH]c12]<br>(1S,2S)-2-fluoro-N-(6-(6-fluoro-7-(methylthio)-1H-indazol-4-yl)benzo[d]thiazol-2-yl)cyclopropane-1-carboxamide | ¹H NMR (400 MHz, DMSO-$d_6$) δ 13.56 (s, 1 H) 12.81 (s, 1 H) 8.42 (s, 1 H) 8.34 (s, 1 H) 7.89-7.82 (m, 2 H) 7.29 (d, J = 10.4 Hz, 1 H) 5.14-4.97 (m, 1 H) 2.49 (s, 3 H) 2.28-2.23 (m, 1 H) 1.80-1.73 (m, 1 H) 1.35-1.30 (m, 1 H); LCMS(electrospray) m/z 416.9 (M + H+). | B |

TABLE 1-continued

Compounds of Examples

| Ex # | Structure/Name | ¹H NMR/MS (M + 1) | Method |
|---|---|---|---|
| 142 | 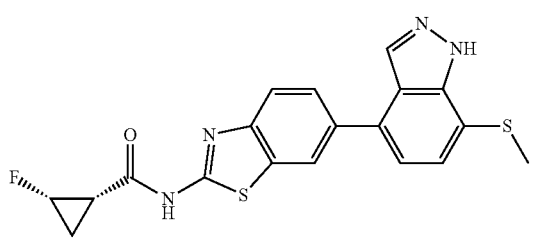<br>(1S,2S)-2-fluoro-N-(6-(7-(methylthio)-1H-indazol-4-yl)benzo[d]thiazol-2-yl)cyclopropane-1-carboxamide | ¹H NMR (400 MHz, DMSO-$d_6$) δ 13.21-13.61 (m, 1 H) 12.76 (s, 1 H) 8.35 (d, J = 1.50 Hz, 1 H) 8.31 (s, 1 H) 7.85-7.89 (m, 1 H) 7.79 (dd, J = 8.38, 1.75 Hz, 1 H) 7.34-7.39 (m, 1 H) 7.27-7.32 (m, 1 H) 4.93-5.17 (m, 1 H) 3.17 (s, 1 H) 2.62 (s, 3 H) 2.20-2.29 (m, 1 H) 1.70-1.82 (m, 1 H) 1.32 (ddt, J = 12.77, 8.93, 6.35, 6.35 Hz, 1 H); LCMS(electrospray) m/z 399.0 (M + H+). | B |
| 143 | 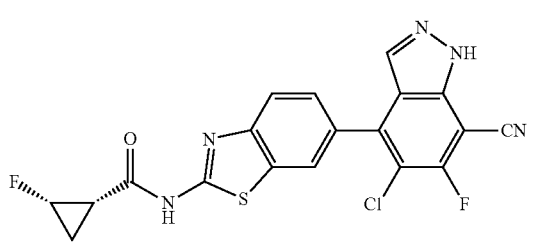 [SMILES: N#Cc1c(F)c(Cl)c(-c2ccc3nc(NC(=O)[C@@H]4C[C@@H]4F)sc3c2)c2cn[nH]c12]<br>(1S,2S)-N-(6-(5-chloro-7-cyano-6-fluoro-1H-indazol-4-yl)benzo[d]thiazol-2-yl)-2-fluorocyclopropane-1-carboxamide | ¹H NMR (400 MHz, DMSO-$d_6$) δ 12.77 (br s, 1H), 8.15-7.99 (m, 2H), 7.83 (br d, J = 8.3 Hz, 1H), 7.45 (br d, J = 8.1 Hz, 1H), 7.18 (br s, 1H), 5.17-4.93 (m, 1H), 2.33 (s, 3H), 2.25 (br s, 1H), 1.84-1.70 (m, 1H), 1.37-1.27 (m, 1H); LCMS(electrospray) m/z 346.1(M + H+). | B |
| 144 | 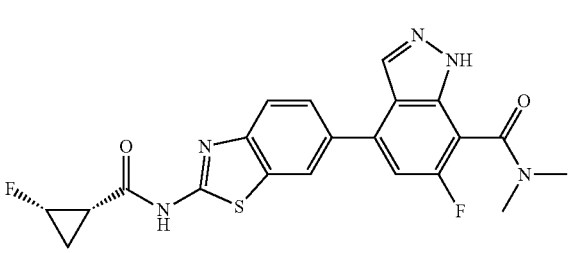 [SMILES: CN(C)C(=O)c1c(F)cc(-c2ccc3nc(NC(=O)[C@@H]4C[C@@H]4F)sc3c2)c2cn[nH]c12]<br>6-fluoro-4-(2-((1S,2S)-2-fluorocyclopropane-1-carboxamido)benzo[d]thiazol-6-yl)-N,N-dimethyl-1H-indazole-7-carboxamide | ¹H NMR (400 MHz, DMSO-$d_6$) δ 13.42 (br s, 1H), 12.82 (br s, 1H), 8.11 (s, 1H), 7.98 (s, 1H), 7.85 (d, J = 8.3 Hz, 1H), 7.55 (td, J = 2.1, 8.3 Hz, 1H), 7.47 (dd, J = 0.7, 9.7 Hz, 1H), 5.18-4.90 (m, 1H), 2.79 (s, 3H), 2.63 (d, J = 1.0 Hz, 3H), 2.24 (td, J = 6.9, 13.6 Hz, 1H), 1.85-1.67 (m, 1H), 1.39-1.25 (m, 1H); LCMS(electrospray) m/z 442.2 (M + H+). | B |
| 145 | 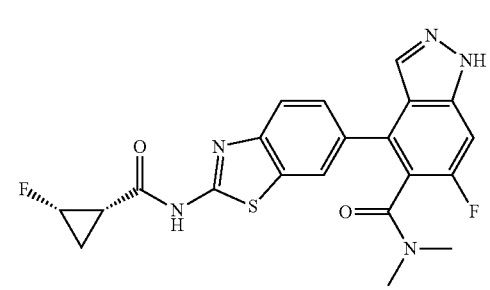 [SMILES: CN(C)C(=O)c1c(F)cc2[nH]ncc2c1-c1ccc2nc(NC(=O)[C@@H]3C[C@@H]3F)sc2c1]<br>6-fluoro-4-(2-((1S,2S)-2-fluorocyclopropane-1-carboxamido)benzo[d]thiazol-6-yl)-N,N-dimethyl-1H-indazole-5-carboxamide | ¹H NMR (400 MHz, DMSO-$d_6$) δ 13.42 (br s, 1H), 12.82 (br s, 1H), 8.11 (s, 1H), 7.98 (s, 1H), 7.85 (d, J = 8.3 Hz, 1H), 7.55 (td, J = 2.1, 8.3 Hz, 1H), 7.47 (dd, J = 0.7, 9.7 Hz, 1H), 5.18-4.90 (m, 1H), 2.79 (s, 3H), 2.63 (d, J = 1.0 Hz, 3H), 2.24 (td, J = 6.9, 13.6 Hz, 1H), 1.85-1.67 (m, 1H), 1.39-1.25 (m, 1H); LCMS(electrospray) m/z 442.2 (M + H+). | B |

TABLE 1-continued

Compounds of Examples

| Ex # | Structure/Name | ¹H NMR/MS (M + 1) | Method |
|---|---|---|---|
| 146 | 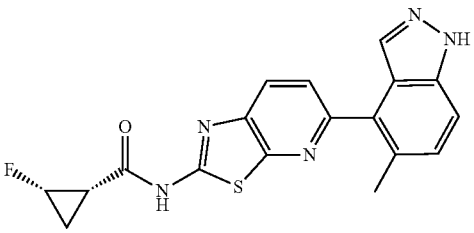 [SMILES: Cc1ccc2[nH]ncc2c1-c1ccc2nc(NC(=O)[C@@H]3C[C@@H]3F)sc2n1]<br><br>(1S,2S)-2-fluoro-N-(5-(5-methyl-1H-indazol-4-yl)thiazolo[5,4-b]pyridin-2-yl)cyclopropane-1-carboxamide | ¹H NMR (400 MHz, DMSO-$d_6$) δ 13.04 (s, 1H), 12.86 (s, 1H), 8.19 (d, J = 8.8 Hz, 1H), 7.74 (s, 1H), 7.65 (d, J = 8.4 Hz, 1H), 7.48 (d, J = 8.4 Hz, 1H), 7.29 (d, J = 8.4 Hz, 1H), 5.14-4.93 (m, 1H), 2.35 (s, 3H), 2.29-2.20 (m, 1H), 1.77-1.70 (m, 1H), 1.35-1.26 (m, 1H); LCMS (electrospray) m/z 368.1 (M + H)+. | D |
| 147 | 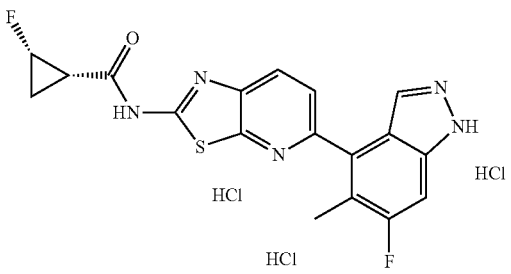 [SMILES: Cc1c(F)cc2[nH]ncc2c1-c1ccc2nc(NC(=O)[C@@H]3C[C@@H]3F)sc2n1 ; Cl ; Cl ; Cl]<br><br>(1S,2S)-2-fluoro-N-(5-(6-fluoro-5-methyl-1H-indazol-4-yl)thiazolo[5,4-b]pyridin-2-yl)cyclopropane-1-carboxamide. 3 HCl | ¹H NMR (400 MHz, DMSO-$d_6$) δ 12.96 (s, 1H), 8.25 (d, J = 8.0 Hz, 1H), 7.80 (s, 1H), 7.71 (d, J = 8.4 Hz, 1H), 7.42 (d, J = 10.0 Hz, 1H), 5.17-4.98 (m, 1H), 2.69 (s, 3H), 2.28-2.21 (m, 1H), 1.81-1.71 (m, 1H), 1.37-1.28 (m, 1H); LCMS (electrospray) m/z 386.1 (M + H)+. | D |
| 148 | 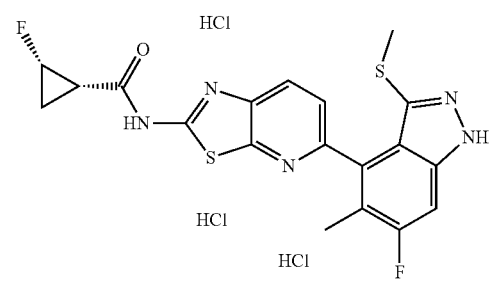 [SMILES: Cl ; CSc1n[nH]c2cc(F)c(C)c(-c3ccc4nc(NC(=O)[C@@H]5C[C@@H]5F)sc4n3)c12 ; Cl ; Cl]<br><br>(1S,2S)-2-fluoro-N-(5-(6-fluoro-5-methyl-3-(methylthio)-1H-indazol-4-yl)thiazolo[5,4-b]pyridin-2-yl)cyclopropane-1-carboxamide. 3 HCl | ¹H NMR (400 MHz, DMSO-$d_6$) δ 13.10 (br s, 1H), 12.95 (s, 1H), 8.21 (d, J = 8.0 Hz, 1H), 7.53 (d, J = 8.0 Hz, 1H), 7.37 (d, J = 10.1 Hz, 1H), 5.18-4.97 (m, 1H), 2.27 (s, 3H), 2.16 (td, J = 6.9, 13.8 Hz, 1H), 1.74-1.60 (m, 1H), 1.25-1.11 (m, 1H); LCMS (electrospray) m/z 432.1 (M + H)+. | D |
| 149 | 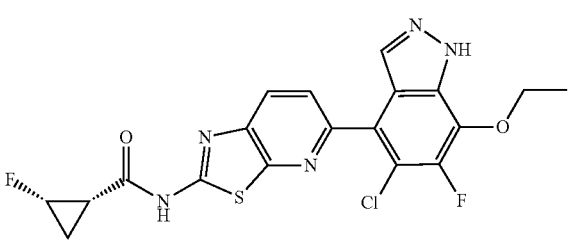<br><br>(1S,2S)-N-(5-(5-chloro-7-ethoxy-6-fluoro-1H-indazol-4-yl)thiazolo[5,4-b]pyridin-2-yl)-2-fluorocyclopropane-1-carboxamide. 2 TFA | ¹H NMR (400 MHz, DMSO-$d_6$) δ 13.77 (s, 1H), 12.97 (s, 1H), 8.27 (d, J = 8.4 Hz, 1H), 7.93 (s, 1H), 7.82 (d, J = 8.5 Hz, 1H), 5.20-4.95 (m, 1H), 4.40 (q, J = 7.0 Hz, 2H), 2.31-2.23 (m, 1H), 1.85-1.71 (m, 1H), 1.41 (t, J = 6.9 Hz, 3H), 1.38-1.30 (m, 1H); LCMS (electrospray) m/z 450.2 (M + H)+. | C |

TABLE 1-continued

Compounds of Examples

| Ex # | Structure/Name | ¹H NMR/MS (M + 1) | Method |
|---|---|---|---|
| 150 | 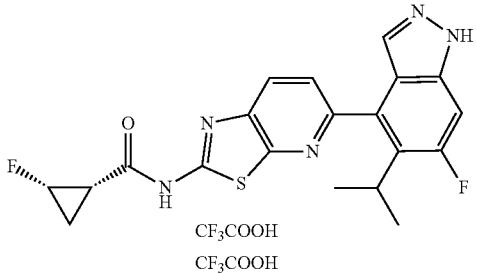 [SMILES: CC(C)c1c(F)cc2[nH]ncc2c1-c1ccc2nc(NC(=O)[C@@H]3C[C@@H]3F)sc2n1 ; "CF3COOH" ; "CF3COOH"]<br>(1S,2S)-2-fluoro-N-(5-(6-fluoro-5-isopropyl-1H-indazol-4-yl)thiazolo[5,4-b]pyridin-2-yl)cyclopropane-1-carboxamide. 2 TFA | ¹H NMR (400 MHz, DMSO-$d_6$) δ 12.93 (s, 1 H), 8.25 (d, J = 8.31 Hz, 1 H), 7.64-7.59 (m, 2 H), 7.39 (d, J = 11.62 Hz, 1 H), 5.19-4.96 (m, 1 H), 3.08 (dt, J = 14.15, 7.17 Hz, 1 H), 2.30-2.23 (m, 1 H), 1.83-1.71 (m, 1 H), 1.40-1.32 (m, 1 H), 1.31-1.23 (m, 6 H); LCMS (electrospray) m/z 414.2 (M + H)+. | D |
| 151 | 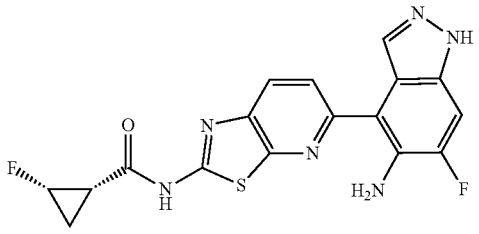 [SMILES: Nc1c(F)cc2[nH]ncc2c1-c1ccc2nc(NC(=O)[C@@H]3C[C@@H]3F)sc2n1]<br>(1S,2S)-N-(5-(5-amino-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 12.91 (s, 1 H), 8.25 (d, J = 8.56 Hz, 1 H), 8.00 (s, 1 H), 7.95 (d, J = 8.44 Hz, 1 H), 7.40 (d, J = 10.88 Hz, 1 H), z, 1 H), 5.21-4.94 (m, 1 H), 2.30-2.23 (m, 1 H), 1.84-1.69 (m, 1 H), 1.41-1.28 (m, 1 H); LCMS (electrospray) m/z 387.2 (M + H)+. | D |
| 152 | 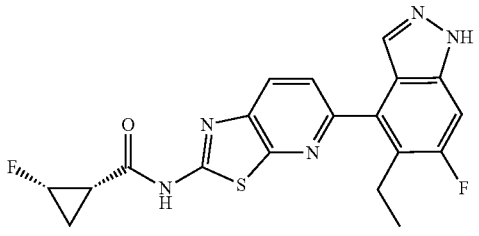 [SMILES: CCc1c(F)cc2[nH]ncc2c1-c1ccc2nc(NC(=O)[C@@H]3C[C@@H]3F)sc2n1]<br>(1S,2S)-N-(5-(5-ethyl-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.18 (br s, 1H), 12.94 (br s, 1H), 8.26 (d, J = 8.2 Hz, 1H), 7.72 (s, 1H), 7.68 (d, J = 8.3 Hz, 1H), 7.42 (d, J = 10.1 Hz, 1H), 5.20-4.95 (m, 1H), 2.65 (dq, J = 2.4, 7.2 Hz, 2H), 2.27 (m, 1H), 1.85-1.69 (m, 1H), 1.34 (m, 1H), 1.11 (t, J = 7.0 Hz, 3H); LCMS (electrospray) m/z 400.4 (M + H)+. | D |
| 153 | 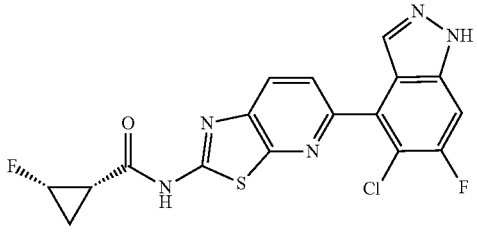<br>(1S,2S)-N-(5-(5-chloro-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 12.99 (s, 1H), 8.29 (d, J = 8.4 Hz, 1H), 7.91 (d, J = 0.9 Hz, 1H), 7.84 (d, J = 8.4 Hz, 1H), 7.71 (dd, J = 0.9, 9.2 Hz, 1H), 5.20-4.96 (m, 1H), 2.31-2.23 (m, 1H), 1.84-1.71 (m, 1H), 1.40-1.31 (m, 1H); LCMS (electrospray) m/z 406.3 (M + H)+. | D |

TABLE 1-continued

Compounds of Examples

| Ex # | Structure/Name | ¹H NMR/MS (M + 1) | Method |
|---|---|---|---|
| 154 | 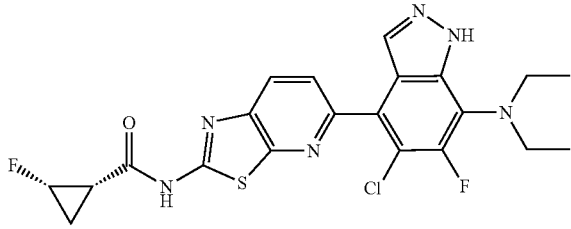 [SMILES: CCN(CC)c1c(F)c(Cl)c(-c2ccc3nc(NC(=O)[C@@H]4C[C@@H]4F)sc3n2)c2cn[nH]c12]<br>(1S,2S)-N-(5-(5-chloro-7-(diethylamino)-6-fluoro-1H-indazol-4-yl)thiazolo[5,4-b]pyridin-2-yl)-2-fluorocyclopropane-1-carboxamide | ¹H NMR (400 MHz, DMSO-d₆) δ 13.44 (br s, 1H), 12.96 (s, 1H), 8.26 (d, J = 8.3 Hz, 1H), 7.89 (s, 1H), 7.83 (d, J = 8.3 Hz, 1H), 5.21-4.95 (m, 1H), 3.30 (q, J = 6.4 Hz, 4H), 2.31-2.22 (m, 1H), 1.84-1.71 (m, 1H), 1.41-1.27 (m, 2H), 1.02 (t, J = 7.1 Hz, 6H); LCMS (electrospray) m/z 477.3 (M + H)+. | D |
| 155 | 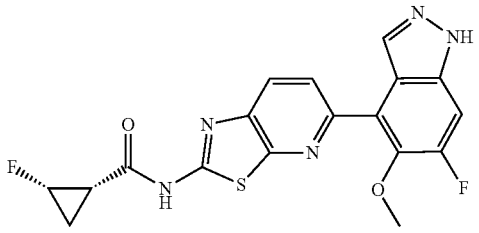<br>(1S,2S)-2-fluoro-N-(5-(6-fluoro-5-methoxy-1H-indazol-4-yl)thiazolo[5,4-b]pyridin-2-yl)cyclopropane-1-carboxamide | ¹H NMR (400 MHz, DMSO-d₆)) δ 12.93 (s, 1H), 8.25 (d, J = 8.6 Hz, 1H), 8.16 (s, 1H), 7.98 (d, J = 8.4 Hz, 1H), 7.55 (d, J = 10.6 Hz, 1H), 5.22-4.93 (m, 1H), 3.73 (s, 3H), 2.31-2.22 (m, 1H), 1.85-1.70 (m, 1H), 1.41-1.28 (m, 1H); LCMS (electrospray) m/z 402.4 (M + H+). | D |
| 156 | 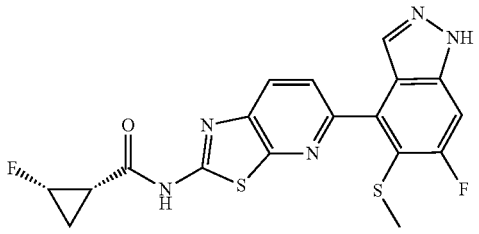<br>(1S,2S)-2-fluoro-N-(5-(6-fluoro-5-(methylthio)-1H-indazol-4-yl)thiazolo[5,4-b]pyridin-2-yl)cyclopropane-1-carboxamide | ¹H NMR (400 MHz, DMSO-d₆) δ 12.94 (s, 1H), 8.29-8.21 (m, 1H), 7.80 (d, J = 0.8 Hz, 1H), 7.74 (d, J = 8.4 Hz, 1H), 7.55 (dd, J = 0.8, 9.5 Hz, 1H), 5.20-4.95 (m, 1H), 2.32-2.27 (m, 1H), 2.26 (s, 3H), 1.84-1.71 (m, 1H), 1.35 (tdd, J = 6.4, 8.9, 13.0 Hz, 1H); LCMS(electrospray) m/z 418.3 (M + H+). | D |
| 157 | 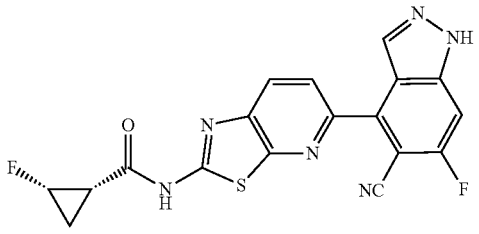 [SMILES: N#Cc1c(F)cc2[nH]ncc2c1-c1ccc2nc(NC(=O)[C@@H]3C[C@@H]3F)sc2n1]<br>(1S,2S)-N-(5-(5-cyano-6-fluoro-1H-indazol-4-yl)thiazolo[5,4-b]pyridin-2-yl)-2-fluorocyclopropane-1-carboxamide | ¹H NMR (400 MHz, DMSO-d₆) δ 13.84 (br s, 1H), 13.07 (s, 1H), 8.39-8.30 (m, 2H), 8.08 (d, J = 8.4 Hz, 1H), 7.77 (d, J = 9.5 Hz, 1H), 5.21-4.97 (m, 1H), 2.29 (td, J = 6.9, 13.4 Hz, 1H), 1.86-1.71 (m, 1H), 1.43-1.28 (m, 1H); LCMS(electrospray) m/z 397.4 (M + H+). | D |

TABLE 1-continued

Compounds of Examples

| Ex # | Structure/Name | ¹H NMR/MS (M + 1) | Method |
|------|----------------|-------------------|--------|
| 158 | 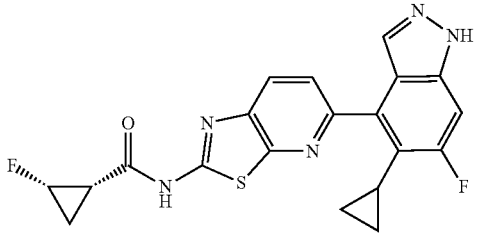 [SMILES: O=C(Nc1nc2ccc(-c3c(C4CC4)c(F)cc4[nH]ncc34)nc2s1)[C@@H]1C[C@@H]1F]<br>(1S,2S)-N-(5-(5-cyclopropyl-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.17 (br s, 1H), 12.83 (br s, 1H), 8.22 (d, J = 8.4 Hz, 1H), 7.87 (s, 1H), 7.81 (d, J = 8.4 Hz, 1H), 7.38 (d, J = 10.2 Hz, 1H), 5.20-4.95 (m, 1H), 2.31-2.23 (m, 1H), 2.07-1.98 (m, 1H), 1.84-1.69 (m, 1H), 1.34 (tdd, J = 6.4, 8.9, 12.8 Hz, 1H), 0.72-0.61 (m, 2H), 0.17-0.06 (m, 2H); LCMS(electrospray) m/z 412.4 (M + H+). | D |
| 159 | 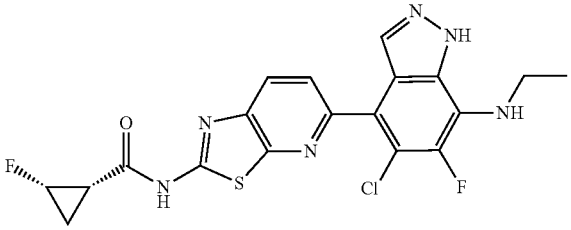 [SMILES: CCNc1c(F)c(Cl)c(-c2ccc3nc(NC(=O)[C@@H]4C[C@@H]4F)sc3n2)c2cn[nH]c12]<br>(1S,2S)-N-(5-(5-chloro-7-(ethylamino)-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 12.93 (s, 1H), 8.21 (d, J = 8.4 Hz, 1H), 7.93 (br s, 1H), 7.78 (d, J = 8.5 Hz, 1H), 5.19-4.96 (m, 1H), 2.31-2.22 (m, 1H), 1.84-1.70 (m, 1H), 1.39-1.27 (m, 1H), 1.22 (t, J = 7.1 Hz, 3H); LCMS(electrospray) m/z 449.3 (M + H+). | D |
| 160 | 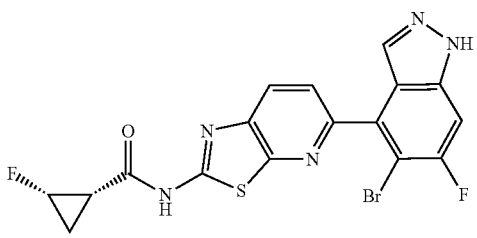<br>(1S,2S)-N-(5-(5-bromo-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.46 (br s, 1H), 12.97 (s, 1H), 8.29 (d, J = 8.3 Hz, 1H), 7.83 (s, 1H), 7.78 (d, J = 8.4 Hz, 1H), 7.67 (d, J = 8.8 Hz, 1H), 5.20-4.96 (m, 1H), 2.31-2.23 (m, 1H), 1.84-1.71 (m, 1H), 1.35 (tdd, J = 6.4, 9.0, 13.0 Hz, 1H); LCMS(electrospray) m/z 452.0 (M + H+). | D |
| 161 | 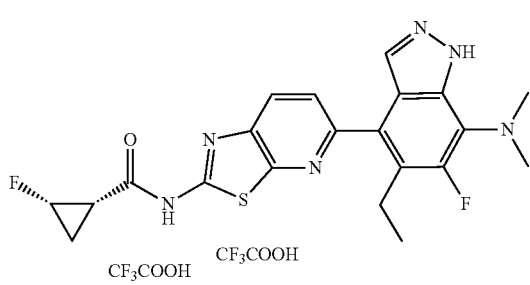 [SMILES: CCc1c(F)c(N(C)C)c2[nH]ncc2c1-c1ccc2nc(NC(=O)[C@@H]3C[C@@H]3F)sc2n1 ; "CF3COOH" ; "CF3COOH"]<br>(1S,2S)-N-(5-(7-(dimethylamino)-5-ethyl-6-fluoro-1H-indazol-4-yl)thiazolo[5,4-b]pyridin-2-yl)-2-fluorocyclopropane-1-carboxamide. 2 TFA | ¹H NMR (400 MHz, DMSO-$d_6$) δ 12.91 (s, 1H), 8.23 (d, J = 8.4 Hz, 1H), 7.72 (s, 1H), 7.64 (d, J = 8.4 Hz, 1H), 5.24-4.90 (m, 1H), 2.99 (s, 3H), 2.98 (s, 3H), 2.70-2.58 (m, 2H), 2.31-2.21 (m, 1H), 1.86-1.67 (m, 1H), 1.41-1.26 (m, 1H), 1.12 (t, J = 7.4 Hz, 3H); LCMS(electrospray) m/z 443.2 (M + H+). | D |

TABLE 1-continued

Compounds of Examples

| Ex # | Structure/Name | ¹H NMR/MS (M + 1) | Method |
|---|---|---|---|
| 162 | 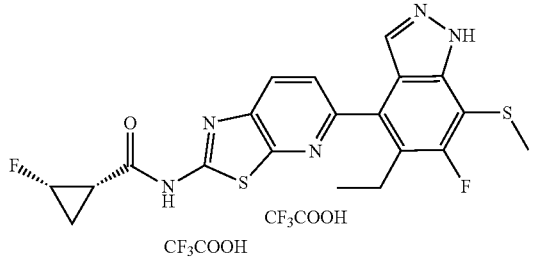<br><br>(1S,2S)-N-(5-(5-ethyl-6-fluoro-7-(methylthio)-1H-indazol-4-yl)thiazolo[5,4-b]pyridin-2-yl)-2-fluorocyclopropane-1-carboxamide. 2 TFA | ¹H NMR (400 MHz, DMSO-$d_6$) δ 13.47 (br s, 1H), 12.95 (s, 1H), 8.27 (d, J = 8.4 Hz, 1H), 7.79 (s, 1H), 7.69 (d J = 8.3 Hz, 1H), 5.18-4.96 (m, 1H), 2.67-2.64 (m, 2H), 2.53 (br s, 3H), 2.30-2.22 (m, 1H), 1.82-1.71 (m, 1H), 1.35 (tdd, J = 6.5, 8.8, 12.9 Hz, 1H), 1.12 (t, J = 7.4 Hz, 3H); LCMS(electrospray) m/z 446.3 (M + H+). | D |
| 163 | 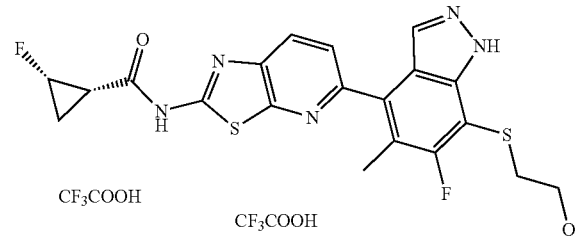<br><br>(1S,2S)-2-fluoro-N-(5-(6-fluoro-7-((2-hydroxyethyl)thio)-5-methyl-1H-indazol-4-yl)thiazolo[5,4-b]pyridin-2-yl)cyclopropane-1-carboxamide. 2TFA | ¹H NMR (400 MHz, CHLOROFORM-d) δ 13.46 (br s, 1H), 12.98 (s, 1H), 8.27 (d, J = 8.4 Hz, 1H), 7.88 (s, 1H), 7.73 (d, J = 8.4 Hz, 1H), 5.24-4.95 (m, 1H), 3.51 (br t, J = 6.9 Hz, 3H), 3.03 (br t, J = 6.6 Hz, 2H), 2.28 (br d, J = 2.6 Hz, 4H), 1.84-1.71 (m, 1H), 1.80-1.30 (m, 1H), 1.41-1.30 (m, 1H); LCMS(electrospray) m/z 462.1 (M + H+). | D |
| 164 | 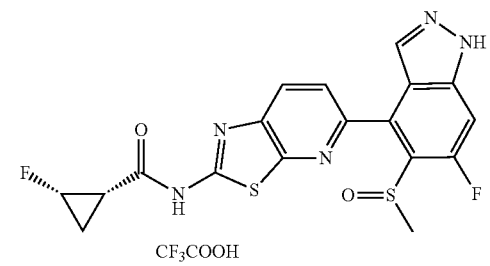<br><br>(1S,2S)-2-fluoro-N-(5-(6-fluoro-5-(methylsulfinyl)-1H-indazol-4-yl)thiazolo[5,4-b]pyridin-2-yl)cyclopropane-1-carboxamide. 2 TFA | ¹H NMR (400 MHz, DMSO-$d_6$) δ 13.65 (br s, 1H), 13.02 (s, 1H), 8.30 (d, J = 8.4 Hz, 1H), 8.10 (s, 1H), 7.92 (d, J = 8.4 Hz, 1H), 7.67 (d, J = 11.2 Hz, 1H), 5.19-4.97 (m, 1H), 3.18 (d, J = 1.0 Hz, 3H), 2.31-2.25 (m, 1H), 1.84-1.71 (m, 1H), 1.41-1.29 (m, 1H); LCMS(electrospray) m/z 434 (M + H+). | D |
| 165 | 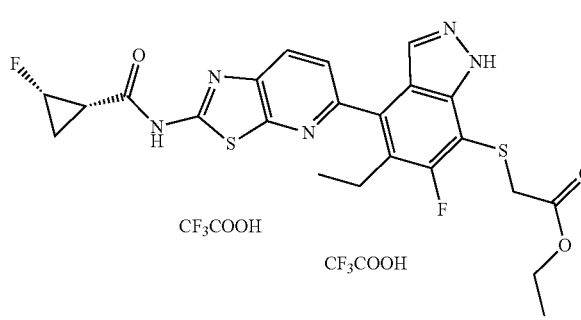<br><br>ethyl 2-((5-ethyl-6-fluoro-4-(2-((1S,2S)-2-fluorocyclopropane-1-carboxamido)thiazolo[5,4-b]pyridin-5-yl)-1H-indazol-7-yl)thio)acetate. 2 TFA | ¹H NMR (400 MHz, DMSO-$d_6$) δ 13.52 (br s, 1H), 13.33 (br s, 1H), 12.97 (s, 1H), 8.28 (d, J = 8.4 Hz, 1H), 8.09 (s, 1H), 7.81 (s, 1H), 7.71 (br s, 1H), 7.68 (d, J = 8.4 Hz, 1H), 5.25-4.96 (m, 1H), 3.97 (q, J = 7.1 Hz, 2H), 3.93-3.87 (m, 1H), 3.78 (s, 2H), 3.70 (s, 1H), 2.72-2.62 (m, 3H), 2.32-2.23 (m, 1H), 1.84-1.71 (m, 1H), 1.41-1.31 (m, 1H), 1.21 (t, J = 7.5 Hz, 1H), 1.12 (t, J = 7.4 Hz, 3H), 1.01 (t, J = 7.1 Hz, 3H), 0.94 (t, J = 7.1 Hz, 1H); LCMS(electrospray) m/z 518.3 (M + H+). | D |

TABLE 1-continued

Compounds of Examples

| Ex # | Structure/Name | ¹H NMR/MS (M + 1) | Method |
|---|---|---|---|
| 166 | 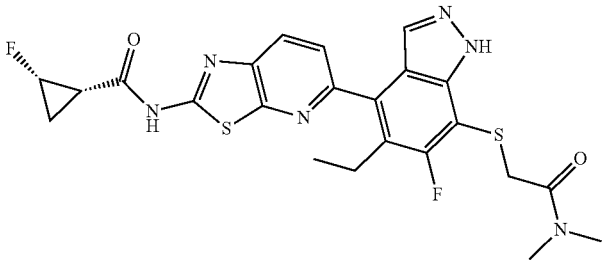 [SMILES: CCc1c(F)c(SCC(=O)N(C)C)c2[nH]ncc2c1-c1ccc2nc(NC(=O)[C@@H]3C[C@@H]3F)sc2n1]<br><br>(1S,2S)-N-(5-(7-((2-(dimethylamino)-2-oxoethyl)thio)-5-ethyl-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.48 (s, 1H), 8.10 (d, J = 8.2 Hz, 1H), 7.81 (s, 1H), 7.58 (d, J = 8.2 Hz, 1H), 5.19-4.84 (m, 1H), 3.97 (s, 2H), 3.02 (s, 3H), 2.91-2.76 (m, 6H), 2.74-2.62 (m, 2H), 2.21-2.10 (m, 1H), 1.81-1.64(m, 1H), 1.29-1.19 (m, 1H), 1.13 (t, J = 7.3 Hz, 3H); LCMS(electrospray) m/z 517.1 (M + H+). | D |
| 167 | 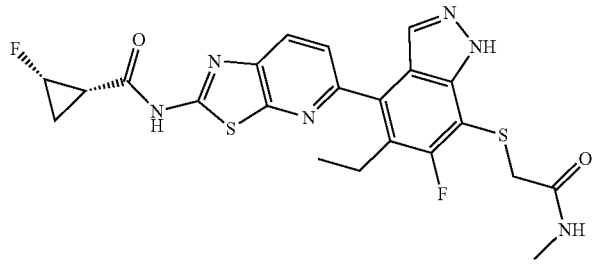 [SMILES: CCc1c(F)c(SCC(=O)NC)c2[nH]ncc2c1-c1ccc2nc(NC(=O)[C@@H]3C[C@@H]3F)sc2n1]<br><br>(1S,2S)-N-(5-(5-ethyl-6-fluoro-7-((2-(methylamino)-2-oxoethyl)thio)-1H-indazol-4-yl)thiazolo[5,4-b]pyridin-2-yl)-2-fluorocyclopropane-1-carboxamide | ¹H NMR (400 MHz, DMSO-$d_6$) δ 7.82 (d, J = 7.9 Hz, 1H), 7.72 (s, 1H), 7.41 (d, J = 8.2 Hz, 1H), 5.03-4.68 (m, 1H), 3.18 (s, 1H), 2.86 (s, 1H), 2.70-2.63 (m, 2H), 2.01-1.91 (m, 1H), 1.72-1.57 (m, 1H), 1.12 (t, J = 7.3 Hz, 3H), 1.05-0.96 (m, 1H); LCMS(electrospray) m/z 503.3 (M + H+). | D |
| 168 | 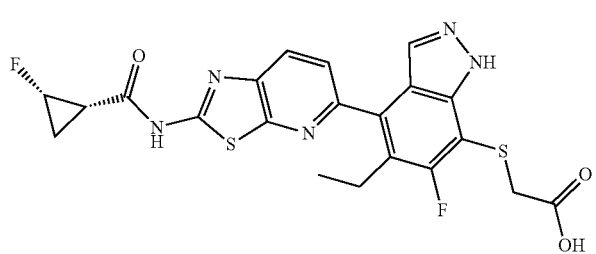 [SMILES: CCc1c(F)c(SCC(=O)O)c2[nH]ncc2c1-c1ccc2nc(NC(=O)[C@@H]3C[C@@H]3F)sc2n1]<br><br>2-((5-ethyl-6-fluoro-4-(2-((1S,2S)-2-fluorocyclopropane-1-carboxamido)thiazolo[5,4-b]pyridin-5-yl)-1H-indazol-7-yl)thio)acetic acid | ¹H NMR (400 MHz, DMSO-$d_6$) δ 7.82 (d, J = 7.9 Hz, 1H), 7.72 (s, 1H), 7.41 (d, J = 8.2 Hz, 1H), 5.03-4.68 (m, 1H), 3.18 (s, 1H), 2.86 (s, 1H), 2.70-2.63 (m, 2H), 2.01-1.91 (m, 1H), 1.72-1.57 (m, 1H), 1.12 (t, J = 7.3 Hz, 3H), 1.05-0.96 (m, 1H); LCMS(electrospray) m/z 490.3 (M + H+). | D |
| 169 | 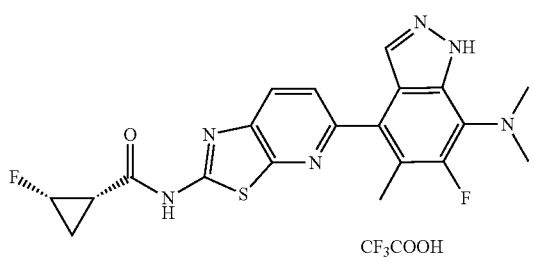<br><br>(1S,2S)-N-(5-(7-(dimethylamino)-6-fluoro-5-methyl-1H-indazol-4-yl)thiazolo[5,4-b]pyridin-2-yl)-2-fluorocyclopropane-1-carboxamide. 2 TFA | ¹H NMR (400 MHz, CHLOROFORM-d) δ 8.15 (d, J = 8.3 Hz, 1H), 7.89 (br s, 1H), 7.60 (d, J = 8.3 Hz, 1H), 5.10-4.76 (m, 1H), 3.13 (d, J = 1.6 Hz, 6H), 2.35 (d, J = 3.4 Hz, 3H), 2.12-2.01 (m, 2H), 1.49-1.33 (m, 1H); LCMS(electrospray) m/z429.1 (M + H+). | D |

TABLE 1-continued

Compounds of Examples

| Ex # | Structure/Name | ¹H NMR/MS (M + 1) | Method |
|---|---|---|---|
| 170 | 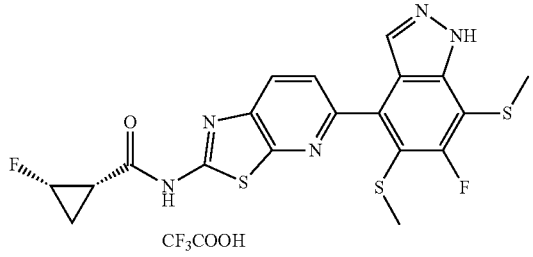<br><br>(1S,2S)-2-fluoro-N-(5-(6-fluoro-5,7-bis(methylthio)-1H-indazol-4-yl)thiazolo[5,4-b]pyridin-2-yl)cyclopropane-1-carboxamide. 2 TFA | ¹H NMR (400 MHz, DMSO-$d_6$) δ 13.65 (s, 1H), 12.94 (br s, 1H), 8.25 (d, J = 8.4 Hz, 1H), 7.89-7.84 (m, 1H), 7.75 (d, J = 8.3 Hz, 1H), 5.20-4.94 (m, 1H), 2.56 (s, 3H), 2.28 (s, 3H), 2.27-2.23 (m, 1H), 1.84-1.72 (m, 1H), 1.41-1.30 (m, 1H); LCMS(electrospray) m/z 464.0 (M + H+). | D |
| 171 | 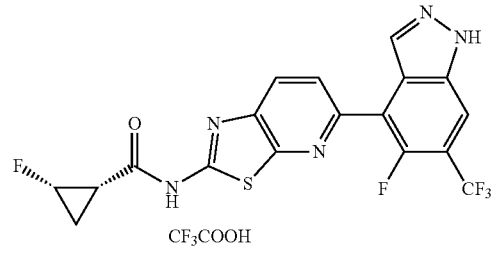<br><br>(1S,2S)-2-fluoro-N-(5-(5-fluoro-6-(trifluoromethyl)-1H-indazol-4-yl)thiazolo[5,4-b]pyridin-2-yl)cyclopropane-1-carboxamide. TFA | ¹H NMR (400 MHz, DMSO-$d_6$) δ 13.96 (s, 1H), 12.92 (s, 1H), 8.41 (d, J = 6.5 Hz, 1H), 8.38 (d, J = 1.2 Hz, 1H), 8.29 (d, J = 8.6 Hz, 1H), 8.15 (d, J = 7.7 Hz, 1H), 5.21-4.94 (m, 1H), 2.24 (s, 1H), 1.88-1.69 (m, 1H), 1.41-1.29 (m, 1H); LCMS(electrospray) m/z 0.887, 440.1 (M + H+). | D |
| 172 | 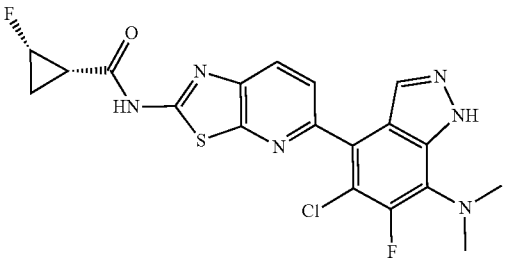 [SMILES: CN(C)c1c(F)c(Cl)c(-c2ccc3nc(NC(=O)[C@@H]4C[C@@H]4F)sc3n2)c2cn[nH]c12]<br><br>(1S,2S)-N-(5-(5-chloro-7-(dimethylamino)-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.56-13.42 (m, 1H), 8.24 (d, J = 8.4 Hz, 1H), 7.90 (br s, 1H), 7.79 (d, J = 8.4 Hz, 1H), 5.20-4.95 (m, 1H), 3.02 (br d, J = 1.7 Hz, 6H), 2.27 (ddd, J = 2.0, 4.6, 6.7 Hz, 1H), 1.85-1.71 (m, 1H), 1.38-1.30 (m, 1H), 1.30 (s, 1H); LCMS(electrospray) m/z 449.1 (M + H+). | D |
| 173 | 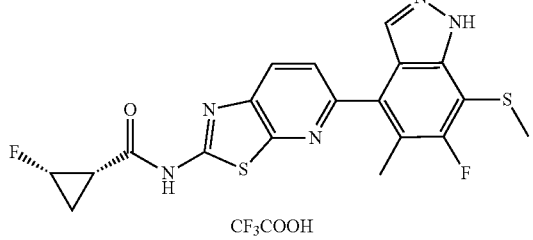<br><br>(1S,2S)-2-fluoro-N-(5-(6-fluoro-5-methyl-7-(methylthio)-1H-indazol-4-yl)thiazolo[5,4-b]pyridin-2-yl)cyclopropane-1-carboxamide. 2 TFA | ¹H NMR (400 MHz, DMSO-$d_6$) δ 13.57-13.32 (m, 1H), 8.25 (dd, J = 3.0, 8.3 Hz, 1H), 7.86 (br s, 1H), 7.70 (dd, J = 2.9, 8.3 Hz, 1H), 5.22-4.91 (m, 1H), 2.53 (br s, 3H), 2.27 (br s, 3H), 1.83-1.70 (m, 1H), 1.40-1.27 (m, 1H), 1.21 (br d, J = 10.5 Hz, 2H); LCMS(electrospray) m/z 431.07 (M + H+). | D |

TABLE 1-continued

Compounds of Examples

| Ex # | Structure/Name | ¹H NMR/MS (M + 1) | Method |
|---|---|---|---|
| 174 | 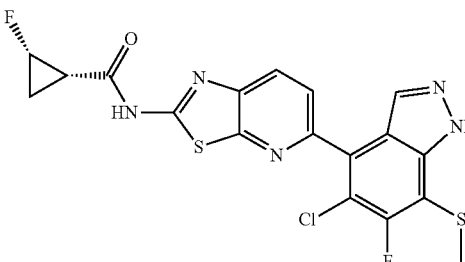<br>(1S,2S)-N-(5-(5-chloro-6-fluoro-7-(methylthio)-1H-indazol-4-yl)thiazolo[5,4-b]pyridin-2-yl)-2-fluorocyclopropane-1-carboxamide | ¹H NMR (400 MHz, DMSO-d$_6$) δ 13.76 (s, 1H), 12.98 (s, 1H), 8.29 (d, J = 8.4 Hz, 1H), 7.98 (d, J = 1.3 Hz, 1H), 7.85 (d, J = 8.4 Hz, 1H), 5.21-4.96 (m, 1H), 2.58 (s, 3H), 2.31-2.25 (m, 1H), 1.84-1.72 (m, 1H), 1.37-1.30 (m, 1H); LCMS(electrospray) m/z 452 (M + H+). | D |
| 175 | 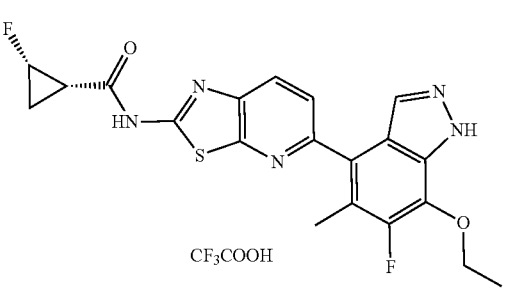 [SMILES: CCOc1c(F)c(C)c(-c2ccc3nc(NC(=O)[C@@H]4C[C@@H]4F)sc3n2)c2cn[nH]c12 ; "CF3COOH"]<br>(1S,2S)-N-(5-(7-ethoxy-6-fluoro-5-methyl-1H-indazol-4-yl)thiazolo[5,4-b]pyridin-2-yl)-2-fluorocyclopropane-1-carboxamide. 1 TFA | ¹H NMR (400 MHz, DMSO-d$_6$) δ 13.54-13.33 (m, 1H), 12.92 (s, 1H), 8.23 (d, J = 8.3 Hz, 1H), 7.82 (s, 1H), 7.68 (d, J = 8.3 Hz, 1H), 5.19-4.96 (m, 1H), 4.33 (q, J = 7.0 Hz, 2H), 2.30-2.25 (m, 4H), 1.83-1.72 (m, 1H), 1.39 (t, J = 7.0 Hz, 3H), 1.36-1.32 (m, 1H); LCMS(electrospray) m/z 430.2 (M + H+). | D |
| 176 | 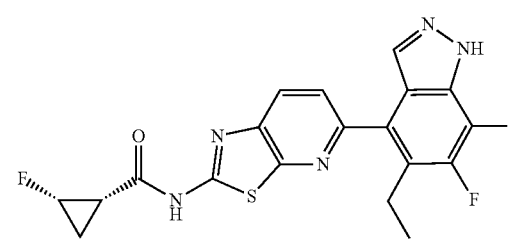<br>(1S,2S)-N-(5-(5-ethyl-6,7-difluoro-1H-indazol-4-yl)thiazolo[5,4-b]pyridin-2-yl)-2-fluorocyclopropane-1-carboxamide | ¹H NMR (400 MHz, DMSO-d$_6$) δ 13.90-13.81 (m, 1H), 12.94 (br s, 1H), 8.26 (d, J = 8.4 Hz, 1H), 7.87-7.80 (m, 1H), 7.67 (d, J = 8.3 Hz, 1H), 5.17-4.95 (m, 1H), 2.76-2.68 (m, 2H), 2.27-2.19 (m, 1H), 1.82-1.73 (m, 1H), 1.57-1.42 (m, 1H), 1.15-1.11 (m, 3H); LCMS(electrospray) m/z 418 (M + H+). | D |
| 177 | 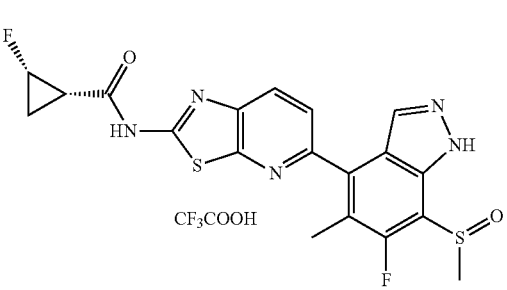 [SMILES: Cc1c(F)c(S(C)=O)c2[nH]ncc2c1-c1ccc2nc(NC(=O)[C@@H]3C[C@@H]3F)sc2n1 ; "CF3COOH"]<br>(1S,2S)-2-fluoro-N-(5-(6-fluoro-5-methyl-7-(methylsulfinyl)-1H-indazol-4-yl)thiazolo[5,4-b]pyridin-2-yl)cyclopropane-1-carboxamide. 1 TFA | ¹H NMR (400 MHz, DMSO-d$_6$) δ 13.36 (s, 1H), 12.97 (s, 1H), 8.29 (d, J = 8.3 Hz, 1H), 7.92 (s, 1H), 7.74 (d, J = 8.3 Hz, 1H), 5.20-4.96 (m, 1H), 3.14 (s, 3H), 2.31-2.23 (m, 4H), 1.84-1.71 (m, 1H), 1.35 (tdd, J = 6.4, 8.9, 13.0 Hz, 1H); LCMS(electrospray) m/z 447.9 (M + H+). | D |

TABLE 1-continued

Compounds of Examples

| Ex # | Structure/Name | ¹H NMR/MS (M + 1) | Method |
|---|---|---|---|
| 178 | 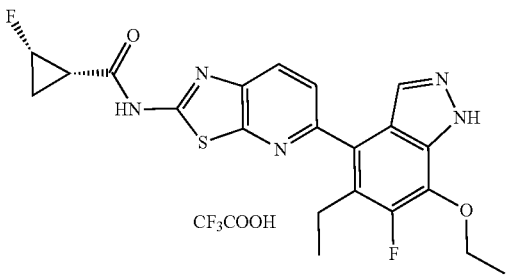 [SMILES: CCOc1c(F)c(CC)c(-c2ccc3nc(NC(=O)[C@@H]4C[C@@H]4F)sc3n2)c2cn[nH]c12 ; "CF3COOH"]<br>(1S,2S)-N-(5-(7-ethoxy-5-ethyl-6-fluoro-1H-indazol-4-yl)thiazolo[5,4-b]pyridin-2-yl)-2-fluorocyclopropane-1-carboxamide. 1 TFA | ¹H NMR (400 MHz, DMSO-$d_6$) δ 13.47 (s, 1H), 12.93 (s, 1H), 8.25 (d, J = 8.0 Hz, 1H), 7.76 (s, 1H), 7.67-7.65 (m, 1H), 5.21-4.96 (m, 1H), 4.37-4.31 (m, 2H), 2.68-2.64 (m, 2H), 2.34-2.33 (m, 1H), 1.81-1.68 (m, 1H), 1.40 (t, J = 6.8 Hz, 3H), 1.19-1.15 (m, 1H), 1.13 (t, J = 7.6 Hz, 3H); LCMS(electrospray) m/z 444.2 (M + H+). | D |
| 179 | 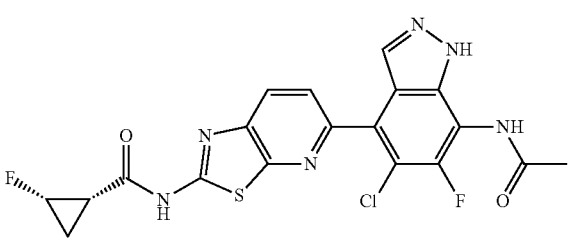<br>(1S,2S)-N-(5-(7-acetamido-5-chloro-6-fluoro-1H-indazol-4-yl)thiazolo[5,4-b]pyridin-2-yl)-2-fluorocyclopropane-1-carboxamide. 1 TFA | ¹H NMR (400 MHz, DMSO-$d_6$) δ 13.27 (br s, 1H), 12.97 (s, 1H), 10.16 (s, 1H), 8.29 (d, J = 8.4 Hz, 1H), 7.91 (s, 1H), 7.85 (d, J = 8.3 Hz, 1H), 5.18-4.98 (m, 1H), 2.28 (ddd, J = 2.4, 4.3, 6.6 Hz, 1H), 2.19 (s, 3H), 1.82-1.73 (m, 1H), 1.35 (ddd, J = 2.6, 6.3, 12.9 Hz, 1H); LCMS(electrospray) m/z 463.1(M + H+). | D |
| 180 | 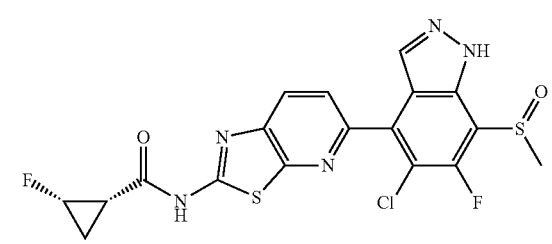 [SMILES: CS(=O)c1c(F)c(Cl)c(-c2ccc3nc(NC(=O)[C@@H]4C[C@@H]4F)sc3n2)c2cn[nH]c12]<br>(1S,2S)-N-(5-(5-chloro-6-fluoro-7-(methylsulfinyl)-1H-indazol-4-yl)thiazolo[5,4-b]pyridin-2-yl)-2-fluorocyclopropane-1-carboxamide | ¹H NMR (400 MHz, DMSO-$d_6$) δ 13.68 (br s, 1H), 13.02 (s, 1H), 8.32 (d, J = 8.4 Hz, 1H), 8.05 (br s, 1H), 7.87 (d, J = 8.4 Hz, 1H), 5.20-4.98 (m, 1H), 3.19 (s, 3H), 2.31-2.25 (m, 1H), 1.85-1.71 (m, 1H), 1.36 (tdd, J = 6.6, 8.8, 13.0 Hz, 1H); LCMS(electrospray) m/z 468 (M + H+). | D |
| 181 | 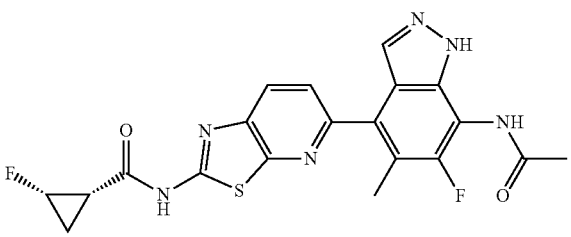<br>(1S,2S)-N-(5-(7-acetamido-6-fluoro-5-methyl-1H-indazol-4-yl)thiazolo[5,4-b]pyridin-2-yl)-2-fluorocyclopropane-1-carboxamide. 1 TFA | ¹H NMR (400 MHz, DMSO-$d_6$) δ 12.96-12.91 (m, 2H), 9.96 (s, 1H), 8.26 (d, J = 8.4 Hz, 1H), 7.79 (s, 1H), 7.71 (d, J = 8.3 Hz, 1H), 5.20-4.94 (m, 1H), 2.27 (d, J = 2.9 Hz, 3H), 2.17 (s, 4H), 1.84-1.71 (m, 1H), 1.42-1.30 (m, 1H); LCMS(electrospray) m/z 442.10 (M + H+). | D |

TABLE 1-continued

Compounds of Examples

| Ex # | Structure/Name | ¹H NMR/MS (M + 1) | Method |
|---|---|---|---|
| 182 | 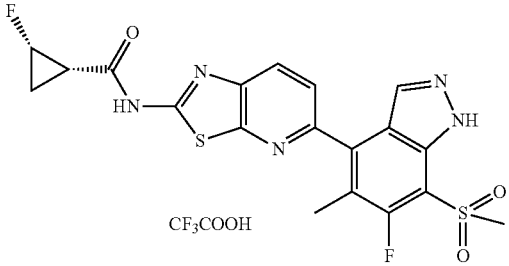 [SMILES: Cc1c(F)c(S(C)(=O)=O)c2[nH]ncc2c1-c1ccc2nc(NC(=O)[C@@H]3C[C@@H]3F)sc2n1 ; "CF3COOH"]<br>(1S,2S)-2-fluoro-N-(5-(6-fluoro-5-methyl-7-(methylsulfonyl)-1H-indazol-4-yl)thiazolo[5,4-b]pyridin-2-yl)cyclopropane-1-carboxamide. 1 TFA | ¹H NMR (400 MHz, DMSO-$d_6$) δ 13.19 (s, 1H), 12.99 (s, 1H), 8.31 (d, J = 8.4 Hz, 1H), 7.97 (s, 1H), 7.76 (d, J = 8.3 Hz, 1H), 5.21-4.95 (m, 1H), 3.51 (s, 3H), 2.33-2.25 (m, 4H), 1.85-1.71 (m, 1H), 1.41-1.28 (m, 1H); LCMS(electrospray) m/z 463.06 (M + H+). | D |
| 183 | 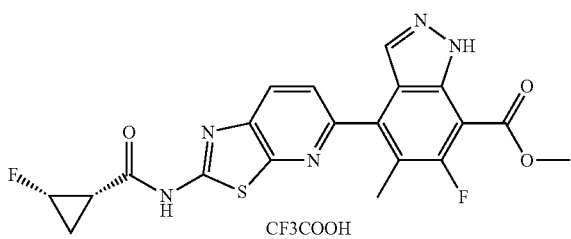<br>methyl 6-fluoro-4-(2-(((1S,2S)-2-fluorocyclopropane-1-carboxamido)thiazolo[5,4-b]pyridin-5-yl)-5-methyl-1H-indazole-7-carboxylate. 1 TFA | ¹H NMR (400 MHz, DMSO-$d_6$) δ 13.44-13.24 (m, 1H), 12.99 (s, 1H), 8.30 (d, J = 8.3 Hz, 1H), 7.98-7.86 (m, 1H), 7.76 (d, J = 8.4 Hz, 1H), 5.27-4.90 (m, 1H), 3.99 (s, 3H), 2.31-2.24 (m, 4H), 1.82-1.70 (m, 1H), 1.44-1.27 (m, 1H); LCMS(electrospray) m/z 444.0 (M + H+). | D |
| 184 | 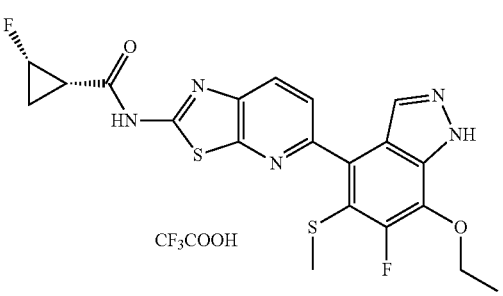 [SMILES: CCOc1c(F)c(SC)c(-c2ccc3nc(NC(=O)[C@@H]4C[C@@H]4F)sc3n2)c2cn[nH]c12 ; "CF3COOH"]<br>(1S,2S)-N-(5-(7-ethoxy-6-fluoro-5-(methylthio)-1H-indazol-4-yl)thiazolo[5,4-b]pyridin-2-yl)-2-fluorocyclopropane-1-carboxamide. 1 TFA | ¹H NMR (400 MHz, DMSO-$d_6$) δ 13.83-13.51 (m, 1H), 12.93 (s, 1H), 8.23 (d, J = 8.4 Hz, 1H), 7.84 (s, 1H), 7.73 (d, J = 8.4 Hz, 1H), 5.22-4.93 (m, 1H), 4.51-4.26 (m, 2H), 2.30-2.28 (m, 1H), 2.06-2.03 (m, 1H), 1.86-1.73 (m, 1H), 1.64-1.52 (m, 1H), 1.42 (t, J = 7.0 Hz, 3H), 1.33 (m, J = 6.7, 14.0 Hz, 1H); LCMS(electrospray) m/z 462.2 (M + H+). | D |
| 185 | 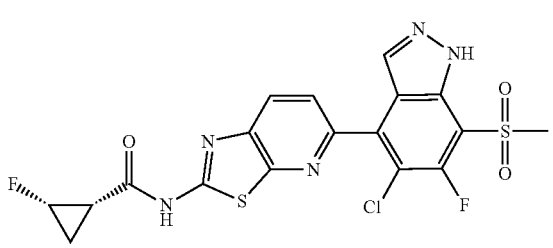<br>(1S,2S)-N-(5-(5-chloro-6-fluoro-7-(methylsulfonyl)-1H-indazol-4-yl)thiazolo[5,4-b]pyridin-2-yl)-2-fluorocyclopropane-1-carboxamide. 1 TFA | ¹H NMR (400 MHz, DMSO-$d_6$) δ 13.48 (s, 1H), 13.03 (s, 1H), 8.34 (d, J = 8.3 Hz, 1H), 8.09 (d, J = 1.3 Hz, 1H), 7.89 (d, J = 8.3 Hz, 1H), 5.20-4.98 (m, 1H), 3.57 (s, 3H), 2.31-2.25 (m, 1H), 1.85-1.73 (m, 1H), 1.41-1.31 (m, 1H); LCMS(electrospray) m/z 484 (M + H+). | D |

TABLE 1-continued

Compounds of Examples

| Ex # | Structure/Name | ¹H NMR/MS (M + 1) | Method |
|---|---|---|---|
| 186 | 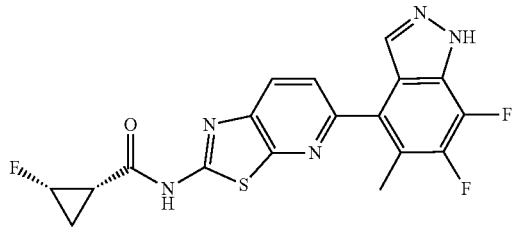<br>CF3COOH<br><br>(1S,2S)-N-(5-(6,7-difluoro-5-methyl-1H-indazol-4-yl)thiazolo[5,4-b]pyridin-2-yl)-2-fluorocyclopropane-1-carboxamide. 1 TFA | ¹H NMR (400 MHz, DMSO-$d_6$) δ 13.92-13.91 (m, 1H), 13.91-13.90 (m, 1H), 13.86 (br s, 1H), 8.23 (d, J = 8.3 Hz, 1H), 7.93 (br d, J = 2.7 Hz, 1H), 7.68 (d, J = 8.3 Hz, 1H), 5.17-4.95 (m, 1H), 2.32-2.31 (m, 1H), 2.31 (d, J = 2.9 Hz, 2H), 2.26 (dt, J = 2.2, 4.5 Hz, 1H), 1.84-1.73 (m, 1H), 1.32-1.25 (m, 1H); LCMS(electrospray) m/z 404.2 (M + H+). | D |
| 187 | 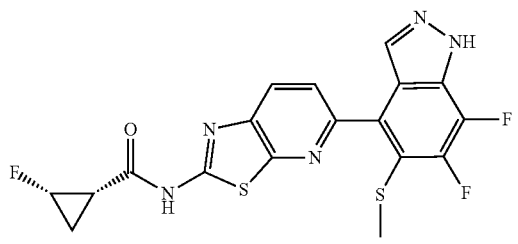 [SMILES: CSc1c(F)c(F)c2[nH]ncc2c1-c1ccc2nc(NC(=O)[C@@H]3C[C@@H]3F)sc2n1]<br><br>(1S,2S)-N-(5-(6,7-difluoro-5-(methylthio)-1H-indazol-4-yl)thiazolo[5,4-b]pyridin-2-yl)-2-fluorocyclopropane-1-carboxamide | ¹H NMR (400 MHz, DMSO-$d_6$) δ 8.42 (d, J = 8.3 Hz, 1H), 8.14 (d, J = 3.2 Hz, 1H), 7.91 (d, J = 8.4 Hz, 1H), 5.38-5.15 (m, 1H), 2.71-2.70 (m, 3H), 2.45 (br s, 1H), 2.03-1.89 (m, 1H), 1.41 (s, 1H); LCMS(electrospray) m/z 436.1 (M + H+). | D |
| 188 | 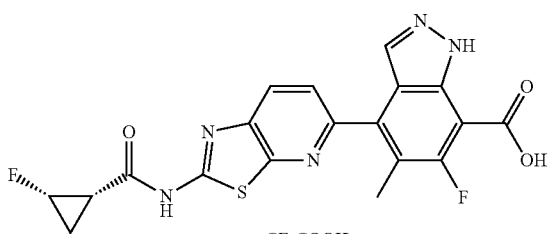<br>CF₃COOH<br><br>6-fluoro-4-(2-((1S,2S)-2-fluorocyclopropane-1-carboxamido)thiazolo[5,4-b]pyridin-5-yl)-5-methyl-1H-indazole-7-carboxylic acid. 1 TFA | ¹H NMR (400 MHz, METHANOL-$d_4$) δ 8.25 (d, J = 8.4 Hz, 1H), 7.84 (s, 1H), 7.71 (d, J = 8.3 Hz, 1H), 5.04 (dt, J = 3.9, 6.2 Hz, 1H), 2.32 (d, J = 3.3 Hz, 3H), 2.24-2.16 (m, 1H), 1.98-1.84 (m, 1H), 1.34-1.29 (m, 1H); LCMS(electrospray) m/z 429.9 (M + H+). | D |
| 189 | 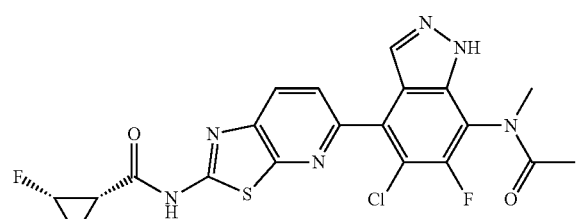<br><br>(1S,2S)-N-(5-(5-chloro-6-fluoro-7-(N-methylacetamido)-1H-indazol-4-yl)thiazolo[5,4-b]pyridin-2-yl)-2-fluorocyclopropane-1-carboxamide | ¹H NMR (400 MHz, DMSO-$d_6$) δ 14.34 (s, 1H), 8.31-8.28 (m, 1H), 8.05 (s, 1H), 7.88 (d, J = 8.4 Hz, 1H), 5.17-4.98 (m, 1H), 3.25 (s, 3H), 2.28 (ddd, J = 1.8, 4.7, 6.8 Hz, 1H), 1.83 (s, 3H), 1.75 (dt, J = 3.8, 6.9 Hz, 1H), 1.38-1.32 (m, 1H); LCMS(electrospray) m/z 477.0 (M + H+). | D |

TABLE 1-continued

Compounds of Examples

| Ex # | Structure/Name | ¹H NMR/MS (M + 1) | Method |
|---|---|---|---|
| 190 | 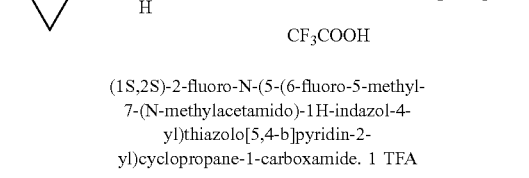<br>(1S,2S)-2-fluoro-N-(5-(6-fluoro-5-methyl-7-(N-methylacetamido)-1H-indazol-4-yl)thiazolo[5,4-b]pyridin-2-yl)cyclopropane-1-carboxamide. 1 TFA | ¹H NMR (400 MHz, DMSO-d₆) δ 13.61 (br s, 1H), 12.99-12.91 (m, 1H), 8.31-8.24 (m, 1H), 7.94-7.88 (m, 1H), 7.77-7.70 (m, 1H), 5.23-4.96 (m, 1H), 3.22 (s, 3H), 2.30 (d, J = 2.8 Hz, 3H), 2.28-2.23 (m, 1H), 1.80 (s, 3H), 1.77-1.70 (m, 1H), 1.41-1.29 (m, 1H); LCMS(electrospray) m/z 456.12 (M + H+). | D |
| 191 | 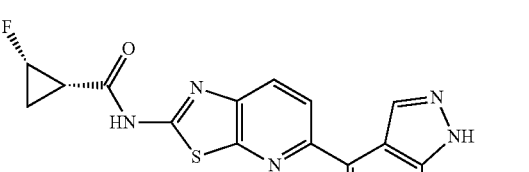<br>(1S,2S)-N-(5-(5-chloro-6-fluoro-7-(2-methylhydrazineyl)-1H-indazol-4-yl)thiazolo[5,4-b]pyridin-2-yl)-2-fluorocyclopropane-1-carboxamide | ¹H NMR (400 MHz, DMSO-d₆) δ 12.90 (br, 2H), 8.20 (d, J = 8.0 Hz, 1H), 7.83 (s, 1H), 7.76 (d, J = 8.4 Hz, 1H), 7.49 (s, 1H), 5.15-4.98 (m, 1H), 5.04 (d, J = 5.2 Hz, 1H), 3.24 (s, 3H), 2.32-2.26 (m, 2H), 1.80-1.73 (m, 1H), 1.35-1.23 (m, 1H); LCMS (electrospray) m/z 450.1 (M + H)+. | D |
| 192 | 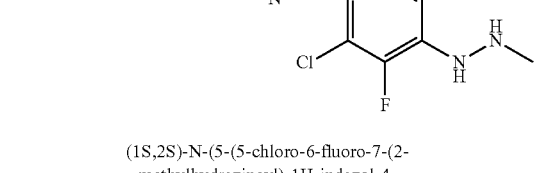<br>tert-butyl 2-(5-chloro-6-fluoro-4-(2-((1S,2S)-2-fluorocyclopropane-1-carboxamido)thiazolo[5,4-b]pyridin-5-yl)-1H-indazol-7-yl)-1-methylhydrazine-1-carboxylate | ¹H NMR (400 MHz, DMSO-d₆) δ 12.94 (s, 1H), 12.88 (s, 1H), 8.37 (s, 1H), 8.22 (d, J = 8.4 Hz, 1H), 7.90 (s, 1H), 7.77 (d, J = 8.4 Hz, 1H), 5.15-4.98 (m, 1H), 2.60 (d, J = 5.2 Hz, 3H), 2.18-2.13 (m, 1H), 1.71-1.63 (m, 1H), 1.35-1.12 (m, 10H); LCMS (electrospray) m/z 550.1 (M + H)+. | D |
| 193 | 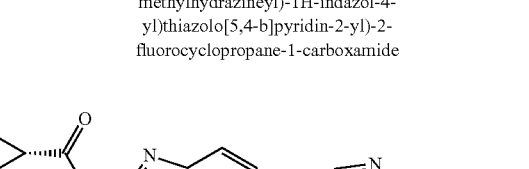<br>5-chloro-6-fluoro-4-(2-((1S,2S)-2-fluorocyclopropane-1-carboxamido)thiazolo[5,4-b]pyridin-5-yl)-N,N-dimethyl-1H-indazole-7-carboxamide | ¹H NMR (400 MHz, DMSO-d₆) δ 13.87-13.62 (m, 1H), 8.29 (d, J = 8.5 Hz, 1H), 7.98 (s, 1H), 7.86 (d, J = 8.5 Hz, 1H), 5.18-4.95 (m, 1H), 3.12 (s, 3H), 2.93 (s, 3H), 2.27 (ddd, J = 2.0, 4.6, 6.7 Hz, 1H), 1.82-1.71 (m, 1H), 1.34 (ddd, J = 2.6, 6.3, 13.0 Hz, 1H); LCMS(electrospray) m/z 476.9 (M + H+). | D |

TABLE 1-continued

Compounds of Examples

| Ex # | Structure/Name | ¹H NMR/MS (M + 1) | Method |
|---|---|---|---|
| 194 | 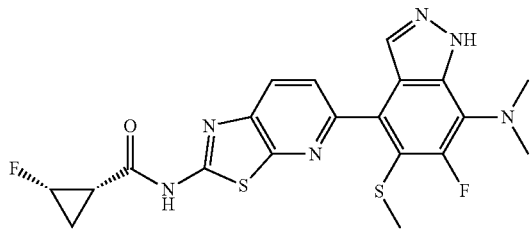 [SMILES: CSc1c(F)c(N(C)C)c2[nH]ncc2c1-c1ccc2nc(NC(=O)[C@@H]3C[C@@H]3F)sc2n1]<br>(1S,2S)-N-(5-(7-(dimethylamino)-6-fluoro-5-(methylthio)-1H-indazol-4-yl)thiazolo[5,4-b]pyridin-2-yl)-2-fluorocyclopropane-1-carboxamide | ¹H NMR (400 MHz, DMSO-$d_6$) δ 13.36 (br s, 1H), 12.90 (br s, 1H), 8.21 (d, J = 8.8 Hz, 1H), 7.77 (s, 1H), 7.70 (d, J = 8.4 Hz, 1H), 5.19-4.95 (m, 1H), 2.99 (s, 6H), 2.27 (s, 4H), 1.84-1.70 (m, 1H), 1.40-1.28 (m, 1H); LCMS(electrospray) m/z 461 (M + H+). | D |
| 195 | 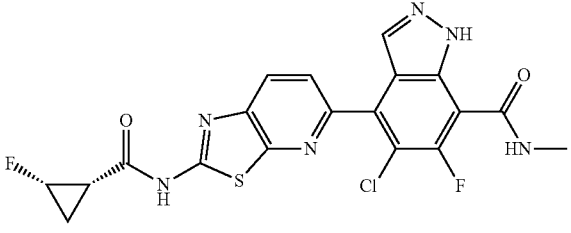 [SMILES: CNC(=O)c1c(F)c(Cl)c(-c2ccc3nc(NC(=O)[C@@H]4C[C@@H]4F)sc3n2)c2cn[nH]c12]<br>5-chloro-6-fluoro-4-(2-((1S,2S)-2-fluorocyclopropane-1-carboxamido)thiazolo[5,4-b]pyridin-5-yl)-N-methyl-1H-indazole-7-carboxamide | ¹H NMR (400 MHz, DMSO-$d_6$) δ 8.65 (br d, J = 3.3 Hz, 1H), 8.19-8.12 (m, 1H), 7.95 (s, 1H), 7.77 (d, J = 8.3 Hz, 1H), 5.17-4.89 (m, 1H), 2.91 (d, J = 4.5 Hz, 3H), 2.23-2.14 (m, 1H), 1.85-1.63 (m, 1H), 1.35-1.17 (m, 1H); LCMS(electrospray) m/z 462.9 (M + H+). | D |
| 196 | 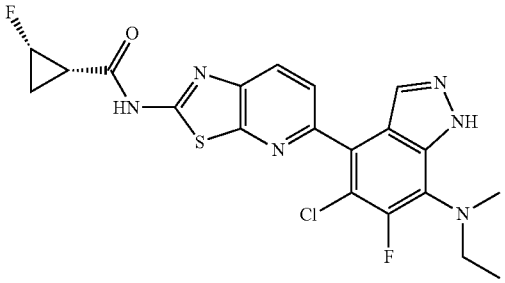<br>(1S,2S)-N-(5-(5-chloro-7-(ethyl(methyl)amino)-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.53-13.38 (m, 1H), 13.59-13.37 (m, 1H), 8.31-8.23 (m, 1H), 7.96-7.87 (m, 1H), 7.85-7.76 (m, 1H), 5.21-4.96 (m, 1H), 3.31 (br s, 2H), 3.09-2.92 (m, 3H), 2.35-2.23 (m, 1H), 1.87-1.72 (m, 1H), 1.42-1.30 (m, 1H), 1.14-1.05 (m, 3H); LCMS(electrospray) m/z 463.7 (M + H+). | D |
| 197 | 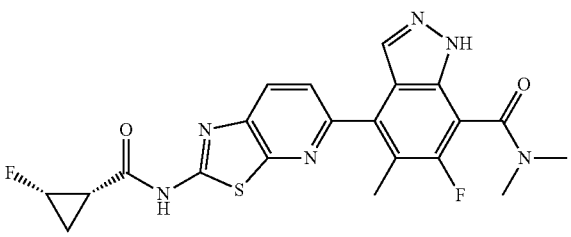<br>6-fluoro-4-(2-((1S,2S)-2-fluorocyclopropane-1-carboxamido)thiazolo[5,4-b]pyridin-5-yl)-N,N,5-trimethyl-1H-indazole-7-carboxamide | ¹H NMR (400 MHz, DMSO-$d_6$) δ 13.48-13.33 (m, 1H), 8.24 (d, J = 8.4 Hz, 1H), 7.86 (s, 1H), 7.72 (d, J = 8.4 Hz, 1H), 5.19-4.93 (m, 1H), 3.12 (s, 3H), 2.92 (s, 3H), 2.28 (d, J = 2.9 Hz, 3H), 2.27-2.22 (m, 1H), 1.82-1.69 (m, 1H), 1.39-1.28 (m, 1H); LCMS(electrospray) m/z 457.1 (M + H+). | D |

TABLE 1-continued

Compounds of Examples

| Ex # | Structure/Name | ¹H NMR/MS (M + 1) | Method |
|---|---|---|---|
| 198 | 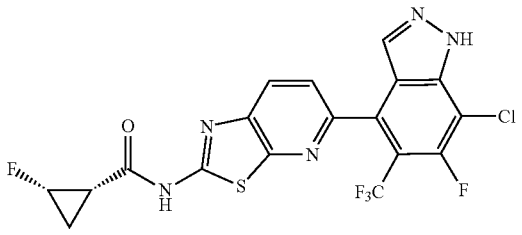 [SMILES: O=C(Nc1nc2ccc(-c3c(C(F)(F)F)c(F)c(Cl)c4[nH]ncc34)nc2s1)[C@@H]1C[C@@H]1F]<br><br>(1S,2S)-N-(5-(7-chloro-6-fluoro-5-(trifluoromethyl)-1H-indazol-4-yl)thiazolo[5,4-b]pyridin-2-yl)-2-fluorocyclopropane-1-carboxamide | ¹H NMR (400 MHz, DMSO-$d_6$) δ 8.35 (s, 1H), 8.22 (d, J = 8.4 Hz, 1H), 7.96 (s, 1H), 7.65 (d, J = 8.4 Hz, 1H), 5.17-4.91 (m, 1H), 2.30-2.19 (m, 1H), 1.83-1.69 (m, 1H), 1.39-1.28 (m, 1H); LCMS(electrospray) m/z 474.1 (M + H+). | D |
| 199 | <br><br>CF3COOH<br><br>(1S,2S)-2-fluoro-N-(5-(6-fluoro-5,7-dimethyl-1H-indazol-4-yl)thiazolo[5,4-b]pyridin-2-yl)cyclopropane-1-carboxamide. 1 TFA | ¹H NMR (400 MHz, DMSO-$d_6$) δ 13.01-12.83 (m, 1H), 8.30-8.14 (m, 1H), 7.98-7.94 (m, 1H), 7.80 (s, 1H), 7.71-7.59 (m, 1H), 5.28-4.88 (m, 1H), 2.49-2.48 (m, 3H), 2.27-2.24 (m, 4H), 1.83-1.72 (m, 1H), 1.39-1.30 (m, 1H); LCMS(electrospray) m/z 400.0 (M + H+). | D |
| 200 | 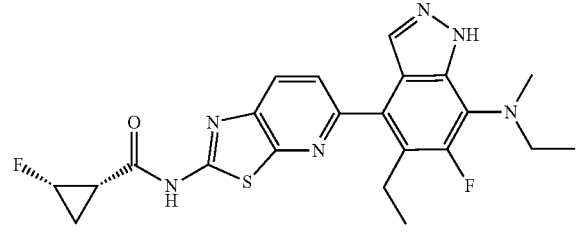 [SMILES: CCc1c(F)c(N(C)CC)c2[nH]ncc2c1-c1ccc2nc(NC(=O)[C@@H]3C[C@@H]3F)sc2n1]<br><br>(1S,2S)-N-(5-(5-ethyl-7-(ethyl(methyl)amino)-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.15 (s, 1H), 13.03-12.78 (m, 1H), 8.23 (d, J = 8.4 Hz, 1H), 7.74-7.61 (m, 2H), 5.20-4.94 (m, 1H), 3.23 (br d, J = 7.1 Hz, 2H), 2.95 (d, J = 1.8 Hz, 3H), 2.63 (br d, J = 5.8 Hz, 2H), 2.29-2.24 (m, 1H), 1.83-1.71 (m, 1H), 1.40-1.29 (m, 1H), 1.12 (t, J = 7.4 Hz, 3H), 1.06 (t, J = 7.1 Hz, 3H); LCMS(electrospray) m/z 457.0 (M + H+). | D |
| 201 | 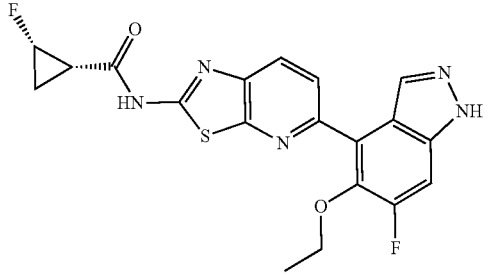 [SMILES: CCOc1c(F)cc2[nH]ncc2c1-c1ccc2nc(NC(=O)[C@@H]3C[C@@H]3F)sc2n1]<br><br>(1S,2S)-N-(5-(5-ethoxy-6-fluoro-1H-indazol-4-yl)thiazolo[5,4-b]pyridin-2-yl)-2-fluorocyclopropane-1-carboxamide | ¹H NMR (400 MHz, DMSO-$d_6$) δ 13.19 (br s, 1H), 12.89 (br s, 1H), 8.24 (d, J = 8.5 Hz, 1H), 8.15 (s, 1H), 8.01 (d, J = 8.5 Hz, 1H), 7.53 (d, J = 10.5 Hz, 1H), 5.19-4.96 (m, 1H), 3.91 (q, J = 7.0 Hz, 2H), 2.31-2.23 (m, 1H), 1.84-1.72 (m, 1H), 1.39-1.30 (m, 1H), 1.15 (t, J = 6.9 Hz, 3H); LCMS(electrospray) m/z 416.0 (M + H+). | D |

TABLE 1-continued

Compounds of Examples

| Ex # | Structure/Name | ¹H NMR/MS (M + 1) | Method |
|---|---|---|---|
| 202 | 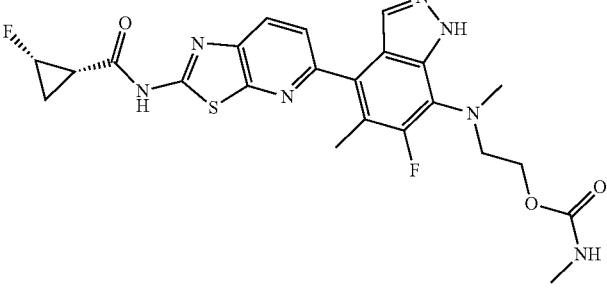<br>2-((6-fluoro-4-(2-((1S,2S)-2-fluorocyclopropane-1-carboxamido)thiazolo[5,4-b]pyridin-5-yl)-5-methyl-1H-indazol-7-yl)(methyl)amino)ethyl methylcarbamate | ¹H NMR (400 MHz, DMSO-$d_6$) δ 13.20-13.00 (m, 1H), 12.95-12.86 (m, 1H), 8.23 (d, J = 8.3 Hz, 1H), 7.80 (s, 1H), 7.67 (d, J = 8.4 Hz, 1H), 6.98-6.89 (m, 1H), 5.21-4.94 (m, 1H), 4.09 (br t, J = 5.9 Hz, 2H), 3.38-3.33 (m, 2H), 3.04-2.98 (m, 3H), 2.57-2.52 (m, 3H), 2.28 (br dd, J = 2.1, 4.4 Hz, 1H), 2.26-2.26 (m, 1H), 2.25 (d, J = 3.1 Hz, 3H), 1.83-1.71 (m, 1H), 1.39-1.30 (m, 1H); LCMS(electrospray) m/z 516.1 (M + H+). | D |
| 203 | 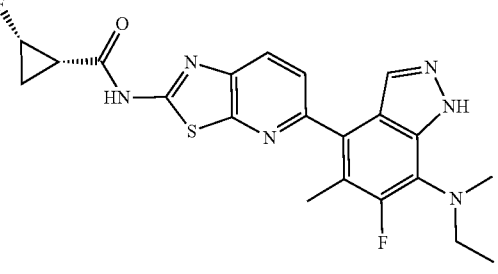<br>(1S,2S)-N-(5-(7-(ethyl(methyl)amino)-6-fluoro-5-methyl-1H-indazol-4-yl)thiazolo[5,4-b]pyridin-2-yl)-2-fluorocyclopropane-1-carboxamide | ¹H NMR (400 MHz, DMSO-$d_6$) δ 13.13 (s, 1H), 8.23 (d, J = 8.3 Hz, 1H), 7.77 (s, 1H), 7.68 (d, J = 8.3 Hz, 1H), 5.23-4.94 (m, 1H), 3.22 (q, J = 6.9 Hz, 2H), 2.95 (d, J = 2.1 Hz, 3H), 2.30-2.27 (m, 1H), 2.25 (d, J = 3.2 Hz, 3H), 1.87-1.68 (m, 1H), 1.35 (tdd, J = 6.5, 8.7, 13.1 Hz, 1H), 1.06 (t, J = 7.2 Hz, 3H); LCMS(electrospray) m/z 442.14 (M + H+). | D |
| 204 | 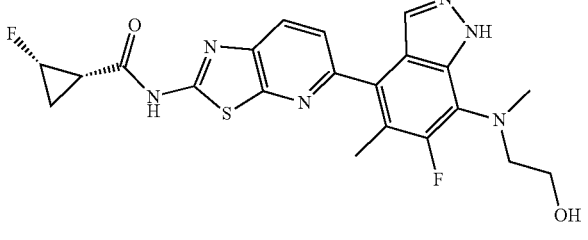<br>(1S,2S)-2-fluoro-N-(5-(6-fluoro-7-((2-hydroxyethyl)(methyl)amino)-5-methyl-1H-indazol-4-yl)thiazolo[5,4-b]pyridin-2-yl)cyclopropane-1-carboxamide | ¹H NMR (400 MHz, DMSO-$d_6$) δ 13.27-13.06 (m, 1H), 8.21 (br d, J = 8.1 Hz, 1H), 7.78 (br s, 1H), 7.66 (br d, J = 8.4 Hz, 1H), 5.19-4.95 (m, 1H), 4.91 (br s, 1H), 3.65-3.55 (m, 2H), 3.27-3.14 (m, 2H), 3.04-2.94 (m, 3H), 2.28-2.19 (m, 4H), 1.82-1.68 (m, 1H), 1.38-1.26 (m, 1H); LCMS(electrospray) m/z 459.1 (M + H+). | D |
| 205 | 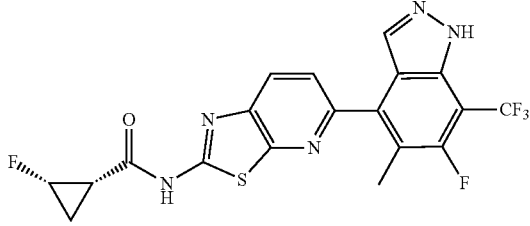<br>(1S,2S)-2-fluoro-N-(5-(6-fluoro-5-methyl-7-(trifluoromethyl)-1H-indazol-4-yl)thiazolo[5,4-b]pyridin-2-yl)cyclopropane-1-carboxamide | ¹H NMR (400 MHz, DMSO-$d_6$) δ 13.63 (br s, 1H), 8.27 (d, J = 8.3 Hz, 1H), 7.99 (s, 1H), 7.74 (d, J = 8.3 Hz, 1H), 5.19-4.95 (m, 1H), 2.29 (d, J = 2.9 Hz, 3H), 2.28-2.22 (m, 1H), 1.84-1.70 (m, 1H), 1.39-1.27 (m, 1H); LCMS(electrospray) m/z 454.2 (M + H+). | D |

TABLE 1-continued

Compounds of Examples

| Ex # | Structure/Name | ¹H NMR/MS (M + 1) | Method |
|---|---|---|---|
| 206 | 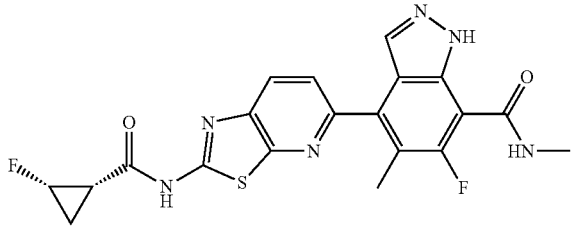<br>6-fluoro-4-(2-(((1S,2S)-2-fluorocyclopropane-1-carboxamido)thiazolo[5,4-b]pyridin-5-yl)-N,5-dimethyl-1H-indazole-7-carboxamide | ¹H NMR (400 MHz, DMSO-d₆) δ 13.24 (br d, J = 2.9 Hz, 1H), 8.50-8.44 (m, 1H), 8.18 (d, J = 8.3 Hz, 1H), 7.84 (s, 1H), 7.67 (d, J = 8.2 Hz, 1H), 5.17-4.89 (m, 1H), 2.91 (d, J = 4.4 Hz, 3H), 2.29 (d, J = 2.8 Hz, 3H), 2.24-2.18 (m, 1H), 1.83-1.67 (m, 1H), 1.35-1.21 (m, 1H); LCMS(electrospray) m/z 442.10 (M + H+). | D |
| 207 | 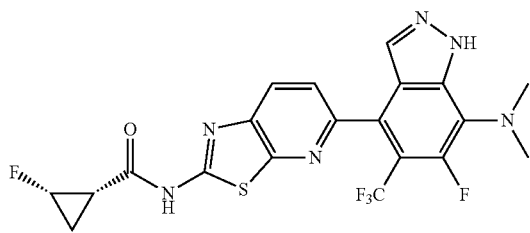<br>CF₃COOH<br>(1S,2S)-N-(5-(7-(dimethylamino)-6-fluoro-5-(trifluoromethyl)-1H-indazol-4-yl)thiazolo[5,4-b]pyridin-2-yl)-2-fluorocyclopropane-1-carboxamide. 1 TFA | ¹H NMR (400 MHz, DMSO-d₆) δ 13.86-13.56 (m, 1H), 12.95 (s, 1H), 8.24 (d, J = 8.3 Hz, 1H), 7.73 (s, 1H), 7.62 (d, J = 8.3 Hz, 1H), 5.19-4.96 (m, 1H), 3.03 (d, J = 2.2 Hz, 6H), 2.32-2.21 (m, 1H), 1.83-1.71 (m, 1H), 1.41-1.31 (m, 1H); LCMS(electrospray) m/z 483.2 (M + H+). | D |
| 208 | 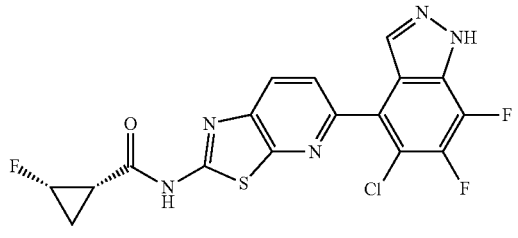<br>CF₃COOH<br>(1S,2S)-N-(5-(5-chloro-6,7-difluoro-1H-indazol-4-yl)thiazolo[5,4-b]pyridin-2-yl)-2-fluorocyclopropane-1-carboxamide 2,2,2-trifluoroacetate. 1 TFA | ¹H NMR (400 MHz, METHANOL-d₄) δ 8.23 (d, J = 8.4 Hz, 1H), 7.98 (d, J = 3.3 Hz, 1H), 7.82 (d, J = 8.4 Hz, 1H), 5.04 (dt, J = 3.9, 6.2 Hz, 1H), 2.20 (dtd, J = 4.3, 6.9, 9.1 Hz, 1H), 1.95-1.84 (m, 1H), 1.37-1.29 (m, 1H); LCMS(electrospray) m/z 424.1 (M + H+). | D |
| 209 | 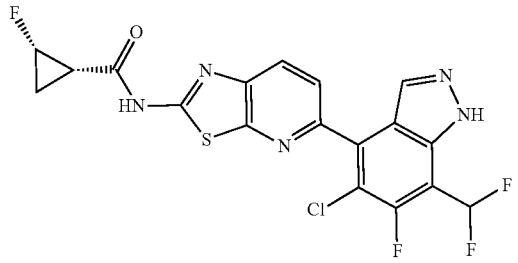 [SMILES: O=C(Nc1nc2ccc(-c3c(Cl)c(F)c(C(F)F)c4[nH]ncc34)nc2s1)[C@@H]1C[C@@H]1F]<br>(1S,2S)-N-(5-(5-chloro-7-(difluoromethyl)-6-fluoro-1H-indazol-4-yl)thiazolo[5,4-b]pyridin-2-yl)-2-fluorocyclopropane-1-carboxamide | ¹H NMR (400 MHz, DMSO-d₆) δ 1.27-1.40 (m, 1 H), 1.71-1.83 (m, 1 H), 2.27 (br s, 1 H), 4.95-5.19 (m, 1 H), 7.51 (s, 1 H), 7.65 (s, 1 H), 7.78 (br s, 1 H), 7.87 (br d, J = 8.68 Hz, 1 H), 8.05 (br s, 1 H), 8.21-8.38 (m, 1 H), 12.77-13.42 (m, 1 H), 13.77-14.05 (m, 1 H); LCMS(electrospray) m/z 456.1 (M + H+). | D |

TABLE 1-continued

Compounds of Examples

| Ex # | Structure/Name | ¹H NMR/MS (M + 1) | Method |
|---|---|---|---|
| 210 | 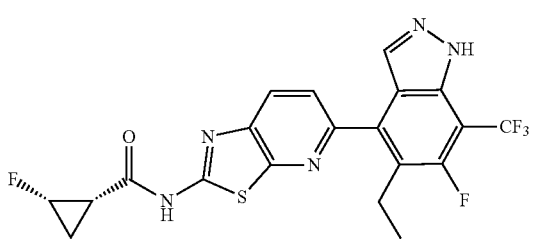 [SMILES: CCc1c(F)c(C(F)(F)F)c2[nH]ncc2c1-c1ccc2nc(NC(=O)[C@@H]3C[C@@H]3F)sc2n1]<br>(1S,2S)-N-(5-(5-ethyl-6-fluoro-7-(trifluoromethyl)-1H-indazol-4-yl)thiazolo[5,4-b]pyridin-2-yl)-2-fluorocyclopropane-1-carboxamide | ¹H NMR (400 MHz, DMSO-$d_6$) δ 1.12 (br t, J = 7.40 Hz, 3 H), 1.27-1.42 (m, 1 H), 1.68-1.85 (m, 1 H), 2.22-2.31 (m, 1 H), 2.68 (br d, J = 7.28 Hz, 2 H), 4.90-5.23 (m, 1 H), 7.73 (d, J = 8.41 Hz, 1 H), 7.93 (br s, 1 H), 8.30 (d, J = 8.28 Hz, 1 H), 12.60-13.33 (m, 1 H), 13.48-13.91 (m, 1 H); LCMS(electrospray) m/z 468.2 (M + H+). | D |
| 211 | 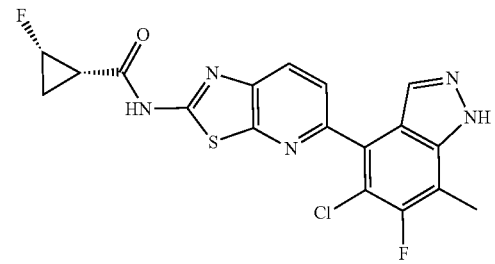 [SMILES: Cc1c(F)c(Cl)c(-c2ccc3nc(NC(=O)[C@@H]4C[C@@H]4F)sc3n2)c2cn[nH]c12]<br>(1S,2S)-N-(5-(5-chloro-6-fluoro-7-methyl-1H-indazol-4-yl)thiazolo[5,4-b]pyridin-2-yl)-2-fluorocyclopropane-1-carboxamide | ¹H NMR (400 MHz, DMSO-$d_6$) δ 13.79-13.40 (m, 1H), 13.10-12.67 (m, 1H), 8.75-8.46 (m, 1H), 8.39-8.10 (m, 1H), 8.01-7.71 (m, 1H), 5.24-4.92 (m, 1H), 2.65-2.55 (m, 3H), 2.32-2.22 (m, 1H), 2.35-2.22 (m, 2H), 1.88-1.63 (m, 1H), 1.49-1.19 (m, 2H); LCMS(electrospray) m/z 420.0 (M + H+). | D |
| 212 | 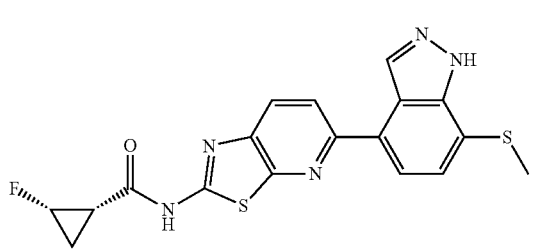 [SMILES: CSc1ccc(-c2ccc3nc(NC(=O)[C@@H]4C[C@@H]4F)sc3n2)c2cn[nH]c12]<br>(1S,2S)-2-fluoro-N-(5-(7-(methylthio)-1H-indazol-4-yl)thiazolo[5,4-b]pyridin-2-yl)cyclopropane-1-carboxamide | ¹H NMR (400 MHz, DMSO-$d_6$) δ 13.15-13.72 (m, 1 H) 12.88 (s, 1 H) 8.74 (s, 1 H) 8.13-8.21 (m, 2 H) 7.77 (d, J = 7.75 Hz, 1 H) 7.35 (d, J = 7.75 Hz, 1 H) 4.92-5.19 (m, 1 H) 3.17 (s, 1 H) 2.65 (s, 3 H) 2.23-2.31 (m, 1H) 1.74-1.84 (m, 2 H) 1.31-1.39 (m, 1 H); LCMS(electrospray) m/z 400.0 (M + H+). | D |
| 213 | 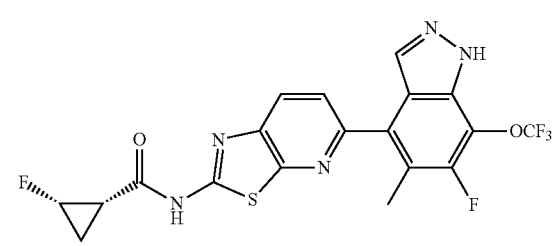 [SMILES: Cc1c(F)c(OC(F)(F)F)c2[nH]ncc2c1-c1ccc2nc(NC(=O)[C@@H]3C[C@@H]3F)sc2n1]<br>(1S,2S)-2-fluoro-N-(5-(6-fluoro-5-methyl-7-(trifluoromethoxy)-1H-indazol-4-yl)thiazolo[5,4-b]pyridin-2-yl)cyclopropane-1-carboxamide | ¹H NMR (400 MHz, DMSO-$d_6$) δ 13.93 (s, 1H), 8.26 (d, J = 8.4 Hz, 1H), 7.96 (s, 1H), 7.74 (d, J = 8.3 Hz, 1H), 5.25-4.89 (m, 1H), 2.31 (d, J = 2.8 Hz, 3H), 2.29-2.22 (m, 1H), 1.84-1.70 (m, 1H), 1.29-1.36 (m, J = 2.6, 6.2, 12.8 Hz, 1H); LCMS(electrospray) m/z 470.2 (M + H+). | D |

TABLE 1-continued

Compounds of Examples

| Ex # | Structure/Name | ¹H NMR/MS (M + 1) | Method |
|------|----------------|-------------------|--------|
| 214 | 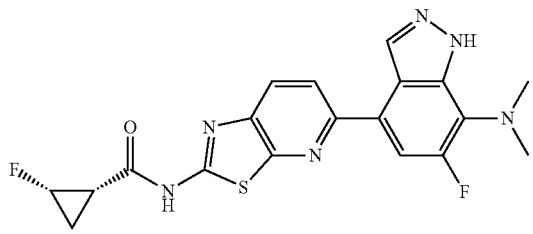 [SMILES: CN(C)c1c(F)cc(-c2ccc3nc(NC(=O)[C@@H]4C[C@@H]4F)sc3n2)c2cn[nH]c12]<br>(1S,2S)-N-(5-(7-(dimethylamino)-6-fluoro-1H-indazol-4-yl)thiazolo[5,4-b]pyridin-2-yl)-2-fluorocyclopropane-1-carboxamide | ¹H NMR (400 MHz, DMSO-d₆) δ 13.27 (br s, 1H), 13.01-12.74 (m, 1H), 8.68 (br s, 1H), 8.55 (d, J = 8.6 Hz, 1H), 8.22 (d, J = 8.5 Hz, 1H), 8.15 (q, J = 8.6 Hz, 2H), 7.61 (d, J = 14.3 Hz, 1H), 5.18-4.96 (m, 1H), 2.99 (br s, 6H), 2.30-2.23 (m, 1H), 1.83-1.72 (m, 1H), 1.38-1.31 (m, 1H); LCMS(electrospray) m/z 415.2 (M + H+). | D |
| 215 | 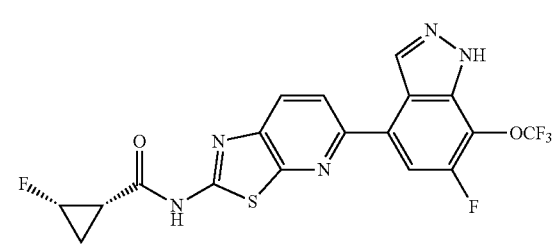<br>(1S,2S)-2-fluoro-N-(5-(6-fluoro-7-(trifluoromethoxy)-1H-indazol-4-yl)thiazolo[5,4-b]pyridin-2-yl)cyclopropane-1-carboxamide | ¹H NMR (400 MHz, DMSO-d₆) δ 14.03 (s, 1H), 12.97 (s, 1H), 8.82 (s, 1H), 8.26 (s, 2H), 7.90 (d, J = 12.0 Hz, 1H), 5.24-4.94 (m, 1H), 2.28 (ddd, J = 2.0, 4.6, 6.7 Hz, 1H), 1.87-1.70 (m, 1H), 1.32-1.36 (m, J = 2.6, 6.2, 12.7 Hz, 1H); LCMS(electrospray) m/z 456.2 (M + H+). | D |
| 216 | 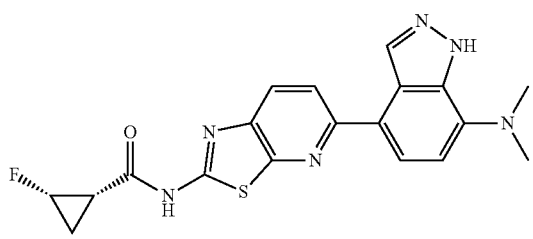 [SMILES: CN(C)c1ccc(-c2ccc3nc(NC(=O)[C@@H]4C[C@@H]4F)sc3n2)c2cn[nH]c12]<br>(1S,2S)-N-(5-(7-(dimethylamino)-1H-indazol-4-yl)thiazolo[5,4-b]pyridin-2-yl)-2-fluorocyclopropane-1-carboxamide | ¹H NMR (400 MHz, DMSO-d₆) δ 13.30-12.94 (m, 1H), 8.73-8.65 (m, 1H), 8.15-8.08 (m, 1H), 8.07-8.01 (m, 1H), 7.66 (d, J = 7.9 Hz, 1H), 6.82-6.73 (m, 1H), 5.29-4.92 (m, 1H), 3.13-2.82 (m, 6H), 2.29-2.18 (m, 1H), 2.07 (s, 1H), 1.84-1.69 (m, 1H), 1.39-1.25 (m, 1H); LCMS(electrospray) m/z 397.1 (M + H+). | D |
| 217 | 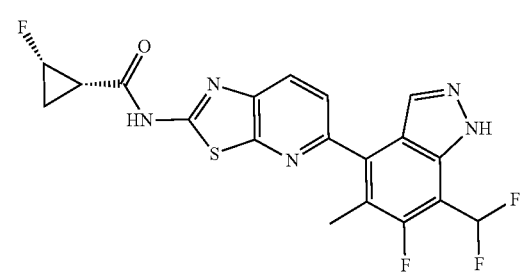<br>(1S,2S)-N-(5-(7-(difluoromethyl)-6-fluoro-5-methyl-1H-indazol-4-yl)thiazolo[5,4-b]pyridin-2-yl)-2-fluorocyclopropane-1-carboxamide | ¹H NMR (400 MHz, DMSO-d₆) δ 13.94-13.07 (m, 1H), 8.24 (d, J = 8.3 Hz, 1H), 7.92 (s, 1H), 7.74-7.44 (m, 2H), 5.18-4.91 (m, 1H), 2.27 (d, J = 2.6 Hz, 3H), 2.26-2.22 (m, 1H), 1.82-1.71 (m, 1H), 1.37-1.28 (m, 1H); LCMS(electrospray) m/z 436.1 (M + H+). | D |

TABLE 1-continued

Compounds of Examples

| Ex # | Structure/Name | ¹H NMR/MS (M + 1) | Method |
|---|---|---|---|
| 218 | 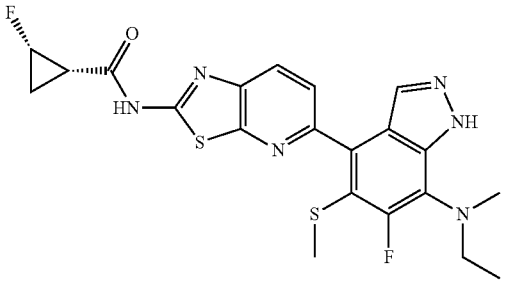 [SMILES: CCN(C)c1c(F)c(SC)c(-c2ccc3nc(NC(=O)[C@@H]4C[C@@H]4F)sc3n2)c2cn[nH]c12]<br>(1S,2S)-N-(5-(7-(ethyl(methyl)amino)-6-fluoro-5-(methylthio)-1H-indazol-4-yl)thiazolo[5,4-b]pyridin-2-yl)-2-fluorocyclopropane-1-carboxamide | ¹H NMR (400 MHz, DMSO-$d_6$) δ 13.33 (br s, 1H), 8.19 (d, J = 8.4 Hz, 1H), 7.77 (s, 1H), 7.70 (d, J = 8.4 Hz, 1H), 5.19-4.95 (m, 1H), 3.25 (br d, J = 7.7 Hz, 2H), 2.97 (d, J = 1.6 Hz, 3H), 2.26 (s, 3H), 1.85-1.70 (m, 1H), 1.40-1.21 (m, 2H), 1.10-1.04 (m, 3H); LCMS(electrospray) m/z 475 (M + H+). | D |
| 219 | 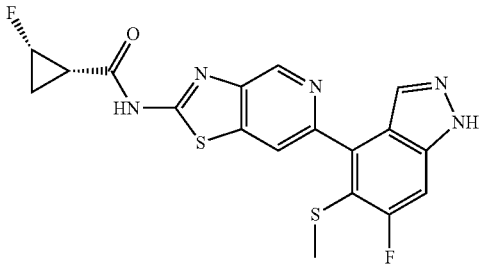 [SMILES: CSc1c(F)cc2[nH]ncc2c1-c1cc2sc(NC(=O)[C@@H]3C[C@@H]3F)nc2cn1]<br>(1S,2S)-2-fluoro-N-(6-(6-fluoro-5-(methylthio)-1H-indazol-4-yl)thiazolo[4,5-c]pyridin-2-yl)cyclopropane-1-carboxamide | ¹H NMR (400 MHz, DMSO-$d_6$) δ 13.32 (s, 1H), 13.04 (s, 1H), 9.13 (s, 1H), 8.31 (s, 1H), 7.79 (s, 1H), 7.52 (d, J = 9.3 Hz, 1H), 5.23-4.94 (m, 1H), 2.35-2.17 (m, 4H), 1.86-1.68 (m, 1H), 1.41-1.29 (m, 1H); LCMS(electrospray) m/z 418.0 (M + H+). | D |
| 220 | 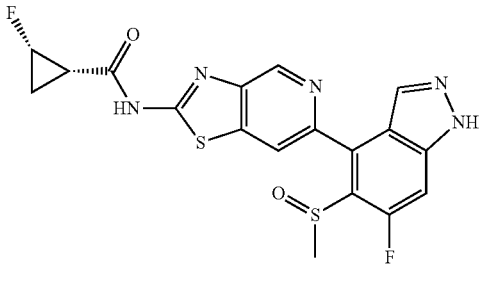 [SMILES: CS(=O)c1c(F)cc2[nH]ncc2c1-c1cc2sc(NC(=O)[C@@H]3C[C@@H]3F)nc2cn1]<br>(1S,2S)-2-fluoro-N-(6-(6-fluoro-5-(methylsulfinyl)-1H-indazol-4-yl)thiazolo[4,5-c]pyridin-2-yl)cyclopropane-1-carboxamide | ¹H NMR (400 MHz, DMSO-$d_6$) δ 13.60 (s, 1H), 13.10 (s, 1H), 9.12 (s, 1H), 8.53 (s, 1H), 8.14 (s, 1H), 7.63 (d, J = 11.5 Hz, 1H), 5.19-4.96 (m, 1H), 3.17 (s, 3H), 2.29-2.21 (m, 1H), 1.86-1.68 (m, 1H), 1.39-1.29 (m, 1H); LCMS(electrospray) m/z 434.0 (M + H+). | D |
| 221 | 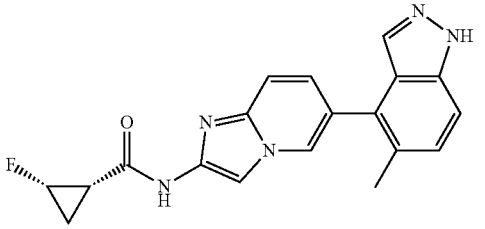 [SMILES: Cc1ccc2[nH]ncc2c1-c1ccc2nc(NC(=O)[C@@H]3C[C@@H]3F)cn2c1]<br>(1S,2S)-2-fluoro-N-(6-(5-methyl-1H-indazol-4-yl)imidazo[1,2-a]pyridin-2-yl)cyclopropane-1-carboxamide | ¹H NMR (400 MHz, DMSO-$d_6$) δ 12.77 (s, 1H), 9.70 (s, 1H), 9.00 (s, 1H), 8.66 (d, J = 9.2 Hz, 1H), 8.59 (s, 1H), 8.55 (d, J = 9.2 Hz, 1H), 8.33 (d, J = 8.0 Hz, 1H), 8.14 (d, J = 8.8 Hz, 1H), 5.91~5.71 (m, 1H), 3.11 (s, 3H), 3.05~3.00 (m, 1H), 2.54~2.48 (m, 1H), 2.07~2.03 (m, 1H); LCMS (electrospray) m/z 350.0 (M + H)+. | E |

TABLE 1-continued

Compounds of Examples

| Ex # | Structure/Name | ¹H NMR/MS (M + 1) | Method |
|---|---|---|---|
| 222 | (1S,2S)-N-(6-(1H-indazol-4-yl)imidazo[1,2-a]pyridin-2-yl)-2-fluorocyclopropane-1-carboxamide | ¹H NMR (400 MHz, DMSO-$d_6$) δ 13.23 (s, 1H), 11.01 (s, 1H), 8.93 (s, 1H), 8.17 (s, 1H), 7.59~7.51 (m, 3H), 7.42 (t, J = 7.8 Hz, 1H), 7.26 (d, J = 6.4 Hz, 1H), 5.00~4.79 (m, 1H), 2.13~2.10 (m, 1H), 1.67~1.60 (m, 1H), 1.17~1.09 (m, 1H); LCMS (electrospray) m/z 335.9 (M + H)+. | E |
| 223 | N-(6-(5-chloro-1H-indazol-4-yl)imidazo[1,2-a]pyridin-2-yl)cyclopropanecarboxamide. 2 HCl salt | ¹H NMR (400 MHz, METHANOL-$d_4$) δ 8.92 (s, 1H), 8.13 (s, 1H), 7.99-7.91 (m, 3H), 7.68 (dd, J = 1.0, 8.9 Hz, 1H), 7.58 (d, J = 8.9 Hz, 1H), 1.95-1.87 (m, 1H), 1.12-1.07 (m, 2H), 1.05-0.98 (m, 2H); LCMS (electrospray) m/z 352.0 (M + H)+. | F |
| 224 | N-(6-(5-methoxy-1H-indazol-4-yl)imidazo[1,2-a]pyridin-2-yl)cyclopropanecarboxamide. 2 HCl salt | ¹H NMR (400 MHz, METHANOL-$d_4$) δ 8.98 (s, 1H), 8.17-8.09 (m, 3H), 7.94 (d, J = 9.2 Hz, 1H), 7.71 (d, J = 9.2 Hz, 1H), 7.54-7.48 (m, 1H), 3.90 (s, 3H), 1.94-1.85 (m, 1H), 1.12-1.06 (m, 2H), 1.05-0.99 (m, 2H); LCMS (electrospray) m/z 348.0 (M + H)+. | F |
| 225 | N-(6-(5-amino-1H-indazol-4-yl)imidazo[1,2-a]pyridin-2-yl)cyclopropanecarboxamide. 3 TFA salt | ¹H NMR (400 MHz, METHANOL-$d_4$) δ 8.76 (s, 1H), 7.88-7.83 (m, 2H), 7.75 (dd, J = 1.5, 9.2 Hz, 1H), 7.66 (dd, J = 0.8, 8.9 Hz, 1H), 7.36 (d, J = 8.9 Hz, 1H), 1.96-1.88 (m, 1H), 1.09-1.04 (m, 2H), 1.02-0.95 (m, 2H); LCMS (electrospray) m/z 333.2 | F |

TABLE 1-continued

Compounds of Examples

| Ex # | Structure/Name | ¹H NMR/MS (M + 1) | Method |
|---|---|---|---|
| 226 | 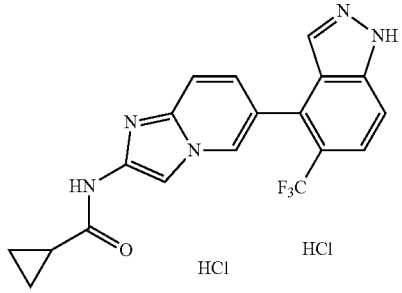 [SMILES: O=C(Nc1cn2cc(-c3c(C(F)(F)F)ccc4[nH]ncc34)ccc2n1)C1CC1 ; Cl ; Cl]<br>N-(6-(5-(trifluoromethyl)-1H-indazol-4-yl)imidazo[1,2-a]pyridin-2-yl)cyclopropanecarboxamide. 2 HCl salt | ¹H NMR (400 MHz, DMSO-$d_6$) δ 11.43 (br s, 1H), 8.80 (s, 1H), 8.16 (s, 1H), 7.93 (s, 1H), 7.84-7.76 (m, 2H), 7.69 (d, J = 9.4 Hz, 1H), 7.45 (br d, J = 8.9 Hz, 1H), 1.97 (quin, J = 6.2 Hz, 1H), 0.86 (d, J = 6.0 Hz, 4H); LCMS (electrospray) m/z 386.1 (M + H)+. | F |
| 227 | 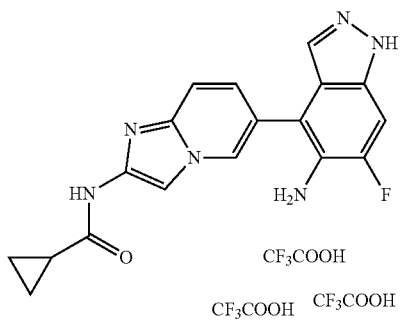 [SMILES: Nc1c(F)cc2[nH]ncc2c1-c1ccc2nc(NC(=O)C3CC3)cn2c1 ; "CF3COOH" ; "CF3COOH" ; "CF3COOH"]<br>N-(6-(5-amino-6-fluoro-1H-indazol-4-yl)imidazo[1,2-a]pyridin-2-yl)cyclopropanecarboxamide. 3TFA salt | ¹H NMR (400 MHz, DMSO-$d_6$) δ 11.40 (br s, 1H), 8.83 (s, 1H), 8.14 (s, 1H), 7.75 (d, J = 9.0 Hz, 1H), 7.68 (s, 1H), 7.61 (d, J = 9.0 Hz, 1H), 7.37 (d, J = 10.9 Hz, 1H), 6.90-5.46 (m, 6H), 1.94 (quin, J = 6.2 Hz, 1H), 0.95-0.82 (m, 4H); LCMS (electrospray) m/z 351.2 (M + H)+. | F |
| 228 | 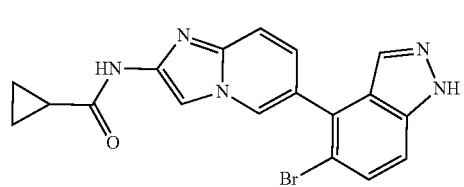 [SMILES: O=C(Nc1cn2cc(-c3c(Br)ccc4[nH]ncc34)ccc2n1)C1CC1]<br>N-(6-(5-bromo-1H-indazol-4-yl)imidazo[1,2-a]pyridin-2-yl)cyclopropanecarboxamide | ¹H NMR (400 MHz, METHANOL-$d_4$) δ 8.56-8.53 (m, 1H), 8.11 (s, 1H), 7.82 (s, 1H), 7.68 (d, J = 8.9 Hz, 1H), 7.58-7.50 (m, 2H), 7.38 (dd, J = 1.7, 9.2 Hz, 1H), 1.97-1.88 (m, 1H), 1.02-0.97 (m, 2H), 0.93-0.88 (m, 2H); LCMS (electrospray) m/z 397.9 (M + H)+. | F |
| 229 | 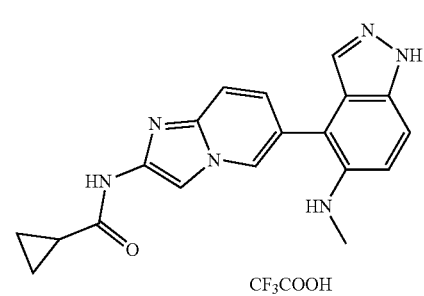<br>N-(6-(5-(methylamino)-1H-indazol-4-yl)imidazo[1,2-a]pyridin-2-yl)cyclopropanecarboxamide. 3 TFA salt | ¹H NMR (400 MHz, METHANOL-$d_4$) δ 8.82 (br s, 1H), 7.89 (br d, J = 8.8 Hz, 1H), 7.82-7.73 (m, 3H), 7.45 (d, J = 8.9 Hz, 1H), 2.98 (s, 3H), 1.98-1.86 (m, 1H), 1.12-0.95 (m, 4H); LCMS (electrospray) m/z 347.0 (M + H)+. | F |

TABLE 1-continued

Compounds of Examples

| Ex # | Structure/Name | ¹H NMR/MS (M + 1) | Method |
|---|---|---|---|
| 230 | 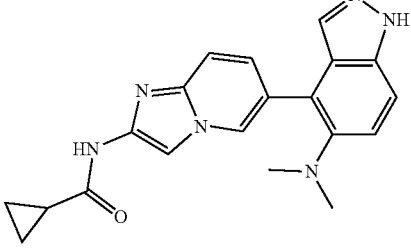<br>N-(6-(5-(dimethylamino)-1H-indazol-4-yl)imidazo[1,2-a]pyridin-2-yl)cyclopropanecarboxamide | ¹H NMR (400 MHz, METHANOL-$d_4$) δ 8.60-8.57 (m, 1H), 8.09 (s, 1H), 7.87 (s, 1H), 7.58-7.49 (m, 3H), 7.48-7.44 (m, 1H), 2.62 (s, 6H), 1.97-1.89 (m, 1H), 1.03-0.97 (m, 2H), 0.94-0.88 (m, 2H); LCMS (electrospray) m/z 361.2 (M + H)+. | F |
| 231 | 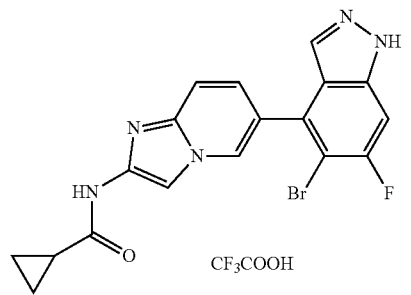<br>N-(6-(5-bromo-6-fluoro-1H-indazol-4-yl)imidazo[1,2-a]pyridin-2-yl)cyclopropanecarboxamide. 2 TFA salt | ¹H NMR (400 MHz, DMSO-$d_6$) δ 13.49 (br s, 1H), 11.05 (s, 1H), 8.78 (s, 1H), 8.14 (s, 1H), 7.92 (s, 1H), 7.64 (d, J = 8.7 Hz, 1H), 7.57 (d, J = 9.2 Hz, 1H), 7.32 (dd, J = 1.7, 9.2 Hz, 1H), 2.05-1.86 (m, 1H), 0.85-0.79 (m, 4H); LCMS (electrospray) m/z 414.1 (M + H)+. | G |
| 232 | 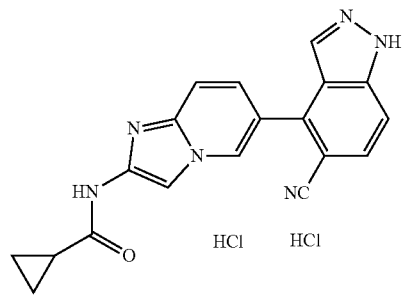 [SMILES: N#Cc1ccc2[nH]ncc2c1-c1ccc2nc(NC(=O)C3CC3)cn2c1 ; Cl ; Cl]<br>N-(6-(5-cyano-1H-indazol-4-yl)imidazo[1,2-a]pyridin-2-yl)cyclopropanecarboxamide. 2 HCl salt | ¹H NMR (400 MHz, METHANOL-$d_4$) δ 9.17 (s, 1H), 8.22 (s, 1H), 8.21-8.18 (m, 1H), 8.06 (d, J = 9.3 Hz, 1H), 7.84 (s, 2H), 1.94-1.87 (m, 1H), 1.14-1.09 (m, 2H), 1.07-1.01 (m, 2H); LCMS (electrospray) m/z 343.0 (M + H)+. | F |
| 233 | 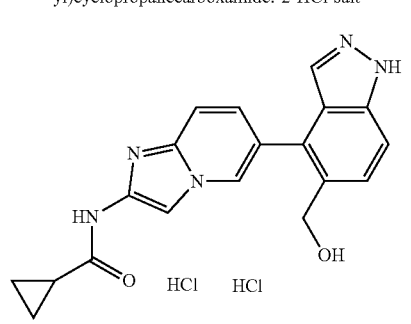<br>N-(6-(5-(hydroxymethyl)-1H-indazol-4-yl)imidazo[1,2-a]pyridin-2-yl)cyclopropanecarboxamide. 2 HCl salt | ¹H NMR (400 MHz, METHANOL-$d_4$) δ 8.91 (s, 1H), 8.10 (s, 1H), 8.07-8.03 (m, 1H), 8.00-7.96 (m, 1H), 7.91 (s, 1H), 7.72-7.65 (m, 2H), 4.61 (s, 2H), 3.61 (s, 1H), 1.93-1.86 (m, 1H), 1.13-1.08 (m, 2H), 1.07-1.01 (m, 2H); LCMS (electrospray) m/z 348.2 (M + H)+. | F |

TABLE 1-continued

Compounds of Examples

| Ex # | Structure/Name | $^1$H NMR/MS (M + 1) | Method |
|---|---|---|---|
| 234 | 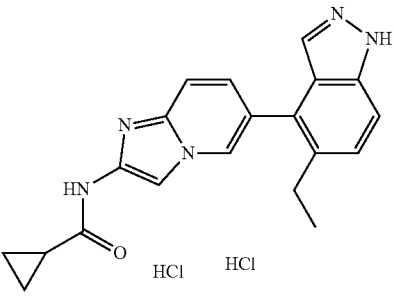 [SMILES: CCc1ccc2[nH]ncc2c1-c1ccc2nc(NC(=O)C3CC3)cn2c1 ; Cl ; Cl]<br>N-(6-(5-ethyl-1H-indazol-4-yl)imidazo[1,2-a]pyridin-2-yl)cyclopropanecarboxamide. 2 HCl salt | $^1$H NMR (400 MHz, METHANOL-d$_4$) δ 8.82 (s, 1H), 8.10 (s, 1H), 8.01-7.95 (m, 1H), 7.95-7.89 (m, 1H), 7.78 (s, 1H), 7.64 (d, J = 8.7 Hz, 1H), 7.50 (d, J = 8.7 Hz, 1H), 2.69 (q, J = 7.5 Hz, 2H), 1.93-1.85 (m, 1H), 1.19 (t, J = 7.5 Hz, 3H), 1.13-1.07 (m, 2H), 1.07-0.98 (m, 2H); LCMS (electrospray) m/z 346.2 (M + H)+. | F |
| 235 | 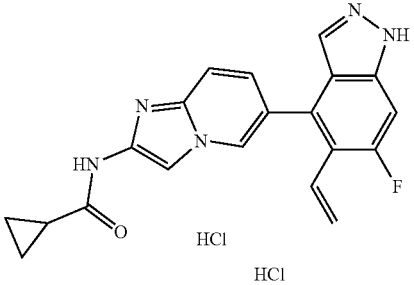 [SMILES: C=Cc1c(F)cc2[nH]ncc2c1-c1ccc2nc(NC(=O)C3CC3)cn2c1 ; Cl ; Cl]<br>N-(6-(6-fluoro-5-vinyl-1H-indazol-4-yl)imidazo[1,2-a]pyridin-2-yl)cyclopropanecarboxamide. 2 HCl salt | $^1$H NMR (400 MHz, DMSO-d$_6$) δ 11.82 (br s, 1H), 8.90 (s, 1H), 8.19 (s, 1H), 7.91 (d, J = 0.6 Hz, 1H), 7.83 (d, J = 9.2 Hz, 1H), 7.63 (br d, J = 9.2 Hz, 1H), 7.50 (d, J = 11.4 Hz, 1H), 6.54 (dd, J = 11.9, 17.9 Hz, 1H), 5.63 (br d, J = 17.9 Hz, 1H), 5.42 (br d, J = 11.6 Hz, 1H), 2.06-1.94 (m, 1H), 0.95-0.85 (m, 4H); LCMS (electrospray) m/z 362.1 (M + H)+. | F |
| 236 | 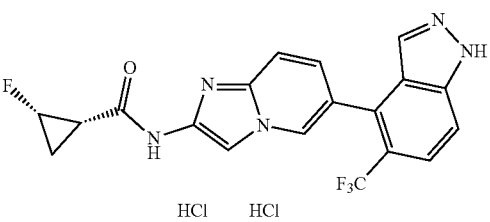 [SMILES: O=C(Nc1cn2cc(-c3c(C(F)(F)F)ccc4[nH]ncc34)ccc2n1)[C@@H]1C[C@@H]1F ; Cl ; Cl]<br>(1S,2S)-2-fluoro-N-(6-(5-(trifluoromethyl)-1H-indazol-4-yl)imidazo[1,2-a]pyridin-2-yl)cyclopropane-1-carboxamide. 2 HCl salt | $^1$H NMR (400 MHz, DMSO-d$_6$) δ 11.46 (br s, 1H), 8.82 (s, 1H), 8.20 (s, 1H), 7.94 (s, 1H), 7.85-7.76 (m, 2H), 7.71 (br d, J = 9.2 Hz, 1H), 7.47 (br d, J = 8.6 Hz, 1H), 5.11-4.85 (m, 1H), 2.20 (td, J = 6.9, 13.9 Hz, 1H), 1.77-1.63 (m, 1H), 1.31-1.16 (m, 1H), 1.31-1.16 (m, 1H); LCMS (electrospray) m/z 403.8 (M + H)+. | F |
| 237 | 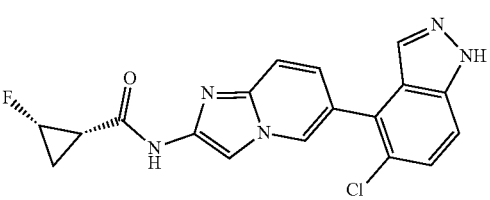 [SMILES: O=C(Nc1cn2cc(-c3c(Cl)ccc4[nH]ncc34)ccc2n1)[C@@H]1C[C@@H]1F]<br>(1S,2S)-N-(6-(5-chloro-1H-indazol-4-yl)imidazo[1,2-a]pyridin-2-yl)-2-fluorocyclopropane-1-carboxamide | $^1$H NMR (400 MHz, DMSO-d$_6$) δ 13.40 (s, 1H), 11.05 (s, 1H), 8.77 (s, 1H), 8.16 (s, 1H), 7.91 (s, 1H), 7.62 (d, J = 9.7 Hz, 1H), 7.58-7.48 (m, 2H), 7.34 (dd, J = 1.7, 9.2 Hz, 1H), 5.04-4.80 (m, 1H), 2.20-2.10 (m, 1H), 1.73-1.59(m, 1H), 1.23-1.10 (m, 1H); LCMS (electrospray) m/z 370.1 (M + H)+. | F |

TABLE 1-continued

Compounds of Examples

| Ex # | Structure/Name | ¹H NMR/MS (M + 1) | Method |
|---|---|---|---|
| 238 | 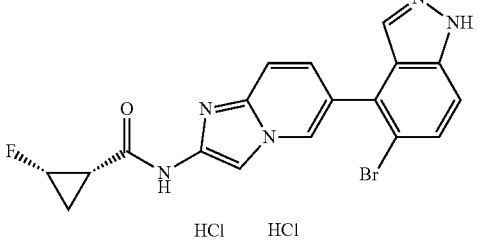<br>(1S,2S)-N-(6-(5-bromo-1H-indazol-4-yl)imidazo[1,2-a]pyridin-2-yl)-2-fluorocyclopropane-1-carboxamide. 2 HCl salt | ¹H NMR (400 MHz, DMSO-$d_6$) δ 11.49 (br s, 1H), 8.88 (br s, 1H), 8.20 (s, 1H), 7.90 (s, 1H), 7.73 (br d, J = 9.2 Hz, 1H), 7.69-7.64 (m, 1H), 7.63-7.53 (m, 2H), 5.11-4.86 (m, 1H), 2.19 (br s, 1H), 1.77-1.62 (m, 1H), 1.22 (br d, J = 2.9 Hz, 1H); LCMS (electrospray) m/z 415.8 (M + H)+. | F |
| 239 | 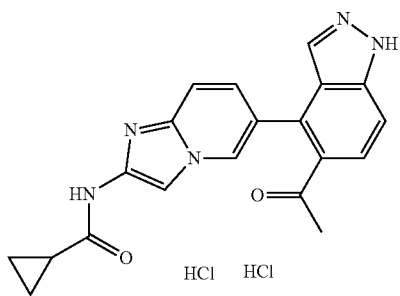 [SMILES: CC(=O)c1ccc2[nH]ncc2c1-c1ccc2nc(NC(=O)C3CC3)cn2c1 ; Cl ; Cl]<br>N-(6-(5-acetyl-1H-indazol-4-yl)imidazo[1,2-a]pyridin-2-yl)cyclopropanecarboxamide. 2 HCl salt | ¹H NMR (400 MHz, DMSO-$d_6$) δ 11.69 (br s, 1H), 8.84 (s, 1H), 8.17 (s, 1H), 8.04 (s, 1H), 7.88 (d, J = 8.8 Hz, 1H), 7.77 (br d, J = 9.0 Hz, 1H), 7.71 (d, J = 8.8 Hz, 1H), 7.59 (br d, J = 8.8 Hz, 1H), 2.40 (s, 3H), 2.03-1.95 (m, 1H), 0.95-0.87 (m, 4H); LCMS (electrospray) m/z 359.9 (M + H)+. | F |
| 240 | 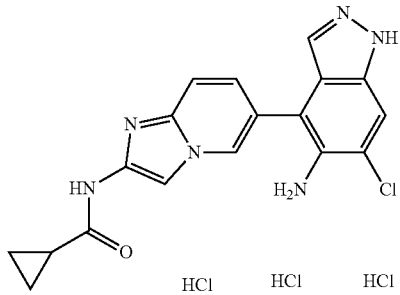 [SMILES: Nc1c(Cl)cc2[nH]ncc2c1-c1ccc2nc(NC(=O)C3CC3)cn2c1 ; Cl ; Cl ; Cl]<br>N-(6-(5-amino-6-chloro-1H-indazol-4-yl)imidazo[1,2-a]pyridin-2-yl)cyclopropanecarboxamide. 3 HCl salt | ¹H NMR (400 MHz, DMSO-$d_6$) δ 12.27 (s, 1H), 8.99 (s, 1H), 8.21 (s, 1H), 7.98 (d, J = 9.2 Hz, 1H), 7.85 (dd, J = 1.5, 9.1 Hz, 1H), 7.69 (dd, J = 1.0, 8.1 Hz, 2H), 6.23-5.16 (m, 6H), 2.13-2.00 (m, 1H), 1.04-0.87 (m, 4H); LCMS (electrospray) m/z 367.0 (M + H+) | F |
| 241 | 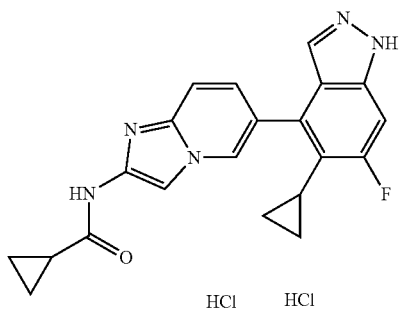 [SMILES: O=C(Nc1cn2cc(-c3c(C4CC4)c(F)cc4[nH]ncc34)ccc2n1)C1CC1 ; Cl ; Cl]<br>N-(6-(5-cyclopropyl-6-fluoro-1H-indazol-4-yl)imidazo[1,2-a]pyridin-2-yl)cyclopropanecarboxamide. 2 HCl salt | ¹H NMR (400 MHz, DMSO-$d_6$) δ 12.09 (br s, 1H), 9.04 (s, 1H), 8.22 (s, 1H), 7.97-7.86 (m, 3H), 7.41 (d, J = 10.5 Hz, 1H), 2.07-2.00 (m, 1H), 1.99-1.91 (m, 1H), 1.99-1.91 (m, 1H), 0.97-0.87 (m, 4H), 0.78-0.68 (m, 2H), 0.26 (br d, J = 4.5 Hz, 2H); LCMS (electrospray) m/z 376.1 (M + H+) | F |

TABLE 1-continued

Compounds of Examples

| Ex # | Structure/Name | ¹H NMR/MS (M + 1) | Method |
|---|---|---|---|
| 242 | 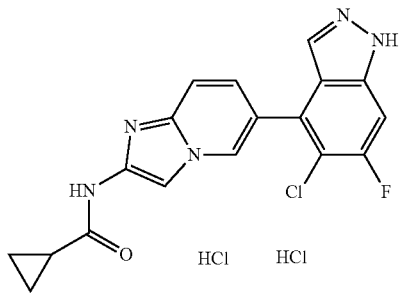 [SMILES: O=C(Nc1cn2cc(-c3c(Cl)c(F)cc4[nH]ncc34)ccc2n1)C1CC1 ; Cl ; Cl]<br>N-(6-(5-chloro-6-fluoro-1H-indazol-4-yl)imidazo[1,2-a]pyridin-2-yl)cyclopropanecarboxamide. 2 HCl salt | ¹H NMR (400 MHz, DMSO-d$_6$) δ 13.50 (br s, 1H), 11.17 (s, 1H), 8.68 (d, J = 7.2 Hz, 1H), 7.92 (s, 1H), 7.79 (d, J = 1.0 Hz, 1H), 7.68 (dd, J = 0.9, 9.0 Hz, 1H), 6.97 (s, 1H), 6.96 (d, J = 2.0 Hz, 1H), 6.96-6.93 (m, 1H), 2.13-2.00 (m, 1H), 1.04-0.87 (m, 4H); LCMS (electrospray)m/z 370.8 (M + H+) | F |
| 243 | 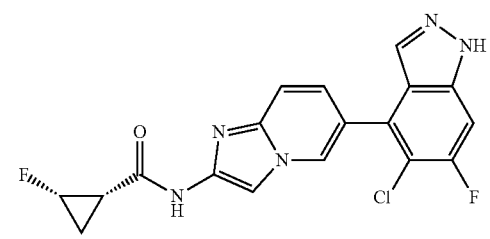<br>(1S,2S)-N-(6-(5-chloro-6-fluoro-1H-indazol-4-yl)imidazo[1,2-a]pyridin-2-yl)-2-fluorocyclopropane-1-carboxamide. 2 HCl salt | ¹H NMR (400 MHz, DMSO-d$_6$) δ 11.91-11.45 (m, 1H), 9.05-8.93 (m, 1H), 8.24 (br s, 1H), 8.00 (s, 1H), 7.87-7.59 (m, 3H), 5.07 (br s, 1H), 4.91 (br s, 1H), 2.22 (br s, 1H), 1.79-1.63 (m, 1H), 1.23 (br s, 1H); LCMS (electrospray) m/z 388.0 (M + H+) | F |
| 244 | 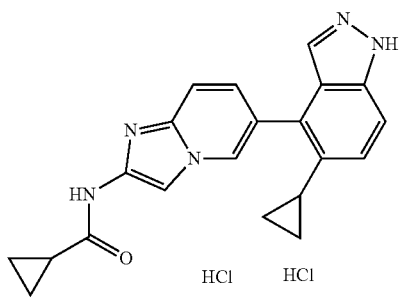 [SMILES: O=C(Nc1cn2cc(-c3c(C4CC4)ccc4[nH]ncc34)ccc2n1)C1CC1 ; Cl ; Cl]<br>N-(6-(5-cyclopropyl-1H-indazol-4-yl)imidazo[1,2-a]pyridin-2-yl)cyclopropanecarboxamide. 2 HCl salt | ¹H NMR (400 MHz, DMSO-d$_6$) δ 11.99 (br s, 1H), 8.99 (s, 1H), 8.23 (s, 1H), 7.95-7.85 (m, 2H), 7.82 (d, J = 0.9 Hz, 1H), 7.55 (d, J = 8.7 Hz, 1H), 7.08 (d, J = 8.7 Hz, 1H), 2.07-1.89 (m, 2H), 0.98-0.90 (m, 4H), 0.87-0.81 (m, 2H), 0.69-0.63 (m, 2H); LCMS (electrospray) m/z 358.0 (M + H+) | F |
| 245 | 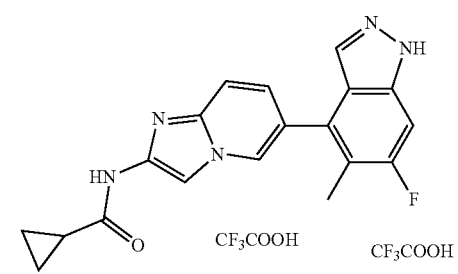 [SMILES: Cc1c(F)cc2[nH]ncc2c1-c1ccc2nc(NC(=O)C3CC3)cn2c1 ; "CF3COOH" ; "CF3COOH"]<br>N-(6-(6-fluoro-5-methyl-1H-indazol-4-yl)imidazo[1,2-a]pyridin-2-yl)cyclopropanecarboxamide. 2 TFA salt | ¹H NMR (400 MHz, DMSO-d$_6$) δ 11.27 (br s, 1H), 8.78 (s, 1H), 8.14 (s, 1H), 7.82 (s, 1H), 7.67 (br d, J = 9.0 Hz, 1H), 7.46 (br d, J = 9.0 Hz, 1H), 7.40 (br d, J = 9.8 Hz, 1H), 2.21 (br d, J = 1.2 Hz, 3H), 2.00-1.88 (m, 1H), 0.86 (br d, J = 5.7 Hz, 4H); LCMS (electrospray) m/z 350.2 (M + H+) | F |

TABLE 1-continued

Compounds of Examples

| Ex # | Structure/Name | ¹H NMR/MS (M + 1) | Method |
|---|---|---|---|
| 246 | 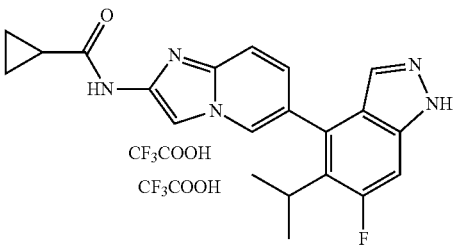 [SMILES: CC(C)c1c(F)cc2[nH]ncc2c1-c1ccc2nc(NC(=O)C3CC3)cn2c1 ; "CF3COOH" ; "CF3COOH"]<br>N-(6-(6-fluoro-5-isopropyl-1H-indazol-4-yl)imidazo[1,2-a]pyridin-2-yl)cyclopropanecarboxamide. 2 TFA salt | ¹H NMR (400 MHz, DMSO-d₆) δ 11.30 (s, 1H), 8.73 (s, 1H), 8.15 (s, 1H), 7.71-7.65 (m, 2H), 7.40 (br d, J = 11.8 Hz, 2H), 3.04 (td, J = 7.0, 14.1 Hz, 1H), 1.98-1.92 (m, 1H), 1.28 (dd, J = 6.9, 17.4 Hz, 6H), 0.87 (d, J = 6.1 Hz, 4H); LCMS (electrospray) m/z 378.1 (M + H+) | F |
| 247 | 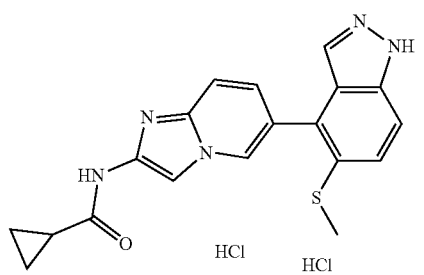 [SMILES: CSc1ccc2[nH]ncc2c1-c1ccc2nc(NC(=O)C3CC3)cn2c1 ; Cl ; Cl]<br>N-(6-(5-(methylthio)-1H-indazol-4-yl)imidazo[1,2-a]pyridin-2-yl)cyclopropanecarboxamide. 2 HCl salt | ¹H NMR (400 MHz, DMSO-d₆) δ 12.22 (s, 1H), 8.99 (s, 1H), 8.24 (s, 1H), 7.98-7.91 (m, 1H), 7.90-7.84 (m, 2H), 7.71-7.65 (m, 1H), 7.62-7.57 (m, 1H), 2.40 (s, 3H), 2.11-1.99 (m, 1H), 1.05-0.87 (m, 4H); LCMS (electrospray) m/z 364.1 (M + H+) | F |
| 248 | 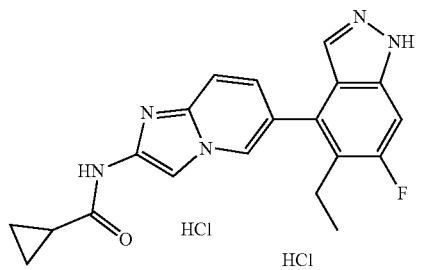 [SMILES: CCc1c(F)cc2[nH]ncc2c1-c1ccc2nc(NC(=O)C3CC3)cn2c1 ; Cl ; Cl]<br>N-(6-(5-ethyl-6-fluoro-1H-indazol-4-yl)imidazo[1,2-a]pyridin-2-yl)cyclopropanecarboxamide. 2 HCl salt | ¹H NMR (400 MHz, DMSO-d₆) δ 12.18 (s, 1H), 8.95 (s, 1H), 8.24 (s, 1H), 7.95 (d, J = 9.0 Hz, 1H), 7.81-7.74 (m, 2H), 7.46 (d, J = 10.3 Hz, 1H), 2.58 (q, J = 6.8 Hz, 2H), 2.09-2.00 (m, 1H), 1.09 (t, J = 7.3 Hz, 3H), 0.98-0.87 (m, 4H); LCMS (electrospray) m/z 364.1 (M + H+) | F |
| 249 | 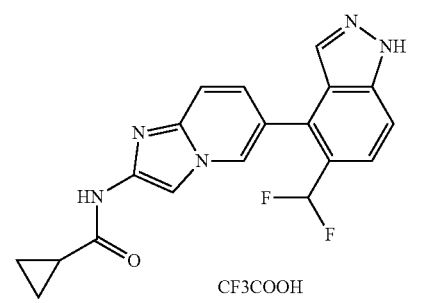<br>N-(6-(5-(difluoromethyl)-1H-indazol-4-yl)imidazo[1,2-a]pyridin-2-yl)cyclopropanecarboxamide. 2 TFA salt | ¹H NMR (400 MHz, DMSO-d₆) δ 13.53 (br s, 1H), 11.13 (s, 1H), 8.72 (s, 1H), 8.15 (s, 1H), 7.97 (s, 1H), 7.78-7.74 (m, 1H), 7.73-7.69 (m, 1H), 7.63 (d, J = 9.2 Hz, 1H), 7.34 (d, J = 9.0 Hz, 1H), 7.11-6.80 (m, 1H), 2.00-1.91 (m, 1H), 0.87-0.81 (m, 4H); LCMS (electrospray) m/z 368.2 (M + H+) | F |

TABLE 1-continued

Compounds of Examples

| Ex # | Structure/Name | $^1$H NMR/MS (M + 1) | Method |
|---|---|---|---|
| 250 | 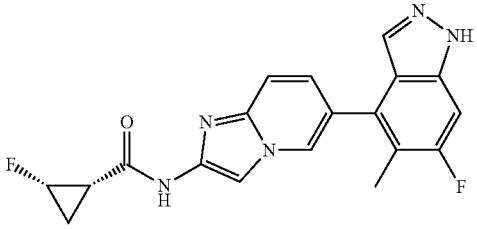 [SMILES: Cc1c(F)cc2[nH]ncc2c1-c1ccc2nc(NC(=O)[C@@H]3C[C@@H]3F)cn2c1]<br>(1S,2S)-2-fluoro-N-(6-(6-fluoro-5-methyl-1H-indazol-4-yl)imidazo[1,2-a]pyridin-2-yl)cyclopropane-1-carboxamide | $^1$H NMR (400 MHz, DMSO-d$_6$) δ 13.16 (s, 1H), 11.06 (s, 1H), 8.70 (s, 1H), 8.15 (s, 1H), 7.80 (s, 1H), 7.56 (d, J = 9.2 Hz, 1H), 7.38 (d, J = 9.8 Hz, 1H), 7.29 (dd, J = 1.7, 9.2 Hz, 1H), 5.09-4.77 (m, 1H), 2.22 (d, J = 2.4 Hz, 3H), 2.18-2.11 (m, 1H), 1.75-1.58 (m, 1H), 1.24-1.06 (m, 1H); LCMS (electrospray) m/z 368.1 (M + H+) | F |
| 251 | 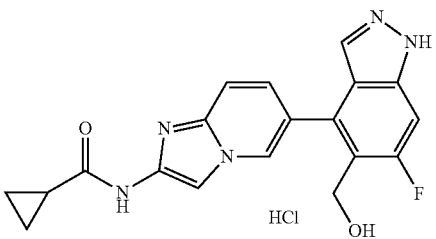<br>N-(6-(6-fluoro-5-(hydroxymethyl)-1H-indazol-4-yl)imidazo[1,2-a]pyridin-2-yl)cyclopropanecarboxamide. 2 HCl salt | $^1$H NMR (400 MHz, DMSO-d$_6$) δ 11.92 (br s, 1H), 8.99 (s, 1H), 8.21 (s, 1H), 7.96-7.81 (m, 3H), 7.46 (d, J = 9.9 Hz, 1H), 4.43 (s, 2H), 2.07-1.96 (m, 1H), 0.96-0.87 (m, 4H); LCMS (electrospray) m/z 366.1 (M + H+) | F |
| 252 | 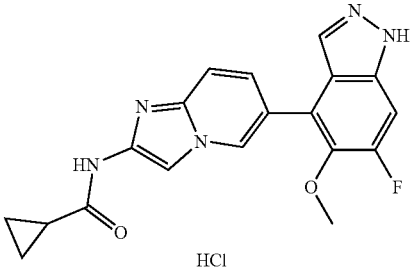<br>N-(6-(6-fluoro-5-methoxy-1H-indazol-4-yl)imidazo[1,2-a]pyridin-2-yl)cyclopropanecarboxamide. 2 HCl salt | $^1$H NMR (400 MHz, METHANOL-d$_4$) δ 9.03 (s, 1H), 8.18-8.14 (m, 1H), 8.05 (s, 1H), 7.99 (d, J = 9.2 Hz, 1H), 7.49 (d, J = 10.6 Hz, 1H), 3.77 (s, 3H), 1.95-1.82 (m, 1H), 1.15-1.07 (m, 2H), 1.06-1.00 (m, 2H); LCMS (electrospray) m/z 366.1 (M + H+) | F |
| 253 | 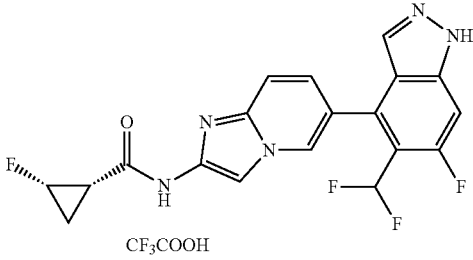<br>(1S,2S)-N-(6-(5-(difluoromethyl)-6-fluoro-1H-indazol-4-yl)imidazo[1,2-a]pyridin-2-yl)-2-fluorocyclopropane-1-carboxamide. 2 TFA salt | $^1$H NMR (400 MHz, DMSO-d$_6$) δ 13.64 (s, 1H), 11.16 (s, 1H), 8.76 (s, 1H), 8.19 (s, 1H), 7.98 (s, 1H), 7.66-7.57 (m, 2H), 7.29 (dd, J = 1.8, 9.1 Hz, 1H), 7.13-6.78 (m, 1H), 5.07-4.80 (m, 1H), 2.16 (td, J = 6.9, 13.9 Hz, 1H), 1.74-1.61 (m, 1H), 1.24-1.13 (m, 1H); LCMS (electrospray) m/z 404.0 (M + H+) | F |

TABLE 1-continued

Compounds of Examples

| Ex # | Structure/Name | ¹H NMR/MS (M + 1) | Method |
|---|---|---|---|
| 254 | 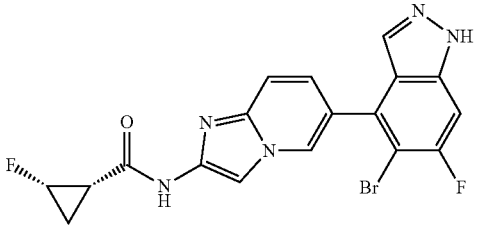 [SMILES: O=C(Nc1cn2cc(-c3c(Br)c(F)cc4[nH]ncc34)ccc2n1)[C@@H]1C[C@@H]1F]<br>(1S,2S)-N-(6-(5-bromo-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.50 (s, 1H), 11.11 (s, 1H), 8.79 (s, 1H), 8.17 (s, 1H), 7.93 (s, 1H), 7.65 (d, J = 8.8 Hz, 1H), 7.57 (d, J = 9.2 Hz, 1H), 7.32 (dd, J = 1.6, 7.6 Hz, 1H), 5.02 (m, 0.5H), 4.85 (m, 0.5H), 2.16 (m, 1H), 1.66 (m, 1H), 1.16 (m, 1H), LCMS (electrospray) m/z 433.00 (M + H)+. | F |
| 255 | 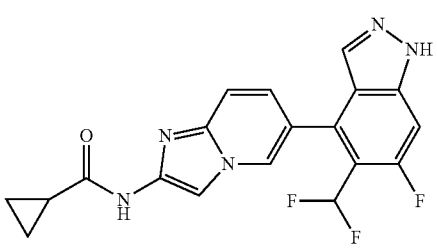 [SMILES: O=C(Nc1cn2cc(-c3c(C(F)F)c(F)cc4[nH]ncc34)ccc2n1)C1CC1]<br>N-(6-(5-(difluoromethyl)-6-fluoro-1H-indazol-4-yl)imidazo[1,2-a]pyridin-2-yl)cyclopropanecarboxamide | ¹H NMR (400 MHz, DMSO-d₆) δ 13.59 (br s, 1H), 11.04 (s, 1H), 8.72 (s, 1H), 8.15 (s, 1H), 7.97 (s, 1H), 7.62-7.56 (m, 2H), 7.23 (dd, J = 1.7, 9.1 Hz, 1H), 7.11-6.80 (m, 1H), 2.01-1.92 (m, 1H), 0.85-0.79 (m, 4H); LCMS (electrospray) m/z 386.1 (M + H+) | F |
| 256 | 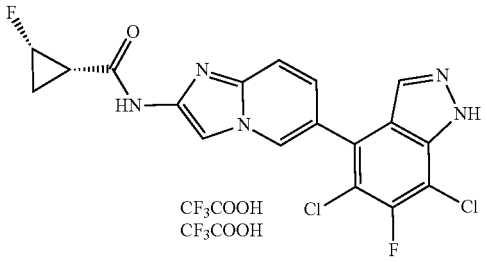 [SMILES: O=C(Nc1cn2cc(-c3c(Cl)c(F)c(Cl)c4[nH]ncc34)ccc2n1)[C@@H]1C[C@@H]1F ; "CF3COOH" ; "CF3COOH"]<br>(1S,2S)-N-(6-(5,7-dichloro-6-fluoro-1H-indazol-4-yl)imidazo[1,2-a]pyridin-2-yl)-2-fluorocyclopropane-1-carboxamide. 2 TFA salt | ¹H NMR (400 MHz, DMSO-d₆) δ 14.14 (s, 1H), 11.13 (s, 1H), 8.87-8.83 (m, 1H), 8.19 (s, 1H), 8.15 (br s, 1H), 7.61 (d, J = 9.3 Hz, 1H), 7.40 (dd, J = 1.8, 9.2 Hz, 1H), 5.04-4.83 (m, 1H), 2.19-2.13 (m, 1H), 1.72-1.62 (m, 1H), 1.23-1.15 (m, 1H); LCMS (electrospray) m/z 422.1 (M + H)+. | F |
| 257 | 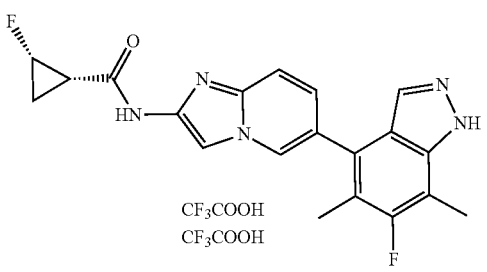 [SMILES: Cc1c(F)c(C)c2[nH]ncc2c1-c1ccc2nc(NC(=O)[C@@H]3C[C@@H]3F)cn2c1 ; "CF3COOH" ; "CF3COOH"]<br>(1S,2S)-2-fluoro-N-(6-(6-fluoro-5,7-dimethyl-1H-indazol-4-yl)imidazo[1,2-a]pyridin-2-yl)cyclopropane-1-carboxamide. 2 TFA salt | ¹H NMR (400 MHz, DMSO-d₆) δ 13.36 (s, 1H), 11.19 (br s, 1H), 8.72 (s, 1H), 8.16 (s, 1H), 7.80 (s, 1H), 7.62 (d, J = 9.2 Hz, 1H), 7.37 (br d, J = 9.2 Hz, 1H), 5.10-4.79 (m, 1H), 2.48 (d, J = 1.7 Hz, 3H), 2.21 (d, J = 2.8 Hz, 3H), 2.18-2.10 (m, 1H), 1.75-1.61 (m, 1H), 1.27-1.10 (m, 1H); LCMS (electrospray) m/z 382.4 (M + H)+. | F |

TABLE 1-continued

Compounds of Examples

| Ex # | Structure/Name | ¹H NMR/MS (M + 1) | Method |
|---|---|---|---|
| 258 | (1S,2S)-N-(6-(5-chloro-7-(dimethylamino)-6-fluoro-1H-indazol-4-yl)imidazo[1,2-a]pyridin-2-yl)-2-fluorocyclopropane-1-carboxamide. 2 TFA salt | ¹H NMR (400 MHz, DMSO-d₆)) δ 13.55 (br s, 1H), 11.21 (s, 1H), 8.80 (s, 1H), 8.17 (s, 1H), 7.95 (s, 1H), 7.62 (d, J = 9.2 Hz, 1H), 7.43 (d, J = 9.2 Hz, 1H), 5.08-4.77 (m, 1H), 3.01 (s, 3H), 3.00 (s, 3H), 2.16 (td, J = 7.0, 13.8 Hz, 1H), 1.76-1.57 (m, 1H), 1.27-1.11 (m, 1H); LCMS (electrospray) m/z 431.2 (M + H)+. | H |
| 259 | (1S,2S)-N-(6-(5-chloro-7-(dimethylphosphoryl)-6-fluoro-1H-indazol-4-yl)imidazo[1,2-a]pyridin-2-yl)-2-fluorocyclopropane-1-carboxamide. 2 TFA salt | ¹H NMR (400 MHz, DMSO-d₆) δ 11.20 (br s, 1H), 8.88 (s, 1H), 8.21 (s, 1H), 8.09 (d, J = 1.1 Hz, 1H), 7.66 (br d, J = 8.3 Hz, 1H), 7.46 (br d, J = 8.8 Hz, 1H), 5.11-4.81 (m, 1H), 2.23-2.11 (m, 1H), 1.96 (s, 3H), 1.93 (s, 3H), 1.75-1.62 (m, 1H), 1.25-1.13 (m, 1H); LCMS (electrospray) m/z 464.1 (M + H)+. | H |
| 260 | (1S,2S)-N-(6-(7-chloro-6-fluoro-5-methyl-1H-indazol-4-yl)imidazo[1,2-a]pyridin-2-yl)-2-fluorocyclopropane-1-carboxamide. 2 TFA salt | ¹H NMR (400 MHz, DMSO-d₆) δ 14.17-13.29 (m, 1H), 11.18 (s, 1H), 8.75 (s, 1H), 8.16 (s, 1H), 7.97 (s, 1H), 7.61 (d, J = 9.0 Hz, 1H), 7.36 (dd, J = 1.3, 9.2 Hz, 1H), 5.12-4.77 (m, 1H), 2.26 (d, J = 2.9 Hz, 3H), 2.16 (td, J = 7.0, 14.0 Hz, 1H), 1.76-1.58 (m, 1H), 1.25-1.10 (m, 1H); LCMS (electrospray) m/z 402.0 (M + H)+. | H |
| 261 | (1S,2S)-N-(6-(7-bromo-5-chloro-6-fluoro-1H-indazol-4-yl)imidazo[1,2-a]pyridin-2-yl)-2-fluorocyclopropane-1-carboxamide. 2 HCl salt | ¹H NMR (400 MHz, DMSO-d₆) δ 11.29 (s, 1H), 8.89 (s, 1H), 8.20 (s, 1H), 8.17 (s, 1H), 7.67 (d, J = 9.0 Hz, 1H), 7.50 (br d, J = 9.4 Hz, 1H), 5.09-4.82 (m, 1H), 2.18 (td, J = 6.9, 13.9 Hz, 1H), 1.75-1.62 (m, 1H), 1.26-1.14 (m, 1H); LCMS (electrospray) m/z 466.1 (M + H)+. | H |

TABLE 1-continued

Compounds of Examples

| Ex # | Structure/Name | ¹H NMR/MS (M + 1) | Method |
|---|---|---|---|
| 262 | 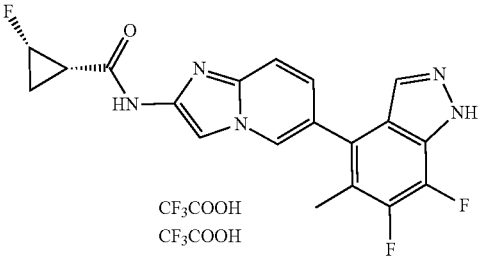 [SMILES: Cc1c(F)c(F)c2[nH]ncc2c1-c1ccc2nc(NC(=O)[C@@H]3C[C@@H]3F)cn2c1 ; "CF3COOH" ; "CF3COOH"]<br>CF₃COOH<br>CF₃COOH<br><br>(1S,2S)-N-(6-(6,7-difluoro-5-methyl-1H-indazol-4-yl)imidazo[1,2-a]pyridin-2-yl)-2-fluorocyclopropane-1-carboxamide. 2 TFA salt | ¹H NMR (400 MHz, DMSO-d₆) δ 11.19 (s, 1H), 8.73 (s, 1H), 8.15 (s, 1H), 7.95 (br s, 1H), 7.61 (d, J = 9.3 Hz, 1H), 7.35 (d, J = 7.8 Hz, 1H), 5.17-4.75 (m, 1H), 2.25 (d, J = 2.9 Hz, 3H), 2.28-2.12 (m, 1H), 1.72-1.59 (m, 1H), 1.24-1.10 (m, 1H); LCMS (electrospray) m/z 386.3 (M + H)+. | H |
| 263 | 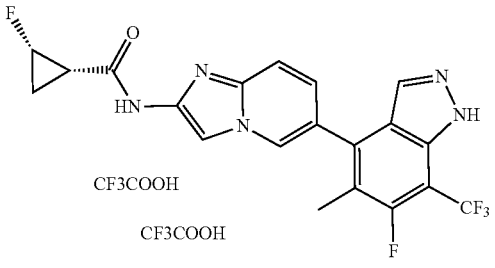 [SMILES: Cc1c(F)c(C(F)(F)F)c2[nH]ncc2c1-c1ccc2nc(NC(=O)[C@@H]3C[C@@H]3F)cn2c1 ; "CF3COOH" ; "CF3COOH"]<br>CF3COOH<br>CF3COOH<br><br>(1S,2S)-2-fluoro-N-(6-(6-fluoro-5-methyl-7-(trifluoromethyl)-1H-indazol-4-yl)imidazo[1,2-a]pyridin-2-yl)cyclopropane-1-carboxamide. 2 TFA salt | ¹H NMR (400 MHz, METHANOL-d₄) δ 8.78 (s, 1H), 7.93 (s, 1H), 7.85 (d, J = 9.2 Hz, 1H), 7.71 (d, J = 9.5 Hz, 1H), 5.06-4.94 (m, 1H), 2.31 (d, J = 3.1 Hz, 3H), 2.16-2.09 (m, 1H), 1.93-1.79 (m, 1H), 1.33-1.22 (m, 1H); LCMS (electrospray) m/z 436.0 (M + H)+. | H |
| 264 | 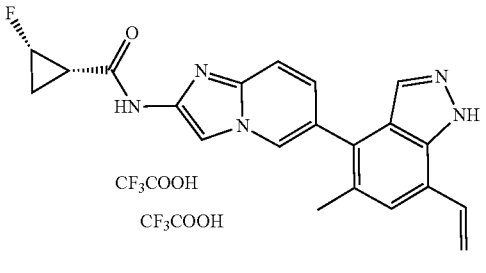 [SMILES: C=Cc1cc(C)c(-c2ccc3nc(NC(=O)[C@@H]4C[C@@H]4F)cn3c2)c2cn[nH]c12 ; "CF3COOH" ; "CF3COOH"]<br>CF₃COOH<br>CF₃COOH<br><br>(1S,2S)-2-fluoro-N-(6-(5-methyl-7-vinyl-1H-indazol-4-yl)imidazo[1,2-a]pyridin-2-yl)cyclopropane-1-carboxamide. 2TFA salt | ¹H NMR (400 MHz, DMSO-d₆) δ 13.38 (br s, 1H), 11.28 (br s, 1H), 8.75 (s, 1H), 8.16 (s, 1H), 7.85 (s, 1H), 7.64 (d, J = 9.0 Hz, 1H), 7.52 (s, 1H), 7.44 (br d, J = 9.0 Hz, 1H), 7.14 (dd, J = 11.4, 17.7 Hz, 1H), 6.12 (br d, J = 17.9 Hz, 1H), 5.51 (d, J = 11.5 Hz, 1H), 5.07-4.86 (m, 1H), 2.34 (s, 3H), 2.16 (td, J = 7.0, 13.8 Hz, 1H), 1.76-1.60 (m, 1H), 1.20 (tdd, J = 6.4, 9.1, 12.3 Hz, 1H); LCMS (electrospray) m/z 376.1 (M + H)+. | H |
| 265 | 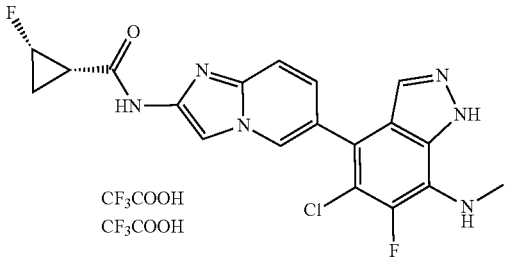 [SMILES: CNc1c(F)c(Cl)c(-c2ccc3nc(NC(=O)[C@@H]4C[C@@H]4F)cn3c2)c2cn[nH]c12 ; "CF3COOH" ; "CF3COOH"]<br>CF₃COOH<br>CF₃COOH<br><br>(1S,2S)-N-(6-(5-chloro-6-fluoro-7-(methylamino)-1H-indazol-4-yl)imidazo[1,2-a]pyridin-2-yl)-2-fluorocyclopropane-1-carboxamide. 2 TFA salt | ¹H NMR (400 MHz, DMSO-d₆) δ 13.09 (br s, 1H), 11.12 (s, 1H), 8.72 (s, 1H), 8.15 (s, 1H), 7.90 (br s, 1H), 7.56 (d, J = 9.2 Hz, 1H), 7.35 (br d, J = 9.2 Hz, 1H), 5.11-4.75 (m, 1H), 3.17 (br d, J = 2.1 Hz, 3H), 2.16 (td, J = 6.9, 13.8 Hz, 1H), 1.74-1.60 (m, 1H), 1.25-1.11 (m, 1H); LCMS (electrospray) m/z 417.1 (M + H)+. | H |

TABLE 1-continued

Compounds of Examples

| Ex # | Structure/Name | ¹H NMR/MS (M + 1) | Method |
|---|---|---|---|
| 266 | (1S,2S)-N-(6-(5-chloro-6-fluoro-7-(methylthio)-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 13.79 (br s, 1H), 11.14 (s, 1H), 8.84 (s, 1H), 8.19 (s, 1H), 8.06 (s, 1H), 7.61 (d, J = 9.3 Hz, 1H), 7.41 (dd, J = 1.6, 9.3 Hz, 1H), 5.08-4.80 (m, 1H), 2.58 (s, 3H), 2.22-2.11 (m, 1H), 1.74-1.60 (m, 1H), 1.18 (tdd, J = 6.2, 9.1, 12.4 Hz, 1H); LCMS (electrospray) m/z 434.2 (M + H)+. | H |
| 267 | (1S,2S)-N-(6-(5-chloro-6-fluoro-7-(methylsulfonyl)-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 13.52 (br s, 1H), 11.19 (s, 1H), 8.90 (s, 1H), 8.22 (d, J = 3.4 Hz, 2H), 7.65 (d, J = 9.3 Hz, 1H), 7.44 (dd, J = 1.7, 9.3 Hz, 1H), 5.07-4.80 (m, 1H), 3.56 (s, 3H), 2.21-2.14 (m, 1H), 1.72-1.62 (m, 1H), 1.24-1.15 (m, 1H); LCMS (electrospray) m/z 466.1 (M + H)+. | H |
| 268 | (1S,2S)-N-(6-(7-bromo-6-fluoro-5-methyl-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 11.29 (s, 1H), 8.78 (s, 1H), 8.17 (s, 1H), 7.99 (s, 1H), 7.65 (d, J = 9.1 Hz, 1H), 7.42 (dd, J = 1.6, 9.1 Hz, 1H), 5.08-4.84 (m, 1H), 2.26 (d, J = 3.0 Hz, 3H), 2.21-2.11 (m, 1H), 1.75-1.62 (m, 1H), 1.20 (tdd, J = 6.3, 9.0, 12.4 Hz, 1H); LCMS (electrospray) m/z 446.2 (M + H)+. | H |
| 269 | (1S,2S)-2-fluoro-N-(6-(6-fluoro-5-methyl-7-(methylthio)-1H-indazol-4-yl)imidazo[1,2-a]pyridin-2-yl)cyclopropane-1-carboxamide. 2 TFA salt | ¹H NMR (400 MHz, DMSO-$d_6$) δ 11.22 (s, 1H), 8.76 (s, 1H), 8.16 (s, 1H), 7.89 (s, 1H), 7.64 (d, J = 9.0 Hz, 1H), 7.41 (dd, J = 1.6, 9.1 Hz, 1H), 5.06-5.02 (m, 1H), 4.90-4.84 (m, 1H), 2.52 (s, 3H), 2.23 (d, J = 2.9 Hz, 3H), 2.20-2.12 (m, 1H), 1.75-1.63 (m, 1H), 1.26-1.14 (m, 1H); LCMS (electrospray) m/z 414.1 (M + H)+. | H |

TABLE 1-continued

Compounds of Examples

| Ex # | Structure/Name | ¹H NMR/MS (M + 1) | Method |
|---|---|---|---|
| 270 | 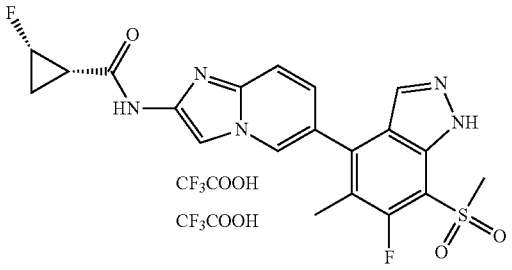 [SMILES: Cc1c(F)c(S(C)(=O)=O)c2[nH]ncc2c1-c1ccc2nc(NC(=O)[C@@H]3C[C@@H]3F)cn2c1 ; "CF3COOH" ; "CF3COOH"]<br>(1S,2S)-2-fluoro-N-(6-(6-fluoro-5-methyl-7-(methylsulfonyl)-1H-indazol-4-yl)imidazo[1,2-a]pyridin-2-yl)cyclopropane-1-carboxamide. 2 TFA salt | ¹H NMR (400 MHz, DMSO-$d_6$) δ 13.23 (br s, 1H), 11.20 (s, 1H), 8.79 (s, 1H), 8.19 (s, 1H), 8.03 (s, 1H), 7.64 (d, J = 9.2 Hz, 1H), 7.37 (dd, J = 1.7, 9.1 Hz, 1H), 5.06-4.84 (m, 1H), 3.50 (br s, 3H), 2.27 (d, J = 2.8 Hz, 3H), 2.21-2.12 (m, 1H), 1.73-1.62 (m, 1H), 1.23-1.14 (m, 1H); LCMS (electrospray) m/z 446.2 (M + H)+. | H |
| 271 | 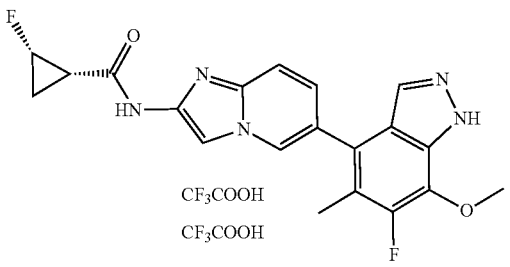 [SMILES: COc1c(F)c(C)c(-c2ccc3nc(NC(=O)[C@@H]4C[C@@H]4F)cn3c2)c2cn[nH]c12 ; "CF3COOH" ; "CF3COOH"]<br>(1S,2S)-2-fluoro-N-(6-(6-fluoro-7-methoxy-5-methyl-1H-indazol-4-yl)imidazo[1,2-a]pyridin-2-yl)cyclopropane-1-carboxamide. 2 TFA salt | ¹H NMR (400 MHz, DMSO-$d_6$) δ 13.54 (br s, 1H), 11.27 (s, 1H), 8.73 (s, 1H), 8.16 (s, 1H), 7.84 (s, 1H), 7.64 (d, J = 9.3 Hz, 1H), 7.41 (dd, J = 1.4, 9.1 Hz, 1H), 5.13-4.79 (m, 1H), 4.08 (d, J = 1.0 Hz, 3H), 2.22 (d, J = 3.1 Hz, 3H), 2.20-2.10 (m, 1H), 1.77-1.60 (m, 1H), 1.20 (tdd, J = 6.3, 9.1, 12.4 Hz, 1H); LCMS (electrospray) m/z 398.2 (M + H)+. | H |
| 272 | <br>(1S,2S)-N-(6-(5-chloro-6-fluoro-7-methoxy-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 13.81 (br s, 1H), 11.15 (s, 1H), 8.80 (s, 1H), 8.17 (s, 1H), 8.00 (s, 1H), 7.61 (d, J = 9.3 Hz, 1H), 7.39 (dd, J = 1.6, 9.2 Hz, 1H), 5.12-4.81 (m, 1H), 4.16 (d, J = 1.5 Hz, 3H), 2.22-2.11 (m, 1H), 1.75-1.60 (m, 1H), 1.18 (tdd, J = 6.3, 9.1, 12.4 Hz, 1H); LCMS (electrospray) m/z 418.2 (M + H)+. | H |
| 273 | 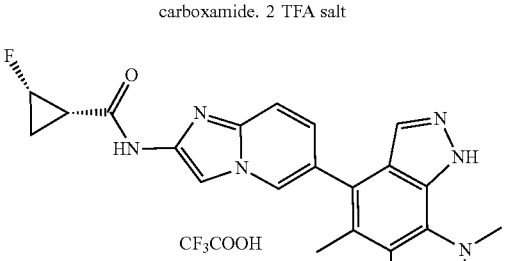<br>(1S,2S)-N-(6-(7-(dimethylamino)-6-fluoro-5-methyl-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 10.90 (br s, 1H), 8.63 (s, 1H), 8.13 (s, 1H), 7.73 (s, 1H), 7.61 (d, J = 9.0 Hz, 1H), 7.36 (d, J = 9.2 Hz, 1H), 5.03-4.80 (m, 1H), 3.00 (s, 6H), 2.19 (d, J = 2.9 Hz, 3H), 2.18-2.14 (m, 1H), 1.78-1.65 (m, 1H), 1.24-1.14 (m, 1H); LCMS (electrospray) m/z 411.2 (M + H)+. | H |

TABLE 1-continued

Compounds of Examples

| Ex # | Structure/Name | ¹H NMR/MS (M + 1) | Method |
|---|---|---|---|
| 274 | 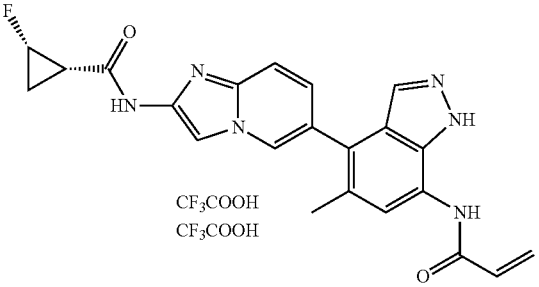 [SMILES: C=CC(=O)Nc1cc(C)c(-c2ccc3nc(NC(=O)[C@@H]4C[C@@H]4F)cn3c2)c2cn[nH]c12 ; "CF3COOH" ; "CF3COOH"]<br>(1S,2S)-N-(6-(7-acrylamido-5-methyl-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 11.29 (s, 1H), 10.19 (s, 1H), 8.75 (s, 1H), 8.16 (s, 1H), 7.82 (s, 1H), 7.66 (s, 1H), 7.64 (s, 1H), 7.45 (br d, J = 9.9 Hz, 1H), 6.61-6.51 (m, 1H), 6.35 (dd, J = 1.8, 16.9 Hz, 1H), 5.89-5.84 (m, 1H), 5.08-5.03 (m, 1H), 4.89 (dt, J = 3.8, 6.3 Hz, 1H), 2.32 (s, 3H), 2.21-2.12 (m, 1H), 1.76-1.60 (m, 1H), 1.27-1.14 (m, 1H); LCMS (electrospray) m/z 419.3 (M + H)+. | H |
| 275 | 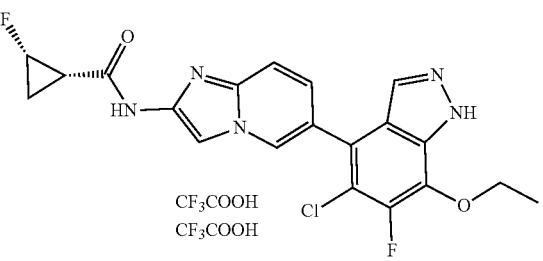 [SMILES: CCOc1c(F)c(Cl)c(-c2ccc3nc(NC(=O)[C@@H]4C[C@@H]4F)cn3c2)c2cn[nH]c12 ; "CF3COOH" ; "CF3COOH"]<br>(1S,2S)-N-(6-(5-chloro-7-ethoxy-6-fluoro-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 13.80 (br s, 1H), 11.18 (s, 1H), 8.82 (s, 1H), 8.17 (s, 1H), 8.00 (s, 1H), 7.62 (d, J = 9.2 Hz, 1H), 7.42 (dd, J = 1.5, 9.3 Hz, 1H), 5.11-4.81 (m, 1H), 4.40 (q, J = 7.1 Hz, 2H), 2.21-2.10 (m, 1H), 1.74-1.61 (m, 1H), 1.41 (t, J = 7.0 Hz, 3H), 1.25-1.09 (m, 1H); LCMS (electrospray) m/z 432.3 (M + H)+. | H |
| 276 | 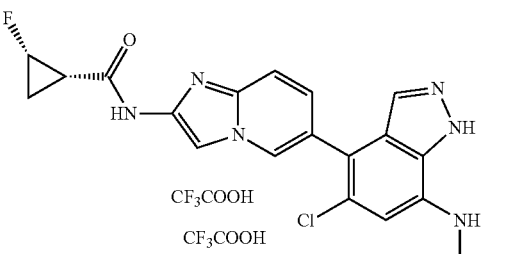<br>(1S,2S)-N-(6-(7-acrylamido-5-chloro-1H-indazol-4-yl)imidazo[1,2-a]pyridin-2-yl)-2-fluorocyclopropane-1-carboxamide. 2 TFA salt | ¹H NMR (400 MHz, DMSO-$d_6$) δ 11.23-11.08 (m, 1H), 10.40-10.29 (m, 1H), 8.80 (s, 1H), 8.17 (s, 1H), 8.01 (br d, J = 7.9 Hz, 2H), 7.59 (br d, J = 9.0 Hz, 1H), 7.46-7.36 (m, 1H), 6.66-6.49 (m, 1H), 6.41-6.36 (m, 1H), 5.95-5.85 (m, 1H), 5.12-4.78 (m, 1H), 2.22-2.08 (m, 1H), 1.77-1.58 (m, 1H), 1.27-1.10 (m, 1H); LCMS (electrospray) m/z 439.2 (M + H)+. | H |
| 277 | 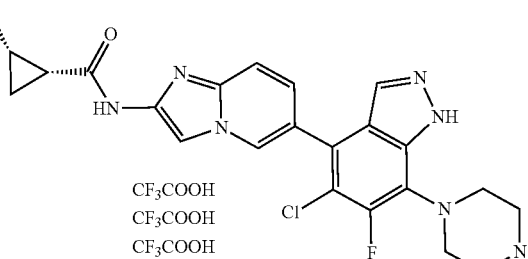<br>(1S,2S)-N-(6-(5-chloro-6-fluoro-7-(4-methylpiperazin-1-yl)-1H-indazol-4-yl)imidazo[1,2-a]pyridin-2-yl)-2-fluorocyclopropane-1-carboxamide. 3 TFA | ¹H NMR (400 MHz, DMSO-$d_6$) δ 11.14 (s, 1H), 9.88 (br d, J = 6.7 Hz, 1H), 8.77 (dd, J = 1.0, 1.6 Hz, 1H), 8.19 (s, 1H), 8.03 (br s, 1H), 7.60 (d, J = 9.2 Hz, 1H), 7.36 (dd, J = 1.8, 9.2 Hz, 1H), 5.05-5.00 (m, 1H), 4.86 (dt, J = 3.9, 6.2 Hz, 1H), 3.58 (br d, J = 11.0 Hz, 4H), 3.53-3.44 (m, 2H), 3.39-3.26 (m, 2H), 2.93 (br d, J = 2.7 Hz, 3H), 2.20-2.12 (m, 1H), 1.73-1.61 (m, 1H), 1.24-1.13 (m, 1H); LCMS (electrospray) m/z 486.2 (M + H)+. | H |

TABLE 1-continued

Compounds of Examples

| Ex # | Structure/Name | ¹H NMR/MS (M + 1) | Method |
|---|---|---|---|
| 278 | 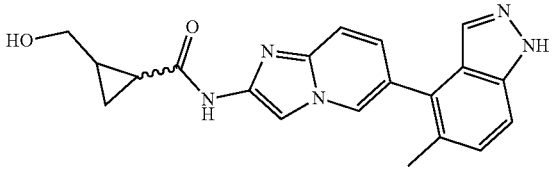 [SMILES: Cc1ccc2[nH]ncc2c1-c1ccc2nc(NC(=O)C3CC3CO)cn2c1]<br>2-(hydroxymethyl)-N-(6-(5-methyl-1H-indazol-4-yl)imidazo[1,2-a]pyridin-2-yl)cyclopropane-1-carboxamide | ¹H NMR (400 MHz, DMSO-$d_6$) δ 13.09 (br s, 1H), 10.92 (s, 1H), 8.64 (s, 1H), 8.13 (s, 1H), 7.75 (s, 1H), 7.52 (d, J = 9.2 Hz, 1H), 7.48 (d, J = 8.3 Hz, 1H), 7.32 (d, J = 8.6 Hz, 1H), 7.26 (dd, J = 1.7, 9.2 Hz, 1H), 4.46 (t, J = 5.2 Hz, 1H), 3.69-3.60 (m, 1H), 3.55-3.48 (m, 1H), 2.32 (s, 3H), 2.08-1.99 (m, 1H), 1.49-1.39 (m, 1H), 1.02-0.96 (m, 1H), 0.95-0.90 (m, 1H); LCMS (electrospray) m/z 362.3 (M + H)+. | H |
| 279 | 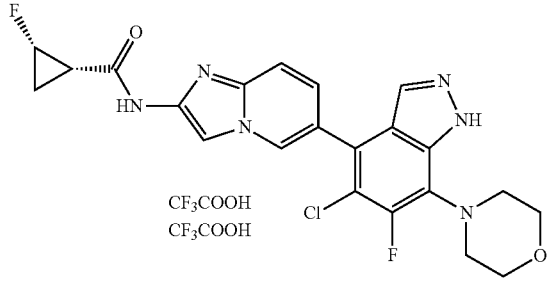 [SMILES: O=C(Nc1cn2cc(-c3c(Cl)c(F)c(N4CCOCC4)c4[nH]ncc34)ccc2n1)[C@@H]1C[C@@H]1F ; "CF3COOH" ; "CF3COOH"]<br>(1S,2S)-N-(6-(5-chloro-6-fluoro-7-morpholino-1H-indazol-4-yl)imidazo[1,2-a]pyridin-2-yl)-2-fluorocyclopropane-1-carboxamide. 2 TFA | ¹H NMR (400 MHz, DMSO-$d_6$) δ 13.54 (br s, 1H), 11.21 (s, 1H), 8.81 (s, 1H), 8.18 (s, 1H), 7.98 (s, 1H), 7.62 (d, J = 9.3 Hz, 1H), 7.43 (dd, J = 1.6, 9.2 Hz, 1H), 5.07-4.84 (m, 1H), 3.84-3.82 (m, 4H), 3.29 (br s, 4H), 2.21-2.12 (m, 1H), 1.74-1.61(m, 1H), 1.19 (tdd, J = 6.4, 9.1, 12.4 Hz, 1H); LCMS (electrospray) m/z 473.2 (M + H)+. | H |
| 280 | 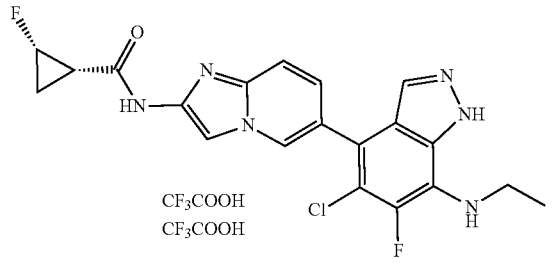 [SMILES: CCNc1c(F)c(Cl)c(-c2ccc3nc(NC(=O)[C@@H]4C[C@@H]4F)cn3c2)c2cn[nH]c12 ; "CF3COOH" ; "CF3COOH"]<br>(1S,2S)-N-(6-(5-chloro-7-(ethylamino)-6-fluoro-1H-indazol-4-yl)imidazo[1,2-a]pyridin-2-yl)-2-fluorocyclopropane-1-carboxamide. 2 TFA | ¹H NMR (400 MHz, DMSO-$d_6$) δ 11.23 (1 H, s) 8.78 (1 H, s) 8.16 (1 H, s) 7.93 (1 H, br s) 7.61 (1 H, d, J = 9.20 Hz) 7.44 (1 H, br d, J = 9.40 Hz) 5.16-4.71 (1 H, m) 2.17 (1 H, dt, J = 14.07, 6.97 Hz) 1.76-1.61 (1 H, m) 1.27-1.17 (4 H, m); LCMS (electrospray) m/z 431.0 (M + H)+. | H |
| 281 | 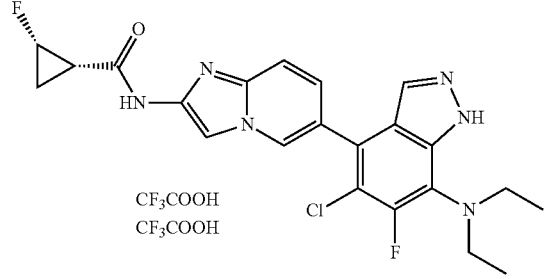 [SMILES: CCN(CC)c1c(F)c(Cl)c(-c2ccc3nc(NC(=O)[C@@H]4C[C@@H]4F)cn3c2)c2cn[nH]c12 ; "CF3COOH" ; "CF3COOH"]<br>(1S,2S)-N-(6-(5-chloro-7-(diethylamino)-6-fluoro-1H-indazol-4-yl)imidazo[1,2-a]pyridin-2-yl)-2-fluorocyclopropane-1-carboxamide. 2 TFA | ¹H NMR (400 MHz, DMSO-$d_6$) δ 13.50 (1 H, br s) 11.38-11.10 (1 H, m) 8.99-8.77 (1 H, m) 8.17 (1 H, s) 7.96 (1 H, s) 7.77-7.57 (1 H, m) 7.53-7.35 (1 H, m) 5.14-4.79 (1 H, m) 3.39-3.37 (1 H, m) 3.30 (4 H, q, J = 7.01 Hz) 2.17 (1 H, dt, J = 13.88, 7.00 Hz) 1.79-1.59 (1 H, m) 1.27-1.12 (1 H, m) 1.06-0.95 (6 H, m); LCMS (electrospray) m/z 459.0 (M + H)+. | H |

TABLE 1-continued

Compounds of Examples

| Ex # | Structure/Name | ¹H NMR/MS (M + 1) | Method |
|---|---|---|---|
| 282 | (1S,2S)-N-(6-(5-chloro-6-fluoro-7-(pyrrolidin-1-yl)-1H-indazol-4-yl)imidazo[1,2-a]pyridin-2-yl)-2-fluorocyclopropane-1-carboxamide. 2 TFA | ¹H NMR (400 MHz, DMSO-d₆) δ 13.15 (br s, 1H), 11.16 (s, 1H), 8.74 (s, 1H), 8.16 (s, 1H), 7.93 (br s, 1H), 7.58 (d, J = 9.0 Hz, 1H), 7.37 (dd, J = 1.5, 9.2 Hz, 1H), 5.07-4.82 (m, 1H), 3.72 (br s, 4H), 2.21-2.12 (m, 1H), 1.98-1.93 (m, 4H), 1.73-1.62 (m, 1H), 1.24-1.13 (m, 1H); LCMS (electrospray) m/z 457.3 (M + H)+. | H |
| 283 | (1S,2S)-N-(6-(7-(azetidin-1-yl)-5-chloro-6-fluoro-1H-indazol-4-yl)imidazo[1,2-a]pyridin-2-yl)-2-fluorocyclopropane-1-carboxamide | ¹H NMR (400 MHz, DMSO-d₆) δ13.08 (br s, 1H), 11.08 (s, 1H), 8.70 (s, 1H), 8.14 (s, 1H), 7.89 (br s, 1H), 7.54 (d, J = 9.3 Hz, 1H), 7.30 (dd, J = 1.6, 9.3 Hz, 1H), 5.06-4.79 (m, 1H), 4.39 (br t, J = 5.7 Hz, 4H), 2.39-2.32 (m, 2H), 2.15 (td, J = 7.0, 13.7 Hz, 1H), 1.72-1.61 (m, 1H), 1.22-1.13 (m, 1H); LCMS (electrospray) m/z 443.4 (M + H)+. | H |
| 284 | (1S,2S)-N-(6-(6-amino-5-chloro-1H-indazol-4-yl)imidazo[1,2-a]pyridin-2-yl)-2-fluorocyclopropane-1-carboxamide. 2 TFA | ¹H NMR (400 MHz, DMSO-d₆) δ 11.22-11.10 (m, 1H), 8.76 (br s, 1H), 8.17 (s, 1H), 7.62-7.56 (m, 2H), 7.43-7.32 (m, 1H), 6.87 (s, 1H), 5.07-4.83 (m, 1H), 2.21-2.10 (m, 1H), 1.75-1.60 (m, 1H), 1.25-1.13 (m, 1H); LCMS(electrospray) m/z 385.4 (M + H+). | H |
| 285 | (1S,2S)-2-fluoro-N-(6-(7-methoxy-5-methyl-1H-indazol-4-yl)imidazo[1,2-a]pyridin-2-yl)cyclopropane-1-carboxamide. 2 TFA | ¹H NMR (400 MHz, DMSO-d₆) δ 13.36 (br s, 1H), 11.28 (s, 1H), 8.69 (s, 1H), 8.15 (s, 1H), 7.73 (s, 1H), 7.63 (d, J = 9.1 Hz, 1H), 7.43 (br d, J = 9.1 Hz, 1H), 6.83 (s, 1H), 5.08-4.86 (m, 1H), 3.99 (s, 3H), 2.32 (s, 3H), 2.21-2.12 (m, 1H), 1.75-1.63 (m, 1H), 1.27-1.12 (m, 1H); LCMS(electrospray) m/z 380.5 (M + H+). | H |

TABLE 1-continued

Compounds of Examples

| Ex # | Structure/Name | $^1$H NMR/MS (M + 1) | Method |
|---|---|---|---|
| 286 | 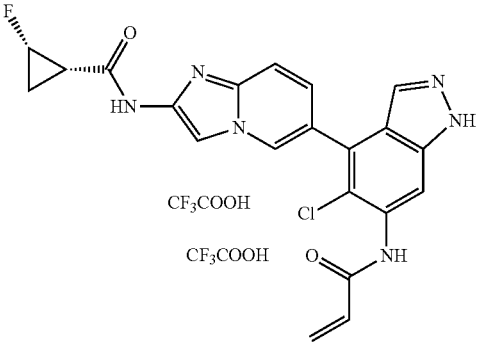 [SMILES: C=CC(=O)Nc1cc2[nH]ncc2c(-c2ccc3nc(NC(=O)[C@@H]4C[C@@H]4F)cn3c2)c1Cl ; "CF3COOH" ; "CF3COOH"]<br>(1S,2S)-N-(6-(6-acrylamido-5-chloro-1H-indazol-4-yl)imidazo[1,2-a]pyridin-2-yl)-2-fluorocyclopropane-1-carboxamide. 2 TFA | $^1$H NMR (400 MHz, DMSO-d$_6$) δ 13.53-13.11 (m, 1H), 11.23-11.11 (m, 1H), 9.82 (s, 1H), 8.80 (br s, 1H), 8.17 (d, J = 11.5 Hz, 2H), 7.89 (s, 1H), 7.65-7.57 (m, 1H), 7.43-7.32 (m, 1H), 6.72 (dd, J = 10.3, 17.1 Hz, 1H), 6.32 (dd, J = 1.9, 17.0 Hz, 1H), 5.85-5.80 (m, 1H), 5.07-4.83 (m, 1H), 2.20-2.12 (m, 1H), 1.73-1.61 (m, 1H), 1.23-1.14 (m, 1H); LCMS (electrospray) m/z 439.3 (M + H+). | H |
| 287 | 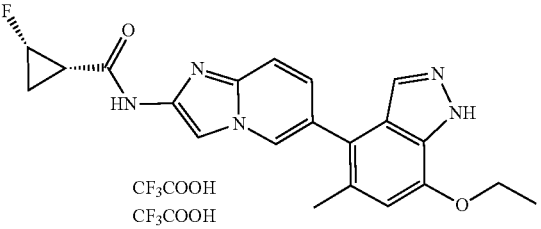 [SMILES: CCOc1cc(C)c(-c2ccc3nc(NC(=O)[C@@H]4C[C@@H]4F)cn3c2)c2cn[nH]c12 ; "CF3COOH" ; "CF3COOH"]<br>(1S,2S)-N-(6-(7-ethoxy-5-methyl-1H-indazol-4-yl)imidazo[1,2-a]pyridin-2-yl)-2-fluorocyclopropane-1-carboxamide. 2 TFA | $^1$H NMR (400 MHz, DMSO-d$_6$) δ 13.30 (br s, 1H), 11.29 (s, 1H), 8.69 (s, 1H), 8.15 (s, 1H), 7.73 (s, 1H), 7.63 (d, J = 9.2 Hz, 1H), 7.43 (br d, J = 8.4 Hz, 1H), 6.82 (s, 1H), 5.07-4.86 (m, 1H), 4.28 (q, J = 6.9 Hz, 3H), 2.31 (s, 3H), 2.20-2.12 (m, 1H), 1.75-1.63 (m, 1H), 1.46 (t, J = 7.0 Hz, 3H), 1.21 (tdd, J = 6.3, 9.0, 12.5 Hz, 1H); LCMS(electrospray) m/z 394.1 (M + H+). | H |
| 288 | 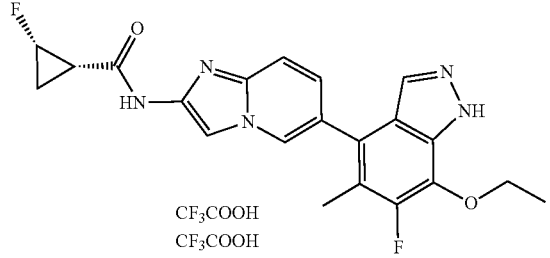 [SMILES: CCOc1c(F)c(C)c(-c2ccc3nc(NC(=O)[C@@H]4C[C@@H]4F)cn3c2)c2cn[nH]c12 ; "CF3COOH" ; "CF3COOH"]<br>(1S,2S)-N-(6-(7-ethoxy-6-fluoro-5-methyl-1H-indazol-4-yl)imidazo[1,2-a]pyridin-2-yl)-2-fluorocyclopropane-1-carboxamide. 2 TFA | $^1$H NMR (400 MHz, DMSO-d$_6$) δ 13.48 (br s, 1H), 11.21 (s, 1H), 8.71 (s, 1H), 8.15 (s, 1H), 7.83 (s, 1H), 7.61 (d, J = 9.2 Hz, 1H), 7.38 (dd, J = 1.3, 9.2 Hz, 1H), 5.12-4.79 (m, 1H), 4.31 (q, J = 7.0 Hz, 2H), 2.22 (d, J = 3.1 Hz, 3H), 2.20-2.11 (m, 1H), 1.74-1.60 (m, 1H), 1.39 (t, J = 7.0 Hz, 3H), 1.19 (tdd, J = 6.4, 9.1, 12.4 Hz, 1H); LCMS(electrospray) m/z 412.1 (M + H+). | H |

TABLE 1-continued

Compounds of Examples

| Ex # | Structure/Name | ¹H NMR/MS (M + 1) | Method |
|---|---|---|---|
| 289 | 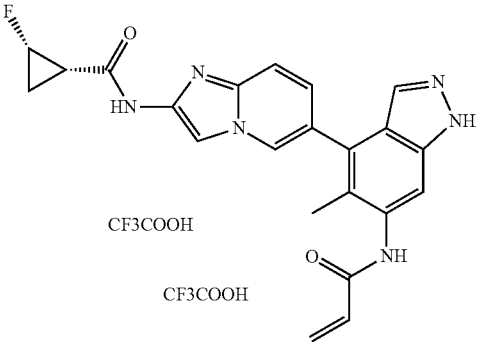 [SMILES: C=CC(=O)Nc1cc2[nH]ncc2c(-c2ccc3nc(NC(=O)[C@@H]4C[C@@H]4F)cn3c2)c1C ; "CF3COOH" ; "CF3COOH"]<br><br>(1S,2S)-N-(6-(6-acrylamido-5-methyl-1H-indazol-4-yl)imidazo[1,2-a]pyridin-2-yl)-2-fluorocyclopropane-1-carboxamide. 2 TFA | ¹H NMR (400 MHz, METHANOL-d₄) δ 8.72 (s, 1H), 7.88-7.81 (m, 2H), 7.79 (s, 1H), 7.73 (br d, J = 8.8 Hz, 1H), 6.64-6.55 (m, 1H), 6.49-6.41 (m, 1H), 5.87 (br d, J = 11.6 Hz, 1H), 5.07-4.97 (m, 2H), 2.26 (s, 3H), 2.19-2.09 (m, 1H), 1.94-1.81 (m, 1H), 1.35-1.23 (m, 1H); LCMS(electrospray) m/z 419.2 (M + H+). | H |
| 290 | 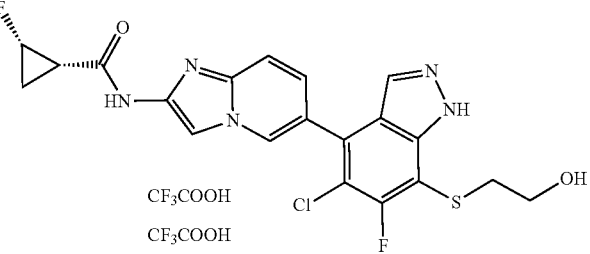<br><br>(1S,2S)-N-(6-(5-chloro-6-fluoro-7-((2-hydroxyethyl)thio)-1H-indazol-4-yl)imidazo[1,2-a]pyridin-2-yl)-2-fluorocyclopropane-1-carboxamide. 2 TFA | ¹H NMR (400 MHz, DMSO-d₆) δ 13.80 (br s, 1H), 11.19 (s, 1H), 8.87 (s, 1H), 8.18 (s, 1H), 8.07 (s, 1H), 7.63 (d, J = 9.2 Hz, 1H), 7.46 (dd, J = 1.7, 9.2 Hz, 1H), 5.06-4.83 (m, 1H), 3.51-3.50 (m, 2H), 3.08 (t, J = 6.7 Hz, 2H), 2.22-2.12 (m, 1H), 1.74-1.61 (m, 1H), 1.19 (tdd, J = 6.3, 9.1, 12.3 Hz, 1H); LCMS(electrospray) m/z 464 (M + H+). | H |
| 291 | 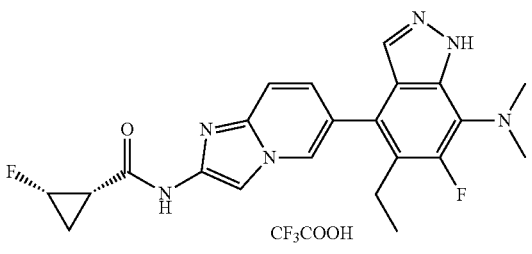<br><br>(1S,2S)-N-(6-(7-(dimethylamino)-5-ethyl-6-fluoro-1H-indazol-4-yl)imidazo[1,2-a]pyridin-2-yl)-2-fluorocyclopropane-1-carboxamide. 2 TFA | ¹H NMR (400 MHz, DMSO-d₆) δ 11.54-11.33 (m, 1H), 8.73 (br d, J = 3.3 Hz, 1H), 8.18 (d, J = 1.6 Hz, 1H), 7.78-7.61 (m, 2H), 7.47 (br t, J = 9.4 Hz, 1H), 5.12-4.85 (m, 1H), 2.98 (s, 3H), 2.97 (s, 3H), 2.56 (br d, J = 7.3 Hz, 2H), 2.17 (td, J = 6.9, 13.7 Hz, 1H), 1.78-1.59 (m, 1H), 1.29-1.21 (m, 1H), 1.10 (t, J = 7.4 Hz, 3H); LCMS(electrospray) m/z 425.2 (M + H+). | H |

TABLE 1-continued

Compounds of Examples

| Ex # | Structure/Name | ¹H NMR/MS (M + 1) | Method |
|---|---|---|---|
| 292 | 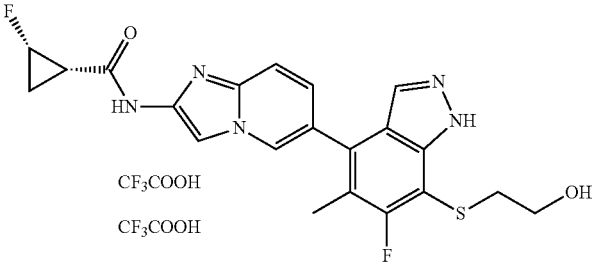 [SMILES: Cc1c(F)c(SCCO)c2[nH]ncc2c1-c1ccc2nc(NC(=O)[C@@H]3C[C@@H]3F)cn2c1 ; "CF3COOH" ; "CF3COOH"]<br>(1S,2S)-2-fluoro-N-(6-(6-fluoro-7-((2-hydroxyethyl)thio)-5-methyl-1H-indazol-4-yl)imidazo[1,2-a]pyridin-2-yl)cyclopropane-1-carboxamide. 2 TFA | ¹H NMR (400 MHz, DMSO-d₆) δ 13.45 (br s, 1H), 11.22 (s, 1H), 8.77 (s, 1H), 8.16 (s, 1H), 7.90 (s, 1H), 7.63 (d, J = 9.2 Hz, 1H), 7.41 (dd, J = 1.5, 9.2 Hz, 1H), 5.06-4.85 (m, 1H), 3.50 (t, J = 6.9 Hz, 2H), 3.02 (t, J = 6.9 Hz, 2H), 2.23 (d, J = 2.9 Hz, 3H), 2.19-2.13 (m, 1H), 1.74-1.60 (m, 1H), 1.19 (tdd, J = 6.3, 9.0, 12.3 Hz, 1H); LCMS(electrospray) m/z 444 (M + H+). | H |
| 293 | 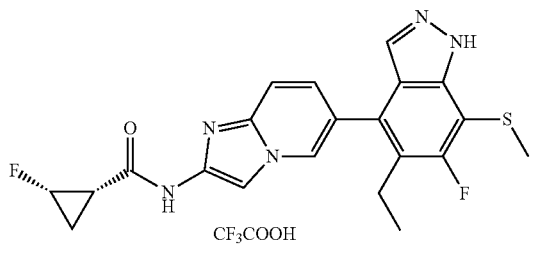<br>(1S,2S)-N-(6-(5-ethyl-6-fluoro-7-(methylthio)-1H-indazol-4-yl)imidazo[1,2-a]pyridin-2-yl)-2-fluorocyclopropane-1-carboxamide. 2 TFA | ¹H NMR (400 MHz, DMSO-d₆) δ 13.89-13.08 (m, 1H), 11.22 (br s, 1H), 8.72 (s, 1H), 8.17 (s, 1H), 7.81 (s, 1H), 7.63 (br d, J = 9.1 Hz, 1H), 7.35 (br d, J = 9.1 Hz, 1H), 5.07-4.83 (m, 1H), 2.62-2.58 (m, 2H), 2.53 (s, 3H), 2.16 (td, J = 6.9, 13.9 Hz, 1H), 1.74-1.60 (m, 1H), 1.24-1.15 (m, 1H), 1.10 (t, J = 7.4 Hz, 3H); LCMS(electrospray) m/z 428.3 (M + H+). | H |
| 294 | 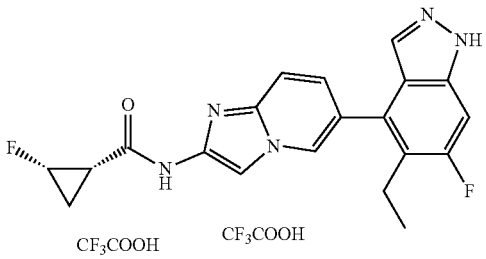 [SMILES: CCc1c(F)cc2[nH]ncc2c1-c1ccc2nc(NC(=O)[C@@H]3C[C@@H]3F)cn2c1 ; "CF3COOH" ; "CF3COOH"]<br>(1S,2S)-N-(6-(5-ethyl-6-fluoro-1H-indazol-4-yl)imidazo[1,2-a]pyridin-2-yl)-2-fluorocyclopropane-1-carboxamide. 2 TFA | ¹H NMR (400 MHz, CHLOROFORM-d) δ 11.24 (s, 1H), 8.73 (s, 1H), 8.18 (s, 1H), 7.75 (s, 1H), 7.64 (d, J = 9.0 Hz, 1H), 7.42 (d, J = 10.4 Hz, 1H), 7.36 (br d, J = 9.0 Hz, 1H), 5.12-4.76 (m, 1H), 2.61 (br d, J = 7.3 Hz, 2H), 2.23-2.12 (m, 1H), 1.77-1.62 (m, 1H), 1.22-1.16 (m, 1H), 1.10 (t, J = 7.4 Hz, 3H); LCMS(electrospray) m/z 382.3 (M + H+). | H |
| 295 | 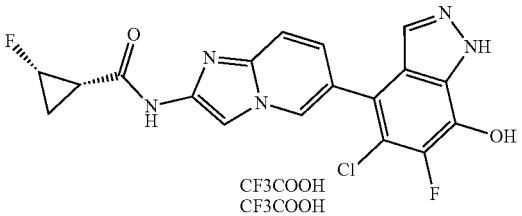 [SMILES: O=C(Nc1cn2cc(-c3c(Cl)c(F)c(O)c4[nH]ncc34)ccc2n1)[C@@H]1C[C@@H]1F ; "CF3COOH" ; "CF3COOH"]<br>(1S,2S)-N-(6-(5-chloro-6-fluoro-7-hydroxy-1H-indazol-4-yl)imidazo[1,2-a]pyridin-2-yl)-2-fluorocyclopropane-1-carboxamide. 2 TFA | ¹H NMR (400 MHz, METHANOL-d₄) δ 8.51 (d, J = 7.2 Hz, 1H), 7.85 (s, 1H), 7.66 (s, 1H), 7.00-6.91 (m, 2H), 5.03-4.96 (m, 1H), 2.16-2.07 (m, 1H), 1.89-1.78 (m, 1H), 1.30-1.17 (m, 1H); LCMS(electrospray) m/z 404.1 (M + H+). | H |

TABLE 1-continued

Compounds of Examples

| Ex # | Structure/Name | ¹H NMR/MS (M + 1) | Method |
|---|---|---|---|
| 296 | 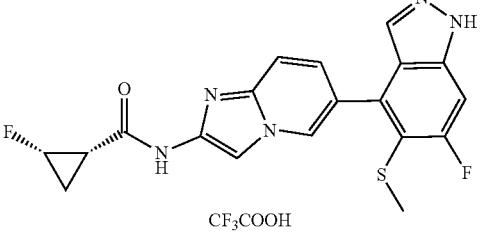<br>(1S,2S)-2-fluoro-N-(6-(6-fluoro-5-(methylthio)-1H-indazol-4-yl)imidazo[1,2-a]pyridin-2-yl)cyclopropane-1-carboxamide. 2 TFA | ¹H NMR (400 MHz, CHLOROFORM-d) δ 11.23 (s, 1H), 8.77 (s, 1H), 8.17 (s, 1H), 7.90 (s, 1H), 7.61 (d, J = 9.0 Hz, 1H), 7.54 (d, J = 9.3 Hz, 1H), 7.45 (br d, J = 9.3 Hz, 1H), 5.12-4.81 (m, 1H), 2.25 (s, 3H), 2.21-2.11 (m, 1H), 1.75-1.61 (m, 1H), 1.25-1.21 (m, 1H); LCMS(electrospray) m/z 400.2 (M + H+). | H |
| 297 | 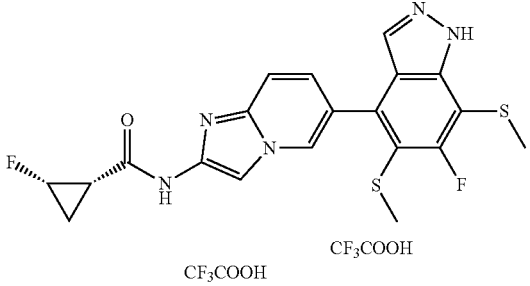 [SMILES: CSc1c(F)c(SC)c2[nH]ncc2c1-c1ccc2nc(NC(=O)[C@@H]3C[C@@H]3F)cn2c1 ; "CF3COOH" ; "CF3COOH"]<br>(1S,2S)-2-fluoro-N-(6-(6-fluoro-5,7-bis(methylthio)-1H-indazol-4-yl)imidazo[1,2-a]pyridin-2-yl)cyclopropane-1-carboxamide. 2 TFA | ¹H NMR (400 MHz, DMSO-d₆) δ 11.17 (s, 1H), 8.75 (d, J = 0.7 Hz, 1H), 8.17 (s, 1H), 7.97 (s, 1H), 7.59 (br d, J = 9.2 Hz, 1H), 7.44-7.39 (m, 1H), 5.16-4.80 (m, 1H), 2.56-2.54 (m, 3H), 2.38-2.30 (m, 1H), 2.27 (s, 3H), 2.21-2.11 (m, 1H), 1.77-1.62 (m, 1H), 1.25-1.12 (m, 1H); LCMS(electrospray) m/z 446.0 (M + H+). | H |
| 298 | 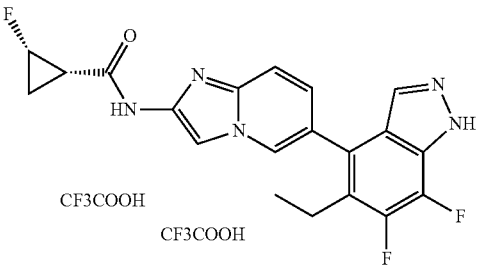 [SMILES: CCc1c(F)c(F)c2[nH]ncc2c1-c1ccc2nc(NC(=O)[C@@H]3C[C@@H]3F)cn2c1 ; "CF3COOH" ; "CF3COOH"]<br>(1S,2S)-N-(6-(5-ethyl-6,7-difluoro-1H-indazol-4-yl)imidazo[1,2-a]pyridin-2-yl)-2-fluorocyclopropane-1-carboxamide. 2 TFA | ¹H NMR (400 MHz, CHLOROFORM-d) δ 13.00 (s, 1 H), 8.34-8.22 (m, 2 H), 7.92 (d, J = 9.17 Hz, 1 H), 7.71-7.61 (m, 2 H), 5.01-4.74 (m, 1 H), 2.67 (br d, J = 7.34 Hz, 2 H), 2.20-2.15 (m, 1 H), 2.06-1.96 (m, 2 H), 1.33-1.23 (m, 1 H), 1.17 (t, J = 7.46 Hz, 3 H); LCMS(electrospray) m/z 400.0 (M + H+). | H |
| 299 | 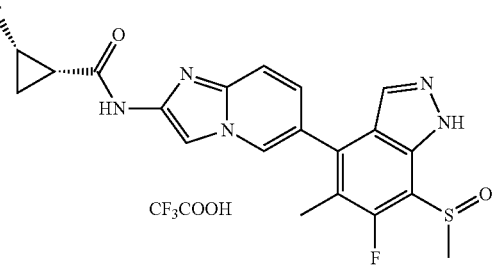<br>(1S,2S)-2-fluoro-N-(6-(6-fluoro-5-methyl-7-(methylsulfinyl)-1H-indazol-4-yl)imidazo[1,2-a]pyridin-2-yl)cyclopropane-1-carboxamide. 1 TFA | ¹H NMR (400 MHz, DMSO-d₆) δ 11.16 (s, 1H), 8.74 (s, 1H), 8.18 (s, 1H), 7.97 (s, 1H), 7.62 (d, J = 9.2 Hz, 1H), 7.36 (br d, J = 8.9 Hz, 1H), 5.09-4.78 (m, 1H), 3.13 (s, 3H), 2.23 (d, J = 2.8 Hz, 3H), 2.20-2.11 (m, 1H), 1.73-1.62 (m, 1H), 1.24-1.12 (m, 1H); LCMS(electrospray) m/z 429.11 (M + H+). | H |

TABLE 1-continued

Compounds of Examples

| Ex # | Structure/Name | ¹H NMR/MS (M + 1) | Method |
|---|---|---|---|
| 300 | (1S,2S)-N-(6-(7-(dimethylamino)-6-fluoro-5-(methylthio)-1H-indazol-4-yl)imidazo[1,2-a]pyridin-2-yl)-2-fluorocyclopropane-1-carboxamide. 1 TFA | ¹H NMR (400 MHz, DMSO-d₆) δ 13.42 (br s, 1H), 11.22 (s, 1H), 8.71 (s, 1H), 8.16 (s, 1H), 7.86 (s, 1H), 7.60 (d, J = 9.2 Hz, 1H), 7.43 (br d, J = 9.0 Hz, 1H), 5.08-4.85 (m, 1H), 2.99 (d, J = 2.3 Hz, 6H), 2.27 (s, 3H), 2.21-2.12 (m, 1H), 1.76-1.61 (m, 1H), 1.26-1.16 (m, 1H); LCMS(electrospray) m/z 443 (M + H+). | H |
| 301 | (1S,2S)-N-(6-(7-acetamido-5-chloro-6-fluoro-1H-indazol-4-yl)imidazo[1,2-a]pyridin-2-yl)-2-fluorocyclopropane-1-carboxamide. 1 TFA | ¹H NMR (400 MHz, DMSO-d₆) δ 11.20 (s, 1H), 10.15 (s, 1H), 8.87 (s, 1H), 8.19 (s, 1H), 7.98 (s, 1H), 7.64 (d, J = 9.3 Hz, 1H), 7.46 (dd, J = 1.5, 9.2 Hz, 1H), 5.08-4.82 (m, 1H), 2.18 (s, 3H), 2.17-2.11 (m, 1H), 1.74-1.62 (m, 1H), 1.26-1.15 (m, 1H); LCMS(electrospray) m/z 445.2 (M + H+). | H |
| 302 | (1S,2S)-2-fluoro-N-(6-(6-fluoro-5-methyl-7-(methylsulfonyl)-1H-indazol-4-yl)imidazo[1,2-a]pyridin-2-yl)cyclopropane-1-carboxamide. 1 TFA | ¹H NMR (400 MHz, DMSO-d₆) δ 13.38-13.09 (m, 1H), 11.19 (s, 1H), 8.80 (s, 1H), 8.19 (s, 1H), 8.03 (s, 1H), 7.64 (d, J = 9.1 Hz, 1H), 7.38 (dd, J = 1.6, 9.2 Hz, 1H), 5.09-4.78 (m, 1H), 3.50 (s, 3H), 2.27 (d, J = 2.8 Hz, 3H), 2.21-2.12 (m, 1H), 1.74-1.61 (m, 1H), 1.19 (tdd, J = 6.3, 9.0, 12.4 Hz, 1H); LCMS(electrospray) m/z 446.0 (M + H+). | H |
| 303 | (1S,2S)-N-(6-(5-chloro-6-fluoro-7-(methylsulfinyl)-1H-indazol-4-yl)imidazo[1,2-a]pyridin-2-yl)-2-fluorocyclopropane-1-carboxamide. 1 TFA | ¹H NMR (400 MHz, DMSO-d₆) δ 11.15 (s, 1H), 8.87 (d, J = 0.6 Hz, 1H), 8.20 (s, 1H), 8.15 (s, 1H), 7.63 (d, J = 9.3 Hz, 1H), 7.42 (dd, J = 1.7, 9.3 Hz, 1H), 5.07-4.82 (m, 1H), 3.19 (s, 3H), 2.21-2.11 (m, 1H), 1.74-1.61 (m, 1H), 1.24-1.12 (m, 1H); LCMS(electrospray) m/z 450 (M + H+). | H |

TABLE 1-continued

Compounds of Examples

| Ex # | Structure/Name | ¹H NMR/MS (M + 1) | Method |
|---|---|---|---|
| 304 | 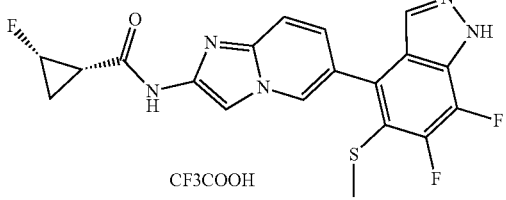<br>(1S,2S)-N-(6-(6,7-difluoro-5-(methylthio)-1H-indazol-4-yl)imidazo[1,2-a]pyridin-2-yl)-2-fluorocyclopropane-1-carboxamide. 1 TFA | ¹H NMR (400 MHz, DMSO-$d_6$) δ 11.28 (br s, 1H), 8.77 (s, 1H), 8.17 (s, 1H), 8.05 (br d, J = 2.0 Hz, 1H), 7.63 (br d, J = 9.1 Hz, 1H), 7.45 (br d, J = 9.1 Hz, 1H), 5.06-5.02 (m, 1H), 4.89-4.87 (m, 1H), 2.30 (s, 3H), 2.21-2.12 (m, 1H), 1.75-1.61 (m, 1H), 1.24-1.13 (m, 1H); LCMS(electrospray) m/z 418 (M + H+). | H |
| 305 | 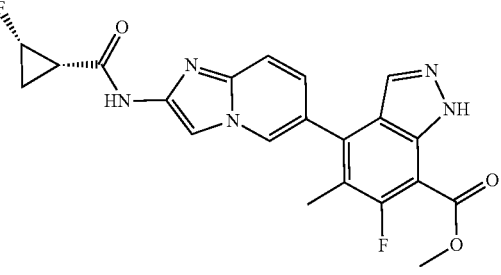<br>methyl 6-fluoro-4-(2-((1S,2S)-2-fluorocyclopropane-1-carboxamido)imidazo[1,2-a]pyridin-6-yl)-5-methyl-1H-indazole-7-carboxylate | ¹H NMR (400 MHz, METHANOL-$d_4$) δ 8.80 (s, 1H), 7.89-7.86 (m, 2H), 7.77 (d, J = 8.9 Hz, 1H), 5.05-4.96 (m, 1H), 4.06 (s, 3H), 2.30 (d, J = 3.1 Hz, 3H), 2.13 (ddd, J = 2.3, 4.5, 6.6 Hz, 1H), 1.91-1.81 (m, 1H), 1.31-1.25 (m, 1H); LCMS(electrospray) m/z 426.2 (M + H+). | H |
| 306 | 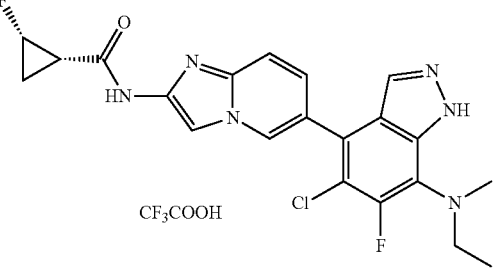<br>(1S,2S)-N-(6-(5-chloro-7-(ethyl(methyl)amino)-6-fluoro-1H-indazol-4-yl)imidazo[1,2-a]pyridin-2-yl)-2-fluorocyclopropane-1-carboxamide. 1 TFA | ¹H NMR (400 MHz, DMSO-$d_6$) δ 11.27 (s, 1H), 8.84 (s, 1H), 8.17 (s, 1H), 7.95 (s, 1H), 7.65 (d, J = 9.2 Hz, 1H), 7.49 (dd, J = 1.6, 9.2 Hz, 1H), 5.04 (dt, J = 3.8, 6.2 Hz, 1H), 4.89-4.85 (m, 1H), 3.27 (q, J = 6.9 Hz, 2H), 2.98 (d, J = 2.6 Hz, 3H), 2.20-2.12 (m, 1H), 1.73-1.63 (m, 1H), 1.20 (tdd, J = 6.3, 9.0, 12.4 Hz, 1H), 1.08 (t, J = 7.1 Hz, 3H); LCMS(electrospray) m/z 445.2 (M + H+). | H |
| 307 | 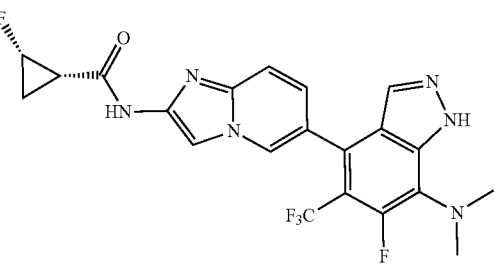<br>(1S,2S)-N-(6-(7-(dimethylamino)-6-fluoro-5-(trifluoromethyl)-1H-indazol-4-yl)imidazo[1,2-a]pyridin-2-yl)-2-fluorocyclopropane-1-carboxamide | ¹H NMR (400 MHz, DMSO-$d_6$) δ 11.14 (s, 1H), 8.68 (s, 1H), 8.13 (s, 1H), 7.86 (br d, J = 3.4 Hz, 1H), 7.55 (d, J = 9.2 Hz, 1H), 7.24 (d, J = 9.2 Hz, 1H), 5.06-4.79 (m, 1H), 3.02 (d, J = 2.0 Hz, 6H), 2.21-2.11 (m, 1H), 1.73-1.61 (m, 1H), 1.21 1.11 (m, 1H); LCMS(electrospray) m/z 465.1 (M + H+). | H |

TABLE 1-continued

Compounds of Examples

| Ex # | Structure/Name | ¹H NMR/MS (M + 1) | Method |
|---|---|---|---|
| 308 | 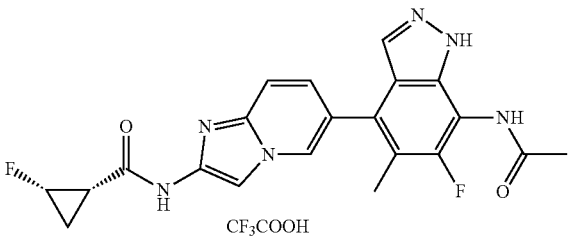 [SMILES: CC(=O)Nc1c(F)c(C)c(-c2ccc3nc(NC(=O)[C@@H]4C[C@@H]4F)cn3c2)c2cn[nH]c12 ; "CF3COOH"]<br>(1S,2S)-N-(6-(7-acetamido-6-fluoro-5-methyl-1H-indazol-4-yl)imidazo[1,2-a]pyridin-2-yl)-2-fluorocyclopropane-1-carboxamide. 1 TFA | ¹H NMR (400 MHz, DMSO-$d_6$) δ 13.14-12.81 (m, 1H), 11.30-11.11 (m, 1H), 9.94 (s, 1H), 8.75 (s, 1H), 8.16 (s, 1H), 7.80 (s, 1H), 7.66-7.59 (m, 1H), 7.43-7.32 (m, 1H), 5.07-4.81 (m, 1H), 2.22 (d, J = 2.9 Hz, 3H), 2.16 (s, 4H), 1.74-1.62 (m, 1H), 1.27-1.12 (m, 1H); LCMS(electrospray) m/z 424.15 (M + H+). | H |
| 309 | 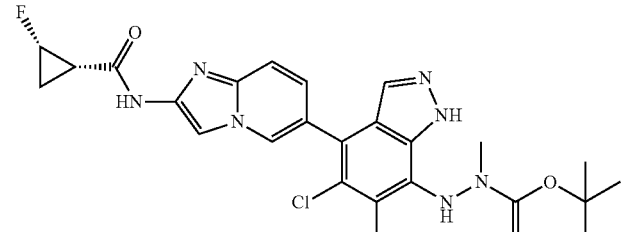<br>tert-butyl 2-(5-chloro-6-fluoro-4-(2-(((1S,2S)-2-fluorocyclopropane-1-carboxamido)imidazo[1,2-a]pyridin-6-yl)-1H-indazol-7-yl)-1-methylhydrazine-1-carboxylate | ¹H NMR (400 MHz, DMSO-$d_6$) δ 13.29 (s, 1H), 11.07 (s, 1H), 8.74 (s, 1H), 8.41 (s, 1H), 7.93 (s, 1H), 7.54 (d, J = 9.2 Hz, 1H), 7.29 (d, J = 9.2 Hz, 1H), 5.01-4.83 (m, 1H), 3.22 (s, 3H), 2.23-2.16 (m, 1H), 1.78-1.61 (m, 1H), 1.23 (br, 9H), 1.28-1.12 (m, 1H); LCMS (electrospray) m/z 532.1 (M + H)+. | H |
| 310 | 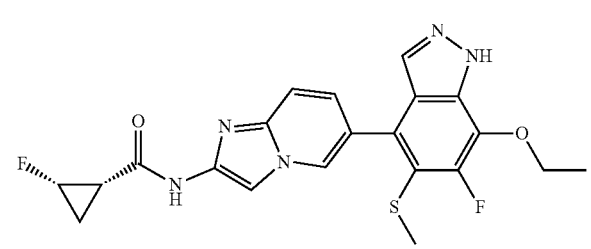<br>(1S,2S)-N-(6-(7-ethoxy-6-fluoro-5-(methylthio)-1H-indazol-4-yl)imidazo[1,2-a]pyridin-2-yl)-2-fluorocyclopropane-1-carboxamide. 1 TFA | ¹H NMR (400 MHz, DMSO-$d_6$) δ 14.02-13.34 (m, 1H), 11.15 (s, 1H), 8.61 (d, J = 7.0 Hz, 1H), 7.85 (s, 1H), 7.65 (s, 1H), 6.93 (s, 1H), 6.89 (dd, J = 1.8, 7.1 Hz, 1H), 5.11-4.78 (m, 1H), 4.35 (q, J = 7.0 Hz, 2H), 2.28 (s, 3H), 2.19-2.12 (m, 1H), 1.68 (m, J = 3.2, 6.8, 19.9 Hz, 1H), 1.41 (t, J = 7.0 Hz, 3H), 1.26-1.11 (m, 1H); LCMS(electrospray) m/z 444.2 (M + H+). | H |
| 311 | 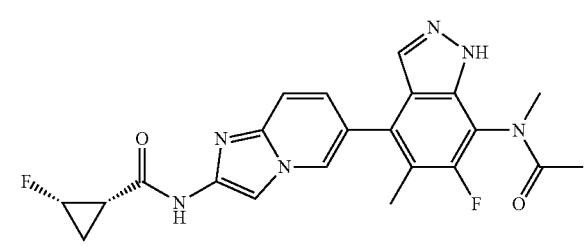<br>(1S,2S)-2-fluoro-N-(6-(6-fluoro-5-methyl-7-(N-methylacetamido)-1H-indazol-4-yl)imidazo[1,2-a]pyridin-2-yl)cyclopropane-1-carboxamide. 1 TFA | ¹H NMR (400 MHz, DMSO-$d_6$) δ 10.85 (br s, 1H), 8.70 (s, 1H), 8.15 (s, 1H), 7.89 (s, 1H), 7.60 (d, J = 9.0 Hz, 1H), 7.36 (dd, J = 1.5, 9.1 Hz, 1H), 5.05-4.79 (m, 2H), 2.27 (br d, J = 2.6 Hz, 3H), 1.80 (s, 3H), 1.77-1.63 (m, 1H), 1.18 (tdd, J = 6.3, 9.2, 12.2 Hz, 1H); LCMS(electrospray) m/z 438.16 (M + H+). | H |

TABLE 1-continued

Compounds of Examples

| Ex # | Structure/Name | ¹H NMR/MS (M + 1) | Method |
|---|---|---|---|
| 312 | 2-((6-fluoro-4-(2-((1S,2S)-2-fluorocyclopropane-1-carboxamido)imidazo[1,2-a]pyridin-6-yl)-5-methyl-1H-indazol-7-yl)thio)ethyl methylcarbamate. 1 TFA | ¹H NMR (400 MHz, METHANOL-d₄) δ 8.78 (s, 1H), 7.91-7.83 (m, 3H), 7.80-7.75 (m, 1H), 5.01 (dt, J = 3.9, 6.2 Hz, 1H), 4.13 (br t, J = 6.5 Hz, 2H), 3.17 (br t, J = 6.7 Hz, 2H), 2.63 (s, 3H), 2.29 (d, J = 2.9 Hz, 3H), 2.17-2.09 (m, 1H), 1.92-1.81 (m, 1H), 1.31-1.26 (m, 1H); LCMS(electrospray) m/z501.3 (M + H+). | H |
| 313 | 6-fluoro-4-(2-((1S,2S)-2-fluorocyclopropane-1-carboxamido)imidazo[1,2-a]pyridin-6-yl)-5-methyl-1H-indazole-7-carboxylic acid. 1 TFA | ¹H NMR (400 MHz, DMSO-d₆) δ 13.19(br s, 1H), 11.16 (s, 1H), 8.79 (s, 1H), 8.17 (s, 1H), 7.91 (s, 1H), 7.61 (d, J = 9.0 Hz, 1H), 7.36 (br d, J = 8.9 Hz, 1H), 5.04-4.85(m, 1H), 2.23 (d, J = 3.1 Hz, 3H), 2.19-2.16 (m, 1H), 1.72-1.63 (m, 1H), 1.18 (ddd, J = 2.6, 6.2, 9.2 Hz, 1H); LCMS(electrospray) m/z 412.1 (M + H+). | H |
| 314 | 5-chloro-6-fluoro-4-(2-((1S,2S)-2-fluorocyclopropane-1-carboxamido)imidazo[1,2-a]pyridin-6-yl)-1H-indazole-7-carboxylic acid. 1 TFA | ¹H NMR (400 MHz, DMSO-d₆) δ 13.49 (br s, 1H), 11.13 (s, 1H), 8.88 (s, 1H), 8.19 (s, 1H), 8.08 (s, 1H), 7.61 (d, J = 9.3 Hz, 1H), 7.41 (dd, J = 1.8, 9.2 Hz, 1H), 5.06-4.83 (m, 1H), 2.22-2.12 (m, 1H), 1.74-1.57 (m, 1H), 1.29-1.06 (m, 1H); LCMS(electrospray) m/z 432.2 (M + H+). | H |
| 315 | methyl 5-chloro-6-fluoro-4-(2-((1S,2S)-2-fluorocyclopropane-1-carboxamido)imidazo[1,2-a]pyridin-6-yl)-1H-indazole-7-carboxylate. 1 TFA | ¹H NMR (400 MHz, DMSO-d₆) δ 13.69-13.54 (m, 1H), 11.16 (s, 1H), 8.90 (s, 1H), 8.20 (s, 1H), 8.13 (s, 1H), 7.63 (br d, J = 9.2 Hz, 1H), 7.44 (br d, J = 9.4 Hz, 1H), 5.12 (d, J = 6.5 Hz, 1H), 4.01 (s, 3H), 2.23-2.11 (m, 1H), 1.76-1.61 (m, 1H), 1.28-1.08 (m, 1H); LCMS(electrospray) m/z 446.2 (M + H+). | H |

TABLE 1-continued

Compounds of Examples

| Ex # | Structure/Name | ¹H NMR/MS (M + 1) | Method |
|---|---|---|---|
| 316 | (1S,2S)-N-(6-(5-chloro-6-fluoro-7-(N-methylacetamido)-1H-indazol-4-yl)imidazo[1,2-a]pyridin-2-yl)-2-fluorocyclopropane-1-carboxamide. 1 TFA | ¹H NMR (400 MHz, DMSO-$d_6$) δ 14.22-13.73 (m, 1H), 11.15 (s, 1H), 8.87-8.86 (m, 1H), 8.19 (s, 1H), 8.13 (s, 1H), 7.62 (d, J = 9.3 Hz, 1H), 7.47-7.40 (m, 1H), 5.04-4.84 (m, 1H), 3.23 (s, 3H), 2.17 (ddd, J = 2.0, 5.0, 6.9 Hz, 1H), 1.82 (s, 3H), 1.71-1.63 (m, 1H), 1.19-1.13 (m, 1H); LCMS(electrospray) m/z 459.1 (M + H+). | H |
| 317 | (1S,2S)-N-(6-(5-chloro-6-fluoro-7-(2-methylhydrazineyl)-1H-indazol-4-yl)imidazo[1,2-a]pyridin-2-yl)-2-fluorocyclopropane-1-carboxamide | ¹H NMR (400 MHz, DMSO-$d_6$) δ 12.93 (s, 1H), 11.06 (s, 1H), 8.70 (s, 1H), 8.14 (s, 1H), 7.79 (s, 1H), 7.52 (d, J = 9.2 Hz, 1H), 7.38 (s, 1H), 7.31 (d, J = 9.2 Hz, 1H), 5.01-4.83 (m, 1H), 5.01 (s, 1H), 2.60 (s, 3H), 2.23-2.16 (m, 1H), 1.78-1.61 (m, 1H), 1.28-1.12 (m, 1H); LCMS (electrospray) m/z 432.1 (M + H)+. | H |
| 318 | (1S,2S)-N-(6-(7-ethoxy-5-ethyl-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.60-13.32 (m, 1H), 11.06 (s, 1H), 8.63 (s, 1H), 8.15 (s, 1H), 7.74 (s, 1H), 7.54 (d, J = 9.1 Hz, 1H), 7.21 (dd, J = 1.6, 9.1 Hz, 1H), 5.04-4.82 (m, 1H), 4.32 (q, J = 7.0 Hz, 2H), 2.60 (br d, J = 6.6 Hz, 2H), 2.20-2.11 (m, 1H), 1.72-1.61 (m, 1H), 1.39 (t, J = 6.9 Hz, 3H), 1.20-1.13 (m, 1H), 1.10 (t, J = 7.4 Hz, 3H); LCMS(electrospray) m/z 426.0 (M + H+). | H |
| 319 | (1S,2S)-N-(6-(7-acetyl-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.73 (s, 1H), 11.13 (s, 1H), 8.89 (s, 1H), 8.22 (s, 1H), 8.10 (s, 1H), 7.62 (d, J = 9.2 Hz, 1H), 7.40 (dd, J = 1.5, 9.2 Hz, 1H), 5.08-4.81 (m, 1H), 2.77 (d, J = 6.1 Hz, 3H), 2.25-2.12 (m, 1H), 1.76-1.61 (m, 1H), 1.13-1.19 (m, J = 2.9, 6.1, 12.1 Hz, 1H); LCMS(electrospray) m/z 430.3(M + H+). | H |

TABLE 1-continued

Compounds of Examples

| Ex # | Structure/Name | ¹H NMR/MS (M + 1) | Method |
|---|---|---|---|
| 320 | 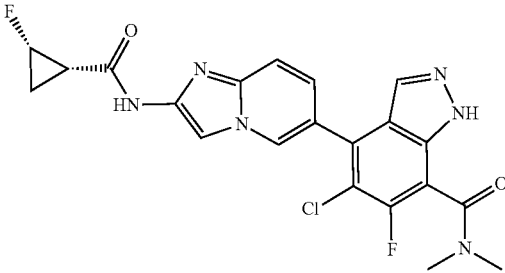 [SMILES: CN(C)C(=O)c1c(F)c(Cl)c(-c2ccc3nc(NC(=O)[C@@H]4C[C@@H]4F)cn3c2)c2cn[nH]c12]<br>5-chloro-6-fluoro-4-(2-((1S,2S)-2-fluorocyclopropane-1-carboxamido)imidazo[1,2-a]pyridin-6-yl)-N,N-dimethyl-1H-indazole-7-carboxamide | ¹H NMR (400 MHz, DMSO-$d_6$) δ 11.10 (s, 1H), 8.89 (s, 1H), 8.19 (s, 1H), 8.06 (s, 1H), 7.60 (d, J = 9.3 Hz, 1H), 7.39 (dd, J = 1.7, 9.3 Hz, 1H), 5.10-4.79 (m, 1H), 3.13 (s, 3H), 2.93 (s, 3H), 2.21-2.12 (m, 1H), 1.75-1.60 (m, 1H), 1.08 (s, 1H); LCMS(electrospray) m/z 459.0 (M + H+). | H |
| 321 | 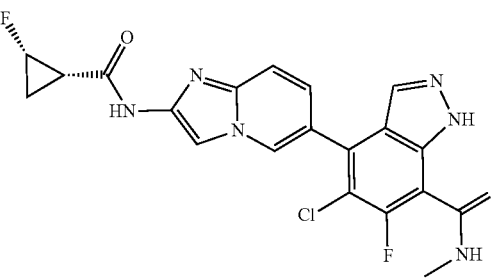<br>5-chloro-6-fluoro-4-(2-((1S,2S)-2-fluorocyclopropane-1-carboxamido)imidazo[1,2-a]pyridin-6-yl)-N-methyl-1H-indazole-7-carboxamide | ¹H NMR (400 MHz, DMSO-$d_6$) δ 11.19-11.05 (m, 1H), 8.90-8.81 (m, 1H), 8.69-8.61 (m, 1H), 8.49-8.44 (m, 1H) 8.26-8.16 (m, 1H) 8.07-8.00 (m, 1H), 7.68-7.54 (m, 1H), 7.42-7.31 (m, 1H), 5.15-4.75 (m, 1H), 2.91 (d, J = 4.2 Hz, 3H), 2.23-2.11 (m, 1H), 1.76 (br d, J = 4.8 Hz, 1H), 1.27-1.10 (m, 1H); LCMS(electrospray) m/z 445.3 (M + H+). | H |
| 322 | 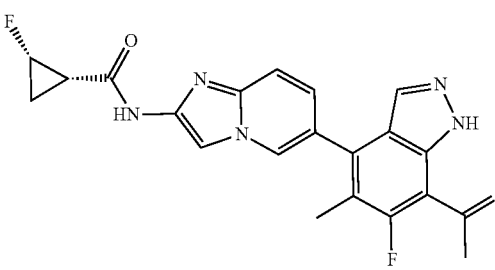<br>(1S,2S)-N-(6-(7-acetyl-6-fluoro-5-methyl-1H-indazol-4-yl)imidazo[1,2-a]pyridin-2-yl)-2-fluorocyclopropane-1-carboxamide | ¹H NMR (400 MHz, DMSO-$d_6$) δ 13.43 (s, 1H), 11.10 (s, 1H), 8.77 (s, 1H), 8.18 (s, 1H), 7.92 (s, 1H), 7.59 (d, J = 9.2 Hz, 1H), 7.31 (dd, J = 1.6, 9.2 Hz, 1H), 5.08-4.79 (m, 1H), 2.74 (d, J = 6.2 Hz, 3H), 2.28 (d, J = 3.2 Hz, 3H), 2.16 (td, J = 6.9, 13.9 Hz, 1H), 1.75-1.58 (m, 1H), 1.17 (tdd, J = 6.3, 9.1, 12.2 Hz, 1H); LCMS(electrospray) m/z 409.14 (M + H+). | H |
| 323 | 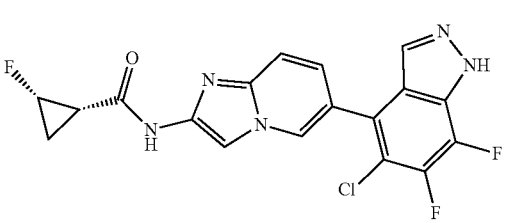 [SMILES: O=C(Nc1cn2cc(-c3c(Cl)c(F)c(F)c4[nH]ncc34)ccc2n1)[C@@H]1C[C@@H]1F]<br>(1S,2S)-N-(6-(5-chloro-6,7-difluoro-1H-indazol-4-yl)imidazo[1,2-a]pyridin-2-yl)-2-fluorocyclopropane-1-carboxamide | ¹H NMR (400 MHz, DMSO-$d_6$) δ 11.21-11.16 (m, 1H), 8.83 (s, 1H), 8.18 (s, 1H), 8.15 (br s, 1H), 7.71-7.59 (m, 1H), 7.41 (dd, J = 1.6, 9.2 Hz, 1H), 5.06-4.83 (m, 1H), 2.22-2.11 (m, 1H), 1.74-1.59 (m, 1H), 1.19 (tdd, J = 6.4, 9.1, 12.4 Hz, 1H); LCMS(electrospray) m/z 406.1 (M + H+). | H |

TABLE 1-continued

Compounds of Examples

| Ex # | Structure/Name | ¹H NMR/MS (M + 1) | Method |
|---|---|---|---|
| 324 | 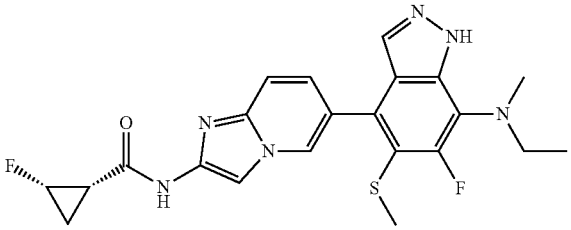 [SMILES: CCN(C)c1c(F)c(SC)c(-c2ccc3nc(NC(=O)[C@@H]4C[C@@H]4F)cn3c2)c2cn[nH]c12]<br>(1S,2S)-N-(6-(7-(ethyl(methyl)amino)-6-fluoro-5-(methylthio)-1H-indazol-4-yl)imidazo[1,2-a]pyridin-2-yl)-2-fluorocyclopropane-1-carboxamide | ¹H NMR (400 MHz, DMSO-d₆) δ 13.38 (br s, 1H), 11.06 (s, 1H), 8.66 (s, 1H), 8.13 (s, 1H), 7.84 (br s, 1H), 7.51 (d, J = 9.1 Hz, 1H), 7.30 (br d, J = 8.5 Hz, 1H), 5.06-4.81 (m, 1H), 3.25-3.20 (m, 2H), 2.95 (br s, 3H), 2.25 (s, 3H), 2.16-2.15 (m, 1H), 1.70-1.63 (m, 1H), 1.19-1.13 (m, 1H), 1.07 (t, J = 7.1 Hz, 3H); LCMS(electrospray) m/z 457 (M + H+). | H |
| 325 | 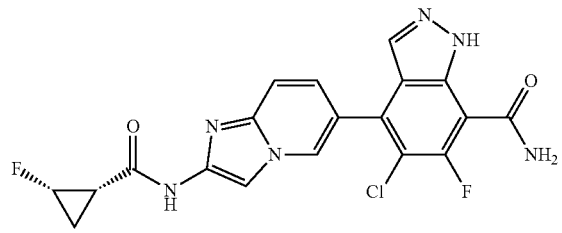 [SMILES: NC(=O)c1c(F)c(Cl)c(-c2ccc3nc(NC(=O)[C@@H]4C[C@@H]4F)cn3c2)c2cn[nH]c12]<br>5-chloro-6-fluoro-4-(2-((1S,2S)-2-fluorocyclopropane-1-carboxamido)imidazo[1,2-a]pyridin-6-yl)-1H-indazole-7-carboxamide | ¹H NMR (400 MHz, DMSO-d₆) δ 13.55 (s, 1H), 11.12 (s, 1H), 8.86 (s, 1H), 8.20 (s, 1H), 8.05 (d, J = 16.9 Hz, 3H), 7.61 (d, J = 9.2 Hz, 1H), 7.38 (dd, J = 1.6, 9.2 Hz, 1H), 5.11-4.79 (m, 1H), 2.24-2.08 (m, 1H), 1.78-1.57 (m, 1H), 1.21-1.14 (m, 1H); LCMS(electrospray) m/z 431.1 (M + H+). | H |
| 326 | 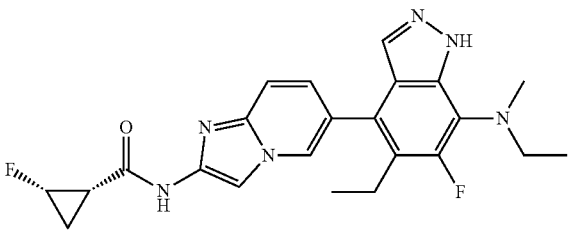 [SMILES: CCc1c(F)c(N(C)CC)c2[nH]ncc2c1-c1ccc2nc(NC(=O)[C@@H]3C[C@@H]3F)cn2c1]<br>(1S,2S)-N-(6-(5-ethyl-7-(ethyl(methyl)amino)-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.16 (br s, 1H), 11.06 (s, 1H), 8.63 (s, 1H), 8.14 (s, 1H), 7.68 (s, 1H), 7.53 (d, J = 9.2 Hz, 1H), 7.22 (d, J = 9.3 Hz, 1H), 5.06-4.78 (m, 1H), 3.27-3.11 (m, 2H), 2.94 (s, 4H), 2.57 (br d, J = 6.8 Hz, 2H), 2.21-2.09 (m, 1H), 1.76-1.58 (m, 1H), 1.25-1.14 (m, 1H), 1.11-1.04 (m, 6H); LCMS(electrospray) m/z 439.2 (M + H+). | H |
| 327 | 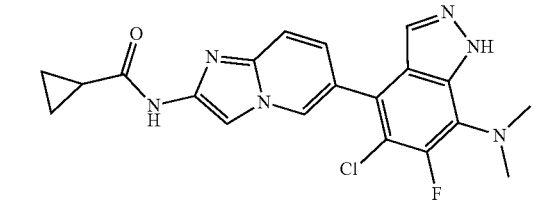 [SMILES: CN(C)c1c(F)c(Cl)c(-c2ccc3nc(NC(=O)C4CC4)cn3c2)c2cn[nH]c12]<br>N-(6-(5-chloro-7-(dimethylamino)-6-fluoro-1H-indazol-4-yl)imidazo[1,2-a]pyridin-2-yl)cyclopropanecarboxamide | ¹H NMR (400 MHz, DMSO-d₆) δ 13.52 (br s, 1H), 11.08 (s, 1H), 8.76 (s, 1H), 8.13 (s, 1H), 7.93 (s, 1H), 7.58 (d, J = 9.2 Hz, 1H), 7.37 (d, J = 9.3 Hz, 1H), 3.00 (d, J = 1.7 Hz, 6H), 2.01-1.90 (m, 1H), 0.92-0.78 (m, 4H); LCMS(electrospray) m/z 413.0 (M + H+). | H |

TABLE 1-continued

Compounds of Examples

| Ex # | Structure/Name | ¹H NMR/MS (M + 1) | Method |
|---|---|---|---|
| 328 | 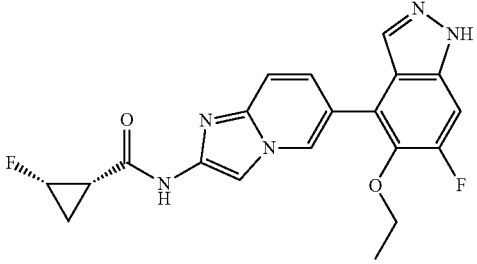 [SMILES: CCOc1c(F)cc2[nH]ncc2c1-c1ccc2nc(NC(=O)[C@@H]3C[C@@H]3F)cn2c1]<br>(1S,2S)-N-(6-(5-ethoxy-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.24 (br s, 1H), 11.07 (s, 1H), 8.84 (s, 1H), 8.19 (s, 1H), 8.02 (s, 1H), 7.58-7.54 (m, 1H), 7.50-7.44 (m, 2H), 5.04-4.81 (m, 1H), 3.85 (q, J = 7.0 Hz, 2H), 2.20-2.12 (m, 1H), 1.67 (tdd, J = 3.3, 6.8, 20.0 Hz, 1H), 1.21-1.14 (m, 1H), 1.10 (t, J = 7.0 Hz, 3H); LCMS(electrospray) m/z 398.1 (M + H+). | H |
| 329 | 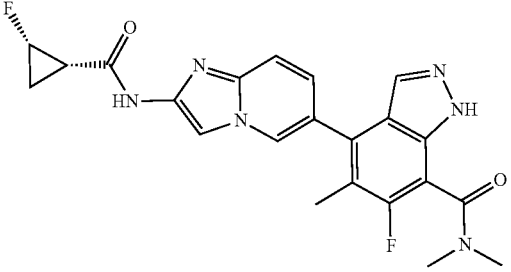 [SMILES: Cc1c(F)c(C(=O)N(C)C)c2[nH]ncc2c1-c1ccc2nc(NC(=O)[C@@H]3C[C@@H]3F)cn2c1]<br>6-fluoro-4-(2-((1S,2S)-2-fluorocyclopropane-1-carboxamido)imidazo[1,2-a]pyridin-6-yl)-N,N,5-trimethyl-1H-indazole-7-carboxamide | ¹H NMR (400 MHz, DMSO-d₆) δ 13.41 (br s, 1H), 11.08 (s, 1H), 8.73 (s, 1H), 8.16 (s, 1H), 7.88 (s, 1H), 7.57 (d, J = 9.1 Hz, 1H), 7.31 (dd, J = 1.4, 9.3 Hz, 1H), 5.08-4.81 (m, 1H), 3.12 (s, 3H), 2.92 (s, 3H), 2.24 (d, J = 2.8 Hz, 3H), 2.19-2.11 (m, 1H), 1.72-1.59 (m, 1H), 1.19-1.15 (m, 1H); LCMS(electrospray) m/z 439.3 (M + H+). | H |
| 330 | 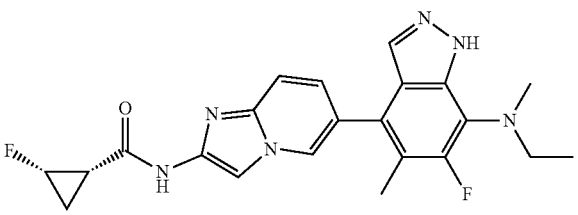 [SMILES: CCN(C)c1c(F)c(C)c(-c2ccc3nc(NC(=O)[C@@H]4C[C@@H]4F)cn3c2)c2cn[nH]c12]<br>(1S,2S)-N-(6-(7-(ethyl(methyl)amino)-6-fluoro-5-methyl-1H-indazol-4-yl)imidazo[1,2-a]pyridin-2-yl)-2-fluorocyclopropane-1-carboxamide | ¹H NMR (400 MHz, DMSO-d₆) δ 13.15 (s, 1H), 11.05 (s, 1H), 8.65 (s, 1H), 8.13 (s, 1H), 7.76 (s, 1H), 7.53 (d, J = 9.0 Hz, 1H), 7.27 (dd, J = 1.6, 9.2 Hz, 1H), 5.07-4.79 (m, 1H), 3.20 (q, J = 6.6 Hz, 2H), 2.92 (s, 3H), 2.21-2.12 (m, 4H), 1.73-1.59 (m, 1H), 1.25-1.10 (m, 1H), 1.05 (t, J = 7.1 Hz, 3H); LCMS(electrospray) m/z 424.18 (M + H+). | H |
| 331 | 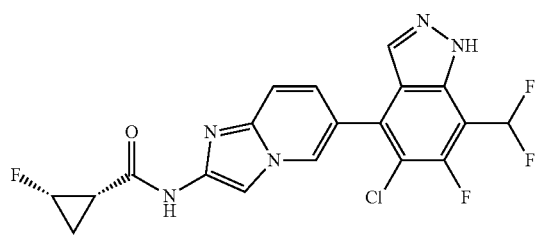 [SMILES: O=C(Nc1cn2cc(-c3c(Cl)c(F)c(C(F)F)c4[nH]ncc34)ccc2n1)[C@@H]1C[C@@H]1F]<br>(1S,2S)-N-(6-(5-chloro-7-(difluoromethyl)-6-fluoro-1H-indazol-4-yl)imidazo[1,2-a]pyridin-2-yl)-2-fluorocyclopropane-1-carboxamide | ¹H NMR (400 MHz, DMSO-d₆) δ 1.12-1.22 (m, 1 H), 1.60-1.73 (m, 1 H), 2.12-2.21 (m, 1 H), 4.81-5.05 (m, 1 H), 7.39 (dd, J = 9.26, 1.75 Hz, 1 H), 7.50 (s, 1 H) 7.58-7.64 (m, 1 H), 7.77 (s, 1 H), 8.14 (s, 1 H), 8.19 (s, 1 H), 8.87 (s, 1 H), 11.11 (s, 1 H), 13.86-13.91 (m, 1 H); LCMS(electrospray) m/z 438.1 (M + H+). | H |

TABLE 1-continued

Compounds of Examples

| Ex # | Structure/Name | ¹H NMR/MS (M + 1) | Method |
|---|---|---|---|
| 332 | 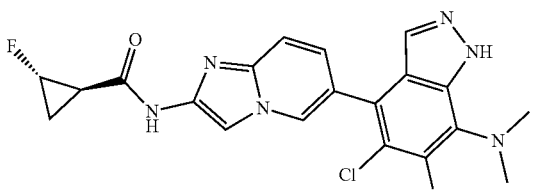<br>(1R,2S)-N-(6-(5-chloro-7-(dimethylamino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.49 (br s, 1H), 11.19 (s, 1H), 8.74 (s, 1H), 8.11 (s, 1H), 8.00-7.84 (m, 1H), 7.56 (d, J = 9.3 Hz, 1H), 7.33 (dd, J = 1.4, 9.2 Hz, 1H), 5.04-4.78 (m, 1H), 3.00 (br s, 6H), 2.46-2.41 (m, 1H), 1.61-1.44 (m, 1H), 1.25 (qd, J = 6.6, 13.1 Hz, 1H); LCMS(electrospray) m/z 431.0 (M + H+). | H |
| 333 | 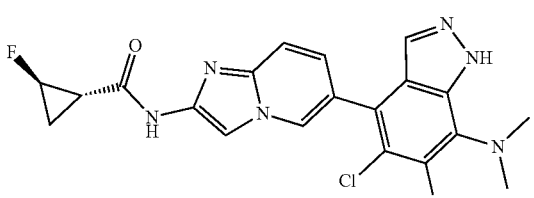<br>(1S,2R)-N-(6-(5-chloro-7-(dimethylamino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.99-13.12 (m, 1H), 11.27 (s, 1H), 8.78 (s, 1H), 8.13 (s, 1H), 7.93 (s, 1H), 7.60 (d, J = 9.3 Hz, 1H), 7.39 (d, J = 9.3 Hz, 1H), 5.05-4.75 (m, 1H), 3.00 (d, J = 2.4 Hz, 6H), 2.44 (br s, 1H), 1.63-1.46 (m, 1H), 1.26 (qd, J = 6.4, 13.2 Hz, 1H); LCMS(electrospray) m/z 431.1 (M + H+). | H |
| 334 | 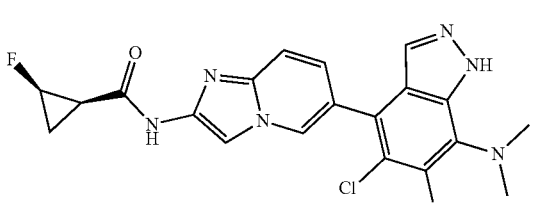<br>(1R,2R)-N-(6-(5-chloro-7-(dimethylamino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.77-13.25 (m, 1H), 11.15 (s, 1H), 8.78 (s, 1H), 8.17 (s, 1H), 7.94 (s, 1H), 7.59 (d, J = 9.2 Hz, 1H), 7.38 (d, J = 9.3 Hz, 1H), 5.09-4.80 (m, 1H), 3.00 (d, J = 2.3 Hz, 6H), 2.16 (td, J = 6.8, 13.6 Hz, 1H), 1.73-1.58 (m, 1H), 1.24-1.10 (m, 1H); LCMS(electrospray) m/z 431.1 (M + H+). | H |
| 335 | 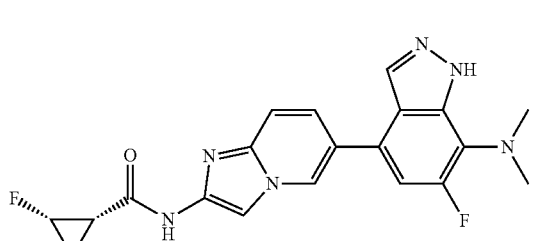<br>(1S,2S)-N-(6-(7-(dimethylamino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.34 (br s, 1H), 11.05 (s, 1H), 8.93 (s, 1H), 8.29 (s, 1H), 8.19 (s, 1H), 7.60-7.56 (m, 1H), 7.55-7.51 (m, 1H), 7.15 (d, J = 13.7 Hz, 1H), 5.06-4.80 (m, 1H), 2.95 (d, J = 1.2 Hz, 6H), 2.22-2.09 (m, 1H), 1.75-1.59 (m, 1H), 1.16 (br s, 1H); LCMS(electrospray) m/z 397.2 (M + H+). | H |

TABLE 1-continued

Compounds of Examples

| Ex # | Structure/Name | ¹H NMR/MS (M + 1) | Method |
|---|---|---|---|
| 336 | 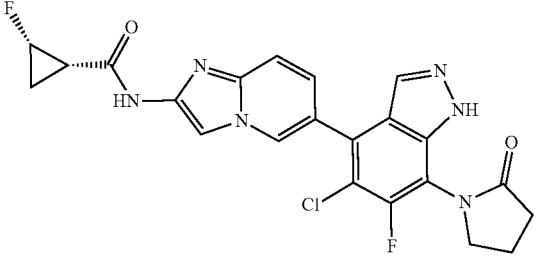 [SMILES: O=C(Nc1cn2cc(-c3c(Cl)c(F)c(N4CCCC4=O)c4[nH]ncc34)ccc2n1)[C@@H]1C[C@@H]1F]<br>(1S,2S)-N-(6-(5-chloro-6-fluoro-7-(2-oxopyrrolidin-1-yl)-1H-indazol-4-yl)imidazo[1,2-a]pyridin-2-yl)-2-fluorocyclopropane-1-carboxamide | ¹H NMR (400 MHz, DMSO-$d_6$) δ 13.68 (s, 1H), 11.09 (s, 1H), 8.83 (s, 1H), 8.18 (s, 1H), 8.08 (s, 1H), 7.59 (d, J = 9.2 Hz, 1H), 7.38 (dd, J = 9.0 Hz, J = 1.8 Hz, 1H), 5.03-4.83 (m, 1H), 3.84 (t, J = 6.8 Hz, 2H), 2.52 (t, J = 7.4 Hz, 2H), 2.31-2.24 (m, 2H), 2.18-2.13 (m, 1H), 1.71-1.63 (m, 1H), 1.23-1.12 (m, 1H); LCMS (electrospray) m/z 471.1 (M + H)+. | H |
| 337 | 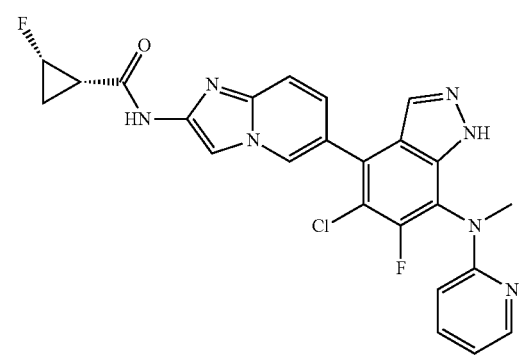 [SMILES: CN(c1ccccn1)c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(methyl(pyridin-2-yl)amino)-1H-indazol-4-yl)imidazo[1,2-a]pyridin-2-yl)-2-fluorocyclopropane-1-carboxamide | ¹H NMR (400 MHz, DMSO-$d_6$) δ 13.62 (s, 1H), 11.06 (s, 1H), 8.82 (s, 1H), 8.16 (s, 1H), 8.11 (br, 1H), 8.08 (s, 1H), 7.59-7.55 (m, 2H), 7.38 (dd, J = 9.0 Hz, J = 1.8 Hz, 1H), 6.73 (d, J = 8.0 Hz, 1H), 6.54 (d, J = 8.0 Hz, 1H), 5.03-4.83 (m, 1H), 3.41 (s, 3H), 2.18-2.13 (m, 1H), 1.71-1.63 (m, 1H), 1.23-1.12 (m, 1H); LCMS (electrospray) m/z 494.1 (M + H)+. | H |
| 338 | 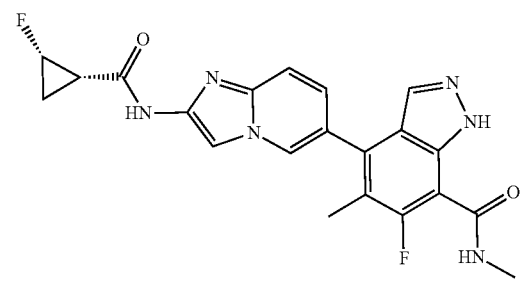 [SMILES: CNC(=O)c1c(F)c(C)c(-c2ccc3nc(NC(=O)[C@@H]4C[C@@H]4F)cn3c2)c2cn[nH]c12]<br>6-fluoro-4-(2-((1S,2S)-2-fluorocyclopropane-1-carboxamido)imidazo[1,2-a]pyridin-6-yl)-N,5-dimethyl-1H-indazole-7-carboxamide | ¹H NMR (400 MHz, DMSO-$d_6$) δ 13.22 (s, 1H), 11.07 (s, 1H), 8.79-8.65 (m, 1H), 8.46-8.34 (m, 1H), 8.17 (s, 1H), 7.90-7.78 (m, 1H), 7.65-7.51 (m, 1H), 7.36-7.22 (m, 1H), 5.08-4.78 (m, 1H), 2.89 (br d, J = 4.5 Hz, 3H), 2.24 (br d, J = 2.8 Hz, 3H), 2.19-2.13 (m, 1H), 1.74-1.58 (m, 1H), 1.23-1.11 (m, 1H); LCMS(electrospray) m/z 425.1 (M + H+). | H |

TABLE 1-continued

Compounds of Examples

| Ex # | Structure/Name | ¹H NMR/MS (M + 1) | Method |
|---|---|---|---|
| 339 | (1S,2S)-N-(6-(5-ethyl-6-fluoro-7-(trifluoromethyl)-1H-indazol-4-yl)imidazo[1,2-a]pyridin-2-yl)-2-fluorocyclopropane-1-carboxamide | ¹H NMR (400 MHz, DMSO-d$_6$) δ 13.67 (br s, 1H), 11.10 (s, 1H), 8.73 (s, 1H), 8.18 (s, 1H), 7.97 (s, 1H), 7.60 (d, J = 9.1 Hz, 1H), 7.27 (dd, J = 1.6, 9.1 Hz, 1H), 5.05-4.81 (m, 1H), 2.66 (br d, J = 7.3 Hz, 2H), 2.22-2.11 (m, 1H), 1.74-1.61 (m, 1H), 1.20-1.14 (m, 1H), 1.10 (t, J = 7.4 Hz, 3H); LCMS(electrospray) m/z 450.2 (M + H+). | H |
| 340 | (1S,2S)-2-fluoro-N-(6-(7-(methylthio)-1H-indazol-4-yl)imidazo[1,2-a]pyridin-2-yl)cyclopropane-1-carboxamide | ¹H NMR (400 MHz, DMSO-d$_6$) δ 13.48 (br s, 1H) 11.05 (s, 1 H) 8.94 (s, 1 H) 8.36 (br s, 1 H) 8.21 (s, 1 H) 7.52-7.62 (m, 2 H) 7.37 (br d, J = 7.25 Hz, 1 H) 7.29 (d, J = 7.50 Hz, 1 H) 4.81-5.04 (m, 1 H) 2.62 (s, 3 H) 2.12-2.20 (m, 1 H) 1.61-1.73 (m, 1 H) 1.12-1.23 (m, 1 H); LCMS(electrospray) m/z 382.1 (M + H+). | H |
| 341 | 5-chloro-N-ethyl-6-fluoro-4-(2-((1S,2S)-2-fluorocyclopropane-1-carboxamido)imidazo[1,2-a]pyridin-6-yl)-N-methyl-1H-indazole-7-carboxamide | ¹H NMR (400 MHz, DMSO-d$_6$) δ 13.70 (s, 1 H), 11.06 (s, 1 H), 8.81 (s, 1 H), 8.14(s, 1 H), 8.01 (s, 1 H), 7.54 (s, 1 H), 7.37-7.34 (m, 1 H), 4.98-4.80 (m, 1 H), 3.23-3.17 (q, J = 7.0 Hz, 1H), 2.87 (s, 3 H), 2.14-2.10 (m, 1 H), 1.66-1.59 (m, 1 H), 1.16-1.10 (m, 1 H), 1.00 (t, J = 6.9 Hz, 3 H); LCMS(electrospray) m/z 473.1 (M + H+). | H |
| 342 | (1S,2S)-2-fluoro-N-(6-(6-fluoro-7-(methylthio)-1H-indazol-4-yl)imidazo[1,2-a]pyridin-2-yl)cyclopropane-1-carboxamide | ¹H NMR (400 MHz, DMSO-d$_6$) δ 13.63 (s, 1 H) 11.17 (s, 1 H) 9.07 (s, 1 H) 8.43(s, 1 H) 8.21 (s, 1 H) 7.72-7.61 (m, 2 H) 7.32 (d, J = 10.4 Hz, 1 H) 5.05-4.85 (m, 1 H) 2.51 (s, 3 H) 2.20-2.15 (m, 1 H) 1.72-1.65 (m, 1 H) 1.22-1.16 (m, 1 H); LCMS(electrospray) m/z 400.0 (M + H+). | H |

TABLE 1-continued

Compounds of Examples

| Ex # | Structure/Name | $^1$H NMR/MS (M + 1) | Method |
|---|---|---|---|
| 343 | (1S,2S)-N-(6-(7-(difluoromethyl)-6-fluoro-5-methyl-1H-indazol-4-yl)imidazo[1,2-a]pyridin-2-yl)-2-fluorocyclopropane-1-carboxamide | $^1$H NMR (400 MHz, DMSO-d$_6$) δ 13.54 (s, 1H), 11.09 (s, 1H), 8.75 (s, 1H), 8.16 (s, 1H), 7.94 (d, J = 1.0 Hz, 1H), 7.73-7.43(m, 2H), 7.30 (dd, J = 1.6, 9.2 Hz, 1H), 5.10-4.79 (m, 1H), 2.24 (d, J = 2.6 Hz, 3H), 2.19-2.12 (m, 1H), 1.74-1.61 (m, 1H), 1.17 (ddd, J = 2.9, 6.2, 12.2 Hz, 1H); LCMS(electrospray) m/z 418.1 (M + H+). | H |
| 344 | (1S,2S)-2-fluoro-N-(6-(6-fluoro-7-(trifluoromethoxy)-1H-indazol-4-yl)imidazo[1,2-a]pyridin-2-yl)cyclopropane-1-carboxamide | $^1$H NMR (400 MHz, DMSO-d$_6$) δ 14.08 (br s, 1H), 11.11 (s, 1H), 9.05 (s, 1H), 8.49 (s, 1H), 8.21 (s, 1H), 7.68-7.63 (m, 1H), 7.61-7.57 (m, 1H), 7.48 (d, J = 11.6 Hz, 1H), 5.12-4.84 (m, 1H), 2.25-2.12 (m, 1H), 1.83-1.60 (m, 1H), 1.27-1.08 (m, 1H); LCMS(electrospray) m/z 438.2 (M + H+). | H |
| 345 | (1S,2S)-2-fluoro-N-(6-(6-fluoro-5-methyl-7-(trifluoromethoxy)-1H-indazol-4-yl)imidazo[1,2-a]pyridin-2-yl)cyclopropane-1-carboxamide | $^1$H NMR (400 MHz, DMSO-d$_6$) δ 13.94 (s, 1H), 11.09 (s, 1H), 8.74 (s, 1H), 8.15 (s, 1H), 7.99 (s, 1H), 7.57 (d, J = 9.2 Hz, 1H), 7.31 (dd, J = 1.7, 9.2 Hz, 1H), 5.08-4.77 (m, 1H), 2.26 (d, J = 2.8 Hz, 3H), 2.20-2.11 (m, 1H), 1.73-1.59 (m, 1H), 1.23-1.10 (m, 1H); LCMS(electrospray) m/z 452.3 (M + H+). | H |
| 346 | (1S,2S)-N-(6-(5-chloro-6-fluoro-7-(methyl(pyrimidin-2-yl)amino)-1H-indazol-4-yl)imidazo[1,2-a]pyridin-2-yl)-2-fluorocyclopropane-1-carboxamide | $^1$H NMR (400 MHz, DMSO-d$_6$) δ 13.61 (s, 1H), 11.10 (s, 1H), 8.86 (s, 1H), 8.63-8.47 (br, 2H), 8.20 (s, 1H), 8.03 (s, 1H), 7.60 (d, J = 9.6 Hz, 1H), 7.43 (t, J = 4.6 Hz, 1H), 6.86 (t, J = 6.0 Hz, 1H), 5.04-4.83 (m, 1H), 3.53 (s, 3H), 2.20-2.13 (m, 1H), 1.72-1.62 (m, 1H), 1.23-1.13 (m, 1H); LCMS (electrospray) m/z 495.1 (M + H)+. | H |

TABLE 1-continued

Compounds of Examples

| Ex # | Structure/Name | $^1$H NMR/MS (M + 1) | Method |
|---|---|---|---|
| 347 | 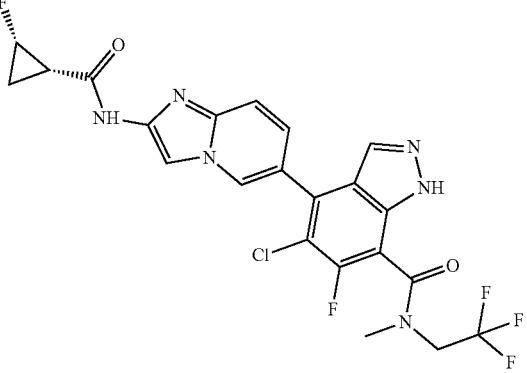<br>5-chloro-6-fluoro-4-(2-((1S,2S)-2-fluorocyclopropane-1-carboxamido)imidazo[1,2-a]pyridin-6-yl)-N-methyl-N-(2,2,2-trifluoroethyl)-1H-indazole-7-carboxamide | $^1$H NMR (400 MHz, ACETONE-d$_6$) δ 13.30 (s, 1H), 10.52 (s, 1H), 9.23 (s, 1H), 8.72 (s, 1H), 8.61 (s, 1H), 8.04 (d, J = 9.3 Hz, 1H), 7.90 (d, J = 9.1 Hz, 1H), 5.47-5.26 (m, 1H), 4.96-4.73 (m, 2H), 3.75 (s, 3H), 2.76-2.71 (m, 1H), 2.33-2.24 (m, 1H), 1.70-1.63 (m, 1H); LCMS(electrospray) m/z 527.1 (M + H+). | H |
| 348 | 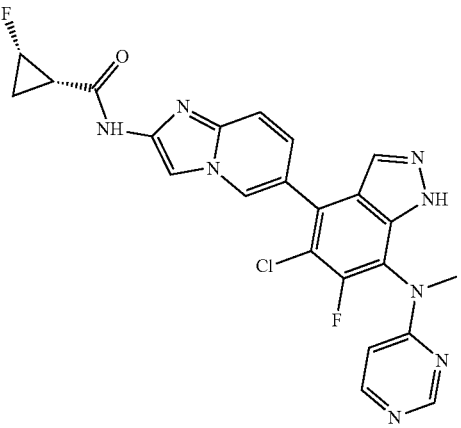 [SMILES: CN(c1ccncn1)c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(methyl(pyrimidin-4-yl)amino)-1H-indazol-4-yl)imidazo[1,2-a]pyridin-2-yl)-2-fluorocyclopropane-1-carboxamide | $^1$H NMR (400 MHz, DMSO-d$_6$) δ 13.61 (s, 1H), 11.10 (s, 1H), 8.86 (s, 1H), 8.63 (br, 1H), 8.47 (br, 1H), 8.20 (s, 1H), 8.08 (s, 1H), 7.60 (d, J = 9.6 Hz, 1H), 7.55 (br, 1H), 7.42 (t, J = 8.0 Hz, 1H), 5.04-4.83 (m, 1H), 3.48 (s, 3H), 2.20-2.15 (m, 1H), 1.72-1.62 (m, 1H), 1.23-1.13 (m, 1H); LCMS (electrospray) m/z 495.1 (M + H)+. | H |
| 349 | 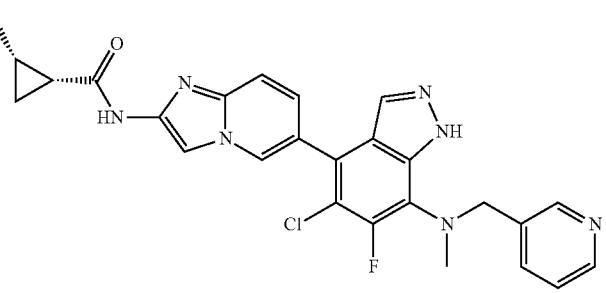<br>(1S,2S)-N-(6-(5-chloro-6-fluoro-7-(methyl(pyridin-3-ylmethyl)amino)-1H-indazol-4-yl)imidazo[1,2-a]pyridin-2-yl)-2-fluorocyclopropane-1-carboxamide | $^1$H NMR (400 MHz, DMSO-d$_6$) δ 13.66 (s, 1H), 11.09 (s, 1H), 8.77 (s, 1H), 8.59 (s, 1H), 8.46 (s, 1H), 8.20 (s, 1H), 7.96 (s, 1H), 7.82 (d, J = 6.8 Hz, 1H), 7.56 (d, J = 8.8 Hz, 1H), 7.34 (t, J = 8.2 Hz, 2H), 5.04-4.83 (m, 1H), 4.45 (s, 2H), 2.90 (s, 3H), 2.20-2.15 (m, 1H), 1.72-1.62 (m, 1H), 1.23-1.13 (m, 1H); LCMS (electrospray) m/z 508.1 (M + H)+. | H |

TABLE 1-continued

Compounds of Examples

| Ex # | Structure/Name | ¹H NMR/MS (M + 1) | Method |
|---|---|---|---|
| 350 | (1S,2S)-N-(6-(5-chloro-6-fluoro-7-(1-methyl-1H-tetrazol-5-yl)-1H-indazol-4-yl)imidazo[1,2-a]pyridin-2-yl)-2-fluorocyclopropane-1-carboxamide | ¹H NMR (400 MHz, DMSO-$d_6$) δ 14.18-13.20 (m, 1H), 11.22 (s, 1H), 8.74 (d, J = 7.2 Hz, 1H), 8.15 (s, 1H), 7.89 (s, 1H), 7.10-6.94 (m, 2H), 5.16-4.74 (m, 1H), 4.12 (s, 3H), 2.25-2.09 (m, 1H), 1.78-1.54 (m, 1H), 1.29-1.05 (m, 1H); LCMS(electrospray) m/z 470.2 (M + H+). | H |
| 351 | (1S,2S)-N-(6-(5-chloro-7-cyano-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 14.75-14.36 (m, 1H), 11.13 (s, 1H), 8.90 (s, 1H), 8.27 (s, 1H), 8.21 (s, 1H), 7.62 (d, J = 9.2 Hz, 1H), 7.41 (dd, J = 1.5, 9.3 Hz, 1H), 5.09-4.80 (m, 1H), 2.22-2.13 (m, 1H), 1.74-1.59 (m, 1H), 1.12-1.20 (m, J = 2.9, 6.1, 12.3 Hz, 1H); LCMS(electrospray) m/z 413.2 (M + H+). | H |
| 352 | (1S,2S)-N-(6-(7-(dimethylamino)-1H-indazol-4-yl)imidazo[1,2-a]pyridin-2-yl)-2-fluorocyclopropane-1-carboxamide | ¹H NMR (400 MHz, DMSO-$d_6$) δ 13.25-13.17 (m, 1H), 11.02 (s, 1H), 8.84 (s, 1H), 8.31-8.24 (m, 1H), 8.18 (s, 1H), 7.57-7.50 (m, 2H), 7.16 (d, J = 7.6 Hz, 1H), 6.80 (br d, J = 3.8 Hz, 1H), 5.07-4.78 (m, 1H), 2.92 (br s, 6H), 2.23-2.09 (m, 1H), 1.76-1.58 (m, 1H), 1.27-1.08 (m, 1H); LCMS(electrospray) m/z 379.1 (M + H+). | H |
| 353 | (1S,2S)-N-(6-(5-chloro-6-fluoro-7-(methyl(pyridin-4-ylmethyl)amino)-1H-indazol-4-yl)imidazo[1,2-a]pyridin-2-yl)-2-fluorocyclopropane-1-carboxamide | ¹H NMR (400 MHz, DMSO-$d_6$) δ 13.69 (s, 1H), 11.08 (s, 1H), 8.76 (s, 1H), 8.52 (s, 2H), 8.15 (s, 1H), 7.97 (s, 1H), 7.54 (s, 1H), 7.46 (s, 2H), 7.33 (br, 1H), 5.04-4.83 (m, 1H), 4.48 (s, 2H), 2.91 (s, 3H), 2.20-2.15 (m, 1H), 1.72-1.62 (m, 1H), 1.23-1.13 (m, 1H); LCMS (electrospray) m/z 508.1 (M + H)+. | H |

TABLE 1-continued

Compounds of Examples

| Ex # | Structure/Name | ¹H NMR/MS (M + 1) | Method |
|---|---|---|---|
| 354 | 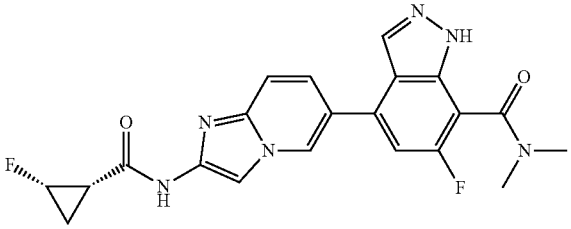 [SMILES: CN(C)C(=O)c1c(F)cc(-c2ccc3nc(NC(=O)[C@@H]4C[C@@H]4F)cn3c2)c2cn[nH]c12]<br>6-fluoro-4-(2-((1S,2S)-2-fluorocyclopropane-1-carboxamido)imidazo[1,2-a]pyridin-6-yl)-N,N-dimethyl-1H-indazole-7-carboxamide | ¹H NMR (400 MHz, DMSO-$d_6$) δ 13.45 (s, 1H), 11.10 (s, 1H), 8.71 (s, 1H), 8.20 (s, 1H), 8.09 (s, 1H), 7.52 (t, J = 9.7 Hz, 2H), 7.28 (td, J = 2.4, 8.9 Hz, 1H), 5.05-4.80 (m, 1H), 2.85 (s, 3H), 2.72 (s, 3H), 2.16 (br s, 1H), 1.74-1.58 (m, 1H), 1.23-1.12 (m, 1H); LCMS(electrospray) m/z 425.2 (M + H+). | H |
| 355 | 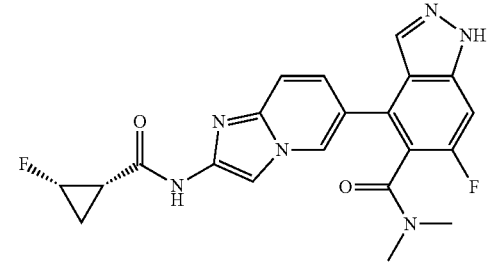 [SMILES: CN(C)C(=O)c1c(F)cc2[nH]ncc2c1-c1ccc2nc(NC(=O)[C@@H]3C[C@@H]3F)cn2c1]<br>6-fluoro-4-(2-((1S,2S)-2-fluorocyclopropane-1-carboxamido)imidazo[1,2-a]pyridin-6-yl)-N,N-dimethyl-1H-indazole-5-carboxamide | ¹H NMR (400 MHz, DMSO-$d_6$) δ 13.45 (s, 1H), 11.10 (s, 1H), 8.71 (s, 1H), 8.20 (s, 1H), 8.09 (s, 1H), 7.52 (t, J = 9.7 Hz, 2H), 7.28 (td, J = 2.4, 8.9 Hz, 1H), 5.05-4.80 (m, 1H), 2.85 (s, 3H), 2.72 (s, 3H), 2.16 (br s, 1H), 1.74-1.58 (m, 1H), 1.23-1.12 (m, 1H); LCMS(electrospray) m/z 425.2 (M + H+). | H |
| 356 | 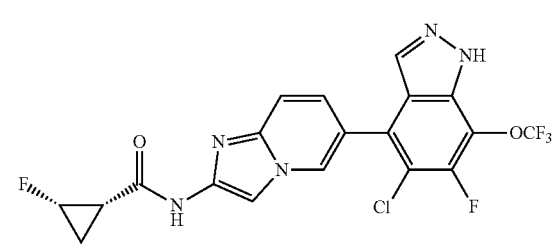 [SMILES: O=C(Nc1cn2cc(-c3c(Cl)c(F)c(OC(F)(F)F)c4[nH]ncc34)ccc2n1)[C@@H]1C[C@@H]1F]<br>(1S,2S)-N-(6-(5-chloro-6-fluoro-7-(trifluoromethoxy)-1H-indazol-4-yl)imidazo[1,2-a]pyridin-2-yl)-2-fluorocyclopropane-1-carboxamide | ¹H NMR (400 MHz, DMSO-$d_6$) δ 13.98 (s, 1H), 11.08 (s, 1H), 8.81 (s, 1H), 8.23-8.18 (m, 2H), 7.55 (d, J = 8.8 Hz, 1H), 7.42 (d, J = 8.8 Hz, 1H), 5.03-4.82 (m, 1H), 3.88 (q, J = 7.0 Hz, 2H), 2.17-2.14 (m, 1H), 1.70-1.63 (m, 1H), 1.19-1.16 (m, 1H), 1.10 (t, J = 7.0 Hz, 3H); LCMS(electrospray) m/z 416.1 (M + H+). | H |
| 357 | 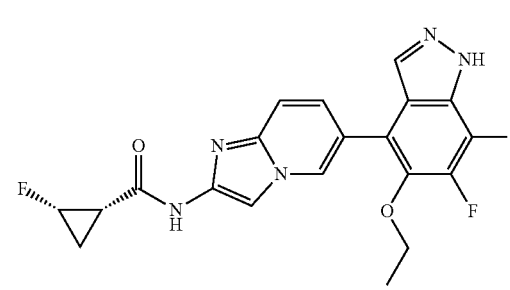<br>(1S,2S)-N-(6-(5-ethoxy-6,7-difluoro-1H-indazol-4-yl)imidazo[1,2-a]pyridin-2-yl)-2-fluorocyclopropane-1-carboxamide | ¹H NMR (400 MHz, DMSO-$d_6$) δ 13.98 (s, 1H), 11.08 (s, 1H), 8.81 (s, 1H), 8.23-8.18 (m, 2H), 7.55 (d, J = 8.8 Hz, 1H), 7.42 (d, J = 8.8 Hz, 1H), 5.03-4.82 (m, 1H), 3.88 (q, J = 7.0 Hz, 2H), 2.17-2.14 (m, 1H), 1.70-1.63 (m, 1H), 1.19-1.16 (m, 1H), 1.10 (t, J = 7.0 Hz, 3H); LCMS(electrospray) m/z 416.1 (M + H+). | H |

TABLE 1-continued

Compounds of Examples

| Ex # | Structure/Name | ¹H NMR/MS (M + 1) | Method |
|---|---|---|---|
| 358 | 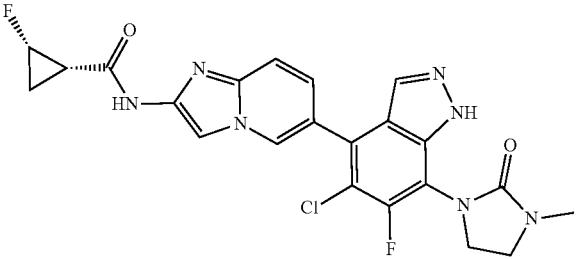 [SMILES: CN1CCN(c2c(F)c(Cl)c(-c3ccc4nc(NC(=O)[C@@H]5C[C@@H]5F)cn4c3)c3cn[nH]c23)C1=O]<br>(1S,2S)-N-(6-(5-chloro-6-fluoro-7-(3-methyl-2-oxoimidazolidin-1-yl)-1H-indazol-4-yl)imidazo[1,2-a]pyridin-2-yl)-2-fluorocyclopropane-1-carboxamide | ¹H NMR (400 MHz, DMSO-$d_6$) δ 13.64 (s, 1H), 11.12 (s, 1H), 8.83 (s, 1H), 8.18 (s, 1H), 8.03 (s, 1H), 7.59 (d, J = 9.6 Hz, 1H), 7.38 (dd, J = 1.6, 9.2 Hz, 1H), 5.03-4.84 (m, 1H), 3.83 (t, J = 7.8 Hz, 2H), 3.60 (t, J = 8.0 Hz, 2H), 2.82 (s, 3H), 2.16 (m, 1H), 1.69-1.64 (m, 1H), 1.21-1.15 (m, 1H); LCMS (electrospray) m/z 486.10 (M + H)+. | H |
| 359 | 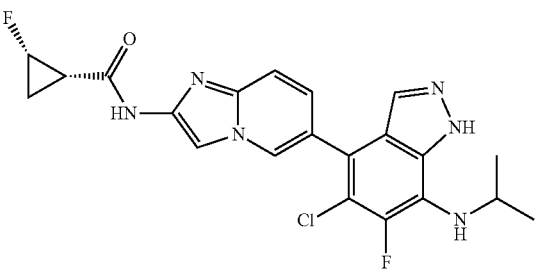<br>(1S,2S)-N-(6-(5-chloro-6-fluoro-7-(isopropylamino)-1H-indazol-4-yl)imidazo[1,2-a]pyridin-2-yl)-2-fluorocyclopropane-1-carboxamide | ¹H NMR (400 MHz, DMSO-$d_6$) δ 13.26 (s, 1H), 11.08 (s, 1H), 8.73 (s, 1H), 8.14 (s, 1H), 7.90 (s, 1H), 7.53 (d, J = 9.2 Hz, 1H), 7.32 (dd, J = 1.6, 9.2 Hz, 1 H), 5.16 (dd, J = 2.6, 9.8 Hz, 1H), 5.03-4.83 (m, 1H), 4.08 (s, 1H), 2.19-2.12 (m, 1H), 1.71-1.61 (m, 1H), 1.22 (d, J = 6.8 Hz, 6H), 1.19-1.12 (m, 1H); LCMS (electrospray) m/z 445.10 (M + H)+. | H |
| 360 | 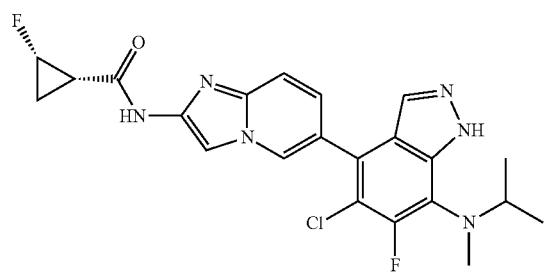<br>(1S,2S)-N-(6-(5-chloro-6-fluoro-7-(isopropyl(methyl)amino)-1H-indazol-4-yl)imidazo[1,2-a]pyridin-2-yl)-2-fluorocyclopropane-1-carboxamide | ¹H NMR (400 MHz, DMSO-$d_6$) δ 13.42 (s, 1H), 11.11 (s, 1H), 8.78 (s, 1H), 8.16 (s, 1H), 7.95 (s, 1H), 7.56 (d, J = 9.2 Hz, 1H), 7.36 (dd, J = 1.8, 9.4 Hz, 1H), 5.02-4.85 (m, 1H), 3.54 (s, 1H), 2.89 (d, J = 3.2 Hz, 3H), 2.19-2.12 (m, 1H), 1.71-1.61 (m, 1H), 1.21-1.13 (m, 7H); LCMS (electrospray) m/z 459.10 (M + H)+. | H |
| 361 | 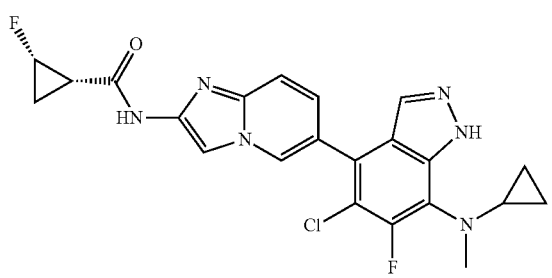 [SMILES: CN(c1c(F)c(Cl)c(-c2ccc3nc(NC(=O)[C@@H]4C[C@@H]4F)cn3c2)c2cn[nH]c12)C1CC1]<br>(1S,2S)-N-(6-(5-chloro-7-(cyclopropyl(methyl)amino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.40 (s, 1H), 11.10 (s, 1H), 8.77 (s, 1H), 8.15 (s, 1H), 7.92 (s, 1H), 7.56 (d, J = 8.8 Hz, 1H), 7.35 (dd, J = 9.2 Hz, J = 2.0 Hz, 1H), 5.03-4.83 (m, 1H), 3.01-2.98 (br, 4H), 2.17-2.14 (m, 1H), 1.69-1.62 (m, 1H), 1.19-1.14 (m, 1H) 0.64-0.59 (m, 2H), 0.48-0.45 (m, 2H); LCMS (electrospray) m/z 457.1 (M + H)+. | H |

TABLE 1-continued

Compounds of Examples

| Ex # | Structure/Name | $^1$H NMR/MS (M + 1) | Method |
|---|---|---|---|
| 362 | 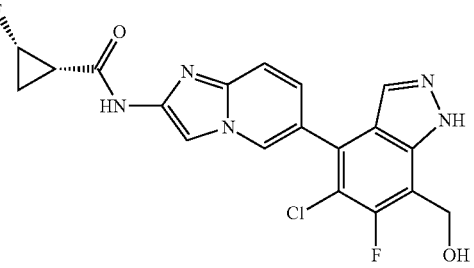<br>(1S,2S)-N-(6-(5-chloro-6-fluoro-7-(hydroxymethyl)-1H-indazol-4-yl)imidazo[1,2-a]pyridin-2-yl)-2-fluorocyclopropane-1-carboxamide | $^1$H NMR (400 MHz, DMSO-$d_6$) δ 13.54 (s, 1H), 11.10 (s, 1H), 8.81 (s, 1H), 8.18 (s, 1H), 7.96 (d, J = 1.6 Hz, 1H), 7.58 (d, J = 9.6 Hz, 1H), 7.35 (dd, J = 1.6, 9.2 Hz, 1H), 5.47 (t, J = 5.6 Hz, 1H), 5.03-4.83 (m, 3H), 2.19-2.12 (m, 1H), 1.70-1.63 (m, 1H), 1.19-1.12 (m, 1H); LCMS (electrospray) m/z 419.10 (M + H)+. | H |
| 363 | 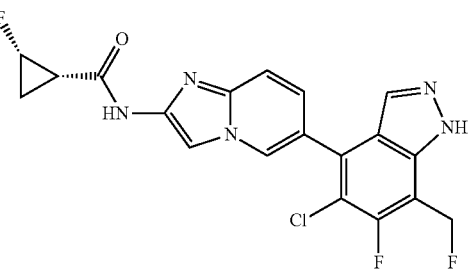<br>(1S,2S)-N-(6-(5-chloro-6-fluoro-7-(fluoromethyl)-1H-indazol-4-yl)imidazo[1,2-a]pyridin-2-yl)-2-fluorocyclopropane-1-carboxamide | $^1$H NMR (400 MHz, DMSO-$d_6$) δ 13.90 (s, 1H), 11.12 (s, 1H), 8.85 (s, 1H), 8.18 (s, 1H), 8.07 (d, J = 1.2 Hz, 1H), 7.59 (d, J = 9.6 Hz, 1H), 7.38 (dd, J = 2.0, 9.2 Hz, 1H), 5.93 (s, 1H), 5.81 (s, 1H), 5.04-4.83 (m, 1H), 2.19-2.12 (m, 1H), 1.71-1.61 (m, 1H), 1.19-1.13 (m, 1H); LCMS (electrospray) m/z 420.05 (M + H)+. | H |
| 364 | 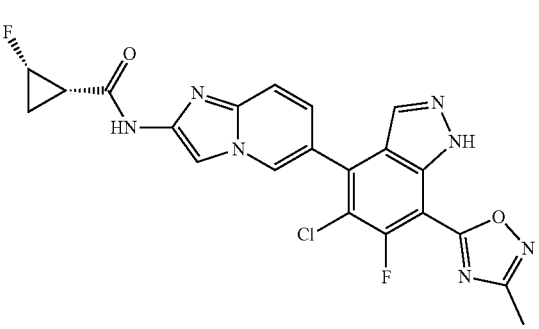 [SMILES: Cc1noc(-c2c(F)c(Cl)c(-c3ccc4nc(NC(=O)[C@@H]5C[C@@H]5F)cn4c3)c3cn[nH]c23)n1]<br>(1S,2S)-N-(6-(5-chloro-6-fluoro-7-(3-methyl-1,2,4-oxadiazol-5-yl)-1H-indazol-4-yl)imidazo[1,2-a]pyridin-2-yl)-2-fluorocyclopropane-1-carboxamide | $^1$H NMR (400 MHz, DMSO-$d_6$) δ 13.73 (s, 1H), 11.15 (s, 1H), 8.93 (s, 1H), 8.23 (s, 1H), 8.21 (s, 1H), 7.63 (d, J = 9.2 Hz, 1H), 7.45 (d, J = 9.2 Hz, 1H), 5.03-4.84 (m, 1H), 2.55 (s, 3H), 2.16-2.14 (m, 1H), 1.69-1.63 (m, 1H), 1.20-1.15 (m, 1H); LCMS (electrospray) m/z 470.10 (M + H)+. | H |
| 365 | 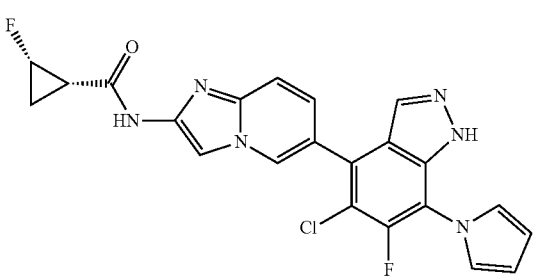 [SMILES: O=C(Nc1cn2cc(-c3c(Cl)c(F)c(-n4cccc4)c4[nH]ncc34)ccc2n1)[C@@H]1C[C@@H]1F]<br>(1S,2S)-N-(6-(5-chloro-6-fluoro-7-(1H-pyrrol-1-yl)-1H-indazol-4-yl)imidazo[1,2-a]pyridin-2-yl)-2-fluorocyclopropane-1-carboxamide | $^1$H NMR (400 MHz, DMSO-$d_6$) δ 13.56-14.07 (1H), 11.12 (s, 1H), 8.84 (d, J = 1.1 Hz, 1H), 8.20 (s, 1H), 8.17 (s, 1H), 7.61 (d, J = 9.3 Hz, 1H), 7.39 (dd, J = 9.1, 1.9 Hz, 1H), 7.28 (s, 2H), 6.41 (t, J = 2.2 Hz, 2H), 5.04-4.84 (m, 1H), 2.20-2.13 (m, 1H), 1.70-1.64 (m, 1H), 1.20-1.13 (m, 1H); LCMS (electrospray) m/z 453.10 (M + H)+. | H |

TABLE 1-continued

Compounds of Examples

| Ex # | Structure/Name | ¹H NMR/MS (M + 1) | Method |
|---|---|---|---|
| 366 | 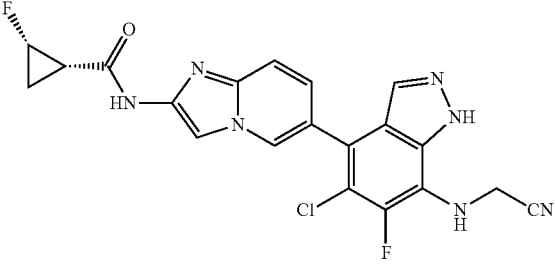 [SMILES: N#CCNc1c(F)c(Cl)c(-c2ccc3nc(NC(=O)[C@@H]4C[C@@H]4F)cn3c2)c2cn[nH]c12]<br>(1S,2S)-N-(6-(5-chloro-7-((cyanomethyl)amino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.35 (s, 1H), 11.09 (s, 1H), 8.77 (s, 1H), 8.14 (s, 1H), 7.97 (s, 1H), 7.54 (d, J = 8.8 Hz, 1H), 7.35 (dd, J = 9.3, 1.6 Hz, 1H), 6.79-6.22 (m, 1H), 5.10-4.47 (m, 3H), 2.25-2.09 (m, 1H), 1.76-1.57 (m, 1H), 1.21-1.09 (m, 1H); LCMS (electrospray) m/z 442.10 (M + H)+. | H |
| 367 | 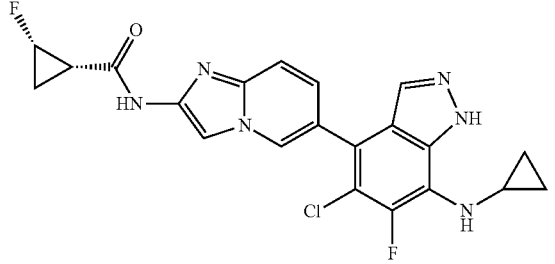<br>(1S,2S)-N-(6-(5-chloro-7-(cyclopropylamino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.03 (s, 1H), 11.07 (s, 1H), 8.71 (s, 1H), 8.16 (d, J = 13.2 Hz, 1H), 7.86 (s, 1H), 7.53 (d, J = 9.3 Hz, 1H), 7.30 (dd, J = 8.8, 1.6 Hz, 1H), 6.08 (s, 1H), 5.09-4.81 (m, 1H), 3.12 (s, 1H), 2.17-2.08 (m, 1H), 1.66 (d, J = 23.1 Hz, 1H), 1.23-1.14 (m, 1H), 0.80 (d, J = 5.5 Hz, 2H), 0.63 (d, J = 3.3 Hz, 2H); LCMS(electrospray) m/z 443.1 (M + H+). | H |
| 368 | 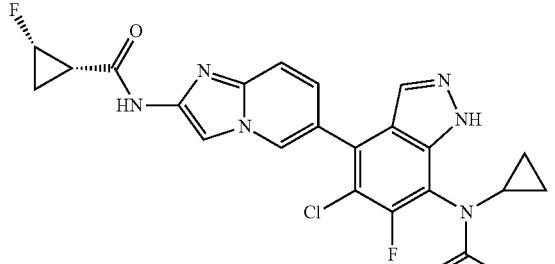<br>(1S,2S)-N-(6-(5-chloro-7-(N-cyclopropyl-2,2,2-trifluoroacetamido)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.96 (s, 1H), 11.12 (s, 1H), 8.93-8.83 (m, 1H), 8.17-8.12 (m, 2H), 7.69-7.57 (m, 1H), 7.46-7.36 (m, 1H), 5.04-4.83 (m, 1H), 3.44 (qd, J = 7.2, 3.7 Hz, 1H), 2.19-2.12 (m, 1H), 1.71-1.61 (m, 1H), 1.23-1.13 (m, 1H), 0.98-0.55 (m, 4H); LCMS(electrospray) m/z 539.1 (M + H+). | H |
| 369 | 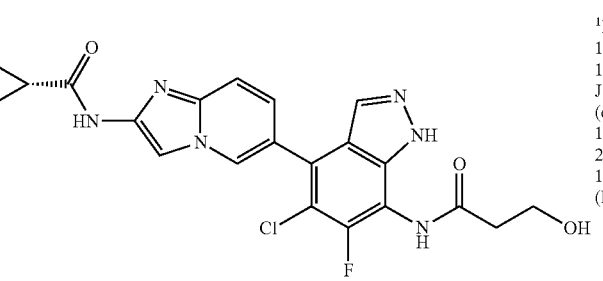<br>(1S,2S)-N-(6-(5-chloro-6-fluoro-7-(3-hydroxypropanamido)-1H-indazol-4-yl)imidazo[1,2-a]pyridin-2-yl)-2-fluorocyclopropane-1-carboxamide | ¹H NMR (400 MHz, DMSO-$d_6$) δ 13.16 (s, 1H), 11.11 (s, 1H), 10.16 (s, 1H), 8.83 (d, J = 1.1 Hz, 1H), 8.18 (s, 1H), 7.98 (d, J = 1.6 Hz, 1H), 7.58 (d, J = 9.3 Hz, 1H), 7.37 (dd, J = 9.1, 1.9 Hz, 1H), 4.93 (ddd, J = 66.2, 9.9, 6.3 Hz, 1H), 4.76 (t, J = 5.5 Hz, 1H), 3.79 (q, J = 6.2 Hz, 2H), 2.65 (t, J = 6.6 Hz, 2H), 2.19-2.08 (m, 1H), 1.70-1.61 (m, 1H), 1.23-1.13 (m, 1H); LCMS(electrospray) m/z 475.1 (M + H+). | H |

TABLE 1-continued

Compounds of Examples

| Ex # | Structure/Name | $^1$H NMR/MS (M + 1) | Method |
|---|---|---|---|
| 370 | 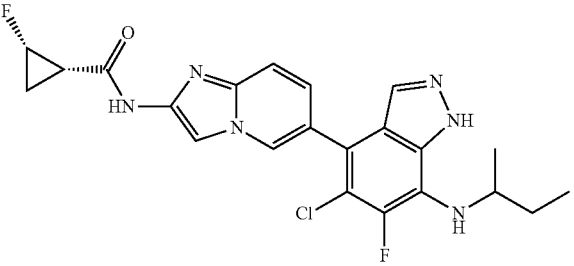 [SMILES: CCC(C)Nc1c(F)c(Cl)c(-c2ccc3nc(NC(=O)[C@@H]4C[C@@H]4F)cn3c2)c2cn[nH]c12]<br>(1S,2S)-N-(6-(7-(sec-butylamino)-5-chloro-6-fluoro-1H-indazol-4-yl)imidazo[1,2-a]pyridin-2-yl)-2-fluorocyclopropane-1-carboxamide | $^1$H NMR (400 MHz, DMSO-$d_6$) δ 13.12-13.48 (1H), 11.08 (s, 1H), 8.72 (s, 1H), 8.14 (s, 1H), 7.90 (s, 1H), 7.52 (d, J = 9.3 Hz, 1H), 7.31 (dd, J = 9.1, 1.9 Hz, 1H), 5.16 (d, J = 6.9 Hz, 1H), 5.03-4.83 (m, 1H), 3.90 (s, 1H), 2.19-2.12 (m, 1H), 1.71-1.58 (m, 2H), 1.53-1.46 (m, 1H), 1.23-1.12 (m, 4H), 0.94 (t, J = 7.4 Hz, 3H); LCMS (electrospray) m/z 459.10 (M + H)+. | H |
| 371 | 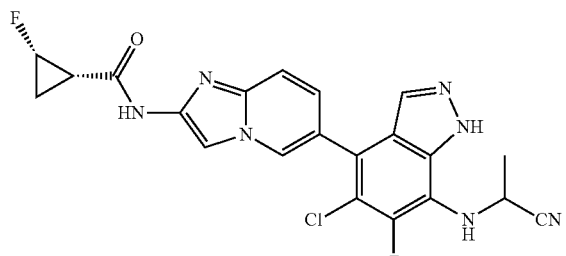<br>(1S,2S)-N-(6-(5-chloro-7-((1-cyanoethyl)amino)-6-fluoro-1H-indazol-4-yl)imidazo[1,2-a]pyridin-2-yl)-2-fluorocyclopropane-1-carboxamide | $^1$H NMR (400 MHz, DMSO-$d_6$) δ 13.38 (s, 1H), 11.10 (s, 1H), 8.77 (d, J = 12.6 Hz, 1H), 8.14 (d, J = 8.2 Hz, 1H), 7.97 (s, 1H), 7.54 (t, J = 9.3 Hz, 1H), 7.35 (d, J = 9.3 Hz, 1H), 6.66-6.46 (m, 0.5H), 6.11 (d, J = 9.3 Hz, 1H), 5.99-5.80 (m, 0.5H), 5.10-4.77 (m, 2H), 2.24-2.09 (m, 1H), 1.81-1.58 (m, 4H), 1.21-1.06 (m, 1H); LCMS (electrospray) m/z 456.10 (M + H)+. | H |
| 372 | 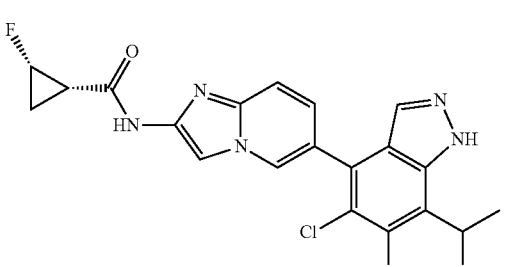<br>(1S,2S)-N-(6-(5-chloro-6-fluoro-7-(1-hydroxyethyl)-1H-indazol-4-yl)imidazo[1,2-a]pyridin-2-yl)-2-fluorocyclopropane-1-carboxamide | $^1$H NMR (400 MHz, DMSO-$d_6$) δ 13.28 (s, 1H), 11.11 (s, 1H), 8.80 (t, J = 1.4 Hz, 1H), 8.18 (s, 1H), 7.94 (d, J = 1.6 Hz, 1H), 7.58 (d, J = 9.3 Hz, 1H), 7.35 (dd, J = 9.1, 1.9 Hz, 1H), 5.83 (d, J = 3.8 Hz, 1H), 5.43-5.37 (m, 1H), 5.04-4.83 (m, 1H), 2.19-2.12 (m, 1H), 1.70-1.62 (m, 1H), 1.54 (d, J = 6.6 Hz, 3H), 1.23-1.13 (m, 1H); LCMS (electrospray) m/z 433.10 (M + H)+. | H |
| 373 | 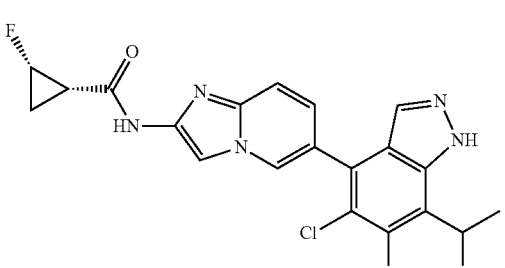<br>(1S,2S)-N-(6-(5-chloro-6-fluoro-7-(1-methoxyethyl)-1H-indazol-4-yl)imidazo[1,2-a]pyridin-2-yl)-2-fluorocyclopropane-1-carboxamide | $^1$H NMR (400 MHz, DMSO-$d_6$) δ 13.40 (s, 1H), 11.11 (s, 1H), 8.82 (t, J = 1.4 Hz, 1H), 8.17 (s, 1H), 7.99 (s, 1H), 7.61-7.57 (m, 1H), 7.38 (dd, J = 9.3, 1.6 Hz, 1H), 5.07-4.83 (m, 2H), 3.23 (s, 3H), 2.19-2.12 (m, 1H), 1.71-1.61 (m, 1H), 1.57 (t, J = 6.3 Hz, 4H), 1.21-1.13 (m, 2H); LCMS (electrospray) m/z 447.10 (M + H)+. | H |

TABLE 1-continued

Compounds of Examples

| Ex # | Structure/Name | ¹H NMR/MS (M + 1) | Method |
|---|---|---|---|
| 374 | 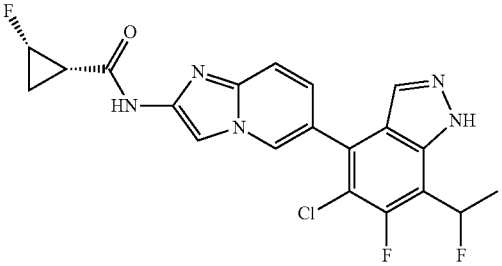 [SMILES: CC(F)c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(1-fluoroethyl)-1H-indazol-4-yl)imidazo[1,2-a]pyridin-2-yl)-2-fluorocyclopropane-1-carboxamide | ¹H NMR (400 MHz, DMSO-d₆) δ 13.68 (s, 1H), 11.11 (s, 1H), 8.83 (t, J = 1.4 Hz, 1H), 8.18 (s, 1H), 8.05 (s, 1H), 7.61-7.58 (m, 1H), 7.37 (dd, J = 9.1, 1.9 Hz, 1H), 6.43-6.27 (m, 1H), 5.04-4.83 (m, 1H), 2.20-2.13 (m, 1H), 1.83 (dd, J = 23.9, 6.3 Hz, 3H), 1.72-1.61 (m, 1H), 1.21-1.13 (m, 1H); LCMS (electrospray) m/z 435.10 (M + H)+. | H |
| 375 | 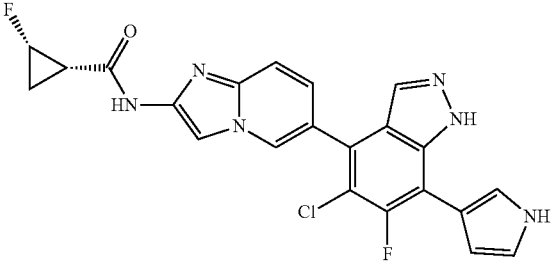 [SMILES: O=C(Nc1cn2cc(-c3c(Cl)c(F)c(-c4cc[nH]c4)c4[nH]ncc34)ccc2n1)[C@@H]1C[C@@H]1F]<br>(1S,2S)-N-(6-(5-chloro-6-fluoro-7-(1H-pyrrol-3-yl)-1H-indazol-4-yl)imidazo[1,2-a]pyridin-2-yl)-2-fluorocyclopropane-1-carboxamide | ¹H NMR (400 MHz, DMSO-d₆) δ 13.37 (s, 1H), 11.44 (s, 1H), 11.11 (s, 1H), 8.82 (d, J = 1.1 Hz, 1H), 8.18 (s, 1H), 8.01 (s, 1H), 7.58 (d, J = 9.3 Hz, 1H), 7.49 (s, 1H), 7.39 (dd, J = 9.1, 1.9 Hz, 1H), 7.01 (s, 1H), 6.68 (s, 1H), 5.04-4.84 (m, 1H), 2.20-2.13 (m, 1H), 1.71-1.61 (m, 1H), 1.23-1.13 (m, 1H); LCMS (electrospray) m/z 454.10 (M + H)+. | H |
| 376 | 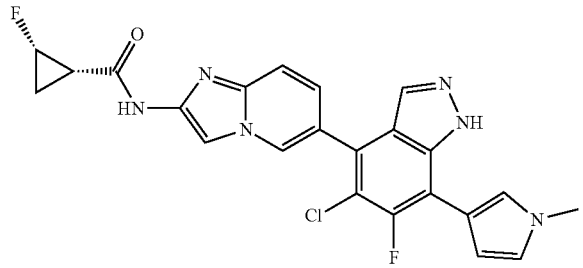 [SMILES: Cn1ccc(-c2c(F)c(Cl)c(-c3ccc4nc(NC(=O)[C@@H]5C[C@@H]5F)cn4c3)c3cn[nH]c23)c1]<br>(1S,2S)-N-(6-(5-chloro-6-fluoro-7-(1-methyl-1H-pyrrol-3-yl)-1H-indazol-4-yl)imidazo[1,2-a]pyridin-2-yl)-2-fluorocyclopropane-1-carboxamide | ¹H NMR (400 MHz, DMSO-d₆) δ 13.35 (s, 1H), 11.11 (s, 1H), 8.82 (d, J = 1.6 Hz, 1H), 8.18 (s, 1H), 8.01 (s, 1H), 7.58 (d, J = 8.8 Hz, 1H), 7.46 (s, 1H), 7.38 (dd, J = 9.1, 1.9 Hz, 1H), 6.96 (s, 1H), 6.64 (s, 1H), 5.04-4.83 (m, 1H), 3.75 (s, 3H), 2.20-2.13 (m, 1H), 1.71-1.61 (m, 1H), 1.23-1.13 (m, 1H); LCMS (electrospray) m/z 468.10 (M + H)+. | H |
| 377 | 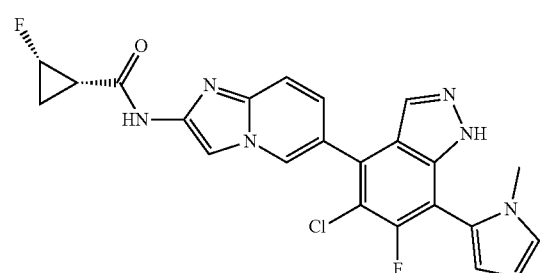<br>(1S,2S)-N-(6-(5-chloro-6-fluoro-7-(1-methyl-1H-pyrrol-2-yl)-1H-indazol-4-yl)imidazo[1,2-a]pyridin-2-yl)-2-fluorocyclopropane-1-carboxamide | ¹H NMR (400 MHz, DMSO-d₆) δ 13.44 (s, 1H), 11.12 (s, 1H), 8.87 (t, J = 1.4 Hz, 1H), 8.19 (s, 1H), 8.04 (s, 1H), 7.60 (d, J = 9.3 Hz, 1H), 7.42 (dd, J = 9.1, 1.9 Hz, 1H), 7.08 (s, 1H), 6.39-6.37 (m, 1H), 6.26 (t, J = 3.0 Hz, 1H), 5.04-4.84 (m, 1H), 3.54 (d, J = 1.1 Hz, 3H), 2.20-2.13 (m, 1H), 1.72-1.62 (m, 1H), 1.23-1.13 (m, 1H); LCMS (electrospray) m/z 468.10 (M + H)+. | H |

TABLE 1-continued

Compounds of Examples

| Ex # | Structure/Name | ¹H NMR/MS (M + 1) | Method |
|---|---|---|---|
| 378 | 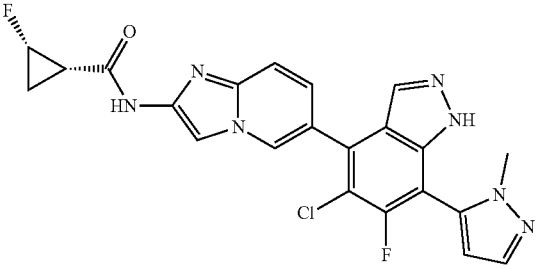 [SMILES: Cn1nccc1-c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(1-methyl-1H-pyrazol-5-yl)-1H-indazol-4-yl)imidazo[1,2-a]pyridin-2-yl)-2-fluorocyclopropane-1-carboxamide | ¹H NMR (400 MHz, DMSO-d₆) δ 13.57 (s, 1H), 11.12 (s, 1H), 8.88 (t, J = 1.1 Hz, 1H), 8.21 (s, 1H), 8.10 (s, 1H), 7.70 (d, J = 1.6 Hz, 1H), 7.62 (d, J = 9.3 Hz, 1H), 7.43 (dd, J = 9.1, 1.9 Hz, 1H), 6.64 (d, J = 1.4 Hz, 1H), 5.04-4.84 (m, 1H), 3.76 (s, 3H), 2.20-2.13 (m, 1H), 1.71-1.62 (m, 1H), 1.23-1.13 (m, 1H); LCMS (electrospray) m/z 469.10 (M + H)+. | H |
| 379 | 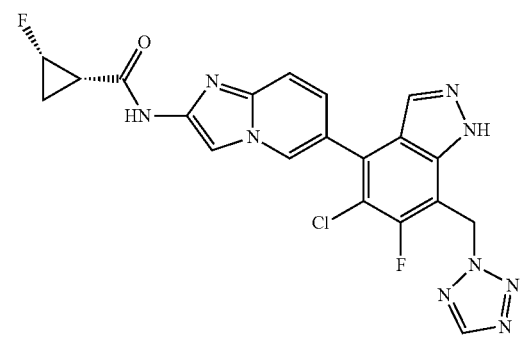<br>(1S,2S)-N-(6-(7-((2H-tetrazol-2-yl)methyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.94 (s, 1H), 11.11 (s, 1H), 9.01 (s, 1H), 8.86 (s, 1H), 8.17 (s, 1H), 8.09 (s, 1H), 7.59 (d, J = 9.1 Hz, 1H), 7.39 (dd, J = 9.2, 1.5 Hz, 1H), 6.36 (s, 2H), 5.02-4.85 (m, 1H), 2.18-2.14 (m, 1H), 1.70-1.63 (m, 1H), 1.20-1.14 (m, 1H); LCMS (electrospray) m/z 470.10 (M + H)+. | I |
| 380 | 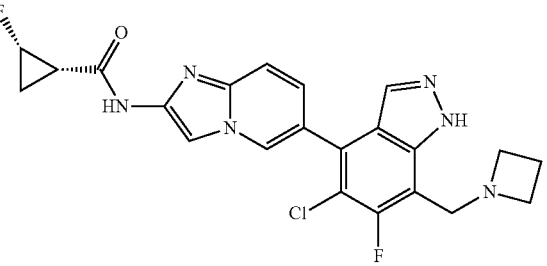<br>(1S,2S)-N-(6-(7-(azetidin-1-ylmethyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.56 (s, 1H), 11.10 (s, 1H), 8.82 (d, J = 1.1 Hz, 1H), 8.17 (s, 1H), 7.96 (s, 1H), 7.57 (d, J = 9.3 Hz, 1H), 7.36 (dd, J = 9.1, 1.9 Hz, 1H), 5.04-4.83 (m, 1H), 3.91 (d, J = 1.1 Hz, 2H), 3.20 (q, J = 6.8 Hz, 4H), 2.19-2.12 (m, 1H), 2.00-1.93 (m, 2H), 1.71-1.61 (m, 1H), 1.23-1.13 (m, 1H); LCMS (electrospray) m/z 457.10 (M + H)+. | H |
| 381 | 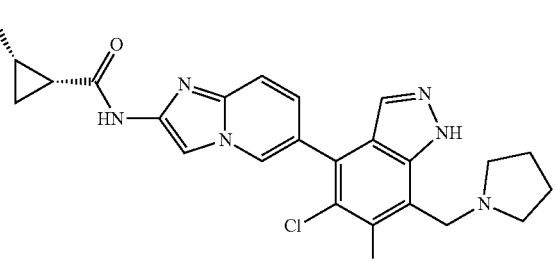<br>(1S,2S)-N-(6-(5-chloro-6-fluoro-7-(pyrrolidin-1-ylmethyl)-1H-indazol-4-yl)imidazo[1,2-a]pyridin-2-yl)-2-fluorocyclopropane-1-carboxamide | ¹H NMR (400 MHz, DMSO-d₆) δ 13.50 (s, 1H), 11.11 (s, 1H), 8.82 (d, J = 1.1 Hz, 1H), 8.18 (s, 1H), 7.98 (s, 1H), 7.58 (d, J = 9.3 Hz, 1H), 7.37 (dd, J = 9.3, 1.6 Hz, 1H), 5.04-4.84 (m, 1H), 4.00 (d, J = 1.1 Hz, 2H), 2.53-2.49 (m, 4H), 2.20-2.13 (m, 1H), 1.70-1.62 (m, 5H), 1.24-1.13 (m, 1H); LCMS (electrospray) m/z 472.10 (M + H)+. | H |

TABLE 1-continued

Compounds of Examples

| Ex # | Structure/Name | ¹H NMR/MS (M + 1) | Method |
|---|---|---|---|
| 382 | 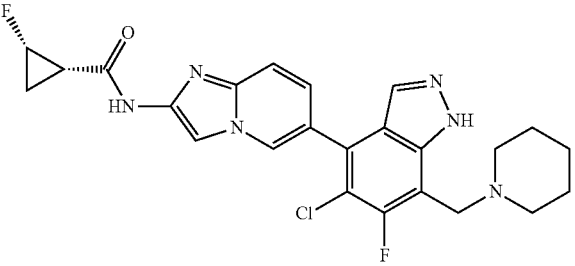 [SMILES: O=C(Nc1cn2cc(-c3c(Cl)c(F)c(CN4CCCCC4)c4[nH]ncc34)ccc2n1)[C@@H]1C[C@@H]1F]<br>(1S,2S)-N-(6-(5-chloro-6-fluoro-7-(piperidin-1-ylmethyl)-1H-indazol-4-yl)imidazo[1,2-a]pyridin-2-yl)-2-fluorocyclopropane-1-carboxamide | ¹H NMR (400 MHz, DMSO-$d_6$) δ 13.41 (s, 1H), 11.11 (s, 1H), 8.83 (t, J = 1.1 Hz, 1H), 8.17 (s, 1H), 7.97 (s, 1H), 7.58 (d, J = 9.3 Hz, 1H), 7.38 (dd, J = 9.1, 1.9 Hz, 1H), 5.04-4.83 (m, 1H), 3.84 (s, 2H), 2.44 (s, 4H), 2.19-2.12 (m, 1H), 1.70-1.62 (m, 1H), 1.51-1.37 (m, 6H), 1.23-1.13 (m, 1H); LCMS (electrospray) m/z 486.10 (M + H)+. | H |
| 383 | 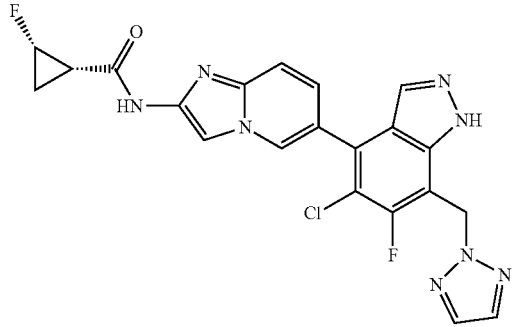 [SMILES: O=C(Nc1cn2cc(-c3c(Cl)c(F)c(Cn4nccn4)c4[nH]ncc34)ccc2n1)[C@@H]1C[C@@H]1F]<br>(1S,2S)-N-(6-(7-((2H-1,2,3-triazol-2-yl)methyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.92 (s, 1H), 11.11 (s, 1H), 8.85 (d, J = 1.1 Hz, 1H), 8.17 (s, 1H), 8.07 (s, 1H), 7.81 (s, 2H), 7.58 (d, J = 9.3 Hz, 1H), 7.38 (dd, J = 9.1, 1.9 Hz, 1H), 6.07 (s, 2H), 5.04-4.83 (m, 1H), 2.19-2.12 (m, 1H), 1.71-1.61 (m, 1H), 1.21-1.13 (m, 1H); LCMS (electrospray) m/z 469.10 (M + H)+. | I |
| 384 | 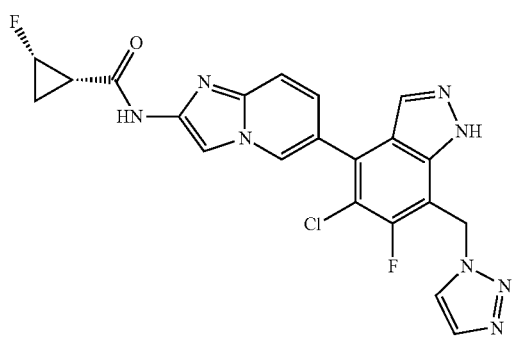 [SMILES: O=C(Nc1cn2cc(-c3c(Cl)c(F)c(Cn4ccnn4)c4[nH]ncc34)ccc2n1)[C@@H]1C[C@@H]1F]<br>(1S,2S)-N-(6-(7-((1H-1,2,3-triazol-1-yl)methyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.95 (s, 1H), 11.11 (s, 1H), 8.83 (t, J = 1.4 Hz, 1H), 8.31 (d, J = 1.4 Hz, 1H), 8.17 (s, 1H), 8.09 (s, 1H), 7.75 (d, J = 1.1 Hz, 1H), 7.58 (d, J = 9.3 Hz, 1H), 7.37 (dd, J = 9.1, 1.9 Hz, 1H), 6.03 (s, 2H), 5.04-4.83 (m, 1H), 2.19-2.12 (m, 1H), 1.71-1.61 (m, 1H), 1.21-1.13 (m, 1H); LCMS (electrospray) m/z 469.10 (M + H)+. | I |

| Ex # | Structure/Name | ¹H NMR/MS (M + 1) | Method |
|---|---|---|---|
| 385 | 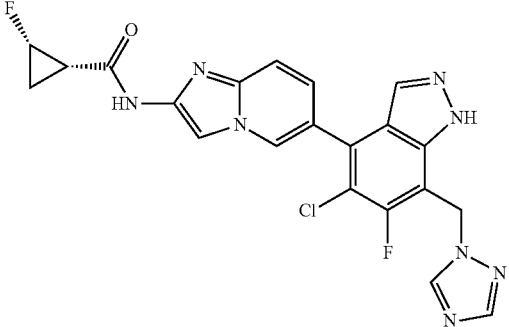 [SMILES: O=C(Nc1cn2cc(-c3c(Cl)c(F)c(Cn4cncn4)c4[nH]ncc34)ccc2n1)[C@@H]1C[C@@H]1F]<br>(1S,2S)-N-(6-(7-((1H-1,2,4-triazol-1-yl)methyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.92 (s, 1H), 11.11 (s, 1H), 8.83 (d, J = 1.1 Hz, 1H), 8.79 (s, 1H), 8.16 (s, 1H), 8.07 (s, 1H), 7.96 (s, 1H), 7.58 (d, J = 9.3 Hz, 1H), 7.37 (dd, J = 9.1, 1.9 Hz, 1H), 5.83 (s, 2H), 5.04-4.83 (m, 1H), 2.19-2.12 (m, 1H), 1.71-1.61 (m, 1H), 1.21-1.13 (m, 1H); LCMS (electrospray) m/z 469.10 (M + H)+. | I |
| 386 | 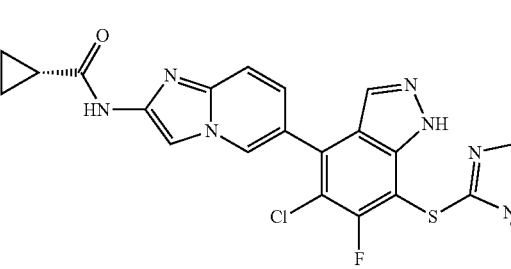<br>(1S,2S)-N-(6-(5-chloro-6-fluoro-7-((1-methyl-1H-imidazol-2-yl)thio)-1H-indazol-4-yl)imidazo[1,2-a]pyridin-2-yl)-2-fluorocyclopropane-1-carboxamide | ¹H NMR (400 MHz, DMSO-$d_6$) δ 13.86 (s, 1H), 11.12 (s, 1H), 8.85 (s, 1H), 8.17 (s, 1H), 8.08 (s, 1H), 7.58 (d, J = 9.6 Hz, 1H), 7.38 (dd, J = 9.3, 1.6 Hz, 1H), 7.33 (d, J = 1.1 Hz, 1H), 6.93-6.91 (m, 1H), 5.04-4.83 (m, 1H), 3.80 (d, J = 15.4 Hz, 3H), 2.19-2.12 (m, 1H), 1.70-1.62 (m, 1H), 1.23-1.13 (m, 1H); LCMS (electrospray) m/z 501.10 (M + H)+. | H |
| 387 | 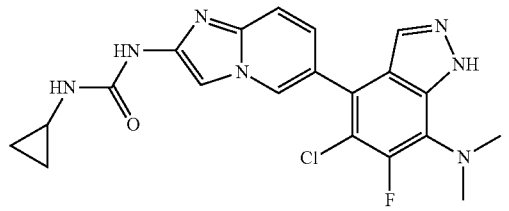 [SMILES: CN(C)c1c(F)c(Cl)c(-c2ccc3nc(NC(=O)NC4CC4)cn3c2)c2cn[nH]c12]<br>1-(6-(5-chloro-7-(dimethylamino)-6-fluoro-1H-indazol-4-yl)imidazo[1,2-a]pyridin-2-yl)-3-cyclopropylurea | ¹H NMR (400 MHz, DMSO-$d_6$) δ 13.20-13.84 (s, 1 H) 8.84 (s, 1 H) 8.71 (d, J = 9.4 Hz, 1 H) 7.92 (s, 1 H) 7.87 (s, 1 H) 7.49 (d, J = 9.13 Hz, 1 H) 7.27 (dd, J = 9.26, 1.75 Hz, 1 H) 6.87 (br s, 1 H) 3.00 (d, J = 2.38 Hz, 6 H) 2.66-2.70 (m, 1 H) 0.61-0.71 (m, 2 H) 0.39-0.46 (m, 2 H); LCMS (electrospray) m/z 428.1 (M + H+). | H |
| 388 | 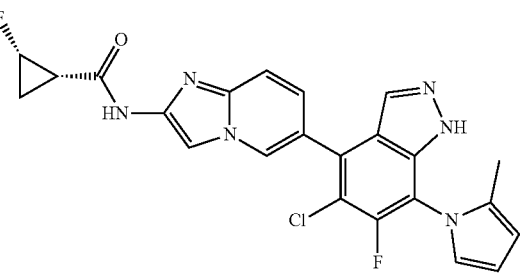<br>(1S,2S)-N-(6-(5-chloro-6-fluoro-7-(2-methyl-1H-pyrrol-1-yl)-1H-indazol-4-yl)imidazo[1,2-a]pyridin-2-yl)-2-fluorocyclopropane-1-carboxamide | ¹H NMR (400 MHz, DMSO-$d_6$) δ 11.12 (s, 1H), 8.89 (s, 1H), 8.21 (s, 1H), 8.15 (s, 1H), 7.62 (d, J = 9.2 Hz, 1H), 7.44 (dd, J = 1.6, 9.3 Hz, 1H), 6.95 (br s, 1H), 6.27 (t, J = 3.1 Hz, 1H), 6.14 (br s, 1H), 5.13-4.80 (m, 1H), 2.18 (td, J = 7.0, 13.9 Hz, 1H), 2.07 (s, 3H), 1.74-1.61 (m, 1H), 1.23-1.13 (m, 1H); LCMS (electrospray) m/z 467.1 (M + H+). | H |

TABLE 1-continued

Compounds of Examples

| Ex # | Structure/Name | ¹H NMR/MS (M + 1) | Method |
|---|---|---|---|
| 389 | 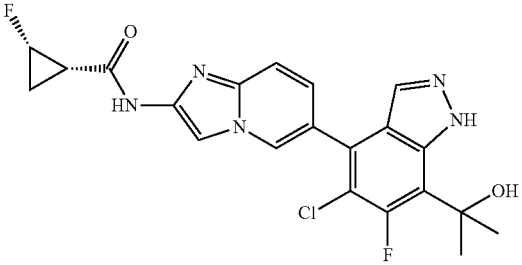 [SMILES: CC(C)(O)c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(2-hydroxypropan-2-yl)-1H-indazol-4-yl)imidazo[1,2-a]pyridin-2-yl)-2-fluorocyclopropane-1-carboxamide | ¹H NMR (400 MHz, DMSO-d₆) δ 13.70-11.96 (m, 1H), 11.08 (s, 1H), 8.79 (s, 1H), 8.17 (s, 1H), 7.89 (s, 1H), 7.57 (d, J = 9.2 Hz, 1H), 7.35 (dd, J = 1.7, 9.2 Hz, 1H), 6.56-5.57 (m, 1H), 5.21-4.65 (m, 1H), 2.25-2.09 (m, 1H), 1.69 (d, J = 1.4 Hz, 6H), 1.65-1.59 (m, 1H), 1.17 (tdd, J = 6.3, 9.1, 12.3 Hz, 1H); LCMS (electrospray) m/z 446.0 (M + H+). | H |
| 390 | 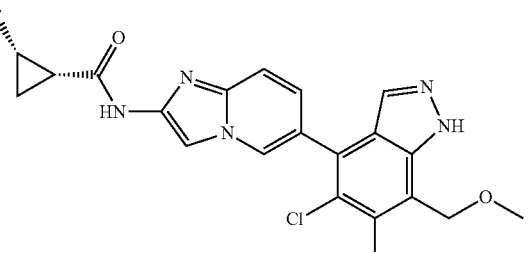<br>(1S,2S)-N-(6-(5-chloro-6-fluoro-7-(methoxymethyl)-1H-indazol-4-yl)imidazo[1,2-a]pyridin-2-yl)-2-fluorocyclopropane-1-carboxamide | ¹H NMR (400 MHz, DMSO-d₆) δ 13.66 (s, 1H), 11.11 (s, 1H), 8.83 (s, 1H), 8.18 (s, 1H), 8.00 (d, J = 1.1 Hz, 1H), 7.59 (d, J = 9.3 Hz, 1H), 7.37 (dd, J = 9.1, 1.9 Hz, 1H), 5.04-4.83 (m, 3H), 3.36 (s, 3H), 2.19-2.12 (m, 1H), 1.71-1.61 (m, 1H), 1.23-1.13 (m, 1H); LCMS (electrospray) m/z 432.10 (M + H)+. | H |
| 391 | 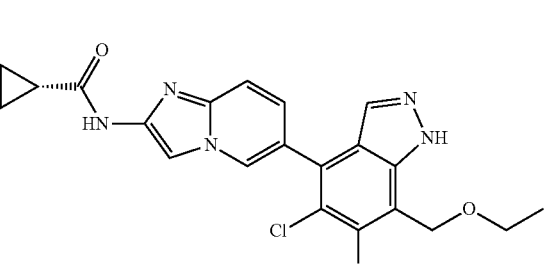<br>(1S,2S)-N-(6-(5-chloro-7-(ethoxymethyl)-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.65 (s, 1H), 11.11 (s, 1H), 8.83 (d, J = 1.1 Hz, 1H), 8.18 (s, 1H), 8.00 (d, J = 1.6 Hz, 1H), 7.59 (d, J = 9.3 Hz, 1H), 7.37 (dd, J = 9.3, 1.6 Hz, 1H), 5.04-4.83 (m, 3H), 3.57 (q, J = 7.1 Hz, 2H), 2.19-2.12 (m, 1H), 1.66 (dtd, J = 23.3, 6.7, 3.5 Hz, 1H), 1.39 (s, 0H), 1.24-1.13 (m, 4H); LCMS (electrospray) m/z 446.10 (M + H)+. | H |
| 392 | 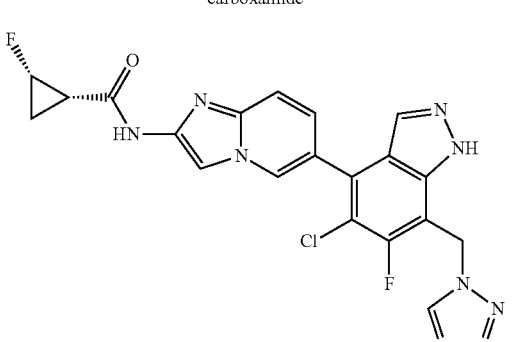<br>(1S,2S)-N-(6-(7-((1-tetrazol-1-yl)methyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.76-14.21 (1H), 11.11 (s, 1H), 9.64 (s, 1H), 8.84 (s, 1H), 8.17 (s, 1H), 8.09 (s, 1H), 7.59 (d, J = 9.3 Hz, 1H), 7.38 (d, J = 8.8 Hz, 1H), 6.11 (s, 2H), 5.01-4.85 (m, 1H), 2.19-2.12 (m, 1H), 1.69-1.63 (m, 1H), 1.19-1.13 (m, 1H); LCMS (electrospray) m/z 470.10 (M + H)+. | I |

TABLE 1-continued

Compounds of Examples

| Ex # | Structure/Name | ¹H NMR/MS (M + 1) | Method |
|---|---|---|---|
| 393 | 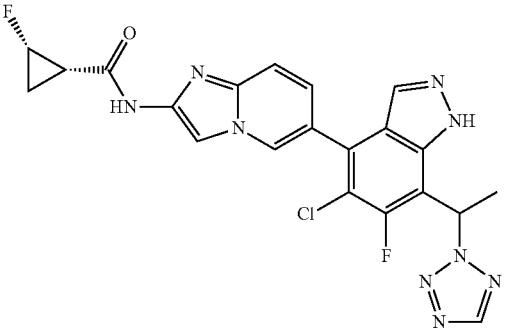 [SMILES: CC(c1c(F)c(Cl)c(-c2ccc3nc(NC(=O)[C@@H]4C[C@@H]4F)cn3c2)c2cn[nH]c12)n1ncnn1]<br>(1S,2S)-N-(6-(7-(1-(2H-tetrazol-2-yl)ethyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.54-13.94 (s, 1H), 11.06 (d, J = 7.7 Hz, 1H), 8.98 (d, J = 11.5 Hz, 1H), 8.80 (s, 1H), 8.12 (s, 2H), 7.58-7.54 (m, 1H), 7.35 (dd, J = 9.3, 1.6 Hz, 1H), 6.74 (q, J = 7.1 Hz, 1H), 5.00-4.79 (m, 1H), 2.24-2.20 (m, 3H), 2.16-2.09 (m, 1H), 1.68-1.57 (m, 1H), 1.18-1.09 (m, 1H); LCMS (electrospray) m/z 485.10 (M + H)+. | I |
| 394 | 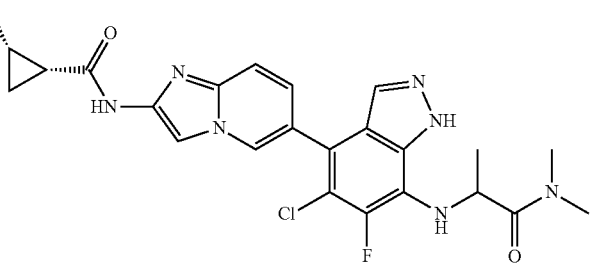<br>(1S,2S)-N-(6-(5-chloro-7-((1-(dimethylamino)-1-oxopropan-2-yl)amino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.42 (s, 1H), 11.06 (d, J = 6.6 Hz, 1H), 8.71 (d, J = 7.7 Hz, 1H), 8.13 (d, J = 7.7 Hz, 1H), 7.88 (d, J = 1.1 Hz, 1H), 7.52 (t, J = 8.5 Hz, 1H), 7.31 (dd, J = 9.3, 1.6 Hz, 1H), 5.56-5.52 (m, 1H), 5.03-4.82 (m, 2H), 3.09 (s, 3H), 2.85 (s, 3H), 2.19-2.12 (m, 1H), 1.71-1.61 (m, 1H), 1.34 (d, J = 6.6 Hz, 3H), 1.21-1.12 (m, 1H); LCMS (electrospray) m/z 503.15 (M + H)+. | H |
| 395 | 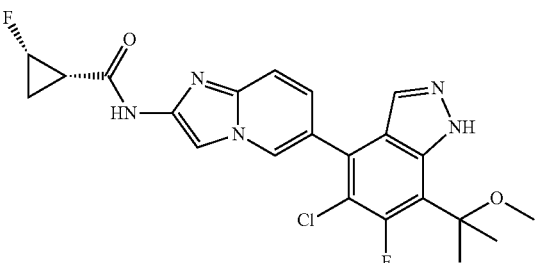<br>(1S,2S)-N-(6-(5-chloro-6-fluoro-7-(2-methoxypropan-2-yl)-1H-indazol-4-yl)imidazo[1,2-a]pyridin-2-yl)-2-fluorocyclopropane-1-carboxamide | ¹H NMR (400 MHz, DMSO-$d_6$) δ13.01 (s, 1H), 11.09 (s, 1H), 8.81 (s, 1H), 8.16 (s, 1H), 7.94 (s, 1H), 7.58 (d, J = 9.3 Hz, 1H), 7.37 (dd, J = 1.7, 9.3 Hz, 1H), 5.08-4.80 (m, 1H), 3.18 (s, 3H), 2.15 (br d, J = 7.0 Hz, 1H), 1.71 (br d, J = 2.7 Hz, 6H), 1.64 (br s, 1H), 1.17 (br dd, J = 8.9, 12.1 Hz, 1H); LCMS (electrospray) m/z 460.2 (M + H)+. | H |

TABLE 1-continued

Compounds of Examples

| Ex # | Structure/Name | $^1$H NMR/MS (M + 1) | Method |
|---|---|---|---|
| 396 | 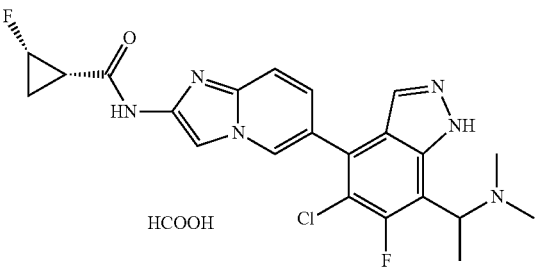 [SMILES: CC(c1c(F)c(Cl)c(-c2ccc3nc(NC(=O)[C@@H]4C[C@@H]4F)cn3c2)c2cn[nH]c12)N(C)C ; "HCOOH"]<br>(1S,2S)-N-(6-(5-chloro-7-(1-(dimethylamino)ethyl)-6-fluoro-1H-indazol-4-yl)imidazo[1,2-a]pyridin-2-yl)-2-fluorocyclopropane-1-carboxamide. Formaic acid salt | $^1$H NMR (400 MHz, DMSO-$d_6$) δ 13.37-12.98 (m, 1H), 11.09 (s, 1H), 8.82 (s, 1H), 8.22 (s, 1H), 8.16 (s, 1H), 7.95 (s, 1H), 7.57 (d, J = 9.2 Hz, 1H), 7.37 (dd, J = 1.7, 9.2 Hz, 1H), 5.03-4.82 (m, 1H), 3.87 (q, J = 6.6 Hz, 1H), 2.21 (s, 6H), 2.16 (br dd, J = 6.1, 7.6 Hz, 1H), 1.72-1.61 (m, 1H), 1.49 (d, J = 6.8 Hz, 3H), 1.23-1.13 (m, 1H); LCMS (electrospray) m/z 459.2 (M + H)+. | H |
| 397 | 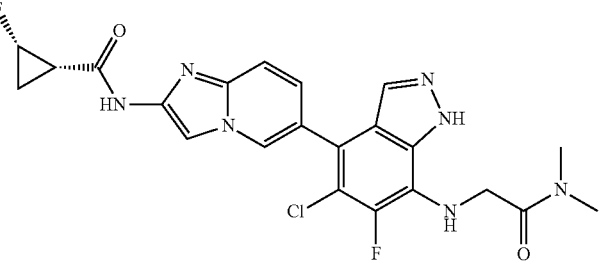<br>(1S,2S)-N-(6-(5-chloro-7-((2-(dimethylamino)-2-oxoethyl)amino)-6-fluoro-1H-indazol-4-yl)imidazo[1,2-a]pyridin-2-yl)-2-fluorocyclopropane-1-carboxamide | $^1$H NMR (400 MHz, DMSO-$d_6$) δ 13.26-13.88 (1H), 11.08 (s, 1H), 8.71 (d, J = 1.6 Hz, 1H), 8.15 (s, 1H), 7.94 (s, 1H), 7.53 (d, J = 9.3 Hz, 1H), 7.30 (dd, J = 9.3, 1.6 Hz, 1H), 5.75 (d, J = 3.3 Hz, 1H), 5.03-4.83 (m, 1H), 4.42 (d, J = 4.4 Hz, 2H), 3.02 (s, 3H), 2.88 (s, 3H), 2.19-2.12 (m, 1H), 1.71-1.61 (m, 1H), 1.23-1.12 (m, 1H); LCMS (electrospray) m/z 488.1 (M + H)+. | H |
| 398 | 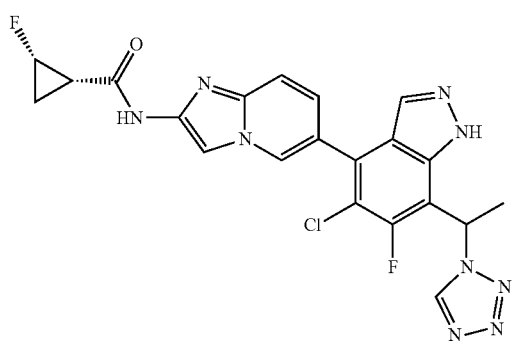 [SMILES: CC(c1c(F)c(Cl)c(-c2ccc3nc(NC(=O)[C@@H]4C[C@@H]4F)cn3c2)c2cn[nH]c12)n1cnnn1]<br>(1S,2S)-N-(6-(7-(1-(1H-tetrazol-1-yl)ethyl)-5-chloro-6-fluoro-1H-indazol-4-yl)imidazo[1,2-a]pyridin-2-yl)-2-fluorocyclopropane-1-carboxamide | $^1$H NMR (400 MHz, DMSO-$d_6$) δ 13.53-14.00 (1H), 11.12 (s, 1H), 9.77 (s, 1H), 8.83 (s, 1H), 8.20-8.17 (m, 2H), 7.59 (d, J = 9.1 Hz, 1H), 7.38 (dd, J = 9.3, 1.6 Hz, 1H), 6.59 (q, J = 7.1 Hz, 1H), 5.04-4.83 (m, 1H), 2.21 (d, J = 7.1 Hz, 3H), 2.17-2.12 (m, 1H), 1.70-1.63 (m, 1H), 1.20-1.13 (m, 1H); LCMS (electrospray) m/z 484.10 (M + H)+. | I |

TABLE 1-continued

Compounds of Examples

| Ex # | Structure/Name | $^1$H NMR/MS (M + 1) | Method |
|---|---|---|---|
| 399 | 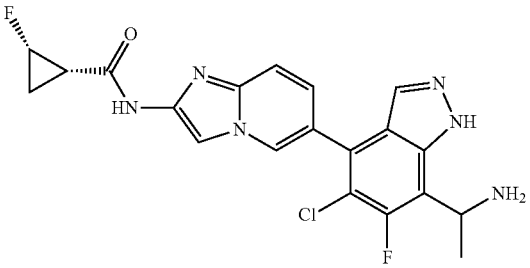 [SMILES: CC(N)c1c(F)c(Cl)c(-c2ccc3nc(NC(=O)[C@@H]4C[C@@H]4F)cn3c2)c2cn[nH]c12]<br><br>(1S,2S)-N-(6-(7-(1-aminoethyl)-5-chloro-6-fluoro-1H-indazol-4-yl)imidazo[1,2-a]pyridin-2-yl)-2-fluorocyclopropane-1-carboxamide | $^1$H NMR (400 MHz, DMSO-$d_6$) δ 11.10 (s, 1H), 8.79 (s, 1H), 8.20 (d, J = 15.8 Hz, 2H), 8.00 (s, 1H), 7.58 (d, J = 9.2 Hz, 1H), 7.34 (dd, J = 1.8, 9.2 Hz, 1H), 5.03-4.84 (m, 1H), 4.81-4.75 (m, 1H), 2.22-2.09 (m, 1H), 1.75-1.59 (m, 1H), 1.54 (d, J = 6.8 Hz, 3H), 1.27-1.12 (m, 1H); LCMS (electrospray) m/z 431.1 (M + H)+. | H |
| 400 | 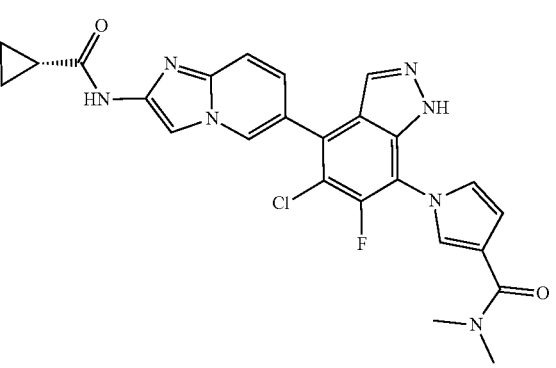<br><br>1-(5-chloro-6-fluoro-4-(2-((1S,2S)-2-fluorocyclopropane-1-carboxamido)imidazo[1,2-a]pyridin-6-yl)-1H-indazol-7-yl)-N,N-dimethyl-1H-pyrrole-3-carboxamide | $^1$H NMR (400 MHz, DMSO-$d_6$) δ 14.12-13.82 (m, 1H), 11.11 (s, 1H), 8.84 (s, 1H), 8.27-8.14 (m, 1H), 7.64 (s, 1H), 7.61 (d, J = 9.2 Hz, 1H), 7.39 (dd, J = 9.1, 1.8 Hz, 1H), 7.27 (s, 1H), 6.66 (dd, J = 2.9, 1.6 Hz, 1H) 5.10-4.79 (m, 1H), 3.22-3.00 (m, 6H), 2.21-2.12 (m, 1H), 1.74-1.61(m, 1H), 1.24-1.12 (m, 1H); LCMS (electrospray) m/z 524.1 (M + H)+. | H |
| 401 | 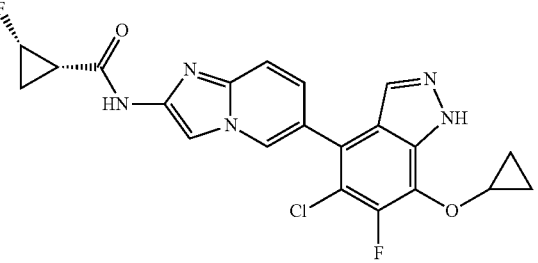<br><br>(1S,2S)-N-(6-(5-chloro-7-cyclopropoxy-6-fluoro-1H-indazol-4-yl)imidazo[1,2-a]pyridin-2-yl)-2-fluorocyclopropane-1-carboxamide | $^1$H NMR (400 MHz, DMSO-$d_6$) δ 13.79 (s, 1 H) 11.18 (s, 1 H) 8.67 (d, J = 7.09 Hz, 1 H) 7.93 (s, 1 H) 7.77 (s, 1 H) 6.92-6.99 (m, 2 H) 4.82-5.08 (m, 1 H) 4.53 (s, 1 H) 2.15 (m, 1 H) 1.61-1.75 (m, 1 H) 1.12-1.27 (m, 1 H) 0.92 (br s, 2 H) 0.68-0.77 (m, 2 H); LCMS (electrospray) m/z 444.0 (M + H)+. | H |

TABLE 1-continued

Compounds of Examples

| Ex # | Structure/Name | ¹H NMR/MS (M + 1) | Method |
|---|---|---|---|
| 402 | 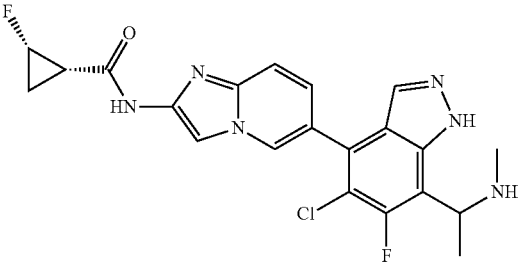 [SMILES: CNC(C)c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(1-(methylamino)ethyl)-1H-indazol-4-yl)imidazo[1,2-a]pyridin-2-yl)-2-fluorocyclopropane-1-carboxamide | ¹H NMR (400 MHz, DMSO-d$_6$) δ 11.08 (s, 1H), 8.81 (s, 1H), 8.27 (br s, 1H), 8.16 (s, 1H), 7.96 (s, 1H), 7.57 (d, J = 9.3 Hz, 1H), 7.37 (dd, J = 1.7, 9.3 Hz, 1H), 5.12-4.75 (m, 1H), 4.33 (d, J = 6.8 Hz, 1H), 2.22-2.12 (m, 4H), 1.74-1.59 (m, 1H), 1.47 (d, J = 6.7 Hz, 3H), 1.22-1.12 (m, 1H); LCMS (electrospray) m/z 445.2 (M + H)+. | H |
| 403 | 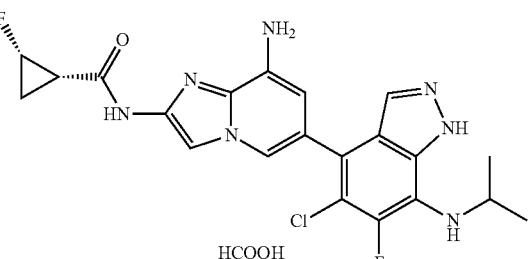<br>(1S,2S)-N-(8-amino-6-(5-chloro-6-fluoro-7-(isopropylamino)-1H-indazol-4-yl)imidazo[1,2-a]pyridin-2-yl)-2-fluorocyclopropane-1-carboxamide. 1 formic acid | ¹H NMR (400 MHz, DMSO-d$_6$) δ 13.35-13.11 (m, 1H), 10.33 (s, 1H), 8.40 (s, 1H), 7.96-7.72 (m, 1H), 7.44 (s, 2H), 6.36 (d, J = 1.4 Hz, 1H), 5.79 (s, 2H), 5.09 (dd, J = 2.4, 9.4 Hz, 1H), 5.05-4.81 (m, 1H), 4.17-3.92 (m, 1H), 4.14-2.74 (m, 1H), 2.17-2.05 (m, 1H), 1.71-1.55 (m,12H), 1.23 (d, J = 6.3 Hz, 6H), 1.21-1.08 (m, 1H); LCMS (electrospray) m/z 460.2 (M + H)+. | H |
| 404 | 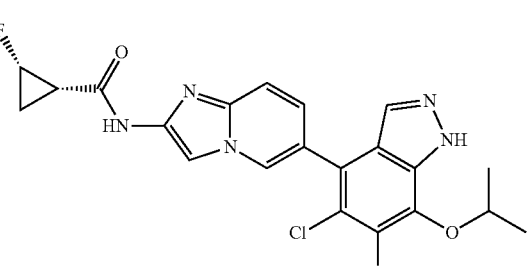<br>(1S,2S)-N-(6-(5-chloro-6-fluoro-7-isopropoxy-1H-indazol-4-yl)imidazo[1,2-a]pyridin-2-yl)-2-fluorocyclopropane-1-carboxamide | ¹H NMR (400 MHz, DMSO-d$_6$) δ 14.17-13.33 (m, 1H), 11.08 (s, 1H), 8.79 (s, 1H), 8.16 (s, 1H), 8.00 (s, 1H), 7.56 (d, J = 9.3 Hz, 1H), 7.35 (dd, J = 1.5, 9.2 Hz, 1H), 5.06-4.81 (m, 1H), 4.73 (br d, J = 1.1 Hz, 1H), 2.16 (td, J = 6.9, 13.8 Hz, 1H), 2.07 (s, 1H), 1.76-1.56 (m, 1H), 1.37 (d, J = 6.0 Hz, 6H), 1.17 (tdd, J = 6.2, 9.0, 12.3 Hz, 1H); LCMS (electrospray) m/z 446.1 (M + H)+. | H |
| 405 | 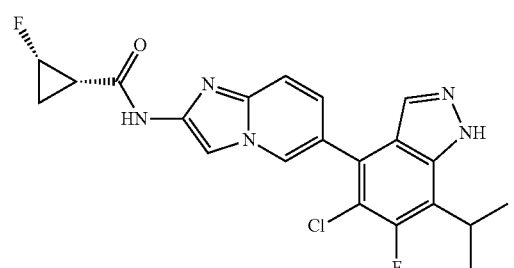<br>(1S,2S)-N-(6-(5-chloro-6-fluoro-7-isopropyl-1H-indazol-4-yl)imidazo[1,2-a]pyridin-2-yl)-2-fluorocyclopropane-1-carboxamide | ¹H NMR (400 MHz, DMSO-d$_6$) δ 13.55 (br s, 1H), 11.08 (s, 1H), 8.78 (d, J = 1.0 Hz, 1H), 8.16 (s, 1H), 7.96 (s, 1H), 7.57 (d, J = 9.3 Hz, 1H), 7.35 (dd, J = 1.8, 9.3 Hz, 1H), 5.05-4.80 (m, 1H), 3.67-3.55 (m, 1H), 2.16 (td, J = 7.0, 14.0 Hz, 1H), 1.73-1.59 (m, 1H), 1.45 (d, J = 7.0 Hz, 6H), 1.17 (tdd, J = 6.1, 9.1, 12.1 Hz, 1H); LCMS (electrospray) m/z 430.2 (M + H)+. | H |

TABLE 1-continued

Compounds of Examples

| Ex # | Structure/Name | $^1$H NMR/MS (M + 1) | Method |
|------|----------------|----------------------|--------|
| 406 | 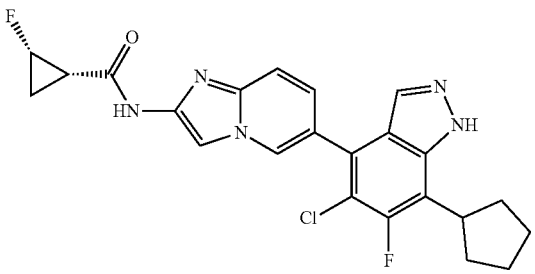 [SMILES: O=C(Nc1cn2cc(-c3c(Cl)c(F)c(C4CCCC4)c4[nH]ncc34)ccc2n1)[C@@H]1C[C@@H]1F]<br>(1S,2S)-N-(6-(5-chloro-7-cyclopentyl-6-fluoro-1H-indazol-4-yl)imidazo[1,2-a]pyridin-2-yl)-2-fluorocyclopropane-1-carboxamide | $^1$H NMR (400 MHz, DMSO-d$_6$) δ 13.54 (s, 1H), 11.11 (s, 1H), 8.79 (s, 1H), 8.17 (s, 1H), 7.96 (d, J = 1.1 Hz, 1H), 7.57 (d, J = 9.3 Hz, 1H), 7.35 (dd, J = 9.3, 1.6 Hz, 1H), 5.04-4.83 (m, 1H), 3.61 (q, J = 8.8 Hz, 1H), 2.19-1.91 (m, 8H), 1.73-1.61 (m, 3H), 1.24-1.07 (m, 1H); LCMS (electrospray) m/z 456.10 (M + H)+. | H |
| 407 | 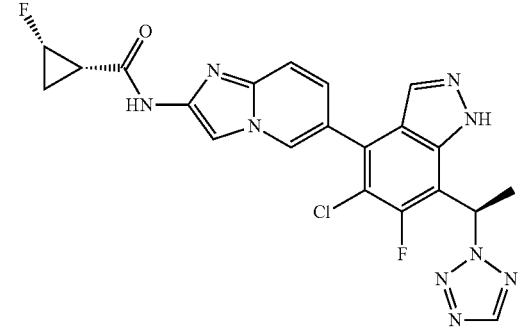 [SMILES: C[C@H](c1c(F)c(Cl)c(-c2ccc3nc(NC(=O)[C@@H]4C[C@@H]4F)cn3c2)c2cn[nH]c12)n1ncnn1]<br>(1S,2S)-N-(6-(7-((R)-1-(2H-tetrazol-2-yl)ethyl)-5-chloro-6-fluoro-1H-indazol-4-yl)imidazo[1,2-a]pyridin-2-yl)-2-fluorocyclopropane-1-carboxamide | $^1$H NMR (400 MHz, DMSO-d$_6$) δ 14.18-13.49 (m, 1H), 11.09 (s, 1H), 9.02 (s, 1H), 8.83 (s, 1H), 8.28-7.99 (m, 2H), 7.58 (d, J = 9.2 Hz, 1H), 7.38 (dd, J = 1.7, 9.2 Hz, 1H), 6.78 (q, J = 6.9 Hz, 1H), 5.10-4.74 (m, 1H), 2.27 (d, J = 7.0 Hz, 3H), 2.21-2.11 (m, 1H), 1.74-1.59 (m, 1H), 1.22-1.12 (m, 1H); LCMS (electrospray) m/z 484.1 (M + H)+. | I |
| 408 | 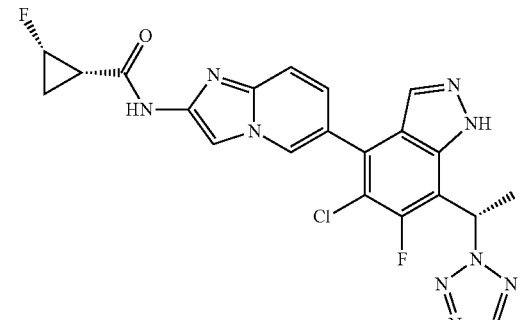<br>(1S,2S)-N-(6-(7-((S)-1-(2H-tetrazol-2-yl)ethyl)-5-chloro-6-fluoro-1H-indazol-4-yl)imidazo[1,2-a]pyridin-2-yl)-2-fluorocyclopropane-1-carboxamide | $^1$H NMR (400 MHz, DMSO-d$_6$) δ 14.19-13.48 (m, 1H), 11.09 (s, 1H), 9.02 (s, 1H), 8.83 (s, 1H), 8.31-7.98 (m, 2H), 7.59 (d, J = 9.2 Hz, 1H), 7.38 (dd, J = 1.7, 9.2 Hz, 1H), 6.78 (q, J = 7.1 Hz, 1H), 5.09-4.68 (m, 1H), 2.27 (d, J = 7.0 Hz, 3H), 2.20-2.10 (m, 1H), 1.67 (tdd, J = 3.2, 6.8, 19.9 Hz, 1H), 1.23-1.13 (m, 1H); LCMS (electrospray) m/z 484.1 (M + H)+. | I |

TABLE 1-continued

Compounds of Examples

| Ex # | Structure/Name | ¹H NMR/MS (M + 1) | Method |
|---|---|---|---|
| 409 | 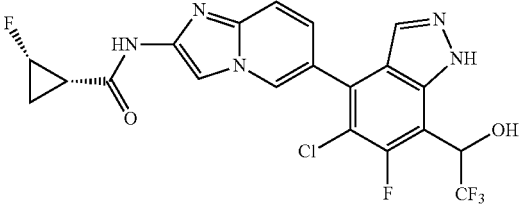 [SMILES: O=C(Nc1cn2cc(-c3c(Cl)c(F)c(C(O)C(F)(F)F)c4[nH]ncc34)ccc2n1)[C@@H]1C[C@@H]1F]<br>(1S,2S)-N-(6-(5-chloro-6-fluoro-7-(2,2,2-trifluoro-1-hydroxyethyl)-1H-indazol-4-yl)imidazo[1,2-a]pyridin-2-yl)-2-fluorocyclopropane-1-carboxamide | ¹H NMR (400 MHz, DMSO-d₆) δ 13.38 (s, 1H), 11.10 (s, 1H), 8.86 (s, 1H), 8.17 (s, 1H), 8.01 (d, J = 1.6 Hz, 1H), 7.59 (q, J = 9.7 Hz, 2H), 7.40 (dd, J = 9.3, 1.6 Hz, 1H), 5.82-5.75 (m, 1H), 5.04-4.83 (m, 1H), 2.20-2.13 (m, 1H), 1.72-1.62 (m, 1H), 1.28-1.11 (m, 1H); LCMS (electrospray) m/z 487.1 (M + H)+. | H |
| 410 | 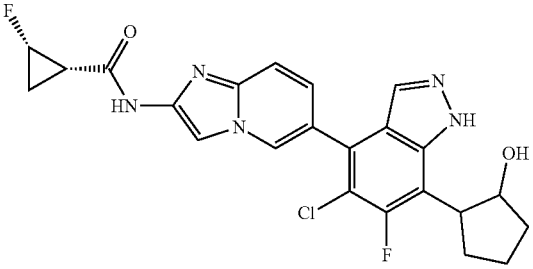 [SMILES: O=C(Nc1cn2cc(-c3c(Cl)c(F)c(C4CCCC4O)c4[nH]ncc34)ccc2n1)[C@@H]1C[C@@H]1F]<br>(1S,2S)-N-(6-(5-chloro-6-fluoro-7-(2-hydroxycyclopentyl)-1H-indazol-4-yl)imidazo[1,2-a]pyridin-2-yl)-2-fluorocyclopropane-1-carboxamide | ¹H NMR (400 MHz, DMSO-d₆) δ 13.51 (s, 1H), 11.08 (s, 1H), 8.77 (s, 1H), 8.18 (s, 1H), 7.95 (s, 1H), 7.57 (d, J = 9.3 Hz, 1H), 7.34 (dd, J = 9.3, 1.6 Hz, 1H), 5.03-4.83 (m, 2H), 4.50-4.42 (m, 3H), 3.51-3.38 (m, 6H), 2.20-2.07 (m, 3H), 1.99-1.83 (m, 3H), 1.72-1.61 (m, 2H), 1.23-1.13 (m, 4H); LCMS (electrospray) m/z 472.10 (M + H)+. | H |
| 411 | 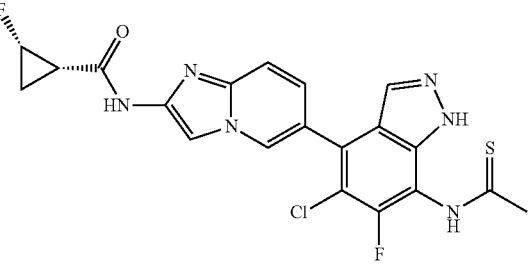<br>(1S,2S)-N-(6-(5-chloro-7-ethanethioamido-6-fluoro-1H-indazol-4-yl)imidazo[1,2-a]pyridin-2-yl)-2-fluorocyclopropane-1-carboxamide | ¹H NMR (400 MHz, DMSO-d₆) δ 8.62-8.72 (m, 1 H) 8.12-8.25 (m, 1 H) 7.83-7.96 (m, 1 H) 7.56-7.62 (m, 1 H) 7.43-7.52 (m, 1 H) 4.95-4.98 (m, 0.5 H) 4.77-4.81 (m, 0.5 H) 2.70-2.80 (m, 3 H) 2.07-2.17 (m, 1H) 1.73-1.88 (m, 1 H) 1.18-1.31 (m, 1 H); LCMS (electrospray) m/z 461.3 (M + H)+. | H |
| 412 | 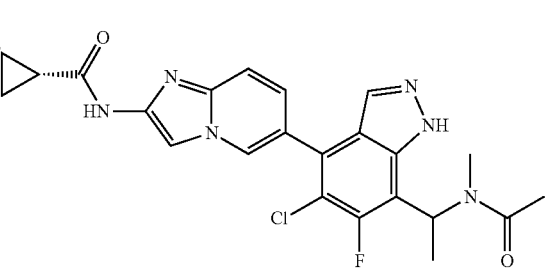<br>(1S,2S)-N-(6-(5-chloro-6-fluoro-7-(1-(N-methylacetamido)ethyl)-1H-indazol-4-yl)imidazo[1,2-a]pyridin-2-yl)-2-fluorocyclopropane-1-carboxamide | ¹H NMR (400 MHz, DMSO-d₆) δ 13.54-12.76 (m, 1H), 11.09 (s, 1H), 8.80 (s, 1H), 8.36 (s, 1H), 8.17 (s, 1H), 8.07-7.97 (m, 1H), 7.58 (d, J = 9.2 Hz, 1H), 7.36 (br d, J = 9.0 Hz, 1H), 7.23 (br d, J = 6.8 Hz, 1H), 6.87 (br d, J = 5.0 Hz, 1H), 6.07 (q, J = 6.7 Hz, 1H), 5.82-5.67 (m, 1H), 5.13-4.80 (m, 1H), 3.02 (s, 3H), 2.78 (br s, 1H), 2.20-2.14 (m, 1H), 2.10-2.00 (m, 3H), 1.86-1.75 (m, 1H), 1.71-1.64 (m, 3H), 1.28-1.07 (m, 1H); LCMS (electrospray) m/z 487.1 (M + H)+. | H |

TABLE 1-continued

Compounds of Examples

| Ex # | Structure/Name | ¹H NMR/MS (M + 1) | Method |
|---|---|---|---|
| 413 | 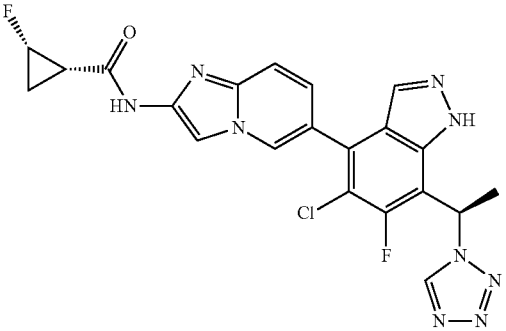<br>(1S,2S)-N-(6-7-((R)-1-(1H-tetrazol-1-yl)ethyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 11.10 (s, 1H), 9.77 (s, 1H), 8.82 (s, 1H), 8.24-8.00 (m, 2H), 7.58 (d, J = 9.1 Hz, 1H), 7.37 (dd, J = 1.6, 9.3 Hz, 1H), 6.62 (d, J = 7.4 Hz, 1H), 5.11-4.74 (m, 1H), 2.25-2.15 (m, 4H), 1.79-1.56 (m, 1H), 1.27-1.10 (m, 1H); LCMS (electrospray) m/z 484.1 (M + H)+. | I |
| 414 | 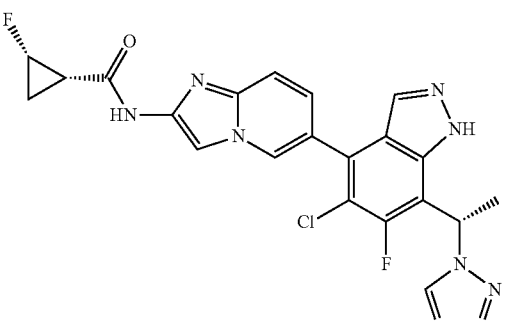<br>(1S,2S)-N-(6-(7-((S)-1-(1H-tetrazol-1-yl)ethyl)-5-chloro-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.75 (br s, 1H), 11.09 (s, 1H), 9.75 (s, 1H), 8.82 (s, 1H), 8.17 (s, 1H), 8.08 (s, 1H), 7.59 (br d, J = 8.9 Hz, 1H), 7.37 (dd, J = 1.7, 9.2 Hz, 1H), 6.59 (br d, J = 6.8 Hz, 1H), 5.12-4.75 (m, 1H), 2.26-2.07 (m, 4H), 1.75-1.60 (m, 1H), 1.21-1.15 (m, 1H); LCMS (electrospray) m/z 484.1 (M + H)+. | I |
| 415 | 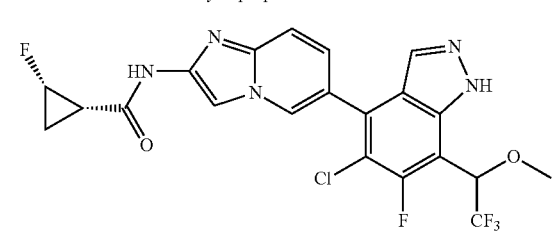<br>(1S,2S)-N-(6-(5-chloro-6-fluoro-7-(2,2,2-trifluoro-1-methoxyethyl)-1H-indazol-4-yl)imidazo[1,2-a]pyridin-2-yl)-2-fluorocyclopropane-1-carboxamide | ¹H NMR (400 MHz, DMSO-$d_6$) δ 13.40-13.49 (1H), 11.06-11.17 (1H), 8.83-8.91 (1H), 8.15-8.21 (1H), 8.02-8.09 (1H), 7.57-7.64 (1H), 7.38-7.46 (1H), 5.72-5.82 (1H), 4.82-5.07 (1H), 3.46-3.55 (3H), 2.12-2.21 (1H), 1.61-1.74 (1H), 1.13-1.22 (1H); LCMS (electrospray) m/z 501.1 (M + H)+. | H |
| 416 | 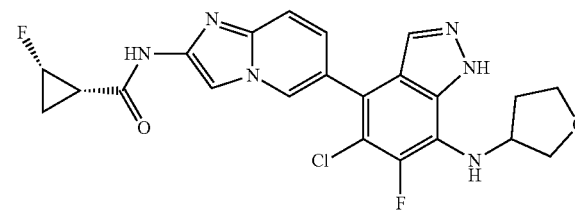<br>(1S,2S)-N-(6-(5-chloro-6-fluoro-7-((tetrahydrofuran-3-yl)amino)-1H-indazol-4-yl)imidazo[1,2-a]pyridin-2-yl)-2-fluorocyclopropane-1-carboxamide | ¹H NMR (400 MHz, DMSO-$d_6$) δ 13.23 (s, 1H), 11.06 (s, 1H), 8.72 (s, 1H), 8.16 (s, 1H), 7.88 (d, J = 1.1 Hz, 1H), 7.54 (d, J = 9.3 Hz, 1H), 7.32 (dd, J = 9.3, 1.6 Hz, 1H), 5.60-5.58 (m, 1H), 5.04-4.83 (m, 1H), 4.55 (s, 1H), 3.95 (q, J = 7.7 Hz, 1H), 3.87 (dd, J = 9.1, 5.8 Hz, 1H), 3.79-3.71 (m, 2H), 2.27-2.13 (m, 2H), 1.91 (s, 1H), 1.67 (dtd, J = 23.5, 6.9, 3.7 Hz, 1H), 1.22-1.13 (m, 1H); LCMS (electrospray) m/z 474.1 (M + H)+. | H |

TABLE 1-continued

Compounds of Examples

| Ex # | Structure/Name | $^1$H NMR/MS (M + 1) | Method |
|---|---|---|---|
| 417 | 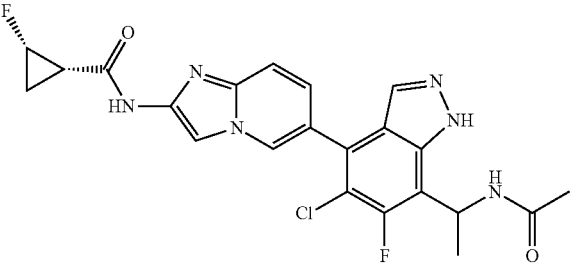<br>(1S,2S)-N-(6-(7-(1-acetamidoethyl)-5-chloro-6-fluoro-1H-indazol-4-yl)imidazo[1,2-a]pyridin-2-yl)-2-fluorocyclopropane-1-carboxamide | $^1$H NMR (400 MHz, DMSO-d$_6$) δ 13.67-13.49 (m, 1H), 11.10 (s, 1H), 8.79 (s, 1H), 8.52 (d, J = 6.8 Hz, 1H), 8.16 (s, 1H), 7.98 (s, 1H), 7.57 (d, J = 9.3 Hz, 1H), 7.35 (dd, J = 1.6, 9.3 Hz, 1H), 5.45 (quin, J = 7.1 Hz, 1H), 5.07-4.81 (m, 1H), 2.22-2.11 (m, 1H), 1.85 (s, 3H), 1.73-1.61 (m, 1H), 1.55 (d, J = 7.3 Hz, 3H), 1.17 (tdd, J = 6.3, 9.1, 12.3 Hz, 1H); LCMS (electrospray) m/z 473.2 (M + H)+. | H |
| 418 | 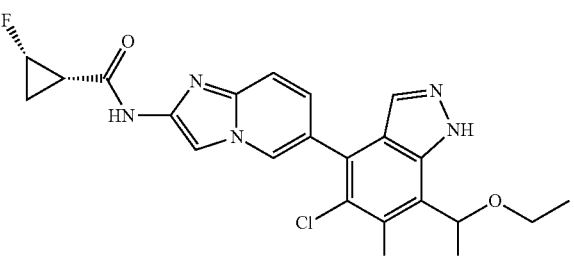<br>(1S,2S)-N-(6-(5-chloro-7-(1-ethoxy-2,2,2-trifluoroethyl)-6-fluoro-1H-indazol-4-yl)imidazo[1,2-a]pyridin-2-yl)-2-fluorocyclopropane-1-carboxamide | $^1$H NMR (400 MHz, DMSO-d$_6$) δ 13.40 (s, 1H), 11.10 (s, 1H), 8.87 (s, 1H), 8.16-8.04 (m, 2H), 7.59 (d, J = 8.8 Hz, 1H), 7.41 (dd, J = 9.1, 1.9 Hz, 1H), 5.81 (q, J = 7.1 Hz, 1H), 5.04-4.83 (m, 1H), 3.79-3.58 (m, 2H), 2.20-2.13 (m, 1H), 1.67 (dtd, J = 23.4, 6.8, 3.6 Hz, 1H), 1.23 (t, J = 7.1 Hz, 3H), 1.19-1.13 (m, 1H); LCMS (electrospray) m/z 514.7 (M + H)+. | H |
| 419 | 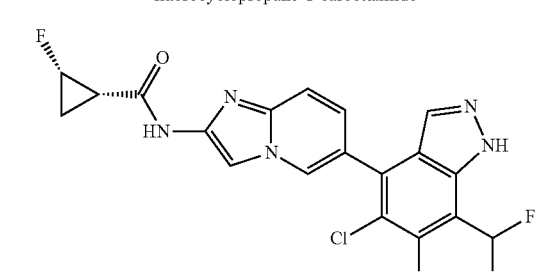<br>(1S,2S)-N-(6-(5-chloro-6-fluoro-7-(1,2,2,2-tetrafluoroethyl)-1H-indazol-4-yl)imidazo[1,2-a]pyridin-2-yl)-2-fluorocyclopropane-1-carboxamide | $^1$H NMR (400 MHz, DMSO-d$_6$) δ 13.78 (s, 1H), 11.12 (s, 1H), 8.89 (t, J = 1.4 Hz, 1H), 8.18 (s, 1H), 8.12 (s, 1H), 7.61 (d, J = 9.3 Hz, 1H), 7.42 (dd, J = 9.1, 1.9 Hz, 1H), 7.06 (dt, J = 41.2, 6.7 Hz, 1H), 5.05-4.84 (m, 1H), 2.21-2.14 (m, 1H), 1.68 (dtd, J = 23.5, 6.9, 3.5 Hz, 1H), 1.24-1.14 (m, 1H); LCMS (electrospray) m/z 488.7 (M + H)+. | H |
| 420 | 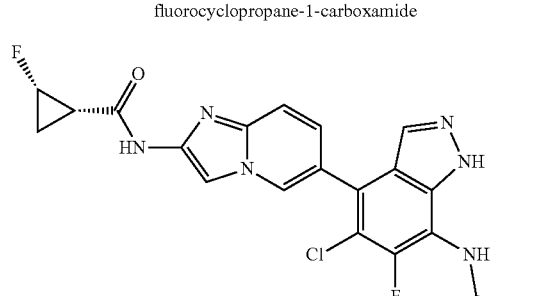<br>(1S,2S)-N-(6-(5-chloro-7-((1-cyclopropylethyl)amino)-6-fluoro-1H-indazol-4-yl)imidazo[1,2-a]pyridin-2-yl)-2-fluorocyclopropane-1-carboxamide | $^1$H NMR (400 MHz, DMSO-d$_6$) δ 13.30 (br s, 1H), 11.05 (s, 1H), 8.72 (s, 1H), 8.14 (s, 1H), 7.87 (br s, 1H), 7.52 (d, J = 9.2 Hz, 1H), 7.31 (dd, J = 1.5, 9.2 Hz, 1H), 5.34 (br s, 1H), 5.04-4.82 (m, 1H), 2.16 (td, J = 7.0, 13.9 Hz, 1H), 1.73-1.61 (m, 1H), 1.26 (d, J = 6.3 Hz, 3H), 1.16 (ddd, J = 2.8, 6.2, 12.1 Hz, 1H), 1.00 (br s, 1H), 0.46-0.37 (m, 2H), 0.30-0.20 (m, 2H); LCMS (electrospray) m/z 471.2 (M + H)+. | H |

TABLE 1-continued

Compounds of Examples

| Ex # | Structure/Name | ¹H NMR/MS (M + 1) | Method |
|---|---|---|---|
| 421 | (1S,2S)-N-(6-(5-chloro-7-((cyclopropylmethyl)amino)-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.22 (br s, 1H), 11.06 (s, 1H), 8.71 (s, 1H), 8.14 (s, 1H), 7.86 (s, 1H), 7.52 (d, J = 9.1 Hz, 1H), 7.30 (d, J = 9.3 Hz, 1H), 5.57 (m, 1H), 4.92 (m, 1H), 3.30 (s, 2H), 2.15 (m, 1H), 1.66 (m, 1H), 1.16 (m, 1H), 1.07 (m, 1H), 0.48 (m, 2H), 0.27 (m, 2H); LCMS (electrospray) m/z 457.1 (M + H)+. | H |
| 422 | (1S,2S)-N-(6-(5-chloro-6-fluoro-7-((R)-1-methoxypropan-2-yl)-1H-indazol-4-yl)imidazo[1,2-a]pyridin-2-yl)-2-fluorocyclopropane-1-carboxamide | ¹H NMR (400 MHz, DMSO-d₆) δ 13.52-13.66 (m, 1H), 11.09 (s, 1H), 8.80 (s, 1H), 8.16 (s, 1H), 7.97 (s, 1H), 7.57 (d, J = 9.2 Hz, 1H), 7.36 (dd, J = 1.6 Hz, 1.6 Hz, 1H), 5.04-4.83 (m, 1H), 3.82-3.74 (m, 3H), 3.68 (s, 1H), 2.20-2.14 (m, 1H), 1.71-1.63 (m, 1H), 1.22 (d, J = 7.4 Hz, 3H), 1.2-1.14(m, 2H); LCMS (electrospray) m/z 460.0 (M + H)+; SFC RT = 0.640. | H |
| 423 | (1S,2S)-N-(6-(5-chloro-6-fluoro-7-((S)-1-methoxypropan-2-yl)-1H-indazol-4-yl)imidazo[1,2-a]pyridin-2-yl)-2-fluorocyclopropane-1-carboxamide | ¹H NMR (400 MHz, DMSO-d₆) δ 13.57 (s, 1H), 11.09 (s, 1H), 8.80 (s, 1H), 8.16 (s, 1H), 7.98 (s, 1H), 7.57 (d, J = 9.2 Hz, 1H), 7.35 (d, J = 1.6 Hz, 1H), 5.04-4.83 (m, 1H), 3.82-3.74 (m, 3H), 2.20-2.14 (m, 1H), 1.41-1.39 (m, 1H), 1.22 (d, J = 14.4 Hz, 3H), 1.2-1.17(m, 2H); LCMS (electrospray) m/z 460.0 (M + H)+; SFC RT = 1.252. | H |

TABLE 1-continued

Compounds of Examples

| Ex # | Structure/Name | ¹H NMR/MS (M + 1) | Method |
|------|----------------|-------------------|--------|
| 424 | 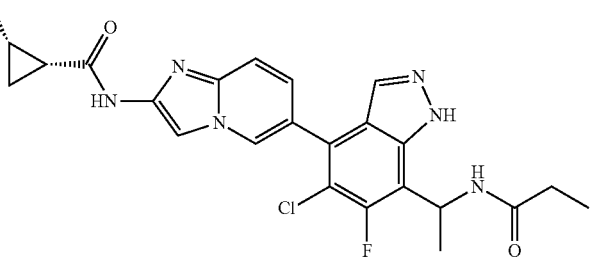<br>(1S,2S)-N-(6-(5-chloro-6-fluoro-7-(1-propionamidoethyl)-1H-indazol-4-yl)imidazo[1,2-a]pyridin-2-yl)-2-fluorocyclopropane-1-carboxamide | ¹H NMR (400 MHz, DMSO-d₆) δ 13.64-13.32 (m, 1H), 11.09 (s, 1H), 8.79 (s, 1H), 8.32 (br d, J = 6.3 Hz, 1H), 8.16 (s, 1H), 7.98 (s, 1H), 7.57 (d, J = 9.3 Hz, 1H), 7.35 (dd, J = 1.7, 9.2 Hz, 1H), 5.46 (br t, J = 7.0 Hz, 1H), 5.05-4.81 (m, 1H), 2.19-2.07 (m, 3H), 1.74-1.60 (m, 1H), 1.55 (d, J = 7.3 Hz, 3H), 1.24-1.11 (m, 1H), 0.95 (t, J = 7.6 Hz, 3H); LCMS (electrospray) m/z 487.2 (M + H)+. | H |
| 425 | 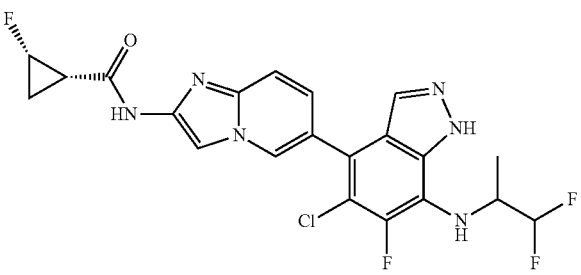 [SMILES: CC(Nc1c(F)c(Cl)c(-c2ccc3nc(NC(=O)[C@@H]4C[C@@H]4F)cn3c2)c2cn[nH]c12)C(F)F]<br>(1S,2S)-N-(6-(5-chloro-7-((1,1-difluoropropan-2-yl)amino)-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.55-13.09 (m, 1H), 11.07 (s, 1H), 8.73 (s, 1H), 8.16 (s, 1H), 8.07-7.83 (m, 1H), 7.54 (d, J = 9.1 Hz, 1H), 7.32 (dd, J = 1.7, 9.1 Hz, 1H), 6.30-5.95 (m, 1H), 5.65-5.44 (m, 1H), 5.11-4.76 (m, 1H), 4.54-3.95 (m, 1H), 2.20-2.12 (m, 1H), 1.75-1.59 (m, 1H), 1.33 (d, J = 6.7 Hz, 3H), 1.17 (ddt J = 6.2, 6.2, 9.1, 12.2 Hz, 1H); LCMS (electrospray) m/z 481.0 (M + H)+. | H |
| 426 | 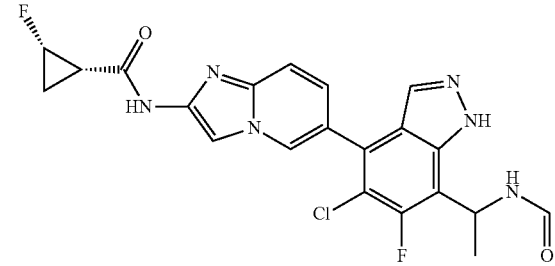 [SMILES: CC(NC=O)c1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-(1-formamidoethyl)-1H-indazol-4-yl)imidazo[1,2-a]pyridin-2-yl)-2-fluorocyclopropane-1-carboxamide | ¹H NMR (400 MHz, DMSO-d₆) δ 13.66-13.47 (m, 1H), 11.09 (s, 1H), 8.80 (s, 1H), 8.67 (br d, J = 6.8 Hz, 1H), 8.16 (s, 1H), 8.06 (s, 1H), 8.00 (br s, 1H), 7.57 (d, J = 9.3 Hz, 1H), 7.35 (dd, J = 1.4, 9.3 Hz, 1H), 5.62-5.48 (m, 1H), 5.09-4.80 (m, 1H), 2.16 (quin, J = 6.9 Hz, 1H), 1.73-1.61 (m, 1H), 1.57 (d, J = 7.0 Hz, 3H), 1.22-1.10 (m, 1H); LCMS (electrospray) m/z 458.9 (M + H)+. | H |
| 427 | 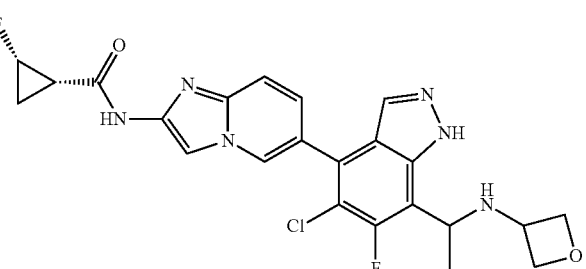<br>(1S,2S)-N-(6-(5-chloro-6-fluoro-7-(1-(oxetan-3-ylamino)ethyl)-1H-indazol-4-yl)imidazo[1,2-a]pyridin-2-yl)-2-fluorocyclopropane-1-carboxamide | ¹H NMR (400 MHz, DMSO-d₆) δ 13.74-13.07 (m, 1H), 11.09 (s, 1H), 8.80 (s, 1H), 8.43 (s, 1H), 8.16 (s, 1H), 7.96 (s, 1H), 7.57 (d, J = 9.2 Hz, 1H), 7.35 (dd, J = 1.7, 9.2 Hz, 1H), 5.06-4.80 (m, 1H), 4.60 (t, J = 6.4 Hz, 1H), 4.50-4.39 (m, 2H), 4.32 (t, J = 6.5 Hz, 1H), 4.15 (t, J = 6.2 Hz, 1H), 3.75 (br t, J = 6.7 Hz, 1H), 2.22-2.11 (m, 1H), 1.73-1.60 (m, 1H), 1.49 (d, J = 6.7 Hz, 3H), 1.24-1.11 (m, 1H); LCMS (electrospray) m/z 487.3 (M + H)+. | H |

TABLE 1-continued

Compounds of Examples

| Ex # | Structure/Name | ¹H NMR/MS (M + 1) | Method |
|---|---|---|---|
| 428 | (1S,2S)-N-(6-(5-chloro-6-fluoro-7-(1-(2,2,2-trifluoroacetamido)ethyl)-1H-indazol-4-yl)imidazo[1,2-a]pyridin-2-yl)-2-fluorocyclopropane-1-carboxamide | ¹H NMR (400 MHz, DMSO-$d_6$) δ 13.30 (br s, 1H), 11.19 (s, 1H), 10.04 (d, J = 4.5 Hz, 1H), 8.84 (s, 1H), 8.16 (s, 1H), 8.04 (s, 1H), 7.62 (d, J = 9.1 Hz, 1H), 7.49-7.39 (m, 1H), 5.70-5.46 (m, 1H), 5.11-4.78 (m, 1H), 2.17 (td, J = 6.9, 13.8 Hz, 1H), 1.69 (d, J = 7.0 Hz, 3H), 1.67-1.59 (m, 1H), 1.29-1.09 (m, 1H); LCMS (electrospray) m/z 527.1 (M + H)+. | H |
| 429 | (1S,2S)-N-(6-(5-chloro-7-(1-((1-cyanocyclopropyl)amino)ethyl)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.30 (br s, 1H), 11.05 (s, 1H), 8.72 (s, 1H), 8.14 (s, 1H), 7.91 (s, 1H), 7.58 (d, J = 9.0 Hz, 1H), 7.38-7.32 (m, 1H), 5.09-4.81 (m, 1H), 4.08-3.99 (m, 1H), 2.19-2.13 (m, 1H), 1.71-1.62 (m, 1H), 1.51 (d, J = 6.7 Hz, 3H), 1.32-1.23 (m, 1H), 1.21-1.13 (m, 1H), 1.04-0.94 (m, 1H), 0.69-0.56 (m, 1H); LCMS (electrospray) m/z 496.3 (M + H)+. | H |
| 430 | N-(1-(5-chloro-6-fluoro-4-(2-((1S,2S)-2-fluorocyclopropane-1-carboxamido)imidazo[1,2-a]pyridin-6-yl)-1H-indazol-7-yl)ethyl)cyclobutanecarboxamide | ¹H NMR (400 MHz, DMSO-$d_6$) δ 13.99-13.36 (m, 1H), 11.09 (s, 1H), 8.79 (s, 1H), 8.51-8.44 (m, 1H), 8.46 (s, 1H), 8.41 (br d, J = 6.7 Hz, 1H), 8.15 (s, 1H), 7.97 (s, 1H), 7.57 (d, J = 9.2 Hz, 1H), 7.35 (dd, J = 1.7, 9.3 Hz, 1H), 5.45 (br t, J = 7.0 Hz, 1H), 5.07-4.76 (m, 1H), 3.14-3.03 (m, 1H), 2.10 (br d, J = 8.7 Hz, 1H), 2.21-2.01 (m, 1H), 2.00-1.81 (m, 4H), 1.64 (dt, J = 4.2, 6.7 Hz, 1H), 1.75-1.60 (m, 1H), 1.55 (br d, J = 7.2 Hz, 3H), 1.17 (ddd, J = 2.8, 6.2, 12.3 Hz, 1H); LCMS (electrospray) m/z 513.3 (M + H)+. | H |
| 431 | (1S,2S)-N-(6-(5-chloro-6-fluoro-7-(1H-imidazol-5-yl)-1H-indazol-4-yl)imidazo[1,2-a]pyridin-2-yl)-2-fluorocyclopropane-1-carboxamide | ¹H NMR (400 MHz, DMSO-$d_6$) δ 13.37 (br s, 1H), 11.25 (s, 1H), 8.92 (s, 1H), 8.81 (d, J = 5.7 Hz, 1H), 8.22 (s, 1H), 8.19 (s, 1H), 8.10 (s, 1H), 7.66 (d, J = 9.2 Hz, 1H), 7.49 (d, J = 9.4 Hz, 1H), 5.06-4.89 (m, 1H), 2.24-2.15 (m, 1H), 1.78-1.62 (m, 1H), 1.26-1.17 (m, 1H), 0.30-0.20 (m, 2H); LCMS (electrospray) m/z 453.9 (M + H)+. | H |

TABLE 1-continued

Compounds of Examples

| Ex # | Structure/Name | ¹H NMR/MS (M + 1) | Method |
|---|---|---|---|
| 432 | (1S,2S)-N-(6-(5-chloro-7-((4,5-dihydro-1H-imidazol-2-yl)amino)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.18 (s, 1H), 11.08 (s, 1H), 8.68 (s, 1H), 8.19 (s, 1H), 7.81 (s, 1H), 7.54 (d, J = 9.3 Hz, 1H), 7.30 (dd, J = 9.3, 1.6 Hz, 1H), 6.48 (d, J = 18.1 Hz, 2H), 4.93 (ddd, J = 66.4, 10.0, 6.2 Hz, 1H), 3.40 (s, 4H), 2.19-2.12 (m, 1H), 1.71-1.62 (m, 1H), 1.19-1.12 (m, 1H); LCMS (electrospray) m/z 472.10 (M + H)+. | H |
| 433 | (1S,2S)-N-(6-(5-chloro-6-fluoro-7-(1-(methylamino)-1-oxopropan-2-yl)-1H-indazol-4-yl)imidazo[1,2-a]pyridin-2-yl)-2-fluorocyclopropane-1-carboxamide | ¹H NMR (400 MHz, DMSO-$d_6$) δ 1H-NMR (400 MHz, DMSO-D6) δ 13.31 (s, 1H), 11.11 (s, 1H), 8.79 (d, J = 1.6 Hz, 1H), 8.19 (s, 1H), 7.98 (d, J = 1.6 Hz, 1H), 7.94 (d, J = 4.9 Hz, 1H), 7.58 (d, J = 9.3 Hz, 1H), 7.35 (dd, J = 9.1, 1.9 Hz, 1H), 4.93 (ddd, J = 66.2, 10.2, 6.3 Hz, 1H), 4.25 (q, J = 7.1 Hz, 1H), 2.67-2.60 (m, 3H), 2.19-2.08 (m, 1H), 1.71-1.61 (m, 1H), 1.55 (d, J = 7.1 Hz, 3H), 1.24-1.10 (m, 1H); LCMS (electrospray) m/z 473.10 (M + H)+. | H |
| 434 | (1S,2S)-N-(6-(5-chloro-6-fluoro-7-((methylthio)methyl)-1H-indazol-4-yl)imidazo[1,2-a]pyridin-2-yl)-2-fluorocyclopropane-1-carboxamide | ¹H NMR (400 MHz, DMSO-$d_6$) δ 13.70 (s, 1H), 11.13 (s, 1H), 8.85 (s, 1H), 8.18 (s, 1H), 8.04-8.01 (m, 1H), 7.59 (d, J = 9.3 Hz, 1H), 7.39 (dd, J = 9.3, 1.6 Hz, 1H), 5.05-4.84 (m, 1H), 4.10 (d, J = 12.6 Hz, 2H), 2.20-2.13 (m, 1H), 2.08 (d, J = 9.3 Hz, 3H), 1.67 (dtd, J = 23.3, 6.8, 3.7 Hz, 1H), 1.24-1.14 (m, 1H), LCMS (electrospray) m/z 449.05 (M + H)+. | H |
| 435 | (1S,2S)-N-(6-(5-chloro-7-(1,3-dimethylureido)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.71 (s, 1H), 11.12 (s, 1H), 8.79 (s, 1H), 8.23 (s, 1H), 8.03 (d, J = 1.1 Hz, 1H), 7.60 (d, J = 9.3 Hz, 1H), 7.36 (dd, J = 9.3, 1.6 Hz, 1H), 6.42 (s, 1H), 5.04-4.84 (m, 1H), 3.21 (s, 3H), 2.58 (d, J = 4.4 Hz, 3H), 2.20-2.13 (m, 1H), 1.70-1.63 (m, 1H), 1.19-1.13 (m, 1H) m/z 474.10 (M + H)+. | H |

TABLE 1-continued

Compounds of Examples

| Ex # | Structure/Name | ¹H NMR/MS (M + 1) | Method |
|---|---|---|---|
| 436 | 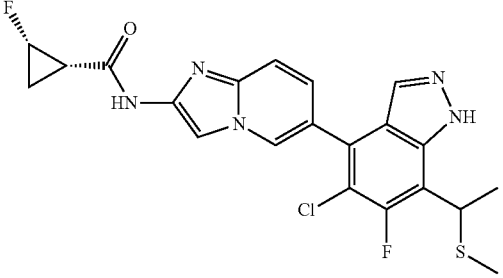<br>(1S,2S)-N-(6-(5-chloro-6-fluoro-7-(1-(methylthio)ethyl)-1H-indazol-4-yl)imidazo[1,2-a]pyridin-2-yl)-2-fluorocyclopropane-1-carboxamide | ¹H NMR (400 MHz, DMSO-$d_6$) δ 13.58 (s, 1H), 11.12 (s, 1H), 8.82 (t, J = 1.4 Hz, 1H), 8.18 (d, J = 12.1 Hz, 1H), 8.01 (s, 1H), 7.58 (d, J = 9.3 Hz, 1H), 7.38 (dd, J = 9.3, 1.6 Hz, 1H), 5.04-4.83 (m, 1H), 4.64 (q, J = 7.1 Hz, 1H), 2.19-2.12 (m, 1H), 2.02-1.96 (m, 3H), 1.81-1.77 (m, 3H), 1.66 (dtd, J = 23.3, 6.9, 3.8 Hz, 1H), 1.21-1.13 (m, 1H), LCMS (electrospray) m/z 463.00 (M + H)+. | H |
| 437 | 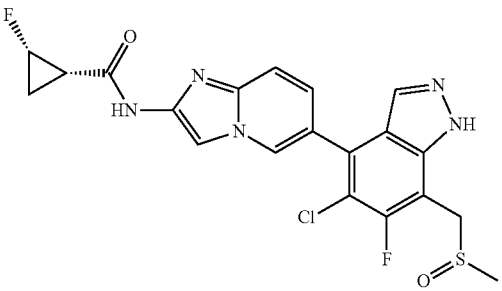 [SMILES: CS(=O)Cc1c(F)c(Cl)c(-c2ccc3nc(NC(=O)[C@@H]4C[C@@H]4F)cn3c2)c2cn[nH]c12]<br>(1S,2S)-N-(6-(5-chloro-6-fluoro-7-((methylsulfinyl)methyl)-1H-indazol-4-yl)imidazo[1,2-a]pyridin-2-yl)-2-fluorocyclopropane-1-carboxamide | ¹H NMR (400 MHz, DMSO-$d_6$) δ 13.71 (s, 1H), 11.12 (s, 1H), 8.85 (d, J = 1.1 Hz, 1H), 8.21-8.16 (m, 1H), 8.03 (d, J = 1.1 Hz, 1H), 7.59 (d, J = 9.3 Hz, 1H), 7.39 (dd, J = 9.3, 1.6 Hz, 1H), 5.04-4.83 (m, 1H), 4.54-4.43 (m, 2H), 2.68 (d, J = 13.7 Hz, 3H), 2.20-2.13 (m, 1H), 1.67 (dtd, J = 23.3, 6.9, 3.8 Hz, 1H), 1.20-1.13 (m, 1H) LCMS (electrospray) m/z 465.00 (M + H)+. | H |
| 438 | 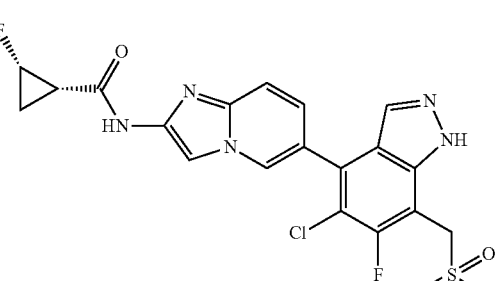<br>(1S,2S)-N-(6-(5-chloro-6-fluoro-7-((methylsulfonyl)methyl)-1H-indazol-4-yl)imidazo[1,2-a]pyridin-2-yl)-2-fluorocyclopropane-1-carboxamide | ¹H NMR (400 MHz, DMSO-$d_6$) δ 13.69 (s, 1H), 11.12 (s, 1H), 8.85 (t, J = 1.4 Hz, 1H), 8.18 (s, 1H), 8.04 (s, 1H), 7.59 (d, J = 9.3 Hz, 1H), 7.39 (dd, J = 9.3, 1.6 Hz, 1H), 5.04-4.83 (m, 3H), 3.11 (s, 3H), 2.19-2.12 (m, 1H), 1.66 (dtd, J = 23.5, 6.7, 3.5 Hz, 1H), 1.22-1.13 (m, 1H), LCMS (electrospray) m/z 481.00 (M + H)+. | H |
| 439 | 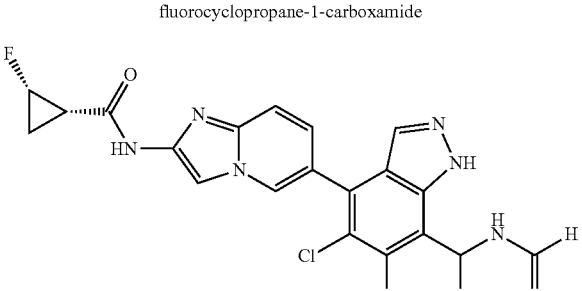<br>(1S,2S)-N-(6-(5-chloro-7-(cyano(formamido)methyl)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.81 (s, 1H), 11.14 (s, 1H), 9.65 (d, J = 6.0 Hz, 1H), 8.86 (s, 1H), 8.21 (d, J = 8.8 Hz, 2H), 8.13 (s, 1H), 7.61 (d, J = 9.3 Hz, 1H), 7.39 (dd, J = 9.1, 1.4 Hz, 1H), 6.69 (d, J = 6.6 Hz, 1H), 5.05-4.84 (m, 1H), 2.21-2.14 (m, 1H), 1.73-1.62 (m, 1H), 1.22-1.14 (m, 1H), LCMS (electrospray) m/z 471.00 (M + H)+. | H |

TABLE 1-continued

Compounds of Examples

| Ex # | Structure/Name | ¹H NMR/MS (M + 1) | Method |
|---|---|---|---|
| 440 | 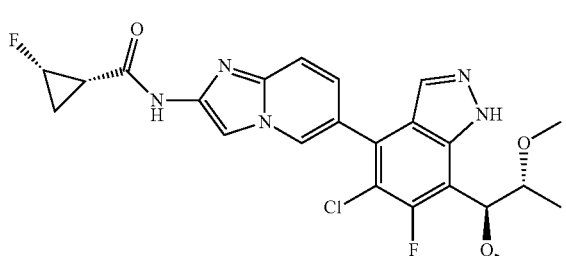<br>(1S,2S)-N-(6-(5-chloro-7-((1S,2R)-1,2-dimethoxypropyl)-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.33 (s, 1H), 11.12 (s, 1H), 8.85 (t, J = 1.4 Hz, 1H), 8.16 (s, 1H), 7.97 (d, J = 0.8 Hz, 1H), 7.58 (d, J = 8.8 Hz, 1H), 7.39 (dd, J = 9.3, 1.6 Hz, 1H), 5.04-4.83 (m, 2H), 3.93-3.87 (m, 1H), 3.38 (d, J = 3.3 Hz, 2H), 3.24 (s, 3H), 2.16 (dt, J = 14.4, 6.7 Hz, 1H), 1.66 (dtd, J = 23.2, 6.9, 3.8 Hz, 1H), 1.24-1.13 (m, 1H), 0.95 (d, J = 6.0 Hz, 3H); LCMS (electrospray) m/z 490.10 (M + H)+. | H |
| 441 | 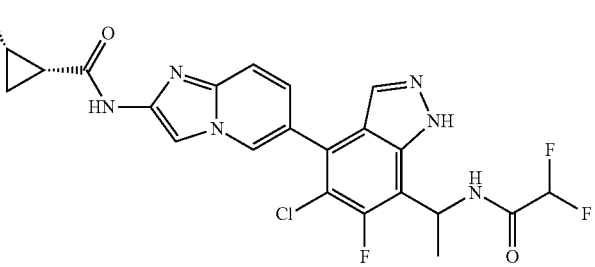<br>(1S,2S)-N-(6-(5-chloro-7-(1-(2,2-difluoroacetamido)ethyl)-6-fluoro-1H-indazol-4-yl)imidazo[1,2-a]pyridin-2-yl)-2-fluorocyclopropane-1-carboxamide | ¹H NMR (400 MHz, DMSO-d₆) δ 13.60 (br s, 1H), 11.08 (s, 1H), 9.39 (br d, J = 6.5 Hz, 1H), 8.80 (s, 1H), 8.16 (s, 1H), 8.02 (br s, 1H), 7.57 (d, J = 9.3 Hz, 1H), 7.36 (dd, J = 1.8, 9.2 Hz, 1H), 6.28 (t, J = 53.6 Hz, 1H), 5.55 (br t, J = 6.8 Hz, 1H), 5.04-4.81 (m, 1H), 2.23-2.10 (m, 1H), 1.73-1.67 (m, 1H), 1.65 (d, J = 7.2 Hz, 3H), 1.17 (tdd, J = 6.2, 9.1, 12.3 Hz, 1H); LCMS (electrospray) m/z 509.2 (M + H)+. | H |
| 442 | 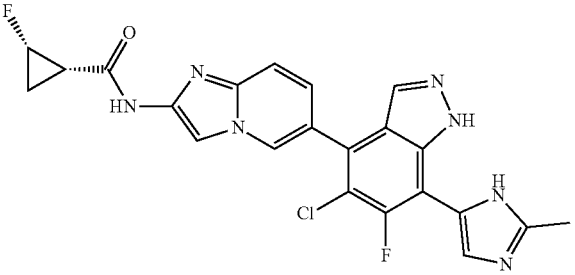 [SMILES: Cc1ncc(-c2c(F)c(Cl)c(-c3ccc4nc(NC(=O)[C@@H]5C[C@@H]5F)cn4c3)c3cn[nH]c23)[nH]1]<br>(1S,2S)-N-(6-(5-chloro-6-fluoro-7-(2-methyl-1H-imidazol-5-yl)-1H-indazol-4-yl)imidazo[1,2-a]pyridin-2-yl)-2-fluorocyclopropane-1-carboxamide | ¹H NMR (400 MHz, DMSO-d₆) δ 13.20 (s, 1H), 12.37 (d, J = 1.3 Hz, 1H), 11.08 (s, 1H), 8.85 (s, 1H), 8.18 (s, 1H), 8.00 (s, 1H), 7.67 (d, J = 3.1 Hz, 1H), 7.58 (d, J = 9.2 Hz, 1H), 7.40 (dd, J = 1.7, 9.2 Hz, 1H), 4.93 (m, 1H), 2.48 (s, 3H), 2.16 (m, 2H), 1.67 (m, 2H), 1.17 (m, 2H); LCMS (electrospray) m/z 468.1 (M + H)+. | H |
| 443 | 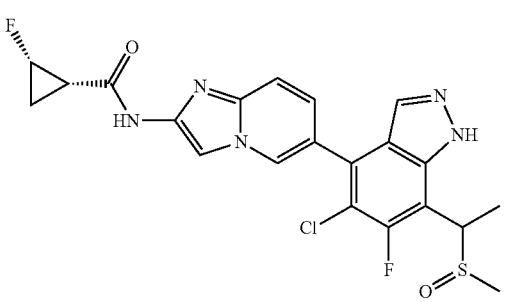 [SMILES: CC(c1c(F)c(Cl)c(-c2ccc3nc(NC(=O)[C@@H]4C[C@@H]4F)cn3c2)c2cn[nH]c12)S(C)=O]<br>(1S,2S)-N-(6-(5-chloro-6-fluoro-7-(1-(methylsulfinyl)ethyl)-1H-indazol-4-yl)imidazo[1,2-a]pyridin-2-yl)-2-fluorocyclopropane-1-carboxamide | ¹H NMR (400 MHz, DMSO-d₆) δ 13.68 (s, 1H), 11.11 (s, 1H), 8.81 (d, J = 1.1 Hz, 1H), 8.17 (d, J = 9.3 Hz, 1H), 8.05 (d, J = 1.1 Hz, 1H), 7.59 (d, J = 9.3 Hz, 1H), 7.37 (dd, J = 9.1, 1.9 Hz, 1H), 5.04-4.83 (m, 1H), 4.64-4.59 (m, 1H), 2.48 (s, 2H), 2.19-2.12 (m, 1H), 1.83-1.81 (m, 3H), 1.71-1.61 (m, 1H), 1.20-1.13 (m, 1H); LCMS (electrospray) m/z 478.1 (M + H)+. | H |

TABLE 1-continued

Compounds of Examples

| Ex # | Structure/Name | ¹H NMR/MS (M + 1) | Method |
|---|---|---|---|
| 444 | 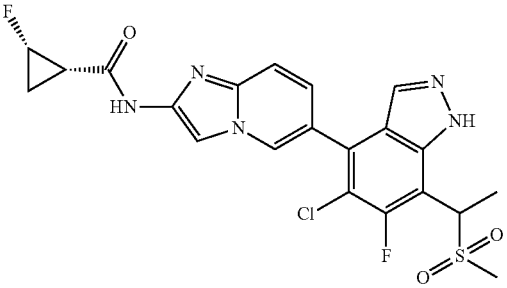 [SMILES: CC(c1c(F)c(Cl)c(-c2ccc3nc(NC(=O)[C@@H]4C[C@@H]4F)cn3c2)c2cn[nH]c12)S(C)(=O)=O]<br>(1S,2S)-N-(6-(5-chloro-6-fluoro-7-(1-(methylsulfonyl)ethyl)-1H-indazol-4-yl)imidazo[1,2-a]pyridin-2-yl)-2-fluorocyclopropane-1-carboxamide | ¹H NMR (400 MHz, DMSO-$d_6$) δ 13.54 (s, 1H), 11.12 (s, 1H), 8.84 (s, 1H), 8.18 (s, 1H), 8.04 (s, 1H), 7.60 (d, J = 9.3 Hz, 1H), 7.38 (dd, J = 9.3, 1.6 Hz, 1H), 5.15 (d, J = 7.1 Hz, 1H), 5.04-4.83 (m, 1H), 3.06 (s, 3H), 2.20-2.13 (m, 1H), 1.97-1.91 (m, 3H), 1.72-1.62 (m, 1H), 1.20-1.13 (m, 1H); LCMS (electrospray) m/z 494.1 (M + H)+. | H |
| 445 | 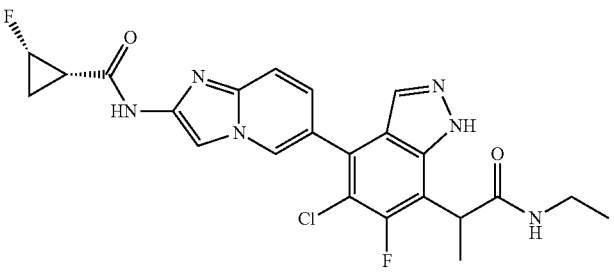 [SMILES: CCNC(=O)C(C)c1c(F)c(Cl)c(-c2ccc3nc(NC(=O)[C@@H]4C[C@@H]4F)cn3c2)c2cn[nH]c12]<br>(1S,2S)-N-(6-(5-chloro-7-(1-(ethylamino)-1-oxopropan-2-yl)-6-fluoro-1H-indazol-4-yl)imidazo[1,2-a]pyridin-2-yl)-2-fluorocyclopropane-1-carboxamide | ¹H NMR (400 MHz, DMSO-$d_6$) δ 13.26 (s, 1H), 11.08 (s, 1H), 8.79 (s, 1H), 8.18 (s, 1H), 8.00 (d, J = 23.6 Hz, 2H), 7.58 (d, J = 8.8 Hz, 1H), 7.35 (dd, J = 9.1, 1.9 Hz, 1H), 5.04-4.83 (m, 1H), 4.24 (q, J = 7.1 Hz, 1H), 3.11 (td, J = 12.6, 7.1 Hz, 2H), 2.20-2.13 (m, 1H), 1.70-1.63 (m, 1H), 1.54 (d, J = 7.1 Hz, 3H), 1.21-1.13 (m, 1H), 1.01 (t, J = 7.1 Hz, 3H); LCMS (electrospray) m/z 487.1 (M + H)+. | H |
| 446 | 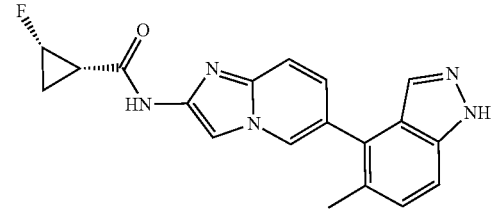 [SMILES: Cc1ccc2[nH]ncc2c1-c1ccc2nc(NC(=O)[C@@H]3C[C@@H]3F)cn2c1]<br>(1S,2S)-2-fluoro-N-(5-(5-methyl-1H-indazol-4-yl)pyrazolo[1,5-a]pyridin-2-yl)cyclopropane-1-carboxamide | ¹H NMR (400 MHz, DMSO-$d_6$) δ 13.09 (s, 1H), 11.13 (s, 1H), 8.61 (d, J = 7.1 Hz, 1H), 7.74 (s, 1H), 7.63 (d, J = 0.9 Hz, 1H), 7.49 (d, J = 8.6 Hz, 1H), 7.32 (d, J = 8.6 Hz, 1H), 6.91 (s, 1H), 6.86 (dd, J = 1.9, 7.0 Hz, 1H), 5.06-4.98 (m, 1H), 4.88-4.84 (m, 1H), 2.34 (s, 3H), 2.15 (td, J = 6.9, 13.8 Hz, 1H), 1.74-1.61 (m, 1H), 1.21-1.13 (m, 1H); LCMS (electrospray) m/z 350.1 (M + H)+. | J |
| 447 | 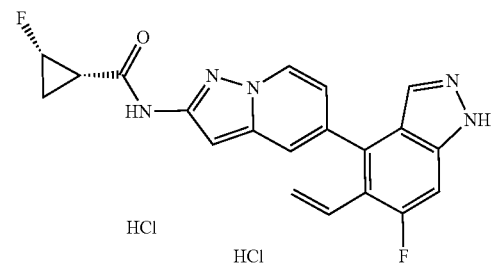 [SMILES: C=Cc1c(F)cc2[nH]ncc2c1-c1ccn2nc(NC(=O)[C@@H]3C[C@@H]3F)cc2c1 ; Cl ; Cl]<br>(1S,2S)-2-fluoro-N-(5-(6-fluoro-5-vinyl-1H-indazol-4-yl)pyrazolo[1,5-a]pyridin-2-yl)cyclopropane-1-carboxamide. 2 HCl | ¹H NMR (400 MHz, DMSO-$d_6$) δ 11.16 (s, 1H), 8.63 (d, J = 7.1 Hz, 1H), 7.82 (s, 1H), 7.65 (d, J = 0.9 Hz, 1H), 7.45 (d, J = 11.5 Hz, 1H), 6.93 (s, 1H), 6.81 (dd, J = 1.8, 7.1 Hz, 1H), 6.56 (dd, J = 11.8, 17.9 Hz, 1H), 5.63 (br d, J = 18.0 Hz, 1H), 5.46-5.36 (m, 1H), 5.06-4.82 (m, 1H), 2.15 (td, J = 7.0, 13.8 Hz, 1H), 1.73-1.59 (m, 1H), 1.17 (tdd, J = 6.3, 9.0, 12.3 Hz, 1H)); LCMS (electrospray) m/z 380.1 (M + H)+. | J |

TABLE 1-continued

Compounds of Examples

| Ex # | Structure/Name | ¹H NMR/MS (M + 1) | Method |
|---|---|---|---|
| 448 | 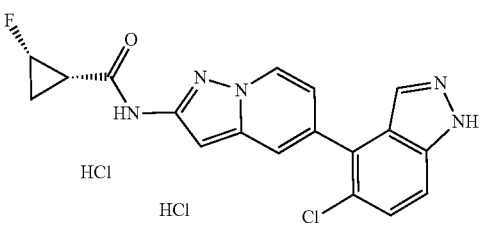 [SMILES: O=C(Nc1cc2cc(-c3c(Cl)ccc4[nH]ncc34)ccn2n1)[C@@H]1C[C@@H]1F ; Cl ; Cl]<br>(1S,2S)-N-(5-(5-chloro-1H-indazol-4-yl)pyrazolo[1,5-a]pyridin-2-yl)-2-fluorocyclopropane-1-carboxamide. 2 HCl | ¹H NMR (400 MHz, DMSO-d₆) δ 11.16 (s, 1H), 8.65 (d, J = 7.1 Hz, 1H), 7.88 (d, J = 1.0 Hz, 1H), 7.75 (d, J = 1.0 Hz, 1H), 7.63 (dd, J = 1.0, 8.8 Hz, 1H), 7.51 (d, J = 8.8 Hz, 1H), 6.95 (s, 1H), 6.92 (dd, J = 2.0, 7.1 Hz, 1H), 5.05-4.83 (m, 1H), 2.15 (td, J = 7.0, 13.8 Hz, 1H), 1.74-1.60 (m, 1H), 1.17 (tdd, J = 6.3, 9.0, 12.3 Hz, 1H); LCMS (electrospray) m/z 370.1 (M + H)+. | J |
| 449 | 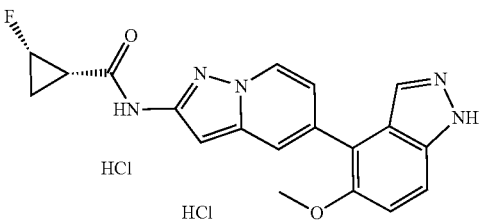 [SMILES: COc1ccc2[nH]ncc2c1-c1ccn2nc(NC(=O)[C@@H]3C[C@@H]3F)cc2c1 ; Cl ; Cl]<br>(1S,2S)-2-fluoro-N-(5-(5-methoxy-1H-indazol-4-yl)pyrazolo[1,5-a]pyridin-2-yl)cyclopropane-1-carboxamide. 2 HCl | ¹H NMR (400 MHz, DMSO-d₆) δ 11.10 (s, 1H), 8.56 (br d, J = 7.0 Hz, 1H), 7.90 (s, 1H), 7.74 (s, 1H), 7.58 (br d, J = 9.2 Hz, 1H), 7.35 (d, J = 8.9 Hz, 1H), 6.98 (br d, J = 7.1 Hz, 1H), 6.89 (s, 1H), 5.08-4.80 (m, 1H), 3.80 (s, 3H), 2.19-2.08 (m, 1H), 1.75-1.60 (m, 1H), 1.26-1.07 (m, 1H); LCMS (electrospray) m/z 366.1 (M + H)+. | J |
| 450 | 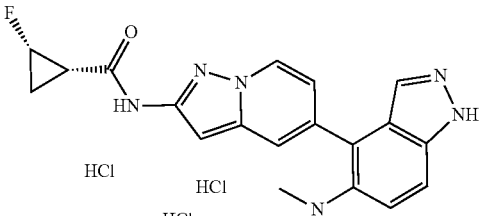<br>(1S,2S)-N-(5-(5-(dimethylamino)-1H-indazol-4-yl)pyrazolo[1,5-a]pyridin-2-yl)-2-fluorocyclopropane-1-carboxamide. 3 HCl | ¹H NMR (400 MHz, DMSO-d₆) δ 11.18 (br s, 1H), 8.68 (br s, 1H), 8.12-7.54 (m, 5H), 7.04-6.85 (m, 2H), 5.05-4.84 (m, 1H), 3.10 (br s, 6H), 2.16 (td, J = 7.0, 14.0 Hz, 1H), 1.73-1.62 (m, 1H), 1.23-1.14 (m, 1H); LCMS (electrospray) m/z 379.1 (M + H)+. | J |
| 451 | 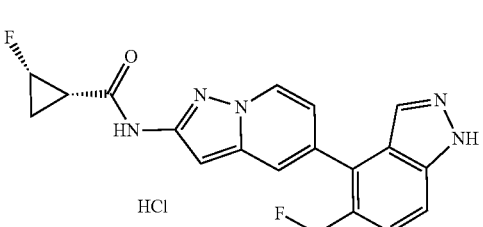<br>(1S,2S)-2-fluoro-N-(5-(5-(trifluoromethyl)-1H-indazol-4-yl)pyrazolo[1,5-a]pyridin-2-yl)cyclopropane-1-carboxamide. 2 HCl | ¹H NMR (400 MHz, DMSO-d₆) δ 14.19-13.15 (m, 1H), 11.17 (s, 1H), 8.64 (d, J = 7.1 Hz, 1H), 7.87 (s, 1H), 7.82-7.74 (m, 2H), 7.64 (s, 1H), 6.93 (s, 1H), 6.83 (dd, J = 1.8, 7.1 Hz, 1H), 5.08-4.81 (m, 1H), 2.20-2.10 (m, 1H), 1.74-1.59 (m, 1H), 1.17 (tdd, J = 6.2, 9.0, 12.4 Hz, 1H); LCMS (electrospray) m/z 404.1 (M + H)+. | J |

TABLE 1-continued

Compounds of Examples

| Ex # | Structure/Name | ¹H NMR/MS (M + 1) | Method |
|---|---|---|---|
| 452 | 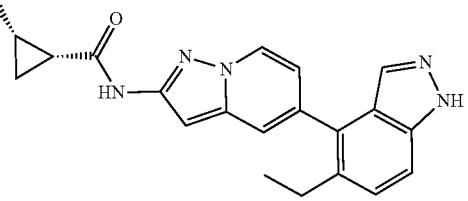<br>(1S,2S)-N-(5-(5-ethyl-1H-indazol-4-yl)pyrazolo[1,5-a]pyridin-2-yl)-2-fluorocyclopropane-1-carboxamide | ¹H NMR (400 MHz, DMSO-$d_6$) δ 13.10 (br s, 1H), 11.13 (s, 1H), 8.61 (d, J = 7.1 Hz, 1H), 7.68 (s, 1H), 7.59 (d, J = 1.0 Hz, 1H), 7.53 (d, J = 8.6 Hz, 1H), 7.36 (d, J = 8.7 Hz, 1H), 6.90 (s, 1H), 6.81 (dd, J = 1.9, 7.0 Hz, 1H), 5.06-4.81 (m, 1H), 2.70-2.59 (m, 2H), 2.20-2.10 (m, 1H), 1.75-1.58 (m, 1H), 1.18 (td, J = 3.1, 6.1 Hz, 1H), 1.12 (t, J = 7.5 Hz, 3H); LCMS (electrospray) m/z 364.2 (M + H)+. | J |
| 453 | 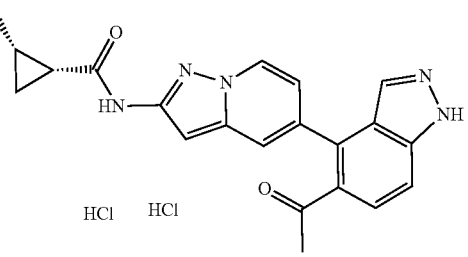<br>(1S,2S)-N-(5-(5-acetyl-1H-indazol-4-yl)pyrazolo[1,5-a]pyridin-2-yl)-2-fluorocyclopropane-1-carboxamide. 2 HCl | ¹H NMR (400 MHz, DMSO-$d_6$) δ 11.16 (s, 1H), 8.61 (d, J = 7.1 Hz, 1H), 7.97 (d, J = 0.7 Hz, 1H), 7.77 (d, J = 8.8 Hz, 1H), 7.69-7.64 (m, 1H), 7.61 (d, J = 1.1 Hz, 1H), 6.92 (s, 1H), 6.82 (dd, J = 2.0, 7.1 Hz, 1H), 5.06-4.82 (m, 1H), 2.33 (s, 3H), 2.21-2.11 (m, 1H), 1.73-1.61 (m, 1H), 1.18 (tdd, J = 6.1, 8.9, 12.3 Hz, 1H); LCMS (electrospray) m/z 378.2 (M + H)+. | J |
| 454 | 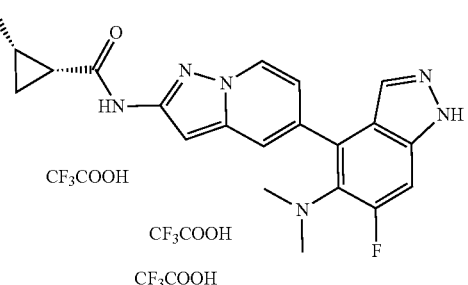<br>(1S,2S)-N-(5-(5-(dimethylamino)-6-fluoro-1H-indazol-4-yl)pyrazolo[1,5-a]pyridin-2-yl)-2-fluorocyclopropane-1-carboxamide. 3 TFA | ¹H NMR (400 MHz, DMSO-$d_6$) δ 11.11 (s, 1H), 8.58 (d, J = 7.1 Hz, 1H), 7.82 (s, 1H), 7.66 (s, 1H), 7.40 (d, J = 12.0 Hz, 1H), 6.93-6.87 (m, 2H), 5.05-4.82 (m, 1H), 2.67 (s, 6H), 2.19-2.09 (m, 1H), 1.73-1.61 (m, 1H), 1.22-1.12 (m, 1H); LCMS (electrospray) m/z = 397.1 (M + H+) | J |
| 455 | 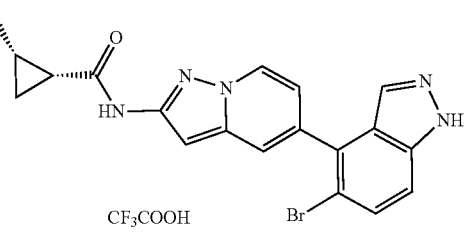<br>(1S,2S)-N-(5-(5-bromo-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.43 (br s, 1H), 11.15 (s, 1H), 8.65 (d, J = 7.1 Hz, 1H), 7.83 (s, 1H), 7.70 (dd, J = 0.8, 1.8 Hz, 1H), 7.67-7.63 (m, 1H), 7.58-7.55 (m, 1H), 6.95 (s, 1H), 6.88 (dd, J = 1.9, 7.2 Hz, 1H), 5.05-4.83 (m, 1H), 2.20-2.10 (m, 1H), 1.72-1.61 (m, 1H), 1.18 (qd, J = 6.2, 15.1 Hz, 1H); LCMS (electrospray) m/z = 414.0 (M + H+) | J |

TABLE 1-continued

Compounds of Examples

| Ex # | Structure/Name | ¹H NMR/MS (M + 1) | Method |
|---|---|---|---|
| 456 | 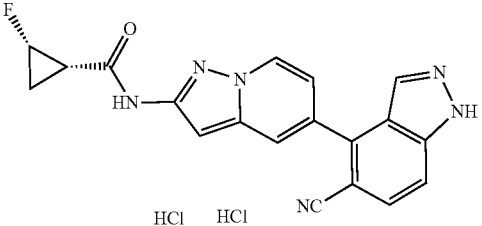 [SMILES: N#Cc1ccc2[nH]ncc2c1-c1ccn2nc(NC(=O)[C@@H]3C[C@@H]3F)cc2c1 ; Cl ; Cl]<br>(1S,2S)-N-(5-(5-cyano-1H-indazol-4-yl)pyrazolo[1,5-a]pyridin-2-yl)-2-fluorocyclopropane-1-carboxamide. 2 HCl | ¹H NMR (400 MHz, DMSO-$d_6$) δ 11.21 (s, 1H), 8.73 (d, J = 7.2 Hz, 1H), 8.19 (s, 1H), 7.94 (d, J = 1.2 Hz, 1H), 7.85-7.73 (m, 2H), 7.09 (dd, J = 2.0, 7.1 Hz, 1H), 7.02 (s, 1H), 5.08-4.82 (m, 1H), 2.16 (td, J = 7.0, 13.8 Hz, 1H), 1.74-1.62 (m, 1H), 1.18 (tdd, J = 6.3, 9.1, 12.3 Hz, 1H); LCMS (electrospray): m/z = 361.1 (M + H+) | J |
| 457 | 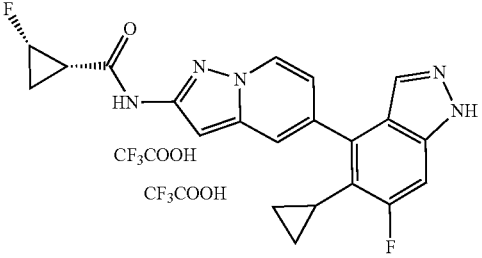 [SMILES: O=C(Nc1cc2cc(-c3c(C4CC4)c(F)cc4[nH]ncc34)ccn2n1)[C@@H]1C[C@@H]1F ; "CF3COOH" ; "CF3COOH"]<br>(1S,2S)-N-(5-(5-cyclopropyl-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 11.14 (s, 1H), 8.62 (d, J = 7.1 Hz, 1H), 7.83 (s, 1H), 7.74 (d, J = 0.9 Hz, 1H), 7.34 (d, J = 10.5 Hz, 1H), 6.98 (dd, J = 1.8, 7.1 Hz, 1H), 6.92 (s, 1H), 5.06-4.99 (m, 1H), 4.90-4.82 (m, 1H), 2.15 (td, J = 7.0, 13.6 Hz, 1H), 2.01-1.93 (m, 1H), 1.74-1.61 (m, 1H), 1.22-1.13 (m, 1H), 0.77-0.69 (m, 2H), 0.33-0.25 (m, 2H); LCMS (electrospray) m/z = 394.1 (M + H+) | J |
| 458 | 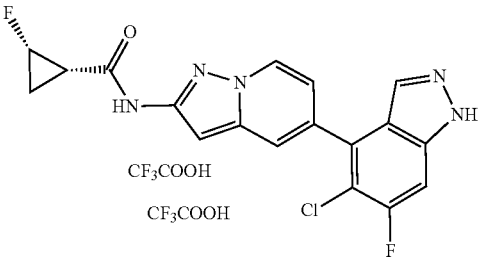 [SMILES: O=C(Nc1cc2cc(-c3c(Cl)c(F)cc4[nH]ncc34)ccn2n1)[C@@H]1C[C@@H]1F ; "CF3COOH" ; "CF3COOH"]<br>(1S,2S)-N-(5-(5-chloro-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.50 (br s, 1H), 11.17 (s, 1H), 8.68 (d, J = 7.2 Hz, 1H), 7.92 (s, 1H), 7.79 (d, J = 1.0 Hz, 1H), 7.68 (dd, J = 0.9, 9.0 Hz, 1H), 6.97 (s, 1H), 6.96 (d, J = 2.0 Hz, 1H), 6.96-6.93 (m, 1H), 5.06-5.00 (m, 1H), 4.88-4.84 (m, 1H), 2.18-2.12 (m, 1H), 1.75-1.59 (m, 1H), 1.22-1.14 (tdd, J = 6.2, 9.2, 12.4 Hz, 1H); LCMS (electrospray)m/z = 388.0 (M + H+) | J |
| 459 | 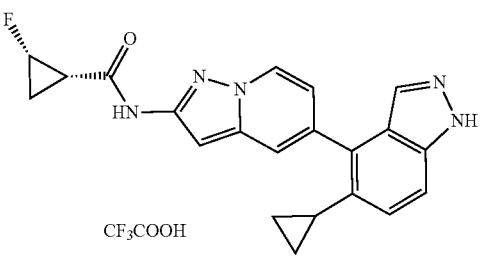<br>(1S,2S)-N-(5-(5-cyclopropyl-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.10 (s, 1H), 11.15 (s, 1H), 8.62 (d, J = 7.1 Hz, 1H), 7.75-7.67 (m, 2H), 7.48 (d, J = 8.8 Hz, 1H), 7.02 (d, J = 8.8 Hz, 1H), 6.96-6.88 (m, 2H), 5.07-4.82 (m, 1H), 2.20-2.08 (m, 1H), 2.03-1.94 (m, 1H), 1.74-1.60 (m, 1H), 1.22-1.11 (m, 1H), 0.90-0.78 (m, 2H), 0.70-0.60 (m, 2H); LCMS (electrospray) m/z = 376.1 (M + H+) | J |

TABLE 1-continued

Compounds of Examples

| Ex # | Structure/Name | ¹H NMR/MS (M + 1) | Method |
|---|---|---|---|
| 460 | 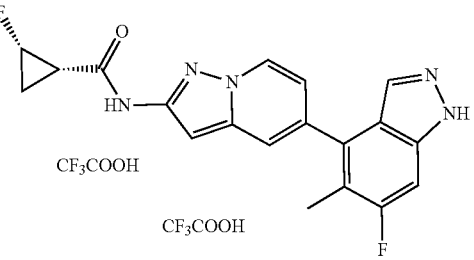<br>(1S,2S)-2-fluoro-N-(5-(6-fluoro-5-methyl-1H-indazol-4-yl)pyrazolo[1,5-a]pyridin-2-yl)cyclopropane-1-carboxamide. 2 TFA | ¹H NMR (400 MHz, DMSO-$d_6$) δ 13.17 (br s, 1H), 11.15 (s, 1H), 8.64 (d, J = 7.1 Hz, 1H), 7.77 (s, 1H), 7.67 (d, J = 0.9 Hz, 1H), 7.38 (d, J = 9.9 Hz, 1H), 6.93 (s, 1H), 6.87 (dd, J = 2.0, 7.1 Hz, 1H), 5.06-4.81 (m, 1H), 2.23 (d, J = 2.6 Hz, 3H), 2.15 (td, J = 6.9, 13.8 Hz, 1H), 1.75-1.59 (m, 1H), 1.17 (tdd, J = 6.3, 9.1, 12.3 Hz, 1H); LCMS (electrospray) m/z = 368.1 (M + H+) | J |
| 461 | 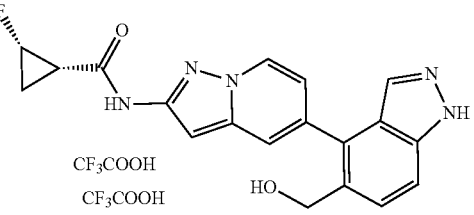<br>(1S,2S)-2-fluoro-N-(5-(5-(hydroxymethyl)-1H-indazol-4-yl)pyrazolo[1,5-a]pyridin-2-yl)cyclopropane-1-carboxamide. 2 TFA | ¹H NMR (400 MHz, DMSO-$d_6$) δ 13.18 (br s, 1H), 11.14 (s, 1H), 8.62 (d, J = 7.1 Hz, 1H), 7.82 (s, 1H), 7.69 (s, 1H), 7.58 (s, 2H), 6.94 (dd, J = 1.9, 7.0 Hz, 1H), 6.91 (s, 1H), 5.09-4.80 (m, 1H), 4.50 (s, 2H), 2.22-2.09 (m, 1H), 1.75-1.58 (m, 1H), 1.24-1.11 (m, 1H); LCMS (electrospray) m/z = 366.0 (M + H+) | J |
| 462 | 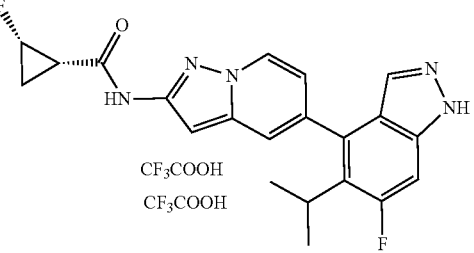<br>(1S,2S)-2-fluoro-N-(5-(6-fluoro-5-isopropyl-1H-indazol-4-yl)pyrazolo[1,5-a]pyridin-2-yl)cyclopropane-1-carboxamide. 2 TFA | ¹H NMR (400 MHz, DMSO-$d_6$) δ 11.14 (s, 1H), 8.63 (d, J = 7.0 Hz, 1H), 7.64 (d, J = 3.1 Hz, 1H), 7.59 (d, J = 0.8 Hz, 1H), 7.36 (d, J = 12.3 Hz, 1H), 6.92 (s, 1H), 6.78 (dd, J = 1.8, 7.1 Hz, 1H), 5.07-4.97 (m, 1H), 4.88-4.84 (m, 1H), 3.13-3.00 (m, 1H), 2.18-2.11 (m, 1H), 1.74-1.60 (m, 1H), 1.28 (dd, J = 7.1, 11.6 Hz, 6H), 1.21-1.08 (m, 1H); LCMS (electrospray) m/z = 396.1 (M + H+) | J |
| 463 | 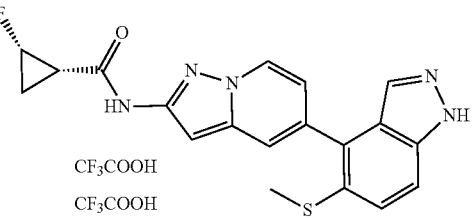<br>(1S,2S)-2-fluoro-N-(5-(5-(methylthio)-1H-indazol-4-yl)pyrazolo[1,5-a]pyridin-2-yl)cyclopropane-1-carboxamide. 2 TFA | ¹H NMR (400 MHz, DMSO-$d_6$) δ 13.25 (br s, 1H), 11.33-10.98 (m, 1H), 11.13 (s, 1H), 8.61 (d, J = 7.0 Hz, 1H), 7.76 (s, 1H), 7.66-7.59 (m, 2H), 7.56-7.51 (m, 1H), 6.92 (s, 1H), 6.87 (dd, J = 1.8, 7.1 Hz, 1H), 5.23-4.71 (m, 1H), 2.39 (s, 3H), 2.20-2.10 (m, 1H), 1.75-1.58 (m, 1H), 1.17 (tdd, J = 6.2, 9.1, 12.2 Hz, 1H); LCMS (electrospray) m/z = 382.1 (M + H+) | J |

TABLE 1-continued

Compounds of Examples

| Ex # | Structure/Name | $^1$H NMR/MS (M + 1) | Method |
|---|---|---|---|
| 464 | 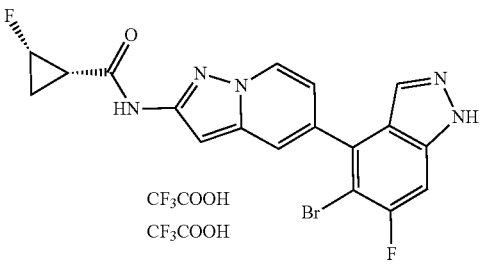 [SMILES: O=C(Nc1cc2cc(-c3c(Br)c(F)cc4[nH]ncc34)ccn2n1)[C@@H]1C[C@@H]1F ; "CF3COOH" ; "CF3COOH"]<br>(1S,2S)-N-(5-(5-bromo-6-fluoro-1H-indazol-4-yl)pyrazolo[1,5-a]pyridin-2-yl)-2-fluorocyclopropane-1-carboxamide. 2 TFA | $^1$H NMR (400 MHz, DMSO-d$_6$) δ 13.48 (br s, 1H), 11.17 (s, 1H), 8.67 (d, J = 7.1 Hz, 1H), 7.86 (s, 1H), 7.74 (d, J = 1.0 Hz, 1H), 7.66-7.61 (m, 1H), 6.96 (s, 1H), 6.90 (dd, J = 2.0, 7.1 Hz, 1H), 5.08-4.80 (m, 1H), 2.14 (br d, J = 7.2 Hz, 1H), 1.75-1.60 (m, 1H), 1.21-1.14 (m, 1H); LCMS (electrospray) m/z = 432.0 (M + H+) | J |
| 465 | 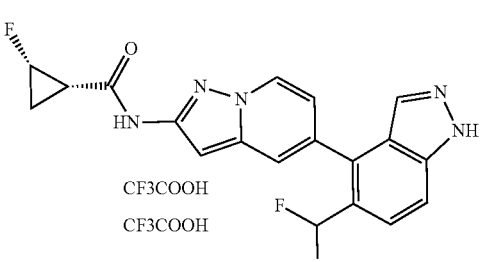<br>(1S,2S)-N-(5-(5-(difluoromethyl)-1H-indazol-4-yl)pyrazolo[1,5-a]pyridin-2-yl)-2-fluorocyclopropane-1-carboxamide. 2 TFA | $^1$H NMR (400 MHz, DMSO-d$_6$) δ 13.52 (br s, 1H), 11.17 (s, 1H), 8.67 (d, J = 7.0 Hz, 1H), 7.94 (s, 1H), 7.78-7.74 (m, 1H), 7.73-7.69 (m, 1H), 7.66 (s, 1H), 7.11-6.80 (m, 3H), 5.07-4.83 (m, 1H), 2.19-2.10 (m, 1H), 1.74-1.62 (m, 1H), 1.18 (tdd, J = 6.4, 9.0, 12.3 Hz, 1H); LCMS (electrospray) m/z = 386.2 (M + H+) | J |
| 466 | 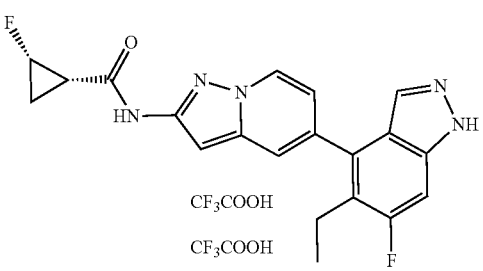 [SMILES: CCc1c(F)cc2[nH]ncc2c1-c1ccn2nc(NC(=O)[C@@H]3C[C@@H]3F)cc2c1 ; "CF3COOH" ; "CF3COOH"]<br>(1S,2S)-N-(5-(5-ethyl-6-fluoro-1H-indazol-4-yl)pyrazolo[1,5-a]pyridin-2-yl)-2-fluorocyclopropane-1-carboxamide. 2 TFA | $^1$H NMR (400 MHz, DMSO-d$_6$) δ 11.15 (s, 1H), 8.64 (d, J = 7.1 Hz, 1H), 7.70 (s, 1H), 7.63 (s, 1H), 7.39 (d, J = 10.4 Hz, 1H), 6.93 (s, 1H), 6.82 (dd, J = 1.8, 7.0 Hz, 1H), 5.06-4.81 (m, 1H), 2.66-2.57 (m, 2H), 2.20-2.09 (m, 1H), 1.74-1.60 (m, 1H), 1.22-1.14 (m, 1H), 1.10 (t, J = 7.4 Hz, 3H); LCMS (electrospray) m/z = 382.1 (M + H+) | J |
| 467 | 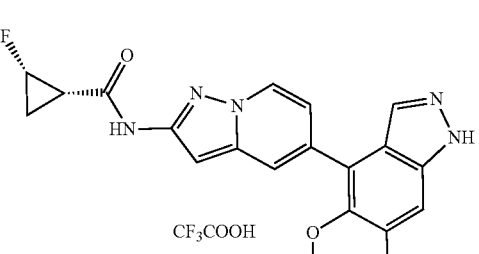<br>(1S,2S)-2-fluoro-N-(5-(6-fluoro-5-methoxy-1H-indazol-4-yl)pyrazolo[1,5-a]pyridin-2-yl)cyclopropane-1-carboxamide. 2 TFA | $^1$H NMR (400 MHz, DMSO-d$_6$) δ 13.27 (s, 1H), 11.15 (s, 1H), 8.67-8.61 (m, 1H), 7.97 (s, 1H), 7.84-7.80 (m, 1H), 7.56-7.48 (m, 1H), 7.05-6.99 (m, 1H), 6.95 (s, 1H), 5.08-4.82 (m, 1H), 3.67 (s, 2H), 3.71-3.63 (m, 1H), 2.07 (s, 1H), 1.75-1.61 (m, 1H), 1.26-1.09 (m, 1H); LCMS (electrospray) m/z = 384.1 (M + H+) | J |

TABLE 1-continued

Compounds of Examples

| Ex # | Structure/Name | ¹H NMR/MS (M + 1) | Method |
|---|---|---|---|
| 468 | 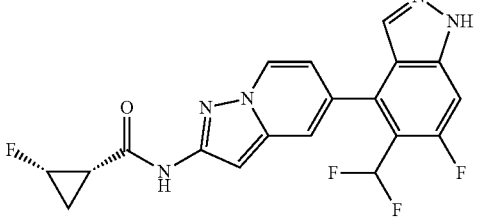<br>(1S,2S)-N-(5-(5-(difluoromethyl)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.60 (br s, 1H), 11.21 (s, 1H), 8.68 (d, J = 7.1 Hz, 1H), 7.93 (s, 1H), 7.69 (s, 1H), 7.60 (d, J = 11.2 Hz, 1H), 7.09-6.79 (m, 3H), 5.08-4.81 (m, 1H), 2.19-2.11 (m, 1H), 1.73-1.61 (m, 1H), 1.23-1.14 (m, 1H); LCMS (electrospray) m/z = 404.1 (M + H+) | J |
| 469 | 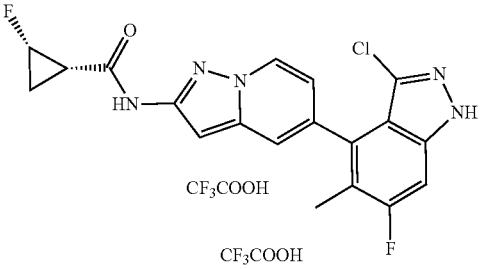 [SMILES: Cc1c(F)cc2[nH]nc(Cl)c2c1-c1ccn2nc(NC(=O)[C@@H]3C[C@@H]3F)cc2c1 ; "CF3COOH" ; "CF3COOH"]<br>(1S,2S)-N-(5-(3-chloro-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.40 (s, 1H), 11.14 (br d, J = 3.1 Hz, 1H), 8.62 (d, J = 7.0 Hz, 1H), 7.52 (s, 1H), 7.44 (d, J = 9.8 Hz, 1H), 6.90 (s, 1H), 6.74 (dd, J = 1.8, 7.1 Hz, 1H), 5.09-4.79 (m, 1H), 2.19-2.12 (m, 1H), 2.09 (t, J = 2.4 Hz, 3H), 1.75-1.60 (m, 1H), 1.23-1.09 (m, 1H); LCMS (electrospray) m/z = 402.0 (M + H+) | J |
| 470 | 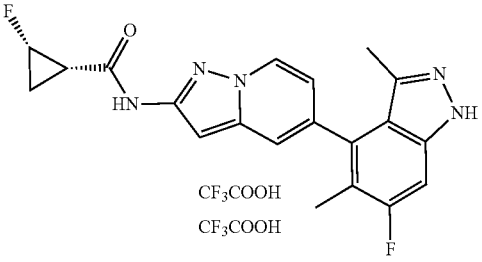 [SMILES: Cc1c(F)cc2[nH]nc(C)c2c1-c1ccn2nc(NC(=O)[C@@H]3C[C@@H]3F)cc2c1 ; "CF3COOH" ; "CF3COOH"]<br>(1S,2S)-2-fluoro-N-(5-(6-fluoro-3,5-dimethyl-1H-indazol-4-yl)pyrazolo[1,5-a]pyridin-2-yl)cyclopropane-1-carboxamide. 2 TFA s | ¹H NMR (400 MHz, DMSO-d$_6$) δ 11.16 (d, J = 3.5 Hz, 1H), 8.63 (d, J = 7.0 Hz, 1H), 7.53 (d, J = 0.7 Hz, 1H), 7.29 (d, J = 10.0 Hz, 1H), 6.91 (s, 1H), 6.75 (dd, J = 1.8, 7.0 Hz, 1H), 5.11-4.79 (m, 1H), 2.15 (td, J = 6.8, 13.4 Hz, 1H), 2.07 (t, J = 2.4 Hz, 3H), 1.90 (d, J = 4.3 Hz, 3H), 1.74-1.59 (m, 1H), 1.24-1.10 (m, 1H); LCMS (electrospray) m/z 382.0 (M + H)+. | J |
| 471 | 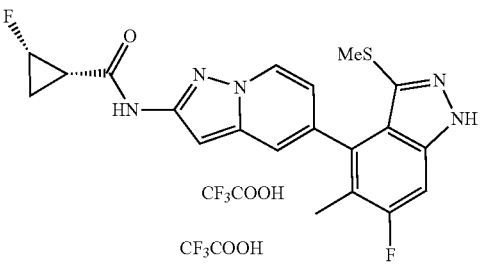 [SMILES: CSc1n[nH]c2cc(F)c(C)c(-c3ccn4nc(NC(=O)[C@@H]5C[C@@H]5F)cc4c3)c12 ; "CF3COOH" ; "CF3COOH"]<br>(1S,2S)-2-fluoro-N-(5-(6-fluoro-5-methyl-3-(methylthio)-1H-indazol-4-yl)pyrazolo[1,5-a]pyridin-2-yl)cyclopropane-1-carboxamide. 2 TFA | ¹H NMR (400 MHz, DMSO-d$_6$) δ 13.37 (s, 1H), 11.15 (s, 1H), 8.59 (d, J = 7.1 Hz, 1H), 7.60 (d, J = 1.0 Hz, 1H), 6.95 (d, J = 10.1 Hz, 1H), 6.91 (s, 1H), 6.88 (dd, J = 2.0, 7.1 Hz, 1H), 5.11-4.77 (m, 1H), 2.43 (s, 6H), 2.14 (td, J = 6.9, 13.9 Hz, 1H), 1.74-1.60 (m, 1H), 1.24-1.11 (m, 1H); LCMS (electrospray) m/z 414.4 (M + H)+. | J |

TABLE 1-continued

Compounds of Examples

| Ex # | Structure/Name | ¹H NMR/MS (M + 1) | Method |
|---|---|---|---|
| 472 | 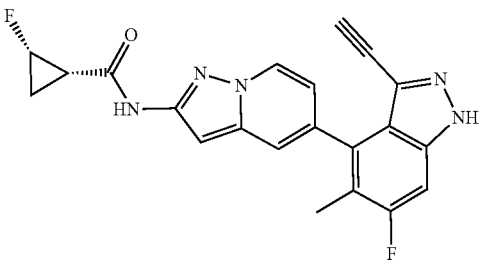 [SMILES: C#Cc1n[nH]c2cc(F)c(C)c(-c3ccn4nc(NC(=O)[C@@H]5C[C@@H]5F)cc4c3)c12]<br>(1S,2S)-N-(5-(3-ethynyl-6-fluoro-5-methyl-1H-indazol-4-yl)pyrazolo[1,5-a]pyridin-2-yl)-2-fluorocyclopropane-1-carboxamide | ¹H NMR (400 MHz, DMSO-$d_6$) δ 13.53 (s, 1H), 11.15 (br d, J = 5.6 Hz, 1H), 8.59 (d, J = 7.0 Hz, 1H), 7.52 (s, 1H), 7.45 (d, J = 9.7 Hz, 1H), 6.90 (s, 1H), 6.75 (dd, J = 1.7, 7.0 Hz, 1H), 5.09-4.80 (m, 1H), 3.79 (d, J = 2.9 Hz, 1H), 2.20-2.14 (m, 1H), 2.12 (br d, J = 1.7 Hz, 3H), 1.74-1.59 (m, 1H), 1.27-1.08 (m, 1H); LCMS (electrospray) m/z 392.2 (M + H+) | J |
| 473 | 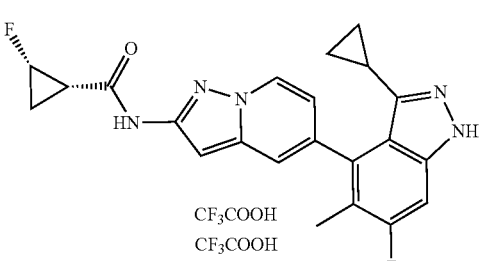<br>(1S,2S)-N-(5-(3-cyclopropyl-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, METHANOL-$d_4$) δ 8.49 (d, J = 7.2 Hz, 1H), 7.51 (s, 1H), 7.17 (d, J = 9.7 Hz, 1H), 6.80 (br d, J = 5.4 Hz, 1H), 4.98-4.76 (m, 1H), 2.15 (s, 3H), 2.12-2.03 (m, 1H), 1.87-1.73 (m, 1H), 1.40-1.30 (m, 1H), 1.27-1.15 (m, 1H), 0.83-0.74 (m, 1H), 0.69 (br s, 1H), 0.55-0.40 (m, 2H); LCMS (electrospray) m/z 408.4 (M + H+) | J |
| 474 | 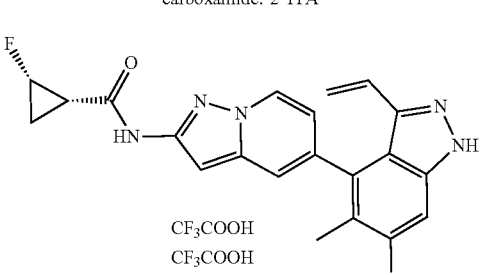<br>(1S,2S)-2-fluoro-N-(5-(6-fluoro-5-methyl-3-vinyl-1H-indazol-4-yl)pyrazolo[1,5-a]pyridin-2-yl)cyclopropane-1-carboxamide. 2 TFA | ¹H NMR (400 MHz, DMSO-$d_6$) δ 11.17 (d, J = 4.4 Hz, 1H), 8.67 (d, J = 7.1 Hz, 1H), 7.53 (s, 1H), 7.37 (d, J = 9.8 Hz, 1H), 6.91 (s, 1H), 6.73 (dd, J = 1.8, 7.1 Hz, 1H), 6.04-5.92 (m, 1H), 5.85-5.75 (m, 1H), 5.06-4.82 (m, 2H), 2.15 (br d, J = 6.5 Hz, 1H), 2.07 (t, J = 2.4 Hz, 3H), 1.74-1.60 (m, 1H), 1.24-1.11 (m, 1H); LCMS (electrospray) m/z 394.3 (M + H+) | J |
| 475 | 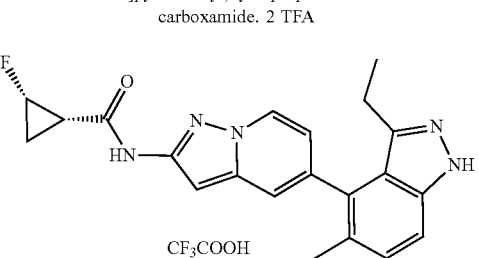<br>(1S,2S)-N-(5-(3-ethyl-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 11.16 (br d, J = 4.8 Hz, 1H), 8.63 (d, J = 7.1 Hz, 1H), 7.55 (s, 1H), 7.29 (d, J = 9.9 Hz, 1H), 6.90 (s, 1H), 6.76 (dd, J = 1.8, 7.0 Hz, 1H), 5.07-4.81 (m, 1H), 2.31-2.24 (m, 2H), 2.14 (br d, J = 6.7 Hz, 1H), 2.06 (t, J = 2.4 Hz, 3H), 1.75-1.59 (m, 1H), 1.24-1.09 (m, 1H), 0.90 (dt, J = 4.0, 7.5 Hz, 3H); LCMS (electrospray) m/z 396.3 (M + H+) | J |

TABLE 1-continued

Compounds of Examples

| Ex # | Structure/Name | ¹H NMR/MS (M + 1) | Method |
|---|---|---|---|
| 476 | (1S,2S)-N-(5-(5,7-dichloro-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 14.12 (br d, J = 0.7 Hz, 1H), 11.18 (s, 1H), 8.69 (d, J = 7.2 Hz, 1H), 8.04 (br s, 1H), 7.80 (s, 1H), 6.98 (s, 1H), 6.95 (dd, J = 1.8, 7.1 Hz, 1H), 5.05-4.84 (m, 1H), 2.18-2.11 (m, 1H), 1.73-1.62 (m, 1H), 1.23-1.15 (m, 1H); LCMS (electrospray) m/z 422.1 (M + H)+. | J |
| 477 | (1S,2S)-2-fluoro-N-(5-(6-fluoro-5,7-dimethyl-1H-indazol-4-yl)pyrazolo[1,5-a]pyridin-2-yl)cyclopropane-1-carboxamide. 2 TFA | ¹H NMR (400 MHz, DMSO-d$_6$) δ 13.31 (br s, 1H), 11.14 (s, 1H), 8.63 (d, J = 7.1 Hz, 1H), 7.77 (s, 1H), 7.63 (d, J = 1.0 Hz, 1H), 6.92 (s, 1H), 6.84 (dd, J = 1.8, 7.1 Hz, 1H), 5.11-4.75 (m, 1H), 2.47 (d, J = 1.6 Hz, 3H), 2.22 (d, J = 2.9 Hz, 3H), 2.15 (td, J = 6.8, 13.8 Hz, 1H), 1.74-1.60 (m, 1H), 1.17 (tdd, J = 6.3, 9.1, 12.4 Hz, 1H); LCMS (electrospray) m/z 382.4 (M + H)+. | J |
| 478 | (1S,2S)-N-(5-(5-chloro-7-(dimethylphosphoryl)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.16-12.54 (m, 1H), 11.20 (s, 1H), 8.71 (d, J = 7.2 Hz, 1H), 8.00 (s, 1H), 7.82 (s, 1H), 7.00 (s, 1H), 6.96 (dd, J = 1.8, 7.2 Hz, 1H), 5.11-4.79 (m, 1H), 2.15 (td, J = 6.9, 13.8 Hz, 1H), 1.96 (s, 3H), 1.92 (s, 3H), 1.76-1.60 (m, 1H), 1.18 (tdd, J = 6.4, 9.1, 12.2 Hz, 1H); LCMS (electrospray) m/z 464.1 (M + H)+. | J |
| 479 | (1S,2S)-N-(5-(7-chloro-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.80 (br s, 1H), 11.17 (s, 1H), 8.66 (d, J = 7.1 Hz, 1H), 7.90 (br s, 1H), 7.69 (s, 1H), 6.94 (s, 1H), 6.87 (dd, J = 2.0, 7.1 Hz, 1H), 5.10-4.78 (m, 1H), 2.27 (d, J = 2.8 Hz, 3H), 2.19-2.07 (m, 1H), 1.74-1.60 (m, 1H), 1.24-1.11 (m, 1H); LCMS (electrospray) m/z 402.0 (M + H)+. | J |

TABLE 1-continued

Compounds of Examples

| Ex # | Structure/Name | $^1$H NMR/MS (M + 1) | Method |
|---|---|---|---|
| 480 | 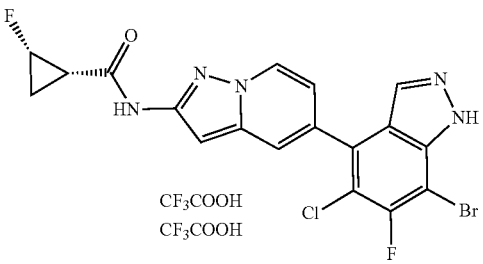 [SMILES: O=C(Nc1cc2cc(-c3c(Cl)c(F)c(Cl)c4[nH]ncc34)ccn2n1)[C@@H]1C[C@@H]1F ; "CF3COOH" ; "CF3COOH"]<br>CF$_3$COOH<br>CF$_3$COOH<br><br>(1S,2S)-N-(5-(7-bromo-5-chloro-6-fluoro-1H-indazol-4-yl)pyrazolo[1,5-a]pyridin-2-yl)-2-fluorocyclopropane-1-carboxamide. 2 TFA | $^1$H NMR (400 MHz, DMSO-d$_6$) δ 14.00 (br s, 1H), 11.18 (s, 1H), 8.68 (d, J = 7.2 Hz, 1H), 8.08 (br s, 1H), 7.80 (d, J = 0.8 Hz, 1H), 6.98 (s, 1H), 6.95 (dd, J = 1.9, 7.2 Hz, 1H), 5.08-4.79 (m, 1H), 2.15 (td, J = 7.0, 13.6 Hz, 1H), 1.75-1.60 (m, 1H), 1.26-1.09 (m, 1H); LCMS (electrospray) m/z 466.3 (M + H)+. | J |
| 481 | 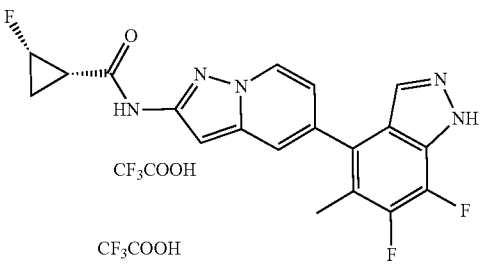 [SMILES: Cc1c(F)c(F)c2[nH]ncc2c1-c1ccn2nc(NC(=O)[C@@H]3C[C@@H]3F)cc2c1 ; "CF3COOH" ; "CF3COOH"]<br>CF$_3$COOH<br>CF$_3$COOH<br><br>(1S,2S)-N-(5-(6,7-difluoro-5-methyl-1H-indazol-4-yl)pyrazolo[1,5-a]pyridin-2-yl)-2-fluorocyclopropane-1-carboxamide. 2 TFA | $^1$H NMR (400 MHz, METHANOL-d$_4$) δ 8.54 (d, J = 7.1 Hz, 1H), 7.85 (d, J = 3.2 Hz, 1H), 7.59 (s, 1H), 6.98 (s, 1H), 6.86 (dd, J = 1.9, 7.2 Hz, 1H), 5.00-4.96 (m, 1H), 2.34 (d, J = 3.2 Hz, 3H), 2.20-2.16 (m, 1H), 1.92-1.72 (m, 1H), 1.30-1.15 (m, 1H); LCMS (electrospray) m/z 386.0 (M + H)+. | J |
| 482 | 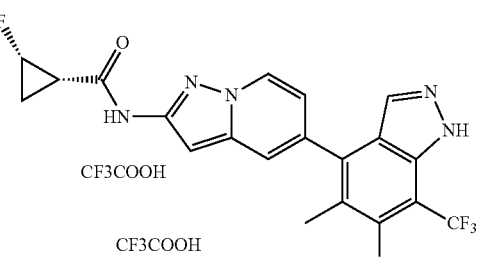<br>CF3COOH<br>CF3COOH<br><br>(1S,2S)-2-fluoro-N-(5-(6-fluoro-5-methyl-7-(trifluoromethyl)-1H-indazol-4-yl)pyrazolo[1,5-a]pyridin-2-yl)cyclopropane-1-carboxamide. 2 TFA | $^1$H NMR (400 MHz, METHANOL-d$_4$) δ 8.55 (d, J = 7.1 Hz, 1H), 7.89 (s, 1H), 7.63 (s, 1H), 7.00 (s, 1H), 6.87 (dd, J = 1.7, 7.1 Hz, 1H), 4.99-4.91 (m, 1H), 2.31 (d, J = 3.1 Hz, 3H), 2.14-2.04 (m, 1H), 1.87-1.75 (m, 1H), 1.27-1.16 (m, 1H); LCMS (electrospray) m/z 435.9 (M + H)+. | J |
| 483 | 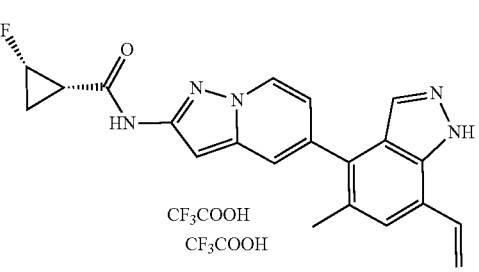 [SMILES: C=Cc1cc(C)c(-c2ccn3nc(NC(=O)[C@@H]4C[C@@H]4F)cc3c2)c2cn[nH]c12 ; "CF3COOH" ; "CF3COOH"]<br>CF$_3$COOH<br>CF$_3$COOH<br><br>(1S,2S)-2-fluoro-N-(5-(5-methyl-7-vinyl-1H-indazol-4-yl)pyrazolo[1,5-a]pyridin-2-yl)cyclopropane-1-carboxamide. 2 TFA | $^1$H NMR (400 MHz, DMSO-d$_6$) δ 13.36 (br s, 1H), 11.16 (s, 1H), 8.63 (d, J = 7.1 Hz, 1H), 7.81 (s, 1H), 7.65 (s, 1H), 7.52 (s, 1H), 7.15 (dd, J = 11.1, 18.0 Hz, 1H), 6.92 (s, 1H), 6.87 (dd, J = 1.8, 7.1 Hz, 1H), 6.11 (br d, J = 17.6 Hz, 1H), 5.51 (d, J = 11.6 Hz, 1H), 5.05-4.85 (m, 1H), 2.36 (s, 3H), 2.14 (br d, J = 8.1 Hz, 1H), 1.72-1.64 (m, 1H), 1.21-1.15 (m, 1H); LCMS (electrospray) m/z 376.1 (M + H)+. | J |

TABLE 1-continued

Compounds of Examples

| Ex # | Structure/Name | ¹H NMR/MS (M + 1) | Method |
|---|---|---|---|
| 484 | (1S,2S)-N-(5-(5-chloro-7-(dimethylamino)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.51 (br s, 1H), 11.16 (s, 1H), 8.64 (d, J = 7.1 Hz, 1H), 7.87 (s, 1H), 7.73 (d, J = 1.0 Hz, 1H), 6.95 (s, 1H), 6.91 (dd, J = 1.9, 7.2 Hz, 1H), 5.10-4.78 (m, 1H), 3.00 (br s, 6H), 2.15 (td, J = 7.0, 13.8 Hz, 1H), 1.74-1.61 (m, 1H), 1.24-1.11 (m, 1H); LCMS (electrospray) m/z 431.1 (M + H)+. | J |
| 485 | (1S,2S)-N-(5-(5-chloro-6-fluoro-7-(methylthio)-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.79 (s, 1H), 11.17 (s, 1H), 8.68 (d, J = 7.1 Hz, 1H), 7.98 (s, 1H), 7.79 (d, J = 1.0 Hz, 1H), 6.98 (s, 1H), 6.94 (dd, J = 2.0, 7.1 Hz, 1H), 5.08-4.77 (m, 1H), 2.57 (s, 3H), 2.15 (td, J = 6.9, 13.9 Hz, 1H), 1.74-1.61 (m, 1H), 1.18 (tdd, J = 6.3, 9.1, 12.3 Hz, 1H); LCMS (electrospray) m/z 434.2 (M + H)+. | J |
| 486 | (1S,2S)-N-(5-(5-chloro-6-fluoro-7-(methylsulfonyl)-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.51 (br s, 1H), 11.20 (s, 1H), 8.72 (d, J = 7.2 Hz, 1H), 8.10 (s, 1H), 7.84 (d, J = 1.0 Hz, 1H), 7.02 (s, 1H), 6.96 (dd, J = 1.9, 7.2 Hz, 1H), 5.07-4.77 (m, 1H), 3.56 (s, 3H), 2.15 (quin, J = 6.9 Hz, 1H), 1.75-1.58 (m, 1H), 1.18 (tdd, J = 6.3, 9.0, 12.3 Hz, 1H); LCMS (electrospray) m/z 466.1 (M + H)+. | J |
| 487 | (1S,2S)-N-(5-(7-bromo-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.69 (br s, 1H), 11.19 (s, 1H), 8.66 (d, J = 7.0 Hz, 1H), 7.92 (br s, 1H), 7.69 (d, J = 1.0 Hz, 1H), 6.94 (s, 1H), 6.87 (dd, J = 1.9, 7.1 Hz, 1H), 5.07-4.82 (m, 1H), 2.27 (d, J = 3.0 Hz, 3H), 2.20-2.10 (m, 1H), 1.74-1.60 (m, 1H), 1.18 (tdd, J = 6.2, 9.1, 12.3 Hz, 1H); LCMS (electrospray) m/z 448.1 (M + H)+. | J |

TABLE 1-continued

Compounds of Examples

| Ex # | Structure/Name | ¹H NMR/MS (M + 1) | Method |
|---|---|---|---|
| 488 | 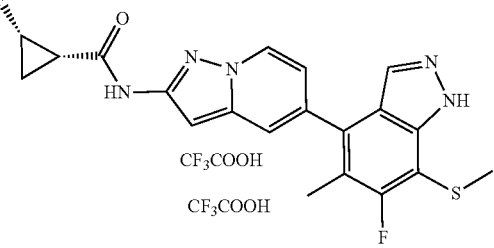<br>(1S,2S)-2-fluoro-N-(5-(6-fluoro-5-methyl-7-(methylthio)-1H-indazol-4-yl)pyrazolo[1,5-a]pyridin-2-yl)cyclopropane-1-carboxamide. 2 TFA | ¹H NMR (400 MHz, DMSO-$d_6$) δ 13.49 (s, 1H), 11.18 (s, 1H), 8.65 (d, J = 7.0 Hz, 1H), 7.84 (s, 1H), 7.68 (s, 1H), 6.93 (s, 1H), 6.87 (dd, J = 1.9, 7.1 Hz, 1H), 5.05-4.84 (m, 1H), 2.52 (br s, 3H), 2.24 (d, J = 2.9 Hz, 3H), 2.19-2.10 (m, 1H), 1.73-1.61 (m, 1H), 1.22-1.13 (m, 1H); LCMS (electrospray) m/z 414.2 (M + H)+. | J |
| 489 | 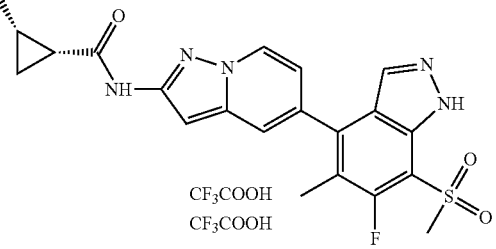<br>(1S,2S)-2-fluoro-N-(5-(6-fluoro-5-methyl-7-(methylsulfonyl)-1H-indazol-4-yl)pyrazolo[1,5-a]pyridin-2-yl)cyclopropane-1-carboxamide. 2 TFA | ¹H NMR (400 MHz, DMSO-$d_6$) δ 13.23 (s, 1H), 11.21 (s, 1H), 8.70 (d, J = 7.2 Hz, 1H), 7.95 (s, 1H), 7.74 (d, J = 0.9 Hz, 1H), 6.97 (s, 1H), 6.90 (dd, J = 1.9, 7.2 Hz, 1H), 5.05-4.84 (m, 1H), 3.50 (s, 3H), 2.27 (d, J = 2.8 Hz, 3H), 2.15 (td, J = 6.9, 13.9 Hz, 1H), 1.73-1.62 (m, 1H), 1.25-1.12 (m, 1H); LCMS (electrospray) m/z 446.2 (M + H)+. | J |
| 490 | 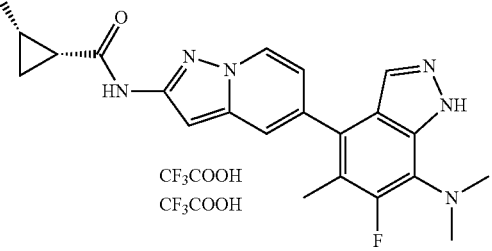<br>(1S,2S)-N-(5-(7-(dimethylamino)-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 11.14 (s, 1H), 8.62 (d, J = 7.2 Hz, 1H), 7.75 (s, 1H), 7.61 (d, J = 1.0 Hz, 1H), 6.90 (s, 1H), 6.84 (dd, J = 1.9, 7.1 Hz, 1H), 5.05-5.00 (m, 1H), 4.88-4.83 (m, 1H), 2.96 (d, J = 2.0 Hz, 6H), 2.20 (d, J = 3.4 Hz, 3H), 2.17-2.09 (m, 1H), 1.73-1.61 (m, 1H), 1.21-1.12 (m, 1H); LCMS (electrospray) m/z 411.2 (M + H)+. | J |
| 491 | 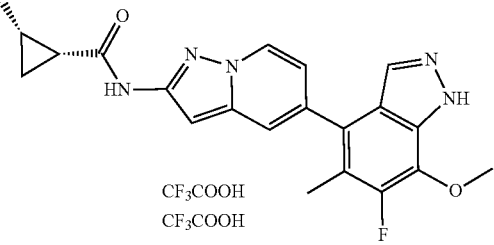<br>(1S,2S)-2-fluoro-N-(5-(6-fluoro-7-methoxy-5-methyl-1H-indazol-4-yl)pyrazolo[1,5-a]pyridin-2-yl)cyclopropane-1-carboxamide. 2 TFA | ¹H NMR (400 MHz, DMSO-$d_6$) δ 13.49 (br s, 1H), 11.14 (s, 1H), 8.62 (d, J = 7.0 Hz, 1H), 7.79 (br s, 1H), 7.62 (d, J = 1.0 Hz, 1H), 6.91 (s, 1H), 6.84 (dd, J = 1.9, 7.1 Hz, 1H), 5.08-4.80 (m, 1H), 4.08 (s, 3H), 2.23 (d, J = 3.1 Hz, 3H), 2.15 (td, J = 6.9, 14.0 Hz, 1H), 1.75-1.59 (m, 1H), 1.24-1.11 (m, 1H); LCMS (electrospray) m/z 398.2 (M + H)+. | J |

TABLE 1-continued

Compounds of Examples

| Ex # | Structure/Name | ¹H NMR/MS (M + 1) | Method |
|---|---|---|---|
| 492 | 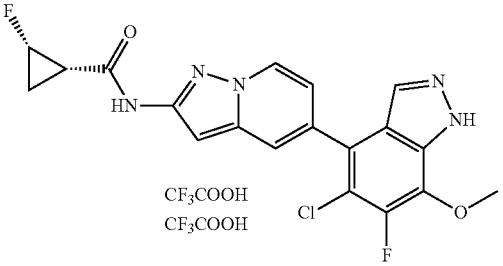 [SMILES: COc1c(F)c(Cl)c(-c2ccn3nc(NC(=O)[C@@H]4C[C@@H]4F)cc3c2)c2cn[nH]c12 ; "CF3COOH" ; "CF3COOH"]<br>(1S,2S)-N-(5-(5-chloro-6-fluoro-7-methoxy-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.84 (br s, 1H), 11.16 (s, 1H), 8.66 (d, J = 7.2 Hz, 1H), 7.94 (s, 1H), 7.77-7.72 (m, 1H), 6.96 (s, 1H), 6.91 (dd, J = 1.9, 7.1 Hz, 1H), 5.09-4.77 (m, 1H), 4.16 (d, J = 1.5 Hz, 3H), 2.15 (td, J = 6.9, 13.7 Hz, 1H), 1.74-1.59 (m, 1H), 1.24-1.10 (m, 1H); LCMS (electrospray) m/z 418.2 (M + H)+. | J |
| 493 | 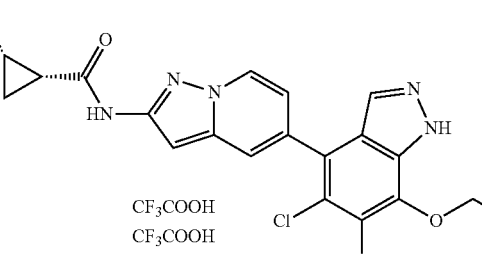<br>(1S,2S)-N-(5-(5-chloro-7-ethoxy-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.80 (br s, 1H), 11.17 (s, 1H), 8.66 (d, J = 7.1 Hz, 1H), 7.94 (br s, 1H), 7.75 (s, 1H), 6.95 (s, 1H), 6.92 (dd, J = 1.8, 7.2 Hz, 1H), 5.13-4.78 (m, 1H), 4.39 (br d, J = 6.5 Hz, 2H), 2.21-2.09 (m, 1H), 1.74-1.60 (m, 1H), 1.41 (t, J = 7.0 Hz, 3H), 1.24-1.12 (m, 1H); LCMS (electrospray) m/z 432.4 (M + H)+. | J |
| 494 | 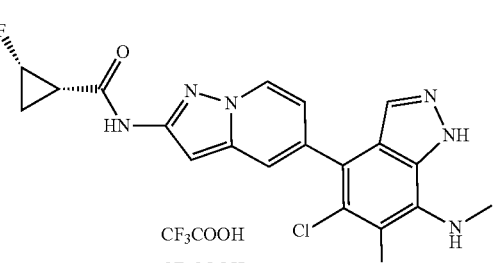<br>(1S,2S)-N-(5-(5-chloro-6-fluoro-7-(methylamino)-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 11.14 (s, 1H), 8.60 (d, J = 7.1 Hz, 1H), 7.88 (s, 1H), 7.68 (dd, J = 0.8, 1.8 Hz, 1H), 6.92 (s, 1H), 6.89 (dd, J = 2.0, 7.1 Hz, 1H), 5.08-4.78 (m, 1H), 3.17 (d, J = 2.8 Hz, 3H), 2.14 (td, J = 7.0, 13.9 Hz, 1H), 1.74-1.58 (m, 1H), 1.17 (tdd, J = 6.3, 9.0, 12.3 Hz, 1H); LCMS (electrospray) m/z 417.4 (M + H)+. | J |
| 495 | 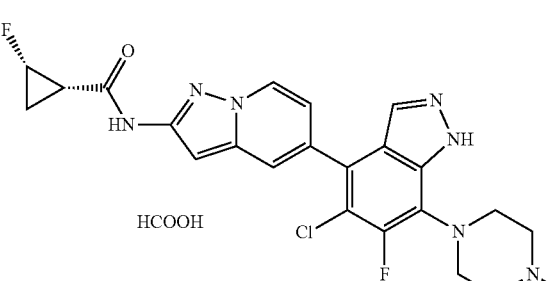<br>(1S,2S)-N-(5-(5-chloro-6-fluoro-7-(4-methylpiperazin-1-yl)-1H-indazol-4-yl)pyrazolo[1,5-a]pyridin-2-yl)-2-fluorocyclopropane-1-carboxamide. 1 FA | ¹H NMR (400 MHz, DMSO-$d_6$) δ 13.44 (br d, J = 2.8 Hz, 1H), 11.18 (s, 1H), 8.65 (d, J = 7.1 Hz, 1H), 8.17 (s, 1H), 7.90 (br s, 1H), 7.77-7.68 (m, 1H), 6.95 (s, 1H), 6.91 (dd, J = 2.0, 7.1 Hz, 1H), 5.06-4.83 (m, 1H), 3.30 (br s, 4H), 2.57 (br s, 4H), 2.28 (s, 3H), 2.19-2.10 (m, 1H), 1.73-1.60 (m, 1H), 1.25-1.11 (m, 1H); LCMS (electrospray) m/z 486.2 (M + H)+. | J |

TABLE 1-continued

Compounds of Examples

| Ex # | Structure/Name | ¹H NMR/MS (M + 1) | Method |
|------|----------------|-------------------|--------|
| 496 | 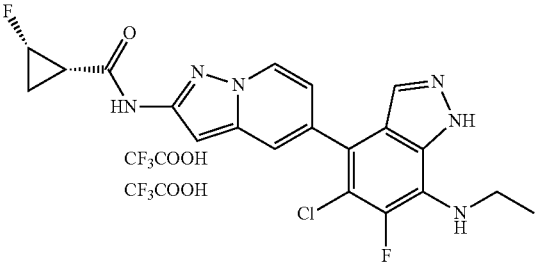 [SMILES: CCNc1c(F)c(Cl)c(-c2ccn3nc(NC(=O)[C@@H]4C[C@@H]4F)cc3c2)c2cn[nH]c12 ; "CF3COOH" ; "CF3COOH"]<br>(1S,2S)-N-(5-(5-chloro-7-(ethylamino)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 11.16 (1 H, s) 8.62 (1 H, d, J = 7.20 Hz) 7.89 (1 H, br s) 7.70 (1 H, d, J = 1.00 Hz) 7.04-6.79 (2 H, m) 5.07-4.70 (1 H, m) 2.15 (1 H, dt, J = 13.85, 7.02 Hz) 1.73-1.61 (1 H, m) 1.25-1.16 (4 H, m); LCMS (electrospray) m/z 431.0 (M + H)+. | J |
| 497 | 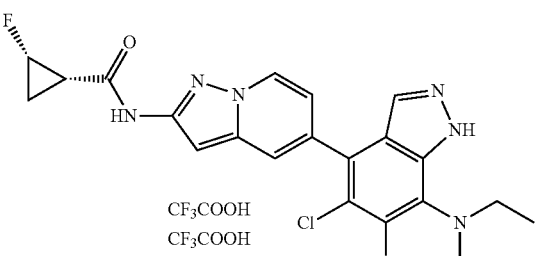<br>(1S,2S)-N-(5-(5-chloro-7-(diethylamino)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.78-13.23 (1 H, m) 11.18 (1 H, s) 8.66 (1 H, d, J = 7.20 Hz) 7.90 (1 H, s) 7.83-7.73 (1 H, m) 7.05-6.90 (2 H, m) 5.10-4.83 (1 H, m) 3.30 (4 H, q, J = 6.65 Hz) 2.15 (1 H, dt, J = 13.77, 6.98 Hz) 1.77-1.61 (1 H, m) 1.27-1.14 (1 H, m) 1.02 (6 H, t, J = 7.09 Hz); LCMS (electrospray) m/z 459.0 (M + H)+. | J |
| 498 | 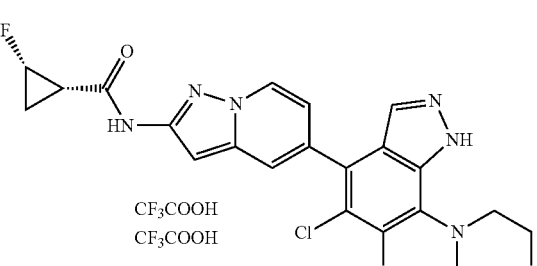<br>(1S,2S)-N-(5-(5-chloro-6-fluoro-7-morpholino-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.53 (br s, 1H), 11.16 (s, 1H), 8.65 (d, J = 7.2 Hz, 1H), 7.90 (br s, 1H), 7.74 (d, J = 1.0 Hz, 1H), 6.95 (s, 1H), 6.93-6.88 (m, 1H), 5.05-4.83 (m, 1H), 3.92-3.76 (m, 4H), 3.30-3.21 (m, 4H), 2.14 (td, J = 6.9, 13.9 Hz, 1H), 1.73-1.61 (m, 1H), 1.18 (tdd, J = 6.2, 9.1, 12.3 Hz, 1H); LCMS (electrospray) m/z 473.3 (M + H)+. | J |
| 499 | 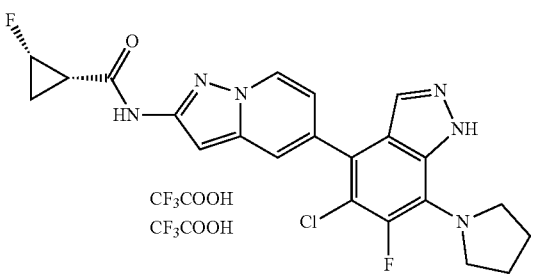 [SMILES: O=C(Nc1cc2cc(-c3c(Cl)c(F)c(N4CCCC4)c4[nH]ncc34)ccn2n1)[C@@H]1C[C@@H]1F ; "CF3COOH" ; "CF3COOH"]<br>(1S,2S)-N-(5-(5-chloro-6-fluoro-7-(pyrrolidin-1-yl)-1H-indazol-4-yl)pyrazolo[1,5-a]pyridin-2-yl)-2-fluorocyclopropane-1-carboxamide. 2 TFA | ¹H NMR (400 MHz, DMSO-d$_6$) δ 13.24 (br s, 1H), 11.14 (s, 1H), 8.61 (d, J = 7.2 Hz, 1H), 7.89 (br s, 1H), 7.69 (d, J = 1.0 Hz, 1H), 6.92 (s, 1H), 6.88 (dd, J = 2.0, 7.1 Hz, 1H), 5.07-4.82 (m, 1H), 3.72 (br s, 4H), 2.19-2.10 (m, 1H), 1.99-1.90 (m, 4H), 1.74-1.61 (m, 1H), 1.23-1.12 (m, 1H); LCMS (electrospray) m/z 457.3 (M + H)+. | J |

TABLE 1-continued

Compounds of Examples

| Ex # | Structure/Name | ¹H NMR/MS (M + 1) | Method |
|---|---|---|---|
| 500 | 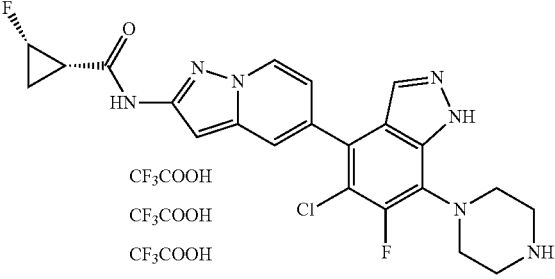 [SMILES: O=C(Nc1cc2cc(-c3c(Cl)c(F)c(N4CCNCC4)c4[nH]ncc34)ccn2n1)[C@@H]1C[C@@H]1F ; "CF3COOH" ; "CF3COOH" ; "CF3COOH"]<br><br>CF₃COOH<br>CF₃COOH<br>CF₃COOH<br><br>(1S,2S)-N-(5-(5-chloro-6-fluoro-7-(piperazin-1-yl)-1H-indazol-4-yl)pyrazolo[1,5-a]pyridin-2-yl)-2-fluorocyclopropane-1-carboxamide. 3 TFA | ¹H NMR (400 MHz, DMSO-d₆) δ 13.61 (br s, 1H), 11.17 (s, 1H), 8.81 (br s, 2H), 8.67 (d, J = 7.1 Hz, 1H), 7.94 (br s, 1H), 7.73 (d, J = 1.0 Hz, 1H), 6.97 (s, 1H), 6.90 (dd, J = 1.9, 7.2 Hz, 1H), 5.08-4.81 (m, 1H), 3.62-3.40 (m, 8H), 2.22-2.09 (m, 1H), 1.74-1.59 (m, 1H), 1.26-1.11 (m, 1H); LCMS (electrospray) m/z 472.3 (M + H)+. | J |
| 501 | 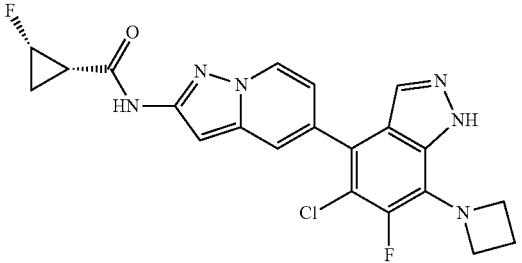 [SMILES: O=C(Nc1cc2cc(-c3c(Cl)c(F)c(N4CCC4)c4[nH]ncc34)ccn2n1)[C@@H]1C[C@@H]1F]<br><br>(1S,2S)-N-(5-(7-(azetidin-1-yl)-5-chloro-6-fluoro-1H-indazol-4-yl)pyrazolo[1,5-a]pyridin-2-yl)-2-fluorocyclopropane-1-carboxamide | ¹H NMR (400 MHz, DMSO-d₆) δ13.10 (br s, 1H), 11.14 (s, 1H), 8.61 (d, J = 7.1 Hz, 1H), 7.88 (br s, 1H), 7.68 (d, J = 0.9 Hz, 1H), 6.92 (s, 1H), 6.88 (dd, J = 1.9, 7.1 Hz, 1H), 5.16-4.74 (m, 1H), 4.51-4.25 (m, 4H), 2.35 (quin, J = 7.3 Hz, 2H), 2.14 (td, J = 6.9, 13.9 Hz, 1H), 1.76-1.57 (m, 1H), 1.29-1.06 (m, 1H); LCMS (electrospray) m/z 443.3 (M + H)+. | J |
| 502 | 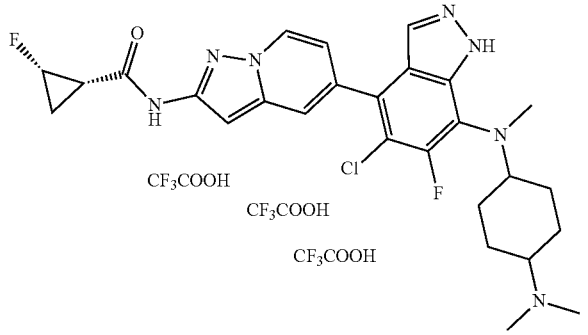 [SMILES: CN(C)C1CCC(N(C)c2c(F)c(Cl)c(-c3ccn4nc(NC(=O)[C@@H]5C[C@@H]5F)cc4c3)c3cn[nH]c23)CC1 ; "CF3COOH" ; "CF3COOH" ; "CF3COOH"]<br><br>CF₃COOH<br>CF₃COOH<br>CF₃COOH<br><br>(1S,2S)-N-(5-(5-chloro-7-((4-(dimethylamino)cyclohexyl)(methyl)amino)-6-fluoro-1H-indazol-4-yl)pyrazolo[1,5-a]pyridin-2-yl)-2-fluorocyclopropane-1-carboxamide. 3 TFA | ¹H NMR (400 MHz, DMSO-d₆) δ 13.45 (br s, 1H), 11.17 (s, 1H), 9.37 (br s, 1H), 8.66 (d, J = 7.1 Hz, 1H), 7.90 (br s, 1H), 7.74 (d, J = 1.0 Hz, 1H), 6.96 (s, 1H), 6.92 (dd, J = 2.0, 7.1 Hz, 1H), 5.05-4.84 (m, 1H), 3.13 (br s, 2H), 2.92 (d, J = 2.4 Hz, 3H), 2.72 (s, 3H), 2.70 (s, 3H), 2.14 (br d, J = 7.1 Hz, 1H), 2.02 (br s, 4H), 1.73-1.62 (m, 1H), 1.48 (br s, 4H), 1.23-1.13 (m, 1H); LCMS(electrospray) m/z542.3 (M + H+). | J |

TABLE 1-continued

Compounds of Examples

| Ex # | Structure/Name | ¹H NMR/MS (M + 1) | Method |
|---|---|---|---|
| 503 | 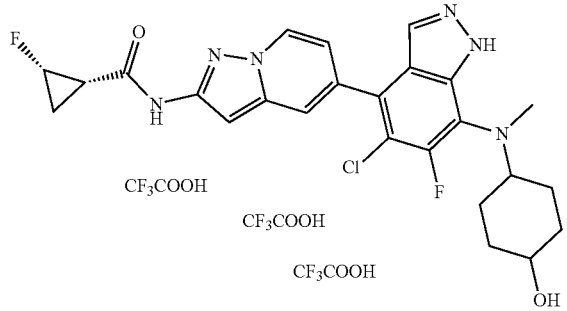 [SMILES: CN(c1c(F)c(Cl)c(-c2ccn3nc(NC(=O)[C@@H]4C[C@@H]4F)cc3c2)c2cn[nH]c12)C1CCC(O)CC1 ; "CF3COOH" ; "CF3COOH" ; "CF3COOH"]<br>CF₃COOH  CF₃COOH  CF₃COOH<br>(1S,2S)-N-(5-(5-chloro-6-fluoro-7-((4-hydroxycyclohexyl)(methyl)amino)-1H-indazol-4-yl)pyrazolo[1,5-a]pyridin-2-yl)-2-fluorocyclopropane-1-carboxamide. 3 TFA | ¹H NMR (400 MHz, DMSO-d₆) δ 13.94-13.16 (m, 1H), 11.18 (s, 1H), 8.66 (d, J = 7.2 Hz, 1H), 7.90 (s, 1H), 7.82-7.71 (m, 1H), 7.84-7.70 (m, 1H), 7.04-6.85 (m, 2H), 5.09-4.82 (m, 1H), 3.44-3.32 (m, 1H), 3.24-3.06 (m, 1H), 2.95-2.81 (m, 3H), 2.23-2.07 (m, 1H), 1.90-1.76 (m, 3H), 1.74-1.34 (m, 6H), 1.26-1.07 (m, 3H); LCMS(electrospray) m/z 515.2 (M + H+). | J |
| 504 | 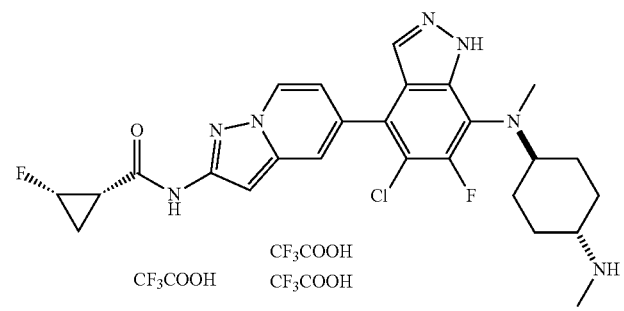<br>CF₃COOH  CF₃COOH  CF₃COOH<br>(1S,2S)-N-(5-(5-chloro-6-fluoro-7-(methyl((1R,4R)-4-(methylamino)cyclohexyl)amino)-1H-indazol-4-yl)pyrazolo[1,5-a]pyridin-2-yl)-2-fluorocyclopropane-1-carboxamide. 3 TFA | ¹H NMR (400 MHz, DMSO-d₆) δ 13.44 (br s, 1H), 11.17 (s, 1H), 8.66 (d, J = 7.1 Hz, 1H), 8.37 (br s, 2H), 7.91 (s, 1H), 7.74 (d, J = 1.0 Hz, 1H), 6.96 (s, 1H), 6.92 (dd, J = 2.0, 7.2 Hz, 1H), 5.07-4.82 (m, 1H), 3.10 (br s, 1H), 2.91 (d, J = 2.6 Hz, 3H), 2.56-2.52 (m, 5H), 2.15 (td, J = 6.9, 13.5 Hz, 1H), 2.06 (br d, J = 9.9 Hz, 2H), 1.99 (br d, J = 11.5 Hz, 2H), 1.72-1.61 (m, 1H), 1.54-1.44 (m, 2H), 1.38-1.26 (m, 2H), 1.21-1.14 (m, 1H); LCMS(electrospray) m/z 528.3 (M + H+). | J |
| 505 | 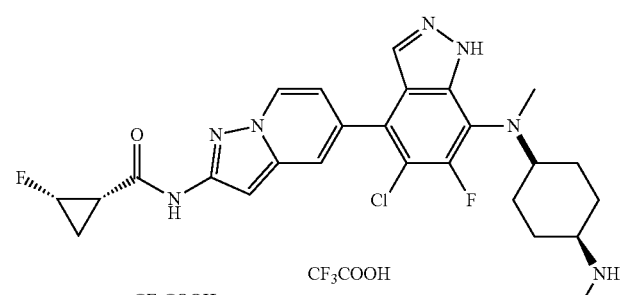<br>CF₃COOH  CF₃COOH  CF₃COOH<br>(1S,2S)-N-(5-(5-chloro-6-fluoro-7-(methyl((1S,4S)-4-(methylamino)cyclohexyl)amino)-1H-indazol-4-yl)pyrazolo[1,5-a]pyridin-2-yl)-2-fluorocyclopropane-1-carboxamide. 3 TFA | ¹H NMR (400 MHz, DMSO-d₆) δ 13.35 (br s, 1H), 11.18 (s, 1H), 8.67 (d, J = 7.2 Hz, 1H), 8.33 (br s, 2H), 7.94 (s, 1H), 7.79-7.75 (m, 1H), 6.97 (s, 1H), 6.94 (dd, J = 2.0, 7.1 Hz, 1H), 5.06-4.84 (m, 1H), 3.08 (br s, 1H), 2.85 (s, 3H), 2.57 (t, J = 5.4 Hz, 3H), 2.54-2.52 (m, 2H), 2.15 (td, J = 7.2, 14.0 Hz, 1H), 1.83 (br s, 4H), 1.72-1.56 (m, 5H), 1.23-1.13 (m, 1H); LCMS(electrospray) m/z 528.3 (M + H+). | J |

TABLE 1-continued

Compounds of Examples

| Ex # | Structure/Name | ¹H NMR/MS (M + 1) | Method |
|---|---|---|---|
| 506 | <br>CF₃COOH<br>CF₃COOH<br><br>(1S,2S)-2-fluoro-N-(5-(7-methoxy-5-methyl-1H-indazol-4-yl)pyrazolo[1,5-a]pyridin-2-yl)cyclopropane-1-carboxamide. 2 TFA | ¹H NMR (400 MHz, DMSO-d₆) δ 13.33 (br s, 1H), 11.11 (s, 1H), 8.58 (d, J = 7.0 Hz, 1H), 7.71 (s, 1H), 7.57 (d, J = 0.9 Hz, 1H), 6.88 (s, 1H), 6.84-6.79 (m, 2H), 5.07-4.80 (m, 1H), 3.99 (s, 3H), 2.35 (s, 3H), 2.14 (td, J = 7.1, 14.0 Hz, 1H), 1.73-1.61 (m, 1H), 1.17 (tdd, J = 6.2, 8.9, 12.3 Hz, 1H); LCMS(electrospray) m/z 380.2 (M + H+). | J |
| 507 | 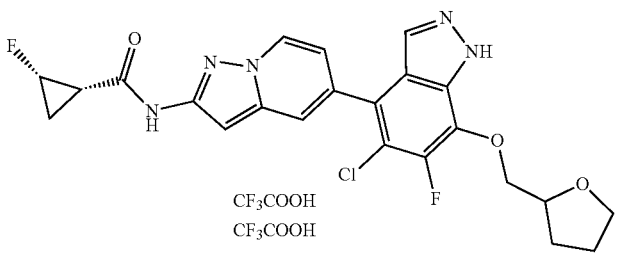 [SMILES: O=C(Nc1cc2cc(-c3c(Cl)c(F)c(OCC4CCCO4)c4[nH]ncc34)ccn2n1)[C@@H]1C[C@@H]1F ; "CF3COOH" ; "CF3COOH"]<br>CF₃COOH<br>CF₃COOH<br><br>(1S,2S)-N-(5-(5-chloro-6-fluoro-7-((tetrahydrofuran-2-yl)methoxy)-1H-indazol-4-yl)pyrazolo[1,5-a]pyridin-2-yl)-2-fluorocyclopropane-1-carboxamide. 2 TFA | ¹H NMR (400 MHz, DMSO-d₆) δ 13.76 (br s, 1H), 11.18 (s, 1H), 8.66 (d, J = 7.1 Hz, 1H), 7.94 (br s, 1H), 7.75 (d, J = 1.0 Hz, 1H), 6.95 (s, 1H), 6.92 (dd, J = 2.0, 7.1 Hz, 1H), 5.06-4.83 (m, 1H), 4.33 (br s, 2H), 4.27-4.20 (m, 1H), 3.81-3.74 (m, 1H), 3.69 (dt, J = 6.1, 7.6 Hz, 1H), 2.18-2.10 (m, 1H), 2.07-1.98 (m, 1H), 1.92-1.81 (m, 2H), 1.80-1.73 (m, 1H), 1.72-1.62 (m, 1H), 1.18 (tdd, J = 6.2, 9.1, 12.3 Hz, 1H); LCMS(electrospray) m/z 488.2 (M + H+). | J |
| 508 | 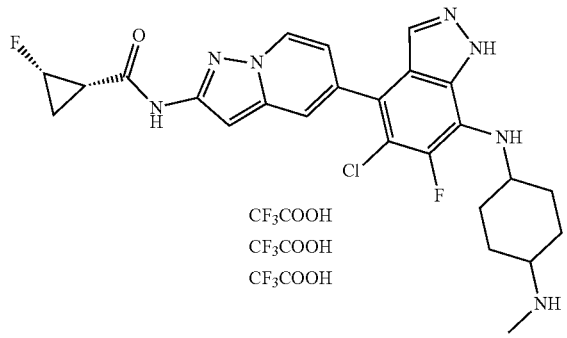 [SMILES: CNC1CCC(Nc2c(F)c(Cl)c(-c3ccn4nc(NC(=O)[C@@H]5C[C@@H]5F)cc4c3)c3cn[nH]c23)CC1 ; "CF3COOH" ; "CF3COOH" ; "CF3COOH"]<br>CF₃COOH<br>CF₃COOH<br>CF₃COOH<br><br>(1S,2S)-N-(5-(5-chloro-6-fluoro-7-((4-(methylamino)cyclohexyl)amino)-1H-indazol-4-yl)pyrazolo[1,5-a]pyridin-2-yl)-2-fluorocyclopropane-1-carboxamide. 3 TFA | ¹H NMR (400 MHz, DMSO-d₆) δ 13.30 (br s, 1H), 11.16 (s, 1H), 8.62 (br d, J = 7.1 Hz, 1H), 8.45 (br s, 2H), 7.85 (s, 1H), 7.70 (s, 1H), 6.93 (s, 1H), 6.89 (dd, J = 2.0, 7.1 Hz, 1H), 5.27 (br d, J = 8.9 Hz, 1H), 5.05-4.83 (m, 1H), 3.60 (br s, 1H), 2.99 (br s, 1H), 2.58 (br t, J = 5.2 Hz, 3H), 2.52 (br s, 1H), 2.18-2.12 (m, 1H), 2.08 (br d, J = 9.8 Hz, 4H), 1.72-1.62 (m, 1H), 1.45-1.32 (m, 4H), 1.23-1.14 (m, 1H); | J |
| 509 | 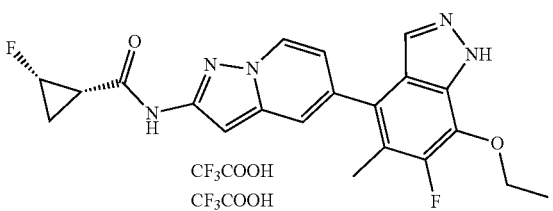 [SMILES: CCOc1c(F)c(C)c(-c2ccn3nc(NC(=O)[C@@H]4C[C@@H]4F)cc3c2)c2cn[nH]c12 ; "CF3COOH" ; "CF3COOH"]<br>CF₃COOH<br>CF₃COOH<br><br>(1S,2S)-N-(5-(7-ethoxy-6-fluoro-5-methyl-1H-indazol-4-yl)pyrazolo[1,5-a]pyridin-2-yl)-2-fluorocyclopropane-1-carboxamide. 2 TFA | ¹H NMR (400 MHz, DMSO-d₆) δ 13.47 (br s, 1H), 11.16 (s, 1H), 8.62 (d, J = 7.1 Hz, 1H), 7.79 (s, 1H), 7.64 (d, J = 0.9 Hz, 1H), 6.91 (s, 1H), 6.85 (dd, J = 2.0, 7.1 Hz, 1H), 5.10-4.81 (m, 1H), 4.31 (br d, J = 6.8 Hz, 2H), 2.23 (d, J = 3.1 Hz, 3H), 2.14 (td, J = 6.9, 13.9 Hz, 1H), 1.73-1.61 (m, 1H), 1.39 (t, J = 7.0 Hz, 3H), 1.17 (tdd, J = 6.2, 9.1, 12.3 Hz, 1H); LCMS(electrospray) m/z 412.2 (M + H+). | J |

TABLE 1-continued

Compounds of Examples

| Ex # | Structure/Name | ¹H NMR/MS (M + 1) | Method |
|---|---|---|---|
| 510 | 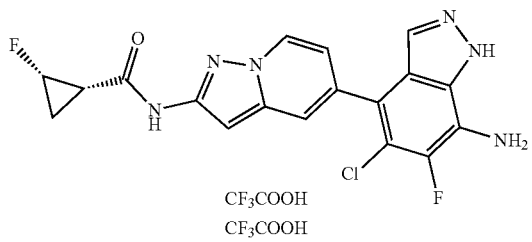 [SMILES: Nc1c(F)c(Cl)c(-c2ccn3nc(NC(=O)[C@@H]4C[C@@H]4F)cc3c2)c2cn[nH]c12 ; "CF3COOH" ; "CF3COOH"]<br>(1S,2S)-N-(5-(7-amino-5-chloro-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.16-12.81 (m, 1H), 11.15 (s, 1H), 8.61 (d, J = 7.1 Hz, 1H), 7.84 (s, 1H), 7.72-7.66 (m, 1H), 6.95-6.86 (m, 2H), 6.00-5.59 (m, 2H), 5.17-4.76 (m, 1H), 2.21-2.09 (m, 1H), 1.76-1.59 (m, 1H), 1.43-1.36 (m, 1H), 1.26-1.11 (m, 1H); LCMS(electrospray) m/z 403.1 (M + H+). | J |
| 511 | 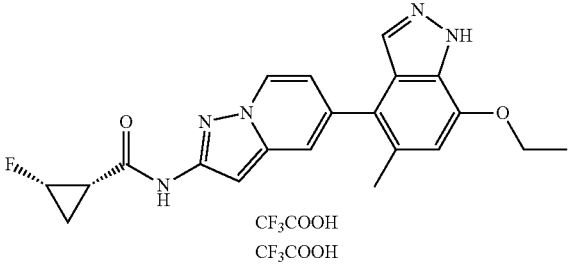 [SMILES: CCOc1cc(C)c(-c2ccn3nc(NC(=O)[C@@H]4C[C@@H]4F)cc3c2)c2cn[nH]c12 ; "CF3COOH" ; "CF3COOH"]<br>(1S,2S)-N-(5-(7-ethoxy-5-methyl-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.28 (s, 1H), 11.12 (s, 1H), 8.58 (d, J = 7.1 Hz, 1H), 7.70 (d, J = 1.2 Hz, 1H), 7.57 (dd, J = 0.9, 1.7 Hz, 1H), 6.87 (s, 1H), 6.84-6.79 (m, 2H), 5.05-4.83 (m, 1H), 4.27 (q, J = 7.0 Hz, 2H), 2.34 (s, 3H), 2.19-2.09 (m, 1H), 1.72-1.61 (m, 1H), 1.46 (t, J = 7.0 Hz, 3H), 1.17 (tdd, J = 6.3, 9.0, 12.3 Hz, 1H); LCMS(electrospray) m/z 393.9 (M + H+). | J |
| 512 | 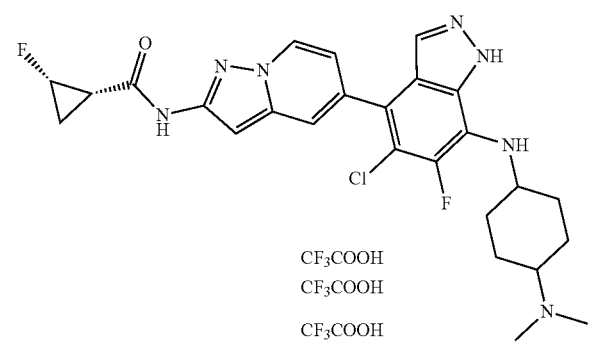 [SMILES: CN(C)C1CCC(Nc2c(F)c(Cl)c(-c3ccn4nc(NC(=O)[C@@H]5C[C@@H]5F)cc4c3)c3cn[nH]c23)CC1 ; "CF3COOH" ; "CF3COOH" ; "CF3COOH"]<br>(1S,2S)-N-(5-(5-chloro-7-((4-(dimethylamino)cyclohexyl)amino)-6-fluoro-1H-indazol-4-yl)pyrazolo[1,5-a]pyridin-2-yl)-2-fluorocyclopropane-1-carboxamide. 3 TFA | ¹H NMR (400 MHz, DMSO-$d_6$) δ 13.27 (br s, 1H), 11.15 (s, 1H), 9.49 (br s, 1H), 8.62 (d, J = 7.1 Hz, 1H), 7.88 (br s, 1H), 7.69 (d, J = 1.0 Hz, 1H), 6.93 (s, 1H), 6.90 (dd, J = 2.0, 7.2 Hz, 1H), 5.33 (br s, 1H), 5.11-4.77 (m, 1H), 3.19 (br d, J = 9.0 Hz, 1H), 2.77 (s, 3H), 2.76 (s, 3H), 2.52 (d, J = 2.0 Hz, 1H), 2.12 (br d, J = 11.7 Hz, 3H), 2.04 (br d, J = 10.8 Hz, 2H), 1.72-1.61 (m, 1H), 1.61-1.51 (m, 2H), 1.46-1.32 (m, 2H), 1.17 (tdd, J = 6.2, 9.0, 12.4 Hz, 1H); LCMS(electrospray) m/z 528.3 (M + H+). | J |

TABLE 1-continued

Compounds of Examples

| Ex # | Structure/Name | ¹H NMR/MS (M + 1) | Method |
|---|---|---|---|
| 513 | 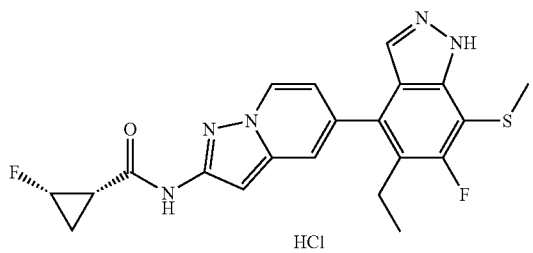<br>(1S,2S)-N-(5-(5-ethyl-6-fluoro-7-(methylthio)-1H-indazol-4-yl)pyrazolo[1,5-a]pyridin-2-yl)-2-fluorocyclopropane-1-carboxamide dihydrochloride. 2 HCl | ¹H NMR (400 MHz, DMSO-$d_6$) δ 13.49 (s, 1H), 11.18 (s, 1H), 8.66 (d, J = 7.2 Hz, 1H), 7.76 (s, 1H), 7.64 (s, 1H), 6.93 (s, 1H), 6.82 (d, J = 7.2 Hz, 1H), 5.04-4.84 (m, 1H), 2.69-2.62 (m, 2H), 2.50 (s, 3H), 2.16-2.12 (m, 1H), 1.70-1.63 (m, 1H), 1.28-1.12 (m, 1H), 1.12-1.08 (m, 3H); LCMS (electrospray) m/z 428.1 (M + H)+. | J |
| 514 | 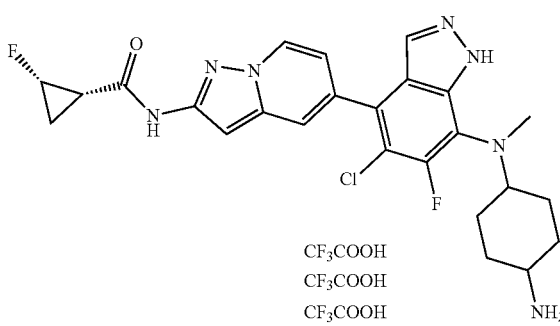 [SMILES: CN(c1c(F)c(Cl)c(-c2ccn3nc(NC(=O)[C@@H]4C[C@@H]4F)cc3c2)c2cn[nH]c12)C1CCC(N)CC1 ; "CF3COOH" ; "CF3COOH" ; "CF3COOH"]<br>(1S,2S)-N-(5-7-((4-aminocyclohexyl)(methyl)amino)-5-chloro-6-fluoro-1H-indazol-4-yl)pyrazolo[1,5-a]pyridin-2-yl)-2-fluorocyclopropane-1-carboxamide. 3 TFA | ¹H NMR (400 MHz, DMSO-$d_6$) δ 13.63-13.08 (m, 1H), 11.19 (s, 1H), 8.67 (td, J = 1.0, 7.1 Hz, 1H), 8.03-7.86 (m, 1H), 7.83-7.56 (m, 4H), 7.06-6.86 (m, 2H), 5.14-4.81 (m, 2H), 3.24-3.15 (m, 1H), 2.95-2.84 (m, 4H), 2.15 (td, J = 7.0, 13.9 Hz, 1H), 2.02-1.91 (m, 2H), 1.86-1.74 (m, 2H), 1.73-1.45 (m, 4H), 1.41-1.28 (m, 1H), 1.25-1.12 (m, 1H); LCMS(electrospray) m/z 514.1 (M + H+). | J |
| 515 | 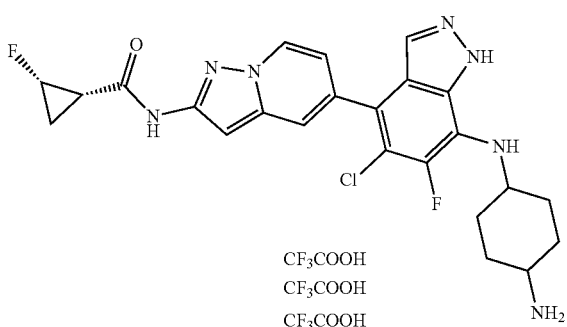<br>(1S,2S)-N-(5-(7-((4-aminocyclohexyl)amino)-5-chloro-6-fluoro-1H-indazol-4-yl)pyrazolo[1,5-a]pyridin-2-yl)-2-fluorocyclopropane-1-carboxamide. 3 TFA | ¹H NMR (400 MHz, DMSO-$d_6$) δ 13.32 (br d, J = 13.8 Hz, 1H), 11.16 (s, 1H), 8.63 (br d, J = 6.9 Hz, 1H), 7.95-7.60 (m, 5H), 6.99-6.79 (m, 2H), 5.35-4.78 (m, 2H), 4.09-3.63 (m, 1H), 4.05-3.45 (m, 1H), 3.24-2.98 (m, 3H), 2.15 (td, J = 6.9, 13.7 Hz, 1H), 2.09-1.93 (m, 2H), 1.77 (br s, 3H), 1.72-1.61 (m, 1H), 1.53-1.34 (m, 2H), 1.26-1.14 (m, 1H); LCMS(electrospray) m/z 500.4 (M + H+). | J |

TABLE 1-continued

Compounds of Examples

| Ex # | Structure/Name | ¹H NMR/MS (M + 1) | Method |
|---|---|---|---|
| 516 | tert-butyl (4-((5-chloro-6-fluoro-4-(2-((1S,2S)-2-fluorocyclopropane-1-carboxamido)pyrazolo[1,5-a]pyridin-5-yl)-1H-indazol-7-yl)amino)cyclohexyl)carbamate. 2 TFA | ¹H NMR (400 MHz, DMSO-$d_6$) δ 14.54-12.40 (m, 1H), 11.16 (s, 1H), 8.62 (d, J = 7.3 Hz, 1H), 7.98-7.77 (m, 1H), 7.71 (br s, 1H), 7.02-6.86 (m, 2H), 6.84-6.66 (m, 1H), 5.07-4.82 (m, 1H), 3.47 (br s, 2H), 3.26 (br s, 1H), 2.15 (td, J = 6.8, 13.6 Hz, 1H), 1.99 (br d, J = 10.3 Hz, 1H), 1.82 (br d, J = 10.4 Hz, 1H), 1.74-1.62 (m, 4H), 1.55 (br d, J = 10.4 Hz, 1H), 1.39 (d, J = 5.1 Hz, 9H), 1.36-1.11 (m, 3H); LCMS(electrospray) m/z 600.1 (M + H+). | J |
| 517 | (1S,2S)-N-(5-(5-chloro-6-fluoro-7-((4-hydroxycyclohexyl)amino)-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.70-12.88 (m, 1H), 11.24-11.06 (m, 1H), 8.71-8.53 (m, 1H), 7.93-7.64 (m, 2H), 7.05-6.57 (m, 2H), 5.10-4.69 (m, 1H), 3.92-3.72 (m, 3H), 2.27-2.08 (m, 1H), 1.81-1.45 (m, 8H), 1.34-1.09 (m, 2H); LCMS(electrospray) m/z 501.1 (M + H+). | J |
| 518 | (1S,2S)-N-(5-(7-(diethylamino)-5-ethyl-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.15 (br s, 1H), 11.15 (s, 1H), 8.62 (d, J = 7.1 Hz, 1H), 7.68 (br s, 1H), 7.62 (s, 1H), 6.91 (s, 1H), 6.83 (dd, J = 1.8, 7.1 Hz, 1H), 5.06-4.82 (m, 1H), 3.26 (br d, J = 6.1 Hz, 4H), 2.61 (br d, J = 7.1 Hz, 2H), 2.19-2.10 (m, 1H), 1.74-1.60 (m, 1H), 1.21-1.14 (m, 1H), 1.10 (t, J = 7.4 Hz, 3H), 0.99 (t, J = 7.1 Hz, 6H); LCMS(electrospray) m/z 453.4(M + H+). | J |
| 519 | (1S,2S)-N-(5-(7-(dimethylamino)-5-ethyl-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.99-12.38 (m, 1H), 11.14 (s, 1H), 8.61 (d, J = 7.1 Hz, 1H), 7.68 (s, 1H), 7.58 (d, J = 0.9 Hz, 1H), 6.90 (s, 1H), 6.79 (dd, J = 1.9, 7.0 Hz, 1H), 5.11-4.76 (m, 1H), 2.97 (s, 3H), 2.97 (s, 3H), 2.65-2.53 (m, 2H), 2.14 (td, J = 6.9, 13.8 Hz, 1H), 1.75-1.60 (m, 1H), 1.22-1.14 (m, 1H), 1.10 (t, J = 7.4 Hz, 3H); LCMS(electrospray) m/z425.2 (M + H+). | J |

TABLE 1-continued

Compounds of Examples

| Ex # | Structure/Name | ¹H NMR/MS (M + 1) | Method |
|---|---|---|---|
| 520 | 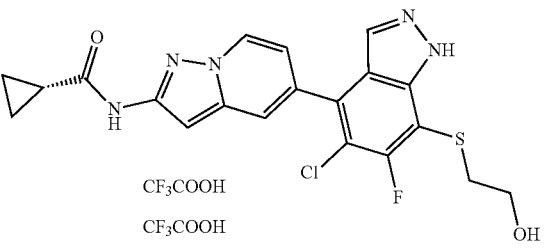<br><br>CF₃COOH<br>CF₃COOH<br><br>(1S,2S)-N-(5-(5-chloro-6-fluoro-7-((2-hydroxyethyl)thio)-1H-indazol-4-yl)pyrazolo[1,5-a]pyridin-2-yl)-2-fluorocyclopropane-1-carboxamide. 2 TFA | ¹H NMR (400 MHz, DMSO-d₆) δ 13.79 (br s, 1H), 11.18 (s, 1H), 8.68 (d, J = 7.2 Hz, 1H), 7.99 (br s, 1H), 7.80 (d, J = 0.7 Hz, 1H), 6.98 (s, 1H), 6.96 (dd, J = 1.9, 7.2 Hz, 1H), 5.06-4.82 (m, 1H), 3.53 (t, J = 6.7 Hz, 2H), 3.12-3.04 (m, 2H), 2.15 (td, J = 7.1, 13.8 Hz, 1H), 1.73-1.61 (m, 1H), 1.18 (tdd, J = 6.2, 9.1, 12.3 Hz, 1H); LCMS(electrospray) m/z 464 (M + H+). | J |
| 521 | 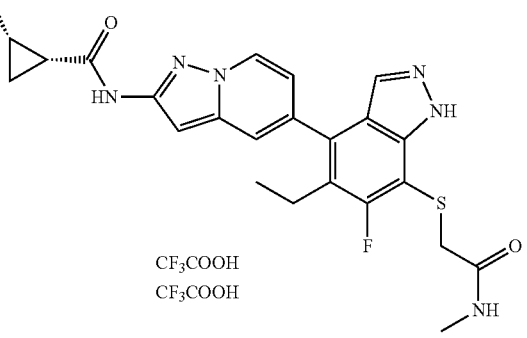<br><br>CF₃COOH<br>CF₃COOH<br><br>(1S,2S)-N-(5-(5-ethyl-6-fluoro-7-((2-(methylamino)-2-oxoethyl)thio)-1H-indazol-4-yl)pyrazolo[1,5-a]pyridin-2-yl)-2-fluorocyclopropane-1-carboxamide bis(2,2,2-trifluoroacetate). 2 TFA | ¹H NMR (400 MHz, DMSO-d₆) δ 13.62 (s, 1H), 11.17 (s, 1H), 8.66 (d, J = 7.1 Hz, 1H), 8.07 (d, 1H), 7.78 (s, 1H), 7.65 (d, 1H), 6.94 (s, 1H), 6.83 (dd, 1H), 5.08-4.83 (m, 1H), 3.64 (s, 2H), 2.63 (d, 2H), 2.60 (d, 3H), 2.20-2.11 (m, 1H), 1.75-1.61 (m, 1H), 1.24-1.15 (m, 1H), 1.11 (t, 3H); LCMS(electrospray) m/z 485.2 (M + H+). | J |
| 522 | 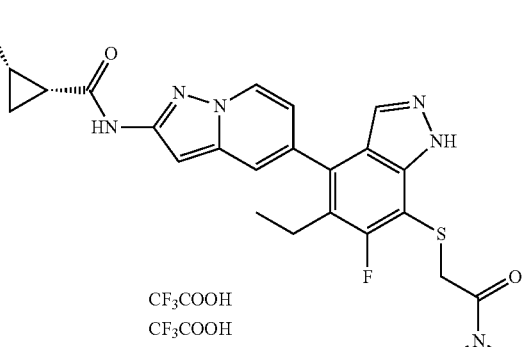<br><br>CF₃COOH<br>CF₃COOH<br><br>(1S,2S)-N-(5-7-((2-(dimethylamino)-2-oxoethyl)thio)-5-ethyl-6-fluoro-1H-indazol-4-yl)pyrazolo[1,5-a]pyridin-2-yl)-2-fluorocyclopropane-1-carboxamide bis(2,2,2-trifluoroacetate). 2 TFA | ¹H NMR (400 MHz, DMSO-d₆) δ 13.72-13.26 (m, 1H), 11.18 (s, 1H), 8.66 (d, J = 7.1 Hz, 1H), 7.78 (s, 1H), 7.64 (d, J = 0.8 Hz, 1H), 6.95 (s, 1H), 6.82 (dd, J = 1.9, 7.1 Hz, 1H), 5.13-4.76 (m, 1H), 3.97 (s, 2H), 3.02 (s, 3H), 2.83 (s, 3H), 2.66-2.59 (m, 2H), 2.19-2.08 (m, 1H), 1.74-1.61 (m, 1H), 1.23-1.15 (m, 1H), 1.11 (t, J = 7.4 Hz, 3H); LCMS(electrospray) m/z 499.4 (M + H+). | J |

TABLE 1-continued

Compounds of Examples

| Ex # | Structure/Name | ¹H NMR/MS (M + 1) | Method |
|---|---|---|---|
| 523 | (1S,2S)-2-fluoro-N-(5-(6-fluoro-7-((2-hydroxyethyl)thio)-5-methyl-1H-indazol-4-yl)pyrazolo[1,5-a]pyridin-2-yl)cyclopropane-1-carboxamide. 2 TFA | ¹H NMR (400 MHz, DMSO-$d_6$) δ 13.46 (s, 1H), 11.16 (s, 1H), 8.65 (d, J = 7.1 Hz, 1H), 7.84 (s, 1H), 7.68 (d, J = 0.7 Hz, 1H), 6.93 (s, 1H), 6.88 (dd, J = 2.0, 7.1 Hz, 1H), 5.08-4.81 (m, 2H), 3.51 (t, J = 6.9 Hz, 2H), 3.01 (br t, J = 6.8 Hz, 2H), 2.24 (d, J = 2.9 Hz, 3H), 2.15 (td, J = 6.9, 14.0 Hz, 1H), 1.73-1.61 (m, 1H), 1.17 (tdd, J = 6.2, 9.0, 12.3 Hz, 1H); LCMS(electrospray) m/z 444.1 (M + H+). | J |
| 524 | (1S,2S)-N-(5-(5-ethyl-7-(ethylamino)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 11.13 (s, 1H), 8.58 (d, J = 7.1 Hz, 1H), 7.67 (s, 1H), 7.55 (d, J = 0.8 Hz, 1H), 6.88 (s, 1H), 6.78 (dd, J = 1.9, 7.1 Hz, 1H), 5.06-4.82 (m, 1H), 3.50 (q, J = 7.0 Hz, 2H), 2.60 (br d, J = 7.6 Hz, 2H), 2.14 (td, J = 7.2, 13.9 Hz, 1H), 1.74-1.59 (m, 1H), 1.22-1.07 (m, 7H); LCMS(electrospray) m/z 425.2 (M + H+). | J |
| 525 | (1S,2S)-N-(5-(5-ethyl-7-(ethyl(methyl)amino)-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.48-12.86 (m, 1H), 11.15 (s, 1H), 8.62 (d, J = 7.0 Hz, 1H), 7.68 (s, 1H), 7.60 (d, J = 0.9 Hz, 1H), 6.91 (s, 1H), 6.81 (dd, J = 1.9, 7.0 Hz, 1H), 5.08-4.79 (m, 1H), 3.23 (q, J = 7.0 Hz, 2H), 2.95 (d, J = 1.6 Hz, 3H), 2.60 (br d, J = 7.1 Hz, 2H), 2.18-2.10 (m, 1H), 1.72-1.61 (m, 1H), 1.20-1.14 (m, 1H), 1.12-1.04 (m, 6H); LCMS(electrospray) m/z 439.2 (M + H+). | J |
| 526 | 2-((5-ethyl-6-fluoro-4-(2-((1S,2S)-2-fluorocyclopropane-1-carboxamido)pyrazolo[1,5-a]pyridin-5-yl)-1H-indazol-7-yl)thio)acetic acid. 2 TFA | ¹H NMR (400 MHz, DMSO-$d_6$) δ 13.70-13.32 (m, 1H), 13.12-12.20 (m, 1H), 11.17 (s, 1H), 8.65 (d, J = 7.1 Hz, 1H), 7.79 (s, 1H), 7.65 (d, J = 0.9 Hz, 1H), 6.94 (s, 1H), 6.83 (dd, J = 2.0, 7.1 Hz, 1H), 5.07-4.82 (m, 1H), 3.77 (br s, 2H), 2.63 (br d, J = 6.8 Hz, 2H), 2.21-2.09 (m, 1H), 1.74-1.61 (m, 1H), 1.24-1.14 (m, 1H), 1.10 (t, J = 7.4 Hz, 3H); LCMS(electrospray) m/z 472.1 (M + H+). | J |

TABLE 1-continued

Compounds of Examples

| Ex # | Structure/Name | ¹H NMR/MS (M + 1) | Method |
|---|---|---|---|
| 527 | 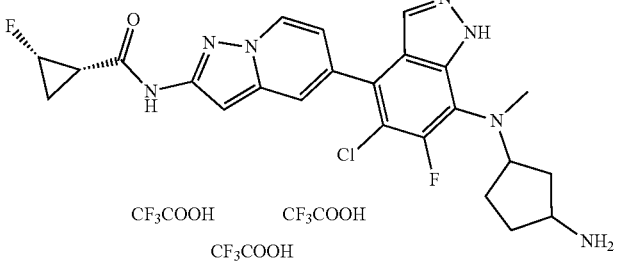<br>(1S,2S)-N-(5-(7-((3-aminocyclopentyl)(methyl)amino)-5-chloro-6-fluoro-1H-indazol-4-yl)pyrazolo[1,5-a]pyridin-2-yl)-2-fluorocyclopropane-1-carboxamide. 2 TFA | ¹H NMR (400 MHz, DMSO-$d_6$) δ 13.64-13.45 (m, 1H), 11.24-11.12 (m, 1H), 8.72-8.62 (m, 1H), 8.02-7.73 (m, 4H), 7.03-6.89 (m, 2H), 5.13-4.83 (m, 1H), 2.88 (br d, J = 17.4 Hz, 2H), 2.08 (s, 5H), 2.04-1.93 (m, 2H), 1.75-1.58 (m, 3H), 1.28-1.18 (m, 3H); LCMS(electrospray) m/z 500.1 (M + H+). | J |
| 528 | 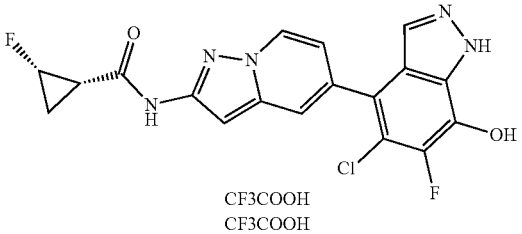 [SMILES: O=C(Nc1cc2cc(-c3c(Cl)c(F)c(O)c4[nH]ncc34)ccn2n1)[C@@H]1C[C@@H]1F ; "CF3COOH" ; "CF3COOH"]<br>(1S,2S)-N-(5-(5-chloro-6-fluoro-7-hydroxy-1H-indazol-4-yl)pyrazolo[1,5-a]pyridin-2-yl)-2-fluorocyclopropane-1-carboxamide. 2 TFA | ¹H NMR (400 MHz, METHANOL-$d_4$) δ 8.75 (s, 1H), 7.88 (s, 1H), 7.82-7.76 (m, 1H), 7.74-7.68 (m, 1H), 2.19-2.11 (m, 1H), 1.92-1.81 (m, 1H), 1.35-1.22 (m, 2H); LCMS(electrospray) m/z 404.1 (M + H+). | J |
| 529 | 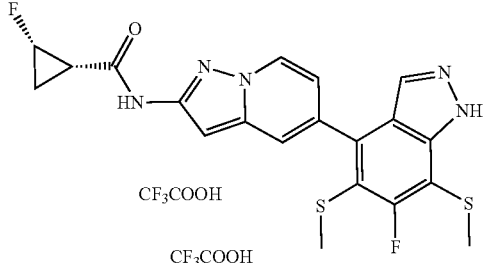<br>(1S,2S)-2-fluoro-N-(5-(6-fluoro-5,7-bis(methylthio)-1H-indazol-4-yl)pyrazolo[1,5-a]pyridin-2-yl)cyclopropane-1-carboxamide. 2 TFA | ¹H NMR (400 MHz, DMSO-$d_6$) δ 13.68 (s, 1H), 11.16 (s, 1H), 8.63 (d, J = 7.1 Hz, 1H), 7.88 (d, J = 1.3 Hz, 1H), 7.68 (d, J = 1.0 Hz, 1H), 6.94 (s, 1H), 6.90 (dd, J = 1.8, 7.1 Hz, 1H), 5.07-4.82 (m, 1H), 2.54 (s, 3H), 2.28 (s, 3H), 2.19-2.10 (m, 1H), 1.79-1.57 (m, 1H), 1.26-1.12 (m, 1H); LCMS(electrospray) m/z 446.0 (M + H+). | J |
| 530 | 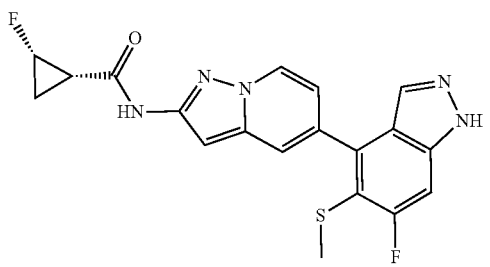 [SMILES: CSc1c(F)cc2[nH]ncc2c1-c1ccn2nc(NC(=O)[C@@H]3C[C@@H]3F)cc2c1]<br>(1S,2S)-2-fluoro-N-(5-(6-fluoro-5-(methylthio)-1H-indazol-4-yl)pyrazolo[1,5-a]pyridin-2-yl)cyclopropane-1-carboxamide | ¹H NMR (400 MHz, CHLOROFORM-d) δ 13.40 (br s, 1H), 11.15 (s, 1H), 8.62 (d, J = 7.1 Hz, 1H), 7.81 (s, 1H), 7.67 (dd, J = 0.7, 1.7 Hz, 1H), 7.52 (dd, J = 0.9, 9.3 Hz, 1H), 6.93 (s, 1H), 6.90 (dd, J = 1.8, 7.1 Hz, 1H), 5.06-4.82 (m, 1H), 2.26 (s, 3H), 2.15 (td, J = 7.0, 13.9 Hz, 1H), 1.75-1.61 (m, 1H), 1.21-1.14 (m, 1H); LCMS(electrospray) m/z 400.1 (M + H+). | J |

TABLE 1-continued

Compounds of Examples

| Ex # | Structure/Name | $^1$H NMR/MS (M + 1) | Method |
|---|---|---|---|
| 531 | 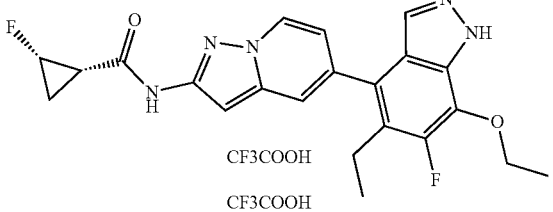<br><br>CF3COOH<br>CF3COOH<br><br>(1S,2S)-N-(5-(7-ethoxy-5-ethyl-6-fluoro-1H-indazol-4-yl)pyrazolo[1,5-a]pyridin-2-yl)-2-fluorocyclopropane-1-carboxamide. 2 TFA | $^1$H NMR (400 MHz, DMSO-d$_6$) δ 13.48 (s, 1H), 11.16 (s, 1H), 8.63 (d, J = 6.8 Hz, 1H), 7.72 (s, 1H), 7.61 (s, 1H), 6.92 (s, 1H), 6.81 (dd, J = 7.2, 2.0 Hz, 1H), 5.04-4.85 (m, 1H), 4.34-4.29 (m, 2H), 2.64-2.60 (m, 2H), 2.17-2.13 (m, 1H), 1.75-1.65 (m, 1H), 1.40 (t, J = 7.2 Hz, 3H), 1.19-1.15 (m, 1H), 1.12 (t, J = 7.2 Hz, 3H); LCMS(electrospray) m/z 426.2 (M + H+). | J |
| 532 | 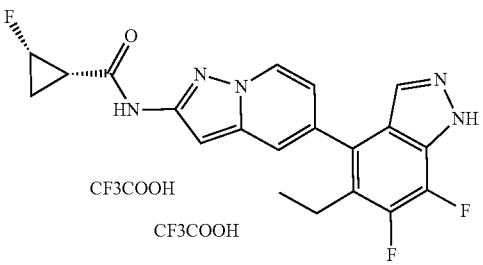 [SMILES: CCc1c(F)c(F)c2[nH]ncc2c1-c1ccn2nc(NC(=O)[C@@H]3C[C@@H]3F)cc2c1 ; "CF3COOH" ; "CF3COOH"]<br><br>CF3COOH<br>CF3COOH<br><br>(1S,2S)-N-(5-(5-ethyl-6,7-difluoro-1H-indazol-4-yl)pyrazolo[1,5-a]pyridin-2-yl)-2-fluorocyclopropane-1-carboxamide. 2 TFA | $^1$H NMR (400 MHz, CHLOROFORM-d) δ 8.46-8.41 (m, 1 H), 8.37 (d, J = 7.09 Hz, 1 H), 7.80-7.74 (m, 1 H), 7.45 (d, J = 0.86 Hz, 1 H), 7.09 (s, 1 H), 6.73 (dd, J = 7.03, 1.90 Hz, 1 H), 5.00-4.72 (m, 1 H), 2.81-2.64 (m, 2 H), 2.01-1.94 (m, 1 H), 1.92-1.89 (m, 1 H), 1.28-1.25 (m, 1 H), 1.18 (t, J = 7.46 Hz, 3 H); LCMS(electrospray) m/z 400.0 (M + H+). | J |
| 533 | 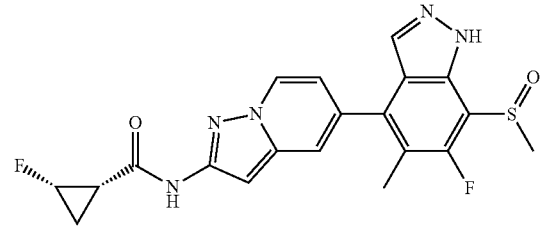<br><br>(1S,2S)-2-fluoro-N-(5-(6-fluoro-5-methyl-7-(methylsulfinyl)-1H-indazol-4-yl)pyrazolo[1,5-a]pyridin-2-yl)cyclopropane-1-carboxamide | $^1$H NMR (400 MHz, DMSO-d$_6$) δ 11.18 (s, 1H), 8.67 (d, J = 7.0 Hz, 1H), 7.91 (s, 1H), 7.71 (s, 1H), 6.96 (s, 1H), 6.89 (dd, J = 1.9, 7.1 Hz, 1H), 5.15-4.65 (m, 1H), 3.13 (s, 3H), 2.24 (d, J = 2.8 Hz, 3H), 2.15 (td, J = 7.0, 14.1 Hz, 1H), 1.76-1.58 (m, 1H), 1.26-1.10 (m, 1H); LCMS(electrospray) m/z 429.11 (M + H+). | J |
| 534 | 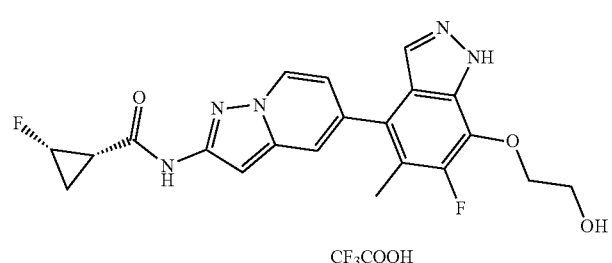<br><br>CF$_3$COOH<br><br>(1S,2S)-2-fluoro-N-(5-(6-fluoro-7-(2-hydroxyethoxy)-5-methyl-1H-indazol-4-yl)pyrazolo[1,5-a]pyridin-2-yl)cyclopropane-1-carboxamide. TFA | $^1$H NMR (400 MHz, DMSO-d$_6$) δ 13.39 (br s, 1H), 14.04-12.74 (m, 1H), 11.15 (s, 1H), 8.63 (d, J = 7.1 Hz, 1H), 7.80 (s, 1H), 7.64 (d, J = 0.9 Hz, 1H), 7.29 (dd, J = 2.0, 7.3 Hz, 1H), 6.96-6.90 (m, 1H), 6.86 (dd, J = 1.8, 7.1 Hz, 1H), 5.06-4.83 (m, 1H), 4.30 (br t, J = 4.9 Hz, 2H), 3.78 (t, J = 5.1 Hz, 2H), 2.24 (d, J = 3.1 Hz, 3H), 2.20-2.08 (m, 1H), 1.75-1.58 (m, 1H), 1.25-1.13 (m, 1H); LCMS(electrospray) m/z 428.0 (M + H+). | J |

TABLE 1-continued

Compounds of Examples

| Ex # | Structure/Name | ¹H NMR/MS (M + 1) | Method |
|---|---|---|---|
| 535 | 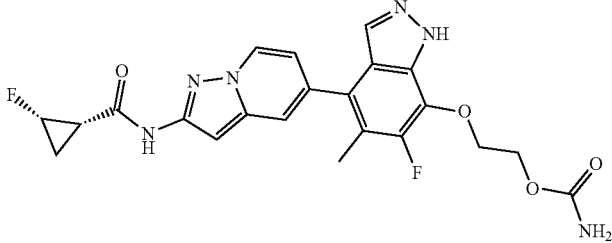 [SMILES: Cc1c(F)c(OCCOC(N)=O)c2[nH]ncc2c1-c1ccn2nc(NC(=O)[C@@H]3C[C@@H]3F)cc2c1]<br>2-((6-fluoro-4-(2-((1S,2S)-2-fluorocyclopropane-1-carboxamido)pyrazolo[1,5-a]pyridin-5-yl)-5-methyl-1H-indazol-7-yl)oxy)ethyl carbamate | ¹H NMR (400 MHz, METHANOL-$d_4$) δ 8.41 (d, J = 7.1 Hz, 1H), 7.66 (s, 1H), 7.44 (s, 1H), 6.83 (s, 1H), 6.74 (dd, J = 1.7, 7.1 Hz, 1H), 4.86 (td, J = 3.1, 6.3 Hz, 1H), 4.69 (dt, J = 3.9, 6.2 Hz, 1H), 4.46-4.38 (m, 2H), 4.33-4.25 (m, 2H), 3.89-3.80 (m, 1H), 2.20-2.16 (m, 1H), 2.18 (d, J = 3.2 Hz, 2H), 2.00 (td, J = 6.9, 13.8 Hz, 1H), 1.78-1.62 (m, 1H), 1.19-1.04 (m, 1H); LCMS(electrospray) m/z 471.1 (M + H+). | J |
| 536 | 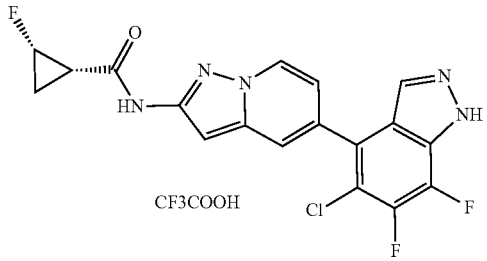 [SMILES: O=C(Nc1cc2cc(-c3c(Cl)c(F)c(F)c4[nH]ncc34)ccn2n1)[C@@H]1C[C@@H]1F ; "CF3COOH"]<br>CF3COOH<br>(1S,2S)-N-(5-(5-chloro-6,7-difluoro-1H-indazol-4-yl)pyrazolo[1,5-a]pyridin-2-yl)-2-fluorocyclopropane-1-carboxamide. 1 TFA | ¹H NMR (400 MHz, DMSO-$d_6$) δ 11.19 (s, 1H), 8.67 (d, J = 7.2 Hz, 1H), 7.67 (s, 1H), 6.96 (s, 1H), 6.87 (s, 1H), 6.79 (dd, J = 2.0, 7.2 Hz, 1H), 5.08-4.79 (m, 1H), 2.19-2.08 (m, 1H), 1.74-1.59 (m, 1H), 1.28-1.09 (m, 2H); LCMS(electrospray) m/z 406.2 (M + H+). | J |
| 537 | 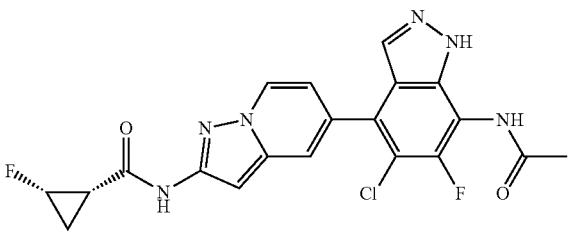<br>CF₃COOH<br>(1S,2S)-N-(5-(7-acetamido-5-chloro-6-fluoro-1H-indazol-4-yl)pyrazolo[1,5-a]pyridin-2-yl)-2-fluorocyclopropane-1-carboxamide. 1 TFA | ¹H NMR (400 MHz, DMSO-$d_6$) δ 13.31 (br s, 1H), 11.27-11.11 (m, 1H), 10.14 (s, 1H), 8.68 (d, J = 7.1 Hz, 1H), 7.91 (s, 1H), 7.80 (d, J = 0.9 Hz, 1H), 6.97 (s, 1H), 6.95 (dd, J = 1.9, 7.2 Hz, 1H), 5.09-4.82 (m, 1H), 2.18 (s, 3H), 2.16-2.10 (m, 1H), 1.75-1.61 (m, 1H), 1.18 (ddd, J = 2.7, 6.1, 12.5 Hz, 1H); LCMS(electrospray) m/z 445.2 (M + H+). | J |
| 538 | 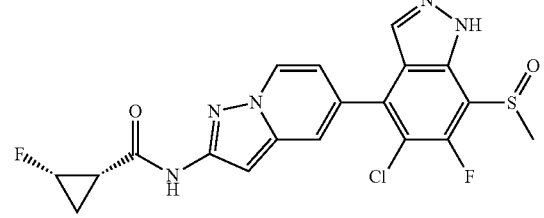<br>(1S,2S)-N-(5-(5-chloro-6-fluoro-7-(methylsulfinyl)-1H-indazol-4-yl)pyrazolo[1,5-a]pyridin-2-yl)-2-fluorocyclopropane-1-carboxamide | ¹H NMR (400 MHz, DMSO-$d_6$) δ 13.73 (br s, 1H), 11.22 (s, 1H), 8.72 (d, J = 7.0 Hz, 1H), 8.06 (s, 1H), 7.83 (d, J = 1.0 Hz, 1H), 7.01 (s, 1H), 6.97 (dd, J = 2.0, 7.2 Hz, 1H), 5.08-4.83 (m, 1H), 3.20 (s, 3H), 2.16 (td, J = 7.0, 14.0 Hz, 1H), 1.75-1.60 (m, 1H), 1.24-1.13 (m, 1H); LCMS(electrospray) m/z 450 (M + H+). | J |

TABLE 1-continued

Compounds of Examples

| Ex # | Structure/Name | ¹H NMR/MS (M + 1) | Method |
|---|---|---|---|
| 539 | 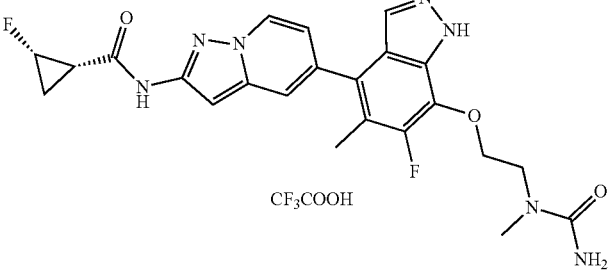<br><br>(1S,2S)-2-fluoro-N-(5-(6-fluoro-5-methyl-7-(2-(1-methylureido)ethoxy)-1H-indazol-4-yl)pyrazolo[1,5-a]pyridin-2-yl)cyclopropane-1-carboxamide. 1 TFA | ¹H NMR (400 MHz, DMSO-d₆) δ 11.15 (s, 1H), 8.62 (d, J = 7.1 Hz, 1H), 7.80 (s, 1H), 7.63 (d, J = 0.7 Hz, 1H), 6.91 (s, 1H), 6.85 (dd, J = 1.9, 7.2 Hz, 1H), 6.06-5.88 (m, 1H), 5.05-4.82 (m, 1H), 4.33 (br t, J = 5.4 Hz, 2H), 3.62 (br t, J = 5.8 Hz, 5H), 2.94 (s, 3H), 2.23 (d, J = 3.1 Hz, 3H), 2.18-2.11 (m, 1H), 1.73-1.61 (m, 1H), 1.20-1.14 (m, 1H); LCMS(electrospray) m/z 484.4 (M + H+). | J |
| 540 | 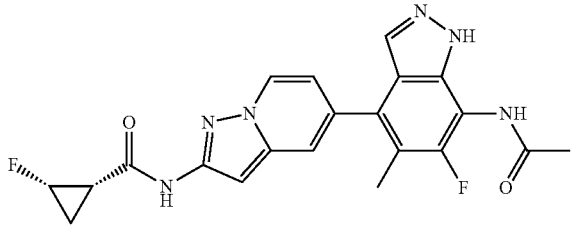<br><br>(1S,2S)-N-(5-(7-acetamido-6-fluoro-5-methyl-1H-indazol-4-yl)pyrazolo[1,5-a]pyridin-2-yl)-2-fluorocyclopropane-1-carboxamide | ¹H NMR (400 MHz, DMSO-d₆) δ 12.95 (s, 1H), 11.16 (s, 1H), 9.93 (s, 1H), 8.64 (d, J = 7.1 Hz, 1H), 7.76 (s, 1H), 7.67 (s, 1H), 6.93 (s, 1H), 6.87 (dd, J = 1.7, 7.1 Hz, 1H), 5.06-4.82 (m, 1H), 2.24 (d, J = 2.6 Hz, 3H), 2.20-2.10 (m, 4H), 1.73-1.60 (m, 1H), 1.17 (tdd, J = 6.4, 9.0, 12.3 Hz, 1H); LCMS(electrospray) m/z 424.15 (M + H+). | J |
| 541 | 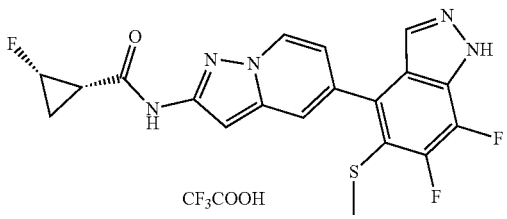 [SMILES: CSc1c(F)c(F)c2[nH]ncc2c1-c1ccn2nc(NC(=O)[C@@H]3C[C@@H]3F)cc2c1 ; "CF3COOH"]<br><br>(1S,2S)-N-(5-(6,7-difluoro-5-(methylthio)-1H-indazol-4-yl)pyrazolo[1,5-a]pyridin-2-yl)-2-fluorocyclopropane-1-carboxamide. 1 TFA | ¹H NMR (400 MHz, DMSO-d₆) δ 11.16 (s, 1H), 8.63 (d, J = 7.1 Hz, 1H), 7.96 (br s, 1H), 7.66 (d, J = 1.0 Hz, 1H), 6.94 (s, 1H), 6.88 (dd, J = 2.0, 7.1 Hz, 1H), 5.06-4.83 (m, 1H), 2.30 (s, 3H), 2.15 (td, J = 7.0, 14.0 Hz, 1H), 1.74-1.60 (m, 1H), 1.17 (tdd, J = 6.3, 9.0, 12.3 Hz, 1H); LCMS(electrospray) m/z 418 (M + H+). | J |
| 542 | 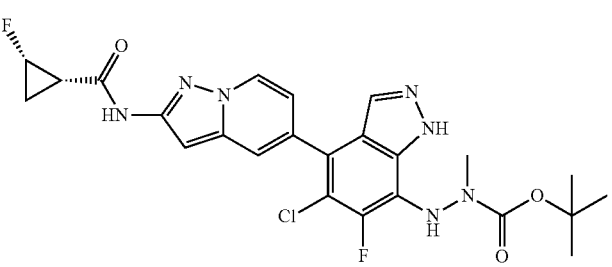 [SMILES: CN(Nc1c(F)c(Cl)c(-c2ccn3nc(NC(=O)[C@@H]4C[C@@H]4F)cc3c2)c2cn[nH]c12)C(=O)OC(C)(C)C]<br><br>tert-butyl 2-(5-chloro-6-fluoro-4-(2-((1S,2S)-2-fluorocyclopropane-1-carboxamido)pyrazolo[1,5-a]pyridin-5-yl)-1H-indazol-7-yl)-1-methylhydrazine-1-carboxylate | ¹H NMR (400 MHz, DMSO-d₆) δ 12.97 (s, 1H), 11.16 (s, 1H), 8.63 (d, J = 7.2 Hz, 1H), 8.35 (s, 1H), 7.88 (s, 1H), 7.71 (s, 1H), 6.93 (s, 1H), 6.89 (d, J = 7.2 Hz, 1H), 5.04-4.85 (m, 1H), 3.23 (s, 3H), 2.16-2.12 (m, 1H), 1.70-1.63 (m, 1H), 1.28-1.12 (m, 1H); LCMS (electrospray) m/z 532.1 (M + H)+. | J |

TABLE 1-continued

Compounds of Examples

| Ex # | Structure/Name | ¹H NMR/MS (M + 1) | Method |
|---|---|---|---|
| 543 | 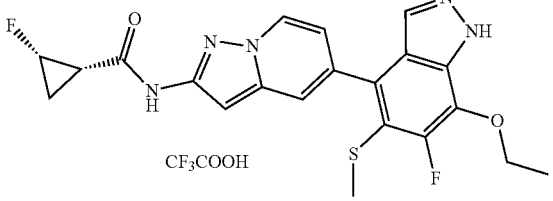<br>(1S,2S)-N-(5-(7-ethoxy-6-fluoro-5-(methylthio)-1H-indazol-4-yl)pyrazolo[1,5-a]pyridin-2-yl)-2-fluorocyclopropane-1-carboxamide. 1 TFA | ¹H NMR (400 MHz, DMSO-$d_6$) δ 14.02-13.34 (m, 1H), 11.15 (s, 1H), 8.61 (d, J = 7.0 Hz, 1H), 7.85 (s, 1H), 7.65 (s, 1H), 6.93 (s, 1H), 6.89 (dd, J = 1.8, 7.1 Hz, 1H), 5.11-4.78 (m, 1H), 4.35 (q, J = 7.0 Hz, 2H), 2.28 (s, 3H), 2.19-2.12 (m, 1H), 1.68 (m, J = 3.2, 6.8, 19.9 Hz, 1H), 1.41 (t, J = 7.0 Hz, 3H), 1.26-1.11 (m, 1H); LCMS(electrospray) m/z 444.2 (M + H+). | J |
| 544 | 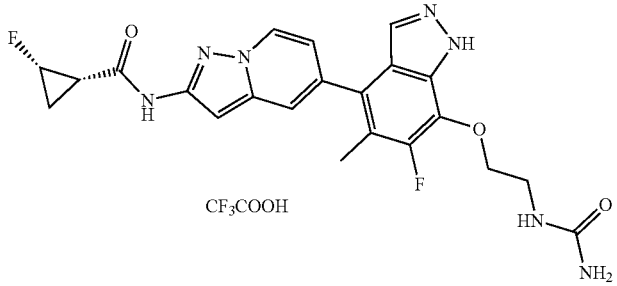 [SMILES: Cc1c(F)c(OCCNC(N)=O)c2[nH]ncc2c1-c1ccn2nc(NC(=O)[C@@H]3C[C@@H]3F)cc2c1 ; "CF3COOH"]<br>(1S,2S)-2-fluoro-N-(5-(6-fluoro-5-methyl-7-(2-ureidoethoxy)-1H-indazol-4-yl)pyrazolo[1,5-a]pyridin-2-yl)cyclopropane-1-carboxamide. 1 TFA | ¹H NMR (400 MHz, DMSO-$d_6$) δ 11.15 (s, 1H), 8.63 (d, J = 7.1 Hz, 1H), 7.80 (s, 1H), 7.64 (d, J = 1.0 Hz, 1H), 6.91 (s, 1H), 6.85 (dd, J = 1.9, 7.1 Hz, 1H), 6.28 (br s, 1H), 5.14-4.71 (m, 1H), 4.22 (t, J = 5.4 Hz, 2H), 3.40 (br d, J = 4.1 Hz, 2H), 2.24 (d, J = 3.0 Hz, 3H), 2.19-2.09 (m, 1H), 1.73-1.59 (m, 1H), 1.24-1.07 (m, 1H); LCMS(electrospray) m/z 470.1 (M + H+). | J |
| 545 | 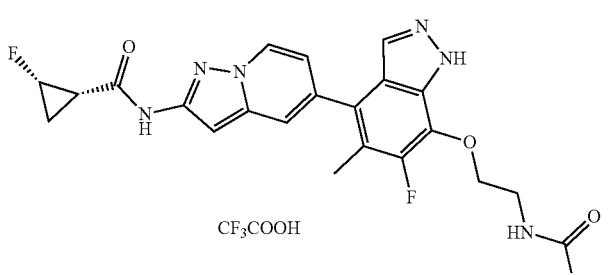<br>(1S,2S)-2-fluoro-N-(5-(6-fluoro-5-methyl-7-(2-(3-methylureido)ethoxy)-1H-indazol-4-yl)pyrazolo[1,5-a]pyridin-2-yl)cyclopropane-1-carboxamide. 1 TFA | ¹H NMR (400 MHz, DMSO-$d_6$) δ 11.24-11.04 (m, 1H), 8.74-8.52 (m, 1H), 7.85-7.75 (m, 1H), 7.64 (d, J = 0.9 Hz, 1H), 6.91 (s, 1H), 6.85 (dd, J = 1.8, 7.1 Hz, 1H), 6.27-6.15 (m, 1H), 6.03-5.80 (m, 1H), 5.09-4.80 (m, 1H), 4.31-4.12 (m, 2H), 3.47-3.34 (m, 2H), 2.57 (s, 3H), 2.23 (d, J = 3.1 Hz, 3H), 2.19-2.08 (m, 1H), 1.75-1.60 (m, 1H), 1.25-1.10 (m, 1H); LCMS(electrospray) m/z 484.2 (M + H+). | J |
| 546 | 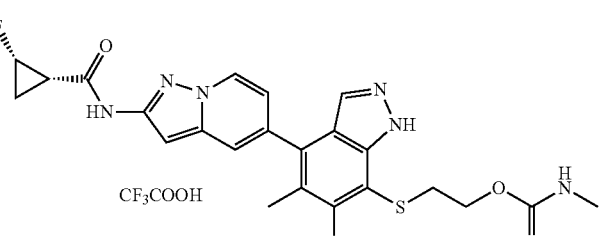<br>2-((6-fluoro-4-(2-((1S,2S)-2-fluorocyclopropane-1-carboxamido)pyrazolo[1,5-a]pyridin-5-yl)-5-methyl-1H-indazol-7-yl)thio)ethyl methylcarbamate. 1 TFA | ¹H NMR (400 MHz, DMSO-$d_6$) δ 13.52-13.40 (m, 1H), 11.16 (s, 1H), 8.64 (d, J = 7.1 Hz, 1H), 7.85 (br s, 1H), 7.68 (s, 1H), 6.94 (s, 1H), 6.89 (dd, J = 1.6, 7.0 Hz, 1H), 5.04-4.83 (m, 1H), 4.05 (br t, J = 6.7 Hz, 2H), 3.16 (br d, J = 5.5 Hz, 2H), 2.53 (br s, 3H), 2.25 (d, J = 2.7 Hz, 3H), 2.17-2.13 (m, 1H), 2.04 (td, J = 2.4, 4.9 Hz, 1H), 1.68 (tdd, J = 3.3, 6.6, 19.7 Hz, 1H), 1.17 (ddd, J = 2.6, 6.2, 12.3 Hz, 1H); LCMS(electrospray) m/z 501.2 (M + H+). | J |

TABLE 1-continued

Compounds of Examples

| Ex # | Structure/Name | ¹H NMR/MS (M + 1) | Method |
|---|---|---|---|
| 547 | 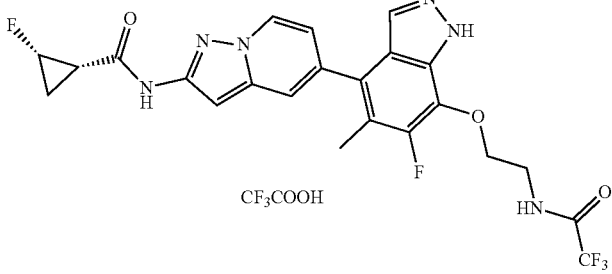<br>(1S,2S)-2-fluoro-N-(5-(6-fluoro-5-methyl-7-(2-(2,2,2-trifluoroacetamido)ethoxy)-1H-indazol-4-yl)pyrazolo[1,5-a]pyridin-2-yl)cyclopropane-1-carboxamide. 1 TFA | ¹H NMR (400 MHz, DMSO-d₆) δ 13.67-13.25 (m, 1H), 11.16 (s, 1H), 9.63 (br t, J = 5.2 Hz, 1H), 8.63 (d, J = 7.1 Hz, 1H), 7.82 (s, 1H), 7.64 (d, J = 0.9 Hz, 1H), 6.92 (s, 1H), 6.85 (dd, J = 1.9, 7.2 Hz, 1H), 5.07-4.83 (m, 1H), 4.38 (s, 2H), 3.66 (q, J = 5.5 Hz, 3H), 2.23 (d, J = 3.1 Hz, 3H), 2.15 (td, J = 7.0, 13.8 Hz, 1H), 1.75-1.61 (m, 1H), 1.18-1.29 (m, J = 2.9, 6.1, 12.3 Hz, 1H); LCMS(electrospray) m/z 523.3 (M + H+). | J |
| 548 | 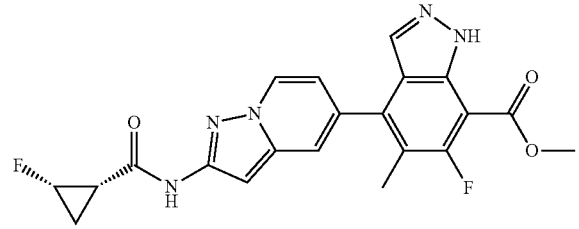<br>methyl 6-fluoro-4-(2-((1S,2S)-2-fluorocyclopropane-1-carboxamido)pyrazolo[1,5-a]pyridin-5-yl)-5-methyl-1H-indazole-7-carboxylate | ¹H NMR (400 MHz, DMSO-d₆) δ 13.32 (s, 1H), 11.19 (s, 1H), 8.68 (d, J = 7.1 Hz, 1H), 7.89 (s, 1H), 7.73 (s, 1H), 6.96 (s, 1H), 6.89 (dd, J = 1.8, 7.1 Hz, 1H), 5.15-4.72 (m, 1H), 3.98 (s, 3H), 2.24 (d, J = 2.9 Hz, 3H), 2.20-2.09 (m, 1H), 1.76-1.59 (m, 1H), 1.18 (ddd, J = 2.8, 6.2, 12.2 Hz, 1H); LCMS(electrospray) m/z 426.2 (M + H+). | J |
| 549 | 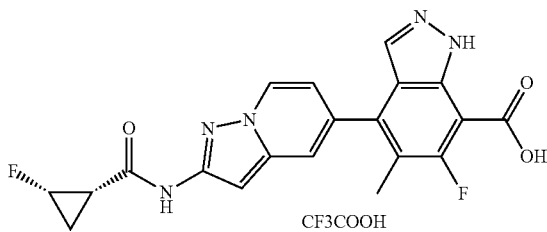<br>6-fluoro-4-(2-((1S,2S)-2-fluorocyclopropane-1-carboxamido)pyrazolo[1,5-a]pyridin-5-yl)-5-methyl-1H-indazole-7-carboxylic acid. 1 TFA | ¹H NMR (400 MHz, DMSO-d₆) δ 13.66-13.38 (m, 1H), 13.19 (br s, 1H), 11.19 (s, 1H), 8.68 (d, J = 7.1 Hz, 1H), 7.85 (s, 1H), 7.72 (s, 1H), 6.96 (s, 1H), 6.89 (dd, J = 1.8, 7.1 Hz, 1H), 5.07-4.84 (m, 1H), 2.24 (d, J = 3.1 Hz, 3H), 2.18-2.13 (m, 1H), 1.72-1.62 (m, 1H), 1.20-1.14 (m, 1H); LCMS(electrospray) m/z 412.2 (M + H+). | J |
| 550 | 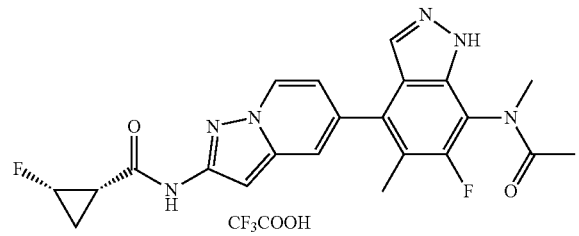<br>(1S,2S)-2-fluoro-N-(5-(6-fluoro-5-methyl-7-(N-methylacetamido)-1H-indazol-4-yl)pyrazolo[1,5-a]pyridin-2-yl)cyclopropane-1-carboxamide. 1 TFA | ¹H NMR (400 MHz, DMSO-d₆) δ 11.22-11.13 (m, 1H), 8.66 (d, J = 7.1 Hz, 1H), 7.95-7.87 (m, 1H), 7.72-7.70 (m, 1H), 6.96-6.93 (m, 1H), 6.92-6.89 (m, 1H), 5.07-4.81 (m, 1H), 3.21 (s, 3H), 2.30-2.25 (m, 3H), 2.25-2.23 (m, 1H), 2.20-2.09 (m, 1H), 1.79 (s, 3H), 1.74-1.63 (m, 1H), 1.28-1.09 (m, 1H); LCMS(electrospray) m/z 438.16 (M + H+) | J |

TABLE 1-continued

Compounds of Examples

| Ex # | Structure/Name | $^1$H NMR/MS (M + 1) | Method |
|---|---|---|---|
| 551 | 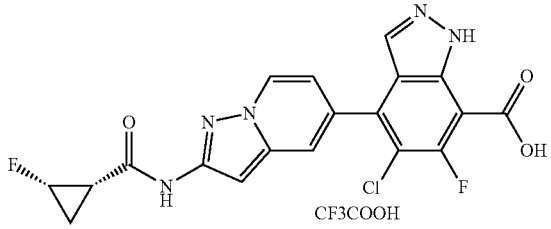 [SMILES: O=C(O)c1c(F)c(Cl)c(-c2ccn3nc(NC(=O)[C@@H]4C[C@@H]4F)cc3c2)c2cn[nH]c12 ; "CF3COOH"]<br>5-chloro-6-fluoro-4-(2-((1S,2S)-2-fluorocyclopropane-1-carboxamido)pyrazolo[1,5-a]pyridin-5-yl)-1H-indazole-7-carboxylic acid. 1 TFA | $^1$H NMR (400 MHz, DMSO-d$_6$) δ 13.47 (br s, 1H), 11.20 (s, 1H), 8.70 (d, J = 7.1 Hz, 1H), 7.99 (s, 1H), 7.83 (d, J = 0.9 Hz, 1H), 7.03-6.95 (m, 2H), 5.10-4.82 (m, 1H), 2.22-2.09 (m, 1H), 1.79-1.60 (m, 1H), 1.26-1.11 (m, 1H); LCMS(electrospray) m/z 432.2 (M + H+). | J |
| 552 | 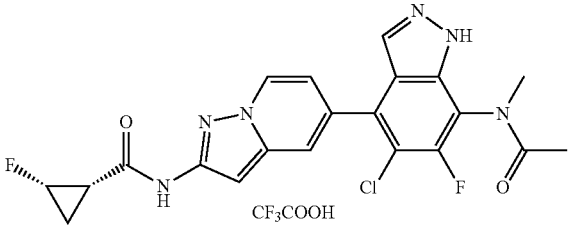<br>(1S,2S)-N-(5-(5-chloro-6-fluoro-7-(N-methylacetamido)-1H-indazol-4-yl)pyrazolo[1,5-a]pyridin-2-yl)-2-fluorocyclopropane-1-carboxamide. 1 TFA | $^1$H NMR (400 MHz, DMSO-d$_6$) δ 14.07-13.87 (m, 1H), 11.19 (s, 1H), 8.69 (br d, J = 7.1 Hz, 1H), 8.07-8.01 (m, 1H), 7.82 (d, J = 0.7 Hz, 1H), 6.99 (s, 1H), 6.97 (br d, J = 2.0 Hz, 1H), 5.05-4.83 (m, 1H), 3.23 (s, 3H), 2.18-2.11 (m, 1H), 1.82 (s, 3H), 1.71-1.64 (m, 1H), 1.22-1.13 (m, 1H); LCMS(electrospray) m/z 459.2 (M + H+). | J |
| 553 | 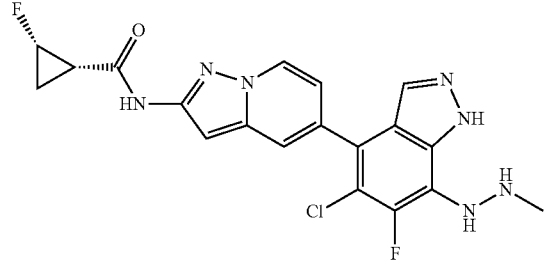<br>(1S,2S)-N-(5-(5-chloro-6-fluoro-7-(2-methylhydrazineyl)-1H-indazol-4-yl)pyrazolo[1,5-a]pyridin-2-yl)-2-fluorocyclopropane-1-carboxamide | $^1$H NMR (400 MHz, DMSO-d$_6$) δ 12.95 (s, 1H), 11.15 (s, 1H), 8.60 (d, J = 7.2 Hz, 1H), 7.77 (s, 1H), 7.68 (s, 1H), 7.42 (s, 1H), 6.91-6.88 (m, 2H), 5.02 (s, 1H), 5.04-4.85 (m, 1H), 2.66 (s, 3H), 2.16-2.12 (m, 1H), 1.70-1.63 (m, 1H), 1.28-1.12 (m, 1H); LCMS (electrospray) m/z 432.1 (M + H+)+. | J |
| 554 | 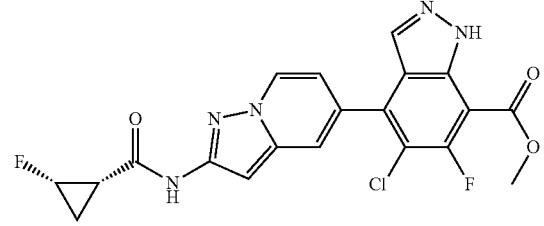 [SMILES: COC(=O)c1c(F)c(Cl)c(-c2ccn3nc(NC(=O)[C@@H]4C[C@@H]4F)cc3c2)c2cn[nH]c12]<br>methyl 5-chloro-6-fluoro-4-(2-((1S,2S)-2-fluorocyclopropane-1-carboxamido)pyrazolo[1,5-a]pyridin-5-yl)-1H-indazole-7-carboxylate | $^1$H NMR (400 MHz, DMSO-d$_6$) δ 11.22 (s, 1H), 8.71 (d, J = 7.1 Hz, 1H), 8.05 (s, 1H), 7.85 (d, J = 1.0 Hz, 1H), 7.00 (s, 1H), 6.97 (dd, J = 2.0, 7.2 Hz, 1H), 5.08-4.81 (m, 1H), 4.00 (s, 3H), 2.19-2.11 (m, 1H), 1.75-1.60 (m, 1H), 1.21-1.13 (m, 1H); LCMS(electrospray) m/z 446.0 (M + H+). | J |

TABLE 1-continued

Compounds of Examples

| Ex # | Structure/Name | ¹H NMR/MS (M + 1) | Method |
|---|---|---|---|
| 555 | 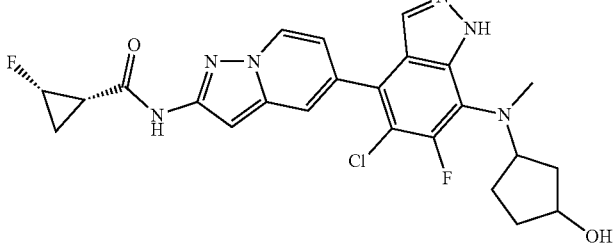<br>(1S,2S)-N-(5-(5-chloro-6-fluoro-7-((3-hydroxycyclopentyl)(methyl)amino)-1H-indazol-4-yl)pyrazolo[1,5-a]pyridin-2-yl)-2-fluorocyclopropane-1-carboxamide | ¹H NMR (400 MHz, DMSO-$d_6$) δ 13.49 (br s, 1H), 11.18 (s, 1H), 8.66 (d, J = 7.0 Hz, 1H), 7.89 (s, 1H), 7.77 (s, 1H), 7.04-6.89 (m, 2H), 5.15-4.82 (m, 1H), 4.58 (d, J = 4.3 Hz, 1H), 4.08 (br d, J = 5.4 Hz, 1H), 3.70 (br s, 1H), 2.90 (s, 3H), 2.11 (dt, J = 7.0, 13.6 Hz, 2H), 1.81-1.62 (m, 5H), 1.59-1.43 (m, 2H), 1.25-1.13 (m, 1H); LCMS(electrospray) m/z 501.2 (M + H+). | J |
| 556 | 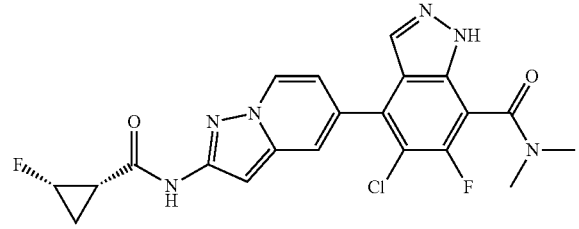 [SMILES: CN(C)C(=O)c1c(F)c(Cl)c(-c2ccn3nc(NC(=O)[C@@H]4C[C@@H]4F)cc3c2)c2cn[nH]c12]<br>5-chloro-6-fluoro-4-(2-((1S,2S)-2-fluorocyclopropane-1-carboxamido)pyrazolo[1,5-a]pyridin-5-yl)-N,N-dimethyl-1H-indazole-7-carboxamide | ¹H NMR (400 MHz, DMSO-$d_6$) δ 13.88-13.56 (m, 1H), 11.20 (s, 1H), 8.70 (d, J = 7.1 Hz, 1H), 8.00 (s, 1H), 7.82 (d, J = 0.7 Hz, 1H), 6.99 (s, 1H), 6.96 (d, J = 2.0 Hz, 1H), 5.05-4.85 (m, 1H), 3.13 (s, 3H), 2.93 (s, 3H), 2.18-2.11 (m, 1H), 1.72-1.62 (m, 1H), 1.18 (ddd, J = 2.9, 6.1, 12.3 Hz, 1H); LCMS(electrospray) m/z459.1(M + H+). | J |
| 557 | 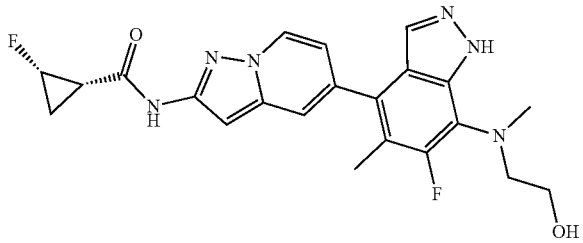 [SMILES: Cc1c(F)c(N(C)CCO)c2[nH]ncc2c1-c1ccn2nc(NC(=O)[C@@H]3C[C@@H]3F)cc2c1]<br>(1S,2S)-2-fluoro-N-(5-(6-fluoro-7-((2-hydroxyethyl)(methyl)amino)-5-methyl-1H-indazol-4-yl)pyrazolo[1,5-a]pyridin-2-yl)cyclopropane-1-carboxamide | ¹H NMR (400 MHz, DMSO-$d_6$) δ 13.18 (br d, J = 2.5 Hz, 1H), 11.14 (s, 1H), 8.62 (d, J = 7.2 Hz, 1H), 7.74 (s, 1H), 7.62 (s, 1H), 6.90 (s, 1H), 6.87-6.81 (m, 1H), 5.17-4.73 (m, 2H), 3.65-3.57 (m, 2H), 3.28-3.18 (m, 2H), 2.97 (d, J = 2.3 Hz, 3H), 2.25-2.10 (m, 4H), 1.76-1.58 (m, 1H), 1.26-1.11 (m, 1H); LCMS(electrospray) m/z 441.1 (M + H+). | J |
| 558 | 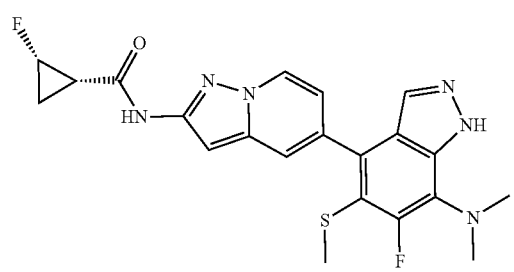 [SMILES: CSc1c(F)c(N(C)C)c2[nH]ncc2c1-c1ccn2nc(NC(=O)[C@@H]3C[C@@H]3F)cc2c1]<br>(1S,2S)-N-(5-(7-(dimethylamino)-6-fluoro-5-(methylthio)-1H-indazol-4-yl)pyrazolo[1,5-a]pyridin-2-yl)-2-fluorocyclopropane-1-carboxamide | ¹H NMR (400 MHz, DMSO-$d_6$) δ 13.43 (br s, 1H), 11.14 (s, 1H), 8.59 (d, J = 7.0 Hz, 1H), 7.78 (s, 1H), 7.62 (s, 1H), 6.91 (s, 1H), 6.87 (dd, J = 1.9, 7.1 Hz, 1H), 5.06-4.82 (m, 1H), 2.97 (d, J = 2.0 Hz, 6H), 2.26 (s, 3H), 2.19-2.10 (m, 1H), 1.73-1.61 (m, 1H), 1.22-1.12 (m, 1H); LCMS(electrospray) m/z 443 (M + H+). | J |

TABLE 1-continued

Compounds of Examples

| Ex # | Structure/Name | $^1$H NMR/MS (M + 1) | Method |
|---|---|---|---|
| 559 | 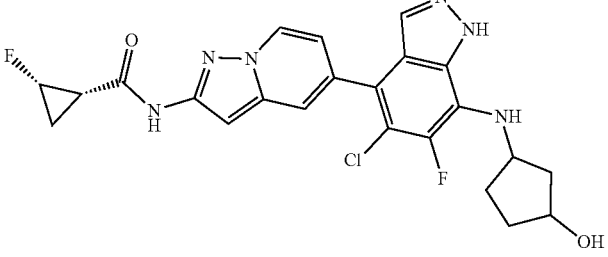<br>(1S,2S)-N-(5-(5-chloro-6-fluoro-7-((3-hydroxycyclopentyl)amino)-1H-indazol-4-yl)pyrazolo[1,5-a]pyridin-2-yl)-2-fluorocyclopropane-1-carboxamide | $^1$H NMR (400 MHz, DMSO-$d_6$) δ 13.29 (br s, 1H), 11.15 (s, 1H), 8.62 (d, J = 7.0 Hz, 1H), 7.86 (br s, 1H), 7.71 (s, 1H), 7.00-6.86 (m, 2H), 5.44 (br s, 1H), 5.11-4.94 (m, 1H), 4.90-4.77 (m, 1H), 4.40-4.11 (m, 2H), 2.25-2.09 (m, 2H), 2.04-1.86 (m, 1H), 1.84-1.57 (m, 5H), 1.30-1.08 (m, 1H); LCMS(electrospray) m/z 487.2 (M + H+). | J |
| 560 | 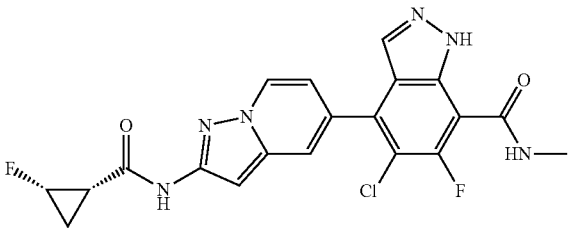<br>5-chloro-6-fluoro-4-(2-((1S,2S)-2-fluorocyclopropane-1-carboxamido)pyrazolo[1,5-a]pyridin-5-yl)-N-methyl-1H-indazole-7-carboxamide | $^1$H NMR (400 MHz, DMSO-$d_6$) δ 13.68-13.53 (m, 1H), 11.24-11.17 (m, 1H), 8.70 (d, J = 7.1 Hz, 1H), 8.67-8.60 (m, 1H), 7.99-7.93 (m, 1H), 7.81 (d, J = 0.9 Hz, 1H), 6.99 (s, 1H), 6.97-6.92 (m, 1H), 5.07-4.81 (m, 1H), 2.91 (d, J = 4.4 Hz, 3H), 2.20-2.10 (m, 1H), 1.75-1.55 (m, 1H), 1.07 (s, 1H); LCMS(electrospray) m/z 445.1(M + H+). | J |
| 561 | 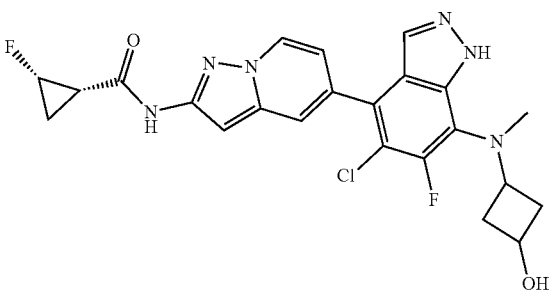 [SMILES: CN(c1c(F)c(Cl)c(-c2ccn3nc(NC(=O)[C@@H]4C[C@@H]4F)cc3c2)c2cn[nH]c12)C1CC(O)C1]<br>(1S,2S)-N-(5-(5-chloro-6-fluoro-7-((3-hydroxycyclobutyl)(methyl)amino)-1H-indazol-4-yl)pyrazolo[1,5-a]pyridin-2-yl)-2-fluorocyclopropane-1-carboxamide | $^1$H NMR (400 MHz, DMSO-$d_6$) δ 11.18 (br s, 1H), 8.65 (d, J = 7.2 Hz, 1H), 7.88 (s, 1H), 7.76 (s, 1H), 7.09-6.87 (m, 2H), 5.08-4.84 (m, 1H), 3.87-3.71 (m, 1H), 3.59-3.43 (m, 1H), 3.60-3.42 (m, 1H), 2.89-2.81 (m, 3H), 2.46-2.39 (m, 2H), 2.21-2.09 (m, 1H), 2.24-2.07 (m, 1H), 2.20-1.95 (m, 1H), 1.99 (br d, J = 4.9 Hz, 3H), 1.79-1.62 (m, 3H), 1.26-1.12 (m, 2H); LCMS(electrospray) m/z 487.2 (M + H+). | J |
| 562 | 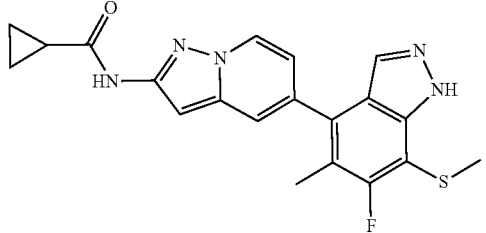 [SMILES: CSc1c(F)c(C)c(-c2ccn3nc(NC(=O)C4CC4)cc3c2)c2cn[nH]c12]<br>N-(5-(6-fluoro-5-methyl-7-(methylthio)-1H-indazol-4-yl)pyrazolo[1,5-a]pyridin-2-yl)cyclopropanecarboxamide | $^1$H NMR (400 MHz, DMSO-$d_6$) δ 13.47 (br s, 1H), 11.11 (s, 1H), 8.64 (d, J = 7.1 Hz, 1H), 7.83 (s, 1H), 7.65 (s, 1H), 6.91 (s, 1H), 6.86 (dd, J = 1.9, 7.1 Hz, 1H), 2.24 (d, J = 2.9 Hz, 3H), 2.00-1.87 (m, 1H), 0.88-0.77 (m, 4H); LCMS(electrospray) m/z 395.12 (M + H+). | J |

TABLE 1-continued

Compounds of Examples

| Ex # | Structure/Name | ¹H NMR/MS (M + 1) | Method |
|---|---|---|---|
| 563 | 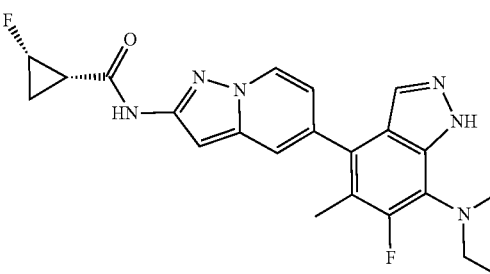<br>(1S,2S)-N-(5-(7-(ethyl(methyl)amino)-6-fluoro-5-methyl-1H-indazol-4-yl)pyrazolo[1,5-a]pyridin-2-yl)-2-fluorocyclopropane-1-carboxamide | ¹H NMR (400 MHz, METHANOL-d₄) δ 8.55-8.47 (m, 1H), 7.79-7.72 (m, 1H), 7.58-7.54 (m, 1H), 7.00-6.93 (m, 1H), 6.89-6.83 (m, 1H), 5.02-4.93 (m, 1H), 4.60-4.56 (m, 1H), 3.29-3.24 (m, 2H), 3.01-2.94 (m, 3H), 2.33-2.25 (m, 3H), 2.17-2.07 (m, 1H), 1.89-1.77 (m, 1H), 1.27-1.19 (m, 1H), 1.15-1.09 (m, 3H); LCMS(electrospray) m/z 425.2 (M + H+). | J |
| 564 | 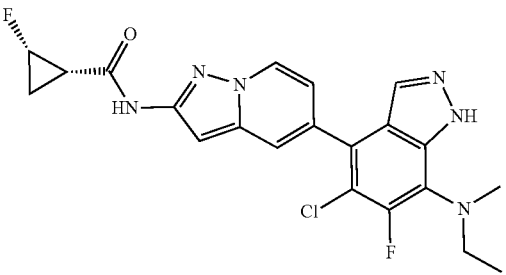 [SMILES: CCN(C)c1c(F)c(Cl)c(-c2ccn3nc(NC(=O)[C@@H]4C[C@@H]4F)cc3c2)c2cn[nH]c12]<br>(1S,2S)-N-(5-(5-chloro-7-(ethyl(methyl)amino)-6-fluoro-1H-indazol-4-yl)pyrazolo[1,5-a]pyridin-2-yl)-2-fluorocyclopropane-1-carboxamide | ¹H NMR (400 MHz, METHANOL-d₄) δ 8.43-8.38 (m, 1H), 7.77-7.72 (m, 1H), 7.59-7.54 (m, 1H), 6.89-6.86 (m, 1H), 6.85-6.81 (m, 1H), 4.88-4.82 (m, 1H), 4.72-4.64 (m, 1H), 3.20-3.15 (m, 2H), 3.20 (br s, 1H), 2.90 (d, J = 1.8 Hz, 2H), 2.95-2.88 (m, 1H), 2.04-1.94 (m, 1H), 1.78-1.65 (m, 1H), 1.17-1.07 (m, 1H), 1.05-0.99 (m, 3H); LCMS(electrospray) m/z 445.2 (M + H+). | J |
| 565 | 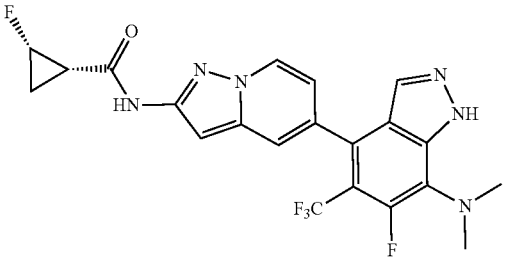 [SMILES: CN(C)c1c(F)c(C(F)(F)F)c(-c2ccn3nc(NC(=O)[C@@H]4C[C@@H]4F)cc3c2)c2cn[nH]c12]<br>(1S,2S)-N-(5-(7-(dimethylamino)-6-fluoro-5-(trifluoromethyl)-1H-indazol-4-yl)pyrazolo[1,5-a]pyridin-2-yl)-2-fluorocyclopropane-1-carboxamide | ¹H NMR (400 MHz, DMSO-d₆) δ 11.18 (s, 1H), 8.62 (d, J = 7.1 Hz, 1H), 7.80 (d, J = 4.8 Hz, 1H), 7.62 (d, J = 0.9 Hz, 1H), 6.92 (s, 1H), 6.80 (dd, J = 1.9, 7.1 Hz, 1H), 5.08-4.70 (m, 1H), 3.02 (d, J = 2.3 Hz, 6H), 2.20-2.12 (m, 1H), 1.73-1.62 (m, 1H), 1.22-1.14 (m, 1H); LCMS(electrospray) m/z 465.1 (M + H+). | J |
| 566 | 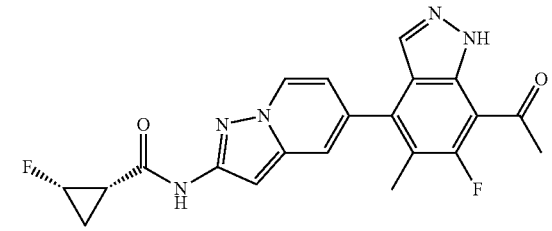 [SMILES: CC(=O)c1c(F)c(C)c(-c2ccn3nc(NC(=O)[C@@H]4C[C@@H]4F)cc3c2)c2cn[nH]c12]<br>(1S,2S)-N-(5-(7-acetyl-6-fluoro-5-methyl-1H-indazol-4-yl)pyrazolo[1,5-a]pyridin-2-yl)-2-fluorocyclopropane-1-carboxamide | ¹H NMR (400 MHz, DMSO-d₆) δ 13.44 (br s, 1H), 11.19 (s, 1H), 8.68 (d, J = 7.1 Hz, 1H), 7.86 (s, 1H), 7.73 (s, 1H), 6.97 (s, 1H), 6.89 (dd, J = 1.9, 7.2 Hz, 1H), 5.07-4.80 (m, 1H), 2.74 (d, J = 6.4 Hz, 3H), 2.28 (d, J = 3.2 Hz, 3H), 2.20-2.09 (m, 1H), 1.74-1.61 (m, 1H), 1.25-1.13 (m, 1H); LCMS(electrospray) m/z 409.14 (M + H+). | J |

TABLE 1-continued

Compounds of Examples

| Ex # | Structure/Name | ¹H NMR/MS (M + 1) | Method |
|---|---|---|---|
| 567 | 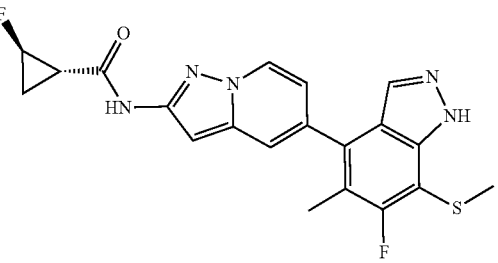<br>(1S,2R)-2-fluoro-N-(5-(6-fluoro-5-methyl-7-(methylthio)-1H-indazol-4-yl)pyrazolo[1,5-a]pyridin-2-yl)cyclopropane-1-carboxamide | ¹H NMR (400 MHz, DMSO-$d_6$) δ 13.47 (br s, 1H), 11.28 (s, 1H), 8.65 (d, J = 7.1 Hz, 1H), 7.83 (s, 1H), 7.67 (s, 1H), 6.89 (s, 1H), 6.87 (d, J = 1.8 Hz, 1H), 5.03-4.81 (m, 1H), 2.23 (d, J = 2.8 Hz, 3H), 1.64-1.45 (m, 1H), 1.27 (qd, J = 6.5, 13.1 Hz, 1H); LCMS(electrospray) m/z 413.11 (M + H+). | J |
| 568 | 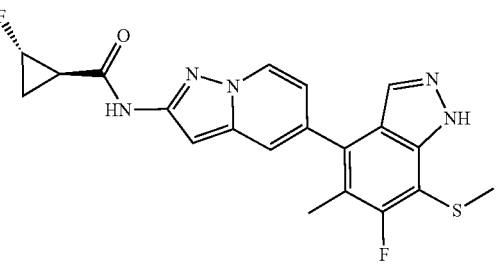 [SMILES: CSc1c(F)c(C)c(-c2ccn3nc(NC(=O)[C@H]4C[C@@H]4F)cc3c2)c2cn[nH]c12]<br>(1R,2S)-2-fluoro-N-(5-(6-fluoro-5-methyl-7-(methylthio)-1H-indazol-4-yl)pyrazolo[1,5-a]pyridin-2-yl)cyclopropane-1-carboxamide | ¹H NMR (400 MHz, DMSO-$d_6$) δ 13.47 (br s, 1H), 11.28 (s, 1H), 8.65 (d, J = 7.1 Hz, 1H), 7.83 (s, 1H), 7.67 (d, J = 0.7 Hz, 1H), 6.88 (s, 1H), 6.87 (d, J = 1.8 Hz, 1H), 5.04-4.79 (m, 1H), 2.49-2.40 (m, 3H), 2.23 (d, J = 2.8 Hz, 3H), 1.62-1.45 (m, 1H), 1.27 (qd, J = 6.4, 13.1 Hz, 1H); LCMS(electrospray) m/z 413.11 (M + H+). | J |
| 569 | 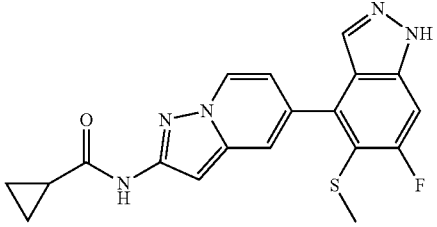 [SMILES: CSc1c(F)cc2[nH]ncc2c1-c1ccn2nc(NC(=O)C3CC3)cc2c1]<br>N-(5-(6-fluoro-5-(methylthio)-1H-indazol-4-yl)pyrazolo[1,5-a]pyridin-2-yl)cyclopropanecarboxamide | ¹H NMR (400 MHz, DMSO-$d_6$) δ 13.45 (br s, 1H), 11.10 (s, 1H), 8.61 (d, J = 7.1 Hz, 1H), 7.81 (s, 1H), 7.66 (s, 1H), 7.52 (d, J = 9.3 Hz, 1H), 6.91 (s, 1H), 6.88 (dd, J = 1.8, 7.1 Hz, 1H), 2.26 (s, 3H), 2.00-1.88 (m, 1H), 0.90-0.77 (m, 4H); LCMS(electrospray) m/z 382.1(M + H+) | J |
| 570 | 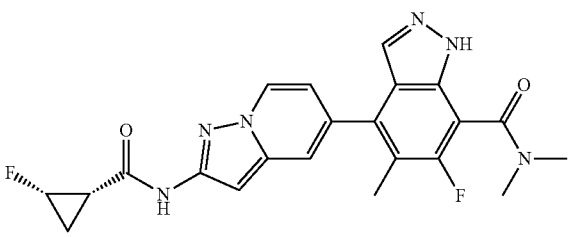 [SMILES: Cc1c(F)c(C(=O)N(C)C)c2[nH]ncc2c1-c1ccn2nc(NC(=O)[C@@H]3C[C@@H]3F)cc2c1]<br>6-fluoro-4-(2-((1S,2S)-2-fluorocyclopropane-1-carboxamido)pyrazolo[1,5-a]pyridin-5-yl)-N,N,5-trimethyl-1H-indazole-7-carboxamide | ¹H NMR (400 MHz, DMSO-$d_6$) δ 13.43 (br s, 1H), 11.17 (s, 1H), 8.66 (d, J = 7.1 Hz, 1H), 7.84 (s, 1H), 7.73-7.67 (m, 1H), 6.94 (s, 1H), 6.89 (dd, J = 2.0, 7.1 Hz, 1H), 5.16-4.74 (m, 1H), 3.12 (s, 3H), 2.92 (s, 3H), 2.24 (d, J = 2.9 Hz, 3H), 2.19-2.10 (m, 1H), 1.74-1.60 (m, 1H), 1.18 (tdd, J = 6.2, 9.1, 12.3 Hz, 1H); LCMS(electrospray) m/z 439.2 (M + H+). | J |

TABLE 1-continued

Compounds of Examples

| Ex # | Structure/Name | ¹H NMR/MS (M + 1) | Method |
|---|---|---|---|
| 571 | 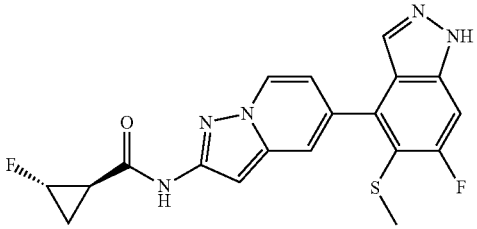 [SMILES: CSc1c(F)cc2[nH]ncc2c1-c1ccn2nc(NC(=O)[C@H]3C[C@@H]3F)cc2c1]<br>(1R,2S)-2-fluoro-N-(5-(6-fluoro-5-(methylthio)-1H-indazol-4-yl)pyrazolo[1,5-a]pyridin-2-yl)cyclopropane-1-carboxamide | ¹H NMR (400 MHz, DMSO-d₆) δ 13.42 (br s, 1H), 11.28 (br s, 1H), 8.63 (d, J = 7.1 Hz, 1H), 7.81 (s, 1H), 7.67 (s, 1H), 7.52 (d, J = 9.3 Hz, 1H), 6.93-6.87 (m, 2H), 5.05-4.81 (m, 1H), 2.48-2.42 (m, 1H), 2.26 (s, 3H), 1.61-1.46 (m, 1H), 1.33-1.20 (m, 1H); LCMS(electrospray) m/z 400.1(M + H+). | J |
| 572 | 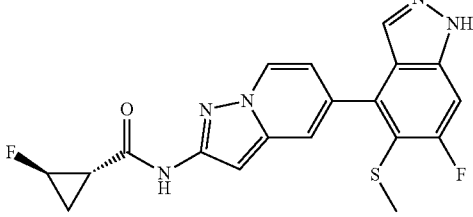<br>(1S,2R)-2-fluoro-N-(5-(6-fluoro-5-(methylthio)-1H-indazol-4-yl)pyrazolo[1,5-a]pyridin-2-yl)cyclopropane-1-carboxamide | ¹H NMR (400 MHz, DMSO-d₆) δ 13.40 (br s, 1H), 11.28 (s, 1H), 8.63 (d, J = 7.0 Hz, 1H), 7.81 (s, 1H), 7.67 (s, 1H), 7.52 (d, J = 9.2 Hz, 1H), 6.93-6.87 (m, 2H), 5.03-4.80 (m, 1H), 2.46-2.42 (m, 1H), 2.26 (s, 3H), 1.61-1.46 (m, 1H), 1.27 (qd, J = 6.3, 13.0 Hz, 1H); LCMS(electrospray) m/z 400.1(M + H+). | J |
| 573 | 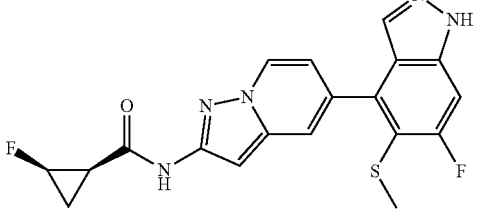<br>(1R,2R)-2-fluoro-N-(5-(6-fluoro-5-(methylthio)-1H-indazol-4-yl)pyrazolo[1,5-a]pyridin-2-yl)cyclopropane-1-carboxamide | ¹H NMR (400 MHz, DMSO-d₆) δ 13.42 (br s, 1H), 11.15 (s, 1H), 8.62 (d, J = 7.0 Hz, 1H), 7.82 (s, 1H), 7.68 (s, 1H), 7.52 (d, J = 9.4 Hz, 1H), 6.93 (s, 1H), 6.90 (dd, J = 1.8, 7.1 Hz, 1H), 5.06-4.83 (m, 1H), 2.26 (s, 3H), 2.15 (td, J = 7.1, 14.1 Hz, 1H), 1.74-1.61 (m, 1H), 1.22-1.12 (m, 1H); LCMS(electrospray) m/z 400.1(M + H+). | J |
| 574 | 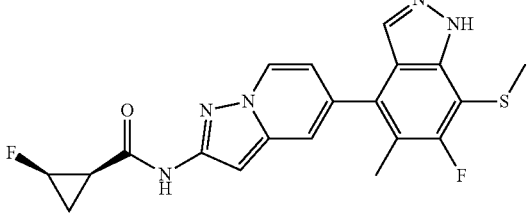<br>(1R,2R)-2-fluoro-N-(5-(6-fluoro-5-methyl-7-(methylthio)-1H-indazol-4-yl)pyrazolo[1,5-a]pyridin-2-yl)cyclopropane-1-carboxamide | ¹H NMR (400 MHz, DMSO-d₆) δ 13.47 (br s, 1H), 11.16 (s, 1H), 8.65 (d, J = 7.1 Hz, 1H), 7.84 (s, 1H), 7.67 (s, 1H), 6.93 (s, 1H), 6.87 (dd, J = 1.8, 7.1 Hz, 1H), 5.08-4.79 (m, 1H), 3.30 (s, 3H), 2.25-2.23 (m, 1H), 2.24 (d, J = 2.9 Hz, 3H), 2.14 (br dd, J = 6.0, 8.1 Hz, 1H), 1.76-1.60 (m, 1H), 1.24-1.13 (m, 1H); LCMS(electrospray) m/z 413.11 (M + H+). | J |

TABLE 1-continued

Compounds of Examples

| Ex # | Structure/Name | $^1$H NMR/MS (M + 1) | Method |
|---|---|---|---|
| 575 | 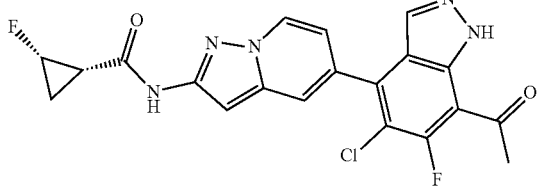<br>(1S,2S)-N-(5-(7-acetyl-5-chloro-6-fluoro-1H-indazol-4-yl)pyrazolo[1,5-a]pyridin-2-yl)-2-fluorocyclopropane-1-carboxamide | $^1$H NMR (400 MHz, DMSO-$d_6$) δ 13.74 (s, 1H), 11.22 (s, 1H), 8.72 (d, J = 7.1 Hz, 1H), 8.40 (s, 1H), 8.02 (s, 1H), 7.85 (d, J = 1.0 Hz, 1H), 7.02 (s, 1H), 6.97 (dd, J = 1.9, 7.2 Hz, 1H), 5.14-4.76 (m, 1H), 2.77 (d, J = 6.1 Hz, 3H), 2.21-2.12 (m, 1H), 1.75-1.61 (m, 1H), 1.26-1.12 (m, 2H); LCMS(electrospray) m/z 430.3 (M + H+). | J |
| 576 | 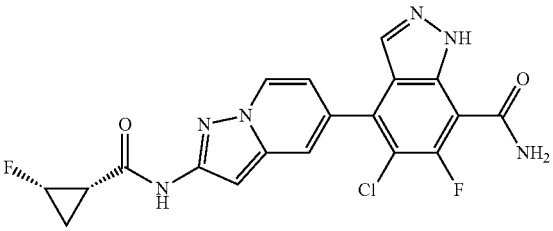 [SMILES: NC(=O)c1c(F)c(Cl)c(-c2ccn3nc(NC(=O)[C@@H]4C[C@@H]4F)cc3c2)c2cn[nH]c12]<br>5-chloro-6-fluoro-4-(2-((1S,2S)-2-fluorocyclopropane-1-carboxamido)pyrazolo[1,5-a]pyridin-5-yl)-1H-indazole-7-carboxamide | $^1$H NMR (400 MHz, DMSO-$d_6$) δ 13.70-13.43 (m, 1H), 11.22 (s, 1H), 8.71 (d, J = 6.8 Hz, 1H), 8.08 (s, 2H), 7.95 (s, 1H), 7.82 (s, 1H), 7.03-6.91 (m, 2H), 5.10-4.81 (m, 1H), 2.15 (d, J = 6.8 Hz, 1H), 1.76-1.59 (m, 1H), 1.18 (d, J = 7.2 Hz, 1H); LCMS(electrospray) m/z 431.1 (M + H+). | J |
| 577 | 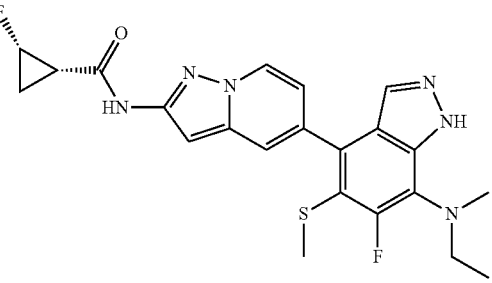<br>(1S,2S)-N-(5-(7-(ethyl(methyl)amino)-6-fluoro-5-(methylthio)-1H-indazol-4-yl)pyrazolo[1,5-a]pyridin-2-yl)-2-fluorocyclopropane-1-carboxamide | $^1$H NMR (400 MHz, DMSO-$d_6$) δ 13.38 (br s, 1H), 11.14 (s, 1H), 8.60 (d, J = 6.9 Hz, 1H), 7.78 (s, 1H), 7.64 (s, 1H), 6.91 (s, 1H), 6.88 (dd, J = 1.6, 7.1 Hz, 1H), 5.06-4.83 (m, 1H), 3.23 (q, J = 6.7 Hz, 2H), 2.95 (s, 3H), 2.26 (s, 3H), 2.19-2.10 (m, 1H), 1.74-1.61 (m, 1H), 1.21-1.14 (m, 1H), 1.07 (t, J = 7.0 Hz, 3H); LCMS(electrospray) m/z 457 (M + H+). | J |
| 578 | 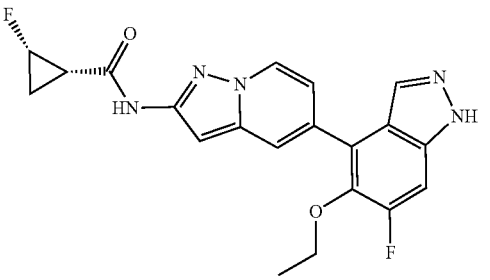 [SMILES: CCOc1c(F)cc2[nH]ncc2c1-c1ccn2nc(NC(=O)[C@@H]3C[C@@H]3F)cc2c1]<br>(1S,2S)-N-(5-(5-ethoxy-6-fluoro-1H-indazol-4-yl)pyrazolo[1,5-a]pyridin-2-yl)-2-fluorocyclopropane-1-carboxamide | $^1$H NMR (400 MHz, DMSO-$d_6$) δ 13.62-12.96 (m, 1H), 11.16 (br s, 1H), 8.64 (d, J = 7.1 Hz, 1H), 7.98 (s, 1H), 7.83 (s, 1H), 7.50 (d, J = 10.4 Hz, 1H), 7.04 (dd, J = 1.8, 7.1 Hz, 1H), 6.95 (s, 1H), 5.06-4.81 (m, 1H), 3.86 (q, J = 6.9 Hz, 2H), 2.15 (td, J = 7.0, 13.6 Hz, 1H), 1.73-1.62 (m, 1H), 1.22-1.15 (m, 1H), 1.11 (t, J = 7.0 Hz, 3H). LCMS: m/z 398.0 (M + H+) | J |

TABLE 1-continued

Compounds of Examples

| Ex # | Structure/Name | $^1$H NMR/MS (M + 1) | Method |
|---|---|---|---|
| 579 | 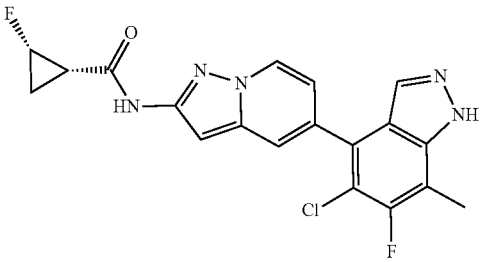 [SMILES: Cc1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-methyl-1H-indazol-4-yl)pyrazolo[1,5-a]pyridin-2-yl)-2-fluorocyclopropane-1-carboxamide | $^1$H NMR (400 MHz, DMSO-$d_6$) δ 11.31-11.12 (m, 1H), 8.82-8.55 (m, 1H), 8.00-7.87 (m, 1H), 7.85-7.70 (m, 1H), 7.03-6.90 (m, 2H), 5.10-4.82 (m, 1H), 2.56-2.53 (m, 3H), 2.24-2.11 (m, 1H), 1.75-1.61 (m, 1H), 1.26-1.13 (m, 1H); LCMS(electrospray) m/z 402.1 (M + H+). | J |
| 580 | 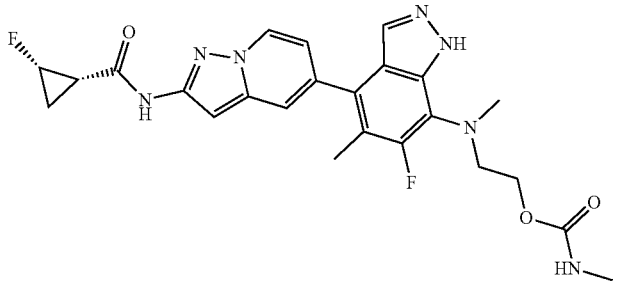 [SMILES: CNC(=O)OCCN(C)c1c(F)c(C)c(-c2ccn3nc(NC(=O)[C@@H]4C[C@@H]4F)cc3c2)c2cn[nH]c12]<br>2-((6-fluoro-4-(2-((1S,2S)-2-fluorocyclopropane-1-carboxamido)pyrazolo[1,5-a]pyridin-5-yl)-5-methyl-1H-indazol-7-yl)(methyl)amino)ethyl methylcarbamate | $^1$H NMR (400 MHz, DMSO-$d_6$) δ 13.31-12.98 (m, 1H), 11.21-11.07 (m, 1H), 8.61 (d, J = 7.0 Hz, 1H), 7.78-7.71 (m, 1H), 7.64-7.58 (m, 1H), 6.93-6.88 (m, 2H), 6.84 (br d, J = 7.1 Hz, 1H), 5.06-4.82 (m, 1H), 4.07 (br t, J = 5.9 Hz, 2H), 3.35-3.27 (m, 2H), 2.98 (s, 3H), 2.53 (d, J = 4.5 Hz, 3H), 2.20 (d, J = 3.0 Hz, 3H), 2.16-2.09 (m, 1H), 1.72-1.61 (m, 1H), 1.20-1.13 (m, 1H); LCMS(electrospray) m/z = 498.2 (M + H+). | J |
| 581 | 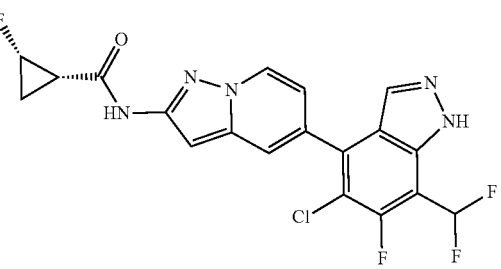<br>(1S,2S)-N-(5-(5-chloro-7-(difluoromethyl)-6-fluoro-1H-indazol-4-yl)pyrazolo[1,5-a]pyridin-2-yl)-2-fluorocyclopropane-1-carboxamide | $^1$H NMR (400 MHz, DMSO-$d_6$) δ 1.12-1.24 (m, 1 H), 1.61-1.74 (m, 1 H), 2.11-2.20 (m, 1 H), 4.82-5.07 (m, 1 H), 6.95-6.98 (m, 1 H), 6.99 (s, 1 H) 7.50 (s, 1 H), 7.63 (s, 1 H), 7.77 (s, 1 H), 7.83 (d, J = 1.00 Hz, 1 H), 8.06 (s, 1 H), 8.71 (d, J = 7.13 Hz, 1 H), 11.20 (s, 1 H), 13.85-13.92 (m, 1 H); LCMS(electrospray) m/z 438.1 (M + H+). | J |
| 582 | 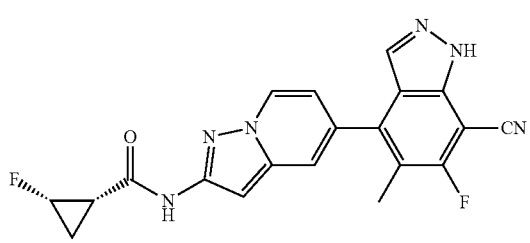 [SMILES: Cc1c(F)c(C#N)c2[nH]ncc2c1-c1ccn2nc(NC(=O)[C@@H]3C[C@@H]3F)cc2c1]<br>(1S,2S)-N-(5-(7-cyano-6-fluoro-5-methyl-1H-indazol-4-yl)pyrazolo[1,5-a]pyridin-2-yl)-2-fluorocyclopropane-1-carboxamide | $^1$H NMR (400 MHz, DMSO-$d_6$) δ 11.19 (s, 1H), 8.69 (d, J = 7.1 Hz, 1H), 8.06 (s, 1H), 7.74 (s, 1H), 6.97 (s, 1H), 6.90 (dd, J = 1.8, 7.1 Hz, 1H), 5.10-4.72 (m, 1H), 2.26 (d, J = 2.6 Hz, 3H), 2.15 (td, J = 6.6, 13.5 Hz, 1H), 1.73-1.60 (m, 1H), 1.25-1.13 (m, 1H); LCMS(electrospray) m/z 393.1 (M + H+). | J |

TABLE 1-continued

Compounds of Examples

| Ex # | Structure/Name | ¹H NMR/MS (M + 1) | Method |
|------|----------------|-------------------|--------|
| 583 | 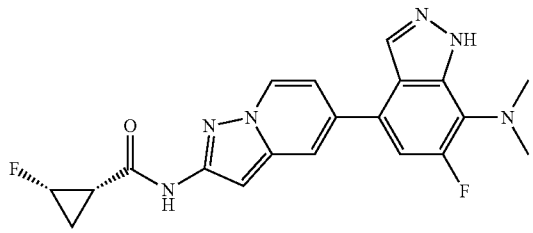 [SMILES: CN(C)c1c(F)cc(-c2ccn3nc(NC(=O)[C@@H]4C[C@@H]4F)cc3c2)c2cn[nH]c12]<br>(1S,2S)-N-(5-(7-(dimethylamino)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.38 (s, 1H), 11.15 (s, 1H), 8.61 (d, J = 7.2 Hz, 1H), 8.29 (s, 1H), 7.93 (d, J = 1.0 Hz, 1H), 7.23 (d, J = 13.7 Hz, 1H), 7.16 (dd, J = 2.0, 7.2 Hz, 1H), 6.94 (s, 1H), 5.06-4.83 (m, 1H), 2.95 (d, J = 2.0 Hz, 6H), 2.14 (br s, 1H), 1.77-1.57 (m, 1H), 1.17 (br s, 1H); LCMS(electrospray) m/z 397.2 (M + H+). | J |
| 584 | 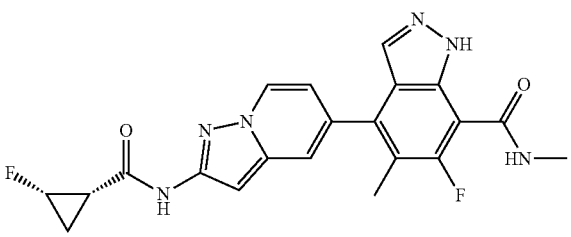<br>6-fluoro-4-(2-((1S,2S)-2-fluorocyclopropane-1-carboxamido)pyrazolo[1,5-a]pyridin-5-yl)-N,5-dimethyl-1H-indazole-7-carboxamide | ¹H NMR (400 MHz, DMSO-d₆) δ 13.31-13.17 (m, 1H), 11.26-11.08 (m, 1H), 8.66 (d, J = 7.1 Hz, 1H), 8.49-8.38 (m, 1H), 7.85-7.76 (m, 1H), 7.70 (s, 1H), 6.95 (s, 1H), 6.88 (s, 1H), 5.07-4.82 (m, 1H), 2.90 (d, J = 4.6 Hz, 3H), 2.25 (d, J = 3.1 Hz, 3H), 2.15 (td, J = 6.7, 13.8 Hz, 1H), 1.74-1.62 (m, 1H), 1.21-1.09 (m, 1H); LCMS(electrospray) m/z 425.1 (M + H+). | J |
| 585 | 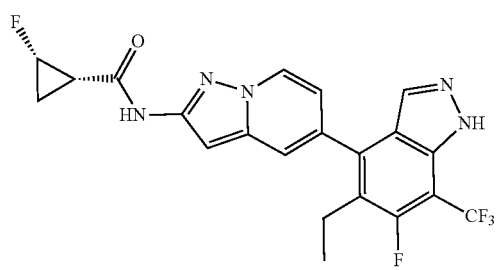 [SMILES: CCc1c(F)c(C(F)(F)F)c2[nH]ncc2c1-c1ccn2nc(NC(=O)[C@@H]3C[C@@H]3F)cc2c1]<br>(1S,2S)-N-(5-(5-ethyl-6-fluoro-7-(trifluoromethyl)-1H-indazol-4-yl)pyrazolo[1,5-a]pyridin-2-yl)-2-fluorocyclopropane-1-carboxamide | ¹H NMR (400 MHz, DMSO-d₆) δ 13.82-13.52 (m, 1H), 11.19 (s, 1H), 8.69 (d, J = 7.0 Hz, 1H), 7.91 (s, 1H), 7.70 (d, J = 0.9 Hz, 1H), 6.96 (s, 1H), 6.86 (dd, J = 1.9, 7.1 Hz, 1H), 5.06-4.83 (m, 1H), 2.68-2.63 (m, 2H), 2.19-2.10 (m, 1H), 1.74-1.62 (m, 1H), 1.20-1.14 (m, 1H), 1.10 (t, J = 7.5 Hz, 3H); LCMS(electrospray) m/z 450.2 (M + H+). | J |
| 586 | 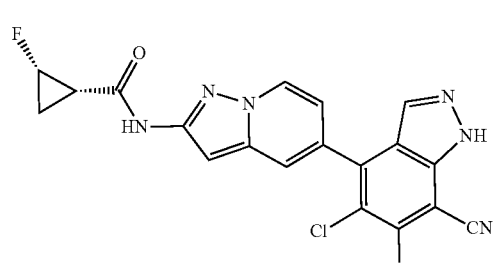<br>(1S,2S)-N-(5-(5-chloro-7-cyano-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 11.21 (s, 1H), 8.73 (d, J = 7.2 Hz, 1H), 8.24 (s, 1H), 7.86 (s, 1H), 7.02 (s, 1H), 6.97 (dd, J = 1.9, 7.2 Hz, 1H), 5.10-4.78 (m, 1H), 2.22-2.10 (m, 1H), 1.76-1.58 (m, 1H), 1.22-1.15 (m, 1H); LCMS(electrospray) m/z 413.2 (M + H+). | J |

TABLE 1-continued

Compounds of Examples

| Ex # | Structure/Name | $^1$H NMR/MS (M + 1) | Method |
|---|---|---|---|
| 587 | 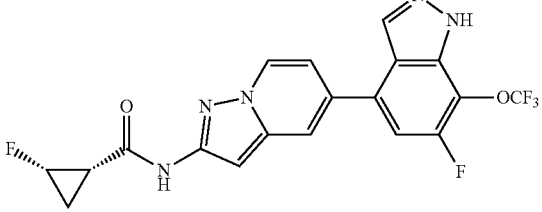<br>(1S,2S)-2-fluoro-N-(5-(6-fluoro-7-(trifluoromethoxy)-1H-indazol-4-yl)pyrazolo[1,5-a]pyridin-2-yl)cyclopropane-1-carboxamide | $^1$H NMR (400 MHz, DMSO-$d_6$) δ 14.11 (s, 1H), 11.17 (s, 1H), 8.68-8.66 (m, 1H), 8.45(s, 1H), 8.04 (s, 1H), 7.52 (d, J = 11.2 Hz, 1H), 7.22-7.21 (m, 1H), 6.99 (s, 1H), 5.02-4.86 (m, 1H), 2.15 (br s, 1H), 1.72-1.70 (m, 1 H) 1.19-1.18 (m, 1 H); LCMS(electrospray) m/z 438.2 (M + H+). | J |
| 588 | 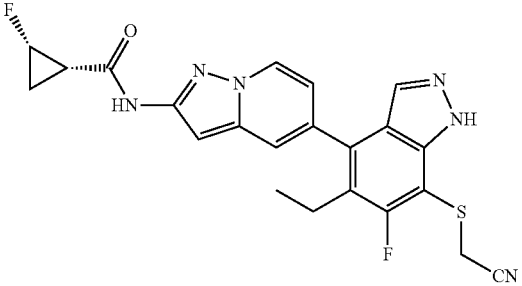 [SMILES: CCc1c(F)c(SCC#N)c2[nH]ncc2c1-c1ccn2nc(NC(=O)[C@@H]3C[C@@H]3F)cc2c1]<br>(1S,2S)-N-(5-(7-((cyanomethyl)thio)-5-ethyl-6-fluoro-1H-indazol-4-yl)pyrazolo[1,5-a]pyridin-2-yl)-2-fluorocyclopropane-1-carboxamide | $^1$H NMR (400 MHz, DMSO-$d_6$) δ 13.84-13.52 (m, 1H), 11.32-11.10 (m, 1H), 8.75-8.60 (m, 1H), 7.97-7.76 (m, 1H), 7.72-7.64 (m, 1H), 6.99-6.91 (m, 1H), 6.89-6.80 (m, 1H), 5.09-4.81 (m, 1H), 4.26-4.07 (m, 2H), 2.75-2.62 (m, 2H), 2.24-2.10 (m, 1H), 1.77-1.62 (m, 1H), 1.23-1.15 (m, 1H), 1.15-1.09 (m, 3H); LCMS(electrospray) m/z 453.1 (M + H+). | J |
| 589 | 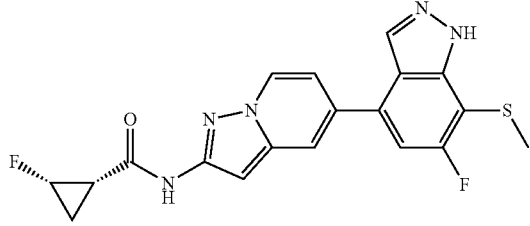 [SMILES: CSc1c(F)cc(-c2ccn3nc(NC(=O)[C@@H]4C[C@@H]4F)cc3c2)c2cn[nH]c12]<br>(1S,2S)-2-fluoro-N-(5-(6-fluoro-7-(methylthio)-1H-indazol-4-yl)pyrazolo[1,5-a]pyridin-2-yl)cyclopropane-1-carboxamide | $^1$H NMR (400 MHz, DMSO-$d_6$) δ 13.64 (s, 1 H) 11.17 (s, 1 H) 8.65 (d, J = 7.2 Hz, 1 H) 8.38 (s, 1 H) 8.02 (s, 1 H) 7.37 (d, J = 8.8 Hz, 1 H) 7.22-7.19 (m, 1 H) 6.98 (s, 1 H) 5.05-4.84 (m, 1 H) 2.52 (s, 3 H) 2.16-2.13 (m, 1H) 1.72-1.64 (m, 1H) 1.20-1.15 (m, 1 H); LCMS(electrospray) m/z 400.1 (M + H+). | J |
| 590 | 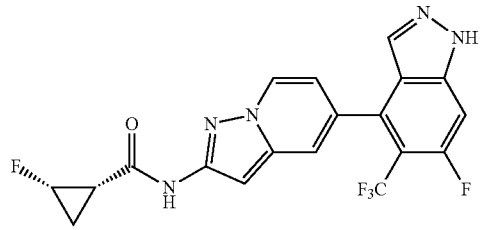 [SMILES: O=C(Nc1cc2cc(-c3c(C(F)(F)F)c(F)cc4[nH]ncc34)ccn2n1)[C@@H]1C[C@@H]1F]<br>(1S,2S)-2-fluoro-N-(5-(6-fluoro-5-(trifluoromethyl)-1H-indazol-4-yl)pyrazolo[1,5-a]pyridin-2-yl)cyclopropane-1-carboxamide | $^1$H NMR (400 MHz, DMSO-$d_6$) δ 13.74 (br s, 1H), 8.24 (d, J = 8.3 Hz, 1H), 7.79 (s, 1H), 7.76 (d, J = 11.9 Hz, 1H), 7.66 (d, J = 8.3 Hz, 1H), 5.19-4.94 (m, 1H), 2.26 (td, J = 6.9, 13.6 Hz, 1H), 1.84-1.70 (m, 1H), 1.39-1.27 (m, 1H); LCMS(electrospray) m/z 440.2 (M + H+). | J |

TABLE 1-continued

Compounds of Examples

| Ex # | Structure/Name | ¹H NMR/MS (M + 1) | Method |
|---|---|---|---|
| 591 | 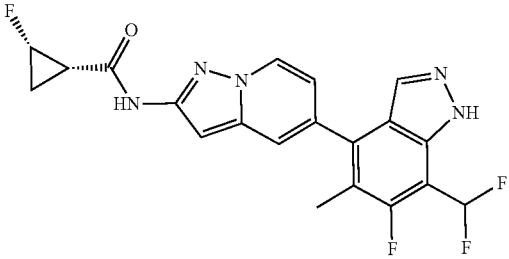 [SMILES: Cc1c(F)c(C(F)F)c2[nH]ncc2c1-c1ccn2nc(NC(=O)[C@@H]3C[C@@H]3F)cc2c1]<br>(1S,2S)-N-(5-(7-(difluoromethyl)-6-fluoro-5-methyl-1H-indazol-4-yl)pyrazolo[1,5-a]pyridin-2-yl)-2-fluorocyclopropane-1-carboxamide | ¹H NMR (400 MHz, DMSO-$d_6$) δ 13.55 (s, 1H), 11.18 (s, 1H), 8.67 (d, J = 7.1 Hz, 1H), 7.89 (d, J = 0.7 Hz, 1H), 7.72-7.41 (m, 2H), 6.95 (s, 1H), 6.89 (dd, J = 1.8, 7.0 Hz, 1H), 5.09-4.81 (m, 1H), 2.24 (d, J = 2.6 Hz, 3H), 2.19-2.11 (m, 1H), 1.76-1.60 (m, 1H), 1.25-1.11 (m, 1H); LCMS(electrospray) m/z 418.1 (M + H+). | J |
| 592 | 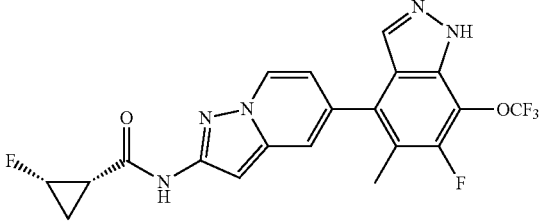 [SMILES: Cc1c(F)c(OC(F)(F)F)c2[nH]ncc2c1-c1ccn2nc(NC(=O)[C@@H]3C[C@@H]3F)cc2c1]<br>(1S,2S)-2-fluoro-N-(5-(6-fluoro-5-methyl-7-(trifluoromethoxy)-1H-indazol-4-yl)pyrazolo[1,5-a]pyridin-2-yl)cyclopropane-1-carboxamide | ¹H NMR (400 MHz, DMSO-$d_6$) δ 13.95 (s, 1H), 11.18 (s, 1H), 8.67 (d, J = 7.1 Hz, 1H), 7.94 (s, 1H), 7.72 (s, 1H), 6.95 (s, 1H), 6.90 (dd, J = 1.8, 7.1 Hz, 1H), 5.11-4.78 (m, 1H), 2.28 (d, J = 2.8 Hz, 3H), 2.20-2.10 (m, 1H), 1.74-1.61 (m, 1H), 1.24-1.12 (m, 1H); LCMS(electrospray) m/z 452.2 (M + H+). | J |
| 593 | 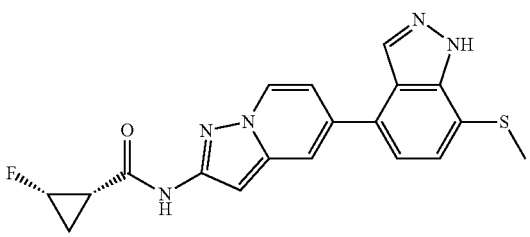 [SMILES: CSc1ccc(-c2ccn3nc(NC(=O)[C@@H]4C[C@@H]4F)cc3c2)c2cn[nH]c12]<br>(1S,2S)-2-fluoro-N-(5-(7-(methylthio)-1H-indazol-4-yl)pyrazolo[1,5-a]pyridin-2-yl)cyclopropane-1-carboxamide | ¹H NMR (400 MHz, DMSO-$d_6$) δ 13.43-13.58 (m, 1 H) 11.13 (s, 1 H) 8.62 (d, J = 7.13 Hz, 1 H) 8.36 (s, 1 H) 7.94 (d, J = 1.25 Hz, 1 H) 7.36 (s, 2 H) 7.17 (dd, J = 7.25, 2.00 Hz, 1 H) 6.95 (s, 1 H) 4.80-5.07 (m, 1 H) 2.63 (s, 3 H) 2.10-2.18 (m, 1 H) 1.62-1.73 (m, 1 H) 1.17 (ddt, J = 12.32, 9.04, 6.27, 6.27 Hz, 1 H); LCMS(electrospray) m/z = 382.1 (M + H+). | J |
| 594 | 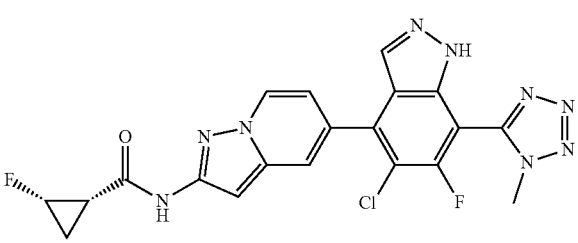 [SMILES: Cn1nnnc1-c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-(1-methyl-1H-tetrazol-5-yl)-1H-indazol-4-yl)pyrazolo[1,5-a]pyridin-2-yl)-2-fluorocyclopropane-1-carboxamide | ¹H NMR (400 MHz, DMSO-$d_6$) δ 13.69 (s, 1H), 11.14 (s, 1H), 8.93 (s, 1H), 8.26-8.23 (m, 2H), 7.65 (d, J = 9.3 Hz, 1H), 7.51-7.39 (m, 1H), 5.11-4.77 (m, 1H), 4.13 (s, 3H), 2.18 (td, J = 6.8, 13.8 Hz, 1H), 1.81-1.59 (m, 1H), 1.27-1.11 (m, 1H); LCMS(electrospray) m/z 470.2 (M + H+). | J |

TABLE 1-continued

Compounds of Examples

| Ex # | Structure/Name | ¹H NMR/MS (M + 1) | Method |
|---|---|---|---|
| 595 | 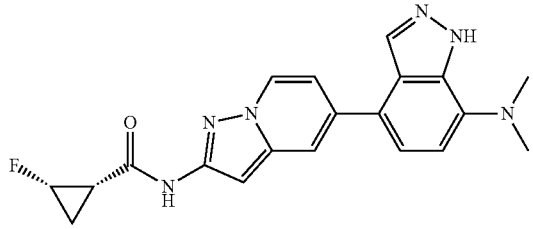 [SMILES: CN(C)c1ccc(-c2ccn3nc(NC(=O)[C@@H]4C[C@@H]4F)cc3c2)c2cn[nH]c12]<br>(1S,2S)-N-(5-(7-(dimethylamino)-1H-indazol-4-yl)pyrazolo[1,5-a]pyridin-2-yl)-2-fluorocyclopropane-1-carboxamide | ¹H NMR (400 MHz, DMSO-d$_6$) δ 13.26 (br s, 1H), 11.11 (s, 1H), 8.57 (br d, J = 7.1 Hz, 1H), 8.28 (s, 1H), 7.84 (s, 1H), 7.26 (br d, J = 7.7 Hz, 1H), 7.13 (dd, J = 2.0, 7.3 Hz, 1H), 6.90 (s, 1H), 6.80 (br d, J = 7.7 Hz, 1H), 5.08-4.79 (m, 1H), 2.93 (s, 6H), 2.14 (quin, J = 6.9 Hz, 1H), 1.74-1.60 (m, 1H), 1.17 (tdd, J = 6.2, 9.0, 12.3 Hz, 1H); LCMS(electrospray) m/z 379.1 (M + H+). | J |
| 596 | 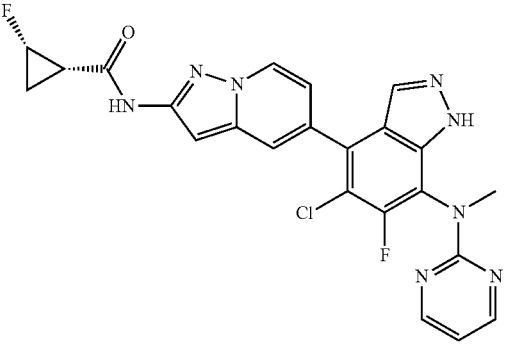 [SMILES: CN(c1ncccn1)c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-(methyl(pyrimidin-2-yl)amino)-1H-indazol-4-yl)pyrazolo[1,5-a]pyridin-2-yl)-2-fluorocyclopropane-1-carboxamide | ¹H NMR (400 MHz, DMSO-d$_6$) δ 13.63 (s, 1H), 11.19 (s, 1H), 8.63 (d, J = 7.2 Hz, 1H), 8.45 (br, 1H), 7.97 (s, 1H), 7.84 (s, 1H), 6.99 (s, 1H), 6.85 (d, J = 7.2 Hz, 1H), 5.04-4.85 (m, 1H), 3.53 (s, 3H), 2.16-2.12 (m, 1H), 1.70-1.63 (m, 1H), 1.28-1.12 (m, 1H); LCMS (electrospray) m/z 495.1 (M + H)+. | J |
| 597 | 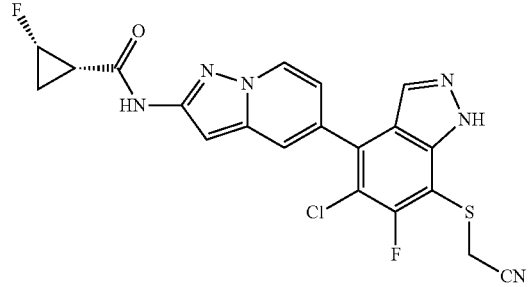 [SMILES: N#CCSc1c(F)c(Cl)c(-c2ccn3nc(NC(=O)[C@@H]4C[C@@H]4F)cc3c2)c2cn[nH]c12]<br>(1S,2S)-N-(5-(5-chloro-7-((cyanomethyl)thio)-6-fluoro-1H-indazol-4-yl)pyrazolo[1,5-a]pyridin-2-yl)-2-fluorocyclopropane-1-carboxamide | ¹H NMR (400 MHz, DMSO-d$_6$) δ 13.67 (s, 1H), 11.19 (s, 1H), 8.67 (d, J = 7.2 Hz, 1H), 7.82 (s, 1H), 7.69 (s, 1H), 6.94 (s, 1H), 6.85 (d, J = 7.2 Hz, 1H), 5.04-4.87 (m, 1H), 4.50 (q, J = 7.2 Hz, 1H), 2.69-2.60 (m, 2H), 4.23 (s, 2H), 2.16-2.12 (m, 1H), 1.70-1.63 (m, 1H), 1.60 (d, J = 12 Hz, 3H), 1.28-1.11 (m, 4H); LCMS (electrospray) m/z 467.1 (M + H)+. | J |
| 598 | 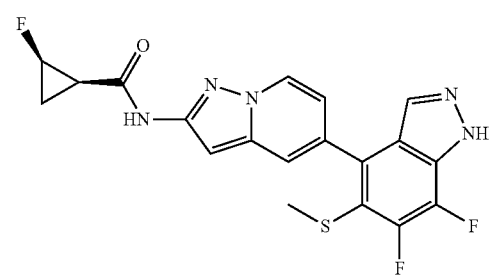 [SMILES: CSc1c(F)c(F)c2[nH]ncc2c1-c1ccn2nc(NC(=O)[C@H]3C[C@H]3F)cc2c1]<br>(1R,2R)-N-(5-(6,7-difluoro-5-(methylthio)-1H-indazol-4-yl)pyrazolo[1,5-a]pyridin-2-yl)-2-fluorocyclopropane-1-carboxamide | ¹H NMR (400 MHz, DMSO-d$_6$) δ 14.15 (s, 1H), 11.17 (s, 1H), 8.63 (d, J = 7.6 Hz, 1H), 7.96 (s, 1H), 7.67 (s, 1H), 6.94 (s, 1H), 6.88 (d, J = 7.2 Hz, 1H), 5.04-4.87 (m, 1H), 2.30 (s, 3H), 2.15-2.13 (m, 1H), 1.71-1.64 (m, 1H), 1.24-1.18 (m, 1H); LCMS (electrospray) m/z 418.10 (M + H)+. | J |

TABLE 1-continued

Compounds of Examples

| Ex # | Structure/Name | ¹H NMR/MS (M + 1) | Method |
|---|---|---|---|
| 599 | (1S,2R)-N-(5-(6,7-difluoro-5-(methylthio)-1H-indazol-4-yl)pyrazolo[1,5-a]pyridin-2-yl)-2-fluorocyclopropane-1-carboxamide | ¹H NMR (400 MHz, DMSO-d₆) δ 14.13 (s, 1H), 11.29 (s, 1H), 8.64 (d, J = 6.0 Hz, 1H), 7.96 (s, 1H), 7.66 (s, 1H), 6.90-6.88 (m, 2H), 5.00-4.84 (m, 1H), 2.50-2.43 (m, 1H), 2.30 (s, 3H), 1.58-1.49 (m, 1H), 1.30-1.24 (m, 1H); LCMS (electrospray) m/z 418.10 (M + H)+. | J |
| 600 | (1R,2S)-N-(5-(6,7-difluoro-5-(methylthio)-1H-indazol-4-yl)pyrazolo[1,5-a]pyridin-2-yl)-2-fluorocyclopropane-1-carboxamide | ¹H NMR (400 MHz, DMSO-d₆) δ 14.11 (s, 1H), 11.29 (s, 1H), 8.64 (d, J = 7.2 Hz, 1H), 7.96 (s, 1H), 7.66 (s, 1H), 6.90-6.88 (m, 2H), 5.00-4.84 (m, 1H), 2.50- 2.43 (m, 1H), 2.30 (s, 3H), 1.57 (m, 1H), 1.29-1.24 (m, 1H); LCMS (electrospray) m/z 418.10 (M + H)+. | J |
| 601 | (1S,2S)-N-(5-(5-chloro-6-fluoro-7-(pyrimidin-2-ylamino)-1H-indazol-4-yl)pyrazolo[1,5-a]pyridin-2-yl)-2-fluorocyclopropane-1-carboxamide | ¹H NMR (400 MHz, DMSO-d₆) δ 13.39 (s, 1H), 11.19 (s, 1H), 9.49 (s, 1H), 8.69 (d, J = 7.2 Hz, 1 H), 8.42 (d, J = 4.4 Hz, 1H), 7.91 (s, 1H), 7.83-7.82 (m, 1H), 6.99-6.97 (m, 1H), 6.86 (t, J = 5.0 Hz, 1H), 5.05-4.85 (m, 1H), 2.17-2.13 (m, 1H), 1.71-1.63 (m, 1H), 1.21-1.15 (m, 1H); LCMS (electrospray) m/z 481.10 (M + H)+. | J |

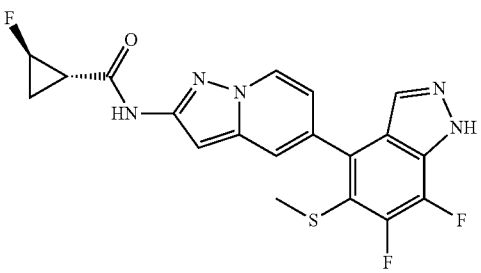 [SMILES: CSc1c(F)c(F)c2[nH]ncc2c1-c1ccn2nc(NC(=O)[C@@H]3C[C@H]3F)cc2c1]

TABLE 1-continued

Compounds of Examples

| Ex # | Structure/Name | ¹H NMR/MS (M + 1) | Method |
|---|---|---|---|
| 602 | 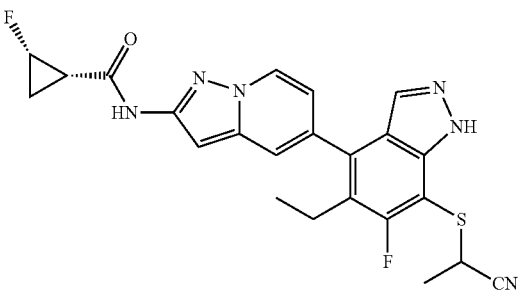<br>(1S,2S)-N-(5-(7-((1-cyanoethyl)thio)-5-ethyl-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.63 (s, 1H), 11.21 (s, 1H), 8.71 (d, J = 7.2 Hz, 1H), 8.05 (s, 1H), 7.85 (s, 1H), 7.00 (s, 1H), 6.98 (d, J = 7.2 Hz, 1H), 5.04-4.87 (m, 1H), 4.23 (s, 2H), 2.16-2.12 (m, 1H), 1.70-1.63 (m, 1H), 1.28-1.12 (m, 1H); LCMS (electrospray) m/z 459.1 (M + H)+. | J |
| 603 | 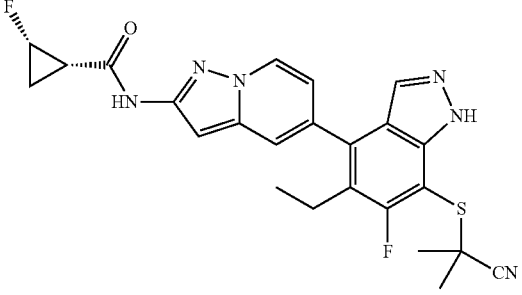 [SMILES: CCc1c(F)c(SC(C)(C)C#N)c2[nH]ncc2c1-c1ccn2nc(NC(=O)[C@@H]3C[C@@H]3F)cc2c1]<br>(1S,2S)-N-(5-(7-((2-cyanopropan-2-yl)thio)-5-ethyl-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.65 (s, 1H), 11.19 (s, 1H), 8.67 (d, J = 7.2 Hz, 1H), 7.81 (s, 1H), 7.71 (s, 1H), 6.94 (s, 1H), 6.87 (d, J = 7.2 Hz, 1H), 5.04-4.84 (m, 1H), 2.66-2.63 (m, 2H), 2.18-2.11 (m, 1H), 1.73 (s, 6H), 1.70-1.62 (m, 1H), 1.28-1.12 (m, 1H), 1.12 (t, J = 5.2 Hz, 3H); LCMS (electrospray) m/z 481.1 (M + H)+. | J |
| 604 | 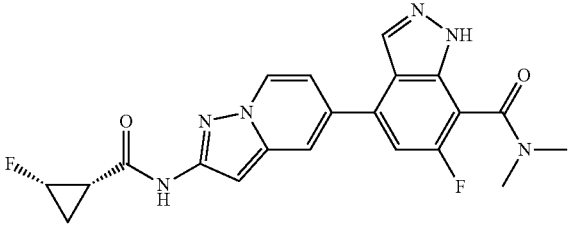 [SMILES: CN(C)C(=O)c1c(F)cc(-c2ccn3nc(NC(=O)[C@@H]4C[C@@H]4F)cc3c2)c2cn[nH]c12]<br>6-fluoro-4-(2-((1S,2S)-2-fluorocyclopropane-1-carboxamido)pyrazolo[1,5-a]pyridin-5-yl)-N,N-dimethyl-1H-indazole-7-carboxamide | ¹H NMR (400 MHz, DMSO-d₆) δ 13.93-13.02 (m, 1H), 11.17 (s, 1H), 8.63 (d, J = 7.2 Hz, 1H), 8.05 (s, 1H), 7.69 (d, J = 1.0 Hz, 1H), 7.52 (dd, J = 0.8, 9.5 Hz, 1H), 6.96 (s, 1H), 6.89 (td, J = 2.2, 7.2 Hz, 1H), 5.14-4.72 (m, 1H), 2.85 (s, 3H), 2.72 (d, J = 1.6 Hz, 3H), 2.14 (td, J = 6.9, 13.8 Hz, 1H), 1.75-1.59 (m, 1H), 1.17 (tdd, J = 6.2, 9.1, 12.3 Hz, 1H); LCMS(electrospray) m/z 425.2 (M + H+). | J |
| 605 | 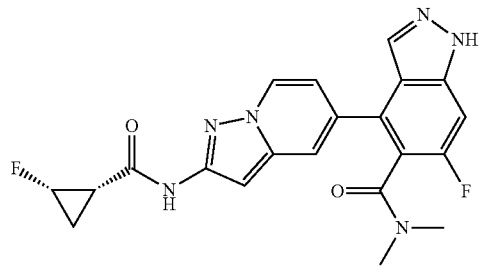 [SMILES: CN(C)C(=O)c1c(F)cc2[nH]ncc2c1-c1ccn2nc(NC(=O)[C@@H]3C[C@@H]3F)cc2c1]<br>6-fluoro-4-(2-((1S,2S)-2-fluorocyclopropane-1-carboxamido)pyrazolo[1,5-a]pyridin-5-yl)-N,N-dimethyl-1H-indazole-5-carboxamide | ¹H NMR (400 MHz, DMSO-d₆) δ 13.93-13.02 (m, 1H), 11.17 (s, 1H), 8.63 (d, J = 7.2 Hz, 1H), 8.05 (s, 1H), 7.69 (d, J = 1.0 Hz, 1H), 7.52 (dd, J = 0.8, 9.5 Hz, 1H), 6.96 (s, 1H), 6.89 (td, J = 2.2, 7.2 Hz, 1H), 5.14-4.72 (m, 1H), 2.85 (s, 3H), 2.72 (d, J = 1.6 Hz, 3H), 2.14 (td, J = 6.9, 13.8 Hz, 1H), 1.75-1.59 (m, 1H), 1.17 (tdd, J = 6.2, 9.1, 12.3 Hz, 1H); LCMS(electrospray) m/z 425.2 (M + H+ | J |

TABLE 1-continued

Compounds of Examples

| Ex # | Structure/Name | ¹H NMR/MS (M + 1) | Method |
|---|---|---|---|
| 606 | 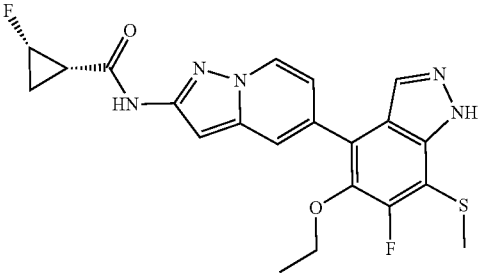 [SMILES: CCOc1c(F)c(SC)c2[nH]ncc2c1-c1ccn2nc(NC(=O)[C@@H]3C[C@@H]3F)cc2c1]<br>(1S,2S)-N-(5-(5-ethoxy-6-fluoro-7-(methylthio)-1H-indazol-4-yl)pyrazolo[1,5-a]pyridin-2-yl)-2-fluorocyclopropane-1-carboxamide | ¹H NMR (400 MHz, DMSO-$d_6$) δ 11.16 (s, 1H), 8.64 (br d, J = 7.1 Hz, 1H), 8.06 (s, 1H), 7.83 (s, 1H), 7.03 (br dd, J = 1.8, 7.1 Hz, 1H), 6.96 (s, 1H), 5.06-4.82 (m, 1H), 3.86 (br d, J = 7.0 Hz, 2H), 2.55 (s, 3H), 2.18-2.12 (m, 1H), 1.73-1.61 (m, 1H), 1.26-1.15 (m, 1H), 1.11 (br t, J = 6.9 Hz, 3H); LCMS(electrospray) m/z 444.2 (M + H+). | J |
| 607 | 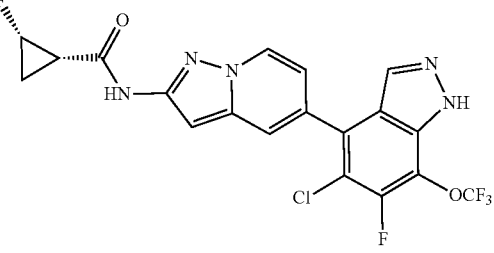<br>(1S,2S)-N-(5-(5-chloro-6-fluoro-7-(trifluoromethoxy)-1H-indazol-4-yl)pyrazolo[1,5-a]pyridin-2-yl)-2-fluorocyclopropane-1-carboxamide | ¹H NMR (400 MHz, DMSO-$d_6$) δ 14.06-13.49 (m, 1H), 10.62 (br s, 1H), 9.03 (d, J = 7.0 Hz, 1H), 8.56 (s, 1H), 8.25 (s, 1H), 7.58 (s, 1H), 7.44 (dd, J = 1.8, 7.1 Hz, 1H), 5.46-5.25 (m, 1H), 2.69 (br s, 1H), 2.27- 2.21 (m, 1H), 1.69-1.61 (m, 1H); LCMS(electrospray) m/z 472.0 (M + H+). | J |
| 608 | 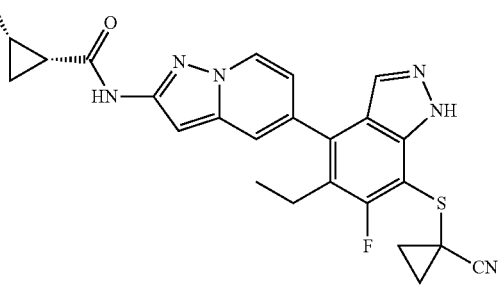<br>(1S,2S)-N-(5-(7-((1-cyanocyclopropyl)thio)-5-ethyl-6-fluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.64 (s, 1H), 11.19 (s, 1H), 8.67 (d, J = 7.2 Hz, 1H), 7.82 (s, 1H), 7.71 (s, 1H), 6.94 (s, 1H), 6.88 (d, J = 7.2 Hz, 1H), 5.04-4.84 (m, 1H), 2.66-2.63 (m, 2H), 2.18-2.11 (m, 1H), 1.73-7.72 (m, 2H), 1.70-1.62 (m, 1H), 1.62-1.60 (m, 1H), 1.28-1.12 (m, 1H), 1.12 (t, J = 5.2 Hz, 3H); LCMS (electrospray) m/z 479.1 (M + H)+. | J |

TABLE 1-continued

Compounds of Examples

| Ex # | Structure/Name | ¹H NMR/MS (M + 1) | Method |
|---|---|---|---|
| 609 | (1S,2S)-N-(5-(5-chloro-6-fluoro-7-(pyridin-4-ylamino)-1H-indazol-4-yl)pyrazolo[1,5-a]pyridin-2-yl)-2-fluorocyclopropane-1-carboxamide | ¹H NMR (400 MHz, DMSO-$d_6$) δ 13.63 (s, 1H), 11.20 (s, 1H), 8.99 (s, 1H), 8.69 (d, J = 7.2 Hz, 1H), 8.21 (d, J = 6.4 Hz, 2H), 7.99 (s, 1H), 7.83-7.82 (m, 1H), 7.01-6.98 (m, 2H), 6.62 (d, J = 4.8 Hz, 2H), 5.04-4.85 (m, 1H), 2.17-2.12 (m, 1H), 1.71-1.63 (m, 1H), 1.21-1.16 (m, 1H); LCMS (electrospray) m/z 480.10 (M + H)+. | J |
| 610 | (1S,2S)-N-(5-(7-(dimethylamino)-5-ethoxy-6-fluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.28 (br s, 1H), 11.15 (s, 1H), 8.60 (d, J = 7.0 Hz, 1H), 7.96 (s, 1H), 7.77 (s, 1H), 7.01 (dd, J = 1.8, 7.3 Hz, 1H), 6.92 (s, 1H), 5.04-4.83 (m, 1H), 3.83 (q, J = 7.0 Hz, 2H), 2.98 (br s, 6H), 2.18-2.11 (m, 1H), 1.72-1.6 (m, 1H), 1.18 (br s, 1H), 1.11 (t, J = 7.0 Hz, 3H); LCMS(electrospray) m/z 441.1 (M + H+). | J |
| 611 | (1S,2S)-N-(5-(5-ethoxy-6,7-difluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.96 (s, 1H), 11.17 (s, 1H), 8.64 (d, J = 7.2 Hz, 1H), 8.18-8.12 (m, 1H), 7.81 (s, 1H), 7.02-6.93 (m, 2H), 5.04-4.84 (m, 1H), 3.96-3.82 (m, 2H), 2.18-2.09 (m, 1H), 1.70-1.60 (m, 1H), 1.20-1.16 (m, 1H), 1.12 (t, J = 6.8 Hz, 3H); LCMS(electrospray) m/z 416.1 (M + H+). | J |

TABLE 1-continued

Compounds of Examples

| Ex # | Structure/Name | ¹H NMR/MS (M + 1) | Method |
|---|---|---|---|
| 612 | 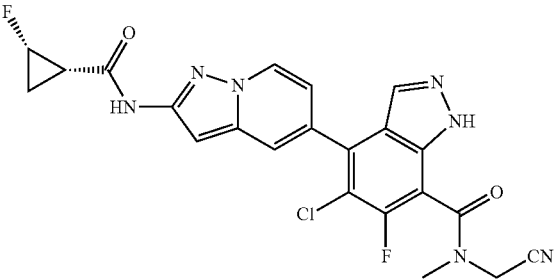 [SMILES: CN(CC#N)C(=O)c1c(F)c(Cl)c(-c2ccn3nc(NC(=O)[C@@H]4C[C@@H]4F)cc3c2)c2cn[nH]c12]<br>5-chloro-N-(cyanomethyl)-6-fluoro-4-(2-((1S,2S)-2-fluorocyclopropane-1-carboxamido)pyrazolo[1,5-a]pyridin-5-yl)-N-methyl-1H-indazole-7-carboxamide | ¹H NMR (400 MHz, DMSO-$d_6$) δ 13.85 (s, 1H), 11.22 (s, 1H), 8.71 (d, J = 7.2 Hz, 1H), 8.01 (s, 1H), 7.82 (s, 1H), 6.99 (s, 1H), 6.97 (s, J = 7.2 Hz, 1H), 5.04-4.84 (m, 1H), 4.72 (s, 2H), 3.03 (s, 3H), 2.18-2.11 (m, 1H), 1.70-1.62 (m, 1H), 1.28-1.12 (m, 1H); LCMS (electrospray) m/z 484.1 (M + H)+. | J |
| 613 | 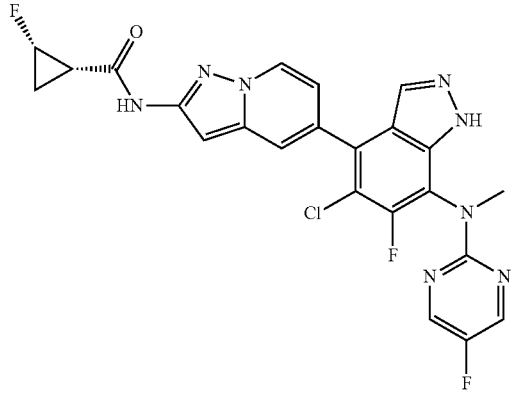 [SMILES: CN(c1ncc(F)cn1)c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-((5-fluoropyrimidin-2-yl)(methyl)amino)-1H-indazol-4-yl)pyrazolo[1,5-a]pyridin-2-yl)-2-fluorocyclopropane-1-carboxamide | ¹H NMR (400 MHz, DMSO-$d_6$) δ 13.62 (s, 1H), 11.21 (s, 1H), 8.70 (d, J = 7.2 Hz, 1H), 8.55 (s, 1H), 7.98 (s, 1H), 7.84 (s, 1H), 7.00-6.99 (m, 2H), 5.03-4.86 (m, 1H), 3.52 (s, 3H), 2.17-2.12 (m, 1H), 1.71-1.64 (m, 1H), 1.21-1.14 (m, 1H); LCMS (electrospray) m/z 513.10 (M + H)+. | J |
| 614 | 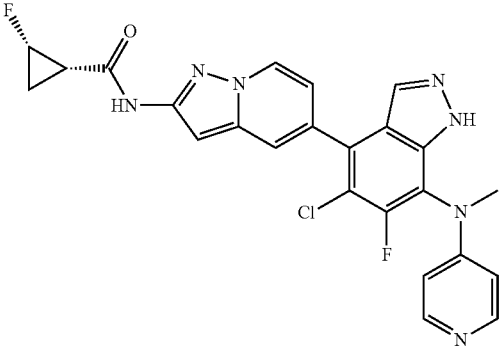 [SMILES: CN(c1ccncc1)c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-(methyl(pyridin-4-yl)amino)-1H-indazol-4-yl)pyrazolo[1,5-a]pyridin-2-yl)-2-fluorocyclopropane-1-carboxamide | ¹H NMR (400 MHz, DMSO-$d_6$) δ 13.75 (s, 1H), 11.20 (s, 1H), 8.71 (d, J = 7.2 Hz, 1H), 8.22 (d, J = 6.8 Hz, 1H), 8.04 (s, 1H), 7.84 (s, 1H), 7.01 (dd, J = 2.2, 7.0 Hz, 2H), 6.60 (d, J = 5.6 Hz, 1H), 5.06-4.86 (m, 1H), 3.41 (s, 3H), 2.19-2.12 (m, 1H), 1.73-1.63 (m, 1H), 1.21-1.17 (m, 1H); LCMS (electrospray) m/z 494.10 (M + H)+. | J |

TABLE 1-continued

Compounds of Examples

| Ex # | Structure/Name | ¹H NMR/MS (M + 1) | Method |
|---|---|---|---|
| 615 | 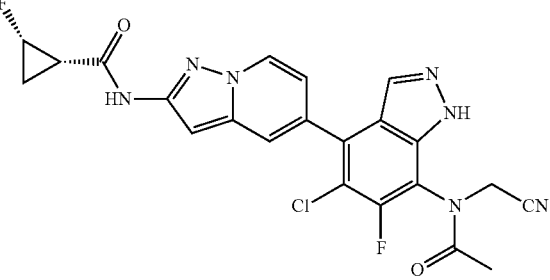<br>(1S,2S)-N-(5-(5-chloro-7-(N-(cyanomethyl)acetamido)-6-fluoro-1H-indazol-4-yl)pyrazolo[1,5-a]pyridin-2-yl)-2-fluorocyclopropane-1-carboxamide | ¹H NMR (400 MHz, DMSO-d$_6$) δ 14.02 (s, 1H), 11.21 (s, 1H), 8.71 (d, J = 7.2 Hz, 1H), 8.09 (s, 1H), 7.83 (s, 1H), 7.00 (s, 1H), 6.97 (s, J = 7.2 Hz, 1H), 5.04-4.84 (m, 1H), 4.79 (dd, J = 18 Hz, 110 Hz, 2H), 2.18-2.11 (m, 1H), 1.90 (s, 3H), 1.70-1.62 (m, 1H), 1.28-1.12 (m, 1H); LCMS (electrospray) m/z 484.1 (M + H)+. | J |
| 616 | 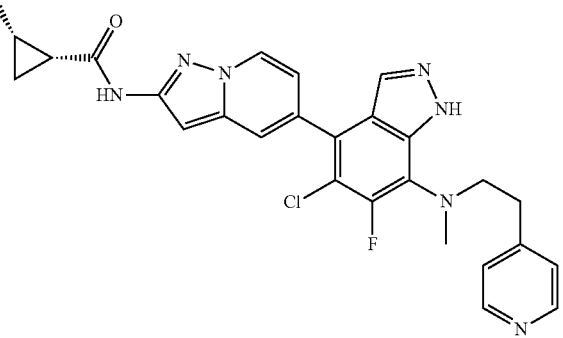<br>(1S,2S)-N-(5-(5-chloro-6-fluoro-7-(methyl(2-(pyridin-4-yl)ethyl)amino)-1H-indazol-4-yl)pyrazolo[1,5-a]pyridin-2-yl)-2-fluorocyclopropane-1-carboxamide | ¹H NMR (400 MHz, DMSO-d$_6$) δ 13.51 (s, 1H), 11.19 (s, 1H), 8.66 (d, J = 7.2 Hz, 1H), 8.38 (dd, J = 1.6, 4.4 Hz, 2H), 7.89 (s, 1H), 7.73-7.72 (m, 1H), 7.21 (d, J = 6.0 Hz, 2H), 6.95 (s, 1H), 6.90 (dd, J = 2.4, 7.2 Hz, 1H), 5.05-4.84 (m, 1H), 3.54 (t, 2H), 3.06 (d, J = 2.0 Hz, 3H), 2.86 (t, J = 7.4 Hz, 2H), 2.18-2.11 (m, 1H), 1.72-1.64 (m, 1H), 1.21-1.13 (m, 1H); LCMS (electrospray) m/z 522.10 (M + H)+. | J |
| 617 | 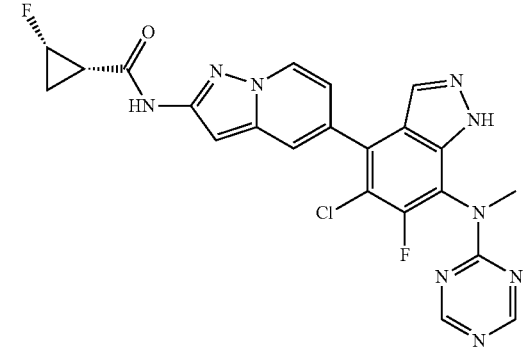 [SMILES: CN(c1ncncn1)c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-(methyl(1,3,5-triazin-2-yl)amino)-1H-indazol-4-yl)pyrazolo[1,5-a]pyridin-2-yl)-2-fluorocyclopropane-1-carboxamide | ¹H NMR (400 MHz, DMSO-d$_6$) δ 13.70 (s, 1H), 11.21 (s, 1H), 8.91 (d, J = 0.8 Hz, 1H), 8.71 (d, J = 7.2 Hz, 1H), 8.58 (d, J = 2.0 Hz, 1H), 8.01 (s, 1H), 7.85 (s, 1H), 7.01-6.99 (m, 2H), 5.04-4.85 (m, 1H), 3.55 (s, 3H), 2.18-2.11 (m, 1H), 1.71-1.64 (m, 1H), 1.21-1.14 (m, 1H); LCMS (electrospray) m/z 496.10 (M + H)+. | J |

TABLE 1-continued

Compounds of Examples

| Ex # | Structure/Name | ¹H NMR/MS (M + 1) | Method |
|---|---|---|---|
| 618 | (1S,2S)-N-(5-(5-chloro-6-fluoro-7-(methyl(1,2,4-triazin-3-yl)amino)-1H-indazol-4-yl)pyrazolo[1,5-a]pyridin-2-yl)-2-fluorocyclopropane-1-carboxamide | ¹H NMR (400 MHz, DMSO-d$_6$) δ 13.67 (s, 1H), 11.21 (s, 1H), 8.88 (d, J = 2.0 Hz, 1H), 8.71 (d, J = 7.2 Hz, 1H), 8.38 (s, 1H), 8.01 (s, 1H), 7.85 (s, 1H), 7.01-6.99 (m, 2H), 5.05-4.84 (m, 1H), 3.63 (s, 3H), 2.18-2.11 (m, 1H), 1.71-1.63 (m, 1H), 1.21-1.11 (m, 1H); LCMS (electrospray) m/z 496.10 (M + H)+. | J |
| 619 | (1S,2S)-N-(5-(5-chloro-6-fluoro-7-(isopropylamino)-1H-indazol-4-yl)pyrazolo[1,5-a]pyridin-2-yl)-2-fluorocyclopropane-1-carboxamide | ¹H NMR (400 MHz, DMSO-d$_6$) δ 13.29 (s, 1H), 11.15 (s, 1H), 8.61 (d, J = 7.3 Hz, 1H), 7.87 (s, 1H), 7.71 (s, 1H), 6.92-6.90 (m, 2H), 5.18-5.17 (m, 1H), 5.03-4.85 (m, 1H), 4.03 (s, 1H), 2.17-2.09 (m, 1H), 1.72-1.62 (m, 1H), 1.23 (d, J = 6.4 Hz, 6H), 1.20-1.15 (m, 1H); LCMS (electrospray) m/z 445.10 (M + H)+. | J |
| 620 | (1S,2S)-N-(5-(5-chloro-7-(cyclobutyl(methyl)amino)-6-fluoro-1H-indazol-4-yl)pyrazolo[1,5-a]pyridin-2-yl)-2-fluorocyclopropane-1-carboxamide | ¹H NMR (400 MHz, DMSO-d$_6$) δ 13.51 (s, 1H), 11.19 (s, 1H), 8.65 (d, J = 7.2 Hz, 1H), 7.88 (s, 1H), 7.76 (s, 1H), 6.94 (s, 1H), 6.92 (s, J = 7.2 Hz, 1H), 5.04-4.84 (m, 1H), 3.93 (t, J = 9.6 Hz, 1H), 2.84 (s, 3H), 2.18-2.07 (m, 3H), 1.96-1.86 (m, 2H), 1.72-1.57 (m, 3H), 1.28-1.12 (m, 1H); LCMS (electrospray) m/z 471.1 (M + H)+. | J |

TABLE 1-continued

Compounds of Examples

| Ex # | Structure/Name | ¹H NMR/MS (M + 1) | Method |
|---|---|---|---|
| 621 | 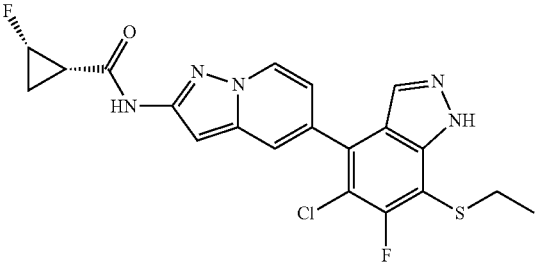 [SMILES: CCSc1c(F)c(Cl)c(-c2ccn3nc(NC(=O)[C@@H]4C[C@@H]4F)cc3c2)c2cn[nH]c12]<br>(1S,2S)-N-(5-(5-chloro-7-(ethylthio)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.81 (s, 1H), 11.21 (s, 1H), 8.69 (d, J = 7.2 Hz, 1H), 7.88 (s, 1H), 7.81 (s, 1H), 6.97 (s, 1H), 6.95 (s, J = 7.2 Hz, 1H), 5.04-4.84 (m, 1H), 3.02 (q, J = 7.3 Hz, 2H), 2.18-2.08 (m, 1H), 1.72-1.62 (m, 1H), 1.22-1.13 (m, 4H); LCMS (electrospray) m/z 448.1 (M + H)+. | J |
| 622 | 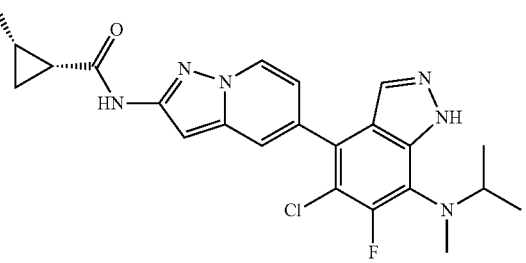<br>(1S,2S)-N-(5-(5-chloro-6-fluoro-7-(isopropyl(methyl)amino)-1H-indazol-4-yl)pyrazolo[1,5-a]pyridin-2-yl)-2-fluorocyclopropane-1-carboxamide | ¹H NMR (400 MHz, DMSO-d₆) δ 13.44 (s, 1H), 11.20 (s, 1H), 8.66 (d, J = 7.2 Hz, 1H), 7.89 (s, 1H), 7.76 (d, J = 1.2 Hz, 1H), 6.95-6.93 (m, 2H), 5.03-4.84 (m, 1H), 3.56 (s, 1H), 2.89 (d, J = 3.6 Hz, 3H), 2.18-2.11 (m, 1H), 1.72-1.62 (m, 1H), 1.22-1.15 (m, 7H); LCMS (electrospray) m/z 459.10 (M + H)+. | J |
| 623 | 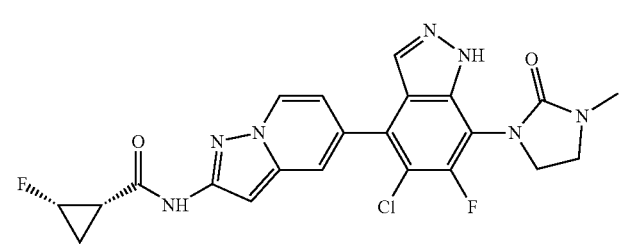 [SMILES: CN1CCN(c2c(F)c(Cl)c(-c3ccn4nc(NC(=O)[C@@H]5C[C@@H]5F)cc4c3)c3cn[nH]c23)C1=O]<br>(1S,2S)-N-(5-(5-chloro-6-fluoro-7-(3-methyl-2-oxoimidazolidin-1-yl)-1H-indazol-4-yl)pyrazolo[1,5-a]pyridin-2-yl)-2-fluorocyclopropane-1-carboxamide | ¹H NMR (400 MHz, DMSO-d₆) δ 13.66 (s, 1H), 11.21 (s, 1H), 8.70 (d, J = 7.2 Hz, 1H), 7.97 (s, 1H), 7.80 (m, 1H), 6.97-6.94 (m, 2H), 5.05-4.85 (m, 1H), 3.84 (t, J = 7.8 Hz, 2H), 3.60 (t, J = 8.0 Hz, 2H), 2.82 (s, 3H), 2.18-2.11 (m, 1H), 1.73-1.62 (m, 1H), 1.21-1.15 (m, 1H); LCMS (electrospray) m/z 486.10 (M + H)+. | J |
| 624 | 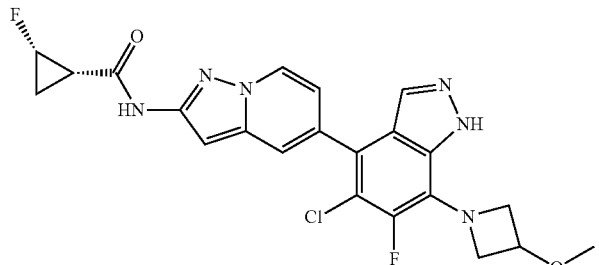<br>(1S,2S)-N-(5-(5-chloro-6-fluoro-7-(3-methoxyazetidin-1-yl)-1H-indazol-4-yl)pyrazolo[1,5-a]pyridin-2-yl)-2-fluorocyclopropane-1-carboxamide | ¹H NMR (400 MHz, DMSO-d₆) δ 13.13 (s, 1H), 11.17 (s, 1H), 8.62 (d, J = 6.8 Hz, 1H), 7.86 (s, 1H), 7.69 (d, J = 0.8 Hz, 1H), 6.96-6.86 (m, 2H), 5.05-4.83 (m, 1H), 4.68-4.58 (m, 2H), 4.37-4.30 (m, 1H), 4.27-4.16 (m, 2H), 3.27 (s, 3H), 2.18-2.09 (m, 1H), 1.73-1.61 (m, 1H), 1.20-1.12 (m, 1H); LCMS (electrospray) m/z 473.1 (M + H)+. | J |

TABLE 1-continued

Compounds of Examples

| Ex # | Structure/Name | ¹H NMR/MS (M + 1) | Method |
|---|---|---|---|
| 625 | 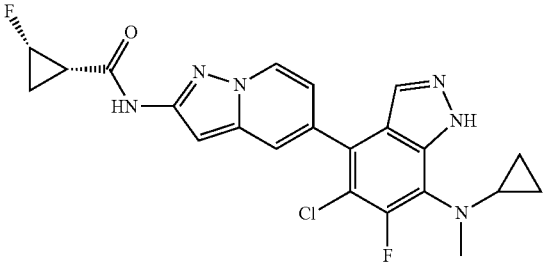 [SMILES: CN(c1c(F)c(Cl)c(-c2ccn3nc(NC(=O)[C@@H]4C[C@@H]4F)cc3c2)c2cn[nH]c12)C1CC1]<br>(1S,2S)-N-(5-(5-chloro-7-(cyclopropyl(methyl)amino)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.41 (s, 1H), 11.19 (s, 1H), 8.65 (d, J = 7.2 Hz, 1H), 7.87 (s, 1H), 7.76 (s, 1H), 6.94 (s, 1H), 6.92 (s, J = 7.2 Hz, 1H), 5.04-4.84 (m, 1H), 3.01-2.98 (m, 4H), 2.18-2.08 (m, 1H), 1.72-1.62 (m, 1H), 1.22-1.13 (m, 4H), 0.63-0.60 (m, 2H), 0.49-0.45 (m, 2H); LCMS (electrospray) m/z 457.1 (M + H)+. | J |
| 626 | 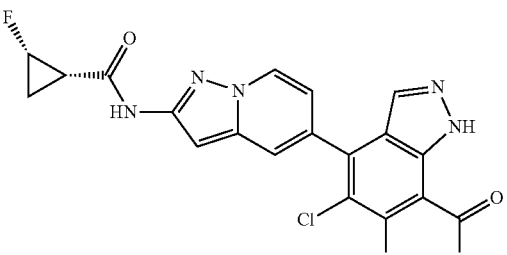<br>(1S,2S)-N-(5-(5-chloro-6-fluoro-7-formyl-1H-indazol-4-yl)pyrazolo[1,5-a]pyridin-2-yl)-2-fluorocyclopropane-1-carboxamide | ¹H NMR (400 MHz, DMSO-d₆) δ 14.02 (s, 1H), 11.24 (s, 1H), 10.49 (s, 1H), 8.73 (d, J = 7.2 Hz, 1H), 8.07 (s, 1H), 7.89-7.87 (m, 1H), 7.02 (s, 1H), 7.00 (dd, J = 7.0, 1.8 Hz, 1H), 5.06-4.85 (m, 1H), 2.19-2.12 (m, 1H), 1.73-1.63 (m, 1H), 1.21-1.15 (m, 1H); LCMS (electrospray) m/z 416.05 (M + H+). | J |
| 627 | 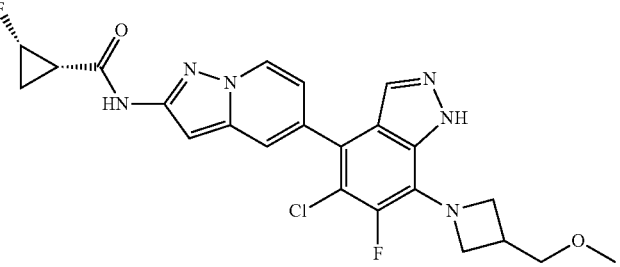<br>(1S,2S)-N-(5-(5-chloro-6-fluoro-7-(3-(methoxymethyl)azetidin-1-yl)-1H-indazol-4-yl)pyrazolo[1,5-a]pyridin-2-yl)-2-fluorocyclopropane-1-carboxamide | ¹H NMR (400 MHz, DMSO-d₆) δ 13.06 (s, 1H), 11.13 (s, 1H), 8.58 (d, J = 6.8 Hz, 1H), 7.81 (s, 1H), 7.64 (s, 1H), 6.90-6.81 (m, 2H), 5.02-4.80 (m, 1H), 4.49-4.40 (m, 2H), 4.20-4.04 (m, 2H), 3.53 (d, J = 6.4 Hz, 2H), 3.25 (s, 3H), 2.99-2.88 (m, 1H), 2.15-2.04 (m, 1H), 1.68-1.57 (m, 1H), 1.17-1.09 (m, 1H); LCMS (electrospray) m/z 487.1 (M + H)+. | J |
| 628 | 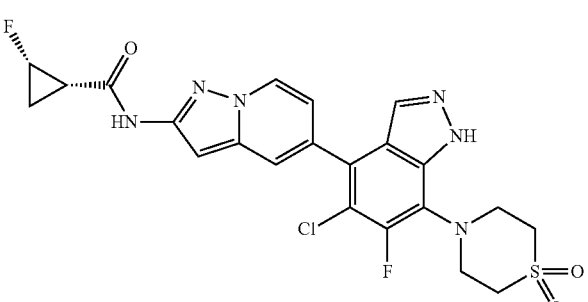<br>(1S,2S)-N-(5-(5-chloro-7-(1,1-dioxidothiomorpholino)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.62 (s, 1H), 11.20 (s, 1H), 8.68 (d, J = 7.2 Hz, 1H), 7.95 (d, J = 2.0 Hz, 1H), 7.74 (d, J = 1.2 Hz, 1H), 6.96 (s, 1H), 6.91 (dd, J = 1.6, 7.2 Hz, 1H), 5.06-4.84 (m, 1H), 3.69-3.61 (m, 4H), 3.47-3.39 (m, 4H), 2.18-2.10 (m, 1H), 1.73-1.61 (m, 1H), 1.21-1.12 (m, 1H); LCMS (electrospray) m/z 521.1 (M + H)+. | J |

TABLE 1-continued

Compounds of Examples

| Ex # | Structure/Name | ¹H NMR/MS (M + 1) | Method |
|---|---|---|---|
| 629 | 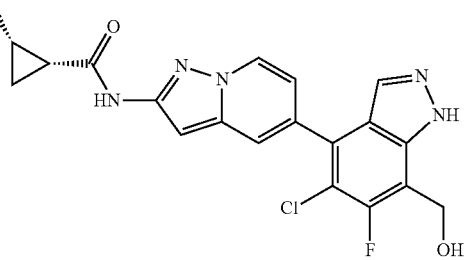<br>(1S,2S)-N-(5-(5-chloro-6-fluoro-7-(hydroxymethyl)-1H-indazol-4-yl)pyrazolo[1,5-a]pyridin-2-yl)-2-fluorocyclopropane-1-carboxamide | ¹H NMR (400 MHz, DMSO-$d_6$) δ 13.57 (s, 1H), 11.20 (s, 1H), 10.49 (s, 1H), 8.68 (d, J = 7.2 Hz, 1H), 8.07 (s, 1H), 7.89-7.87 (m, 1H), 7.02 (s, 1H), 7.00 (dd, J = 7.0, 1.8 Hz, 1H), 5.06-4.85 (m, 1H), 2.19-2.12 (m, 1H), 1.73-1.63 (m, 1H), 1.21-1.15 (m, 1H); LCMS (electrospray) m/z 416.05 (M + H+). | J |
| 630 | 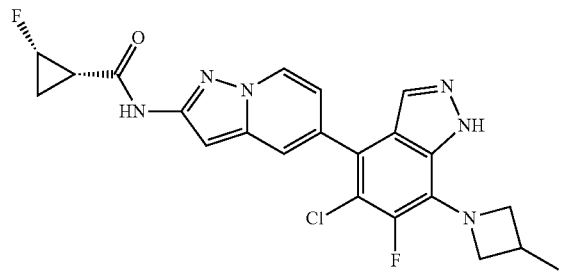 [SMILES: CC1CN(c2c(F)c(Cl)c(-c3ccn4nc(NC(=O)[C@@H]5C[C@@H]5F)cc4c3)c3cn[nH]c23)C1]<br>(1S,2S)-N-(5-(5-chloro-6-fluoro-7-(3-methylazetidin-1-yl)-1H-indazol-4-yl)pyrazolo[1,5-a]pyridin-2-yl)-2-fluorocyclopropane-1-carboxamide | ¹H NMR (400 MHz, DMSO-$d_6$) δ 13.41 (s, 1H), 11.19 (s, 1H), 8.61 (d, J = 7.2 Hz, 1H), 7.91 (s, 1H), 7.76 (s, 1H), 6.94 (s, 1H), 6.87 (s, J = 7.2 Hz, 1H), 5.04-4.84 (m, 1H), 4.55-4.51 (m, 2H), 3.98-3.94 (m, 2H), 2.85-2.80 (m, 1H), 2.15-2.08 (m, 1H), 1.72-1.62 (m, 1H), 1.29-1.12 (m, 4H), 0.86-0.79 (m, 1H); LCMS (electrospray) m/z 457.1 (M + H)+. | J |
| 631 | 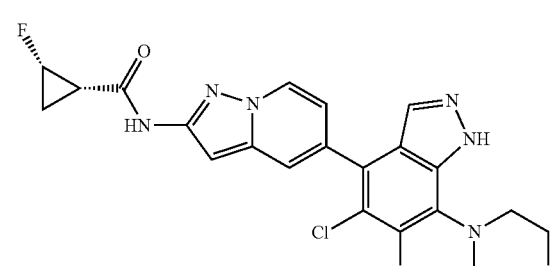<br>(1S,2S)-N-(5-(5-chloro-6-fluoro-7-thiomorpholino-1H-indazol-4-yl)pyrazolo[1,5-a]pyridin-2-yl)-2-fluorocyclopropane-1-carboxamide | ¹H NMR (400 MHz, DMSO-$d_6$) δ 13.49 (s, 1H), 11.19 (s, 1H), 8.66 (d, J = 7.2 Hz, 1H), 7.91 (s, 1H), 7.74 (t, J = 1.2 Hz, 1H), 6.95 (s, 1H), 6.91 (dd, J = 2.4, 7.2 Hz, 1H), 5.06-4.84 (m, 1H), 3.53-3.39 (m, 4H), 2.90-2.82 (m, 4H), 2.19-2.09 (m, 1H), 1.73-1.61 (m, 1H), 1.21-1.12 (m, 1H); LCMS (electrospray) m/z 489.1 (M + H)+. | J |
| 632 | 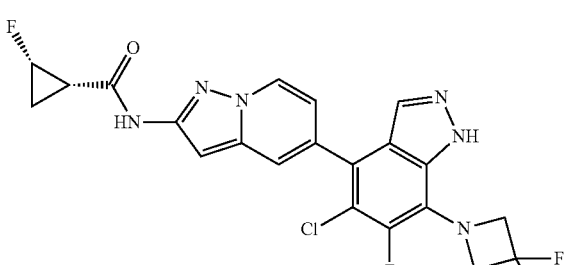<br>(1S,2S)-N-(5-(5-chloro-6-fluoro-7-(3-fluoro-3-methylazetidin-1-yl)-1H-indazol-4-yl)pyrazolo[1,5-a]pyridin-2-yl)-2-fluorocyclopropane-1-carboxamide | ¹H NMR (400 MHz, DMSO-$d_6$) δ 13.41 (s, 1H), 11.20 (s, 1H), 8.61 (d, J = 7.2 Hz, 1H), 7.96 (s, 1H), 7.68 (s, 1H), 6.92 (s, 1H), 6.87 (s, J = 7.2 Hz, 1H), 5.04-4.84 (m, 1H), 4.55-4.44 (m, 4H), 2.15-2.08 (m, 1H), 1.72-1.62 (m, 1H), 1.66 (d, J = 22 Hz, 1H), 1.29-1.12 (m, 1H); LCMS (electrospray) m/z 475.1 (M + H)+. | J |

TABLE 1-continued

Compounds of Examples

| Ex # | Structure/Name | ¹H NMR/MS (M + 1) | Method |
|---|---|---|---|
| 633 | 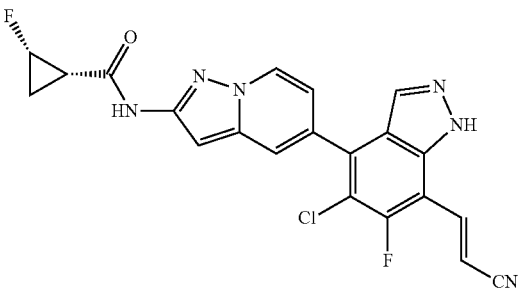 [SMILES: N#C/C=C/c1c(F)c(Cl)c(-c2ccn3nc(NC(=O)[C@@H]4C[C@@H]4F)cc3c2)c2cn[nH]c12]<br>(1S,2S)-N-(5-(5-chloro-7-((E)-2-cyanovinyl)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.90 (br s, 1H), 11.23 (s, 1H), 8.71 (d, J = 7.2 Hz, 1H), 7.99 (d, J = 17.2 Hz, 1H), 7.85-7.83 (m, 1H), 7.00 (s, 1H), 6.97 (dd, J = 7.0, 2.0 Hz, 1H), 5.06-4.85 (m, 1H), 2.18-2.11 (m, 1H), 1.73-1.63 (m, 1H), 1.21-1.14 (m, 1H); LCMS (electrospray) m/z 439.05 (M + H+). | J |
| 634 | 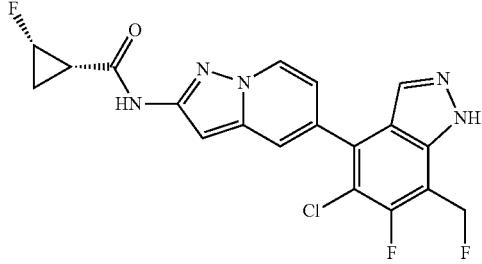 [SMILES: O=C(Nc1cc2cc(-c3c(Cl)c(F)c(CF)c4[nH]ncc34)ccn2n1)[C@@H]1C[C@@H]1F]<br>(1S,2S)-N-(5-(5-chloro-6-fluoro-7-(fluoromethyl)-1H-indazol-4-yl)pyrazolo[1,5-a]pyridin-2-yl)-2-fluorocyclopropane-1-carboxamide | ¹H NMR (400 MHz, DMSO-d₆) δ 13.91 (s, 1H), 11.22 (s, 1H), 8.70 (d, J = 7.2 Hz, 1H), 7.99 (s, 1H), 7.83-7.80 (m, 1H), 6.98 (s, 1H), 6.96 (dd, J = 7.0, 1.8 Hz, 1H), 5.93 (s, 1H), 5.81 (s, 1H), 5.05-4.84 (m, 1H), 2.18-2.11 (m, 1H), 1.72-1.62 (m, 1H), 1.20-1.13 (m, 1H); LCMS (electrospray) m/z 420.00 (M + H+). | J |
| 635 | 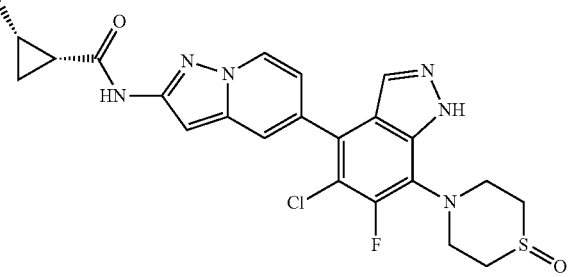<br>(1S,2S)-N-(5-(5-chloro-6-fluoro-7-(1-oxidothiomorpholino)-1H-indazol-4-yl)pyrazolo[1,5-a]pyridin-2-yl)-2-fluorocyclopropane-1-carboxamide | ¹H NMR (400 MHz, DMSO-d₆) δ 13.59 (s, 1H), 11.18 (s, 1H), 8.67 (d, J = 7.1 Hz, 1H), 7.93 (s, 1H), 7.75 (t, J = 1.4 Hz, 1H), 6.96 (s, 1H), 6.92 (dd, J = 7.1, 1.6 Hz, 1H), 5.08-4.80 (m, 1H), 3.89 (t, J = 11.5 Hz, 2H), 3.32-3.24 (m, 2H), 3.24-3.10 (m, 2H), 2.97 (d, J = 11.5 Hz, 2H), 2.22-2.09 (m, 1H), 1.77-1.61 (m, 1H), 1.22-1.11 (m, 1H); LCMS (electrospray) m/z 505.10 (M + H+)+. | J |
| 636 | 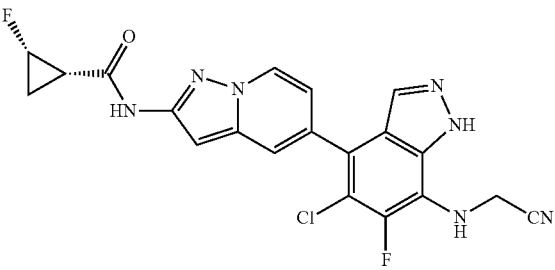 [SMILES: N#CCNc1c(F)c(Cl)c(-c2ccn3nc(NC(=O)[C@@H]4C[C@@H]4F)cc3c2)c2cn[nH]c12]<br>(1S,2S)-N-(5-(5-chloro-7-((cyanomethyl)amino)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.44 (s, 1H), 11.18 (s, 1H), 8.64 (d, J = 7.1 Hz, 1H), 7.75 (s, 1H), 7.03-6.84 (m, 2H), 6.42 (s, 1H), 5.10-4.83 (m, 1H), 4.83-4.49 (m, 2H), 2.24-2.04 (m, 1H), 1.76-1.59 (m, 1H), 1.21-1.05 (m, 1H); LCMS (electrospray) m/z 442.10 (M + H+)+. | J |

TABLE 1-continued

Compounds of Examples

| Ex # | Structure/Name | ¹H NMR/MS (M + 1) | Method |
|---|---|---|---|
| 637 | 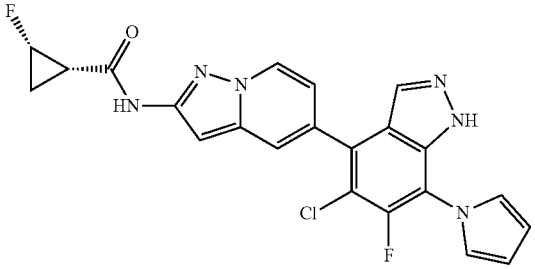 [SMILES: O=C(Nc1cc2cc(-c3c(Cl)c(F)c(-n4cccc4)c4[nH]ncc34)ccn2n1)[C@@H]1C[C@@H]1F]<br>(1S,2S)-N-(5-(5-chloro-6-fluoro-7-(1H-pyrrol-1-yl)-1H-indazol-4-yl)pyrazolo[1,5-a]pyridin-2-yl)-2-fluorocyclopropane-1-carboxamide | ¹H NMR (400 MHz, DMSO-d₆) δ 13.63-14.10 (1H), 11.21 (s, 1H), 8.71 (d, J = 7.1 Hz, 1H), 8.09 (s, 1H), 7.82 (t, J = 1.4 Hz, 1H), 7.28 (s, 2H), 6.99-6.96 (m, 2H), 6.41 (t, J = 2.2 Hz, 2H), 5.06-4.85 (m, 1H), 2.19-2.12 (m, 1H), 1.73-1.63 (m, 1H), 1.21-1.14 (m, 1H); LCMS (electrospray) m/z 453.10 (M + H)+. | J |
| 638 | 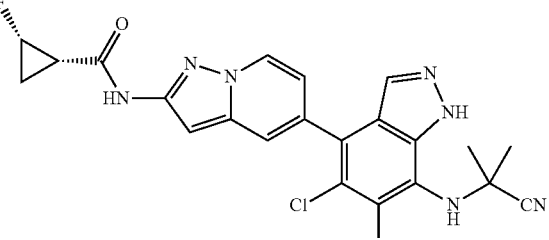<br>(1S,2S)-N-(5-(5-chloro-7-((2-cyanopropan-2-yl)amino)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.51 (s, 1H), 11.20 (s, 1H), 8.67 (d, J = 7.1 Hz, 1H), 7.92 (s, 1H), 7.80 (d, J = 1.1 Hz, 1H), 7.02-6.87 (m, 2H), 5.76 (s, 1H), 5.09-4.81 (m, 1H), 2.23-2.07 (m, 1H), 1.75-1.61 (m, 7H), 1.21-1.10 (m, 2H); LCMS (electrospray) m/z 470.10 (M + H)+. | J |
| 639 | 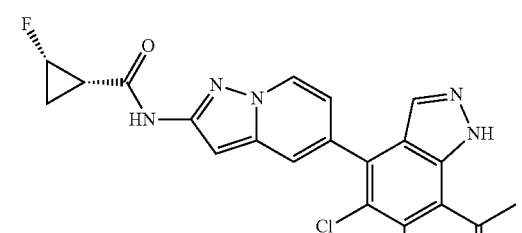<br>(1S,2S)-N-(5-(5-chloro-6-fluoro-7-(prop-1-en-2-yl)-1H-indazol-4-yl)pyrazolo[1,5-a]pyridin-2-yl)-2-fluorocyclopropane-1-carboxamide | ¹H NMR (400 MHz, DMSO-d₆) δ 13.67-13.30 (m, 1H), 11.18 (s, 1H), 8.68 (d, J = 7.1 Hz, 1H), 7.94 (s, 1H), 7.79 (d, J = 1.0 Hz, 1H), 7.05-6.79 (m, 2H), 5.63 (s, 1H), 5.38 (s, 1H), 5.15-4.77 (m, 1H), 2.21 (s, 3H), 2.18-2.09 (m, 1H), 1.74-1.60 (m, 1H), 1.25-1.12 (m, 1H); LCMS (electrospray) m/z 428.1 (M + H+). | J |
| 640 | 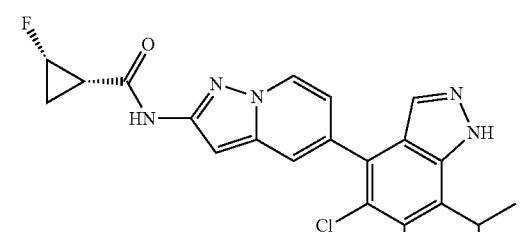<br>(1S,2S)-N-(5-(5-chloro-6-fluoro-7-isopropyl-1H-indazol-4-yl)pyrazolo[1,5-a]pyridin-2-yl)-2-fluorocyclopropane-1-carboxamide | ¹H NMR (400 MHz, DMSO-d₆) δ 13.61 (br d, J = 2.1 Hz, 1H), 11.18 (s, 1H), 8.66 (d, J = 7.2 Hz, 1H), 7.92 (s, 1H), 7.76 (d, J = 0.9 Hz, 1H), 7.07-6.84 (m, 2H), 5.10-4.76 (m, 1H), 3.62 (td, J = 7.0, 14.1 Hz, 1H), 2.15 (td, J = 6.9, 13.8 Hz, 1H), 1.76-1.59 (m, 1H), 1.44 (d, J = 7.0 Hz, 6H), 1.18 (tdd, J = 6.2, 9.0, 12.3 Hz, 1H); LCMS (electrospray) m/z 430.2 (M + H+). | J |

TABLE 1-continued

Compounds of Examples

| Ex # | Structure/Name | ¹H NMR/MS (M + 1) | Method |
|---|---|---|---|
| 641 | 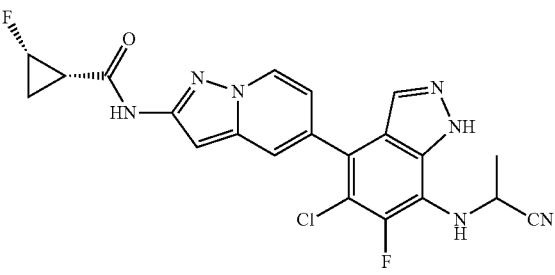 [SMILES: CC(C#N)Nc1c(F)c(Cl)c(-c2ccn3nc(NC(=O)[C@@H]4C[C@@H]4F)cc3c2)c2cn[nH]c12]<br>(1S,2S)-N-(5-(5-chloro-7-((1-cyanoethyl)amino)-6-fluoro-1H-indazol-4-yl)pyrazolo[1,5-a]pyridin-2-yl)-2-fluorocyclopropane-1-carboxamide | ¹H NMR (400 MHz, DMSO-d₆) δ 13.32 (s, 1H), 11.03 (s, 1H), 8.61 (d, J = 7.1 Hz, 1H), 7.95 (s, 1H), 7.73 (s, 1H), 6.98-6.88 (m, 2H), 6.24-5.96 (m, 1H), 5.05-4.81 (m, 1H), 3.34-3.24 (m, 1H), 2.22-2.09 (m, 1H), 1.78-1.58 (m, 4H), 1.22-1.11 (m, 1H); LCMS (electrospray) m/z 456.10 (M + H)+. | J |
| 642 | 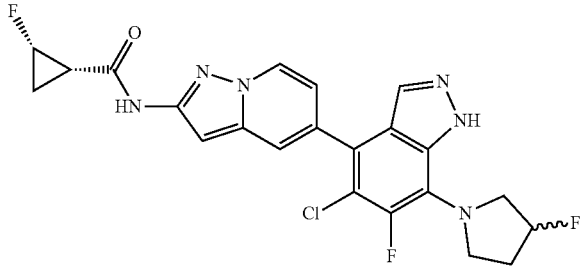 [SMILES: O=C(Nc1cc2cc(-c3c(Cl)c(F)c(N4CCC(F)C4)c4[nH]ncc34)ccn2n1)[C@@H]1C[C@@H]1F]<br>(1S,2S)-N-(5-(5-chloro-6-fluoro-7-(3-fluoropyrrolidin-1-yl)-1H-indazol-4-yl)pyrazolo[1,5-a]pyridin-2-yl)-2-fluorocyclopropane-1-carboxamide | ¹H NMR (400 MHz, DMSO-d₆) δ 13.11 (s, 1H), 10.83 (s, 1H), 8.54 (d, J = 7.1 Hz, 1H), 7.90-7.72 (m, 1H), 7.62 (s, 1H), 6.88 (s, 1H), 6.86-6.79 (m, 1H), 5.56-5.24 (m, 1H), 5.00-4.74 (m, 1H), 4.34-3.50 (m, 4H), 2.38-2.03 (m, 3H), 1.75-1.56 (m, 1H), 1.19-1.04 (m, 1H); LCMS (electrospray) m/z 475.10 (M + H)+. | J |
| 643 | 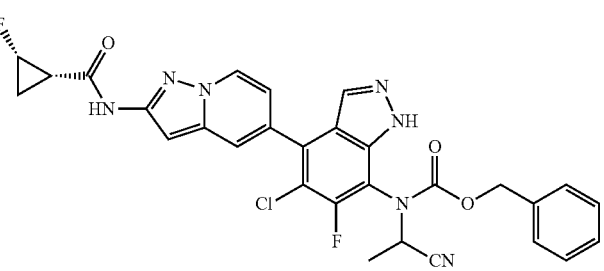<br>benzyl (5-chloro-6-fluoro-4-(2-((1S,2S)-2-fluorocyclopropane-1-carboxamido)pyrazolo[1,5-a]pyridin-5-yl)-1H-indazol-7-yl)(1-cyanoethyl)carbamate | ¹H NMR (400 MHz, DMSO-d₆) δ 13.83 (s, 1H), 11.08 (s, 1H), 8.67 (d, J = 7.1 Hz, 1H), 7.99 (s, 1H), 7.82 (d, J = 5.5 Hz, 1H), 7.67-6.83 (m, 7H), 5.59-5.07 (m, 3H), 5.05-4.79 (m, 1H), 2.23-2.09 (m, 1H), 1.79-1.62 (m, 2H), 1.43 (d, J = 7.1 Hz, 2H), 1.23-1.09 (m, 1H); LCMS (electrospray) m/z 591.20 (M + H)+. | J |
| 644 | 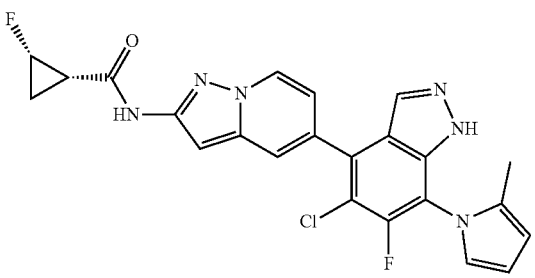 [SMILES: Cc1cccn1-c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-(2-methyl-1H-pyrrol-1-yl)-1H-indazol-4-yl)pyrazolo[1,5-a]pyridin-2-yl)-2-fluorocyclopropane-1-carboxamide | ¹H NMR (400 MHz, DMSO-d₆) δ 11.21 (s, 1H), 8.72 (d, J = 7.2 Hz, 1H), 8.07 (s, 1H), 7.87 (d, J = 1.0 Hz, 1H), 7.05-6.99 (m, 2H), 6.95 (br s, 1H), 6.27 (t, J = 3.2 Hz, 1H), 6.16-6.11 (m, 1H), 5.08-4.84 (m, 1H), 2.16 (td, J = 6.8, 14.1 Hz, 1H), 2.10-2.04 (m, 3H), 1.78-1.63 (m, 1H), 1.23-1.15 (m, 1H); LCMS (electrospray) m/z 467.1 (M + H+). | J |

TABLE 1-continued

Compounds of Examples

| Ex # | Structure/Name | ¹H NMR/MS (M + 1) | Method |
|------|----------------|-------------------|--------|
| 645 | 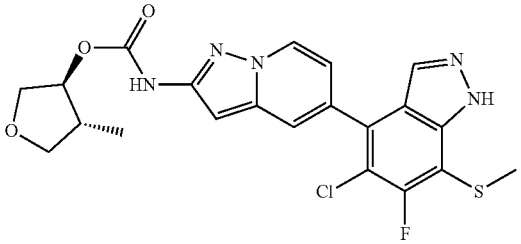 [SMILES: CSc1c(F)c(Cl)c(-c2ccn3nc(NC(=O)O[C@@H]4COC[C@H]4C)cc3c2)c2cn[nH]c12]<br>(3S,4R)-4-methyltetrahydrofuran-3-yl (5-(5-chloro-6-fluoro-7-(methylthio)-1H-indazol-4-yl)pyrazolo[1,5-a]pyridin-2-yl)carbamate | ¹H NMR (400 MHz, DMSO-d$_6$) δ 13.95-13.76 (m, 1H), 10.54 (s, 1H), 8.65 (d, J = 7.1 Hz, 1H), 8.47 (s, 1H), 7.98 (s, 1H), 7.76 (d, J = 1.0 Hz, 1H), 6.91 (dd, J = 2.0, 7.1 Hz, 1H), 6.76 (s, 1H), 4.92-4.85 (m, 1H), 4.03-3.91 (m, 2H), 3.76 (dd, J = 1.3, 10.6 Hz, 1H), 2.57 (s, 3H), 2.38-2.29 (m, 1H), 1.06 (d, J = 7.2 Hz, 3H); LCMS (electrospray) m/z 476.1(M + H+). | J |
| 646 | 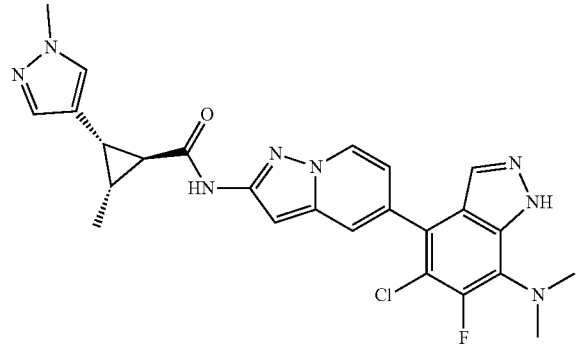 [SMILES: C[C@H]1[C@H](C(=O)Nc2cc3cc(-c4c(Cl)c(F)c(N(C)C)c5[nH]ncc45)ccn3n2)[C@H]1c1cnn(C)c1]<br>(1S,2R,3S)-N-(5-(5-chloro-7-(dimethylamino)-6-fluoro-1H-indazol-4-yl)pyrazolo[1,5-a]pyridin-2-yl)-2-methyl-3-(1-methyl-1H-pyrazol-4-yl)cyclopropane-1-carboxamide | ¹H NMR (400 MHz, DMSO-d$_6$) δ 13.51 (s, 1H), 11.07 (s, 1H), 9.60-9.58 (m, 1H), 8.64 (d, J = 7.1 Hz, 1H), 7.87 (s, 1H), 7.72 (s, 1H), 7.53 (s, 1H), 7.28 (s, 1H), 6.94 (s, 1H), 6.90 (dd, J = 7.1, 1.8 Hz, 1H), 3.80 (s, 3H), 2.99 (7H), 2.32 (dd, J = 9.1, 4.3 Hz, 2H), 2.00-1.95 (m, 1H), 1.68-1.55 (m, 1H), 1.37-1.18 (m, 2H), 0.97 (d J = 6.2 Hz 3H). LCMS (electrospray) m/z 507.1 (M + H)+. | J |
| 647 | 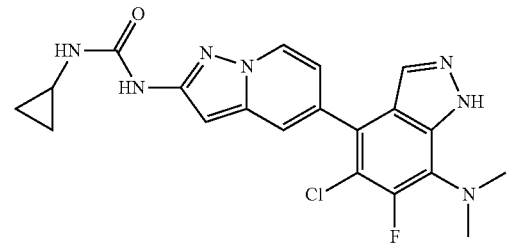 [SMILES: CN(C)c1c(F)c(Cl)c(-c2ccn3nc(NC(=O)NC4CC4)cc3c2)c2cn[nH]c12]<br>1-(5-(5-chloro-7-(dimethylamino)-6-fluoro-1H-indazol-4-yl)pyrazolo[1,5-a]pyridin-2-yl)-3-cyclopropylurea | ¹H NMR (400 MHz, DMSO-d$_6$) δ 13.52 (s, 1H), 9.05 (s, 1H), 8.57 (d, J = 7.0 Hz, 1H), 7.87 (s, 1H), 7.65 (dd, J = 1.77, 0.79 Hz, 1H), 6.85-6.81 (m, 2H), 6.72 (s, 1H), 3.01 (s, 6H), 2.62-2.58 (m, 1H), 0.69-0.65 (m, 2H), 0.46-0.44 (m, 2H); LCMS (electrospray) m/z 428.0 (M + H)+. | J |

TABLE 1-continued

Compounds of Examples

| Ex # | Structure/Name | ¹H NMR/MS (M + 1) | Method |
|---|---|---|---|
| 648 | 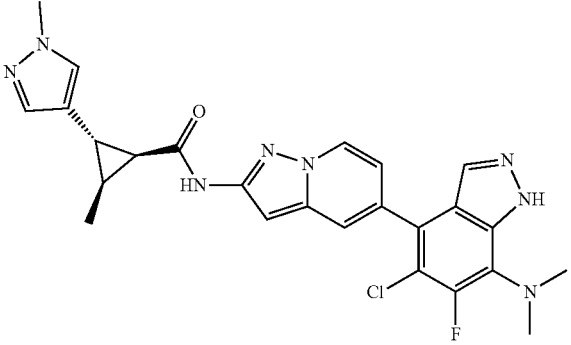<br>(1S,2S,3S)-N-(5-(5-chloro-7-(dimethylamino)-6-fluoro-1H-indazol-4-yl)pyrazolo[1,5-a]pyridin-2-yl)-2-methyl-3-(1-methyl-1H-pyrazol-4-yl)cyclopropane-1-carboxamide | ¹H NMR (400 MHz, DMSO-$d_6$) δ 11.03 (s, 1H), 8.63 (d, J = 7.2 Hz, 1H), 8.55 (s, 1H), 7.87 (s, 1H), 7.71 (s, 1H), 7.53 (s, 1H), 7.26 (s, 1H), 6.97 (s, 1H), 6.90 (dd, J = 7.1, 1.8 Hz, 1H), 3.77 (s, 3H), 3.02 (d, J = 2.2 Hz, 6H), 2.22-2.14 (m, 1H), 2.09 (d, J = 4.5 Hz, 3 H), 1.63-1.54 (m, 1H), 1.26 (d, J = 6.1 Hz, 5H), 1.06 (t, J = 7.0 Hz, 2H); LCMS (electrospray) m/z 507.1 (M + H)+. | J |
| 649 | 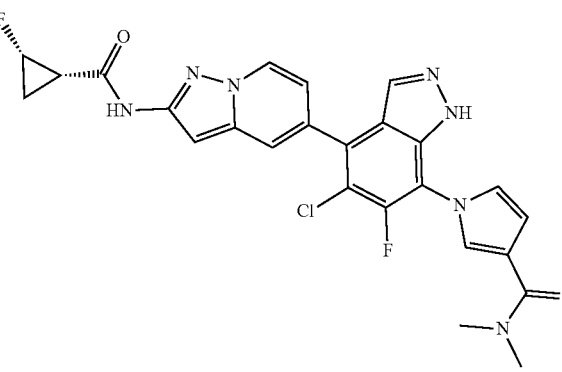<br>1-(5-chloro-6-fluoro-4-(2-((1S,2S)-2-fluorocyclopropane-1-carboxamido)pyrazolo[1,5-a]pyridin-5-yl)-1H-indazol-7-yl)-N,N-dimethyl-1H-pyrrole-3-carboxamide | ¹H NMR (400 MHz, DMSO-$d_6$) δ 11.20 (s, 1H), 8.71 (d, J = 7.1 Hz, 1H), 8.13 (s, 1H), 7.84-7.80 (m, 1H), 7.50-7.38 (m, 1H), 7.00 (s, 1H), 6.97 (dd, J = 7.19, 1.94 Hz, 1 H), 6.66 (dd, J = 2.94, 1.69 Hz, 1 H), 5.09-4.81 (m, 1H), 3.15-2.95 (m, 5H), 2.20-2.11 (m, 1H), 1.75-1.61 (m, 1H), 1.22-1.12 (m, 1H); LCMS (electrospray) m/z 524.1 (M + H)+. | J |
| 650 | 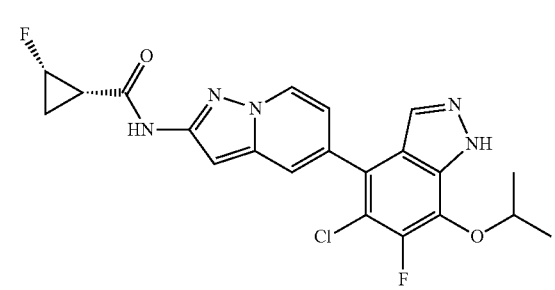 [SMILES: CC(C)Oc1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-isopropoxy-1H-indazol-4-yl)pyrazolo[1,5-a]pyridin-2-yl)-2-fluorocyclopropane-1-carboxamide | ¹H NMR (400 MHz, DMSO-$d_6$) δ 14.17-13.20 (m, 1H), 11.17 (s, 1H), 8.66 (d, J = 7.2 Hz, 1H), 7.94 (s, 1H), 7.76 (s, 1H), 7.00-6.89 (m, 2H), 5.10-4.80 (m, 1H), 4.74 (br s, 1H), 2.15 (quin, J = 6.9 Hz, 1H), 1.77-1.59 (m, 1H), 1.37 (d, J = 6.0 Hz, 6H), 1.26-1.09 (m, 1H); LCMS (electrospray) m/z 446.0 (M + H)+. | J |

TABLE 1-continued

Compounds of Examples

| Ex # | Structure/Name | ¹H NMR/MS (M + 1) | Method |
|---|---|---|---|
| 651 | 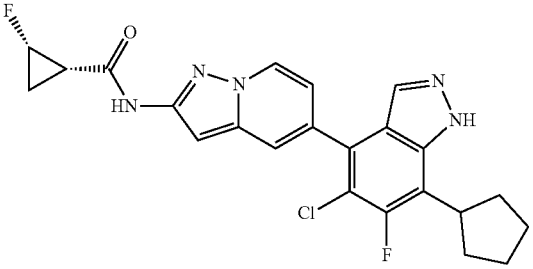 [SMILES: O=C(Nc1cc2cc(-c3c(Cl)c(F)c(C4CCCC4)c4[nH]ncc34)ccn2n1)[C@@H]1C[C@@H]1F]<br>(1S,2S)-N-(5-(5-chloro-7-cyclopentyl-6-fluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.55 (s, 1H), 11.19 (s, 1H), 8.67 (d, J = 7.1 Hz, 1H), 7.90 (d, J = 1.1 Hz, 1H), 7.76 (t, J = 1.1 Hz, 1H), 6.96-6.92 (m, 2H), 5.05-4.84 (m, 1H), 3.59 (q, J = 8.6 Hz, 1H), 2.18-1.91 (m, 8H), 1.72-1.62 (m, 3H), 1.24-1.06 (m, 1H); LCMS (electrospray) m/z 456.1 (M + H)+. | J |
| 652 | 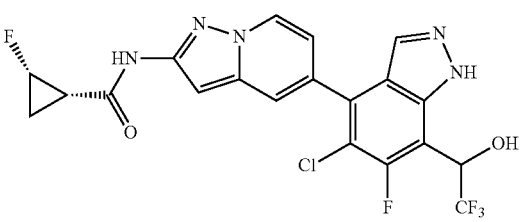 [SMILES: O=C(Nc1cc2cc(-c3c(Cl)c(F)c(C(O)C(F)(F)F)c4[nH]ncc34)ccn2n1)[C@@H]1C[C@@H]1F]<br>(1S,2S)-N-(5-(5-chloro-6-fluoro-7-(2,2,2-trifluoro-1-hydroxyethyl)-1H-indazol-4-yl)pyrazolo[1,5-a]pyridin-2-yl)-2-fluorocyclopropane-1-carboxamide | ¹H NMR (400 MHz, DMSO-$d_6$) δ 13.35 (s, 1H), 11.15 (s, 1H), 8.65 (d, J = 7.1 Hz, 1H), 7.90 (s, 1H), 7.79 (t, J = 1.4 Hz, 1H), 7.59 (s, 1H), 6.93 (dd, J = 6.3, 2.5 Hz, 2H), 5.74 (t, J = 7.4 Hz, 1H), 5.01-4.80 (m, 1H), 2.15-2.08 (m, 1H), 1.64 (dtd, J = 23.2, 6.9, 3.8 Hz, 1H), 1.17-1.10 (m, 1H); LCMS (electrospray) m/z 487.1 (M + H)+. | J |
| 653 | 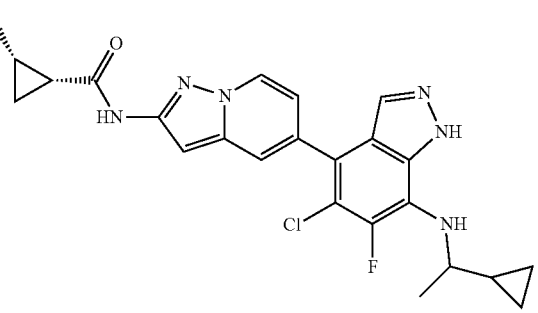<br>(1S,2S)-N-(5-(5-chloro-7-((1-cyclopropylethyl)amino)-6-fluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.25 (br s, 1H), 11.14 (s, 1H), 8.61 (d, J = 7.2 Hz, 1H), 7.85 (br s, 1H), 7.70 (s, 1H), 6.92 (s, 1H), 6.91-6.88 (m, 1H), 5.32 (br d, J = 9.5 Hz, 1H), 5.06-4.82 (m, 1H), 2.21-2.06 (m, 1H), 1.75-1.61 (m, 1H), 1.26 (d, J = 6.4 Hz, 3H), 1.21-1.14 (m, 1H), 1.04 (br s, 1H), 0.48-0.35 (m, 2H), 0.34-0.18 (m, 2H); LCMS (electrospray) m/z 471.1 (M + H)+. | J |
| 654 | 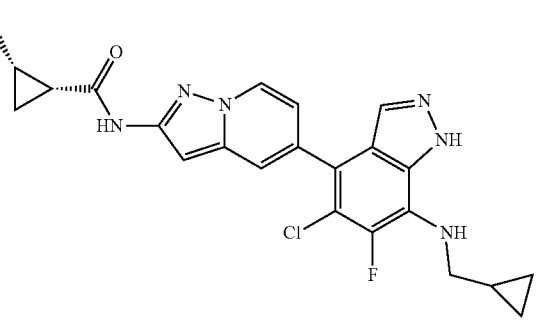<br>(1S,2S)-N-(5-(5-chloro-7-((cyclopropylmethyl)amino)-6-fluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.26 (s, 1H), 11.15 (s, 1H), 8.61 (d, J = 7.0 Hz, 1H), 7.85 (m, 1H), 7.70 (d, J = 1.0 Hz, 1H), 6.91 (m, 2H), 5.65 (m, 1H), 4.95 (m, 1H), 3.31 (s, 2H), 2.14 (m, 1H), 1.67 (m, 1H), 1.18 (m, 1H), 1.08 (m, 1H), 0.48 (d, J = 7.1 Hz, 2H), 0.27 (m, 2H); LCMS (electrospray) m/z 457.1 (M + H)+. | J |

TABLE 1-continued

Compounds of Examples

| Ex # | Structure/Name | ¹H NMR/MS (M + 1) | Method |
|---|---|---|---|
| 655 | 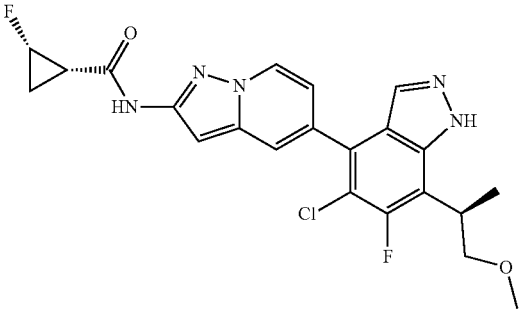 [SMILES: COC[C@H](C)c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-((R)-1-methoxypropan-2-yl)-1H-indazol-4-yl)pyrazolo[1,5-a]pyridin-2-yl)-2-fluorocyclopropane-1-carboxamide | ¹H NMR (400 MHz, DMSO-$d_6$) δ13.56 (br s, 1H), 11.17 (s, 1H), 8.67 (d, J = 7.1 Hz, 1H), 7.91 (s, 1H), 7.78 (s, 1H), 6.96 (br d, J = 2.2 Hz, 1H), 6.95-6.91 (m, 1H), 5.07-4.82 (m, 1H), 3.85-3.74 (m, 2H), 3.67 (br s, 1H), 3.25 (s, 3H), 2.21-2.09 (m, 1H), 1.74-1.60 (m, 1H), 1.40 (br d, J = 6.1 Hz, 3H), 1.22-1.12 (m, 1H); LCMS (electrospray) m/z 460.1 (M + H)+. | J |
| 656 | 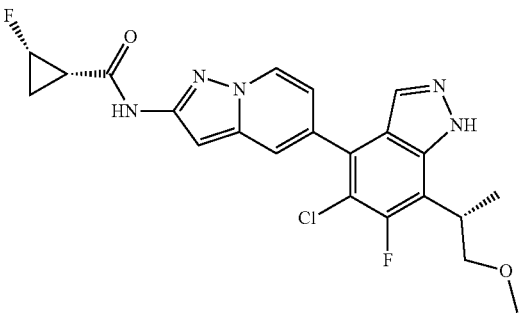 [SMILES: COC[C@@H](C)c1c(F)c(Cl)c(-c2ccn3nc(NC(=O)[C@@H]4C[C@@H]4F)cc3c2)c2cn[nH]c12]<br>(1S,2S)-N-(5-(5-chloro-6-fluoro-7-((S)-1-methoxypropan-2-yl)-1H-indazol-4-yl)pyrazolo[1,5-a]pyridin-2-yl)-2-fluorocyclopropane-1-carboxamide | ¹H NMR (400 MHz, DMSO-$d_6$) δ13.56 (br s, 1H), 11.17 (s, 1H), 8.67 (d, J = 7.1 Hz, 1H), 7.91 (s, 1H), 7.78 (d, J = 1.0 Hz, 1H), 6.96 (d, J = 2.6 Hz, 1H), 6.95-6.92 (m, 1H), 5.07-4.79 (m, 1H), 3.85-3.73 (m, 2H), 3.67 (br s, 1H), 3.25 (s, 3H), 2.15 (td, J = 6.8, 13.7 Hz, 1H), 1.73-1.61 (m, 1H), 1.40 (br d, J = 6.2 Hz, 3H), 1.18 (ddd, J = 2.8, 6.2, 12.3 Hz, 1H); LCMS (electrospray) m/z 460.1 (M + H)+. | J |
| 657 | 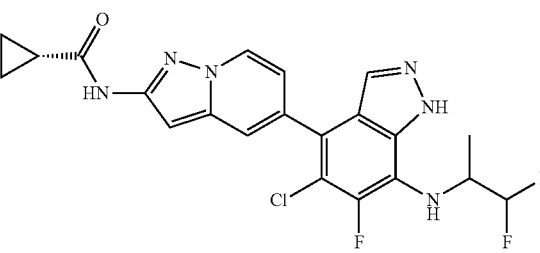<br>(1S,2S)-N-(5-(5-chloro-7-((1,1-difluoropropan-2-yl)amino)-6-fluoro-1H-indazol-4-yl)pyrazolo[1,5-a]pyridin-2-yl)-2-fluorocyclopropane-1-carboxamide | ¹H NMR (400 MHz, DMSO-$d_6$) δ 13.15 (s, 1H), 11.15 (s, 1H), 8.62 (d, J = 7.1 Hz, 1H), 8.04-7.83 (m, 1H), 7.71 (d, J = 1.0 Hz, 1H), 6.92 (s, 1H), 6.90 (dd, J = 7.1, 2.0 Hz, 1H), 6.33-5.92 (m, 1H), 5.67-5.51 (m, 1H), 5.07-4.81 (m, 1H), 4.53-4.03 (m, 1H), 2.21-2.05 (m, 1H), 1.75-1.57 (m, 1H), 1.32 (d, J = 6.6 Hz, 3H), 1.17 (ddt, J = 12.26, 9.07, 6.16, 6.16 Hz, 1 H); LCMS (electrospray) m/z 481.0 (M + H)+. | J |

TABLE 1-continued

Compounds of Examples

| Ex # | Structure/Name | ¹H NMR/MS (M + 1) | Method |
|---|---|---|---|
| 658 | (1S,2S)-N-(5-(5-chloro-6-fluoro-7-(4-hydroxytetrahydrofuran-2-yl)-1H-indazol-4-yl)pyrazolo[1,5-a]pyridin-2-yl)-2-fluorocyclopropane-1-carboxamide | ¹H NMR (400 MHz, DMSO-$d_6$) δ 13.15 (s, 1H), 11.19 (s, 1H), 8.68 (d, J = 7.1 Hz, 1H), 7.92 (s, 1H), 7.78 (d, J = 1.0 Hz, 1H), 6.98 (s, 1H), 6.94 (dd, J = 2.0, 7.1 Hz, 1H), 5.57 (dd, J = 5.4, 10.8 Hz, 1H), 5.18 (d, J = 3.4 Hz, 1H), 5.07-4.83 (m, 1H), 4.55 (dd, J = 3.7 Hz, 1H), 4.47 (dd, J = 4.6, 8.9 Hz, 1H), 3.72 (dd, J = 1.2, 9.0 Hz, 1H), 2.26 (dd, J = 5.4, 12.5 Hz, 1H), 2.20-2.02 (m, 2H), 1.76-1.62 (m, 1H), 1.28-1.12 (m, 2H); LCMS (electrospray) m/z 474.2 (M + H)+. | J |
| 659 | (1S,2S)-N-(5-(5-chloro-6-fluoro-7-(1-formamidoethyl)-1H-indazol-4-yl)pyrazolo[1,5-a]pyridin-2-yl)-2-fluorocyclopropane-1-carboxamide | ¹H NMR (400 MHz, DMSO-$d_6$) δ13.80-13.56 (m, 1H), 11.18 (s, 1H), 8.77 (br d, J = 6.6 Hz, 1H), 8.67 (d, J = 7.1 Hz, 1H), 8.06 (s, 1H), 7.94 (s, 1H), 7.77 (d, J = 0.9 Hz, 1H), 6.96 (s, 1H), 6.93 (dd, J = 1.8, 7.2 Hz, 1H), 5.56 (br t, J = 7.2 Hz, 1H), 5.11-4.78 (m, 1H), 2.15 (td, J = 7.0, 13.8 Hz, 1H), 1.73-1.62 (m, 1H), 1.58 (d, J = 7.2 Hz, 3H), 1.18 (tdd, J = 6.4, 9.0, 12.4 Hz, 1H); LCMS (electrospray) m/z 459.2 (M + H)+. | J |
| 660 | (1S,2S)-N-(5-(5-chloro-6-fluoro-7-(1-propionamidoethyl)-1H-indazol-4-yl)pyrazolo[1,5-a]pyridin-2-yl)-2-fluorocyclopropane-1-carboxamide | ¹H NMR (400 MHz, DMSO-$d_6$) δ13.73-13.44 (m, 1H), 11.17 (s, 1H), 8.67 (d, J = 7.1 Hz, 1H), 8.46-8.32 (m, 1H), 7.92 (s, 1H), 7.77 (s, 1H), 6.96 (s, 1H), 6.93 (dd, J = 2.0, 7.2 Hz, 1H), 5.46 (br t, J = 7.0 Hz, 1H), 5.09-4.77 (m, 1H), 2.20-2.07 (m, 3H), 1.78-1.61 (m, 1H), 1.55 (br d, J = 7.2 Hz, 3H), 1.27-1.07 (m, 1H), 0.95 (t, J = 7.6 Hz, 3H); LCMS (electrospray) m/z 487.2 (M + H)+. | J |
| 661 | N-(1-(5-chloro-6-fluoro-4-(2-((1S,2S)-2-fluorocyclopropane-1-carboxamido)pyrazolo[1,5-a]pyridin-5-yl)-1H-indazol-7-yl)ethyl)cyclobutanecarboxamide | ¹H NMR (400 MHz, DMSO-$d_6$) δ13.77-13.42 (m, 1H), 11.18 (s, 1H), 8.67 (d, J = 7.1 Hz, 1H), 8.54-8.48 (m, 1H), 8.34 (br s, 1H), 7.91 (s, 1H), 7.77 (d, J = 0.7 Hz, 1H), 6.95 (s, 1H), 6.93 (dd, J = 2.0, 7.2 Hz, 1H), 5.45 (br t, J = 7.1 Hz, 1H), 5.05-4.83 (m, 1H), 3.08 (br t, J = 8.3 Hz, 1H), 2.19-2.01 (m, 3H), 1.99-1.83 (m, 3H), 1.75-1.61 (m, 2H), 1.55 (d, J = 7.2 Hz, 3H), 1.17 (ddd, J = 2.8, 6.1, 12.3 Hz, 1H); LCMS (electrospray) m/z 513.2 (M + H)+. | J |

TABLE 1-continued

Compounds of Examples

| Ex # | Structure/Name | ¹H NMR/MS (M + 1) | Method |
|---|---|---|---|
| 662 | 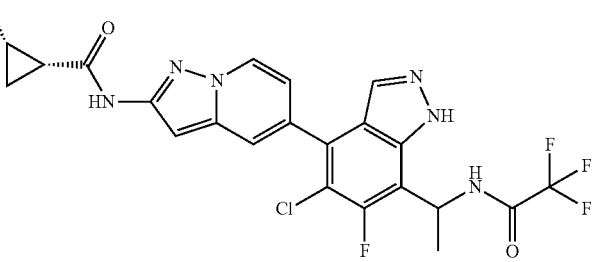<br>(1S,2S)-N-(5-(5-chloro-6-fluoro-7-(1-(2,2,2-trifluoroacetamido)ethyl)-1H-indazol-4-yl)pyrazolo[1,5-a]pyridin-2-yl)-2-fluorocyclopropane-1-carboxamide | ¹H NMR (400 MHz, DMSO-d$_6$) δ14.24-12.89 (m, 1H), 11.19 (s, 1H), 10.54-9.82 (m, 1H), 8.68 (d, J = 7.0 Hz, 1H), 7.97 (s, 1H), 7.00-6.92 (m, 2H), 5.56 (q, J = 7.0 Hz, 1H), 5.07-4.81 (m, 1H), 2.21-2.08 (m, 1H), 1.69 (d, J = 7.0 Hz, 3H), 1.66-1.60 (m, 1H), 1.26-1.09 (m, 1H); LCMS (electrospray) m/z 527.1 (M + H)+. | J |
| 663 | 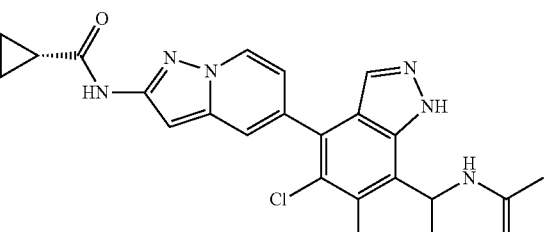<br>(1S,2S)-N-(5-(7-(1-acetamidoethyl)-5-chloro-6-fluoro-1H-indazol-4-yl)pyrazolo[1,5-a]pyridin-2-yl)-2-fluorocyclopropane-1-carboxamide | ¹H NMR (400 MHz, DMSO-d$_6$) δ13.90-13.44 (m, 1H), 11.21-11.13 (m, 1H), 8.94-8.80 (m, 1H), 8.66 (d, J = 7.2 Hz, 1H), 8.56 (s, 1H), 7.96-7.86 (m, 1H), 7.80-7.73 (m, 1H), 6.95 (s, 1H), 6.94-6.91 (m, 1H), 5.54-5.41 (m, 1H), 4.93 (s, 1H), 2.22-2.09 (m, 1H), 1.90-1.82 (m, 3H), 1.73-1.61 (m, 1H), 1.54 (d, J = 7.0 Hz, 3H), 1.21-1.13 (m, 1H); LCMS (electrospray) m/z 473.1 (M + H)+. | J |
| 664 | 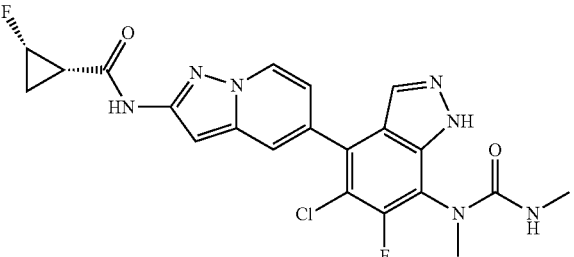<br>(1S,2S)-N-(5-(5-chloro-7-(1,3-dimethylureido)-6-fluoro-1H-indazol-4-yl)pyrazolo[1,5-a]pyridin-2-yl)-2-fluorocyclopropane-1-carboxamide | ¹H NMR (400 MHz, DMSO-d$_6$) δ 13.73 (s, 1H), 11.21 (s, 1H), 8.70 (d, J = 7.1 Hz, 1H), 7.97 (s, 1H), 7.77 (s, 1H), 7.00 (s, 1H), 6.93 (dd, J = 7.1, 2.2 Hz, 1H), 6.40 (s, 1H), 5.05-4.85 (m, 1H), 3.20 (s, 3H), 2.58 (d, J = 4.4 Hz, 3H), 2.18-2.11 (m, 1H), 1.72-1.64 (m, 1H), 1.21-1.15 (m, 1H) m/z 474.10 (M + H)+. | J |
| 665 | 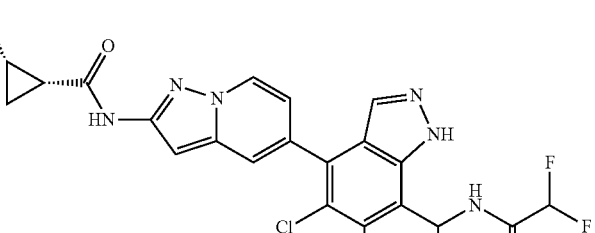<br>(1S,2S)-N-(5-(5-chloro-7-(1-(2,2-difluoroacetamido)ethyl)-6-fluoro-1H-indazol-4-yl)pyrazolo[1,5-a]pyridin-2-yl)-2-fluorocyclopropane-1-carboxamide | ¹H NMR (400 MHz, DMSO-d$_6$) δ 14.06-13.53 (m, 1H), 11.18 (s, 1H), 9.82-9.45 (m, 1H), 8.67 (d, J = 7.1 Hz, 1H), 7.95 (s, 1H), 7.78 (d, J = 0.9 Hz, 1H), 6.99-6.91 (m, 2H), 6.44-6.11 (m, 1H), 5.61-5.51 (m, 1H), 5.05-4.83 (m, 1H), 2.15 (td, J = 7.0, 13.8 Hz, 1H), 1.70 (dt, J = 3.7, 6.9 Hz, 1H), 1.65 (d, J = 7.2 Hz, 3H), 1.24-1.12 (m, 1H); LCMS (electrospray) m/z 509.2 (M + H)+. | J |

TABLE 1-continued

Compounds of Examples

| Ex # | Structure/Name | $^1$H NMR/MS (M + 1) | Method |
|---|---|---|---|
| 666 | 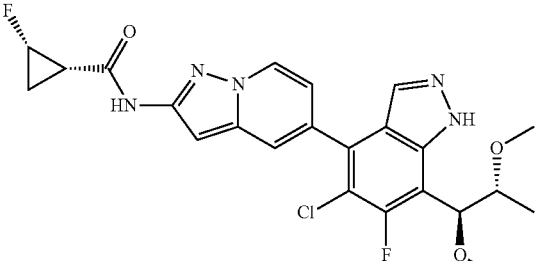<br>(1S,2S)-N-(5-(5-chloro-7-((1S,2R)-1,2-dimethoxypropyl)-6-fluoro-1H-indazol-4-yl)pyrazolo[1,5-a]pyridin-2-yl)-2-fluorocyclopropane-1-carboxamide | $^1$H NMR (400 MHz, DMSO-d$_6$) δ 13.33 (s, 1H), 11.20 (s, 1H), 8.67 (t, J = 8.0 Hz, 1H), 7.91 (s, 1H), 7.82 (t, J = 1.1 Hz, 1H), 6.97 (dd, J = 7.1, 2.2 Hz, 2H), 5.04-4.85 (m, 2H), 3.90 (t, J = 6.3 Hz, 1H), 3.38 (d, J = 6.6 Hz, 3H), 3.25 (s, 3H), 2.14 (t, J = 8.0 Hz, 1H), 1.71-1.64 (m, 1H), 1.18 (dd, J = 12.1, 8.8 Hz, 1H), 0.95 (d, J = 6.6 Hz, 3H); LCMS (electrospray) m/z 490.1 (M + H)+. | J |

Evaluation of Compounds

HPK1 Kinase Assay

HPK1 kinase activity was measured by Promega's ADP-Glo™ kinase assay. In this assay, 5 ng of recombinant human HPK1 (signalchem) is incubated with 5 μL of compounds (0.5% DMSO), 5 μL of MBP (0.5 μg/μl) and 5 μL of ATP (25 μM) in buffer (40 mM Tris, 7.5; 20 mM MgCl$_2$; 0.1 mg/ml BSA; 5 μM DTT). The assay was started by incubating the reaction mixture in a 96-well plate at 30' C for 40 minutes. After the incubation, 25 uL ADP-Glo reagent was added and the reaction was incubated at room temperature for 40-min to stop the reaction and degrade residual ATP. The ADP product was then converted to ATP by adding 50 uL per well of detection reagent. Luminescence was detected after 30-min room temperature incubation with the Molecular device I3X plate reader. The IC$_{50}$ values were calculated from a series of percent inhibition values determined at a range of inhibitor concentration using software routines as implemented in the GraphPad Prism 7 software and SigmaPlot13.0.

Table 2 shows IC$_{50}$ values of the invented compounds which represent + for >1000 nM, ++ for 501-1000 nM, +++ for 101-500 nM, ++++ for <100 nM.

TABLE 2

In vitro activity against HPK1 data

| Example | HPK1 IC$_{50}$ (nM) |
|---|---|
| 1 | +++ |
| 2 | +++ |
| 3 | + |
| 4 | ++ |
| 5 | +++ |
| 6 | +++ |
| 7 | +++ |
| 8 | + |
| 9 | + |
| 10 | + |
| 11 | ++ |
| 12 | + |
| 13 | + |
| 14 | + |
| 15 | +++ |
| 16 | +++ |
| 17 | +++ |
| 18 | + |
| 19 | + |
| 20 | + |
| 21 | + |
| 22 | + |
| 23 | + |
| 24 | +++ |
| 25 | ++ |
| 26 | + |
| 27 | + |
| 28 | +++ |
| 29 | +++ |
| 30 | +++ |
| 31 | + |
| 32 | +++ |
| 33 | +++ |
| 34 | + |
| 35 | +++ |
| 36 | +++ |
| 37 | +++ |
| 38 | + |
| 39 | +++ |
| 40 | ++++ |
| 41 | +++ |
| 42 | +++ |
| 43 | ++++ |
| 44 | ++ |
| 45 | + |
| 46 | ++++ |
| 47 | ++++ |
| 48 | ++++ |
| 49 | ++ |
| 50 | ++++ |
| 51 | ++++ |
| 52 | + |
| 53 | +++ |
| 54 | + |
| 55 | +++ |
| 56 | ++++ |
| 57 | ++++ |
| 58 | ++++ |
| 59 | ++++ |
| 60 | + |
| 61 | ++++ |
| 62 | +++ |
| 63 | ++++ |
| 64 | ++++ |

TABLE 2-continued

In vitro activity against HPK1 data

| Example | HPK1 IC$_{50}$ (nM) |
|---|---|
| 65 | ++++ |
| 66 | ++++ |
| 67 | ++++ |
| 68 | ++++ |
| 69 | ++++ |
| 70 | ++++ |
| 71 | ++++ |
| 72 | +++ |
| 73 | ++++ |
| 74 | +++ |
| 75 | +++ |
| 76 | +++ |
| 77 | ++++ |
| 78 | +++ |
| 79 | ++++ |
| 80 | ++++ |
| 81 | ++++ |
| 82 | ++++ |
| 83 | +++ |
| 84 | ++++ |
| 85 | ++++ |
| 86 | ++++ |
| 87 | ++++ |
| 88 | ++++ |
| 89 | ++++ |
| 90 | ++++ |
| 91 | +++ |
| 92 | ++++ |
| 93 | ++++ |
| 94 | ++++ |
| 95 | ++++ |
| 96 | ++++ |
| 97 | ++++ |
| 98 | ++++ |
| 99 | ++++ |
| 100 | ++++ |
| 101 | ++++ |
| 102 | ++++ |
| 103 | ++++ |
| 104 | ++++ |
| 105 | ++++ |
| 106 | ++++ |
| 107 | ++++ |
| 108 | ++++ |
| 109 | ++++ |
| 110 | ++++ |
| 111 | ++++ |
| 112 | +++ |
| 113 | ++++ |
| 114 | +++ |
| 115 | ++++ |
| 116 | ++++ |
| 117 | ++++ |
| 118 | ++++ |
| 119 | +++ |
| 120 | ++++ |
| 121 | + |
| 122 | ++++ |
| 123 | ++++ |
| 124 | + |
| 125 | ++++ |
| 126 | ++++ |
| 127 | ++++ |
| 128 | +++ |
| 129 | ++++ |
| 130 | ++++ |
| 131 | +++ |
| 132 | +++ |
| 133 | ++++ |
| 134 | ++++ |
| 135 | + |
| 136 | ++++ |
| 137 | ++++ |
| 138 | ++++ |
| 139 | ++++ |
| 140 | + |
| 141 | + |
| 142 | + |
| 143 | ++++ |
| 144 | +++ |
| 145 | + |
| 146 | +++ |
| 147 | ++++ |
| 148 | + |
| 149 | ++++ |
| 150 | ++++ |
| 151 | + |
| 152 | ++++ |
| 153 | ++++ |
| 154 | ++++ |
| 155 | ++++ |
| 156 | ++++ |
| 157 | +++ |
| 158 | +++ |
| 159 | ++++ |
| 160 | ++++ |
| 161 | ++++ |
| 162 | ++++ |
| 163 | ++++ |
| 164 | + |
| 165 | ++++ |
| 166 | ++++ |
| 167 | ++++ |
| 168 | +++ |
| 169 | ++++ |
| 170 | ++++ |
| 171 | + |
| 172 | ++++ |
| 173 | ++++ |
| 174 | ++++ |
| 175 | ++++ |
| 176 | ++++ |
| 177 | +++ |
| 178 | ++++ |
| 179 | ++++ |
| 180 | +++ |
| 181 | +++ |
| 182 | + |
| 183 | ++++ |
| 184 | ++++ |
| 185 | +++ |
| 186 | ++++ |
| 187 | ++++ |
| 188 | + |
| 189 | ++++ |
| 190 | ++++ |
| 191 | ++++ |
| 192 | ++++ |
| 193 | ++++ |
| 194 | ++++ |
| 195 | +++ |
| 196 | ++++ |
| 197 | ++++ |
| 198 | ++++ |
| 199 | ++++ |
| 200 | ++++ |
| 201 | + |
| 202 | ++++ |
| 203 | ++++ |
| 204 | ++++ |
| 205 | ++++ |
| 206 | +++ |
| 207 | ++++ |
| 208 | ++++ |
| 209 | ++++ |
| 210 | ++++ |
| 211 | ++++ |
| 212 | + |
| 213 | + |
| 214 | + |
| 215 | + |
| 216 | + |

TABLE 2-continued

In vitro activity against HPK1 data

| Example | HPK1 IC$_{50}$ (nM) |
|---|---|
| 217 | ++++ |
| 218 | ++++ |
| 219 | +++ |
| 220 | + |
| 221 | +++ |
| 222 | ++ |
| 223 | ++++ |
| 224 | +++ |
| 225 | + |
| 226 | ++++ |
| 227 | + |
| 228 | + |
| 229 | ++++ |
| 230 | + |
| 231 | + |
| 232 | ++++ |
| 233 | ++ |
| 234 | + |
| 235 | ++++ |
| 236 | ++++ |
| 237 | ++++ |
| 238 | ++++ |
| 239 | ++++ |
| 240 | ++ |
| 241 | + |
| 242 | +++ |
| 243 | ++++ |
| 244 | +++ |
| 245 | ++++ |
| 246 | ++++ |
| 247 | ++++ |
| 248 | ++++ |
| 249 | +++ |
| 250 | ++++ |
| 251 | + |
| 252 | ++++ |
| 253 | ++++ |
| 254 | ++++ |
| 255 | ++++ |
| 256 | ++++ |
| 257 | ++++ |
| 258 | ++++ |
| 259 | + |
| 260 | ++++ |
| 261 | ++++ |
| 262 | ++++ |
| 263 | ++++ |
| 264 | ++++ |
| 265 | ++++ |
| 266 | ++++ |
| 267 | +++ |
| 268 | ++++ |
| 269 | ++++ |
| 270 | +++ |
| 271 | ++++ |
| 272 | ++++ |
| 273 | ++++ |
| 274 | ++++ |
| 275 | ++++ |
| 276 | ++++ |
| 277 | +++ |
| 278 | + |
| 279 | ++++ |
| 280 | ++++ |
| 281 | ++++ |
| 282 | ++++ |
| 283 | ++++ |
| 284 | +++ |
| 285 | ++++ |
| 286 | + |
| 287 | ++++ |
| 288 | ++++ |
| 289 | + |
| 290 | ++++ |
| 291 | ++++ |
| 292 | ++++ |
| 293 | ++++ |
| 294 | ++++ |
| 295 | ++++ |
| 296 | ++++ |
| 297 | ++++ |
| 298 | ++++ |
| 299 | +++ |
| 300 | ++++ |
| 301 | ++++ |
| 302 | +++ |
| 303 | ++++ |
| 304 | ++++ |
| 305 | ++++ |
| 306 | ++++ |
| 307 | ++++ |
| 308 | +++ |
| 309 | ++++ |
| 310 | ++++ |
| 311 | ++++ |
| 312 | ++++ |
| 313 | + |
| 314 | + |
| 315 | ++++ |
| 316 | ++++ |
| 317 | ++++ |
| 318 | ++++ |
| 319 | ++++ |
| 320 | ++++ |
| 321 | ++++ |
| 322 | +++ |
| 323 | ++++ |
| 324 | ++++ |
| 325 | + |
| 326 | ++++ |
| 327 | ++++ |
| 328 | ++++ |
| 329 | ++++ |
| 330 | ++++ |
| 331 | ++++ |
| 332 | ++++ |
| 333 | ++++ |
| 334 | ++++ |
| 335 | ++++ |
| 336 | ++++ |
| 337 | ++++ |
| 338 | +++ |
| 339 | ++++ |
| 340 | +++ |
| 341 | ++++ |
| 342 | ++++ |
| 343 | ++++ |
| 344 | +++ |
| 345 | ++++ |
| 346 | ++++ |
| 347 | ++++ |
| 348 | ++++ |
| 349 | ++++ |
| 350 | ++++ |
| 351 | ++++ |
| 352 | +++ |
| 353 | ++++ |
| 354 | + |
| 355 | + |
| 356 | ++++ |
| 357 | ++++ |
| 358 | ++++ |
| 359 | ++++ |
| 360 | ++++ |
| 361 | ++++ |
| 362 | ++++ |
| 363 | ++++ |
| 364 | ++++ |
| 365 | ++++ |
| 366 | ++++ |
| 367 | ++++ |
| 368 | ++++ |

TABLE 2-continued

In vitro activity against HPK1 data

| Example | HPK1 IC$_{50}$ (nM) |
|---|---|
| 369 | ++++ |
| 370 | ++++ |
| 371 | ++++ |
| 372 | ++++ |
| 373 | ++++ |
| 374 | ++++ |
| 375 | ++++ |
| 376 | ++++ |
| 377 | ++++ |
| 378 | ++++ |
| 379 | ++++ |
| 380 | ++++ |
| 381 | ++++ |
| 382 | +++ |
| 383 | ++++ |
| 384 | ++++ |
| 385 | ++++ |
| 386 | ++++ |
| 387 | ++++ |
| 388 | ++++ |
| 389 | ++++ |
| 390 | ++++ |
| 391 | ++++ |
| 392 | ++++ |
| 393 | ++++ |
| 394 | ++++ |
| 395 | ++++ |
| 396 | ++++ |
| 397 | ++++ |
| 398 | ++++ |
| 399 | ++++ |
| 400 | ++++ |
| 401 | ++++ |
| 402 | +++ |
| 403 | + |
| 404 | ++++ |
| 405 | ++++ |
| 406 | ++++ |
| 407 | ++++ |
| 408 | ++++ |
| 409 | ++++ |
| 410 | ++++ |
| 411 | ++++ |
| 412 | ++++ |
| 413 | ++++ |
| 414 | ++++ |
| 415 | ++++ |
| 416 | ++++ |
| 417 | ++++ |
| 418 | ++++ |
| 419 | ++++ |
| 420 | ++++ |
| 421 | ++++ |
| 422 | ++++ |
| 423 | ++++ |
| 424 | ++++ |
| 425 | ++++ |
| 426 | ++++ |
| 427 | ++++ |
| 428 | ++++ |
| 429 | ++++ |
| 430 | ++++ |
| 431 | +++ |
| 432 | ++++ |
| 433 | ++++ |
| 434 | ++++ |
| 435 | ++++ |
| 436 | ++++ |
| 437 | ++++ |
| 438 | ++++ |
| 439 | ++++ |
| 440 | ++++ |
| 441 | ++++ |
| 442 | ++++ |
| 443 | ++++ |
| 444 | ++++ |
| 445 | ++++ |
| 446 | ++++ |
| 447 | ++++ |
| 448 | ++++ |
| 449 | +++ |
| 450 | + |
| 451 | ++++ |
| 452 | ++++ |
| 453 | ++ |
| 454 | +++ |
| 455 | ++++ |
| 456 | ++ |
| 457 | ++++ |
| 458 | ++++ |
| 459 | +++ |
| 460 | ++++ |
| 461 | + |
| 462 | ++++ |
| 463 | ++++ |
| 464 | ++++ |
| 465 | ++++ |
| 466 | ++++ |
| 467 | ++++ |
| 468 | ++++ |
| 469 | ++++ |
| 470 | +++ |
| 471 | +++ |
| 472 | + |
| 473 | + |
| 474 | +++ |
| 475 | + |
| 476 | ++++ |
| 477 | ++++ |
| 478 | ++ |
| 479 | ++++ |
| 480 | ++++ |
| 481 | ++++ |
| 482 | ++++ |
| 483 | ++++ |
| 484 | ++++ |
| 485 | ++++ |
| 486 | ++++ |
| 487 | ++++ |
| 488 | ++++ |
| 489 | ++++ |
| 490 | ++++ |
| 491 | ++++ |
| 492 | ++++ |
| 493 | ++++ |
| 494 | ++++ |
| 495 | ++++ |
| 496 | ++++ |
| 497 | ++++ |
| 498 | ++++ |
| 499 | ++++ |
| 500 | +++ |
| 501 | ++++ |
| 502 | ++++ |
| 503 | ++++ |
| 504 | ++++ |
| 505 | ++++ |
| 506 | ++++ |
| 507 | ++++ |
| 508 | ++++ |
| 509 | ++++ |
| 510 | ++++ |
| 511 | ++++ |
| 512 | ++++ |
| 513 | ++++ |
| 514 | ++++ |
| 515 | ++++ |
| 516 | ++++ |
| 517 | ++++ |
| 518 | ++++ |
| 519 | ++++ |
| 520 | ++++ |

TABLE 2-continued

In vitro activity against HPK1 data

| Example | HPK1 IC$_{50}$ (nM) |
|---|---|
| 521 | ++++ |
| 522 | ++++ |
| 523 | ++++ |
| 524 | ++++ |
| 525 | ++++ |
| 526 | ++++ |
| 527 | ++++ |
| 528 | ++++ |
| 529 | ++++ |
| 530 | ++++ |
| 531 | ++++ |
| 532 | ++++ |
| 533 | ++++ |
| 534 | ++++ |
| 535 | ++++ |
| 536 | ++++ |
| 537 | ++++ |
| 538 | ++++ |
| 539 | ++++ |
| 540 | ++++ |
| 541 | ++++ |
| 542 | ++++ |
| 543 | ++++ |
| 544 | ++++ |
| 545 | ++++ |
| 546 | ++++ |
| 547 | ++++ |
| 548 | ++++ |
| 549 | + |
| 550 | ++++ |
| 551 | + |
| 552 | ++++ |
| 553 | ++++ |
| 554 | ++++ |
| 555 | ++++ |
| 556 | ++++ |
| 557 | ++++ |
| 558 | ++++ |
| 559 | ++++ |
| 560 | ++++ |
| 561 | ++++ |
| 562 | ++++ |
| 563 | ++++ |
| 564 | ++++ |
| 565 | ++++ |
| 566 | +++ |
| 567 | ++++ |
| 568 | ++++ |
| 569 | ++++ |
| 570 | ++++ |
| 571 | ++++ |
| 572 | ++++ |
| 573 | ++++ |
| 574 | ++++ |
| 575 | ++++ |
| 576 | + |
| 577 | ++++ |
| 578 | ++++ |
| 579 | ++++ |
| 580 | ++++ |
| 581 | ++++ |
| 582 | ++++ |
| 583 | ++++ |
| 584 | +++ |
| 585 | ++++ |
| 586 | ++++ |
| 587 | ++++ |
| 588 | ++++ |
| 589 | ++++ |
| 590 | ++++ |
| 591 | ++++ |
| 592 | ++++ |
| 593 | ++++ |
| 594 | ++++ |
| 595 | +++ |
| 596 | ++++ |
| 597 | ++++ |
| 598 | ++++ |
| 599 | ++++ |
| 600 | ++++ |
| 601 | ++++ |
| 602 | ++++ |
| 603 | ++++ |
| 604 | +++ |
| 605 | + |
| 606 | ++++ |
| 607 | ++++ |
| 608 | ++++ |
| 609 | ++++ |
| 610 | ++++ |
| 611 | ++++ |
| 612 | ++++ |
| 613 | ++++ |
| 614 | ++++ |
| 615 | ++++ |
| 616 | ++++ |
| 617 | ++++ |
| 618 | ++++ |
| 619 | ++++ |
| 620 | ++++ |
| 621 | ++++ |
| 622 | ++++ |
| 623 | ++++ |
| 624 | ++++ |
| 625 | ++++ |
| 626 | ++++ |
| 627 | ++++ |
| 628 | ++++ |
| 629 | ++++ |
| 630 | ++++ |
| 631 | ++++ |
| 632 | ++++ |
| 633 | ++++ |
| 634 | ++++ |
| 635 | ++++ |
| 636 | ++++ |
| 637 | ++++ |
| 638 | ++++ |
| 639 | ++++ |
| 640 | ++++ |
| 641 | ++++ |
| 642 | ++++ |
| 643 | +++ |
| 644 | ++++ |
| 645 | ++++ |
| 646 | ++++ |
| 647 | ++++ |
| 648 | ++++ |
| 649 | ++++ |
| 650 | ++++ |
| 651 | ++++ |
| 652 | ++++ |
| 653 | ++++ |
| 654 | ++++ |
| 655 | ++++ |
| 656 | ++++ |
| 657 | ++++ |
| 658 | ++++ |
| 659 | ++++ |
| 660 | ++++ |
| 661 | ++++ |
| 662 | ++++ |
| 663 | ++++ |
| 664 | ++++ |
| 665 | ++++ |
| 666 | +++ |

IFNγ and IL-2 Analysis of Human Peripheral Pan T Cells

Human peripheral blood pan T cells were purchased from STEMCELL™ Technologies Inc. Human peripheral blood pan T cells were thawed and suspended in DMEM media (10% FBS and 10 Penicillin/Streptomycin). 8×10⁴ T cells were seeded in 96-well plate and incubated with various concentration of compounds and 100 nM Prostaglandin E2 for 1 hr. T cells were stimulated with Dynabeads Human T-Activator CD3/CD28 (Life Technologies) at a 1:3 cells: beads ratio. Cytokine secretion was measured after 24 hr post stimulation using MSD V-PLEX human cytokine kit as suggested by the manufacturer. Data were analyzed with an MESO Quickplex SQ120 (Mesoscale Discovery).

In Table 3, the values represent + for >1000 nM, ++ 200-1,000 nM, +++ for <200 nM and − for not determined.

TABLE 3

IFNγ and IL-2 secretion of the invented compounds in human peripheral blood pan T cells

| Example | IFNγ (EC$_{50}$) | IL-2 (EC$_{50}$) |
|---|---|---|
| 104 | ++ | + |
| 105 | ++ | + |
| 107 | ++ | − |
| 110 | +++ | − |
| 111 | ++ | − |
| 118 | +++ | − |
| 123 | ++ | + |
| 125 | +++ | − |
| 134 | +++ | + |
| 152 | ++ | ++ |
| 156 | ++ | ++ |
| 161 | ++ | − |
| 162 | ++ | − |
| 163 | − | − |
| 167 | ++ | + |
| 169 | ++ | + |
| 170 | ++ | + |
| 172 | ++ | − |
| 173 | ++ | − |
| 174 | ++ | − |
| 175 | +++ | − |
| 178 | − | − |
| 184 | +++ | − |
| 193 | ++ | + |
| 194 | ++ | − |
| 196 | ++ | − |
| 199 | ++ | − |
| 258 | +++ | ++ |
| 291 | +++ | ++ |
| 293 | +++ | − |
| 296 | +++ | ++ |
| 297 | +++ | +++ |
| 316 | ++ | + |
| 320 | ++ | − |
| 324 | +++ | ++ |
| 326 | ++ | ++ |
| 327 | +++ | ++ |
| 329 | ++ | ++ |
| 330 | ++ | ++ |
| 332 | ++ | ++ |
| 333 | ++ | ++ |
| 334 | ++ | ++ |
| 359 | ++ | ++ |
| 361 | ++ | + |
| 484 | +++ | ++ |
| 488 | ++ | − |
| 503 | ++ | − |
| 509 | +++ | ++ |
| 520 | ++ | − |
| 521 | +++ | +++ |
| 523 | +++ | − |
| 524 | +++ | +++ |
| 525 | +++ | ++ |
| 529 | +++ | +++ |
| 530 | ++ | ++ |
| 531 | +++ | ++ |
| 532 | ++ | − |
| 534 | +++ | − |
| 541 | ++ | − |
| 543 | +++ | ++ |

TABLE 3-continued

IFNγ and IL-2 secretion of the invented compounds in human peripheral blood pan T cells

| Example | IFNγ (EC$_{50}$) | IL-2 (EC$_{50}$) |
|---|---|---|
| 548 | − | − |
| 550 | ++ | ++ |
| 552 | ++ | ++ |
| 556 | +++ | ++ |
| 557 | +++ | ++ |
| 558 | +++ | ++ |
| 561 | ++ | ++ |
| 562 | ++ | − |
| 563 | ++ | ++ |
| 564 | ++ | ++ |
| 565 | ++ | ++ |
| 569 | ++ | + |
| 570 | +++ | ++ |
| 574 | ++ | ++ |
| 577 | +++ | ++ |
| 579 | +++ | + |
| 588 | +++ | +++ |

What is claimed is:
1. A compound of Formula (I):

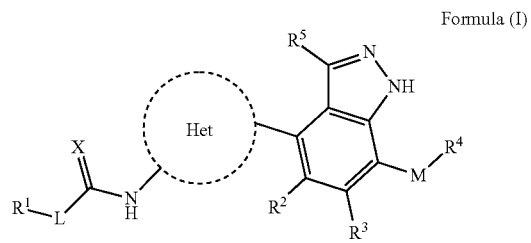

Formula (I)

or a pharmaceutically acceptable salt, hydrate, or solvate, thereof, wherein:
X is O or S;
L is a bond, —O—, —S—, or —NR⁶—;
R¹ is alkyl, cycloalkyl, aryl, heteroaryl, or heterocyclyl, wherein R¹ is optionally substituted with one or more substituents independently selected from R⁷;
R⁶ is —H or C$_{1-6}$ alkyl;
R⁷ is C$_{1-6}$ alkyl, C$_{2-6}$ alkenyl, C$_{2-6}$ alkynyl, cycloalkyl, aryl, heteroaryl, heterocyclyl, halo, oxo, cyano, hydroxy, —C(O)R⁹, —C(O)OR⁹, —C(O)NR¹⁰R¹¹, —OR⁹, —OC(O)R⁹, —OC(O)NR¹⁰R¹¹, —SR⁹, —S(O)R⁹, —S(O)₂R⁹, —S(O)(=NH)R¹⁰, —S(O)₂NR¹⁰R¹¹, —NR¹⁰R¹¹, —N(R⁶)NR¹⁰R¹¹, —N(R⁶)OR⁹, —N(R⁶)C(O)R⁹, —N(R⁶)C(O)OR⁹, —N(R⁶)C(O)NR¹⁰R¹¹, —N(R⁶)S(O)₂R⁹, —N(R⁶)S(O)₂NR¹⁰R¹¹, or —P(O)R¹²R¹³;
R⁹ is —H, C$_{1-6}$ alkyl, C$_{1-6}$ haloalkyl, C$_{2-6}$ alkenyl, C$_{2-6}$ alkynyl, cycloalkyl, aryl, heteroaryl, or heterocyclyl;
Each R¹⁰ and R¹¹ is independently —H, C$_{1-6}$ alkyl, C$_{2-6}$ alkenyl, C$_{2-6}$ alkynyl, cycloalkyl, aryl, heteroaryl, or heterocyclyl, or R¹⁰ and R¹¹ are taken together with the nitrogen atom to which they are attached to form a 4- to 12-membered heterocyclyl optionally substituted with one or more groups selected from the group consisting of halo, hydroxyl, alkyl, alkenyl, alkynyl, haloalkyl, hydroxyalkyl, —CN, —NO₂, —NR¹⁰R¹¹, —NR¹⁰C(=O)R⁹, —NR¹⁰C(=O)NR¹⁰R¹¹, —NR¹⁰C(=O)OR⁹, —OR⁹, —C(=O)R⁹, —C(=O)OR⁹, —C(=O)NR¹⁰R¹¹, —OC(=O)R⁹, —OC(=O)OR⁹, and —OC(=O)NR¹⁰R¹¹;

Each $R^{12}$ and $R^{13}$ is independently $C_{1-6}$ alkyl, $C_{1-6}$ alkoxy, $C_{3-8}$ cycloalkyl, aryl, heteroaryl, heterocyclyl, or $R^{12}$ and $R^{13}$ are taken together with the phosphorus atom to which they are attached to form a 4- to 8-membered heterocyclyl optionally substituted with one or more groups selected from the group consisting of halo, hydroxyl, alkyl, alkenyl, alkynyl, haloalkyl, hydroxyalkyl, —CN, —NO$_2$, —NR$^{10}$R$^{11}$, —NR$^{10}$C(=O)R$^9$, —NR$^{10}$C(=O) NR$^{10}$R$^{11}$, —NR$^{10}$C(=O)OR$^9$, —OR$^9$, —C(=O) R$^9$, —C(=O)OR$^9$, —C(=O)NR$^{10}$R$^{11}$, —OC(=O) R$^9$, —OC(=O)OR$^9$, and —OC(=O)NR$^{10}$R$^{11}$;

Het is selected from the group consisting of:

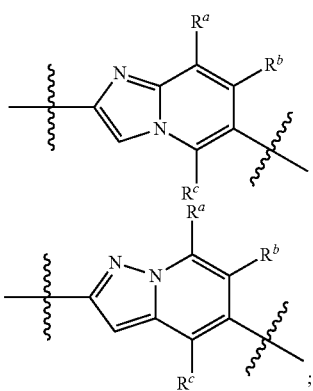

Each of $R^a$, $R^b$ and $R^c$ is independently —H, -D, halo, CF$_3$, CF$_2$H, CH$_2$F, CN, OR$^9$ or NR$^{10}$R$^{11}$;

$R^2$ is —H, -D, —CD$_3$, $C_{1-6}$ alkyl, $C_{2-6}$ alkenyl, $C_{2-6}$ alkynyl, cycloalkyl, aryl, heteroaryl, heterocyclyl, halo, hydroxyl, —CD$_2$OH, —CN, —NO$_2$, haloalkyl, trimethylsilylethoxymethyl, —C(O)R$^9$, —C(O)OR$^9$, —C(O)NR$^{10}$R$^{11}$, —OR$^9$, —OC(O)R$^9$, —OC(O) NR$^{10}$R$^{11}$, —SR$^9$, —S(O)R$^9$, —S(O)$_2$R$^9$, —S(O) (=NH)R$^{10}$, —S(O)$_2$NR$^{10}$R$^{11}$, —NR$^{10}$R$^{11}$, —N(R$^6$) NR$^{10}$R$^{11}$, —N(R$^6$)OR$^9$, —N(R$^6$)C(O)R$^9$, —N(R$^6$)C (O)R$^9$, —N(R$^6$)C(O)OR$^9$, —N(R$^6$)C(O)NR$^{10}$R$^{11}$, —N(R$^6$)S(O)$_2$R$^9$, —N(R$^6$)S(O)$_2$NR$^{10}$R$^{11}$, or —P(O) R$^{12}$R$^{13}$, wherein the $C_{1-6}$ alkyl, $C_{2-6}$ alkenyl, $C_{2-6}$ alkynyl, cycloalkyl, aryl, heteroaryl, or heterocyclyl is optionally substituted with one or more groups selected from the group consisting of halo, hydroxyl, alkyl, alkenyl, alkynyl, haloalkyl, hydroxyalkyl, —CN, —NO$_2$, —NR$^{10}$R$^{11}$, —NR$^{10}$c(=O)R$^9$, —NR$^{10}$C (=O)NR$^{10}$R$^{11}$, —NR$^{10}$C(=O)OR$^9$, —OR$^9$, —C(=O)R$^9$, —C(=O)OR$^9$, —C(=O)NR$^{10}$R$^{11}$, —OC(=O)R$^9$, —OC(=O)OR$^9$, and —OC(=O) NR$^{10}$R$^{11}$;

$R^3$ is —H, -D, —CD$_3$, $C_{1-6}$ alkyl, $C_{2-6}$ alkenyl, $C_{2-6}$ alkynyl, cycloalkyl, aryl, heteroaryl, heterocyclyl, halo, cyano, hydroxy, —CH$_2$OH, —CD$_2$OH, —OH, —CN, —NO$_2$, haloalkyl, —C(O)R$^9$, —C(O)OR$^9$, —C(O)NR$^{10}$R$^{11}$, —OR$^9$, —OC(O)R$^9$, —OC(O) NR$^{10}$R$^{11}$, —SR$^9$, —S(O)R$^9$, —S(O)$_2$R$^9$, —S(O) (=NH)R$^{10}$, —S(O)$_2$NR$^{10}$R$^{11}$, —NR$^{10}$R$^{11}$, —N(R$^6$) NR$^{10}$R$^{11}$, —N(R$^6$)OR$^9$, —N(R$^6$)C(O)R$^9$, —N(R$^6$)C (O)OR$^9$, —N(R$^6$)C(O)NR$^{10}$R$^{11}$, —N(R$^6$)S(O)$_2$R$^9$, —N(R$^6$)S(O)$_2$NR$^{10}$R$^{11}$, or —P(O)R$^{12}$R$^{13}$;

M is a bond, —O—, —S—, or —NR$^6$—;

$R^6$ is —H or $C_{1-6}$ alkyl;

$R^4$ is —H, -D, $C_{1-6}$ alkyl, $C_{2-6}$ alkenyl, $C_{2-6}$ alkynyl, cycloalkyl, aryl, heteroaryl, heterocyclyl, halo, cyano, hydroxy, —C(O)R$^9$, —C(O)OR$^9$, —C(O) NR$^{10}$R$^{11}$, —S(O)$_2$R$^9$, —S(O)(=NH)R$^{10}$, —S(O)$_2$NR$^{10}$R$^{11}$, or —P(O)R$^{12}$R$^{13}$, wherein $C_{1-6}$ alkyl, $C_{2-6}$ alkenyl, $C_{2-6}$ alkynyl, cycloalkyl, aryl, heteroaryl, or heterocyclyl is optionally substituted with one or more groups selected from the group consisting of halo, hydroxyl, alkyl, alkenyl, alkynyl, haloalkyl, hydroxyalkyl, —CN, —CD$_3$, —NO$_2$, —NR$^{10}$R$^{11}$, —NR$^{10}$C(=O)R$^9$, —NR$^{10}$C(=O) NR$^{10}$R$^{11}$, —NR$^{10}$C(=O)OR$^9$, —NR$^{10}$S(O)$_2$R$^9$, —OR$^9$, —C(=O)R$^9$, —C(=O)OR$^9$, —C(=O) NR$^{10}$R$^{11}$, —OC(=O)R$^9$, —OC(=O)OR$^9$, and —OC(=O)NR$^{10}$R$^{11}$; and $R^5$ is —H, -D, —CD$_3$, $C_{1-6}$ alkyl, $C_{2-6}$ alkenyl, $C_{2-6}$ alkynyl, cycloalkyl, halo, hydroxyl, —CH$_2$OH, —CD$_2$OH, —CN or haloalkyl.

2. The compound of claim 1 or a pharmaceutically acceptable salt thereof, wherein L is a bond, and $R^1$ is cycloalkyl which is optionally substituted with one or more groups selected from the group consisting of $C_{1-6}$ alkyl, $C_{2-6}$ alkenyl, $C_{2-6}$ alkynyl, cycloalkyl, halo, cyano, hydroxy, —C(O)R$^9$, —C(O)OR$^9$, —C(O)NR$^{10}$R$^{11}$, —OR$^9$, —OC(O) R$^9$, —OC(O)NR$^{10}$R$^{11}$, —NR$^{10}$R$^{11}$, —N(R$^6$)NR$^{10}$R$^{11}$, —N(R$^6$)OR$^9$, —N(R$^6$)C(O)R$^9$, —N(R$^6$)C(O)OR$^9$, and —N(R$^6$)C(O)NR$^{10}$R$^{11}$.

3. The compound of claim 1 or a pharmaceutically acceptable salt thereof, wherein each of $R^2$ and $R^3$ is independently —H, halo, alkylthio, haloalkyl, or alkyl.

4. The compound of claim 1 or a pharmaceutically acceptable salt thereof, wherein M is a bond, —O—, or —NR$^6$—; and $R^4$ is —H, -D, $C_{1-6}$ alkyl, $C_{2-6}$ alkenyl, $C_{2-6}$ alkynyl, cycloalkyl, aryl, heteroaryl, heterocyclyl, halo, cyano, hydroxy, —C(O)R$^9$, —C(O)NR$^{10}$R$^{11}$, —S(O)$_2$R$^9$, —S(O)(=NH)R$^{10}$, or —S(O)$_2$NR$^{10}$R$^{11}$, wherein the $C_{1-6}$ alkyl, $C_{2-6}$ alkenyl, $C_{2-6}$ alkynyl, cycloalkyl, aryl, heteroaryl, or heterocyclyl is optionally substituted with one or more groups selected from the group consisting of halo, hydroxy, alkyl, alkenyl, alkynyl, haloalkyl, hydroxyalkyl, —CN, —CD$_3$, —NR$^{10}$R$^{11}$, —NR$^{10}$S(O)$_2$R$^9$, and —NR$^{10}$C(=O) R$^9$.

5. The compound of claim 1 or a pharmaceutically acceptable salt thereof, which is a compound of Formula (V):

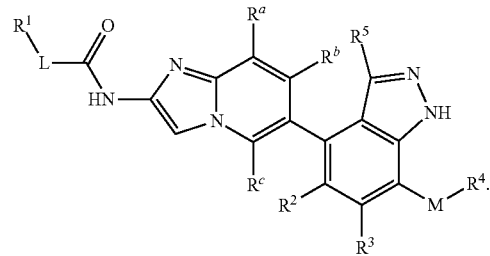

Formula (V)

6. The compound of claim 5 or a pharmaceutically acceptable salt thereof, wherein L is a bond, and $R^1$ is cycloalkyl which is optionally substituted with one or more groups selected from the group consisting of $C_{1-6}$ alkyl, $C_{2-6}$ alkenyl, $C_{2-6}$ alkynyl, cycloalkyl, halo, cyano, hydroxy, —C(O)R$^9$, —C(O)OR$^9$, —C(O)NR$^{10}$R$^{11}$, —OR$^9$, —OC(O) R$^9$, —OC(O)NR$^{10}$R$^{11}$, —NR$^{10}$R$^{11}$, —N(R$^6$)NR$^{10}$R$^{11}$, —N(R$^6$)OR$^9$, —N(R$^6$)C(O)R$^9$, —N(R$^6$)C(O)OR$^9$, and —N(R$^6$)C(O)NR$^{10}$R$^{11}$.

7. The compound of claim 5 or a pharmaceutically acceptable salt thereof, wherein $R^1$ is cycloalkyl which is optionally substituted with one or more groups selected from the group consisting of halo, $C_{1-3}$ alkyl, $C_{1-3}$ hydroxyalkyl and $C_{1-3}$ haloalkyl.

8. The compound of claim 5 or a pharmaceutically acceptable salt thereof, which is selected from the group consisting of:

(1S,2S)-2-fluoro-N-(6-(5-methyl-1H-indazol-4-yl)imidazo[1,2-a]pyridin-2-yl)cyclopropane-1-carboxamide;
(1S,2S)-N-(6-(1H-indazol-4-yl)imidazo[1,2-a]pyridin-2-yl)-2-fluorocyclopropane-1-carboxamide;
N-(6-(5-chloro-1H-indazol-4-yl)imidazo[1,2-a]pyridin-2-yl)cyclopropanecarboxamide;
N-(6-(5-methoxy-1H-indazol-4-yl)imidazo[1,2-a]pyridin-2-yl)cyclopropanecarboxamide;
N-(6-(5-amino-1H-indazol-4-yl)imidazo[1,2-a]pyridin-2-yl)cyclopropanecarboxamide;
N-(6-(5-(trifluoromethyl)-1H-indazol-4-yl)imidazo[1,2-a]pyridin-2-yl)cyclopropanecarboxamide;
N-(6-(5-amino-6-fluoro-1H-indazol-4-yl)imidazo[1,2-a]pyridin-2-yl)cyclopropanecarboxamide;
N-(6-(5-bromo-1H-indazol-4-yl)imidazo[1,2-a]pyridin-2-yl)cyclopropanecarboxamide;
N-(6-(5-(methylamino)-1H-indazol-4-yl)imidazo[1,2-a]pyridin-2-yl)cyclopropanecarboxamide;
N-(6-(5-(dimethylamino)-1H-indazol-4-yl)imidazo[1,2-a]pyridin-2-yl)cyclopropanecarboxamide;
N-(6-(5-bromo-6-fluoro-1H-indazol-4-yl)imidazo[1,2-a]pyridin-2-yl)cyclopropanecarboxamide;
N-(6-(5-cyano-1H-indazol-4-yl)imidazo[1,2-a]pyridin-2-yl)cyclopropanecarboxamide;
N-(6-(5-(hydroxymethyl)-1H-indazol-4-yl)imidazo[1,2-a]pyridin-2-yl)cyclopropanecarboxamide;
N-(6-(5-ethyl-1H-indazol-4-yl)imidazo[1,2-a]pyridin-2-yl)cyclopropanecarboxamide;
N-(6-(6-fluoro-5-vinyl-1H-indazol-4-yl)imidazo[1,2-a]pyridin-2-yl)cyclopropanecarboxamide;
(1S,2S)-2-fluoro-N-(6-(5-(trifluoromethyl)-1H-indazol-4-yl)imidazo[1,2-a]pyridin-2-yl)cyclopropane-1-carboxamide;
(1S,2S)-N-(6-(5-chloro-1H-indazol-4-yl)imidazo[1,2-a]pyridin-2-yl)-2-fluorocyclopropane-1-carboxamide;
(1S,2S)-N-(6-(5-bromo-1H-indazol-4-yl)imidazo[1,2-a]pyridin-2-yl)-2-fluorocyclopropane-1-carboxamide;
N-(6-(5-acetyl-1H-indazol-4-yl)imidazo[1,2-a]pyridin-2-yl)cyclopropanecarboxamide;
N-(6-(5-amino-6-chloro-1H-indazol-4-yl)imidazo[1,2-a]pyridin-2-yl)cyclopropanecarboxamide;
N-(6-(5-cyclopropyl-6-fluoro-1H-indazol-4-yl)imidazo[1,2-a]pyridin-2-yl)cyclopropanecarboxamide;
N-(6-(5-chloro-6-fluoro-1H-indazol-4-yl)imidazo[1,2-a]pyridin-2-yl)cyclopropanecarboxamide;
(1S,2S)-N-(6-(5-chloro-6-fluoro-1H-indazol-4-yl)imidazo[1,2-a]pyridin-2-yl)-2-fluorocyclopropane-1-carboxamide;
N-(6-(5-cyclopropyl-1H-indazol-4-yl)imidazo[1,2-a]pyridin-2-yl)cyclopropanecarboxamide;
N-(6-(6-fluoro-5-methyl-1H-indazol-4-yl)imidazo[1,2-a]pyridin-2-yl)cyclopropanecarboxamide;
N-(6-(6-fluoro-5-isopropyl-1H-indazol-4-yl)imidazo[1,2-a]pyridin-2-yl)cyclopropanecarboxamide;
N-(6-(5-(methylthio)-1H-indazol-4-yl)imidazo[1,2-a]pyridin-2-yl)cyclopropanecarboxamide;
N-(6-(5-ethyl-6-fluoro-1H-indazol-4-yl)imidazo[1,2-a]pyridin-2-yl)cyclopropanecarboxamide;
N-(6-(5-(difluoromethyl)-1H-indazol-4-yl)imidazo[1,2-a]pyridin-2-yl)cyclopropanecarboxamide;
(1S,2S)-2-fluoro-N-(6-(6-fluoro-5-methyl-1H-indazol-4-yl)imidazo[1,2-a]pyridin-2-yl)cyclopropane-1-carboxamide;
N-(6-(6-fluoro-5-(hydroxymethyl)-1H-indazol-4-yl)imidazo[1,2-a]pyridin-2-yl)cyclopropanecarboxamide;
N-(6-(6-fluoro-5-methoxy-1H-indazol-4-yl)imidazo[1,2-a]pyridin-2-yl)cyclopropanecarboxamide;
(1S,2S)-N-(6-(5-(difluoromethyl)-6-fluoro-1H-indazol-4-yl)imidazo[1,2-a]pyridin-2-yl)-2-fluorocyclopropane-1-carboxamide;
(1S,2S)-N-(6-(5-bromo-6-fluoro-1H-indazol-4-yl)imidazo[1,2-a]pyridin-2-yl)-2-fluorocyclopropane-1-carboxamide;
N-(6-(5-(difluoromethyl)-6-fluoro-1H-indazol-4-yl)imidazo[1,2-a]pyridin-2-yl)cyclopropanecarboxamide;
(1S,2S)-N-(6-(5,7-dichloro-6-fluoro-1H-indazol-4-yl)imidazo[1,2-a]pyridin-2-yl)-2-fluorocyclopropane-1-carboxamide;
(1S,2S)-2-fluoro-N-(6-(6-fluoro-5,7-dimethyl-1H-indazol-4-yl)imidazo[1,2-a]pyridin-2-yl)cyclopropane-1-carboxamide;
(1S,2S)-N-(6-(5-chloro-7-(dimethylamino)-6-fluoro-1H-indazol-4-yl)imidazo[1,2-a]pyridin-2-yl)-2-fluorocyclopropane-1-carboxamide;
(1S,2S)-N-(6-(5-chloro-7-(dimethylphosphoryl)-6-fluoro-1H-indazol-4-yl)imidazo[1,2-a]pyridin-2-yl)-2-fluorocyclopropane-1-carboxamide;
(1S,2S)-N-(6-(7-chloro-6-fluoro-5-methyl-1H-indazol-4-yl)imidazo[1,2-a]pyridin-2-yl)-2-fluorocyclopropane-1-carboxamide;
(1S,2S)-N-(6-(7-bromo-5-chloro-6-fluoro-1H-indazol-4-yl)imidazo[1,2-a]pyridin-2-yl)-2-fluorocyclopropane-1-carboxamide;
(1S,2S)-N-(6-(6,7-difluoro-5-methyl-1H-indazol-4-yl)imidazo[1,2-a]pyridin-2-yl)-2-fluorocyclopropane-1-carboxamide;
(1S,2S)-2-fluoro-N-(6-(6-fluoro-5-methyl-7-(trifluoromethyl)-1H-indazol-4-yl)imidazo[1,2-a]pyridin-2-yl)cyclopropane-1-carboxamide;
(1S,2S)-2-fluoro-N-(6-(5-methyl-7-vinyl-1H-indazol-4-yl)imidazo[1,2-a]pyridin-2-yl)cyclopropane-1-carboxamide;
(1S,2S)-N-(6-(5-chloro-6-fluoro-7-(methylamino)-1H-indazol-4-yl)imidazo[1,2-a]pyridin-2-yl)-2-fluorocyclopropane-1-carboxamide;
(1S,2S)-N-(6-(5-chloro-6-fluoro-7-(methylthio)-1H-indazol-4-yl)imidazo[1,2-a]pyridin-2-yl)-2-fluorocyclopropane-1-carboxamide;
(1S,2S)-N-(6-(5-chloro-6-fluoro-7-(methylsulfonyl)-1H-indazol-4-yl)imidazo[1,2-a]pyridin-2-yl)-2-fluorocyclopropane-1-carboxamide;
(1S,2S)-N-(6-(7-bromo-6-fluoro-5-methyl-1H-indazol-4-yl)imidazo[1,2-a]pyridin-2-yl)-2-fluorocyclopropane-1-carboxamide;
(1S,2S)-2-fluoro-N-(6-(6-fluoro-5-methyl-7-(methylthio)-1H-indazol-4-yl)imidazo[1,2-a]pyridin-2-yl)cyclopropane-1-carboxamide;
(1S,2S)-2-fluoro-N-(6-(6-fluoro-5-methyl-7-(methylsulfonyl)-1H-indazol-4-yl)imidazo[1,2-a]pyridin-2-yl)cyclopropane-1-carboxamide;
(1S,2S)-2-fluoro-N-(6-(6-fluoro-7-methoxy-5-methyl-1H-indazol-4-yl)imidazo[1,2-a]pyridin-2-yl)cyclopropane-1-carboxamide;

(1S,2S)-N-(6-(5-chloro-6-fluoro-7-methoxy-1H-indazol-4-yl)imidazo[1,2-a]pyridin-2-yl)-2-fluorocyclopropane-1-carboxamide;
(1S,2S)-N-(6-(7-(dimethylamino)-6-fluoro-5-methyl-1H-indazol-4-yl)imidazo[1,2-a]pyridin-2-yl)-2-fluorocyclopropane-1-carboxamide;
(1S,2S)-N-(6-(7-acrylamido-5-methyl-1H-indazol-4-yl)imidazo[1,2-a]pyridin-2-yl)-2-fluorocyclopropane-1-carboxamide;
(1S,2S)-N-(6-(5-chloro-7-ethoxy-6-fluoro-1H-indazol-4-yl)imidazo[1,2-a]pyridin-2-yl)-2-fluorocyclopropane-1-carboxamide;
(1S,2S)-N-(6-(7-acrylamido-5-chloro-1H-indazol-4-yl)imidazo[1,2-a]pyridin-2-yl)-2-fluorocyclopropane-1-carboxamide;
(1S,2S)-N-(6-(5-chloro-6-fluoro-7-(4-methylpiperazin-1-yl)-1H-indazol-4-yl)imidazo[1,2-a]pyridin-2-yl)-2-fluorocyclopropane-1-carboxamide;
2-(hydroxymethyl)-N-(6-(5-methyl-1H-indazol-4-yl)imidazo[1,2-a]pyridin-2-yl)cyclopropane-1-carboxamide;
(1S,2S)-N-(6-(5-chloro-6-fluoro-7-morpholino-1H-indazol-4-yl)imidazo[1,2-a]pyridin-2-yl)-2-fluorocyclopropane-1-carboxamide;
(1S,2S)-N-(6-(5-chloro-7-(ethylamino)-6-fluoro-1H-indazol-4-yl)imidazo[1,2-a]pyridin-2-yl)-2-fluorocyclopropane-1-carboxamide;
(1S,2S)-N-(6-(5-chloro-7-(diethylamino)-6-fluoro-1H-indazol-4-yl)imidazo[1,2-a]pyridin-2-yl)-2-fluorocyclopropane-1-carboxamide;
(1S,2S)-N-(6-(5-chloro-6-fluoro-7-(pyrrolidin-1-yl)-1H-indazol-4-yl)imidazo[1,2-a]pyridin-2-yl)-2-fluorocyclopropane-1-carboxamide;
(1S,2S)-N-(6-(7-(azetidin-1-yl)-5-chloro-6-fluoro-1H-indazol-4-yl)imidazo[1,2-a]pyridin-2-yl)-2-fluorocyclopropane-1-carboxamide;
(1S,2S)-N-(6-(6-amino-5-chloro-1H-indazol-4-yl)imidazo[1,2-a]pyridin-2-yl)-2-fluorocyclopropane-1-carboxamide;
(1S,2S)-2-fluoro-N-(6-(7-methoxy-5-methyl-1H-indazol-4-yl)imidazo[1,2-a]pyridin-2-yl)cyclopropane-1-carboxamide;
(1S,2S)-N-(6-(6-acrylamido-5-chloro-1H-indazol-4-yl)imidazo[1,2-a]pyridin-2-yl)-2-fluorocyclopropane-1-carboxamide;
(1S,2S)-N-(6-(7-ethoxy-5-methyl-1H-indazol-4-yl)imidazo[1,2-a]pyridin-2-yl)-2-fluorocyclopropane-1-carboxamide;
(1S,2S)-N-(6-(7-ethoxy-6-fluoro-5-methyl-1H-indazol-4-yl)imidazo[1,2-a]pyridin-2-yl)-2-fluorocyclopropane-1-carboxamide;
(1S,2S)-N-(6-(6-acrylamido-5-methyl-1H-indazol-4-yl)imidazo[1,2-a]pyridin-2-yl)-2-fluorocyclopropane-1-carboxamide;
(1S,2S)-N-(6-(5-chloro-6-fluoro-7-((2-hydroxyethyl)thio)-1H-indazol-4-yl)imidazo[1,2-a]pyridin-2-yl)-2-fluorocyclopropane-1-carboxamide;
(1S,2S)-N-(6-(7-(dimethylamino)-5-ethyl-6-fluoro-1H-indazol-4-yl)imidazo[1,2-a]pyridin-2-yl)-2-fluorocyclopropane-1-carboxamide;
(1S,2S)-2-fluoro-N-(6-(6-fluoro-7-(2-hydroxyethyl)thio)-5-methyl-1H-indazol-4-yl)imidazo[1,2-a]pyridin-2-yl)cyclopropane-1-carboxamide;
(1S,2S)-N-(6-(5-ethyl-6-fluoro-7-(methylthio)-1H-indazol-4-yl)imidazo[1,2-a]pyridin-2-yl)-2-fluorocyclopropane-1-carboxamide;
(1S,2S)-N-(6-(5-ethyl-6-fluoro-1H-indazol-4-yl)imidazo[1,2-a]pyridin-2-yl)-2-fluorocyclopropane-1-carboxamide;
(1S,2S)-N-(6-(5-chloro-6-fluoro-7-hydroxy-1H-indazol-4-yl)imidazo[1,2-a]pyridin-2-yl)-2-fluorocyclopropane-1-carboxamide;
(1S,2S)-2-fluoro-N-(6-(6-fluoro-5-(methylthio)-1H-indazol-4-yl)imidazo[1,2-a]pyridin-2-yl)cyclopropane-1-carboxamide;
(1S,2S)-2-fluoro-N-(6-(6-fluoro-5,7-bis(methylthio)-1H-indazol-4-yl)imidazo[1,2-a]pyridin-2-yl)cyclopropane-1-carboxamide;
(1S,2S)-N-(6-(5-ethyl-6,7-difluoro-1H-indazol-4-yl)imidazo[1,2-a]pyridin-2-yl)-2-fluorocyclopropane-1-carboxamide;
(1S,2S)-2-fluoro-N-(6-(6-fluoro-5-methyl-7-(methylsulfinyl)-1H-indazol-4-yl)imidazo[1,2-a]pyridin-2-yl)cyclopropane-1-carboxamide;
(1S,2S)-N-(6-(7-(dimethylamino)-6-fluoro-5-(methylthio)-1H-indazol-4-yl)imidazo[1,2-a]pyridin-2-yl)-2-fluorocyclopropane-1-carboxamide;
(1S,2S)-N-(6-(7-acetamido-5-chloro-6-fluoro-1H-indazol-4-yl)imidazo[1,2-a]pyridin-2-yl)-2-fluorocyclopropane-1-carboxamide;
(1S,2S)-2-fluoro-N-(6-(6-fluoro-5-methyl-7-(methylsulfonyl)-1H-indazol-4-yl)imidazo[1,2-a]pyridin-2-yl)cyclopropane-1-carboxamide;
(1S,2S)-N-(6-(5-chloro-6-fluoro-7-(methylsulfinyl)-1H-indazol-4-yl)imidazo[1,2-a]pyridin-2-yl)-2-fluorocyclopropane-1-carboxamide;
(1S,2S)-N-(6-(6,7-difluoro-5-(methylthio)-1H-indazol-4-yl)imidazo[1,2-a]pyridin-2-yl)-2-fluorocyclopropane-1-carboxamide;
methyl 6-fluoro-4-(2-((1S,2S)-2-fluorocyclopropane-1-carboxamido)imidazo[1,2-a]pyridin-6-yl)-5-methyl-1H-indazole-7-carboxylate;
(1S,2S)-N-(6-(5-chloro-7-(ethyl(methyl)amino)-6-fluoro-1H-indazol-4-yl)imidazo[1,2-a]pyridin-2-yl)-2-fluorocyclopropane-1-carboxamide;
(1S,2S)-N-(6-(7-(dimethylamino)-6-fluoro-5-(trifluoromethyl)-1H-indazol-4-yl)imidazo[1,2-a]pyridin-2-yl)-2-fluorocyclopropane-1-carboxamide;
(1S,2S)-N-(6-(7-acetamido-6-fluoro-5-methyl-1H-indazol-4-yl)imidazo[1,2-a]pyridin-2-yl)-2-fluorocyclopropane-1-carboxamide;
tert-butyl 2-(5-chloro-6-fluoro-4-(2-((1S,2S)-2-fluorocyclopropane-1-carboxamido)imidazo[1,2-a]pyridin-6-yl)-1H-indazol-7-yl)-1-methylhydrazine-1-carboxylate;
(1S,2S)-N-(6-(7-ethoxy-6-fluoro-5-(methylthio)-1H-indazol-4-yl)imidazo[1,2-a]pyridin-2-yl)-2-fluorocyclopropane-1-carboxamide;
(1S,2S)-2-fluoro-N-(6-(6-fluoro-5-methyl-7-(N-methylacetamido)-1H-indazol-4-yl)imidazo[1,2-a]pyridin-2-yl)cyclopropane-1-carboxamide;
2-((6-fluoro-4-(2-((1S,2S)-2-fluorocyclopropane-1-carboxamido)imidazo[1,2-a]pyridin-6-yl)-5-methyl-1H-indazol-7-yl)thio)ethyl methylcarbamate;
6-fluoro-4-(2-((1S,2S)-2-fluorocyclopropane-1-carboxamido)imidazo[1,2-a]pyridin-6-yl)-5-methyl-1H-indazole-7-carboxylic acid;
5-chloro-6-fluoro-4-(2-((1S,2S)-2-fluorocyclopropane-1-carboxamido)imidazo[1,2-a]pyridin-6-yl)-1H-indazole-7-carboxylic acid;
methyl 5-chloro-6-fluoro-4-(2-((1S,2S)-2-fluorocyclopropane-1-carboxamido)imidazo[1,2-a]pyridin-6-yl)-1H-indazole-7-carboxylate;

(1S,2S)-N-(6-(5-chloro-6-fluoro-7-(N-methylacet-amido)-1H-indazol-4-yl)imidazo[1,2-a]pyridin-2-yl)-2-fluorocyclopropane-1-carboxamide;

(1S,2S)-N-(6-(5-chloro-6-fluoro-7-(2-methylhydrazineyl)-1H-indazol-4-yl)imidazo[1,2-a]pyridin-2-yl)-2-fluorocyclopropane-1-carboxamide;

(1S,2S)-N-(6-(7-ethoxy-5-ethyl-6-fluoro-1H-indazol-4-yl)imidazo[1,2-a]pyridin-2-yl)-2-fluorocyclopropane-1-carboxamide;

(1S,2S)-N-(6-(7-acetyl-5-chloro-6-fluoro-1H-indazol-4-yl)imidazo[1,2-a]pyridin-2-yl)-2-fluorocyclopropane-1-carboxamide;

5-chloro-6-fluoro-4-(2-((1S,2S)-2-fluorocyclopropane-1-carboxamido)imidazo[1,2-a]pyridin-6-yl)-N,N-dimethyl-1H-indazole-7-carboxamide;

5-chloro-6-fluoro-4-(2-((1S,2S)-2-fluorocyclopropane-1-carboxamido)imidazo[1,2-a]pyridin-6-yl)-N-methyl-1H-indazole-7-carboxamide;

(1S,2S)-N-(6-(7-acetyl-6-fluoro-5-methyl-1H-indazol-4-yl)imidazo[1,2-a]pyridin-2-yl)-2-fluorocyclopropane-1-carboxamide;

(1S,2S)-N-(6-(5-chloro-6,7-difluoro-1H-indazol-4-yl)imidazo[1,2-a]pyridin-2-yl)-2-fluorocyclopropane-1-carboxamide;

(1S,2S)-N-(6-(7-(ethyl(methyl)amino)-6-fluoro-5-(methylthio)-1H-indazol-4-yl)imidazo[1,2-a]pyridin-2-yl)-2-fluorocyclopropane-1-carboxamide;

5-chloro-6-fluoro-4-(2-((1S,2S)-2-fluorocyclopropane-1-carboxamido)imidazo[1,2-a]pyridin-6-yl)-1H-indazole-7-carboxamide;

(1S,2S)-N-(6-(5-ethyl-7-(ethyl(methyl)amino)-6-fluoro-1H-indazol-4-yl)imidazo[1,2-a]pyridin-2-yl)-2-fluorocyclopropane-1-carboxamide;

N-(6-(5-chloro-7-(dimethylamino)-6-fluoro-1H-indazol-4-yl)imidazo[1,2-a]pyridin-2-yl)cyclopropanecarboxamide;

(1S,2S)-N-(6-(5-ethoxy-6-fluoro-1H-indazol-4-yl)imidazo[1,2-a]pyridin-2-yl)-2-fluorocyclopropane-1-carboxamide;

6-fluoro-4-(2-((1S,2S)-2-fluorocyclopropane-1-carboxamido)imidazo[1,2-a]pyridin-6-yl)-N,N,5-trimethyl-1H-indazole-7-carboxamide;

(1S,2S)-N-(6-(7-(ethyl(methyl)amino)-6-fluoro-5-methyl-1H-indazol-4-yl)imidazo[1,2-a]pyridin-2-yl)-2-fluorocyclopropane-1-carboxamide;

(1S,2S)-N-(6-(5-chloro-7-(difluoromethyl)-6-fluoro-1H-indazol-4-yl)imidazo[1,2-a]pyridin-2-yl)-2-fluorocyclopropane-1-carboxamide;

(1R,2S)-N-(6-(5-chloro-7-(dimethylamino)-6-fluoro-1H-indazol-4-yl)imidazo[1,2-a]pyridin-2-yl)-2-fluorocyclopropane-1-carboxamide;

(1S,2R)-N-(6-(5-chloro-7-(dimethylamino)-6-fluoro-1H-indazol-4-yl)imidazo[1,2-a]pyridin-2-yl)-2-fluorocyclopropane-1-carboxamide;

(1R,2R)-N-(6-(5-chloro-7-(dimethylamino)-6-fluoro-1H-indazol-4-yl)imidazo[1,2-a]pyridin-2-yl)-2-fluorocyclopropane-1-carboxamide;

(1S,2S)-N-(6-(7-(dimethylamino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2-oxopyrrolidin-1-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(methyl(pyridin-2-yl)amino)-1H-indazol-4-yl)imidazo[1,2-a]pyridin-2-yl)-2-fluorocyclopropane-1-carboxamide;

6-fluoro-4-(2-((1S,2S)-2-fluorocyclopropane-1-carboxamido)imidazo[1,2-a]pyridin-6-yl)-N,5-dimethyl-1H-indazole-7-carboxamide;

(1S,2S)-N-(6-(5-ethyl-6-fluoro-7-(trifluoromethyl)-1H-indazol-4-yl)imidazo[1,2-a]pyridin-2-yl)-2-fluorocyclopropane-1-carboxamide;

(1S,2S)-2-fluoro-N-(6-(7-(methylthio)-1H-indazol-4-yl)imidazo[1,2-a]pyridin-2-yl)cyclopropane-1-carboxamide;

5-chloro-N-ethyl-6-fluoro-4-(2-((1S,2S)-2-fluorocyclopropane-1-carboxamido)imidazo[1,2-a]pyridin-6-yl)-N-methyl-1H-indazole-7-carboxamide;

(1S,2S)-2-fluoro-N-(6-(6-fluoro-7-(methylthio)-1H-indazol-4-yl)imidazo[1,2-a]pyridin-2-yl)cyclopropane-1-carboxamide;

(1S,2S)-N-(6-(7-(difluoromethyl)-6-fluoro-5-methyl-1H-indazol-4-yl)imidazo[1,2-a]pyridin-2-yl)-2-fluorocyclopropane-1-carboxamide;

(1S,2S)-2-fluoro-N-(6-(6-fluoro-7-(trifluoromethoxy)-1H-indazol-4-yl)imidazo[1,2-a]pyridin-2-yl)cyclopropane-1-carboxamide;

(1S,2S)-2-fluoro-N-(6-(6-fluoro-5-methyl-7-(trifluoromethoxy)-1H-indazol-4-yl)imidazo[1,2-a]pyridin-2-yl)cyclopropane-1-carboxamide;

(1S,2S)-N-(6-(5-chloro-6-fluoro-7-(methyl(pyrimidin-2-yl)amino)-1H-indazol-4-yl)imidazo[1,2-a]pyridin-2-yl)-2-fluorocyclopropane-1-carboxamide;

5-chloro-6-fluoro-4-(2-((1S,2S)-2-fluorocyclopropane-1-carboxamido)imidazo[1,2-a]pyridin-6-yl)-N-methyl-N-(2,2,2-trifluoroethyl)-1H-indazole-7-carboxamide;

(1S,2S)-N-(6-(5-chloro-6-fluoro-7-(methyl(pyrimidin-4-yl)amino)-1H-indazol-4-yl)imidazo[1,2-a]pyridin-2-yl)-2-fluorocyclopropane-1-carboxamide;

(1S,2S)-N-(6-(5-chloro-6-fluoro-7-(methyl(pyridin-3-ylmethyl)amino)-1H-indazol-4-yl)imidazo[1,2-a]pyridin-2-yl)-2-fluorocyclopropane-1-carboxamide;

(1S,2S)-N-(6-(5-chloro-6-fluoro-7-(1-methyl-1H-tetrazol-5-yl)-1H-indazol-4-yl)imidazo[1,2-a]pyridin-2-yl)-2-fluorocyclopropane-1-carboxamide;

(1S,2S)-N-(6-(5-chloro-7-cyano-6-fluoro-1H-indazol-4-yl)imidazo[1,2-a]pyridin-2-yl)-2-fluorocyclopropane-1-carboxamide;

(1S,2S)-N-(6-(7-(dimethylamino)-1H-indazol-4-yl)imidazo[1,2-a]pyridin-2-yl)-2-fluorocyclopropane-1-carboxamide;

(1S,2S)-N-(6-(5-chloro-6-fluoro-7-(methyl(pyridin-4-ylmethyl)amino)-1H-indazol-4-yl)imidazo[1,2-a]pyridin-2-yl)-2-fluorocyclopropane-1-carboxamide;

6-fluoro-4-(2-((1S,2S)-2-fluorocyclopropane-1-carboxamido)imidazo[1,2-a]pyridin-6-yl)-N,N-dimethyl-1H-indazole-7-carboxamide;

6-fluoro-4-(2-((1S,2S)-2-fluorocyclopropane-1-carboxamido)imidazo[1,2-a]pyridin-6-yl)-N,N-dimethyl-1H-indazole-5-carboxamide;

(1S,2S)-N-(6-(5-chloro-6-fluoro-7-(trifluoromethoxy)-1H-indazol-4-yl)imidazo[1,2-a]pyridin-2-yl)-2-fluorocyclopropane-1-carboxamide;

(1S,2S)-N-(6-(5-ethoxy-6,7-difluoro-1H-indazol-4-yl)imidazo[1,2-a]pyridin-2-yl)-2-fluorocyclopropane-1-carboxamide;

(1S,2S)-N-(6-(5-chloro-6-fluoro-7-(3-methyl-2-oxoimidazolidin-1-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(isopropylamino)-1H-indazol-4-yl)imidazo[1,2-a]pyridin-2-yl)-2-fluorocyclopropane-1-carboxamide;

(1S,2S)-N-(6-(5-chloro-6-fluoro-7-(isopropyl(methyl)amino)-1H-indazol-4-yl)imidazo[1,2-a]pyridin-2-yl)-2-fluorocyclopropane-1-carboxamide;

(1S,2S)-N-(6-(5-chloro-7-(cyclopropyl(methyl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(hydroxymethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(fluoromethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(3-methyl-1,2,4-oxadiazol-5-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(1H-pyrrol-1-yl)-1H-indazol-4-yl)imidazo[1,2-a]pyridin-2-yl)-2-fluorocyclopropane-1-carboxamide;

(1S,2S)-N-(6-(5-chloro-7-((cyanomethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-7-(cyclopropylamino)-6-fluoro-1H-indazol-4-yl)imidazo[1,2-a]pyridin-2-yl)-2-fluorocyclopropane-1-carboxamide;

(1S,2S)-N-(6-(5-chloro-7-(N-cyclopropyl-2,2,2-trifluoroacetamido)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(3-hydroxypropanamido)-1H-indazol-4-yl)imidazo[1,2-a]pyridin-2-yl)-2-fluorocyclopropane-1-carboxamide;

(1S,2S)-N-(6-(7-(sec-butylamino)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-7-((1-cyanoethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-hydroxyethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-methoxyethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-fluoroethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1H-pyrrol-3-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-methyl-1H-pyrrol-3-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-methyl-1H-pyrrol-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-methyl-1H-pyrazol-5-yl)-1H-indazol-4-yl)imidazo[1,2-a]pyridin-2-yl)-2-fluorocyclopropane-1-carboxamide;

(1S,2S)-N-(6-(7-((2H-tetrazol-2-yl)methyl)-5-chloro-6-fluoro-1H-indazol-4-yl)imidazo[1,2-a]pyridin-2-yl)-2-fluorocyclopropane-1-carboxamide;

(1S,2S)-N-(6-(7-(azetidin-1-ylmethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(pyrrolidin-1-ylmethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(piperidin-1-ylmethyl)-1H-indazol-4-yl)imidazo[1,2-a]pyridin-2-yl)-2-fluorocyclopropane-1-carboxamide;

(1S,2S)-N-(6-(7-((2H-1,2,3-triazol-2-yl)methyl)-5-chloro-6-fluoro-1H-indazol-4-yl)imidazo[1,2-a]pyridin-2-yl)-2-fluorocyclopropane-1-carboxamide;

(1S,2S)-N-(6-(7-((1H-1,2,3-triazol-1-yl)methyl)-5-chloro-6-fluoro-1H-indazol-4-yl)imidazo[1,2-a]pyridin-2-yl)-2-fluorocyclopropane-1-carboxamide;

(1S,2S)-N-(6-(7-((1H-1,2,4-triazol-1-yl)methyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-((1-methyl-1H-imidazol-2-yl)thio)-1H-indazol-4-yl)imidazo[1,2-a]pyridin-2-yl)-2-fluorocyclopropane-1-carboxamide;

1-(6-(5-chloro-7-(dimethylamino)-6-fluoro-1H-indazol-4-yl)imidazo[1,2-a]pyridin-2-yl)-3-cyclopropylurea;

(1S,2S)-N-(6-(5-chloro-6-fluoro-7-(2-methyl-1H-pyrrol-1-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(2-hydroxypropan-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(methoxymethyl)-1H-indazol-4-yl)imidazo[1,2-a]pyridin-2-yl)-2-fluorocyclopropane-1-carboxamide;

(1S,2S)-N-(6-(5-chloro-7-(ethoxymethyl)-6-fluoro-1H-indazol-4-yl)imidazo[1,2-a]pyridin-2-yl)-2-fluorocyclopropane-1-carboxamide;

(1S,2S)-N-(6-(7-((1H-tetrazol-1-yl)methyl)-5-chloro-6-fluoro-1H-indazol-4-yl)imidazo[1,2-a]pyridin-2-yl)-2-fluorocyclopropane-1-carboxamide;

(1S,2S)-N-(6-(7-(1-(2H-tetrazol-2-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-7-((1-(dimethylamino)-1-oxopropan-2-yl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2-methoxypropan-2-yl)-1H-indazol-4-yl)imidazo[1,2-a]pyridin-2-yl)-2-fluorocyclopropane-1-carboxamide;

(1S,2S)-N-(6-(5-chloro-7-(1-(dimethylamino)ethyl)-6-fluoro-1H-indazol-4-yl)imidazo[1,2-a]pyridin-2-yl)-2-fluorocyclopropane-1-carboxamide;

(1S,2S)-N-(6-(5-chloro-7-((2-(dimethylamino)-2-oxoethyl)amino)-6-fluoro-1H-indazol-4-yl)imidazo[1,2-a]pyridin-2-yl)-2-fluorocyclopropane-1-carboxamide;

(1S,2S)-N-(6-(7-(1-(1H-tetrazol-1-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(7-(1-aminoethyl)-5-chloro-6-fluoro-1H-indazol-4-yl)imidazo[1,2-a]pyridin-2-yl)-2-fluorocyclopropane-1-carboxamide;

1-(5-chloro-6-fluoro-4-(2-((1S,2S)-2-fluorocyclopropane-1-carboxamido)imidazo[1,2-a]pyridin-6-yl)-1H-indazol-7-yl)-N,N-dimethyl-1H-pyrrole-3-carboxamide;

(1S,2S)-N-(6-(5-chloro-7-cyclopropoxy-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-(methylamino)ethyl)-1H-indazol-4-yl)imidazo[1,2-a]pyridin-2-yl)-2-fluorocyclopropane-1-carboxamide;

(1S,2S)-N-(8-amino-6-(5-chloro-6-fluoro-7-(isopropylamino)-1H-indazol-4-yl)imidazo[1,2-a]pyridin-2-yl)-2-fluorocyclopropane-1-carboxamide;

(1S,2S)-N-(6-(5-chloro-6-fluoro-7-isopropoxy-1H-indazol-4-yl)imidazo[1,2-a]pyridin-2-yl)-2-fluorocyclopropane-1-carboxamide;

(1S,2S)-N-(6-(5-chloro-6-fluoro-7-isopropyl-1H-indazol-4-yl)imidazo[1,2-a]pyridin-2-yl)-2-fluorocyclopropane-1-carboxamide;

(1S,2S)-N-(6-(5-chloro-7-cyclopentyl-6-fluoro-1H-indazol-4-yl)imidazo[1,2-a]pyridin-2-yl)-2-fluorocyclopropane-1-carboxamide;

(1S,2S)-N-(6-(7-((R)-1-(2H-tetrazol-2-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(7-((S)-1-(2H-tetrazol-2-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2,2,2-trifluoro-1-hydroxyethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(2-hydroxycyclopentyl)-1H-indazol-4-yl)imidazo[1,2-a]pyridin-2-yl)-2-fluorocyclopropane-1-carboxamide;

(1S,2S)-N-(6-(5-chloro-7-ethanethioamido-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-(N-methylacetamido)ethyl)-1H-indazol-4-yl)imidazo[1,2-a]pyridin-2-yl)-2-fluorocyclopropane-1-carboxamide;

(1S,2S)-N-(6-(7-((R)-1-(1H-tetrazol-1-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(7-((S)-1-(1H-tetrazol-1-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2,2,2-trifluoro-1-methoxyethyl)-1H-indazol-4-yl)imidazo[1,2-a]pyridin-2-yl)-2-fluorocyclopropane-1-carboxamide;

(1S,2S)-N-(6-(5-chloro-6-fluoro-7-((tetrahydrofuran-3-yl)amino)-1H-indazol-4-yl)imidazo[1,2-a]pyridin-2-yl)-2-fluorocyclopropane-1-carboxamide;

(1S,2S)-N-(6-(7-(1-acetamidoethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-7-(1-ethoxy-2,2,2-trifluoroethyl)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1,2,2,2-tetrafluoroethyl)-1H-indazol-4-yl)imidazo[1,2-a]pyridin-2-yl)-2-fluorocyclopropane-1-carboxamide;

(1S,2S)-N-(6-(5-chloro-7-((1-cyclopropylethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-7-((cyclopropylmethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-((R)-1-methoxypropan-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-((S)-1-methoxypropan-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-propionamidoethyl)-1H-indazol-4-yl)imidazo[1,2-a]pyridin-2-yl)-2-fluorocyclopropane-1-carboxamide;

(1S,2S)-N-(6-(5-chloro-7-((1,1-difluoropropan-2-yl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-formamidoethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-(oxetan-3-ylamino)ethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-(2,2,2-trifluoroacetamido)ethyl)-1H-indazol-4-yl)imidazo[1,2-a]pyridin-2-yl)-2-fluorocyclopropane-1-carboxamide (1S,2S)-N-(6-(5-chloro-7-(1-((1-cyanocyclopropyl)amino)ethyl)-6-fluoro-1H-indazol-4-yl)imidazo[1,2-a]pyridin-2-yl)-2-fluorocyclopropane-1-carboxamide;

N-(1-(5-chloro-6-fluoro-4-(2-((1S,2S)-2-fluorocyclopropane-1-carboxamido)imidazo[1,2-a]pyridin-6-yl)-1H-indazol-7-yl)ethyl)cyclobutanecarboxamide;

(1S,2S)-N-(6-(5-chloro-6-fluoro-7-(1H-imidazol-5-yl)-1H-indazol-4-yl)imidazo[1,2-a]pyridin-2-yl)-2-fluorocyclopropane-1-carboxamide;

(1S,2S)-N-(6-(5-chloro-7-((4,5-dihydro-1H-imidazol-2-yl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-(methylamino)-1-oxopropan-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-((methylthio)methyl)-1H-indazol-4-yl)imidazo[1,2-a]pyridin-2-yl)-2-fluorocyclopropane-1-carboxamide;

(1S,2S)-N-(6-(5-chloro-7-(1,3-dimethylureido)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-(methylthio)ethyl)-1H-indazol-4-yl)imidazo[1,2-a]pyridin-2-yl)-2-fluorocyclopropane-1-carboxamide;

(1S,2S)-N-(6-(5-chloro-6-fluoro-7-((methylsulfinyl)methyl)-1H-indazol-4-yl)imidazo[1,2-a]pyridin-2-yl)-2-fluorocyclopropane-1-carboxamide;

(1S,2S)-N-(6-(5-chloro-6-fluoro-7-((methylsulfonyl)methyl)-1H-indazol-4-yl)imidazo[1,2-a]pyridin-2-yl)-2-fluorocyclopropane-1-carboxamide;

(1S,2S)-N-(6-(5-chloro-7-(cyano(formamido)methyl)-6-fluoro-1H-indazol-4-yl)imidazo[1,2-a]pyridin-2-yl)-2-fluorocyclopropane-1-carboxamide;

(1S,2S)-N-(6-(5-chloro-7-((1S,2R)-1,2-dimethoxypropyl)-6-fluoro-1H-indazol-4-yl)imidazo[1,2-a]pyridin-2-yl)-2-fluorocyclopropane-1-carboxamide;

(1S,2S)-N-(6-(5-chloro-7-(1-(2,2-difluoroacetamido)ethyl)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2-methyl-1H-imidazol-5-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-(methylsulfinyl)ethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-(methylsulfonyl)ethyl)-1H-indazol-4-yl)imidazo[1,2-a]pyridin-2-yl)-2-fluorocyclopropane-1-carboxamide; and (1S,2S)-N-(6-(5-chloro-7-(1-(ethylamino)-1-oxopropan-2-yl)-6-fluoro-1H-indazol-4-yl)imidazo[1,2-a]pyridin-2-yl)-2-fluorocyclopropane-1-carboxamide.

9. The compound of claim 5 or a pharmaceutically acceptable salt thereof, wherein $R^1$ is cyclopropyl which is optionally substituted with one or more groups selected from the group consisting of halo, $C_1$-$C_3$ alkyl, $C_1$-$C_3$ hydroxyalkyl and $C_1$-$C_3$ haloalkyl; $R^2$ is —H, alkyl, alkylthio, haloalkyl, or halo; $R^3$ is —H, alkyl, or halo; M is a bond, —O—, or —NR$^6$—; R$^4$ is —H, halo, alkyl, monoalkylamino, or dialkylamino; R$^5$ is —H, alkyl, or halo.

10. The compound of claim 5 or a pharmaceutically acceptable salt thereof, which is selected from the group consisting of:
    (1S,2S)-N-(6-(5-chloro-7-(dimethylamino)-6-fluoro-1H-indazol-4-yl)imidazo[1,2-a]pyridin-2-yl)-2-fluorocyclopropane-1-carboxamide;
    (1S,2S)-N-(6-(7-(dimethylamino)-6-fluoro-5-methyl-1H-indazol-4-yl)imidazo[1,2-a]pyridin-2-yl)-2-fluorocyclopropane-1-carboxamide;
    (1S,2S)-N-(6-(7-(dimethylamino)-6-fluoro-5-(methylthio)-1H-indazol-4-yl)imidazo[1,2-a]pyridin-2-yl)-2-fluorocyclopropane-1-carboxamide;
    (1S,2S)-N-(6-(7-(dimethylamino)-6-fluoro-5-(trifluoromethyl)-1H-indazol-4-yl)imidazo[1,2-a]pyridin-2-yl)-2-fluorocyclopropane-1-carboxamide;
    (1S,2S)-N-(6-(5-chloro-6-fluoro-7-(isopropylamino)-1H-indazol-4-yl)imidazo[1,2-a]pyridin-2-yl)-2-fluorocyclopropane-1-carboxamide; and
    (1S,2S)-N-(6-(5-chloro-6-fluoro-7-isopropyl-1H-indazol-4-yl)imidazo[1,2-a]pyridin-2-yl)-2-fluorocyclopropane-1-carboxamide.

11. The compound of claim 5 or a pharmaceutically acceptable salt thereof, wherein R$^1$ is cyclopropyl which is optionally substituted with one or more groups selected from the group consisting of halo, C$_{1-3}$ alkyl, C$_{1-3}$ hydroxyalkyl and C$_{1-3}$ haloalkyl; R$^2$ is —H, alkyl, halo, haloalkyl, or alkylthio; R$^3$ is —H, alkyl, or halo; M is a bond, —O—, —S— or —NR$^6$—; R$^4$ is —H, halo, alkyl, hydroxyalkyl, haloalkyl, haloalkenyl, cycloalkyl, monoalkylamino, or dialkylamino; and R$^5$ is —H, alkyl, or halo.

12. The compound of claim 5 or a pharmaceutically acceptable salt thereof, which is selected from the group consisting of:
    (1S,2S)-N-(6-(5-chloro-7-(dimethylamino)-6-fluoro-1H-indazol-4-yl)imidazo[1,2-a]pyridin-2-yl)-2-fluorocyclopropane-1-carboxamide;
    (1S,2S)-N-(6-(7-bromo-5-chloro-6-fluoro-1H-indazol-4-yl)imidazo[1,2-a]pyridin-2-yl)-2-fluorocyclopropane-1-carboxamide;
    (1S,2S)-N-(6-(5-chloro-6-fluoro-7-(methylamino)-1H-indazol-4-yl)imidazo[1,2-a]pyridin-2-yl)-2-fluorocyclopropane-1-carboxamide;
    (1S,2S)-N-(6-(5-chloro-6-fluoro-7-(methylthio)-1H-indazol-4-yl)imidazo[1,2-a]pyridin-2-yl)-2-fluorocyclopropane-1-carboxamide;
    (1S,2S)-2-fluoro-N-(6-(6-fluoro-5-methyl-7-(methylthio)-1H-indazol-4-yl)imidazo[1,2-a]pyridin-2-yl)cyclopropane-1-carboxamide;
    (1S,2S)-N-(6-(5-chloro-6-fluoro-7-methoxy-1H-indazol-4-yl)imidazo[1,2-a]pyridin-2-yl)-2-fluorocyclopropane-1-carboxamide;
    (1S,2S)-N-(6-(5-chloro-7-ethoxy-6-fluoro-1H-indazol-4-yl)imidazo[1,2-a]pyridin-2-yl)-2-fluorocyclopropane-1-carboxamide;
    (1S,2S)-N-(6-(5-chloro-7-(ethylamino)-6-fluoro-1H-indazol-4-yl)imidazo[1,2-a]pyridin-2-yl)-2-fluorocyclopropane-1-carboxamide;
    (1S,2S)-N-(6-(7-ethoxy-6-fluoro-5-methyl-1H-indazol-4-yl)imidazo[1,2-a]pyridin-2-yl)-2-fluorocyclopropane-1-carboxamide;
    (1S,2S)-N-(6-(7-(dimethylamino)-5-ethyl-6-fluoro-1H-indazol-4-yl)imidazo[1,2-a]pyridin-2-yl)-2-fluorocyclopropane-1-carboxamide;
    (1S,2S)-N-(6-(5-ethyl-6-fluoro-7-(methylthio)-1H-indazol-4-yl)imidazo[1,2-a]pyridin-2-yl)-2-fluorocyclopropane-1-carboxamide;
    (1S,2S)-2-fluoro-N-(6-(6-fluoro-5-(methylthio)-1H-indazol-4-yl)imidazo[1,2-a]pyridin-2-yl)cyclopropane-1-carboxamide;
    (1S,2S)-2-fluoro-N-(6-(6-fluoro-5,7-bis(methylthio)-1H-indazol-4-yl)imidazo[1,2-a]pyridin-2-yl)cyclopropane-1-carboxamide;
    (1S,2S)-N-(6-(7-(dimethylamino)-6-fluoro-5-(methylthio)-1H-indazol-4-yl)imidazo[1,2-a]pyridin-2-yl)-2-fluorocyclopropane-1-carboxamide;
    (1S,2S)-N-(6-(6,7-difluoro-5-(methylthio)-1H-indazol-4-yl)imidazo[1,2-a]pyridin-2-yl)-2-fluorocyclopropane-1-carboxamide;
    (1S,2S)-N-(6-(5-chloro-7-(ethyl(methyl)amino)-6-fluoro-1H-indazol-4-yl)imidazo[1,2-a]pyridin-2-yl)-2-fluorocyclopropane-1-carboxamide;
    (1S,2S)-N-(6-(7-ethoxy-6-fluoro-5-(methylthio)-1H-indazol-4-yl)imidazo[1,2-a]pyridin-2-yl)-2-fluorocyclopropane-1-carboxamide;
    (1S,2S)-N-(6-(7-ethoxy-5-ethyl-6-fluoro-1H-indazol-4-yl)imidazo[1,2-a]pyridin-2-yl)-2-fluorocyclopropane-1-carboxamide;
    5-chloro-6-fluoro-4-(2-((1S,2S)-2-fluorocyclopropane-1-carboxamido)imidazo[1,2-a]pyridin-6-yl)-N,N-dimethyl-1H-indazole-7-carboxamide;
    (1S,2S)-N-(6-(7-(ethyl(methyl)amino)-6-fluoro-5-(methylthio)-1H-indazol-4-yl)imidazo[1,2-a]pyridin-2-yl)-2-fluorocyclopropane-1-carboxamide;
    N-(6-(5-chloro-7-(dimethylamino)-6-fluoro-1H-indazol-4-yl)imidazo[1,2-a]pyridin-2-yl)cyclopropanecarboxamide;
    6-fluoro-4-(2-((1S,2S)-2-fluorocyclopropane-1-carboxamido)imidazo[1,2-a]pyridin-6-yl)-N,N,5-trimethyl-1H-indazole-7-carboxamide;
    (1S,2S)-N-(6-(7-(ethyl(methyl)amino)-6-fluoro-5-methyl-1H-indazol-4-yl)imidazo[1,2-a]pyridin-2-yl)-2-fluorocyclopropane-1-carboxamide;
    (1R,2S)-N-(6-(5-chloro-7-(dimethylamino)-6-fluoro-1H-indazol-4-yl)imidazo[1,2-a]pyridin-2-yl)-2-fluorocyclopropane-1-carboxamide;
    (1R,2R)-N-(6-(5-chloro-7-(dimethylamino)-6-fluoro-1H-indazol-4-yl)imidazo[1,2-a]pyridin-2-yl)-2-fluorocyclopropane-1-carboxamide;
    (1S,2S)-N-(6-(5-chloro-6-fluoro-7-(2-oxopyrrolidin-1-yl)-1H-indazol-4-yl)imidazo[1,2-a]pyridin-2-yl)-2-fluorocyclopropane-1-carboxamide;
    5-chloro-N-ethyl-6-fluoro-4-(2-((1S,2S)-2-fluorocyclopropane-1-carboxamido)imidazo[1,2-a]pyridin-6-yl)-N-methyl-1H-indazole-7-carboxamide;
    (1S,2S)-2-fluoro-N-(6-(6-fluoro-5-methyl-7-(trifluoromethoxy)-1H-indazol-4-yl)imidazo[1,2-a]pyridin-2-yl)cyclopropane-1-carboxamide;
    (1S,2S)-N-(6-(5-chloro-6-fluoro-7-(methyl(pyridin-3-ylmethyl)amino)-1H-indazol-4-yl)imidazo[1,2-a]pyridin-2-yl)-2-fluorocyclopropane-1-carboxamide;
    (1S,2S)-N-(6-(5-chloro-6-fluoro-7-(methyl(pyridin-4-ylmethyl)amino)-1H-indazol-4-yl)imidazo[1,2-a]pyridin-2-yl)-2-fluorocyclopropane-1-carboxamide;
    (1S,2S)-N-(6-(5-chloro-6-fluoro-7-(trifluoromethoxy)-1H-indazol-4-yl)imidazo[1,2-a]pyridin-2-yl)-2-fluorocyclopropane-1-carboxamide;
    (1S,2S)-N-(6-(5-chloro-6-fluoro-7-(3-methyl-2-oxoimidazolidin-1-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(isopropylamino)-1H-indazol-4-yl)imidazo[1,2-a]pyridin-2-yl)-2-fluorocyclopropane-1-carboxamide;

(1S,2S)-N-(6-(5-chloro-7-(cyclopropyl(methyl)amino)-6-fluoro-1H-indazol-4-yl)imidazo[1,2-a]pyridin-2-yl)-2-fluorocyclopropane-1-carboxamide;

(1S,2S)-N-(6-(5-chloro-7-((cyanomethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-7-((1-cyanoethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-hydroxyethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-fluoroethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(methoxymethyl)-1H-indazol-4-yl)imidazo[1,2-a]pyridin-2-yl)-2-fluorocyclopropane-1-carboxamide;

(1S,2S)-N-(6-(5-chloro-7-(ethoxymethyl)-6-fluoro-1H-indazol-4-yl)imidazo[1,2-a]pyridin-2-yl)-2-fluorocyclopropane-1-carboxamide;

(1S,2S)-N-(6-(7-(1-(2H-tetrazol-2-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-isopropoxy-1H-indazol-4-yl)imidazo[1,2-a]pyridin-2-yl)-2-fluorocyclopropane-1-carboxamide;

(1S,2S)-N-(6-(5-chloro-6-fluoro-7-isopropyl-1H-indazol-4-yl)imidazo[1,2-a]pyridin-2-yl)-2-fluorocyclopropane-1-carboxamide;

(1S,2S)-N-(6-(7-((S)-1-(2H-tetrazol-2-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2-hydroxycyclopentyl)-1H-indazol-4-yl)imidazo[1,2-a]pyridin-2-yl)-2-fluorocyclopropane-1-carboxamide;

(1S,2S)-N-(6-(7-((S)-1-(1H-tetrazol-1-yl)ethyl)-5-chloro-6-fluoro-1H-indazol-4-yl)imidazo[1,2-a]pyridin-2-yl)-2-fluorocyclopropane-1-carboxamide;

(1S,2S)-N-(6-(7-(1-acetamidoethyl)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1,2,2,2-tetrafluoroethyl)-1H-indazol-4-yl)imidazo[1,2-a]pyridin-2-yl)-2-fluorocyclopropane-1-carboxamide;

(1S,2S)-N-(6-(5-chloro-6-fluoro-7-((R)-1-methoxypropan-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-((S)-1-methoxypropan-2-yl)-1H-indazol-4-yl)imidazo[1,2-a]pyridin-2-yl)-2-fluorocyclopropane-1-carboxamide;

(1S,2S)-N-(6-(5-chloro-7-((1,1-difluoropropan-2-yl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-formamidoethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-(2,2,2-trifluoroacetamido)ethyl)-1H-indazol-4-yl)imidazo[1,2-a]pyridin-2-yl)-2-fluorocyclopropane-1-carboxamide;

N-(1-(5-chloro-6-fluoro-4-(2-((1S,2S)-2-fluorocyclopropane-1-carboxamido)imidazo[1,2-a]pyridin-6-yl)-1H-indazol-7-yl)ethyl)cyclobutanecarboxamide;

(1S,2S)-N-(6-(5-chloro-6-fluoro-7-(1-(methylamino)-1-oxopropan-2-yl)-1H-indazol-4-yl)imidazo[1,2-a]pyridin-2-yl)-2-fluorocyclopropane-1-carboxamide;

(1S,2S)-N-(6-(5-chloro-6-fluoro-7-((methylthio)methyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-(methylthio)ethyl)-1H-indazol-4-yl)imidazo[1,2-a]pyridin-2-yl)-2-fluorocyclopropane-1-carboxamide;

(1S,2S)-N-(6-(5-chloro-7-(cyano(formamido)methyl)-6-fluoro-1H-indazol-4-yl)imidazo[1,2-a]pyridin-2-yl)-2-fluorocyclopropane-1-carboxamide;

(1S,2S)-N-(6-(5-chloro-7-(1-(2,2-difluoroacetamido)ethyl)-6-fluoro-1H-indazol-4-yl)imidazo[1,2-a]pyridin-2-yl)-2-fluorocyclopropane-1-carboxamide; and (1S,2S)-N-(6-(5-chloro-7-(1-(ethylamino)-1-oxopropan-2-yl)-6-fluoro-1H-indazol-4-yl)imidazo[1,2-a]pyridin-2-yl)-2-fluorocyclopropane-1-carboxamide.

13. The compound of claim 5 or a pharmaceutically acceptable salt thereof, wherein $R^1$ is cyclopropyl which is optionally substituted with one or more groups selected from the group consisting of halo, $C_{1-3}$ alkyl, $C_{1-3}$ hydroxyalkyl and $C_{1-3}$ haloalkyl; $R^2$ is —H, alkyl, halo, haloalkyl, or alkylthio; $R^3$ is —H, alkyl, or halo; M is a bond, —O—, —S— or —NR$^6$—; $R^4$ is —H, halo, alkyl, alkylcarbonyl, dialkylaminocarbonyl, oxopyrrolidinyl, hydroxyalkyl, haloalkyl, haloalkenyl, cycloalkyl, pyridinyl, monoalkylamino, or dialkylamino; and $R^5$ is —H, alkyl, or halo.

14. The compound of claim 5 or a pharmaceutically acceptable salt thereof, which is selected from the group consisting of:

(1S,2S)-N-(6-(5-chloro-7-(dimethylamino)-6-fluoro-1H-indazol-4-yl)imidazo[1,2-a]pyridin-2-yl)-2-fluorocyclopropane-1-carboxamide;

(1S,2S)-N-(6-(7-bromo-5-chloro-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(methylamino)-1H-indazol-4-yl)imidazo[1,2-a]pyridin-2-yl)-2-fluorocyclopropane-1-carboxamide;

(1S,2S)-N-(6-(5-chloro-6-fluoro-7-(methylthio)-1H-indazol-4-yl)imidazo[1,2-a]pyridin-2-yl)-2-fluorocyclopropane-1-carboxamide;

(1S,2S)-N-(6-(7-bromo-6-fluoro-5-methyl-1H-indazol-4-yl)imidazo[1,2-a]pyridin-2-yl)-2-fluorocyclopropane-1-carboxamide;

(1S,2S)-2-fluoro-N-(6-(6-fluoro-5-methyl-7-(methylthio)-1H-indazol-4-yl)imidazo[1,2-a]pyridin-2-yl)cyclopropane-1-carboxamide;

(1S,2S)-2-fluoro-N-(6-(6-fluoro-7-methoxy-5-methyl-1H-indazol-4-yl)imidazo[1,2-a]pyridin-2-yl)cyclopropane-1-carboxamide;

(1S,2S)-N-(6-(5-chloro-6-fluoro-7-methoxy-1H-indazol-4-yl)imidazo[1,2-a]pyridin-2-yl)-2-fluorocyclopropane-1-carboxamide;

(1S,2S)-N-(6-(7-(dimethylamino)-6-fluoro-5-methyl-1H-indazol-4-yl)imidazo[1,2-a]pyridin-2-yl)-2-fluorocyclopropane-1-carboxamide;

(1S,2S)-N-(6-(5-chloro-7-ethoxy-6-fluoro-1H-indazol-4-yl)imidazo[1,2-a]pyridin-2-yl)-2-fluorocyclopropane-1-carboxamide;

(1S,2S)-N-(6-(5-chloro-7-(ethylamino)-6-fluoro-1H-indazol-4-yl)imidazo[1,2-a]pyridin-2-yl)-2-fluorocyclopropane-1-carboxamide;

(1S,2S)-N-(6-(5-chloro-7-(diethylamino)-6-fluoro-1H-indazol-4-yl)imidazo[1,2-a]pyridin-2-yl)-2-fluorocyclopropane-1-carboxamide;

(1S,2S)-N-(6-(7-ethoxy-6-fluoro-5-methyl-1H-indazol-4-yl)imidazo[1,2-a]pyridin-2-yl)-2-fluorocyclopropane-1-carboxamide;

(1S,2S)-N-(6-(5-chloro-6-fluoro-7-((2-hydroxyethyl)thio)-1H-indazol-4-yl)imidazo[1,2-a]pyridin-2-yl)-2-fluorocyclopropane-1-carboxamide;

(1S,2S)-N-(6-(7-(dimethylamino)-5-ethyl-6-fluoro-1H-indazol-4-yl)imidazo[1,2-a]pyridin-2-yl)-2-fluorocyclopropane-1-carboxamide;

(1S,2S)-N-(6-(5-ethyl-6-fluoro-7-(methylthio)-1H-indazol-4-yl)imidazo[1,2-a]pyridin-2-yl)-2-fluorocyclopropane-1-carboxamide;

(1S,2S)-2-fluoro-N-(6-(6-fluoro-5-(methylthio)-1H-indazol-4-yl)imidazo[1,2-a]pyridin-2-yl)cyclopropane-1-carboxamide;

(1S,2S)-2-fluoro-N-(6-(6-fluoro-5,7-bis(methylthio)-1H-indazol-4-yl)imidazo[1,2-a]pyridin-2-yl)cyclopropane-1-carboxamide;

(1S,2S)-N-(6-(5-ethyl-6,7-difluoro-1H-indazol-4-yl)imidazo[1,2-a]pyridin-2-yl)-2-fluorocyclopropane-1-carboxamide;

(1S,2S)-N-(6-(7-(dimethylamino)-6-fluoro-5-(methylthio)-1H-indazol-4-yl)imidazo[1,2-a]pyridin-2-yl)-2-fluorocyclopropane-1-carboxamide;

(1S,2S)-N-(6-(6,7-difluoro-5-(methylthio)-1H-indazol-4-yl)imidazo[1,2-a]pyridin-2-yl)-2-fluorocyclopropane-1-carboxamide;

(1S,2S)-N-(6-(5-chloro-7-(ethyl(methyl)amino)-6-fluoro-1H-indazol-4-yl)imidazo[1,2-a]pyridin-2-yl)-2-fluorocyclopropane-1-carboxamide;

(1S,2S)-N-(6-(7-(dimethylamino)-6-fluoro-5-(trifluoromethyl)-1H-indazol-4-yl)imidazo[1,2-a]pyridin-2-yl)-2-fluorocyclopropane-1-carboxamide;

(1S,2S)-N-(6-(7-ethoxy-6-fluoro-5-(methylthio)-1H-indazol-4-yl)imidazo[1,2-a]pyridin-2-yl)-2-fluorocyclopropane-1-carboxamide;

(1S,2S)-N-(6-(5-chloro-6-fluoro-7-(N-methylacetamido)-1H-indazol-4-yl)imidazo[1,2-a]pyridin-2-yl)-2-fluorocyclopropane-1-carboxamide;

(1S,2S)-N-(6-(7-ethoxy-5-ethyl-6-fluoro-1H-indazol-4-yl)imidazo[1,2-a]pyridin-2-yl)-2-fluorocyclopropane-1-carboxamide;

5-chloro-6-fluoro-4-(2-((1S,2S)-2-fluorocyclopropane-1-carboxamido)imidazo[1,2-a]pyridin-6-yl)-N,N-dimethyl-1H-indazole-7-carboxamide;

(1S,2S)-N-(6-(7-(ethyl(methyl)amino)-6-fluoro-5-(methylthio)-1H-indazol-4-yl)imidazo[1,2-a]pyridin-2-yl)-2-fluorocyclopropane-1-carboxamide;

(1S,2S)-N-(6-(5-ethyl-7-(ethyl(methyl)amino)-6-fluoro-1H-indazol-4-yl)imidazo[1,2-a]pyridin-2-yl)-2-fluorocyclopropane-1-carboxamide;

N-(6-(5-chloro-7-(dimethylamino)-6-fluoro-1H-indazol-4-yl)imidazo[1,2-a]pyridin-2-yl)cyclopropanecarboxamide;

6-fluoro-4-(2-((1S,2S)-2-fluorocyclopropane-1-carboxamido)imidazo[1,2-a]pyridin-6-yl)-N,N,5-trimethyl-1H-indazole-7-carboxamide;

(1S,2S)-N-(6-(7-(ethyl(methyl)amino)-6-fluoro-5-methyl-1H-indazol-4-yl)imidazo[1,2-a]pyridin-2-yl)-2-fluorocyclopropane-1-carboxamide;

(1S,2S)-N-(6-(5-chloro-7-(difluoromethyl)-6-fluoro-1H-indazol-4-yl)imidazo[1,2-a]pyridin-2-yl)-2-fluorocyclopropane-1-carboxamide;

(1R,2S)-N-(6-(5-chloro-7-(dimethylamino)-6-fluoro-1H-indazol-4-yl)imidazo[1,2-a]pyridin-2-yl)-2-fluorocyclopropane-1-carboxamide;

(1S,2R)-N-(6-(5-chloro-7-(dimethylamino)-6-fluoro-1H-indazol-4-yl)imidazo[1,2-a]pyridin-2-yl)-2-fluorocyclopropane-1-carboxamide;

(1R,2R)-N-(6-(5-chloro-7-(dimethylamino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(2-oxopyrrolidin-1-yl)-1H-indazol-4-yl)imidazo[1,2-a]pyridin-2-yl)-2-fluorocyclopropane-1-carboxamide;

(1S,2S)-N-(6-(5-ethyl-6-fluoro-7-(trifluoromethyl)-1H-indazol-4-yl)imidazo[1,2-a]pyridin-2-yl)-2-fluorocyclopropane-1-carboxamide;

5-chloro-N-ethyl-6-fluoro-4-(2-((1S,2S)-2-fluorocyclopropane-1-carboxamido)imidazo[1,2-a]pyridin-6-yl)-N-methyl-1H-indazole-7-carboxamide;

(1S,2S)-2-fluoro-N-(6-(6-fluoro-5-methyl-7-(trifluoromethoxy)-1H-indazol-4-yl)imidazo[1,2-a]pyridin-2-yl)cyclopropane-1-carboxamide;

(1S,2S)-N-(6-(5-chloro-6-fluoro-7-(methyl(pyrimidin-2-yl)amino)-1H-indazol-4-yl)imidazo[1,2-a]pyridin-2-yl)-2-fluorocyclopropane-1-carboxamide;

(1S,2S)-N-(6-(5-chloro-6-fluoro-7-(methyl(pyridin-3-ylmethyl)amino)-1H-indazol-4-yl)imidazo[1,2-a]pyridin-2-yl)-2-fluorocyclopropane-1-carboxamide;

(1S,2S)-N-(6-(5-chloro-6-fluoro-7-(methyl(pyridin-4-ylmethyl)amino)-1H-indazol-4-yl)imidazo[1,2-a]pyridin-2-yl)-2-fluorocyclopropane-1-carboxamide;

(1S,2S)-N-(6-(5-chloro-6-fluoro-7-(trifluoromethoxy)-1H-indazol-4-yl)imidazo[1,2-a]pyridin-2-yl)-2-fluorocyclopropane-1-carboxamide;

(1S,2S)-N-(6-(5-chloro-6-fluoro-7-(3-methyl-2-oxoimidazolidin-1-yl)-1H-indazol-4-yl)imidazo[1,2-a]pyridin-2-yl)-2-fluorocyclopropane-1-carboxamide;

(1S,2S)-N-(6-(5-chloro-6-fluoro-7-(isopropylamino)-1H-indazol-4-yl)imidazo[1,2-a]pyridin-2-yl)-2-fluorocyclopropane-1-carboxamide;

(1S,2S)-N-(6-(5-chloro-7-(cyclopropyl(methyl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(hydroxymethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(fluoromethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1H-pyrrol-1-yl)-1H-indazol-4-yl)imidazo[1,2-a]pyridin-2-yl)-2-fluorocyclopropane-1-carboxamide;

(1S,2S)-N-(6-(5-chloro-7-((cyanomethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-7-(cyclopropylamino)-6-fluoro-1H-indazol-4-yl)imidazo[1,2-a]pyridin-2-yl)-2-fluorocyclopropane-1-carboxamide;

(1S,2S)-N-(6-(7-(sec-butylamino)-5-chloro-6-fluoro-1H-indazol-4-yl)imidazo[1,2-a]pyridin-2-yl)-2-fluorocyclopropane-1-carboxamide;

(1S,2S)-N-(6-(5-chloro-7-((1-cyanoethyl)amino)-6-fluoro-1H-indazol-4-yl)imidazo[1,2-a]pyridin-2-yl)-2-fluorocyclopropane-1-carboxamide;

(1S,2S)-N-(6-(5-chloro-6-fluoro-7-(1-hydroxyethyl)-1H-indazol-4-yl)imidazo[1,2-a]pyridin-2-yl)-2-fluorocyclopropane-1-carboxamide;

(1S,2S)-N-(6-(5-chloro-6-fluoro-7-(1-methoxyethyl)-1H-indazol-4-yl)imidazo[1,2-a]pyridin-2-yl)-2-fluorocyclopropane-1-carboxamide;

(1 S,2S)-N-(6-(5-chloro-6-fluoro-7-(1-fluoroethyl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(1-methyl-1 H-pyrrol-2-yl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(1-methyl-1 H-pyrazol-5-yl)-1 H-indazol-4-yl)imidazo[1,2-a]pyridin-2-yl)-2-fluorocyclopropane-1-carboxamide;
(1 S,2S)-N-(6-(7-((2H-tetrazol-2-yl)methyl)-5-chloro-6-fluoro-1 H-indazol-4-yl)imidazo[1,2-a]pyridin-2-yl)-2-fluorocyclopropane-1-carboxamide;
(1 S,2S)-N-(6-(7-((2H-1,2,3-triazol-2-yl)methyl)-5-chloro-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-(2-methyl-1 H-pyrrol-1-yl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(methoxymethyl)-1 H-indazol-4-yl)imidazo[1,2-a]pyridin-2-yl)-2-fluorocyclopropane-1-carboxamide;
(1 S,2S)-N-(6-(5-chloro-7-(ethoxymethyl)-6-fluoro-1 H-indazol-4-yl)imidazo[1,2-a]pyridin-2-yl)-2-fluorocyclopropane-1-carboxamide;
(1 S,2S)-N-(6-(7-(1-(2H-tetrazol-2-yl)ethyl)-5-chloro-6-fluoro-1 H-indazol-4-yl)imidazo[1,2-a]pyridin-2-yl)-2-fluorocyclopropane-1-carboxamide;
(1 S,2S)-N-(6-(7-(1-(1 H-tetrazol-1-yl)ethyl)-5-chloro-6-fluoro-1 H-indazol-4-yl)imidazo[1,2-a]pyridin-2-yl)-2-fluorocyclopropane-1-carboxamide;
(1 S,2S)-N-(6-(5-chloro-7-cyclopropoxy-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-isopropoxy-1 H-indazol-4-yl)imidazo[1,2-a]pyridin-2-yl)-2-fluorocyclopropane-1-carboxamide;
(1 S,2S)-N-(6-(5-chloro-6-fluoro-7-isopropyl-1 H-indazol-4-yl)imidazo[1,2-a]pyridin-2-yl)-2-fluorocyclopropane-1-carboxamide;
(1 S,2S)-N-(6-(5-chloro-7-cyclopentyl-6-fluoro-1 H-indazol-4-yl)imidazo[1,2-a]pyridin-2-yl)-2-fluorocyclopropane-1-carboxamide;
(1 S,2S)-N-(6-(7-((S)-1-(2H-tetrazol-2-yl)ethyl)-5-chloro-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-(2,2,2-trifluoro-1-hydroxyethyl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(2-hydroxycyclopentyl)-1 H-indazol-4-yl)imidazo[1,2-a]pyridin-2-yl)-2-fluorocyclopropane-1-carboxamide;
(1 S,2S)-N-(6-(7-((S)-1-(1 H-tetrazol-1-yl)ethyl)-5-chloro-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-(2,2,2-trifluoro-1-methoxyethyl)-1 H-indazol-4-yl)imidazo[1,2-a]pyridin-2-yl)-2-fluorocyclopropane-1-carboxamide;
(1 S,2S)-N-(6-(7-(1-acetamidoethyl)-5-chloro-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-(1,2,2,2-tetrafluoroethyl)-1 H-indazol-4-yl)imidazo[1,2-a]pyridin-2-yl)-2-fluorocyclopropane-1-carboxamide;
(1 S,2S)-N-(6-(5-chloro-7-((cyclopropylmethyl)amino)-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-((R)-1-methoxypropan-2-yl)-1 H-indazol-4-yl)imidazo[1,2-a]pyridin-2-yl)-2-fluorocyclopropane-1-carboxamide;
(1 S,2S)-N-(6-(5-chloro-6-fluoro-7-((S)-1-methoxypropan-2-yl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(1-propionamidoethyl)-1 H-indazol-4-yl)imidazo[1,2-a]pyridin-2-yl)-2-fluorocyclopropane-1-carboxamide;
(1 S,2S)-N-(6-(5-chloro-7-((1,1-difluoropropan-2-yl)amino)-6-fluoro-1 H-indazol-4-yl)imidazo[1,2-a]pyridin-2-yl)-2-fluorocyclopropane-1-carboxamide;
(1 S,2S)-N-(6-(5-chloro-6-fluoro-7-(1-formamidoethyl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(1-(2,2,2-trifluoroacetamido)ethyl)-1 H-indazol-4-yl)imidazo[1,2-a]pyridin-2-yl)-2-fluorocyclopropane-1-carboxamide;
N-(1-(5-chloro-6-fluoro-4-(2-((1 S,2S)-2-fluorocyclopropane-1-carboxamido)imidazo[1,2-a]pyridin-6-yl)-1 H-indazol-7-yl)ethyl)cyclobutanecarboxamide;
(1 S,2S)-N-(6-(5-chloro-6-fluoro-7-(1-(methylamino)-1-oxopropan-2-yl)-1 H-indazol-4-yl)imidazo[1,2-a]pyridin-2-yl)-2-fluorocyclopropane-1-carboxamide;
(1 S,2S)-N-(6-(5-chloro-6-fluoro-7-((methylthio)methyl)-1 H-indazol-4-yl)imidazo[1,2-a]pyridin-2-yl)-2-fluorocyclopropane-1-carboxamide;
(1 S,2S)-N-(6-(5-chloro-6-fluoro-7-(1-(methylthio)ethyl)-1 H-indazol-4-yl)imidazo[1,2-a]pyridin-2-yl)-2-fluorocyclopropane-1-carboxamide;
(1 S,2S)-N-(6-(5-chloro-7-(cyano(formamido)methyl)-6-fluoro-1 H-indazol-4-yl)imidazo[1,2-a]pyridin-2-yl)-2-fluorocyclopropane-1-carboxamide;
(1 S,2S)-N-(6-(5-chloro-7-(1-(2,2-difluoroacetamido)ethyl)-6-fluoro-1 H-indazol-4-yl)imidazo[1,2-a]pyridin-2-yl)-2-fluorocyclopropane-1-carboxamide; and
(1 S,2S)-N-(6-(5-chloro-7-(1-(ethylamino)-1-oxopropan-2-yl)-6-fluoro-1 H-indazol-4-yl)imidazo[1,2-a]pyridin-2-yl)-2-fluorocyclopropane-1-carboxamide.

15. The compound of claim 1 or a pharmaceutically acceptable salt thereof, which is a compound of Formula (VI):

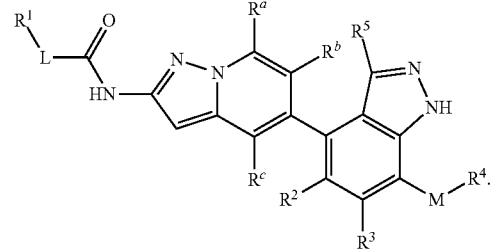

Formula (VI)

16. A pharmaceutical composition comprising a pharmaceutically acceptable carrier or diluent and the compound of claim 1 or a pharmaceutically acceptable salt thereof.

17. The compound of claim 15 or a pharmaceutically acceptable salt thereof, wherein L is a bond, $R^1$ is cyclopropyl which is optionally substituted with one or more groups selected from the group consisting of halo, $C_{1-3}$ alkyl, $C_{1-3}$ hydroxy alkyl and $C_{1-3}$ haloalkyl; $R^2$ is —H, alkyl, halo, haloalkyl, or alkylthio; $R^3$ is —H, alkyl, or halo; M is a bond, —O—, —S— or —NR$^6$—; $R^4$ is —H, halo, alkyl, hydroxyalkyl, haloalkyl, haloalkylamidoalkyl, haloalkylcarbonylaminoalkyl, alkylamidoalkyl, hydroxyhaloalkyl, haloalkenyl, cycloalkyl, cyano, cyanoalkyl, dimethylamino, dimethylaminoethyl, methylaminocarbonyl, dimethylaminocarbonyl, methylaminooxoethyl, am inocarbonylalkyl, acetamindoethyl, dialkylaminocycloalkyl, aminocycloalkyl, methylaminocycloalkyl, cycloalkylalkyl, cycloalkyl(hydroxy)alkyl, cycloalkylamidoalkyl, cycloalkylaminocarbonyl, hydroxycycloalkyl, methoxycycloalkyl, cycloalkyl (methoxy)methyl, alkoxycarbonyl, alkylcarbonyl, alkylamidoalkyl, alkoxyalkyl, alkenyl, methylsulfonamidoethyl, imidazolylethyl, dioxanyl, azetidinyl, azetidin ylmethyl, tetrahydrofuranyl, furanyl, pyrimidinyl, pyridinyl, pyrrolyl, halopyrrolidinyl, pyrrolidinyl, methylpyrrolyl, isoxazolyl, tetrazolylalkyl, triazinyl, methylpyrazolyl, or methylpyrazolylmethyl; and $R^5$ is —H, alkyl, or halo.

18. The compound of claim 15 or a pharmaceutically acceptable salt thereof, which is selected from the group consisting of:
- (1S,2S)-2-fluoro-N-(5-(5-methyl-1H-indazol-4-yl)pyrazolo[1,5-a]pyridin-2-yl)cyclopropane-1-carboxamide;
- (1S,2S)-2-fluoro-N-(5-(6-fluoro-5-vinyl-1H-indazol-4-yl)pyrazolo[1,5-a]pyridin-2-yl)cyclopropane-1-carboxamide;
- (1S,2S)-N-(5-(5-chloro-1H-indazol-4-yl)pyrazolo[1,5-a]pyridin-2-yl)-2-fluorocyclopropane-1-carboxamide;
- (1S,2S)-2-fluoro-N-(5-(5-methoxy-1H-indazol-4-yl)pyrazolo[1,5-a]pyridin-2-yl)cyclopropane-1-carboxamide;
- (1S,2S)-N-(5-(5-(dimethylamino)-1H-indazol-4-yl)pyrazolo[1,5-a]pyridin-2-yl)-2-fluorocyclopropane-1-carboxamide;
- (1S,2S)-2-fluoro-N-(5-(5-(trifluoromethyl)-1H-indazol-4-yl)pyrazolo[1,5-a]pyridin-2-yl)cyclopropane-1-carboxamide;
- (1S,2S)-N-(5-(5-ethyl-1H-indazol-4-yl)pyrazolo[1,5-a]pyridin-2-yl)-2-fluorocyclopropane-1-carboxamide;
- (1S,2S)-N-(5-(5-acetyl-1H-indazol-4-yl)pyrazolo[1,5-a]pyridin-2-yl)-2-fluorocyclopropane-1-carboxamide;
- (1S,2S)-N-(5-(5-(dimethylamino)-6-fluoro-1H-indazol-4-yl)pyrazolo[1,5-a]pyridin-2-yl)-2-fluorocyclopropane-1-carboxamide;
- (1S,2S)-N-(5-(5-bromo-1H-indazol-4-yl)pyrazolo[1,5-a]pyridin-2-yl)-2-fluorocyclopropane-1-carboxamide;
- (1S,2S)-N-(5-(5-cyano-1H-indazol-4-yl)pyrazolo[1,5-a]pyridin-2-yl)-2-fluorocyclopropane-1-carboxamide;
- (1S,2S)-N-(5-(5-cyclopropyl-6-fluoro-1H-indazol-4-yl)pyrazolo[1,5-a]pyridin-2-yl)-2-fluorocyclopropane-1-carboxamide;
- (1S,2S)-N-(5-(5-chloro-6-fluoro-1H-indazol-4-yl)pyrazolo[1,5-a]pyridin-2-yl)-2-fluorocyclopropane-1-carboxamide;
- (1S,2S)-N-(5-(5-cyclopropyl-1H-indazol-4-yl)pyrazolo[1,5-a]pyridin-2-yl)-2-fluorocyclopropane-1-carboxamide;
- (1S,2S)-2-fluoro-N-(5-(6-fluoro-5-methyl-1H-indazol-4-yl)pyrazolo[1,5-a]pyridin-2-yl)cyclopropane-1-carboxamide;
- (1S,2S)-2-fluoro-N-(5-(5-(hydroxymethyl)-1H-indazol-4-yl)pyrazolo[1,5-a]pyridin-2-yl)cyclopropane-1-carboxamide;
- (1 S,2S)-2-fluoro-N-(5-(6-fluoro-5-isopropyl-1 H-indazol-4-yl)pyrazolo[1,5-a]pyridin-2-yl)cyclopropane-1-carboxamide;
- (1 S,2S)-2-fluoro-N-(5-(5-(methylthio)-1 H-indazol-4-yl)pyrazolo[1,5-a]pyridin-2-yl)cyclopropane-1-carboxamide;
- (1 S,2S)-N-(5-(5-bromo-6-fluoro-1 H-indazol-4-yl)pyrazolo[1,5-a]pyridin-2-yl)-2-fluorocyclopropane-1-carboxamide;
- (1 S,2S)-N-(5-(5-(difluoromethyl)-1 H-indazol-4-yl)pyrazolo[1,5-a]pyridin-2-yl)-2-fluorocyclopropane-1-carboxamide;
- (1 S,2S)-N-(5-(5-ethyl-6-fluoro-1 H-indazol-4-yl)pyrazolo[1,5-a]pyridin-2-yl)-2-fluorocyclopropane-1-carboxamide;
- (1 S,2S)-2-fluoro-N-(5-(6-fluoro-5-methoxy-1 H-indazol-4-yl)pyrazolo[1,5-a]pyridin-2-yl)cyclopropane-1-carboxamide;
- (1 S,2S)-N-(5-(5-(difluoromethyl)-6-fluoro-1 H-indazol-4-yl)pyrazolo[1,5-a]pyridin-2-yl)-2-fluorocyclopropane-1-carboxamide;
- (1 S,2S)-N-(5-(3-chloro-6-fluoro-5-methyl-1 H-indazol-4-yl)pyrazolo[1,5-a]pyridin-2-yl)-2-fluorocyclopropane-1-carboxamide;
- (1 S,2S)-2-fluoro-N-(5-(6-fluoro-3,5-dimethyl-1 H-indazol-4-yl)pyrazolo[1,5-a]pyridin-2-yl)cyclopropane-1-carboxamide;
- (1 S,2S)-2-fluoro-N-(5-(6-fluoro-5-methyl-3-(methylthio)-1 H-indazol-4-yl)pyrazolo[1,5-a]pyridin-2-yl)cyclopropane-1-carboxamide;
- (1 S,2S)-N-(5-(3-ethynyl-6-fluoro-5-methyl-1 H-indazol-4-yl)pyrazolo[1,5-a]pyridin-2-yl)-2-fluorocyclopropane-1-carboxamide;
- (1 S,2S)-N-(5-(3-cyclopropyl-6-fluoro-5-methyl-1 H-indazol-4-yl)pyrazolo[1,5-a]pyridin-2-yl)-2-fluorocyclopropane-1-carboxamide;
- (1 S,2S)-2-fluoro-N-(5-(6-fluoro-5-methyl-3-vinyl-1 H-indazol-4-yl)pyrazolo[1,5-a]pyridin-2-yl)cyclopropane-1-carboxamide;
- (1 S,2S)-N-(5-(3-ethyl-6-fluoro-5-methyl-1 H-indazol-4-yl)pyrazolo[1,5-a]pyridin-2-yl)-2-fluorocyclopropane-1-carboxamide;
- (1 S,2S)-N-(5-(5,7-dichloro-6-fluoro-1 H-indazol-4-yl)pyrazolo[1,5-a]pyridin-2-yl)-2-fluorocyclopropane-1-carboxamide;
- (1S,2S)-2-fluoro-N-(5-(6-fluoro-5,7-dimethyl-1H-indazol-4-yl)pyrazolo[1,5-a]pyridin-2-yl)cyclopropane-1-carboxamide;
- (1S,2S)-N-(5-(5-chloro-7-(dimethylphosphoryl)-6-fluoro-1H-indazol-4-yl)pyrazolo[1,5-a]pyridin-2-yl)-2-fluorocyclopropane-1-carboxamide;
- (1S,2S)-N-(5-(7-chloro-6-fluoro-5-methyl-1H-indazol-4-yl)pyrazolo[1,5-a]pyridin-2-yl)-2-fluorocyclopropane-1-carboxamide;
- (1S,2S)-N-(5-(7-bromo-5-chloro-6-fluoro-1H-indazol-4-yl)pyrazolo[1,5-a]pyridin-2-yl)-2-fluorocyclopropane-1-carboxamide;
- (1S,2S)-N-(5-(6,7-difluoro-5-methyl-1H-indazol-4-yl)pyrazolo[1,5-a]pyridin-2-yl)-2-fluorocyclopropane-1-carboxamide;
- (1S,2S)-2-fluoro-N-(5-(6-fluoro-5-methyl-7-(trifluoromethyl)-1H-indazol-4-yl)pyrazolo[1,5-a]pyridin-2-yl)cyclopropane-1-carboxamide;
- (1S,2S)-2-fluoro-N-(5-(5-methyl-7-vinyl-1H-indazol-4-yl)pyrazolo[1,5-a]pyridin-2-yl)cyclopropane-1-carboxamide;
- (1S,2S)-N-(5-(5-chloro-7-(dimethylamino)-6-fluoro-1H-indazol-4-yl)pyrazolo[1,5-a]pyridin-2-yl)-2-fluorocyclopropane-1-carboxamide;
- (1S,2S)-N-(5-(5-chloro-6-fluoro-7-(methylthio)-1H-indazol-4-yl)pyrazolo[1,5-a]pyridin-2-yl)-2-fluorocyclopropane-1-carboxamide;

(1S,2S)-N-(5-(5-chloro-6-fluoro-7-(methylsulfonyl)-1H-indazol-4-yl)pyrazolo[1,5-a]pyridin-2-yl)-2-fluorocyclopropane-1-carboxamide;

(1S,2S)-N-(5-(7-bromo-6-fluoro-5-methyl-1H-indazol-4-yl)pyrazolo[1,5-a]pyridin-2-yl)-2-fluorocyclopropane-1-carboxamide;

(1S,2S)-2-fluoro-N-(5-(6-fluoro-5-methyl-7-(methylthio)-1H-indazol-4-yl)pyrazolo[1,5-a]pyridin-2-yl)cyclopropane-1-carboxamide;

(1S,2S)-2-fluoro-N-(5-(6-fluoro-5-methyl-7-(methylsulfonyl)-1H-indazol-4-yl)pyrazolo[1,5-a]pyridin-2-yl)cyclopropane-1-carboxamide;

(1S,2S)-N-(5-(7-(dimethylamino)-6-fluoro-5-methyl-1H-indazol-4-yl)pyrazolo[1,5-a]pyridin-2-yl)-2-fluorocyclopropane-1-carboxamide;

(1S,2S)-2-fluoro-N-(5-(6-fluoro-7-methoxy-5-methyl-1H-indazol-4-yl)pyrazolo[1,5-a]pyridin-2-yl)cyclopropane-1-carboxamide;

(1 S,2S)-N-(5-(5-chloro-6-fluoro-7-methoxy-1 H-indazol-4-yl)pyrazolo[1,5-a]pyridin-2-yl)-2-fluorocyclopropane-1-carboxamide;

(1 S,2S)-N-(5-(5-chloro-7-ethoxy-6-fluoro-1 H-indazol-4-yl)pyrazolo[1,5-a]pyridin-2-yl)-2-fluorocyclopropane-1-carboxamide;

(1 S,2S)-N-(5-(5-chloro-6-fluoro-7-(methylamino)-1 H-indazol-4-yl)pyrazolo[1,5-a]pyridin-2-yl)-2-fluorocyclopropane-1-carboxamide;

(1 S,2S)-N-(5-(5-chloro-6-fluoro-7-(4-methylpiperazin-1-yl)-1 H-indazol-4-yl)pyrazolo[1,5-a]pyridin-2-yl)-2-fluorocyclopropane-1-carboxamide;

(1 S,2S)-N-(5-(5-chloro-7-(ethylamino)-6-fluoro-1 H-indazol-4-yl)pyrazolo[1,5-a]pyridin-2-yl)-2-fluorocyclopropane-1-carboxamide;

(1 S,2S)-N-(5-(5-chloro-7-(diethylamino)-6-fluoro-1 H-indazol-4-yl)pyrazolo[1,5-a]pyridin-2-yl)-2-fluorocyclopropane-1-carboxamide;

(1 S,2S)-N-(5-(5-chloro-6-fluoro-7-morpholino-1 H-indazol-4-yl)pyrazolo[1,5-a]pyridin-2-yl)-2-fluorocyclopropane-1-carboxamide;

(1 S,2S)-N-(5-(5-chloro-6-fluoro-7-(pyrrolidin-1-yl)-1 H-indazol-4-yl)pyrazolo[1,5-a]pyridin-2-yl)-2-fluorocyclopropane-1-carboxamide;

(1 S,2S)-N-(5-(5-chloro-6-fluoro-7-(piperazin-1-yl)-1 H-indazol-4-yl)pyrazolo[1,5-a]pyridin-2-yl)-2-fluorocyclopropane-1-carboxamide;

(1 S,2S)-N-(5-(7-(azetidin-1-yl)-5-chloro-6-fluoro-1 H-indazol-4-yl)pyrazolo[1,5-a]pyridin-2-yl)-2-fluorocyclopropane-1-carboxamide;

(1 S,2S)-N-(5-(5-chloro-7-((4-(dimethylamino)cyclohexyl)(methyl)amino)-6-fluoro-1 H-indazol-4-yl)pyrazolo[1,5-a]pyridin-2-yl)-2-fluorocyclopropane-1-carboxamide;

(1 S,2S)-N-(5-(5-chloro-6-fluoro-7-((4-hydroxycyclohexyl)(methyl)amino)-1 H-indazol-4-yl)pyrazolo[1,5-a]pyridin-2-yl)-2-fluorocyclopropane-1-carboxamide;

(1 S,2S)-N-(5-(5-chloro-6-fluoro-7-(methyl((1R,4R)-4-(methylamino)cyclohexyl)amino)-1 H-indazol-4-yl)pyrazolo[1,5-a]pyridin-2-yl)-2-fluorocyclopropane-1-carboxamide;

(1 S,2S)-N-(5-(5-chloro-6-fluoro-7-(methyl((1 S,4S)-4-(methylamino)cyclohexyl)amino)-1 H-indazol-4-yl)pyrazolo[1,5-a]pyridin-2-yl)-2-fluorocyclopropane-1-carboxamide;

(1 S,2S)-2-fluoro-N-(5-(7-methoxy-5-methyl-1 H-indazol-4-yl)pyrazolo[1,5-a]pyridin-2-yl)cyclopropane-1-carboxamide;

(1 S,2S)-N-(5-(5-chloro-6-fluoro-7-((tetrahydrofuran-2-yl)methoxy)-1 H-indazol-4-yl)pyrazolo[1,5-a]pyridin-2-yl)-2-fluorocyclopropane-1-carboxamide;

(1 S,2S)-N-(5-(5-chloro-6-fluoro-7-((4-(methylamino)cyclohexyl)amino)-1 H-indazol-4-yl)pyrazolo[1,5-a]pyridin-2-yl)-2-fluorocyclopropane-1-carboxamide;

(1 S,2S)-N-(5-(7-ethoxy-6-fluoro-5-methyl-1 H-indazol-4-yl)pyrazolo[1,5-a]pyridin-2-yl)-2-fluorocyclopropane-1-carboxamide;

(1 S,2S)-N-(5-(7-amino-5-chloro-6-fluoro-1 H-indazol-4-yl)pyrazolo[1,5-a]pyridin-2-yl)-2-fluorocyclopropane-1-carboxamide;

(1 S,2S)-N-(5-(7-ethoxy-5-methyl-1 H-indazol-4-yl)pyrazolo[1,5-a]pyridin-2-yl)-2-fluorocyclopropane-1-carboxamide;

(1 S,2S)-N-(5-(5-chloro-7-((4-(dimethylamino)cyclohexyl)amino)-6-fluoro-1 H-indazol-4-yl)pyrazolo[1,5-a]pyridin-2-yl)-2-fluorocyclopropane-1-carboxamide;

(1 S,2S)-N-(5-(5-ethyl-6-fluoro-7-(methylthio)-1 H-indazol-4-yl)pyrazolo[1,5-a]pyridin-2-yl)-2-fluorocyclopropane-1-carboxamide dihydrochloride;

(1 S,2S)-N-(5-(7-((4-aminocyclohexyl)(methyl)amino)-5-chloro-6-fluoro-1 H-indazol-4-yl)pyrazolo[1,5-a]pyridin-2-yl)-2-fluorocyclopropane-1-carboxamide;

(1 S,2S)-N-(5-(7-((4-aminocyclohexyl)amino)-5-chloro-6-fluoro-1 H-indazol-4-yl)pyrazolo[1,5-a]pyridin-2-yl)-2-fluorocyclopropane-1-carboxamide;

tert-butyl (4-((5-chloro-6-fluoro-4-(2-((1 S,2S)-2-fluorocyclopropane-1-carboxamido) pyrazolo[1,5-a]pyridin-5-yl)-1 H-indazol-7-yl)amino)cyclohexyl)carbamate;

(1 S,2S)-N-(5-(5-chloro-6-fluoro-7-((4-hydroxycyclohexyl)amino)-1 H-indazol-4-yl)pyrazolo[1,5-a]pyridin-2-yl)-2-fluorocyclopropane-1-carboxamide;

(1 S,2S)-N-(5-(7-(diethylamino)-5-ethyl-6-fluoro-1 H-indazol-4-yl)pyrazolo[1,5-a]pyridin-2-yl)-2-fluorocyclopropane-1-carboxamide;

(1 S,2S)-N-(5-(7-(dimethylamino)-5-ethyl-6-fluoro-1 H-indazol-4-yl)pyrazolo[1,5-a]pyridin-2-yl)-2-fluorocyclopropane-1-carboxamide;

(1 S,2S)-N-(5-(5-chloro-6-fluoro-7-((2-hydroxyethyl)thio)-1 H-indazol-4-yl)pyrazolo[1,5-a]pyridin-2-yl)-2-fluorocyclopropane-1-carboxamide;

(1 S,2S)-N-(5-(5-ethyl-6-fluoro-7-((2-(methylamino)-2-oxoethyl)thio)-1 H-indazol-4-yl)pyrazolo[1,5-a]pyridin-2-yl)-2-fluorocyclopropane-1-carboxamide bis(2,2,2-trifluoroacetate);

(1 S,2S)-N-(5-(7-((2-(dimethylamino)-2-oxoethyl)thio)-5-ethyl-6-fluoro-1 H-indazol-4-yl)pyrazolo[1,5-a]pyridin-2-yl)-2-fluorocyclopropane-1-carboxamide bis(2,2,2-trifluoroacetate);

(1 S,2S)-2-fluoro-N-(5-(6-fluoro-7-((2-hydroxyethyl)thio)-5-methyl-1 H-indazol-4-yl)pyrazolo[1,5-a]pyridin-2-yl)cyclopropane-1-carboxamide;

(1 S,2S)-N-(5-(5-ethyl-7-(ethylamino)-6-fluoro-1 H-indazol-4-yl)pyrazolo[1,5-a]pyridin-2-yl)-2-fluorocyclopropane-1-carboxamide;

(1 S,2S)-N-(5-(5-ethyl-7-(ethyl(methyl)amino)-6-fluoro-1 H-indazol-4-yl)pyrazolo[1,5-a]pyridin-2-yl)-2-fluorocyclopropane-1-carboxamide;

2-((5-ethyl-6-fluoro-4-(2-((1S,2S)-2-fluorocyclopropane-1-carboxamido)pyrazolo[1,5-a]pyridin-5-yl)-1H-indazol-7-yl)thio)acetic acid;

(1 S,2S)-N-(5-(7-((3-aminocyclopentyl)(methyl)amino)-5-chloro-6-fluoro-1 H-indazol-4-yl)pyrazolo[1,5-a]pyridin-2-yl)-2-fluorocyclopropane-1-carboxamide;

(1S,2S)-N-(5-(5-chloro-6-fluoro-7-hydroxy-1H-indazol-4-yl)pyrazolo[1,5-a]pyridin-2-yl)-2-fluorocyclopropane-1-carboxamide;

(1S,2S)-2-fluoro-N-(5-(6-fluoro-5,7-bis(methylthio)-1H-indazol-4-yl)pyrazolo[1,5-a]pyridin-2-yl)cyclopropane-1-carboxamide;

(1S,2S)-2-fluoro-N-(5-(6-fluoro-5-(methylthio)-1H-indazol-4-yl)pyrazolo[1,5-a]pyridin-2-yl)cyclopropane-1-carboxamide;

(1S,2S)-N-(5-(7-ethoxy-5-ethyl-6-fluoro-1H-indazol-4-yl)pyrazolo[1,5-a]pyridin-2-yl)-2-fluorocyclopropane-1-carboxamide;

(1S,2S)-N-(5-(5-ethyl-6,7-difluoro-1H-indazol-4-yl)pyrazolo[1,5-a]pyridin-2-yl)-2-fluorocyclopropane-1-carboxamide;

(1S,2S)-2-fluoro-N-(5-(6-fluoro-5-methyl-7-(methylsulfinyl)-1H-indazol-4-yl)pyrazolo[1,5-a]pyridin-2-yl)cyclopropane-1-carboxamide;

(1S,2S)-2-fluoro-N-(5-(6-fluoro-7-(2-hydroxyethoxy)-5-methyl-1H-indazol-4-yl)pyrazolo[1,5-a]pyridin-2-yl)cyclopropane-1-carboxamide;

2-((6-fluoro-4-(2-((1S,2S)-2-fluorocyclopropane-1-carboxamido)pyrazolo[1,5-a]pyridin-5-yl)-5-methyl-1H-indazol-7-yl)oxy)ethyl carbamate;

(1S,2S)-N-(5-(5-chloro-6,7-difluoro-1H-indazol-4-yl)pyrazolo[1,5-a]pyridin-2-yl)-2-fluorocyclopropane-1-carboxamide;

(1S,2S)-N-(5-(7-acetamido-5-chloro-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(methylsulfinyl)-1H-indazol-4-yl)pyrazolo[1,5-a]pyridin-2-yl)-2-fluorocyclopropane-1-carboxamide;

(1S,2S)-2-fluoro-N-(5-(6-fluoro-5-methyl-7-(2-(1-methylureido)ethoxy)-1H-indazol-4-yl)pyrazolo[1,5-a]pyridin-2-yl)cyclopropane-1-carboxamide;

(1S,2S)-N-(5-(7-acetamido-6-fluoro-5-methyl-1H-indazol-4-yl)pyrazolo[1,5-a]pyridin-2-yl)-2-fluorocyclopropane-1-carboxamide;

(1S,2S)-N-(5-(6,7-difluoro-5-(methylthio)-1H-indazol-4-yl)pyrazolo[1,5-a]pyridin-2-yl)-2-fluorocyclopropane-1-carboxamide;

tert-butyl 2-(5-chloro-6-fluoro-4-(2-((1S,2S)-2-fluorocyclopropane-1-carboxamido)pyrazolo[1,5-a]pyridin-5-yl)-1H-indazol-7-yl)-1-methylhydrazine-1-carboxylate;

(1S,2S)-N-(5-(7-ethoxy-6-fluoro-5-(methylthio)-1H-indazol-4-yl)pyrazolo[1,5-a]pyridin-2-yl)-2-fluorocyclopropane-1-carboxamide;

(1S,2S)-2-fluoro-N-(5-(6-fluoro-5-methyl-7-(2-ureidoethoxy)-1H-indazol-4-yl)pyrazolo[1,5-a]pyridin-2-yl)cyclopropane-1-carboxamide;

(1S,2S)-2-fluoro-N-(5-(6-fluoro-5-methyl-7-(2-(3-methylureido)ethoxy)-1H-indazol-4-yl)pyrazolo[1,5-a]pyridin-2-yl)cyclopropane-1-carboxamide;

2-((6-fluoro-4-(2-((1S,2S)-2-fluorocyclopropane-1-carboxamido)pyrazolo[1,5-a]pyridin-5-yl)-5-methyl-1H-indazol-7-yl)thio)ethyl methylcarbamate;

(1S,2S)-2-fluoro-N-(5-(6-fluoro-5-methyl-7-(2-(2,2,2-trifluoroacetamido)ethoxy)-1H-indazol-4-yl)pyrazolo[1,5-a]pyridin-2-yl)cyclopropane-1-carboxamide;

methyl 6-fluoro-4-(2-((1S,2S)-2-fluorocyclopropane-1-carboxamido)pyrazolo[1,5-a]pyridin-5-yl)-5-methyl-1H-indazole-7-carboxylate;

6-fluoro-4-(2-((1S,2S)-2-fluorocyclopropane-1-carboxamido)pyrazolo[1,5-a]pyridin-5-yl)-5-methyl-1H-indazole-7-carboxylic acid;

(1S,2S)-2-fluoro-N-(5-(6-fluoro-5-methyl-7-(N-methylacetamido)-1H-indazol-4-yl)pyrazolo[1,5-a]pyridin-2-yl)cyclopropane-1-carboxamide;

5-chloro-6-fluoro-4-(2-((1S,2S)-2-fluorocyclopropane-1-carboxamido)pyrazolo[1,5-a]pyridin-5-yl)-1H-indazole-7-carboxylic acid;

(1S,2S)-N-(5-(5-chloro-6-fluoro-7-(N-methylacetamido)-1H-indazol-4-yl)pyrazolo[1,5-a]pyridin-2-yl)-2-fluorocyclopropane-1-carboxamide;

(1S,2S)-N-(5-(5-chloro-6-fluoro-7-(2-methylhydrazineyl)-1H-indazol-4-yl)pyrazolo[1,5-a]pyridin-2-yl)-2-fluorocyclopropane-1-carboxamide;

methyl 5-chloro-6-fluoro-4-(2-((1S,2S)-2-fluorocyclopropane-1-carboxamido)pyrazolo[1,5-a]pyridin-5-yl)-1H-indazole-7-carboxylate;

(1S,2S)-N-(5-(5-chloro-6-fluoro-7-((3-hydroxycyclopentyl)(methyl)amino)-1H-indazol-4-yl)pyrazolo[1,5-a]pyridin-2-yl)-2-fluorocyclopropane-1-carboxamide;

5-chloro-6-fluoro-4-(2-((1S,2S)-2-fluorocyclopropane-1-carboxamido)pyrazolo[1,5-a]pyridin-5-yl)-N,N-dimethyl-1H-indazole-7-carboxamide;

(1S,2S)-2-fluoro-N-(5-(6-fluoro-7-((2-hydroxyethyl)(methyl)amino)-5-methyl-1H-indazol-4-yl)pyrazolo[1,5-a]pyridin-2-yl)cyclopropane-1-carboxamide;

(1S,2S)-N-(5-(7-(dimethylamino)-6-fluoro-5-(methylthio)-1H-indazol-4-yl)pyrazolo[1,5-a]pyridin-2-yl)-2-fluorocyclopropane-1-carboxamide;

(1S,2S)-N-(5-(5-chloro-6-fluoro-7-((3-hydroxycyclopentyl)amino)-1H-indazol-4-yl)pyrazolo[1,5-a]pyridin-2-yl)-2-fluorocyclopropane-1-carboxamide;

5-chloro-6-fluoro-4-(2-((1S,2S)-2-fluorocyclopropane-1-carboxamido)pyrazolo[1,5-a]pyridin-5-yl)-N-methyl-1H-indazole-7-carboxamide;

(1S,2S)-N-(5-(5-chloro-6-fluoro-7-((3-hydroxycyclobutyl)(methyl)amino)-1H-indazol-4-yl)pyrazolo[1,5-a]pyridin-2-yl)-2-fluorocyclopropane-1-carboxamide;

N-(5-(6-fluoro-5-methyl-7-(methylthio)-1H-indazol-4-yl)pyrazolo[1,5-a]pyridin-2-yl)cyclopropanecarboxamide;

(1S,2S)-N-(5-(7-(ethyl(methyl)amino)-6-fluoro-5-methyl-1H-indazol-4-yl)pyrazolo[1,5-a]pyridin-2-yl)-2-fluorocyclopropane-1-carboxamide;

(1S,2S)-N-(5-(5-chloro-7-(ethyl(methyl)amino)-6-fluoro-1H-indazol-4-yl)pyrazolo[1,5-a]pyridin-2-yl)-2-fluorocyclopropane-1-carboxamide;

(1S,2S)-N-(5-(7-(dimethylamino)-6-fluoro-5-(trifluoromethyl)-1H-indazol-4-yl)pyrazolo[1,5-a]pyridin-2-yl)-2-fluorocyclopropane-1-carboxamide;

(1S,2S)-N-(5-(7-acetyl-6-fluoro-5-methyl-1H-indazol-4-yl)pyrazolo[1,5-a]pyridin-2-yl)-2-fluorocyclopropane-1-carboxamide;

(1S,2R)-2-fluoro-N-(5-(6-fluoro-5-methyl-7-(methylthio)-1H-indazol-4-yl)pyrazolo[1,5-a]pyridin-2-yl)cyclopropane-1-carboxamide;

(1R,2S)-2-fluoro-N-(5-(6-fluoro-5-methyl-7-(methylthio)-1H-indazol-4-yl)pyrazolo[1,5-a]pyridin-2-yl)cyclopropane-1-carboxamide;

N-(5-(6-fluoro-5-(methylthio)-1H-indazol-4-yl)pyrazolo[1,5-a]pyridin-2-yl)cyclopropanecarboxamide;

6-fluoro-4-(2-((1S,2S)-2-fluorocyclopropane-1-carboxamido)pyrazolo[1,5-a]pyridin-5-yl)-N,N,5-trimethyl-1H-indazole-7-carboxamide;

(1R,2S)-2-fluoro-N-(5-(6-fluoro-5-(methylthio)-1H-indazol-4-yl)pyrazolo[1,5-a]pyridin-2-yl)cyclopropane-1-carboxamide;

(1S,2R)-2-fluoro-N-(5-(6-fluoro-5-(methylthio)-1 H-indazol-4-yl)pyrazolo[1,5-a]pyridin-2-yl)cyclopropane-1-carboxamide;
(1R,2R)-2-fluoro-N-(5-(6-fluoro-5-(methylthio)-1 H-indazol-4-yl)pyrazolo[1,5-a]pyridin-2-yl)cyclopropane-1-carboxamide;
(1R,2R)-2-fluoro-N-(5-(6-fluoro-5-methyl-7-(methylthio)-1 H-indazol-4-yl)pyrazolo[1,5-a]pyridin-2-yl)cyclopropane-1-carboxamide;
(1S,2S)-N-(5-(7-acetyl-5-chloro-6-fluoro-1 H-indazol-4-yl)pyrazolo[1,5-a]pyridin-2-yl)-2-fluorocyclopropane-1-carboxamide;
5-chloro-6-fluoro-4-(2-((1S,2S)-2-fluorocyclopropane-1-carboxamido)pyrazolo[1,5-a]pyridin-5-yl)-1 H-indazole-7-carboxamide;
(1S,2S)-N-(5-(7-(ethyl(methyl)amino)-6-fluoro-5-(methylthio)-1 H-indazol-4-yl)pyrazolo[1,5-a]pyridin-2-yl)-2-fluorocyclopropane-1-carboxamide;
(1S,2S)-N-(5-(5-ethoxy-6-fluoro-1 H-indazol-4-yl)pyrazolo[1,5-a]pyridin-2-yl)-2-fluorocyclopropane-1-carboxamide;
(1S,2S)-N-(5-(5-chloro-6-fluoro-7-methyl-1 H-indazol-4-yl)pyrazolo[1,5-a]pyridin-2-yl)-2-fluorocyclopropane-1-carboxamide;
2-((6-fluoro-4-(2-((1S,2S)-2-fluorocyclopropane-1-carboxamido)pyrazolo[1,5-a]pyridin-5-yl)-5-methyl-1 H-indazol-7-yl)(methyl)amino)ethyl methylcarbamate;
(1S,2S)-N-(5-(5-chloro-7-(difluoromethyl)-6-fluoro-1 H-indazol-4-yl)pyrazolo[1,5-a]pyridin-2-yl)-2-fluorocyclopropane-1-carboxamide;
(1S,2S)-N-(5-(7-cyano-6-fluoro-5-methyl-1 H-indazol-4-yl)pyrazolo[1,5-a]pyridin-2-yl)-2-fluorocyclopropane-1-carboxamide;
(1S,2S)-N-(5-(7-(dimethylamino)-6-fluoro-1 H-indazol-4-yl)pyrazolo[1,5-a]pyridin-2-yl)-2-fluorocyclopropane-1-carboxamide;
6-fluoro-4-(2-((1S,2S)-2-fluorocyclopropane-1-carboxamido)pyrazolo[1,5-a]pyridin-5-yl)-N,5-dimethyl-1 H-indazole-7-carboxamide;
(1S,2S)-N-(5-(5-ethyl-6-fluoro-7-(trifluoromethyl)-1 H-indazol-4-yl)pyrazolo[1,5-a]pyridin-2-yl)-2-fluorocyclopropane-1-carboxamide;
(1S,2S)-N-(5-(5-chloro-7-cyano-6-fluoro-1 H-indazol-4-yl)pyrazolo[1,5-a]pyridin-2-yl)-2-fluorocyclopropane-1-carboxamide;
(1S,2S)-2-fluoro-N-(5-(6-fluoro-7-(trifluoromethoxy)-1 H-indazol-4-yl)pyrazolo[1,5-a]pyridin-2-yl)cyclopropane-1-carboxamide;
(1S,2S)-N-(5-(7-((cyanomethyl)thio)-5-ethyl-6-fluoro-1 H-indazol-4-yl)pyrazolo[1,5-a]pyridin-2-yl)-2-fluorocyclopropane-1-carboxamide;
(1S,2S)-2-fluoro-N-(5-(6-fluoro-7-(methylthio)-1 H-indazol-4-yl)pyrazolo[1,5-a]pyridin-2-yl)cyclopropane-1-carboxamide;
(1S,2S)-2-fluoro-N-(5-(6-fluoro-5-(trifluoromethyl)-1 H-indazol-4-yl)pyrazolo[1,5-a]pyridin-2-yl)cyclopropane-1-carboxamide;
(1S,2S)-N-(5-(7-(difluoromethyl)-6-fluoro-5-methyl-1 H-indazol-4-yl)pyrazolo[1,5-a]pyridin-2-yl)-2-fluorocyclopropane-1-carboxamide;
(1S,2S)-2-fluoro-N-(5-(6-fluoro-5-methyl-7-(trifluoromethoxy)-1 H-indazol-4-yl)pyrazolo[1,5-a]pyridin-2-yl)cyclopropane-1-carboxamide;
(1S,2S)-2-fluoro-N-(5-(7-(methylthio)-1 H-indazol-4-yl)pyrazolo[1,5-a]pyridin-2-yl)cyclopropane-1-carboxamide;
(1S,2S)-N-(5-(5-chloro-6-fluoro-7-(1-methyl-1 H-tetrazol-5-yl)-1 H-indazol-4-yl)pyrazolo[1,5-a]pyridin-2-yl)-2-fluorocyclopropane-1-carboxamide;
(1S,2S)-N-(5-(7-(dimethylamino)-1 H-indazol-4-yl)pyrazolo[1,5-a]pyridin-2-yl)-2-fluorocyclopropane-1-carboxamide;
(1S,2S)-N-(5-(5-chloro-6-fluoro-7-(methyl(pyrimidin-2-yl)amino)-1 H-indazol-4-yl)pyrazolo[1,5-a]pyridin-2-yl)-2-fluorocyclopropane-1-carboxamide;
(1S,2S)-N-(5-(5-chloro-7-((cyanomethyl)thio)-6-fluoro-1 H-indazol-4-yl)pyrazolo[1,5-a]pyridin-2-yl)-2-fluorocyclopropane-1-carboxamide;
(1R,2R)-N-(5-(6,7-difluoro-5-(methylthio)-1 H-indazol-4-yl)pyrazolo[1,5-a]pyridin-2-yl)-2-fluorocyclopropane-1-carboxamide;
(1S,2R)-N-(5-(6,7-difluoro-5-(methylthio)-1 H-indazol-4-yl)pyrazolo[1,5-a]pyridin-2-yl)-2-fluorocyclopropane-1-carboxamide;
(1R,2S)-N-(5-(6,7-difluoro-5-(methylthio)-1 H-indazol-4-yl)pyrazolo[1,5-a]pyridin-2-yl)-2-fluorocyclopropane-1-carboxamide;
(1S,2S)-N-(5-(5-chloro-6-fluoro-7-(pyrimidin-2-ylamino)-1 H-indazol-4-yl)pyrazolo[1,5-a]pyridin-2-yl)-2-fluorocyclopropane-1-carboxamide;
(1S,2S)-N-(5-(7-((1-cyanoethyl)thio)-5-ethyl-6-fluoro-1 H-indazol-4-yl)pyrazolo[1,5-a]pyridin-2-yl)-2-fluorocyclopropane-1-carboxamide;
(1S,2S)-N-(5-(7-((2-cyanopropan-2-yl)thio)-5-ethyl-6-fluoro-1 H-indazol-4-yl)pyrazolo[1,5-a]pyridin-2-yl)-2-fluorocyclopropane-1-carboxamide;
6-fluoro-4-(2-((1S,2S)-2-fluorocyclopropane-1-carboxamido)pyrazolo[1,5-a]pyridin-5-yl)-N,N-dimethyl-1 H-indazole-7-carboxamide;
6-fluoro-4-(2-((1S,2S)-2-fluorocyclopropane-1-carboxamido)pyrazolo[1,5-a]pyridin-5-yl)-N,N-dimethyl-1 H-indazole-5-carboxamide;
(1S,2S)-N-(5-(5-ethoxy-6-fluoro-7-(methylthio)-1 H-indazol-4-yl)pyrazolo[1,5-a]pyridin-2-yl)-2-fluorocyclopropane-1-carboxamide;
(1S,2S)-N-(5-(5-chloro-6-fluoro-7-(trifluoromethoxy)-1 H-indazol-4-yl)pyrazolo[1,5-a]pyridin-2-yl)-2-fluorocyclopropane-1-carboxamide;
(1S,2S)-N-(5-(7-((1-cyanocyclopropyl)thio)-5-ethyl-6-fluoro-1 H-indazol-4-yl)pyrazolo[1,5-a]pyridin-2-yl)-2-fluorocyclopropane-1-carboxamide;
(1S,2S)-N-(5-(5-chloro-6-fluoro-7-(pyridin-4-ylamino)-1 H-indazol-4-yl)pyrazolo[1,5-a]pyridin-2-yl)-2-fluorocyclopropane-1-carboxamide;
(1S,2S)-N-(5-(7-(dimethylamino)-5-ethoxy-6-fluoro-1 H-indazol-4-yl)pyrazolo[1,5-a]pyridin-2-yl)-2-fluorocyclopropane-1-carboxamide;
(1S,2S)-N-(5-(5-ethoxy-6,7-difluoro-1 H-indazol-4-yl)pyrazolo[1,5-a]pyridin-2-yl)-2-fluorocyclopropane-1-carboxamide;
5-chloro-N-(cyanomethyl)-6-fluoro-4-(2-((1S,2S)-2-fluorocyclopropane-1-carboxamido)pyrazolo[1,5-a]pyridin-5-yl)-N-methyl-1 H-indazole-7-carboxamide;
(1S,2S)-N-(5-(5-chloro-6-fluoro-7-((5-fluoropyrimidin-2-yl)(methyl)amino)-1 H-indazol-4-yl)pyrazolo[1,5-a]pyridin-2-yl)-2-fluorocyclopropane-1-carboxamide;
(1S,2S)-N-(5-(5-chloro-6-fluoro-7-(methyl(pyridin-4-yl)amino)-1 H-indazol-4-yl)pyrazolo[1,5-a]pyridin-2-yl)-2-fluorocyclopropane-1-carboxamide;
(1S,2S)-N-(5-(5-chloro-7-(N-(cyanomethyl)acetamido)-6-fluoro-1 H-indazol-4-yl)pyrazolo[1,5-a]pyridin-2-yl)-2-fluorocyclopropane-1-carboxamide;

(1S,2S)-N-(5-(5-chloro-6-fluoro-7-(methyl(2-(pyridin-4-yl)ethyl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(methyl(1,3,5-triazin-2-yl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(methyl(1,2,4-triazin-3-yl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(isopropylamino)-1H-indazol-4-yl)pyrazolo[1,5-a]pyridin-2-yl)-2-fluorocyclopropane-1-carboxamide;

(1S,2S)-N-(5-(5-chloro-7-(cyclobutyl(methyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-7-(ethylthio)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(isopropyl(methyl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-methyl-2-oxoimidazolidin-1-yl)-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-methoxyazetidin-1-yl)-1H-indazol-4-yl)pyrazolo[1,5-a]pyridin-2-yl)-2-fluorocyclopropane-1-carboxamide;

(1S,2S)-N-(5-(5-chloro-7-(cyclopropyl(methyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-formyl-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-(methoxymethyl)azetidin-1-yl)-1H-indazol-4-yl)pyrazolo[1,5-a]pyridin-2-yl)-2-fluorocyclopropane-1-carboxamide;

(1S,2S)-N-(5-(5-chloro-7-(1,1-dioxidothiomorpholino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(hydroxymethyl)-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-methylazetidin-1-yl)-1H-indazol-4-yl)pyrazolo[1,5-a]pyridin-2-yl)-2-fluorocyclopropane-1-carboxamide;

(1S,2S)-N-(5-(5-chloro-6-fluoro-7-thiomorpholino-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-fluoro-3-methylazetidin-1-yl)-1H-indazol-4-yl)pyrazolo[1,5-a]pyridin-2-yl)-2-fluorocyclopropane-1-carboxamide;

(1S,2S)-N-(5-(5-chloro-7-((E)-2-cyanovinyl)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(fluoromethyl)-1H-indazol-4-yl)pyrazolo[1,5-a]pyridin-2-yl)-2-fluorocyclopropane-1-carboxamide;

(1S,2S)-N-(5-(5-chloro-6-fluoro-7-(1-oxidothiomorpholino)-1H-indazol-4-yl)pyrazolo[1,5-a]pyridin-2-yl)-2-fluorocyclopropane-1-carboxamide;

(1S,2S)-N-(5-(5-chloro-7-((cyanomethyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(1H-pyrrol-1-yl)-1H-indazol-4-yl)pyrazolo[1,5-a]pyridin-2-yl)-2-fluorocyclopropane-1-carboxamide;

(1S,2S)-N-(5-(5-chloro-7-((2-cyanopropan-2-yl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(prop-1-en-2-yl)-1H-indazol-4-yl)pyrazolo[1,5-a]pyridin-2-yl)-2-fluorocyclopropane-1-carboxamide;

(1S,2S)-N-(5-(5-chloro-6-fluoro-7-isopropyl-1H-indazol-4-yl)pyrazolo[1,5-a]pyridin-2-yl)-2-fluorocyclopropane-1-carboxamide;

(1S,2S)-N-(5-(5-chloro-7-((1-cyanoethyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-fluoropyrrolidin-1-yl)-1H-indazol-4-yl)pyrazolo[1,5-a]pyridin-2-yl)-2-fluorocyclopropane-1-carboxamide;

benzyl (5-chloro-6-fluoro-4-(2-((1S,2S)-2-fluorocyclopropane-1-carboxamido)pyrazolo[1,5-a]pyridin-5-yl)-1H-indazol-7-yl)(1-cyanoethyl)carbamate;

(1S,2S)-N-(5-(5-chloro-6-fluoro-7-(2-methyl-1H-pyrrol-1-yl)-1H-indazol-4-yl)pyrazolo[1,5-a]pyridin-2-yl)-2-fluorocyclopropane-1-carboxamide;

(3S,4R)-4-methyltetrahydrofuran-3-yl (5-(5-chloro-6-fluoro-7-(methylthio)-1H-indazol-4-yl)pyrazolo[1,5-a]pyridin-2-yl)carbamate;

(1S,2R,3S)-N-(5-(5-chloro-7-(dimethylamino)-6-fluoro-1H-indazol-4-yl)pyrazolo[1,5-a]pyridin-2-yl)-2-methyl-3-(1-methyl-1H-pyrazol-4-yl)cyclopropane-1-carboxamide;

1-(5-(5-chloro-7-(dimethylamino)-6-fluoro-1H-indazol-4-yl)pyrazolo[1,5-a]pyridin-2-yl)-3-cyclopropylurea;

(1S,2S,3S)-N-(5-(5-chloro-7-(dimethylamino)-6-fluoro-1H-indazol-4-yl)pyrazolo[1,5-a]pyridin-2-yl)-2-methyl-3-(1-methyl-1H-pyrazol-4-yl)cyclopropane-1-carboxamide;

1-(5-chloro-6-fluoro-4-(2-((1S,2S)-2-fluorocyclopropane-1-carboxamido)pyrazolo[1,5-a]pyridin-5-yl)-1H-indazol-7-yl)-N,N-dimethyl-1H-pyrrole-3-carboxamide;

(1S,2S)-N-(5-(5-chloro-6-fluoro-7-isopropoxy-1H-indazol-4-yl)pyrazolo[1,5-a]pyridin-2-yl)-2-fluorocyclopropane-1-carboxamide;

(1S,2S)-N-(5-(5-chloro-7-cyclopentyl-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(2,2,2-trifluoro-1-hydroxyethyl)-1H-indazol-4-yl)pyrazolo[1,5-a]pyridin-2-yl)-2-fluorocyclopropane-1-carboxamide;

(1S,2S)-N-(5-(5-chloro-7-((1-cyclopropylethyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-7-((cyclopropylmethyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-((R)-1-methoxypropan-2-yl)-1H-indazol-4-yl)pyrazolo[1,5-a]pyridin-2-yl)-2-fluorocyclopropane-1-carboxamide;

(1S,2S)-N-(5-(5-chloro-6-fluoro-7-((S)-1-methoxypropan-2-yl)-1H-indazol-4-yl)pyrazolo[1,5-a]pyridin-2-yl)-2-fluorocyclopropane-1-carboxamide;

(1S,2S)-N-(5-(5-chloro-7-((1,1-difluoropropan-2-yl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(4-hydroxytetrahydrofuran-2-yl)-1H-indazol-4-yl)pyrazolo[1,5-a]pyridin-2-yl)-2-fluorocyclopropane-1-carboxamide;

(1S,2S)-N-(5-(5-chloro-6-fluoro-7-(1-formamidoethyl)-1H-indazol-4-yl)pyrazolo[1,5-a]pyridin-2-yl)-2-fluorocyclopropane-1-carboxamide;

(1S,2S)-N-(5-(5-chloro-6-fluoro-7-(1-propionamidoethyl)-1H-indazol-4-yl)pyrazolo[1,5-a]pyridin-2-yl)-2-fluorocyclopropane-1-carboxamide;

N-(1-(5-chloro-6-fluoro-4-(2-(((1S,2S)-2-fluorocyclopropane-1-carboxamido)pyrazolo[1,5-a]pyridin-5-yl)-1H-indazol-7-yl)ethyl)cyclobutanecarboxamide;

(1S,2S)-N-(5-(5-chloro-6-fluoro-7-(1-(2,2,2-trifluoroacetamido)ethyl)-1H-indazol-4-yl)pyrazolo[1,5-a]pyridin-2-yl)-2-fluorocyclopropane-1-carboxamide;

(1S,2S)-N-(5-(7-(1-acetamidoethyl)-5-chloro-6-fluoro-1H-indazol-4-yl)pyrazolo[1,5-a]pyridin-2-yl)-2-fluorocyclopropane-1-carboxamide;

(1S,2S)-N-(5-(5-chloro-7-(1,3-dimethylureido)-6-fluoro-1H-indazol-4-yl)pyrazolo[1,5-a]pyridin-2-yl)-2-fluorocyclopropane-1-carboxamide;

(1S,2S)-N-(5-(5-chloro-7-(1-(2,2-difluoroacetamido)ethyl)-6-fluoro-1H-indazol-4-yl)pyrazolo[1,5-a]pyridin-2-yl)-2-fluorocyclopropane-1-carboxamide; and (1S,2S)-N-(5-(5-chloro-7-((1S,2R)-1,2-dimethoxypropyl)-6-fluoro-1H-indazol-4-yl)pyrazolo[1,5-a]pyridin-2-yl)-2-fluorocyclopropane-1-carboxamide.

19. The compound of claim 15 or a pharmaceutically acceptable salt thereof, which is selected from the group consisting of:

(1S,2S)-N-(5-(5-bromo-6-fluoro-1H-indazol-4-yl)pyrazolo[1,5-a]pyridin-2-yl)-2-fluorocyclopropane-1-carboxamide;

(1S,2S)-N-(5-(5-ethyl-6-fluoro-1H-indazol-4-yl)pyrazolo[1,5-a]pyridin-2-yl)-2-fluorocyclopropane-1-carboxamide;

(1S,2S)-2-fluoro-N-(5-(6-fluoro-5-methoxy-1H-indazol-4-yl)pyrazolo[1,5-a]pyridin-2-yl)cyclopropane-1-carboxamide;

(1S,2S)-N-(5-(5,7-dichloro-6-fluoro-1H-indazol-4-yl)pyrazolo[1,5-a]pyridin-2-yl)-2-fluorocyclopropane-1-carboxamide;

(1S,2S)-2-fluoro-N-(5-(6-fluoro-5,7-dimethyl-1H-indazol-4-yl)pyrazolo[1,5-a]pyridin-2-yl)cyclopropane-1-carboxamide;

(1S,2S)-N-(5-(7-bromo-5-chloro-6-fluoro-1H-indazol-4-yl)pyrazolo[1,5-a]pyridin-2-yl)-2-fluorocyclopropane-1-carboxamide;

(1S,2S)-N-(5-(5-chloro-7-(dimethylamino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(methylthio)-1H-indazol-4-yl)pyrazolo[1,5-a]pyridin-2-yl)-2-fluorocyclopropane-1-carboxamide;

(1S,2S)-N-(5-(7-bromo-6-fluoro-5-methyl-1H-indazol-4-yl)pyrazolo[1,5-a]pyridin-2-yl)-2-fluorocyclopropane-1-carboxamide;

(1S,2S)-2-fluoro-N-(5-(6-fluoro-5-methyl-7-(methylthio)-1H-indazol-4-yl)pyrazolo[1,5-a]pyridin-2-yl)cyclopropane-1-carboxamide;

(1S,2S)-N-(5-(7-(dimethylamino)-6-fluoro-5-methyl-1H-indazol-4-yl)pyrazolo[1,5-a]pyridin-2-yl)-2-fluorocyclopropane-1-carboxamide;

(1S,2S)-2-fluoro-N-(5-(6-fluoro-7-methoxy-5-methyl-1H-indazol-4-yl)pyrazolo[1,5-a]pyridin-2-yl)cyclopropane-1-carboxamide;

(1S,2S)-N-(5-(5-chloro-6-fluoro-7-methoxy-1H-indazol-4-yl)pyrazolo[1,5-a]pyridin-2-yl)-2-fluorocyclopropane-1-carboxamide;

(1S,2S)-N-(5-(5-chloro-7-ethoxy-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(methylamino)-1H-indazol-4-yl)pyrazolo[1,5-a]pyridin-2-yl)-2-fluorocyclopropane-1-carboxamide;

(1S,2S)-N-(5-(5-chloro-7-(ethylamino)-6-fluoro-1H-indazol-4-yl)pyrazolo[1,5-a]pyridin-2-yl)-2-fluorocyclopropane-1-carboxamide;

(1S,2S)-N-(5-(5-chloro-7-(diethylamino)-6-fluoro-1H-indazol-4-yl)pyrazolo[1,5-a]pyridin-2-yl)-2-fluorocyclopropane-1-carboxamide;

(1S,2S)-N-(5-(5-chloro-7-((4-(dimethylamino)cyclohexyl)(methyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-((4-hydroxycyclohexyl)(methyl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(methyl((1R,4R)-4-(methylamino)cyclohexyl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(methyl((1S,4S)-4-(methylamino)cyclohexyl)amino)-1H-indazol-4-yl)pyrazolo[1,5-a]pyridin-2-yl)-2-fluorocyclopropane-1-carboxamide;

(1S,2S)-N-(5-(7-ethoxy-6-fluoro-5-methyl-1H-indazol-4-yl)pyrazolo[1,5-a]pyridin-2-yl)-2-fluorocyclopropane-1-carboxamide;

(1S,2S)-N-(5-(5-ethyl-6-fluoro-7-(methylthio)-1H-indazol-4-yl)pyrazolo[1,5-a]pyridin-2-yl)-2-fluorocyclopropane-1-carboxamide dihydrochloride;

(1S,2S)-N-(5-(7-((4-aminocyclohexyl)(methyl)amino)-5-chloro-6-fluoro-1H-indazol-4-yl)pyrazolo[1,5-a]pyridin-2-yl)-2-fluorocyclopropane-1-carboxamide;

(1S,2S)-N-(5-(7-(dimethylamino)-5-ethyl-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-((2-hydroxyethyl)thio)-1H-indazol-4-yl)pyrazolo[1,5-a]pyridin-2-yl)-2-fluorocyclopropane-1-carboxamide;

(1S,2S)-N-(5-(5-ethyl-6-fluoro-7-((2-(methylamino)-2-oxoethyl)thio)-1H-indazol-4-yl)pyrazolo[1,5-a]pyridin-2-yl)-2-fluorocyclopropane-1-carboxamide bis(2,2,2-trifluoroacetate);

(1S,2S)-2-fluoro-N-(5-(6-fluoro-7-((2-hydroxyethyl)thio)-5-methyl-1H-indazol-4-yl)pyrazolo[1,5-a]pyridin-2-yl)cyclopropane-1-carboxamide;

(1S,2S)-N-(5-(5-ethyl-7-(ethylamino)-6-fluoro-1H-indazol-4-yl)pyrazolo[1,5-a]pyridin-2-yl)-2-fluorocyclopropane-1-carboxamide;

(1S,2S)-N-(5-(5-ethyl-7-(ethyl(methyl)amino)-6-fluoro-1H-indazol-4-yl)pyrazolo[1,5-a]pyridin-2-yl)-2-fluorocyclopropane-1-carboxamide;

(1S,2S)-2-fluoro-N-(5-(6-fluoro-5,7-bis(methylthio)-1H-indazol-4-yl)pyrazolo[1,5-a]pyridin-2-yl)cyclopropane-1-carboxamide;

(1S,2S)-2-fluoro-N-(5-(6-fluoro-5-(methylthio)-1H-indazol-4-yl)pyrazolo[1,5-a]pyridin-2-yl)cyclopropane-1-carboxamide;

(1S,2S)-N-(5-(7-ethoxy-5-ethyl-6-fluoro-1H-indazol-4-yl)pyrazolo[1,5-a]pyridin-2-yl)-2-fluorocyclopropane-1-carboxamide;

(1S,2S)-N-(5-(5-ethyl-6,7-difluoro-1H-indazol-4-yl)pyrazolo[1,5-a]pyridin-2-yl)-2-fluorocyclopropane-1-carboxamide;

(1S,2S)-2-fluoro-N-(5-(6-fluoro-7-(2-hydroxyethoxy)-5-methyl-1H-indazol-4-yl)pyrazolo[1,5-a]pyridin-2-yl)cyclopropane-1-carboxamide;

(1S,2S)-N-(5-(6,7-difluoro-5-(methylthio)-1H-indazol-4-yl)pyrazolo[1,5-a]pyridin-2-yl)-2-fluorocyclopropane-1-carboxamide;

(1S,2S)-N-(5-(7-ethoxy-6-fluoro-5-(methylthio)-1H-indazol-4-yl)pyrazolo[1,5-a]pyridin-2-yl)-2-fluorocyclopropane-1-carboxamide;

methyl 6-fluoro-4-(2-(((1S,2S)-2-fluorocyclopropane-1-carboxamido)pyrazolo[1,5-a]pyridin-5-yl)-5-methyl-1H-indazole-7-carboxylate;

(1S,2S)-2-fluoro-N-(5-(6-fluoro-5-methyl-7-(N-methylacetamido)-1H-indazol-4-yl)pyrazolo[1,5-a]pyridin-2-yl)cyclopropane-1-carboxamide;

(1S,2S)-N-(5-(5-chloro-6-fluoro-7-(N-methylacetamido)-1H-indazol-4-yl)pyrazolo[1,5-a]pyridin-2-yl)-2-fluorocyclopropane-1-carboxamide;

5-chloro-6-fluoro-4-(2-((1S,2S)-2-fluorocyclopropane-1-carboxamido)pyrazolo[1,5-a]pyridin-5-yl)-N,N-dimethyl-1H-indazole-7-carboxamide;

(1S,2S)-2-fluoro-N-(5-(6-fluoro-7-((2-hydroxyethyl)(methyl)amino)-5-methyl-1H-indazol-4-yl)pyrazolo[1,5-a]pyridin-2-yl)cyclopropane-1-carboxamide;

(1S,2S)-N-(5-(7-(dimethylamino)-6-fluoro-5-(methylthio)-1H-indazol-4-yl)pyrazolo[1,5-a]pyridin-2-yl)-2-fluorocyclopropane-1-carboxamide;

(1S,2S)-N-(5-(5-chloro-6-fluoro-7-((3-hydroxycyclobutyl)(methyl)amino)-1H-indazol-4-yl)pyrazolo[1,5-a]pyridin-2-yl)-2-fluorocyclopropane-1-carboxamide;

N-(5-(6-fluoro-5-methyl-7-(methylthio)-1H-indazol-4-yl)pyrazolo[1,5-a]pyridin-2-yl)cyclopropanecarboxamide;

(1S,2S)-N-(5-(7-(ethyl(methyl)amino)-6-fluoro-5-methyl-1H-indazol-4-yl)pyrazolo[1,5-a]pyridin-2-yl)-2-fluorocyclopropane-1-carboxamide;

(1S,2S)-N-(5-(5-chloro-7-(ethyl(methyl)amino)-6-fluoro-1H-indazol-4-yl)pyrazolo[1,5-a]pyridin-2-yl)-2-fluorocyclopropane-1-carboxamide;

(1S,2S)-N-(5-(7-(dimethylamino)-6-fluoro-5-(trifluoromethyl)-1H-indazol-4-yl)pyrazolo[1,5-a]pyridin-2-yl)-2-fluorocyclopropane-1-carboxamide;

(1R,2S)-2-fluoro-N-(5-(6-fluoro-5-methyl-7-(methylthio)-1H-indazol-4-yl)pyrazolo[1,5-a]pyridin-2-yl)cyclopropane-1-carboxamide;

N-(5-(6-fluoro-5-(methylthio)-1H-indazol-4-yl)pyrazolo[1,5-a]pyridin-2-yl)cyclopropanecarboxamide;

6-fluoro-4-(2-((1S,2S)-2-fluorocyclopropane-1-carboxamido)pyrazolo[1,5-a]pyridin-5-yl)-N,N,5-trimethyl-1H-indazole-7-carboxamide;

(1R,2S)-2-fluoro-N-(5-(6-fluoro-5-(methylthio)-1H-indazol-4-yl)pyrazolo[1,5-a]pyridin-2-yl)cyclopropane-1-carboxamide;

(1S,2R)-2-fluoro-N-(5-(6-fluoro-5-(methylthio)-1H-indazol-4-yl)pyrazolo[1,5-a]pyridin-2-yl)cyclopropane-1-carboxamide;

(1R,2R)-2-fluoro-N-(5-(6-fluoro-5-(methylthio)-1H-indazol-4-yl)pyrazolo[1,5-a]pyridin-2-yl)cyclopropane-1-carboxamide;

(1R,2R)-2-fluoro-N-(5-(6-fluoro-5-methyl-7-(methylthio)-1H-indazol-4-yl)pyrazolo[1,5-a]pyridin-2-yl)cyclopropane-1-carboxamide;

(1S,2S)-N-(5-(7-(ethyl(methyl)amino)-6-fluoro-5-(methylthio)-1H-indazol-4-yl)pyrazolo[1,5-a]pyridin-2-yl)-2-fluorocyclopropane-1-carboxamide;

(1S,2S)-N-(5-(5-chloro-6-fluoro-7-methyl-1H-indazol-4-yl)pyrazolo[1,5-a]pyridin-2-yl)-2-fluorocyclopropane-1-carboxamide;

(1S,2S)-N-(5-(5-chloro-7-(difluoromethyl)-6-fluoro-1H-indazol-4-yl)pyrazolo[1,5-a]pyridin-2-yl)-2-fluorocyclopropane-1-carboxamide;

(1S,2S)-N-(5-(5-ethyl-6-fluoro-7-(trifluoromethyl)-1H-indazol-4-yl)pyrazolo[1,5-a]pyridin-2-yl)-2-fluorocyclopropane-1-carboxamide;

(1S,2S)-N-(5-(5-chloro-7-cyano-6-fluoro-1H-indazol-4-yl)pyrazolo[1,5-a]pyridin-2-yl)-2-fluorocyclopropane-1-carboxamide;

(1S,2S)-N-(5-(7-((cyanomethyl)thio)-5-ethyl-6-fluoro-1H-indazol-4-yl)pyrazolo[1,5-a]pyridin-2-yl)-2-fluorocyclopropane-1-carboxamide;

(1S,2S)-2-fluoro-N-(5-(6-fluoro-5-methyl-7-(trifluoromethoxy)-1H-indazol-4-yl)pyrazolo[1,5-a]pyridin-2-yl)cyclopropane-1-carboxamide;

(1S,2S)-N-(5-(5-chloro-6-fluoro-7-(methyl(pyrimidin-2-yl)amino)-1H-indazol-4-yl)pyrazolo[1,5-a]pyridin-2-yl)-2-fluorocyclopropane-1-carboxamide;

(1S,2S)-N-(5-(5-chloro-7-((cyanomethyl)thio)-6-fluoro-1H-indazol-4-yl)pyrazolo[1,5-a]pyridin-2-yl)-2-fluorocyclopropane-1-carboxamide;

(1R,2R)-N-(5-(6,7-difluoro-5-(methylthio)-1H-indazol-4-yl)pyrazolo[1,5-a]pyridin-2-yl)-2-fluorocyclopropane-1-carboxamide;

(1S,2R)-N-(5-(6,7-difluoro-5-(methylthio)-1H-indazol-4-yl)pyrazolo[1,5-a]pyridin-2-yl)-2-fluorocyclopropane-1-carboxamide;

(1R,2S)-N-(5-(6,7-difluoro-5-(methylthio)-1H-indazol-4-yl)pyrazolo[1,5-a]pyridin-2-yl)-2-fluorocyclopropane-1-carboxamide;

(1S,2S)-N-(5-(7-((1-cyanoethyl)thio)-5-ethyl-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(trifluoromethoxy)-1H-indazol-4-yl)pyrazolo[1,5-a]pyridin-2-yl)-2-fluorocyclopropane-1-carboxamide;

5-chloro-N-(cyanomethyl)-6-fluoro-4-(2-((1S,2S)-2-fluorocyclopropane-1-carboxamido)pyrazolo[1,5-a]pyridin-5-yl)-N-methyl-1H-indazole-7-carboxamide;

(1S,2S)-N-(5-(5-chloro-7-(N-(cyanomethyl)acetamido)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(methyl(1,3,5-triazin-2-yl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(methyl(1,2,4-triazin-3-yl)amino)-1H-indazol-4-yl)pyrazolo[1,5-a]pyridin-2-yl)-2-fluorocyclopropane-1-carboxamide;

(1S,2S)-N-(5-(5-chloro-6-fluoro-7-(isopropylamino)-1H-indazol-4-yl)pyrazolo[1,5-a]pyridin-2-yl)-2-fluorocyclopropane-1-carboxamide;

(1S,2S)-N-(5-(5-chloro-7-(ethylthio)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(3-methyl-2-oxoimidazolidin-1-yl)-1H-indazol-4-yl)pyrazolo[1,5-a]pyridin-2-yl)-2-fluorocyclopropane-1-carboxamide;

(1S,2S)-N-(5-(5-chloro-7-(cyclopropyl(methyl)amino)-6-fluoro-1H-indazol-4-yl)pyrazolo[1,5-a]pyridin-2-yl)-2-fluorocyclopropane-1-carboxamide;

(1S,2S)-N-(5-(5-chloro-6-fluoro-7-(hydroxymethyl)-1H-indazol-4-yl)pyrazolo[1,5-a]pyridin-2-yl)-2-fluorocyclopropane-1-carboxamide;

(1S,2S)-N-(5-(5-chloro-6-fluoro-7-(fluoromethyl)-1H-indazol-4-yl)pyrazolo[1,5-a]pyridin-2-yl)-2-fluorocyclopropane-1-carboxamide;
(1S,2S)-N-(5-(5-chloro-7-((cyanomethyl)amino)-6-fluoro-1H-indazol-4-yl)pyrazolo[1,5-a]pyridin-2-yl)-2-fluorocyclopropane-1-carboxamide;
(1S,2S)-N-(5-(5-chloro-6-fluoro-7-(1H-pyrrol-1-yl)-1H-indazol-4-yl)pyrazolo[1,5-a]pyridin-2-yl)-2-fluorocyclopropane-1-carboxamide;
(1S,2S)-N-(5-(5-chloro-7-((2-cyanopropan-2-yl)amino)-6-fluoro-1H-indazol-4-yl)pyrazolo[1,5-a]pyridin-2-yl)-2-fluorocyclopropane-1-carboxamide;
(1S,2S)-N-(5-(5-chloro-6-fluoro-7-(prop-1-en-2-yl)-1H-indazol-4-yl)pyrazolo[1,5-a]pyridin-2-yl)-2-fluorocyclopropane-1-carboxamide;
(1S,2S)-N-(5-(5-chloro-6-fluoro-7-isopropyl-1H-indazol-4-yl)pyrazolo[1,5-a]pyridin-2-yl)-2-fluorocyclopropane-1-carboxamide;
(1S,2S)-N-(5-(5-chloro-7-((1-cyanoethyl)amino)-6-fluoro-1H-indazol-4-yl)pyrazolo[1,5-a]pyridin-2-yl)-2-fluorocyclopropane-1-carboxamide;
(1S,2S)-N-(5-(5-chloro-6-fluoro-7-(3-fluoropyrrolidin-1-yl)-1H-indazol-4-yl)pyrazolo[1,5-a]pyridin-2-yl)-2-fluorocyclopropane-1-carboxamide;
(1S,2S)-N-(5-(5-chloro-6-fluoro-7-(2-methyl-1H-pyrrol-1-yl)-1H-indazol-4-yl)pyrazolo[1,5-a]pyridin-2-yl)-2-fluorocyclopropane-1-carboxamide;
(1S,2R,3S)-N-(5-(5-chloro-7-(dimethylamino)-6-fluoro-1H-indazol-4-yl)pyrazolo[1,5-a]pyridin-2-yl)-2-methyl-3-(1-methyl-1H-pyrazol-4-yl)cyclopropane-1-carboxamide;
(1S,2S)-N-(5-(5-chloro-6-fluoro-7-isopropoxy-1H-indazol-4-yl)pyrazolo[1,5-a]pyridin-2-yl)-2-fluorocyclopropane-1-carboxamide;
(1S,2S)-N-(5-(5-chloro-7-cyclopentyl-6-fluoro-1H-indazol-4-yl)pyrazolo[1,5-a]pyridin-2-yl)-2-fluorocyclopropane-1-carboxamide;
(1S,2S)-N-(5-(5-chloro-6-fluoro-7-(2,2,2-trifluoro-1-hydroxyethyl)-1H-indazol-4-yl)pyrazolo[1,5-a]pyridin-2-yl)-2-fluorocyclopropane-1-carboxamide;
(1S,2S)-N-(5-(5-chloro-6-fluoro-7-((R)-1-methoxypropan-2-yl)-1H-indazol-4-yl)pyrazolo[1,5-a]pyridin-2-yl)-2-fluorocyclopropane-1-carboxamide;
(1S,2S)-N-(5-(5-chloro-6-fluoro-7-((S)-1-methoxypropan-2-yl)-1H-indazol-4-yl)pyrazolo[1,5-a]pyridin-2-yl)-2-fluorocyclopropane-1-carboxamide;
(1S,2S)-N-(5-(5-chloro-7-((1,1-difluoropropan-2-yl)amino)-6-fluoro-1H-indazol-4-yl)pyrazolo[1,5-a]pyridin-2-yl)-2-fluorocyclopropane-1-carboxamide;
(1S,2S)-N-(5-(5-chloro-6-fluoro-7-(1-formamidoethyl)-1H-indazol-4-yl)pyrazolo[1,5-a]pyridin-2-yl)-2-fluorocyclopropane-1-carboxamide;
(1S,2S)-N-(5-(5-chloro-6-fluoro-7-(1-propionamidoethyl)-1H-indazol-4-yl)pyrazolo[1,5-a]pyridin-2-yl)-2-fluorocyclopropane-1-carboxamide;
N-(1-(5-chloro-6-fluoro-4-(2-((1S,2S)-2-fluorocyclopropane-1-carboxamido)pyrazolo[1,5-a]pyridin-5-yl)-1H-indazol-7-yl)ethyl)cyclobutanecarboxamide;
(1S,2S)-N-(5-(5-chloro-6-fluoro-7-(1-(2,2,2-trifluoroacetamido)ethyl)-1H-indazol-4-yl)pyrazolo[1,5-a]pyridin-2-yl)-2-fluorocyclopropane-1-carboxamide;
(1S,2S)-N-(5-(7-(1-acetamidoethyl)-5-chloro-6-fluoro-1H-indazol-4-yl)pyrazolo[1,5-a]pyridin-2-yl)-2-fluorocyclopropane-1-carboxamide;
(1S,2S)-N-(5-(5-chloro-7-(1,3-dimethylureido)-6-fluoro-1H-indazol-4-yl)pyrazolo[1,5-a]pyridin-2-yl)-2-fluorocyclopropane-1-carboxamide; and
(1S,2S)-N-(5-(5-chloro-7-(1-(2,2-difluoroacetamido)ethyl)-6-fluoro-1H-indazol-4-yl)pyrazolo[1,5-a]pyridin-2-yl)-2-fluorocyclopropane-1-carboxamide.

\* \* \* \* \*